US011266626B2

United States Patent
(12) United States Patent
Schon et al.

(10) Patent No.: US 11,266,626 B2
(45) Date of Patent: Mar. 8, 2022

(54) REDUCTION OF ER-MAM-LOCALIZED APP-C99 AND METHODS OF TREATING ALZHEIMER'S DISEASE

(71) Applicant: THE TRUSTEES OF COLUMBIA UNIVERSITY IN THE CITY OF NEW YORK, New York, NY (US)

(72) Inventors: Eric A. Schon, Bronx, NY (US); Estela Area-Gomez, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 838 days.

(21) Appl. No.: 15/917,344

(22) Filed: Mar. 9, 2018

(65) Prior Publication Data

US 2018/0271832 A1 Sep. 27, 2018

Related U.S. Application Data

(63) Continuation-in-part of application No. PCT/US2016/051046, filed on Sep. 9, 2016.

(60) Provisional application No. 62/216,198, filed on Sep. 9, 2015.

(51) Int. Cl.

| | |
|---|---|
| ***A61K 31/397*** | (2006.01) |
| ***A61K 31/192*** | (2006.01) |
| ***A61K 31/137*** | (2006.01) |
| ***A61K 31/166*** | (2006.01) |
| ***A61K 31/366*** | (2006.01) |
| ***A61K 31/519*** | (2006.01) |
| ***A61K 31/37*** | (2006.01) |
| ***A61K 31/11*** | (2006.01) |
| ***A61P 25/28*** | (2006.01) |
| ***A61K 31/197*** | (2006.01) |
| ***A61K 31/327*** | (2006.01) |
| ***A61K 31/40*** | (2006.01) |
| ***A61K 31/4188*** | (2006.01) |
| ***A61K 31/513*** | (2006.01) |
| ***A61K 31/55*** | (2006.01) |
| ***A61K 31/566*** | (2006.01) |
| ***A61K 31/675*** | (2006.01) |

(52) U.S. Cl.

CPC ............ *A61K 31/397* (2013.01); *A61K 31/11* (2013.01); *A61K 31/137* (2013.01); *A61K 31/166* (2013.01); *A61K 31/192* (2013.01); *A61K 31/197* (2013.01); *A61K 31/327* (2013.01); *A61K 31/366* (2013.01); *A61K 31/37* (2013.01); *A61K 31/40* (2013.01); *A61K 31/4188* (2013.01); *A61K 31/513* (2013.01); *A61K 31/519* (2013.01); *A61K 31/55* (2013.01); *A61K 31/566* (2013.01); *A61K 31/675* (2013.01); *A61P 25/28* (2018.01)

(58) Field of Classification Search

None

See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,710,384 | A | 12/1987 | Rotman |
| 5,059,595 | A | 10/1991 | Le Grazie |
| 5,073,543 | A | 12/1991 | Marshall et al. |
| 5,120,548 | A | 6/1992 | McClelland et al. |
| 5,236,838 | A | 8/1993 | Rasmussen et al. |
| 5,252,479 | A | 10/1993 | Srivastava |
| 5,328,470 | A | 7/1994 | Nabel et al. |
| 5,354,556 | A | 10/1994 | Sparks et al. |
| 5,492,812 | A | 2/1996 | Vooheis |
| 5,508,167 | A | 4/1996 | Roses et al. |
| 5,580,757 | A | 12/1996 | Desnick et al. |
| 5,591,767 | A | 1/1997 | Mohr et al. |
| 5,639,476 | A | 6/1997 | Oshlack et al. |
| 5,641,670 | A | 6/1997 | Treco et al. |
| 5,674,533 | A | 10/1997 | Santus et al. |
| 5,721,121 | A | 2/1998 | Etcheverry et al. |
| 5,733,566 | A | 3/1998 | Lewis |
| 5,747,469 | A | 5/1998 | Roth et al. |
| 5,766,846 | A | 6/1998 | Schlossmacher et al. |
| 5,795,737 | A | 8/1998 | Seed et al. |
| 5,804,387 | A | 9/1998 | Cormack et al. |
| 5,879,680 | A | 3/1999 | Ginns et al. |
| 5,942,400 | A | 8/1999 | Anderson et al. |
| 5,985,581 | A | 11/1999 | Nixon et al. |

(Continued)

FOREIGN PATENT DOCUMENTS

| | | |
|---|---|---|
| WO | WO-1997/027296 | 7/1997 |
| WO | WO-1999/07409 | 2/1999 |

(Continued)

OTHER PUBLICATIONS

ARA "medications and alzheimer's disease" accessed from alzalaska.org on May 7, 2021 (Year: 2012).*

(Continued)

*Primary Examiner* — Adam Weidner

(74) *Attorney, Agent, or Firm* — Wilmer Cutler Pickering Hale and Dorr LLP

(57) ABSTRACT

The invention provides for methods for treating Alzheimer's Disease in a subject by reducing ER-MAM localized APP-C99.

8 Claims, 98 Drawing Sheets

(27 of 98 Drawing Sheet(s) Filed in Color)

Specification includes a Sequence Listing.

(56) References Cited

U.S. PATENT DOCUMENTS

| | | | |
|---|---|---|---|
| 6,017,524 | A | 1/2000 | Roth et al. |
| 6,083,725 | A | 7/2000 | Selden et al. |
| 6,143,290 | A | 11/2000 | Zhang et al. |
| 6,188,045 | B1 | 2/2001 | Hansen et al. |
| 6,194,153 | B1 | 2/2001 | St. George-Hyslop et al. |
| 6,210,666 | B1 | 4/2001 | Miyamura |
| 6,232,039 | B1 | 5/2001 | Chiang et al. |
| 6,323,039 | B1 | 11/2001 | Dykens et al. |
| 6,395,884 | B1 | 5/2002 | Selden et al. |
| 6,410,010 | B1 | 6/2002 | Zhang et al. |
| 6,451,547 | B1 | 9/2002 | Jackowski et al. |
| 6,451,600 | B1 | 9/2002 | Rasmussen et al. |
| 6,458,574 | B1 | 10/2002 | Selden et al. |
| 6,461,609 | B1 | 10/2002 | Calhoun et al. |
| 6,485,911 | B1 | 11/2002 | St. George-Hyslop et al. |
| 6,495,335 | B2 | 12/2002 | Chojkier et al. |
| 6,511,847 | B1 | 1/2003 | Zhang et al. |
| 6,627,449 | B1 | 9/2003 | Tsien et al. |
| 6,780,975 | B2 | 8/2004 | Tsien et al. |
| 6,800,733 | B2 | 10/2004 | Tsien et al. |
| 6,960,470 | B1 | 11/2005 | Malinow et al. |
| 6,998,467 | B1 | 2/2006 | St. George-Hyslop et al. |
| 7,148,342 | B2 | 12/2006 | Tolentino et al. |
| 7,294,504 | B1 | 11/2007 | Wang |
| 7,422,896 | B1 | 9/2008 | Wang |
| 8,398,968 | B2 | 3/2013 | Mayall |
| 8,404,653 | B2 | 3/2013 | Zsebo |
| 2002/0168673 | A1 | 11/2002 | Fuller et al. |
| 2002/0173478 | A1 | 11/2002 | Gewirtz |
| 2003/0044776 | A1 | 3/2003 | Dykens et al. |
| 2005/0250682 | A1 | 11/2005 | Molina |
| 2006/0154865 | A1* | 7/2006 | Amrein ................ C07K 14/475 514/8.6 |
| 2007/0032548 | A1 | 2/2007 | Ellis |
| 2007/0072204 | A1 | 3/2007 | Hannon et al. |
| 2008/0119488 | A1 | 5/2008 | Bayne et al. |
| 2010/0062457 | A1 | 3/2010 | McIntyre |
| 2011/0256565 | A1 | 10/2011 | Schon et al. |
| 2012/0251459 | A1 | 10/2012 | Lee et al. |
| 2014/0044757 | A1 | 2/2014 | Chang et al. |
| 2014/0288030 | A1* | 9/2014 | Cohen ..................... A61P 25/16 514/171 |

FOREIGN PATENT DOCUMENTS

| | | | |
|---|---|---|---|
| WO | WO-1999/032619 | A1 | 7/1999 |
| WO | WO-2000/01846 | | 1/2000 |
| WO | WO-2000/044895 | A1 | 8/2000 |
| WO | WO-2000/044914 | A1 | 8/2000 |
| WO | WO-2001/029058 | A1 | 4/2001 |
| WO | WO-2001736646 | | 5/2001 |
| WO | WO-2001792337 | | 12/2001 |
| WO | WO-2002/046767 | | 6/2002 |
| WO | WO-2009/158148 | | 12/2009 |
| WO | WO-20097147009 | | 12/2009 |
| WO | WO-2012/040727 | | 3/2012 |
| WO | WO-2013/066764 | | 5/2013 |
| WO | WO 2013149091 | * | 10/2013 |
| WO | WO-2015124576 | | 8/2015 |
| WO | WO-2017044807 | A2 | 3/2017 |
| WO | WO2019173795 | | 9/2019 |

OTHER PUBLICATIONS

Lauritzen "The b-Secretase-Derived C-Terminal Fragment of bAPP, C99, But Not Ab, Is a Key Contributor to Early Intraneuronal Lesions in Triple-Transgenic Mouse Hippocampus" The Journal of Neuroscience, Nov. 14, 2012 • 32(46): 16243-16255 • (Year :2012).*

Zhang "Amyloid-β Production Via Cleavage of Amyloid-β Protein Precursor is Modulated by Cell Density" J Alzheimers Dis. 2010 ; 22(2): 683-984 (Year: 2010).*

Schon "Mitochondria-associated ER membranes in Alzheimer disease" Molecular and Cellular Neuroscience 55 (2013) 26-36 (Year: 2013).*

Gilady, S. et al., "Ero1α requires oxidizing and normoxic conditions to localize to the mitochondria-associated membrane (MAM)", Cell Stress and Chaperones, 15, pp. 619-629 (2010) (11 pages).

Giorgi, C. et al., "PML Regulates Apoptosis at Endoplasmic Reticulum by Modulating Calcium Release", Author manuscript published in final form as: Science, 330(6008), pp. 1247-1251 (Nov. 26, 2010) (11 pages).

Glater, E.E. et al., "Axonal transport of mitochondria requires milton to recruit kinesin heavy chain and is light chain independent", The Journal of Cell Biology, 173(4), pp. 545-557 (May 22, 2006) (13 pages).

Goate, A. et al., "Segregation of a missense mutation in the amyloid precursor protein gene with familial Alzheimer's disease", Nature, 349, pp. 704-706 (Feb. 21, 1991) (3 pages).

Goedert, M. et al., "A Century of Alzheimer's Disease", Science, 314, pp. 777-781 (Nov. 3, 2006) (5 pages).

Goetz, J.G. et al., "Interaction of the smooth endoplasmic reticulum and mitochondria", Biochemical Society Transactions, 34(part 3), pp. 370-373 (2006) (4 pages).

Gong, C-X. et al., "Impaired brain glucose metabolism leads to Alzheimer neurofibrillary degeneration through a decrease in tau O-GlcNAcylation", Journal of Alzheimer's Disease, 9, pp. 1-12 (2006) (12 pages).

Gorziglia, M. et al., "Expression of the OSU Rotavirus Outer Capsid Protein VP4 by an Adenovirus Recombinant," Journal of Virology, 66(7), pp. 4407-4412 (Jul. 1992) (6 pages).

Graham, F.L. et al., "Characteristics of a Human Cell Line Transformed by DNA from Human Adenovirus Type 5", J. gen. Virol., 36, pp. 59-72 (1977) (14 pages).

Green, D.R. et al., "Mitochondria and Apoptosis", Science, 281, pp. 1309-1312, (Aug. 28, 1998) (5 pages).

Grimm, M.O.W. et al., "Intracellular APP Domain Regulates Serine-Palmitoyl-CoA Transferase Expression and is Affected in Alzheimer's Disease", International Journal of Alzheimer's Disease, Article ID 695413, (2011) (8 pages).

Grimm, M.O.W. et al., "Regulation of cholesterol and sphingomyelin metabolism by amyloid-β and presenilin", Nature Cell Biology, 7(11):1118-1123; Supplementary Information pp. 1-4, (Nov. 2005) (10 pages).

Grziwa, B. et al., "The Transmembrane Domain of the Amyloid Precursor Protein In Microsomal Membranes Is on Both Sides Shorter than Predicted", The Journal of Biological Chemistry, 278(9), pp. 6803-6808 (Feb. 28, 2003) (7 pages).

Gu, Y. et al., "The Presenilin Proteins Are Components of Multiple Membrane-bound Complexes That Have Different Biological Activities", The Journal of Biological Chemistry, 279(30), pp. 31329-31336 (Jul. 23, 2004) (9 pages).

Guan, X.L. et al., "Functional Interactions between Sphingolipids and Sterols in Biological Membranes Regulating Cell Physiology", Molecular Biology ofthe Cell, 20, pp. 2083-2095 (Apr. 1, 2009) (13 pages).

Guardia-Laguarta, C. et al., "α-Synuclein Is Localized to Mitochondria-Associated ER Membranes", The Journal of Neuroscience, 34(1), pp. 249-259 (Jan. 1, 2014) (11 pages).

Gulati, S. et al., "Sterols and sphingolipids: Dynamic duo or partners in crime?", Author manuscript published in final edited form as: Prog Lipid Res., 49(4), pp. 353-365 (Oct. 2010) (27 pages).

Gunter, T.E. et al., "The $Ca^{2+}$ transport mechanisms of mitochondria and $Ca^{2+}$ uptake from physiological-type $Ca^{2+}$ transients", Biochimica et Biophysica Acta, 1366, pp. 5-15 (1998) (11 pages).

Gunter, K.K. et al., "Transport of Calcium by Mitochondria", Journal of Bioenergetics and Biomembranes, 26(5), pp. 471-485 (1994) (15 pages).

Guo, Q. et al., "Increased Vulnerability of Hippocampal Neurons from Presenilin-1 Mutant Knock-In Mice to Amyloid β-Peptide Toxicity: Central Roles of Superoxide Production and Caspase Activation", J. Neurochem., 72, pp. 1019-1029 (1999) (11 pages).

Guo, Q. et al., "Increased vulnerability of hippocampal neurons to excitotoxic necrosis in presenilin-1 mutant knock-in mice", Nature Medicine, 5(1), pp. 101-106 (Jan. 1999) (6 pages).

(56) References Cited

OTHER PUBLICATIONS

Guo, X. et al., "The GTPased Miro Is Required for Axonal Transport of Mitochondria to *Drosophila* Synapses", Neuron, 47, pp. 379-393 (Aug. 4, 2005) (15 pages).
Gurskaya, N.G. et al., "Engineering of a monomeric green-to-red photoactivatable fluorescent protein induced by blue light", Nature Biotechnology, 24(4), pp. 461-465 (Apr. 2006) (5 pages).
Gwon, A-R. et al., "Oxidative lipid modification of nicastrin enhances amyloidogenic γ-secretase activity in Alzheimer's disease", Aging Cell., 11(4), pp. 559-568 (Aug. 2012) (10 pages).
Gómez-Ramos, P. et al., "Ultrastructural Localization of Intraneuronal Aβ-Peptide in Alzheimer Disease Brains", Journal of Alzheimer's Disease, 11, pp. 53-59 (2007) (7 pages).
Haass, C. et al., "Trafficking and Proteolytic Processing of APP", Cold Spring Harbor Perspect Med, 2:a006270, (2012) (25 pages).
Hafiane, A. et al., "Novel Apo E-Derived ABCA1 Agonist Peptide (CS-6253) Promotes Reverse Cholesterol Transport and Induces Formation of preβ-1 HDL In Vitro", PLOS One 10(7):e0131997, (Jul. 24, 2015) (32 pages).
Hager, G. et al., "Protein dynamics in the nuclear compartment", Current Opinion in Genetics & Development, 12, pp. 137-141 (2002) (5 pages).
Hajnóczky, G. et al., "Old players in a new role: mitochondria-associated membranes, VDAC, and ryanodine receptors as contributors to calcium signal propagation from endoplasmic reticulum to the mitochondria", Cell Calcium, 32(5-6), pp. 363-377 (2002) (15 pages).
Halima, S.B. et al., "Specific Inhibition of β-Secretase Processing of the Alzheimer Disease Amyloid Precursor Protein", Cell Reports, 14, pp. 2127-2141 (Mar. 8, 2016) (16 pages).
Halliday, G. et al., "Pick Bodies in a Family with Presenilin-1 Alzheimer's Disease", Ann Neurol, 57, pp. 139-143 (2005) (5 pages).
Han, J. et al., "OCIAD2 activates γ-secretase to enhance amyloid β production by interacting with nicastrin", Cell. Mol. Life Sci., 71, pp. 2561-2576 (2014) (16 pages).
Hanashima, S. et al., "Synthesis of N-glycan units for assessment of substrate structural requirements of N-acetylglucosamlnyltransferase III", Bioorganic & Medicinal Chemistry Letters, 24, pp. 4533-4537 (2014) (5 pages).
Hancock, J.F. "Lipid rafts: contentious only from simplistic standpoints", Author manuscript published in final edited form as: Nat Rev Mol Cell Biol., 7(6), pp. 456-462 (Jun. 2006) (16 pages).
Handler, M. et al., "Presenilin-1 regulates neuronal differentiation during neurogenesis", Development, 127, pp. 2593-2606 (2000) (14 pages).
Hanshaw, R.G. et al., "New reagents for phosphatidylserine recognition and detection of apoptosis", Bioorganic & Medicinal Chemistry, 13, pp. 5035-5042 (2005) (8 pages).
Hansson, E.M. et al., "Aph-1 interacts at the cell surface with proteins in the active γ-secretase complex and membrane-tethered Notch", Journal of Neurochemistry, 92, pp. 1010-1020 (2005) (11 pages).
Hansson, C.A. et al., "Nicastrin, Presenilin, APH 1, and PEN-2 Form Active γ-Secretase Complexes in Mitochondria", The Journal of Biological Chemistry, 279(49), pp. 51654-51660 (2004) (8 pages).
Hansson Petersen, C.A. et al., "The amyloid β-peptide is imported into mitochondria via the TOM import machinery and localized to mitochondrial cristae", PNAS, 105(35), pp. 13145-13150 (Sep. 2, 2008) (6 pages).
Hardy, J.A. et al., "Alzheimer's Disease: The Amyloid Cascade Hypothesis", Science, 256, pp. 184-185 (Apr. 10, 1992) (3 pages).
Hardy, J. et al., "The Amyloid Hypothesis of Alzheimer's Disease: Progress and Problems on the Road to Therapeutics", Science, 297, pp. 353-356 (Jul. 19, 2002) (6 pages).
Hardy, J., "Framing β-amyloid". Nature Genetics, 1, pp. 233-234 (Jul. 1992) (2 pages).
Hare, J., "Trafficking of amyloid β-precursor protein products C83 and C99 on the endocytic pathway", Biochemical and Biophysical Research Communications, 401, pp. 219-224 (2010) (6 pages).
Harmon, C.M. et al., "Labeling of Adipocyte Membranes by Sulfo-N-Succinimidyl Derivatives of Long-Chain Fatty Acids: Inhibition of Fatty Acid Transport", J. Membrane Biol., 121, pp. 261-268 (1991) (8 pages).
Hartmann, T. et al., "Alzheimer's disease: the lipid connection", Journal of Neurochemistry, 103(Suppl. 1), pp. 159-170 (2007) (12 pages).
Hashimoto, T. et al., "Colocalization of MCT1, CD147, and LDH in mitochondrial inner membrane of L6 muscle cells: evidence of a mitochondrial lactate oxidation complex", Am. J. Physiol Endocrinol Metab, 290(6), pp. E1237-E1244 (Jan. 24, 2006) (8 pages).
Hayashi, T.et al., "Detergent-Resistant Microdomains Determine the Localization of α-1 Receptors to the Endoplasmic Reticulum-Mitochondria Junction", Molecular Pharmacology, 77(4), pp. 517-528 (2010) (12 pages).
Hayashi, T. et al., "MAM: more than just a housekeeper", Author manuscript published in final edited form as: Trends Cell Biol., 19(2), pp. 81-88 (Feb. 2009) (18 pages).
Hayashi, T. et al., "Sigma-1 Receptor Chaperones at the ER-Mitochondrion Interface Regulate $Ca^{2+}$ Signaling and Cell Survival", Cell, 131, pp. 596-610 (Nov. 2, 2007) (15 pages).
Hayrapetyan, V. et al., "The N-terminus of presenilin-2 increases single channel activity of brain ryanodine receptors through direct protein-protein interaction", Cell Calcium, 44, pp. 507-518 (2008) (12 pages).
He, X. et al., "Deregulation of sphingolipid metabolism in Alzheimer's disease", Author manuscript, published in final edited form as: Neurobiol Aging, 31(3), pp. 398-408 (Mar. 2010) (21 pages).
He, X. et al., "Reduction of Mitochondria-Endoplasmic Reticulum Interactions by Acetylcholine Protects Human Umbilical Vein Endothelial Cells From Hypoxia/Reoxygenation Injury", Arterioscler Thromb Vasc Biol, 35, pp. 1623-1634 (Jul. 2015) (12 pages).
Hedskog, L. et al., "Modulation of the endoplasmic reticulum-mitochondria interface in Alzheimer's disease and related models", PNAS, 110(19), pp. 7916-7921 (May 7, 2013) (6 pages).
Heilig, E.A. et al., "Trans-Dominant Negative Effects of Pathogenic PSEN1 Mutations on γ-Secretase Activity and Aβ Production," The Journal of Neuroscience, 33(28), pp. 11606-11617 (Jul. 10, 2013) (12 pages).
Helseth, E. et al., "Changes in the Transmembrane Region of the Human Immunodeficiency Virus Type 1 gp41 Envelope Glycoprotein Affect Membrane Fusion," Journal of Virology, 64(12), pp. 6314-6318 (Dec. 1990) (5 pages).
Hendriks, L. et al., "Presenile dementia and cerebral haemorrhage linked to a mutation at codon 692 of the β-amyloid precursor protein gene", Nature Genetics, 1, pp. 218-221 (Jun. 1992) (4 pages).
Hansen, J.B., "Towards Selective Kir6.2/SUR1 Potassium Channel Openers, Medicinal Chemistry and Therapeutic Perspectives", Current Medicinal Chemistry, 13(4), pp. 361-376 (2006) (16 pages).
Herms, J. et al., "Cortical dysplasia resembling human type 2 lissencephaly in mice lacking all three APP family members", The EMBO Journal, 23(20), pp. 4106-4115 (2004) (10 pages).
Orrenius, S. and Nicotera, P., "The calcium ion and cell death", J Neural Transm, 43(Suppl), pp. 1-11 (1994) (11 pages).
Oster-Granite, M.L. et al., "Age-Dependent Neuronal and Synaptic Degeneration in Mice Transgenic for the C Terminus of the Amyloid Precursor Protein", The Journal of Neuroscience, 16(21), pp. 6732-6741 (Nov. 1, 1996) (10 pages).
Ostrom, R.S. and Liu, X., "Detergent and Detergent-Free Methods to Define Lipid Rafts and Caveolae", :Methods in Molecular Biology, vol. 400: Methods in Membrane Lipids, pp. 459-468 (2007) (10 pages).
Pack-Chung, E. et al., "Presenilin 2 interacts with Sorcin, a Modulator of the Ryanodine Receptor", The Journal of Biological Chemistry, 275(19), pp. 14440-14445, (May 12, 2000) (7 pages).
Page, K.A. et al., "Construction and Use of a Human Immunodeficiency Virus Vector for Analysis of Virus Infectivity", Journal of Virology, 64(11), pp. 5270-5276 (Nov. 1990) (7 pages).

(56) References Cited

OTHER PUBLICATIONS

Pagliaro, L. et al., "Emerging classes of protein-protein interaction inhibitors and new tools for their development", Current Opinion in Chemical Biology, 8, pp. 442-449 (2004) (8 pages).
Paillard, M. et al., "Depressing Mitochondria-Reticulum Interactions Protects Cardiomyocytes From Lethal Hypoxia-Reoxygenation Injury", Circulation, 128, pp. 1555-1565 (Oct. 1, 2013) (11 pages).
Pani, A. et al., "Accumulation of neutral lipids in peripheral blood mononuclear cells as a distinctive trait of Alzheimer patients and asymptomatic subjects at risk of disease", BMC Medicine, 7(66), doi:10.1186/1741-7015-7-66 (Nov. 2, 2009) (12 pages).
Pani, Al. et al., "Altered Cholesterol Ester Cycle in Skin Fibroblasts from Patients with Alzheimer's Disease", Journal of Alzheimer's Disease, 18, pp. 829-841 (2009) (13 pages).
Papassotiropoulos, A. et al., "A Cluster of Cholesterol-Related Genes Confers Susceptibility for Alzheimer's Disease", J Clin Psychiatry, 66(7), pp. 940-947 (Jul. 2005) (8 pages).
Papassotiropoulos, A. et al., "Cholesterol 25-Hydroxylase on Chromosome 10q Is a Susceptibility Gene for Sporadic Alzheimer's Disease", Neurodegenerative Dis, 2, pp. 233-241 (2005) (9 pages).
Papassotiropoulos, A. et al., "Increased Brain β-Amyloid Load, Phosphorylated Tau, and Risk of Alzheimer Disease Associated With an Intronic CYP46 Polymorphism", Arch Neurol., 60, pp. 29-35 (Jan. 2003) (7 pages).
Park, H.-J. et al., "The stress response neuropeptide CRF increases amyloid-β production by regulating γ-secretase activity", The EMBO Journal, 34(12), pp. 1674-1686 (May 11, 2015) (13 pages).
Pasternak, S.H. et al., "Presenilin-1, Nicastrin, Amyloid Precursor Protein, and y-Secretase Activity Are Co-localized in the Lysosomal Membrane", The Journal of Biological Chemistry, 278(29), pp. 26687-26694 (Jul. 18, 2003) (9 pages).
Peacock, M.L. et al., "Novel polymorphism in the A4 region of the amyloid precursor protein gene in a patient without Alzheimer's disease", Neurology, 43, pp. 1254-1256 (Jun. 1993) (3 pages).
Pellegrini, L. et al., "PAMP and PARL, two novel putative metalloproteases interacting with the CoOH-terminus of Presenilin-1 and -2", Journal of Alzheimer's Disease, 3, pp. 181-190 (2001) (10 pages).
Pera, M. et al., "Distinct patterns of APP processing in the CNS in autosomal-dominant and sporadic Alzheimer disease", Acta Neuropathol, 125, pp. 201-213 (2013) (13 pages).
Pera, M. et al., "Increased localization of APP-C99 in mitochondria-associated ER membranes causes mitochondrial dysfunction in Alzheimer disease", The EMBO Journal, 36(22), pp. 3356-3371 (2017) (16 pages).
Pereira, A.J. et al., "Mitochondrial Association of a Plus End-Directed Microtubule Motor Expressed during Mitosis in *Drosophila*", The Journal of Cell Biology, 136(5), pp. 1081-1090 (Mar. 10, 1997) (10 pages).
Perez-Tur, J. et al., "A mutation in Alzheimer's disease destroying a splice acceptor site in the presenilin-1 gene", NeuroReport, 7(1), pp. 297-301 (Dec. 29, 1995) (5 pages).
Pericak-Vance, M.A. et al., "Linkage Studies in Familial Alzheimer Disease: Evidence for Chromosome 19 Linkage", Am. J. Hum. Genet., 48(6), pp. 1034-1050 (1991) (17 pages).
Petropoulos, C.J. et al., "Using Avian Retroviral Vectors for Gene Transfer", Journal of Virology, 66(6), pp. 3391-3397 (Jun. 1992) (7 pages).
Pettegrew, J.W. et al., "Brain Membrane Phospholipid Alterations in Alzheimer's Disease", Neurochemical Research, 26(7), pp. 771-782 (Jul. 2001) (12 pages).
Pickel, V.M. et al., "Ultrastructural Localization of Sorcin, a 22 kDa Calcium Binding Protein, in the Rat Caudate-Putamen Nucleus: Association With Ryanodine Receptors and Intracellular Calcium Release", The Journal of Comparative Neurology, 386, pp. 625-634 (1997) (10 pages).
Pierrot, N. et al., "Amyloid precursor protein controls cholesterol turnover needed for neuronal activity", EMBO Mol Med, 5, pp. 608-625 (2013) (18 pages).
Pigino, G. et al., "Alzheimer's Presenilin 1 Mutations Impair Kinesin-Based Axonal Transport", The Journal of Neuroscience, 23(11), pp. 4499-4508 (Jun. 1, 2003) (10 pages).
Pike, L.J., "The challenge of lipid rafts", Journal of Lipid Research, 50(Suppl.), pp. S323-S328 (Apr. 2009) (6 pages).
Pilling, A.D. et al., "Kinesin-1 and Dynein Are the Primary Motors for Fast Transport of Mitochondria in *Drosophila* Motor Axons", Molecular Biology of the Cell, 17, pp. 2057-2068 (Apr. 2006) (12 pages).
Pinton, P. et al., "Chapter 15: Biosensors for the Detection of Calcium and pH", Methods in Cell Biology, vol. 80, Elsevier Inc., Cambridge, MA, pp. 297-325 (2007) (29 pages).
Pitas, R.E. et al., "Astrocytes synthesize apolipoprotein E and metabolize apolipoprotein E-containing lipoproteins", Biochimca et Biophysica Acta, 917, pp. 148-161 (1987) (14 pages).
Pitts, K.R. et al., "The Dynamin-like Protein DLP1 Is Essential for Normal Distribution and Morphology of the Endoplasmic Reticulum and Mitochondria in Mammalian Cells", Molecular Biology of the Cell, 10, pp. 4403-4417 (Dec. 1999) (15 pages).
Pizzo, P. and Pozzan, T., "Mitochondria-endoplasmic reticulum choreography: structure and signaling dynamics", Trends in Cell Biology, 17(10), pp. 511-517 (Available online Sep. 11, 2007) (7 pages).
Pohland, M. et al., "MH84 improves mitochondrial dysfunction in a mouse model of early Alzheimer's disease", Alzheimer's Research & Therapy, 10(18), (Available online Feb. 13, 2018) (12 pages).
Pohland, M. et al., "MH84: A Novel γ-Secretase Modulator/PPARγ Agonist-Improves Mitochondrial Dysfunction in a Cellular Model of Alzheimer's Disease", Neurochem Res, 41, pp. 231-242 (2016) (12 pages).
Polzhofer, H., "Linking cholesterol sensing at the plasma membrane to its production at the endoplasmic reticulum", Doctoral Thesis, ETH Zürich, (2010) (157 pages).
Ponting, C.P. et al., "Identification of a novel family of presenilin homologues", Human Molecular Genetics, 11 (9), pp. 1037-1044 (2002) (8 pages).
Porter, D.L. et al., "Chimeric Antigen Receptor-Modified T Cells in Chronic Lymphoid Leukemia", N Engl J Med, 365(8), pp. 725-733 (Aug. 10, 2011); Correction printed N Engl J Med, 374(10), p. 998 (Mar. 10, 2016) (10 pages).
Poston, C.N. et al., "In-depth proteomic analysis of mammalian mitochondria-associated membranes (MAM)", Journal of Proteomics, 79, pp. 219-230 (Jan. 2013) (13 pages).
Pottekat, A. and Menon, A.K., "Subcellular Localization and Targeting of N-Acetylglucosaminyl Phosphatidylinositol De-N-acetylase, the Second Enzyme in the Glycosylphosphatidylinositol Biosynthetic Pathway", The Journal of Biological Chemistry, 279(16), pp. 15743-15751 (Apr. 16, 2004) (10 pages).
Pozzan, T. et al., "Molecular and Cellular Physiology of Intracellular Calcium Stores", Physiological Reviews, 74(3), pp. 595-636 (Jul. 1994) (42 pages).
Praticò, D. et al., "Oxidative Injury in Diseases of the Central Nervous System: Focus on Alzheimer's Disease", Am. J. Med., 109, pp. 577-585 (Nov. 2000) (9 pages).
Prihar, G. et al., "Alzheimer disease PS-1 exon 9 deletion defined", Nature Medicine, 5(10), p. 1090 (Oct. 1999) (1 page).
Priller, C. et al., "Mutant Presenilin 1 Alters Synaptic Transmission in Cultured Hippocampal Neurons", The Journal of Biological Chemistry, 282(2), pp. 1119-1127 (Jan. 12, 2007) (10 pages).
Prinz, W.A. et al., "Mutants Affecting the Structure of the Cortical Endoplasmic Reticulum in *Saccharomyces cerevisiae*", The Journal of Cell Biology, 150(3), pp. 461-474 (Aug. 7, 2000) (14 pages).
Puglielli, L. et al., "Acyl-coenzyme A: cholesterol acyltransferase modulates the generation of the amyloid β-peptide,", Nature Cell Biology, 3, pp. 905-912 (Oct. 2001) (8 pages).
Puglielli, L. et al., "Role of Acyl-Coenzyme A—Cholesterol Acyltransferase Activity in the Processing of the Amyloid Precursor Protein", Journal of Molecular Neuroscience, 24, pp. 93-96 (2004) (4 pages).
Quantin, B. et al., "Adenovirus as an expression vector in muscle cells in vivo", Proc. Natl. Acad. Sci. USA, 89, pp. 2581-2584 (Apr. 1992) (4 pages).

(56) References Cited

OTHER PUBLICATIONS

Rademakers, R. et al., "Tau negative frontal lobe dementia at 17q21: significant finemapping of the candidate region to a 4.8 cM interval", Molecular Psychiatry, 7, pp. 1064-1074 (2002) (11 pages).
Rajendran, L. et al., "Efficient Inhibition of the Alzheimer's Disease β-Secretase by Membrane Targeting," Science, 320, pp. 520-523 (Apr. 25, 2008); Correction, Science, 321, Aug. 15, 2008 (6 pages).
Ranganathan, S .et al., "LRAD3, A Novel Low-Density Lipoprotein Receptor Family Member That Modulates Amyloid Precursor Protein Trafficking", The Journal of Neuroscience, 31(30), pp. 10836-10846 (Jul. 27, 2011) (11 pages).
Registre, M. et al., "The gene product of the gp78/AMFR ubiquitin E3 ligase cDNA is selectively recognized by the 3F3A antibody within a subdomain of the endoplasmic reticulum", Biochemical and Biophysical Research Communications, 320, pp. 1316-1322 (Jul. 2, 2004) ((7 pages).
Renbaum, P. et al., "EGR-1 upregulates the Alzheimer's disease presenilin-2 gene in neuronal cells", Gene, 318, pp. 113-124 (2003) (12 pages).
Ricobaraza, A. et al., "Phenylbutyrate Ameliorates Cognitive Deficit and Reduces Tau Pathology in an Alzheimer's Disease Mouse Model", Neuropsychopharmacology, 34, pp. 1721-1732 (2009) (12 pages).
Rideout, H.J. and Stefanis, L., "Proteasomal Inhibition-Induced Inclusion Formation and Death in Cortical Neurons Require Transcription and Ubiquitination", Molecular and Cellular Neuroscience, 21, pp. 223-238 (2002) (16 pages).
Riekhof, W.R. et al., "Identification and Characterization of the Major Lysophosphatidylethanolamine Acyltransferase in *Saccharomyces cerevisiae*", The Journal of Biological Chemistry, 282(39), p. 28344-28352 (Sep. 28, 2007) (10 pages).
Rigaut, G. et al., "A generic protein purification method for protein complex characterization and proteome exploration", Nature Biotechnology, 17, pp. 1030-1032 (Oct. 1999) (3 pages).
Ringheim, G.E. and Szczepanik, A.M., "Brain Inflammation, Cholesterol, and Glutamate as Interconnected Participants in the Pathology of Alzheimer's Disease", Current Pharmaceutical Design, 12(6), pp. 719-738 (2006) (20 pages).
Rintoul, G. et al., "Glutamate Decreases Mitochondrial Size and Movement in Primary Forebrain Neurons", The Journal of Neuroscience, 23(21), pp. 7881-7888 (Aug. 27, 2003) (8 pages).
Berkner, K.L., "Development of Adenovirus Vectors for the Expression of Heterologous Genes", Biotechniques, 6(7), pp. 616-629 (1988) (11 pages).
Chen, Q. et al., "Loss of Presenilin Function Causes Alzheimer's Disease-Like Neurodegeneration in the Mouse" Journal of Neuroscience Research, 86, pp. 1615-1625 (2008) (11 pages).
Chen, F. et al., "TMP21 is a presenilin complex component that modulates $\gamma$-secretase but not ε-secretase activity", Nature, 440, pp. 1208-1212 (Apr. 27, 2006) (5 pages).
Choi, E-K. et al., "Calsenilin Is a Substrate for Caspase-3 That Preferentially Interacts with the Familial Alzheimer's Disease-associated C-terminal Fragment of Presenilin 2", The Journal of Biological Chemistry, 276(22), pp. 19197-19204 (2001) (9 pages).
Choung, S-Y. et al., "Hemolytic activity of a cyclic peptide Ro09-0198 isolated from *Streptoverticillium*," Biochimica et Biophysica Acta, 940, pp. 171-179 (1988) (9 pages).
Choung, S-Y. et al., "Interaction of a cyclic peptide, Ro09-0198, with phosphatidylethanolamine in liposomal membranes", Biochimica et Biophysica Acta, 940, pp. 180-187 (1988) (8 pages).
Chui, D-H. et al., "Transgenic mice with Alzheimer presenilin 1 mutations show accelerated neurodegeneration without amyloid plaque formation", Nature Medicine, 5(5), pp. 560-564 (May 1999) (5 pages).
Chávez-Gutiérrez, L. et al., "The mechanism of $\gamma$-Secretase dysfunction in familial Alzheimer disease", The EMBO Journal, 31, pp. 2261-2274 (2012) (14 pages).
Cipolat, S. et al., "OPA1 requires mitofusin 1 to promote mitochondrial fusion", Proc. Natl. Acad. Sci. USA, 101(45), pp. 15927-15932 (Nov. 9, 2004) (6 pages).

Citron, M. et al., "Mutant presenilins of Alzheimer's disease increase production of 42-residue amyloid β-protein in both transfected cells and transgenic mice", Nature Medicine, 3(1), pp. 67-72 (Jan. 1997) (6 pages).
Clapham, D.E. "Calcium Signaling", Cell, 80(2), pp. 259-268 (Jan. 27, 1995) (10 pages).
Cleveland, W.L. et al., "Routine Large-Scale Production of Monoclonal Antibodies in a Protein-Free Culture Medium", Journal of Immunological Methods, 56(2), pp. 221-234 (1983) (14 pages).
Coisne, C. et al., "Cyclodextrins as Emerging Therapeutic Tools in the Treatment of Cholesterol-Associated Vascular and Neurodegenerative Diseases", Molecules, 21, (2016) (22 pages).
Colón-Sáez, J. et al., "The α7 nicotinic acetylcholine receptor function in hippocampal neurons is regulated by the lipid composition of the plasma membrane", J. Physiol., 589.13, pp. 3163-3174 (2011) (12 pages).
Coppola, M. et al., "Identification and Characterization of YME1L1, a Novel Paraplegin-Related Gene", Genomics, 66, pp. 48-54 (2000) (7 pages).
Corbett, G.T. et al., "Sodium Phenylbutyrate Enhances Astrocytic Neurotrophin Synthesis via Protein Kinase C (PKC)-mediated Activation of cAMP-response Element-binding Protein (CREB): Implications for Alzheimer Disease Therapy", Journal of Biological Chemistry, 288(12), pp. 8299-8312 (Mar. 22, 2013) (14 pages).
Corder, E.H. et al., "Gene Dose of Apolipoprotein E Type 4 Allele and the Risk of Alzheimer's Disease in Late Onset Families", Science, 261(5123), pp. 921-923 (Aug. 13, 1993) (4 pages).
Cordy, J.M. et al., "The involvement of lipid rafts in Alzheimer's disease (Review)", Molecular Membrane Biology, 23(1), pp. 111-122 (Jan.-Feb. 2006) (12 pages).
DiMauro, S. et al., "Mitochondrial Respiratory-Chain Diseases", The New England Journal of Medicine, 348(26), pp. 2656-2668 (Jun. 26, 2003) (13 pages).
Cossec, C. et al., "Clathrin-dependent APP endocytosis and A secretion are highly sensitive to the level of plasma membrane cholesterol", Biochimica et Biophysica Acta Molecular and Cell Biology of Lipids, Elsevier, 1801 (8) pp. 846-852 (2010) (8 pages).
Cruts, M. et al., "Presenilin mutations in Alzheimer's Disease", Human Mutation, 11, pp. 183-190 (1998) (8 pages).
Cruz-Orive, L.M. et al., "Recent stereological methods for cell biology: a brief survey", Am. J. Physiol., 258, pp. L148-L156 (1990) (9 pages).
Csordás, G. et al., "Sorting of calcium signals at the junctions of endoplasmic reticulum and mitochondria", Cell Calcium, 29(4), pp. 249-262 (published online Jan. 23, 2001) (14 pages).
Csordás, G. et al., "Structural and functional features and significance of the physical linkage between ER and mitochondria", The Journal of Cell Biology, 174(7), pp. 915-921 (Sep. 25, 2006) (7 pages).
Cuadrado-Tejedor, M. et al., "Phenylbutyrate is a Multifaceted Drug that Exerts Neuroprotective Effects and Reverses the Alzheimer's Disease-like Phenotype of a Commonly Used Mouse Model", Current Pharmaceutical Design, 19(28), pp. 5076-5084 (2013) (9 pages).
Cui, W. et al., "Activation of Liver X Receptor Decreases BACE1 Expression and Activity by Reducing Membrane Cholesterol Levels", Neurochem Res, 36, pp. 1910-1921 (2011) (12 pages).
Cui, Z. et al., "Cloning and Expression of a Novel Phosphatidylethanolamine N-methyltransferase: A Specific Biochemicalband Cytological Marker for a Unique Membrane Fraction in Rat Liver", The Journal of Biological Chemistry, 268(22), pp. 16655-16663 (Aug. 5, 1993) (9 pages).
Cupers, P. et al., "The amyloid precursor protein (APP)-cytoplasmic fragment generated by $\gamma$-secretase is rapidly degraded but distributes partially in a nuclear fraction of neurones in culture", Journal of Neurochemistry, 78, pp. 1168-1178 (2001) (11 pages).
Cupers, P. et al., "The discrepancy between presenilin subcellular localization and ν-secretase processing of amyloid precursor protein", The Journal of Cell Biology, 154(4), pp. 731-740 (Aug. 20, 2001) (10 pages).
Cutler, R.G. et al., "Involvement of oxidative stress-induced abnormalities in ceramide and cholesterol metabolism in brain aging and

(56) References Cited

OTHER PUBLICATIONS

Alzheimer's disease", Proc. Natl. Acad. Sci. USA, 101(7), pp. 2070-2075 (Feb. 17, 2004) (6 pages).
Dalla, Y. et al., "Potential of ezetimibe in memory deficits associated with dementia of Alzheimer's type in mice", Indian J Pharmacol, 41 (6), pp. 262-267 (Dec. 2009) (7 pages).
Dallas, A. et al., "RNAi: A novel antisense technology and its therapeutic potential", Med Sci Monit 12(4): RA67-74 (2006) (8 pages).
Das, A. et al., "Three pools of plasma membrane cholesterol and their relation to cholesterol homeostasis", eLife, 3:e02882, (2014)16 pages.
Das, U. et al., "Visualization of APP and BACE-1 approximation in neurons: new insights into the amyloidogenic pathway", Author manuscript published in final edited form as: Nat. Neurosci., 19(1), pp. 55-64 (Jan. 2016) (27 pages).
Dillon, C. et al., "The Actin Cytoskeleton: Integrating Form and Function at the Synapse", Annu. Rev. Neurosci., 28, pp. 25-55 (2005) (34 pages).
Davis Jr., W., "The ATP-binding cassette transporter-2 (ABCA2) regulates esterification of plasma membrane cholesterol by modulation of sphingolipid metabolism", Author manuscript published in final edited form as: Biochim Biophys Acta., 1841(1), pp. 168-179 (Jan. 2014) (32 pages).
Davis Jr., W., "The Cholesterol Transport Inhibitor U18666a Regulates Amyloid Precursor Protein Metabolism and Trafficking in N2aAPP "Swedish" Cells", Current Alzheimer Research, 5, pp. 448-456 (2008) (9 pages).
De Brito, O.M. et al., "Mitofusin 2 tethers endoplasmic reticulum to mitochondria", Nature, 456, pp. 605-610 (Dec. 4, 2008) (7 pages).
De Gasperi, R. et al., "Presenilin-1 regulates induction of hypoxia inducible factor-1α: altered activation by a mutation associated with familial Alzheimer's disease", Molecular Neurodegeneration, 5:38, (2010) (20 pages).
De Jonghe, C. et al., "Aberrant splicing in the presenilin-1 intron 4 mutation causes presenile Alzheimer's disease by increased Aβsecretion", Human Molecular Genetics, 8(8), pp. 1529-1540 (1999) (12 pages).
De Jonghe, C. et al., "Flemish and Dutch Mutations in Amyloid β Precursor Protein Have Different Effects on Amyloid β secretion", Neurobiology of Disease, 5, pp. 281-286 (1998) (6 pages).
De Meis, L. et al., "Fusion of the Endoplasmic Reticulum and Mitochondrial Outer Membrane in Rats Brown Adipose Tissue: Activation of Thermogenesis by $Ca^{2+}$", PLoS ONE, e9439, 5(3), pp. 1-9 (Mar. 2, 2010) (9 pages).
De Strooper, B. et al., "Deficiency of presenilin-1 inhibits the normal cleavage of amyloid precursor protein", Nature, 391, pp. 387-390 (Jan. 22, 1998) (4 pages).
De Strooper, B. et al., "Phosphorylation, Subcellular Localization, and Membrane Orientation of the Alzheimer's Disease-associated Presenilins", The Journal of Biological Chemistry, 272(6), pp. 3590-3598 (Feb. 7, 1997) (10 pages).
De Strooper, B., "Aph-1, Pen-2, and Nicastrin with Presenilin Generate an Active γ-Secretase Complex", Neuron, 38, pp. 9-12 (Apr. 10, 2003) (4 pages).
De Tullio, L. et al., "The initial surface composition and topography modulate sphingomyelinase-driven sphingomyelin to ceramide conversion in lipid monolayers", Cell Biochem. Biophys, 47, pp. 169-177 (Apr. 19, 2007) (9 pages).
De Vos et al., "Tumor necrosis factor induces hyperphosphorylation of kinesin light chain and inhibits kinesin-mediated transport of mitochondria", The Journal of Cell Biology, 149(6), pp. 1207-1214 (Jun. 12, 2000) (8 pages).
Debose-Boyd, R.A., "Feedback Regulation of Cholesterol Synthesis: Sterol-Accelerated Ubiquitination and Degradation of HMG CoA Reductase", Author Manuscript published in final edited form as Cell Res., 18(6), pp. 609-621 (Jun. 2008) (18 pages).
Delettre, C. et al., "Nuclear gene *OPA1*, encoding a mitochondrial dynamin-related protein, is mutated in dominant optic atrophy", Nature Genetics, 26, pp. 207-210 (Oct. 2000) (4 pages).
Delgado, A. et al., "Inhibitors of sphingolipid metabolism enzymes", Biochimica et Biophysica Acta, 1758, pp. 1957-1977 (Sep. 1, 2006) (21 pages).
Delvaux, E. et al., "Differential processing of amyloid precursor protein in brain and in peripheral blood leukocytes", Author manuscript published in final edited form as: Neurobiol Aging., 34(6), pp. 1680-1686 (Jun. 2013) (17 pages).
Dermaut, B. et al., "A Novel Presenilin 1 Mutation Associated with Pick's Disease but Not β-Amyloid Plaques", Annals of Neurology, 55(5), pp. 617-626 (May 2004) (10 pages).
Dermaut, B. et al., "The Glu318Gly Substitution in Presenilin 1 is Not Causally Related to Alzheimer Disease", Am. J. Hum. Genet., 64, pp. 290-292 (1999) (3 pages).
Devi, L. et al., "Mitochondrial dysfunction and accumulation of the β-secretase-cleaved C-terminal fragment of APP in Alzheimer's disease transgenic mice", Author manuscript, published in final edited form as: Neurobiol Dis., 45(1), pp. 417-424 (Jan. 2012) (19 pages).
Devi, G. et al., "Novel Presenilin 1 Mutations Associated with Early Onset of Dementia in a Family With Both Early-Onset and Late-Onset Alzheimer Disease", Arch Neurol, 57, pp. 1454-1457 (Oct. 2000) (4 pages).
Di Paola, M et al., "Ceramide Interaction with the Respiratory Chain of Heart Mitochondria", Biochemistry, 39(22), 6660-6668 (2000) (9 pages).
Di Paolo, G. et al., "Linking Lipids to Alzheimer's Disease: Cholesterol and Beyond", Author Manuscript published in final edited form as: Nat Rev Neurosci., 12(5), pp. 284-296 (May 2011) (24 pages).
Di Scala, C. et al., "Interaction of Alzheimer'β-Amyloid Peptides with Cholesterol: Mechanistic insights into amyloid pore formation", Biochemistry, 53, pp. 4489-4502 (Jul. 7, 2014) (14 pages).
Lessard, C.B. et al., "The overexpression of presenilin2 and Alzheimer's-disease-linked presenilin2 variants influences TRPC6-enhanced $Ca^{2+}$ entry into HEK293 cells", Cellular Signalling, 17, pp. 437-445 (available online Sep. 29, 2004) (9 pages).
Leuenberger, D. et al., "Different import pathways through the mitochondrial intermembrane space for inner membrane proteins", The EMBO Journal, 18(17), pp. 4816-4822 (1999) (7 pages).
Kamal, A. et al., "Kinesin-mediated axonal transport of a membrane compartment containing β-secretase and presenilin-1 requires APP", Nature, 414, pp. 643-648 (Dec. 6, 2001) (6 pages).
Kamino, K. et al., "Linkage and Mutational Analysis of Familial Alzheimer disease Kindreds for the APP Gene Region", Am. J. Hum. Genet., 51, pp. 998-1014 (1992) (17 pages).
Kannan, M. et al., "Phosphatidylserine synthesis at membrane contact sites promotes its transport out of the ER", Journal of Lipid Research, 58, pp. 553-562 (2017) (10 pages).
Katzov, H. et al., "Genetic Variants of ABCA1 Modify Alzheimer Disease Risk and Quantitative Traits Related to β-Amyloid Metabolism", Human Mutation, 23, pp. 358-367 (2004) (10 pages).
Kaufmann, M.R. et al., "Dysregulation of Hypoxia-Inducible Factor by Presenilin/γ-Secretase Loss-of-Function Mutations", The Journal of Neuroscience, 33(5), pp. 1915-1926 (Jan. 30, 2013) (12 pages).
Kawasaki, H. and Kretsinger, R., "Calcium-Binding Proteins 1: EF-Hands", Protein Profile, 1(4), pp. 343-391 (1994) (54 pages).
Kawasaki, H. et al., "Classification and evolution of EF-hand proteins", BioMetals, 11, pp. 277-295 (1998) (19 pages).
Kennedy, M.A. et al., "A Signaling Lipid Associated with Alzheimer's Disease Promotes Mitochondrial Dysfunction", Nature: Scientific Reports, 6(19332), pp. 1-11 (Jan. 13, 2016) (11 pages).
Kennedy, M.E. et al., "The BACE1 inhibitor verubecestat (MK-8931) reduces CNS β-amyloid in animal models and in Alzheimer's disease patients", Sci. Transl. Med. 8:363ra150, Nov. 2, 2016 (14 pages).
Khachaturian, A.S. et al., "Antihypertensive Medication Use and Incident Alzheimer Disease: The Cache County Study", Arch Neurol, 63, pp. 686-692 (May 2006) (7 pages).
Kielar, D. et al., "Adenosine Triphosphate Binding Cassette (ABC) Transporters Are Expressed and Regulated During Terminal Keratinocyte Differentiation: A Potential Role for ABCA7 in Epidermal Lipid Reorganization", The Journal of Investigative Dermatology, 121(3), pp. 465-474 (Sep. 2003) (10 pages).

(56) References Cited

OTHER PUBLICATIONS

Kikuchi, Y. et al., "Cutaneous gene delivery", Journal of Dermatological Science, 50, pp. 87-98 (2008) (12 pages).
Kim, T.-W. et al., "Endoproteolytic Cleavage and Proteasomal Degradation of Presenilin 2 in Transfected Cells", The Journal of Biological Chemistry, 272(17), pp. 11006-11010 (1997) (6 pages).
Kim, S.-K. et al., "ERK1/2 is an endogenous negative regulator of the γsecretase activity", The FASEB Journal, 20, pp. 157-159 (2006) (published online Nov. 17, 2005) (22 pages).
Kim, J. et al., "miR-106b impairs cholesterol efflux and increases Aβ levels by repressing ABCA1 expression", Experimental Neurology, 235, pp. 476-483 (2012) (8 pages).
Kim, W.S. et al., "Role of ABCG1 and ABCA1 in Regulation of Neuronal Cholesterol Efflux to Apolipoprotein E Discs and Suppression of Amyloid-β Peptide Generation", The Journal of Biological Chemistry, 282(5), pp. 2851-2861 (Feb. 2, 2007) (11 pages).
Kim, S.-H. et al., "Subcellular Localization of Presenilins: Association with a Unique Membrane Pool in Cultured Cells", Neurobiology of Disease, 7, pp. 99-117 (2000) (19 pages).
Kimura, N. et al., "Age-related changes in the localization of presenilin-1 in cynomolgus monkey brain", Brain Research, 922, pp. 30-41 (2001) (12 pages).
King, T.D. et al., "Caspase-3 activation induced by inhibition of mitochondrial complex I is facilitated by glycogen synthase kinase-3β and attenuated by lithium", Brain Research, 919, pp. 106-114 (2001) (9 pages).
Kinoshita, T. et al., "Dissecting and manipulating the pathway for glycosylphos-phatidylinositol-anchor biosynthesis", Current Opinion in Chemical Biology, 4, pp. 632-638 (2000) (7 pages).
Kizuka, Y. et al., "An aberrant sugar modification of BACE1 blocks its lysosomal targeting in Alzheimer's disease", EMBO Mol Med, 7(2), pp. 175-189 (Jan. 15, 2015) (15 pages).
Klement, P. et al., "Analysis of Oxidative Phosphorylation Complexes in Cultured Human Fibroblasts and Amniocytes by Blue-Native-Electrophoresis Using Mitoplasts Isolated with the Help of Digitonin", Analytical Biochemistry, 231, pp. 218-224 (1995) (7 pages).
Klivenyi, P. et al., "Mice deficient in dihydrolipoamide dehydrogenase show increased vulnerability to MPTP, malonate and 3-nitropropionic acid neurotoxicity", Journal of Neurochemistry, 88, pp. 1352-1360 (2004) (9 pages).
Kogot-Levin, A. and Saada, A., "Ceramide and the mitochondrial respiratory chain", Biochimie, 100, pp. 88-94 (2014) (available online Aug. 9, 2013) (7 pages).
Kojro, E. et al., "Statins and the Squalene Synthase Inhibitor Zaragozic Acid Stimulate the Non-Amyloidogenic Pathway of Amyloid-β Protein Precursor Processing by Suppression of Cholesterol Synthesis", Journal of Alzheimer's Disease 20, pp. 1215-1231 (2010) (17 pages).
Kolhekar, A.S., "Peptidylglycine α-Hydroxylating Monooxygenase: Active Site Residues, Disulfide Linkages, and a Two-Domain Model of the Catalytic Core", Biochemistry, 36(36), pp. 10901-10909 (1997) (9 pages).
Kopach, O. et al., "Functional coupling between ryanodine receptors, mitochondria and Ca(2+) ATPases In rat submandibular acinar cells", Cell Calcium, 43, pp. 469-481 (Jun. 2008) (14 pages).
Korsmeyer, S.J. et al., "Reactive oxygen species and the regulation of cell death by the Bcl-2 gene family", Biochimica et Biophysica Acta, 1271, pp. 63-66 (1995) (4 pages).
Kosicek, M. et al., "Cholesterol accumulation in Niemann Pick type C (NPC) model cells causes a shift in APP localization to lipid rafts", Biochemical and Biophysical Research Communications, 393, pp. 404-409 (available online Feb. 6, 2010) (6 pages).
Kottgen, M. et al., "Trafficking ofTRPP2 by PACS proteins represents a novel mechanism of ion channel regulation", The EMBO Journal, 24(4), pp. 705-716 (2005) (12 pages).
Koudinova, N. et al., "Alzheimer's $A\beta_{1-40}$ Peptide Modulates Lipid Synthesis in Neuronal Cultures and Intact Rat Fetal Brain Under Normoxic and Oxidative Stress Conditions", Neurochemical Research, 25(5), pp. 653-660 (2000) (8 pages).
Kristián, T. et al., "Isolation of mitochondria with high respiratory control from primary cultures of neurons and astrocytes using nitrogen cavitation", Author manuscript published in final edited form as: J Neurosci Methods, 152(1-2), pp. 136-143 (Apr. 15, 2006) (14 pages).
Kuo, L.H. et al., "Tumor Necrosis Factor-α-elicited Stimulation of γ-Secretase Is Mediated by c-Jun N-terminal Kinase-dependent Phosphorylation of Presenilin and Nicastrin", Molecular Biology of the Cell, 19, pp. 4201-4212 (Oct. 2008) (12 pages).
Lahtinen, U. et al., "Molecular Cloning and Expression of a 58-kDa cis-Golgi and Intermediate Compartment Protein", The Journal of Biological Chemistry, 271(8), pp. 4031-4037 (Feb. 23, 1996) (8 pages).
Lai, J.C.K. and Cooper, A.J.L., "Brain α-Ketoglutarate Dehydrogenase Complex: Kinetic Properties, Regional Distribution, and Effects of Inhibitors", J. Neurochem., 47(5), pp. 1376-1386 (1986) (11 pages).
Lam, K.S., "Application of combinatorial library methods in cancer research and drug discovery", Anti-Cancer Drug Design, 12, pp. 145-167 (1997) (23 pages).
Lamb, B.T. et al., "Amyloid production and deposition in mutant *amyloid precursor protein and presenilin-1 yeast* artificial chromosome transgenic mice", Nature *Neuroscience*, 2(8), pp. 695-697 (Aug. 1999) (3 pages).
Lange, Y. et al., "Regulation of endoplasmic reticulum cholesterol by plasma membrane cholesterol", Journal of Lipid Research, 40, pp. 2264-2270 (1999) (7 pages).
Langer, R. and Peppas, N., "Chemical and Physical Structure of Polymers as Carriers for Controlled Release of Bioactive Agents: A Review", Journal of Macromolecular Science—Reviews in Macromolecular Chemistry and Physics, C23(1), pp. 61-126 (1983) (67 pages).
Langer, R., "New Methods of Drug Delivery", Science, 249, pp. 1527-1533 (Sep. 28, 1990) (8 pages).
Laudon, H. et al., "A Nine-transmembrane Domain Topology for Presenilin 1", The Journal of Biological Chemistry, 280(42), pp. 35352-35360 (Oct. 21, 2005) (10 pages).
Lauritzen, I. et al., "The β-secretase-derived C-terminal fragment of βAPP, C99, but not Aβ, is a key contributor to early intraneuronal lesions in triple-transgenic mouse hippocampus", Author Manuscript published in final form as: J Neurosci., 32(46), pp. 16243-16255a (Nov. 14, 2012) (42 pages).
Lazic, D. et al., "3K3A-activated protein C blocks amyloidogenic BACE1 pathway and improves functional outcome in mice", J. Exp. Med., 216(2), pp. 279-293, S17-S21 (Jan. 15, 2019) (20 pages).
Lebiedzinska, M. et al., "Age-related changes in levels of p66Shc and serine 36-phosphorylated p66Shc in organs and mouse tissues", Archives of Biochemistry and Biophysics, 486, pp. 73-80 (2009) (8 pages).
Lee, J. and Bogyo, M., "Synthesis and evaluation of aza-peptidyl inhibitors of the lysosomal asparaginyl endopeptidase, legumain", Bioorganic & Medicinal Chemistry Letters, 22, pp. 1340-1343, (2012) (4 pages).
Lee, S.J. et al., "A detergent-insoluble membrane compartment contains Aβ in vivo", Nature Medicine, 4(6), pp. 730-734 (Jun. 1998) (5 pages).
Lee, J. et al., "Acid sphingomyelinase modulates the autophagic process by controlling lysosomal biogenesis in Alzheimer's disease", JEM, 211(8), pp. 1551-1570 (2014) (20 pages).
Lee, J.H. et al., "Expanded Genomewide Scan Implicates a Novel Locus at 3q28 Among Caribbean Hispanics with Familial Alzheimer Disease", Arch Neurol, 63, pp. 1591-1598, E1 (Nov. 2006) (9 pages).
Lee, K.W. et al., "Progressive neuronal loss and behavioral impairments of transgenic C57BL/6 inbred mice expressing the carboxy terminus of amyloid precursor protein", Neurobiology of Disease, 22, pp. 10-24 (2006) (15 pages).
Leissring, M.A. et al., "A physiologic signaling role for the γ-secretase-derived intracellular fragment of APP", PNAS, 99(7), pp. 4697-4702 (Apr. 2, 2002) (6 pages).
Leissring, M.A. et al., "Alzheimer's Presenilin-1 Mutation Potentiates Inositol 1,4,5-Trisphosphate-Medlated Calcium Signaling in Xenopus Oocytes", J. Neurochem., 72(3), pp. 1061-1068 (1999) (8 pages).

(56) References Cited

OTHER PUBLICATIONS

Leissring, M.A. et al., "Capacitative Calcium Entry Deficits and Elevated Luminal Calcium Content in Mutant Presenilin-1 Knockin Mice", The Journal of Cell Biology, 149(4), pp. 793-797 (May 15, 2000) (5 pages).
Leissring, M.A. et al., "Presenilin-2 Mutations Modulate Amplitude and Kinetics of Inositol 1,4,5-Trisphosphate-mediated Calcium Signals", The Journal of Biological Chemistry, 274(46), p. 32535-32538 (Nov. 1999) (5 pages).
Levitan, D. and Greenwald, I., "Effects of SEL-12 presenilin on LIN-12 localization and function in Caenorhabditis elegans", Development, 125, pp. 3599-3606 (1998) (8 pages).
Leist, M. and Nicotera, P., "Calcium and Neuronal Death", Rev. Physiol. Biochem. Pharmacol., 132, pp. 79-125 (1998) (47 pages).
Leong, S.F. et al., "The Activities of Some Energy-Metabolising Enzymes in Nonsynaptic (Free) and Synaptic Mitochondria Derived from Selected Brain Regions", Journal of Neurochemistry, 42(5), pp. 1306-1312 (1984) (7 pages).
Tesco, G. and Tanzi, R.E., "GSK3β Forms a Tetrameric Complex with Endogenous PS1-CTF/NTF and β-Catenin: Effects of the D257/D385A and FAD-llnked Mutations", Annals New York Academy of Sciences, 920(1) (Jan. 25, 2006) (7 page).
Thathiah, A. et al., "The Orphan G Protein-Coupled Receptor 3 Modulates Amyloid-Beta Peptide Generation in Neurons", Science, 323, pp. 946-951 (Feb. 13, 2009) (7 pages).
Thathiah, A. et al., "β-arrestin 2 regulates Aβ generation and γ-secretase activity in Alzheimer's disease", Nature Medicine, 19(1), pp. 43-49 (Jan. 2013) (9 pages).
The International Mouse Knockout Consortium, "A Mouse for All Reasons", Cell, 128, pp. 9-13 (Jan. 12, 2007) (5 pages).
Thielke, S. et al., "Association Between Alzheimer Dementia Mortality Rate and Altitude in California Counties", JAMA Psychiatry, 72(12), pp. 1253-1254 (Dec. 2015) (2 pages).
Thinakaran, G. et al., "Endoproteolysis of Presenilin 1 and Accumulation of Processed Derivatives In Vivo", Neuron, 17, pp. 181-190 (Jul. 1996) (10 pages).
Tian, Y. et al., "Adaptor complex AP2/PICALM, through interaction with LC3, targets Alzheimer's APP-CTF for terminal degradation via autophagy", PNAS, 110(42), pp. 17071-17076 (Oct. 15, 2013) (6 pages).
Trinczek, B. et al., "Tau regulates the attachment/detachment but not the speed of motors in microtubule-dependent transport of single vesicles and organelles", Journal of Cell Science, 112, pp. 2355-2367 (1999) (13 pages).
Tsai, A. and Carstens, R.P., "An optimized protocol for protein purification in cultured mammalian cells using a tandem affinity purification approach", Nature Protocols, 1 (6), pp. 2820-2827 (2006) (8 pages).
Tu, H. et al., "Presenilins Form ER $Ca^{2+}$ Leak Channels, a Function Disrupted by Familial Alzheimer's Disease-Linked Mutations", Cell, 126, pp. 981-993 (Sep. 8, 2006) (13 pages).
Tubbs, E. et al., "Mitochondria-Associated Endoplasmic Reticulum Membrane (MAM) Integrity is Required for Insulin Signaling and Is Implicated in Hepatic Insulin Resistance", Diabetes, 63, pp. 3279-3294 (Oct. 2014) (16 pages).
Uchida, R. et al., "Alutenusin, a Specific Neutral Sphingomyelinase Inhibitor, Produced by *Penicillium* sp. FO-7436", The Journal of Antibiotics, 52(6), pp. 572-574 (Jun. 1999) (3 pages).
Urano, Y. et al., "Association of active γ-secretase complex with lipid rafts", Journal of Lipid Research, 46, pp. 904-912 (2005) (9 pages).
Urban, N. et al., "Identification and Validation of Larixyl Acetate as a Potent TRPC6 inhibitor", Mol Pharmacol, 89, pp. 197-213 (Jan. 2016) (17 pages).
Urlaub, G. and Chasin, L.A., "Isolation of Chinese hamster cell mutants deficient in dihydrofolate reductase activity", Proc. Natl. Acad. Sci. USA, 77(7), pp. 4216-4220 (Jul. 1980) (5 pages).
Urlaub, G. et al., "Effect of Gamma Rays at the Dihydrofolate Reductase Locus: Deletions and Inversions", Somatic Cell and Molecular Genetics, 12(6), pp. 555-566 (1986) (12 pages).
Van Echten-Deckert, G. and Walter, J., "Sphingolipids: Critical players in Alzheimer's disease", Progress in Lipid Research, 51, pp. 378-393 (Jul. 23, 2012) (16 pages).
Van Heeke, G. and Schuster, S.M., "Expression of Human Asparagine Synthetase in *Escherichia coli*" The Journal of Biological Chemistry, 264(10), pp. 5503-5509 (Apr. 5, 1989) (7 pages).
Vance, J.E. et al., "Abnormalities in mitochondria-associated membranes and phospholipid biosynthetic enzymes in the *mnd/mnd* mouse model of neuronal ceroid lipofuscinosis", Biochimica et Biophysica Acta, 1344, pp. 286-299 (1997) (14 pages).
Vance, D.E. et al., "Phosphatidylethanolamine N-methyltransferase from liver", Biochimica et Biophysica Acta, 1348, pp. 142-150 (1997) (9 pages).
Vance, J.E., "MAM (mitochondria-associated membranes) in mammalian cells: Lipids and beyond", Biochimica et Biophysica Acta, 1841, pp. 595-609 (2014) (available online Dec. 6, 2013) (15 pages).
Vance, J.E., "Molecular and Cell Biology of Phosphatidylserine and Phosphatidylethanolamine Metabolism", in Progress in Nucleic Acid Research and Molecular Biology, vol. 75, Moldave, K., Editor, Academic Press, San Diego, California, pp. 69-111 (2003) (45 pages).
Vance, J.E., "Phosphatidylserine and phosphatidylethanolamine in mammalian cells: two metabolically related aminophospholipids", Journal of Lipid Research, 49, pp. 1377-1387 (2008) (11 pages).
Vance, J.E., "Phospholipid Synthesis in a Membrane Fraction Associated with Mitochondria", The Journal of Biological Chemistry, 265(13), pp. 7248-7256 (May 5, 1990) (9 pages).
Verma, I.M., "Gene Therapy", Scientific American, pp. 68-72, 81-82, and 84 (Nov. 1990) (10 pages).
Vetrivel, K.S. and Thinakaran, G., "Membrane rafts in Alzheimer's disease beta-amyloid production", Author Manuscript Published in final edited form as: Biochim Biophys Acta, 1801(8), pp. 860-867 (Aug. 2010) (16 pages).
Vetrivel, K.S. et al., "Association of γ-Secretase with Lipid Rafts in Post-Golgi and Endosome Membranes", The Journal of Biological Chemistry, 279(43), pp. 44945-44954 (Oct. 22, 2004) (11 pages).
Vetrivel, K.S. et al., "Spatial segregation of γ-Secretase and Substrates in Distinct Membrane Domains", The Journal of Biological Chemistry, 280(27), pp. 25892-25900 (Jul. 8, 2005) (10 pages).
Vignini, A. et al., "Amyloid precursor protein expression is enhanced in human platelets from subjects with Alzheimer's disease and frontotemporal lobar degeneration: A Real-time PCR study", Experimental Gerontology, 48(12), pp. 1505-1508 (available online Oct. 26, 2013) (5 pages).
Villa, J.C. et al., "Nontranscriptional Role of Hif-1α in activation of γ-Secretase and Notch Signaling in Breast Cancer", Cell Reports, 8, pp. 1-16 (Aug. 21, 2014) (16 pages).
Villani, G. and Attardi, G., "Chapter 5: Polarographic Assays of Respiratory Chain Complex Activity", in Methods in Cell Biology, vol. 80, Pon, et al., Eds., Elsevier Inc., Amsterdam, Netherlands, pp. 121-133 (2001) (13 pages).
Vingtdeux, V. et al. "Phosphorylation of amyloid precursor carboxy-terminal fragments enhances their processing by a gamma-secretase-dependent mechanism", Neurobiology of Disease, 20, pp. 625-637 (2005) (13 pages).
Vives-Bauza, C. et al., "Chapter 7: Assay of Mitochondrial ATP Synthesis in Animal Cells", in Methods in Cell Biology, vol. 80, Pon, et al., Eds., Elsevier Inc., Amsterdam, Netherlands, pp. 155-171 (2007) (17 pages).
Voelker, D.R., "Interorganelle transport of aminoglycerophospholipids", Biochimica et Biophysica Acta, 1486, pp. 97-107 (2000) (11 pages).
Voelker, D.R., "Phosphatidylserine functions as the major precursor of phosphatidylethanolamine in cultured BHK-21 cells", Proc. Natl. Acad. Sci. USA, 81, pp. 2669-2673 (May 1984) (5 pages).
Voelker, D.R., "Protein and lipid motifs regulate phosphatidylserine traffic in yeast", Seventh Yeast Lipid Conference Swansea, Wales, May 12-14, 2005, Biochemical Society Transactions, vol. 33, Part 5, pp. 1141-1145 (2005) (5 pages).
Von Arnim, C.A.F. et al., "GGA1 Acts as a Spatial Switch Altering Amyloid Precursor Protein Trafficking and Processing", The Journal of Neuroscience, 26(39), pp. 9913-9922 (Sep. 27, 2006) (10 pages).

(56) References Cited

OTHER PUBLICATIONS

Waehler, R. et al., "Engineering targeted viral vectors for gene therapy", Nature Reviews Genetics, 8, pp. 573-587 (Aug. 2007) (15 pages).
Walsh, D.M. and Selkoe, D.J., "Deciphering the Molecular Basis of Memory Failure in Alzheimer's Disease", Neuron, 44, pp. 181-193 (Sep. 30, 2004) (13 pages).
Walter, J. et al., "The Alzheimer's Disease-Associated Presenilins Are Differentially Phosphorylated Proteins Located Predominantly within the Endoplasmic Reticulum", Molecular Medicine., 2(6), pp. 673-691 (Nov. 1996) (19 pages).
Walther, T. and Farese, R.V., "The life of lipid droplets", Author Manuscript Published in final edited form as: Biochim Biophys Acta., 1791 (6), pp. 459-466 (Jun. 2009) (17 pages).
Wang, R. et al. "All-trans-retinoic Acid Reduces *BACE1* Expression under Inflammatory Conditions via Modulation of Nuclear Factor κB (NFκB) Signaling", The Journal of Biological Chemistry, 290(37), p. 22532-22542 (Sep. 11, 2015) (11 pages).
Wang, W. et al., "Amyloid precursor protein α- and β-cleaved ectodomains exert opposing control of cholesterol homeostasis viaSREBP2", The FASEB Journal, 28, pp. 849-860 (Feb. 2014) (13 pages).
Wang, N. et al., "ATP-binding Cassette Transporter A7 (ABCA7) Binds Apolipoprotein A-I and Mediates Cellular Phospholipid but Not Cholesterol Efflux", The Journal of Biological Chemistry, 278(44), pp. 42906-42912 (Oct. 31, 2003) (7 pages).
Wang, H. et al., "ATP-Sensitive Potassium Channel Openers and 2,3-Dimethyl-2-Butylamine Derivatives", Current Medicinal Chemistry, 14(2), pp. 133-155 (2007) (23 pages).
Wang, B.-J. et al., "ErbB2 regulates autophagic flux to modulate the proteostasis of APP-CTFs in Alzheimer's disease", PNAS, 114, pp. E3129-E3138 (published online Mar. 28, 2017) (10 pages).
Wang, W. et al., "Evidence of Cholesterol Accumulated In High Curvature Regions: Implication to the Curvature Elastic Energy for Lipid Mixtures", Biophysical Journal, 92(8), pp. 2819-2830 (Apr. 2007) (12 pages).
Wang, J.-Z. et al., "Glycosylation of microtubule-associated protein tau: An abnormal posttranslational modification in Alzheimer's disease", Nature Medicine, 2(8), pp. 871-875 (Aug. 1996) (5 pages).
Wang, S. et al., "Mitochondrial fission proteins in peripheral blood lymphocytes are potential biomarkers for Alzheimer's disease", European Journal of Neurology, 19, pp. 1015-1022 (2012) (8 pages).
Wang, X. et al., "Oxidative Stress and Mitochondrial Dysfunction in Alzheimer's Disease", Author Manuscript Published in final edited form as: Biochim Biophys Acta., 1842(8), pp. 1240-1247 (Aug. 2014) (20 pages).
Wang, J. et al., "TRPC6 specifically interacts with APP to inhibit its cleavage by γ-secretase and reduce Aβ production", DOI:10.1038/ncomms9876, Nature Communications, 6(8876), pp. 1-12 (Nov. 19, 2015) (12 pages).
Wang, R. et al., "Transcriptional regulation of APH-1A and increased γ-secretase cleavage of APP and Notch by HIF-1 and hypoxia", FJ Express Summary, The FASEB Journal, 20:1275-1277, Jun. 2006 (3 pages).
Wang, et al., "Transcriptional regulation of APH-1A and increased γ-secretase cleavage of APP and Notch by HIF-1 and hypoxia", FJ Express Full-Length Article, The FASEB Journal, 20:E614-E622, Jun. 2006 (9 pages).
Warnecke, C. et al., "Activation of the hypoxia-inducible factor pathway and stimulation of angiogenesis by application of prolyl hydroxylase inhibitors", The FASEB Journal, 17, pp. 1186-1188 (published online Apr. 22, 2003) (23 pages).
Wassler, M. and Fries, E., "Proteolytic Cleavage of Haptoglobin Occurs in a Subcompartment of the Endoplasmic Reticulum: Evidence from Membrane Fusion In Vitro", The Journal of Cell Biology, 123(2), pp. 285-291 (Oct. 1993).
Weihofen, A. et al., "Identification of Signal Peptide Peptidase, a Presenilin-Type Aspartic Protease", Science, 296, pp. 2215-2218 (Jun. 21, 2002) (4 pages).
Werner, T. and Nelson, P. J., "Joining high-throughput technology with in silioo modelling advances genome-wide screening towards targeted discovery", Briefing in Functional Genomics and Proteomics, 5(1), pp. 32-36 (5 pages).
Wicher, K.B. and Fries, E., "Prohaptoglobin is proteolytically cleaved in the endoplasmic reticulum by the complement C1r-like protein", PNAS, 101(40), p. 14390-14395 (Oct. 5, 2004) (6 pages).
Abe-Dohmae et al., "Human ABCA7 Supports Apolipoprotein-mediated Release of Cellular Cholesterol and Phospholipid to Generate High Density Lipoprotein," J. Biol. Chem. 279(1), pp. 604-611 (2004) (9 pages).
Achleitner et al., "Association between the endoplasmic reticulum and mitochondria of yeast facilitates interorganelle transport of phospholipids through membrane contact," Eur. J. Biochem., 264, pp. 545-553 (1999) (9 pages).
Achleitner et al., "Synthesis and Intracellular Transport of Aminoglycerophospholipids in Permeabilized Cells ofthe Yeast, *Saocharomyces cerevisiae*," J. Biol. Chem., 270(50), p. 29836-29842 (1995) (8 pages).
Ackerley et al., "Glutamate Slows Axonal Transport of Neurofilaments in Transfected Neurons," J. Cell Biology., 150(1), pp. 165-175 (2000) (11 pages).
Acín-Perez and Enriquez, "The function ofthe respiratory supercomplexes: The plasticity model," Biochim. Biophys. Acta, 1837, pp. 444-450 (2014) (7 pages).
Acín-Pérez et al., "Respiratory Active Mitochondrial Supercomplexes," Mol. Cell, 32, pp. 529-539 (Nov. 21, 2008) (11 pages).
Albrecht et al., "A novel missense mutation in *ABCA1* results in altered protein trafficking and reduced phosphatidylserine translocation in a patient with Scott syndrome," Blood. 2005,106, pp. 542-549 (9 pages).
Alder-Baerens et al. "Headgroup-specific Exposure of Phospholipids in ABCA1-expressing Cells," J. Biol. Chem., 280, p. 26321-26329 (2005) (10 pages).
Allsopp et al., "Unique residues in the ATP gated human P2X7 receptor define a novel allosteric binding pocket for the selective antagonist AZ10606120," Sci. Rep., 7(725), 1-12 (Apr. 7, 2017) (12 pages).
Alonso et al., "Calcium microdomains in mitochondria and nucleus," Cell Calcium, 40, pp. 513-525 (Oct. 25, 2006) (13 pages).
Altaras et al., "Production and Formulation of Adenovirus Vectors," Adv. Blochem. Eng. Biotechnol., 99, pp. 193-260 (2005) (68 pages).
Anandatheerthavarada et al., "Mitochondrial targeting and a novel transmembrane arrest of Alzheimer's amyloid precursor protein impairs mitochondrial function in neuronal cells," J. Cell Biol., 161(1), pp. 41-54 (Apr. 14, 2003) (14 pages).
Ancolio et al., "Unusual phenotypic alteration of β amyloid precursor protein (βAPP) maturation by a new Val-715→ Met βAPP-770 mutation responsible for probable early-onset Alzheimer's disease," Proc. Natl. Acad. Sci. USA, 96, pp. 4119-4124 (Mar. 1999) (6 pages).
Anderson, "Human Gene Therapy," Science, 256, pp. 808-813 (May 8, 1992) (7 pages).
Anderson et al., "Mapping of the Allosteric Site in Cholesterol Hydroxylase CYP46A1 for Efavirenz, a Drug That Stimulates Enzyme Activity," J. Biol. Chem. 291(22), p. 11876-11886 (May 27, 2016) (11 pages).
Andreyev et al., "Mitochondrial Metabolism of Reactive Oxygen Species," Biochemistry (Moscow), 70(2), pp. 200-214 (2005) (15 pages).
Ankarcrona and Hultenby, "Presenilin-1 is located in rat mitochondria," Biochemical Biophysical Research Communications, 295, pp. 766-770 (2002) (5 pages).
Annaert et al., "Presenilin 1 Controls γ-Secretase Processing of Amyloid Precursor Protein in Pre-Golgi Compartments of Hippocampal Neurons," J. Cell Biol., 147(2), pp. 277-294 (Oct. 18, 1999) (18 pages).
Arbel and Solomon, "A Novel Immunotherapy for Alzheimer's Disease: Antibodies against the β-Secretase Cleavage Site of APP," Curr. Alzheimer Res., 4, pp. 437-445 (2007) (9 pages).
Ardail et al., "The mitochondria-associated endoplasmic-reticulum subcompartment (MAM fraction) of rat liver contains highly active

(56) References Cited

OTHER PUBLICATIONS sphingolipid-specific glycosyltransferases," Biochem. J., 371, pp. 1013-1019 (Feb. 11, 2003) (7 pages).
Area et al., "3D structure of the Influenza virus polymerase complex: Localization of subunit domains," Proc. Natl. Acad. Sci. USA, 101(1), pp. 308-313 (Jan. 6, 2004) (6 pages).
Basseri et al., "The chemical chaperone 4-phenylbutyrate inhibits adipogenesis by modulating the unfolded protein response," J. Lipid Res., 50, pp. 2486-2501 (2009) (16 pages).
Area-Gomez et al., "Upregulated function of mitochondria-associated ER membranes in Alzheimer disease," EMBO J., 31(21), pp. 4106-4123 (2012) (18 pages).
Bawaskar et al., "RBC acetyl cholinesterase: A poor man's early diagnostic biomarker for familial alzheimer's and Parkinson's disease dementia," J. Neurosciences Rural Practice, 6(1), pp. 33-38 (Jan.-Mar. 2015) (7 pages).
Area-Gomez, "Chapter Eleven—Assessing the Function of Mitochondria-Associated ER Membranes," Methods Enzymol., 547, pp. 181-197 (2014) (17 pages).
Area-Gomez, et al., "Presenilins Are Enriched in Endoplasmic Reticulum Membranes Associated with Mitochondria", American Journal of Pathology, 175(5):1810-1816, Nov. 2009 (7 pages).
Atamna and Frey II, "Mechanisms of mitochondrial dysfunction and energy deficiency in Alzheimer's disease," Mitochondrion, 7, pp. 297-310 (2007) (14 pages).
Atkins et al., "HIV-1 Nef Binds PACS-2 to Assemble a Multikinase Cascade That Triggers Major Histocompatibility Complex Class I (MHC-I) Down-regulation: Analysis Using Short Interfering RNA and Knock-Out Mice," J. Biol. Chem., 283(17), p. 11772-11784 (Apr. 25, 2008) (14 pages).
Bae et al., "Knock-down of protein L-isoaspartyl O-methyltransferase increases β-amyloid production by decreasing ADAM10 and ADAM17 levels," Acta Pharmacol. Sin., 32, pp. 288-294 (2011) (7 pages).
Bae et al., "Lipid raft proteome reveals ATP synthase complex in the cell surface," Proteomics, 4, pp. 3536-3548 (2004) (13 pages).
Baglietto-Vargas et al., "Mifepristone alters APP processing to preclude Aβ and also reduces tau pathology," Author manuscript published in final edited form as: Biol. Psychiatry, 74(5), pp. 357-366 (2013) (17 pages).
Baki et al., "Presenilin-1 binds cytoplasmic epithelial cadherin, inhibits cadherin/p120 association, and regulates stability and function of the cadherin/catenin adhesion complex," Proc. Natl. Acad. Sci. USA, 98(5), pp. 2381-2386 (Feb. 27, 2001) (6 pages).
Balietti et al., "Early Selective Vulnerability of Synapses and Synaptic Mitochondria in the Hippocampal CA1 Region of the Tg2576 Mouse Model of Alzheimer's Disease," J. Alzheimer's Dis., 34, pp. 887-896 (2013) (10 pages).
Baloh et al., "Altered Axonal Mitochondrial Transport in the Pathogenesis of Charcot-Marie-Tooth Disease from Mitofusin 2 Mutations," The Journal of Neuroscience, 27(2), pp. 422-430 (Jan. 10, 2007) (9 pages).
Bandyopadhyay and Temin, "Expression of Complete Chicken Thymidine Kinase Gene Inserted in a Retrovirus Vector," Mol. Cell Biol., 4(4), pp. 749-754 (Apr. 1984) (6 pages).
Bao et al., "BACE1 SUMOylation increases its stability and escalates the protease activity in Alzheimer's disease," Proc. Natl. Acad. Sci. USA, 115(15), pp. 3954-3959 (Apr. 10, 2018) (6 pages).
Barbero-Camps et al., "Endoplasmic Reticulum Stress Mediates Amyloid β Neurotoxicity via Mitochondrial Cholesterol Trafficking," Am. J. Pathol., 184(7), pp. 2066-2081 (Jul. 2014) (16 pages).
Barrett et al., "The Amyloid Precursor Protein has a Flexible Transmembrane Domain and Binds Cholesterol,"Author Manuscript, Science 336(6085), pp. 1168-1171 (2012) (10 pages).
Barrow et al., "Functional Phenotype in Transgenic Mice Expressing Mutant Human Presenilin-1," Neurobiology of Disease, 7, pp. 119-126 (2000) (8 pages).
Barry et al., "Regulation of glycogen synthase kinase 3 in human platelets: a possible role in platelet function?" FEBS Letters, 553, pp. 173-178 (Sep. 18, 2003) (6 pages).

Ris, L. et al., "Capacltatlve Calcium Entry Induces Hippocampal Long Term Potentiation in the Absence of Presenilin-1", The Journal of Biological Chemistry, 278(45), pp. 44393-44399 (Nov. 7, 2003) (8 pages).
Risselada, H.J. and Marrink, S.J., "The molecular face of lipid rafts in model membranes", PNAS, 105(45), pp. 17367-17372 (Nov. 11, 2008) (6 pages).
Rizzuto, R. et al., "A Gene Specifying Subunit VIII of Human Cytochrome c Oxidase Is Localized to Chromosome 11 and Is Expressed in Both Muscle and Non-muscle Tissues", The Journal of Biological Chemistry, 264(18), pp. 10595-10600 (Jun. 25, 1989) (6 pages).
Rizzuto, R. et al., "Close Contacts with the Endoplasmic Reticulum as Determinants of Mitochondrial $Ca^{2+}$ Responses", Science, 280, pp. 1763-1766 (Jun. 12, 1998) (5 pages).
Rizzuto, R. et al., "Digital imaging microscopy of living cells", Trends in Cell Biology, 8, pp. 288-292 (Jul. 1998) (5 pages).
Robb-Gaspers, L.D. et al., "Integrating cytosolic calcium signals into mitochondrial metabolic responses", The EMBO Journal, 17(17), pp. 4987-5000 (1998) (14 pages).
Roberson, E.D. et al., "Reducing Endogenous Tau Ameliorates Amyloid β-Induced Deficits in an Alzheimer's Disease Mouse Model", Science, 316, pp. 750-754 (May 4, 2007) (6 pages).
Rocca, W.A. et al., "Frequency and Distribution of Alzheimer's Disease in Europe: A Collaborative Study of 1980-1990 Prevalence Findings", Annals of Neurology, 30(3), pp. 381-390 (Sep. 1991) (10 pages).
Rockenstein, E. et al., "High β-Secretase Activity Elicits Neurodegeneration in Transgenic Mice Despite Reductions in Amyloid-β Levels: Implications for the Treatment of Alzheimer Disease", The Journal of Biological Chemistry, 280(38), p. 32957-32967 (Sep. 23, 2005) (12 pages).
Rodrigue-Way, A. et al., "Scavenger receptor CD36 mediates inhibition of cholesterol synthesis via activation of the PPARγ/PGC-1α pathway and lnsig1/2 expression in hepatocytes" The FASEB Journal, 28(4), pp. 1910-1923 (2014) (first published Dec. 26, 2013) (29 pages).
Rogaeva, E. et al., "The neuronal sortilin-related receptor SORL1 is genetically associated with Alzheimer's Disease", Author Manuscript, published in final edited form as: Nat Genet., 39(2), pp. 168-177 (Feb. 2007) (25 pages).
Rose, I.A. and O'Connell, E.L., "Mechanism of Aconitase Action I. the Hydrogen Transfer Reaction", The Journal of Biological Chemistry, 242(8), pp. 1870-1879 (Apr. 25, 1967) (11 pages).
Rosenfeld, M.A. et al., "In Vivo Transfer of the Human Cystic Fibrosis Transmembrane Conductance Regulator Gene to the Airway Epithelium", Cell, 68, pp. 143-155 (Jan. 10, 1992) (13 pages).
Rosenthal, R.E. et al., "Cerebral Ischemia and Reperfusion: Prevention of Brain Mitochondrial Injury by Lidoflazine", Journal of Cerebral Blood Flow and Metabolism, 7(6), pp. 752-758 (1987) (7 pages).
Roth, A.G. et al., "Potent and Selective Inhibition of Acid Sphingomyelinase by Bisphosphonates", Angew. Chem. Int. Ed., 48, pp. 7560-7563 (2009) (4 pages).
Rowland, A.A. et al., "ER contact sites define the position and timing of endosome fission", Author manuscript published in final edited form as: Cell., 159(5), pp. 1027-1041 (Nov. 20, 2014) (25 pages).
Rube, D.A. and van der Bliek, A.M., "Mitochondrial morphology is dynamic and varied", Molecular and Cellular Biochemistry, 256/257, pp. 331-339 (2004) (9 pages).
Runz et al., "Inhibition of intracellular cholesterol transport alters presenilin localization and amyloid precursor protein processing in neuronal cells," The Journal of Neuroscience, 22(5), pp. 1679-1689 (Mar. 1, 2002) (11 pages).
Rusiñol, A.E. et al., "A Unique Mitochondria-associated Membrane Fraction from Rat Liver Has a High Capacity for Lipid Synthesis and Contains Pre-Golgi Secretory Proteins Including Nascent Lipoproteins", The Journal of Biological Chemistry, 269(44), pp. 27494-27502 (Nov. 4, 1994) (9 pages).
Rybalchenko, V. et al., "The cytosolic N-terminus of presenilin-1 potentiates mouse ryanodine receptor single channel activity", The

(56) References Cited

OTHER PUBLICATIONS

International Journal of Biochemistry & Cell Biology, 40, pp. 84-97 (2008) (available online Jul. 13, 2007) (14 pages).
Rüther, U. and Müller-Hill, B., "Easy identification of cDNA clones", The EMBO Journal., 2(10), pp. 1791-1794 (1983) (4 pages).
Saito, T. et al., "Potent amyloidogenicity and pathogenicity of A β 43.", Nature Neuroscience, 14(8), pp. 1023-1032 (Aug. 2011) (50 pages).
Salehi, A. et al., "Decreased Activity of Hippocampal Neurons In Alzheimer's Disease Is Not Related to the Presence of Neurofibrillary Tangles", Journal of Neuropathology and Experimental Neurology, 54(5), pp. 704-709 (Sep. 1995) (6 pages).
Sapoznik, S. et al., "Age-dependent glutamate induction of synaptic plasticity in cultured hippocampal neurons", Learning & Memory, 13, pp. 719-727 (2006) (9 pages).
Sastre, M. et al., "Nonsteroidal anti-inflammatory drugs repress β-secretase gene promoter activity by the activation of PPARγ", PNAS, 103(2), pp. 443-448 (Jan. 10, 2006) (6 pages).
Sato, T et al., "Active γ-Secretase Complexes Contain Only One of Each Component", The Journal of Biological Chemistry, 282(47), pp. 33985-33993 (Nov. 23, 2007) (10 pages).
Sato, S. et al., "Splicing Mutation of *Presenilin-1* Gene for Early-Onset Familial Alzheimer's Disease", Human Mutation Supplement 1, pp. S91-S94 (1998) (4 pages).
Saudek, C.D. et al., "A Preliminary Trial of the Programmable Implantable Medication System for Insulin Delivery", The New England Journal of Medicine, 321(9), pp. 574-579 (Aug. 31, 1989) (6 pages).
Saura, C.A. et al., "Loss of Presenilin Function Causes Impairments of Memory and Synaptic Plasticity Followed by Age-Dependent Neurodegeneration", Neuron, 42, pp. 23-36 (Apr. 8, 2004) (14 pages).
Sawamura, N. et al., "Modulation of Amyloid Precursor Protein Cleavage by Cellular Sphingolipids," J. Biol. Chem. 279(12), pp. 11984-11991 (Mar. 19, 2004) (8 pages).
Schägger, H. and von Jagow, G., "Blue Native Electrophoresis for Isolation of Membrane Protein Complexes in Enzymatically Active Form", Analytical Biochemistry, 199, pp. 223-231 (1991) (9 pages).
Scheek, S. et al., "Sphingomyelin depletion in cultured cells blocks proteolysis of sterol regulatory element binding proteins at site 1", Proc. Natl. Acad. Sci. USA, 94, p. 11179-11183 (Oct. 1997) (5 pages).
Scheff, S.W. et al., "Hippocampal synaptic loss In early Alzheimer's disease and mild cognitive impairment", Neurobiology of Aging, 27, pp. 1372-1384 (2006) (13 pages).
Schmitz, G. and Kaminski, W.E., "ABCA2: a candidate regulator of neural transmembrane lipid transport", Cell. Mol. Life Sci., 59, pp. 1285-1295 (2002) (11 pages).
Schneider, I. et al., "Mutant Presenilins Disturb Neuronal Calcium Homeostasis in the Brain of Transgenic Mice, Decreasing the Threshold for Excitotoxicity and Facilitating Long-term Potentiation", The Journal of Biological Chemistry, 276(15), pp. 11539-11544 (Apr. 13, 2001) (7 pages).
Schnöder, L. et al., "Deficiency of Neuronal p38α MAPK Attenuates Amyloid Pathology in Alzheimer Disease Mouse and Cell Models through Facilitating Lysosomal Degradation of BACE1", Journal of Biological Chemistry, 291 (5), pp. 2067-2079 (Jan. 29, 2016) (13 pages).
Schon, E.A. and Area-Gomez, E., "Is Alzheimer's Disease a Disorder of Mitochondria-Associated Membranes?", Journal of Alzheimer's Disease, 20, pp. S281-S292 (2010) (12 pages).
Schon, E.A. and Area-Gomez, E., "Mitochondria-associated ER membranes in Alzheimer disease", Molecular and Cellular Neuroscience, 55, pp. 26-36 (2013) (11 pages).
Schreiner, B. et al., "Amyloid-β Peptides are Generated in Mitochondria-Associated Endoplasmic Reticulum Membranes", Journal of Alzheimer's Disease, 43, pp. 369-374 (2015) (6 pages).
Schumacher, M.M. et al., "Phosphatidylserine Transport to the Mitochondria Is Regulated by Ubiquitination", The Journal of Biological Chemistry, 277(52), pp. 51033-51042 (Dec. 27, 2002) (11 pages).
Schwarzer, C. et al., "Voltage-dependent anion-selective channel (VDAC) interacts with the dynein light chain Tctex1 and the heat-shock protein PBP74", The International Journal of Biochemistry & Cell Biology, 34, 1059-1070 (2002) (12 pages).
Schwarzman, A.L. et al., "Endogenous presenilin 1 redistributes to the surface of lamellipodia upon adhesion of Jurkat cells to a collagen matrix", Proc. Natl. Acad. Sci. USA, 96, pp. 7932-7937 (Jul. 1999) (6 pages).
Schwerzmann, K. et al., "Molecular Architecture of the Inner Membrane of Mitochondria from Rat Liver: A Combined Biochemical and Stereological Study", The Journal of Cell Biology, 102, pp. 97-103 (1986) (7 pages).
Sefton, M.V., "Implantable Pumps", Critical Reviews in Biomedical Engineering, 14(3), CRC Press, Boca Raton, Florida, pp. 201-240 (1987) (42 pages).
Selak, M.A. et al., "Succinate links TCA cycle dysfunction to oncogenesis by inhibiting HIF-α prolyl hydroxylase", Cancer Cell, 7, pp. 77-85 (Jan. 2005) (9 pages).
Selkoe, D.J., "Alzheimer's Disease Is a Synaptic Failure", Science, 298, pp. 789-791 (Oct. 25, 2002) (4 pages).
Selkoe, D.J., "Deciphering the genesis and fate of amyloid α-protein yields novel therapies for Alzheimer disease", The Journal of Clinical Investigation, 110(10), pp. 1375-1381 (Nov. 2002) (7 pages).
Serban, G. et al., "Cadherins Mediate Both the Association between PS1 and β-Catenin and the Effects of PS1 on β-Catenin Stability", The Journal of Biological Chemistry, 280(43), pp. 36007-36012 (Oct. 28, 2005) (7 pages).
Shah, SA et al., "Novel osmotin inhibits SREBP2 via the AdipoR1/AMPK/SIRT1 pathway to improve Alzheimer's disease neuropathological deficits", Molecular Psychiatry, 22, pp. 407-416 (2017) (published online Mar. 22, 2016) (10 pages).
Shah, Z.H. et al., "The human homologue of the yeast mitochondrial AAA metalloprotease Yme1p complements a yeast *ymef* disruptant", FEBS Letters, 478, pp. 267-270 (2000) (4 pages).
Sharman, M.J. et al., "The Guinea Pig as a Model for Sporadic Alzheimer's Disease (AD): The Impact of Cholesterol Intake on Expression of AD-Related Genes", PLOS One, 8(6), e66235, pp. 1-12 (Jun. 21, 2013) (12 pages).
Shea, K.J., "Molecular Imprinting of Synthetic Network Polymers: The *De Novo* Synthesis of Macromolecular Binding and Catalytic Sites", Trends in Polymer Science 2(5), pp. 166-173 (May 1994) (8 pages).
Shen, J. and Kelleher, R.J., "The presenilin hypothesis of Alzheimer's disease: Evidence for a loss-of function pathogenic mechanism", PNAS, 104(2), pp. 403-409 (Jan. 9, 2007) (7 pages).
Shen, D. et al., "Lipid Storage Disorders Block Lysosomal Trafficking By Inhibiting TRP Channel and Calcium Release", Author Manuscript published in final edited form as: Nat Commun. 3:731,. Doi:10.1038/ncomms1735., pp. 1-20 (Sep. 13, 2012) (20 pages).
Shen, J. et al., "Skeletal and CNS Defects in *Presenilin*-1-Deficient Mice", Cell, 89, pp. 629-639 (May 16, 1997) (11 pages).
Shepherd, D. and Garland, P.B., "The Kinetic Properties of Citrate Synthase from Rat Liver Mitochondria", Biochem. J., 114, pp. 597-610 (1969) (14 pages).
Sherrington, R. et al., "Cloning of a gene bearing missense mutations in early-onset familial Alzheimer's disease", Nature, 375, pp. 754-760 (Jun. 29, 1995) (7 pages).
Herreman, A. et al., "Presenilin 2 deficiency causes a mild pulmonary phenotype and no. changes in amyloid precursor protein processing but enhances the embryonic lethal phenotype of presenilin 1 deficiency", PNAS, 96(21), p. 11872-11877 (Oct. 12, 1999) (6 pages).
Herreman, A. et al., "Total inactivation of γ-secretase activity in presenilin-deficient embryonic stem cells", Nature Cell Biology, 2, pp. 461-462 (Jul. 2000) (2 pages).
Herrera-Rivero, M. et al., "Tau, App, NCT and BACE1 in lymphocytes through cognitively normal ageing and neuropathology", An Acad Bras Cienc, 85(4), pp. 1489-1496 (2013) (8 pages).

(56) References Cited

OTHER PUBLICATIONS

Herrington, J. et al., "Dominant Role of Mitochondria in Clearance of Large $Ca^{2+}$ Loads from Rat Adrenal Chromaffin Cells," Neuron, 16, pp. 219-228 (Jan. 1996) (10 pages).
Herweijer, H. and Wolff, JA, "Gene therapy progress and prospects: Hydrodynamic gene delivery", Gene Therapy, 14 pp. 99-107 (2007), published online Nov. 30, 2006 (9 pages).
Hieke, M. et al., "Design, Synthesis, and Biological Evaluation of a Novel Class of γ-Secretase Modulators with PPARγ Activity", J. Med. Chem., 53, pp. 4691-4700, (2010) (10 pages).
Hirai, K. et al., "Mitochondrial Abnormalities in Alzheimer's Disease", The Journal of Neuroscience, 21(9), pp. 3017-3023 (May 1, 2001) (7 pages).
Holcomb, L. et al., "Accelerated Alzheimer-type phenotype in transgenic mice carrying both mutant amyloid precursor protein and presenilin 1 transgenes", Nature Medicine, 4(1), pp. 97-100 (Jan. 1998) (4 pages).
Hollenbeck, P.J. and Saxton, W.M., "The axonal transport of mitochondria", Journal of Cell Science, 118(23), pp. 5411-5419 (2005) (9 pages).
Hollenbeck, P.J., "Mitochondria and Neurotransmission: Evacuating the Synapse", Neuron, 47, pp. 331-333 (Aug. 4, 2005) (3 pages).
Hollenbeck, P.J., "The Pattern and Mechanism of Mitochondrial Transport in Axons", Frontiers in Bioscience, 1, pp. d91-d102 (Jul. 1, 1996) (12 pages).
Holopainen, J.M. et al., "Sphingomyelinase Induces Lipid Microdomain Formation in a Fluid Phosphatidylcholine/Sphingomyelin Membrane", Biochemistry, 37(50):17562-17570 (1998) (9 pages).
Holsinger, R.M. Damian et al., "Increased Expression of the Amyloid Precursor β-Secretase in Alzheimer's Disease", Annals of Neurology, 51(6), pp. 783-786 (Jun. 2002) (4 pages).
Holtzman, D.M. et al. "Apolipoprotein E and Apolipoprotein E Receptors: Normal Biology and Roles in Alzheimer Disease", Cold Spring Harbor Perspect Med, 2:a006312, (Jan. 10, 2012) (24 pages).
Hong, Y. et al., "Pig-n, a Mammalian Homologue ofYeast Mcd4p, Is Involved in Transferring Phosphoethanolamine to the First Mannose of the Glycosylphosphatidylinositol", The Journal of Biological Chemistry, 274(49), pp. 35099-35106 (Dec. 1999) (9 pages).
Honrath, B. et al., "Glucose-regulated protein 75 determines ER-mitochondrial coupling and sensitivity to oxidative stress in neuronal cells", Cell Death Discovery, 3, pp. 1-13 (2017) (13 pages).
Hosoda, K. et al., "Structure Determination of an Immunopotentiator Peptide, Cinnamycin, Complexed with Lysophosphatidylethanolamine by $^{1}$H-NMR[1]", J. Biochem., 119, pp. 226-230 (1996) (5 pages).
Houacine, J. et al., "Selective neutralization of APP-C99 with monoclonal antibodies reduces the production of Alzheimer's Aβ peptides", Neurobiology of Aging, 33, pp. 2704-2714 (2012) (11 pages).
Howard, III, M.A. et al., "Intracerebral drug delivery in rats with lesion-induced memory deficits", J Neurosurg, 71, pp. 105-112 (Jul. 1989) (8 page).
Hudson, P.J., "Recombinant antibody fragments", Current Opinion in Biotechnology, 9, pp. 395-402 (1998) (8 pages).
Hulce, J.J. et al., "Proteome-wide Mapping of Cholesterol-Interacting Proteins in Mammalian Cells", Author manuscript published in final edited form as: Nat. Methods, 10(3), pp. 259-264 (Mar. 2013) (17 pages).
Hurwitz, R. et al., "The Tricyclic Antidepressant Desipramine Causes Proteolytic Degradation of Lysosomal Sphingomyelinase in Human Fibroblasts", Biol. Chem. Hoppe-Seyler, 375, 447-450 (Jul. 1994) (4 pages).
Hutter-Paier, B. et al. "The ACAT Inhibitor CP-113,818 Markedly Reduces Amyloid Pathology in a Mouse Model of Alzheimer's Disease", Neuron, 44, pp. 227-238 (Oct. 14, 2004) (12 pages).
Ikeda et al., "Posttranscriptional regulation of human ABCA7 and its function for the apoA-l-dependent lipid release", Biochem. Biophys. Res. Commun., 311, pp. 313-318 (2003) (6 pages).
Inouye, S. and Inouye, M. "Up-promoter mutations in the Ipp gene of *Escherichia coli*", Nucleic Acids Research, 13(9):3101-3110 (1985) (10 pages).
International Search Report and Written Opinion issued by the U.S. Patent and Trademark Office as Searching Authority in PCT/US19/21487, dated Sep. 13, 2019 (14 pages).
Isacson, O. et al., "Alzheimer's disease and Down's syndrome: roles of APP, trophic factors and ACh", TRENDS in Neurosciences, 25(2), pp. 79-84 (Feb. 2002) (6 pages).
Isaka, Y. et al., "Electroporation-mediated gene therapy", Expert Opin. Drug Deliv., 4(5), pp. 561-571 (2007) (12 pages).
Ito, E. et al., "Internal $Ca^{2+}$ mobilization is altered in fibroblasts from patients with Alzheimer disease", Proc. Natl. Acad. Sci. USA, 91, pp. 534-538 (Jan. 1994) (5 pages).
Iwamoto, N. et al., "ABCA7 expression is regulated by cellular cholesterol through the SREBP2 pathway and associated with phagocytosis", Journal of Lipid Research, 47, pp. 1915-1927 (2006) (13 pages).
Iwasawa, R. et al., "Fis1 and Bap31 bridge the mitochondria-ER interface to establish a platform for apoptosis induction", The EMBO Journal, 30(3), pp. 556-568 (2011) (13 pages).
Iyer, M. et al., "Two-step transcriptional amplification as a method for imaging reporter gene expression using weak promoters", PNAS, 98(25), pp. 14595-14600 (Dec. 4, 2001) (6 pages).
Jager, L. and Ehrhardt, A., "Emerging Adenoviral Vectors for Stable Correction of Genetic Disorders", Current Gene Therapy, 7(4), pp. 272-283 (2007) (12 pages).
Jang, C. et al., "Calsenilin regulates presenilin 1/γ -secretase-mediated N-cadherin ϵ-cleavage and β-catenin signaling", The FASEB Journal, 25, pp. 4174-4183 (Dec. 2011) (10 pages).
Jaworska, A. et al., "Analysis of calcium homeostasis In fresh lymphocytes from patients with sporadic Alzheimer's disease or mild cognitive impairment", Biochimica et Biophysica Acta, 1833, pp. 1692-1699 (Jan. 24, 2013) (8 pages).
Jehle, A.W. et al., "ATP-binding cassette transporter A7 enhances phagocytosis of apoptotic cells and associated ERK signaling in macrophages", The Journal of Cell Biology, 174(4), pp. 547-556 (Aug. 14, 2006) (10 pages).
Jembrek, M.J. et al., "Ceramides in Alzheimer's Disease: Key Mediators of Neuronal Apoptosis Induced by Oxidative Stress and Aβ Accumulation", Oxidative Medicine and Cellular Longevity, vol. 2015, Article ID: 346783, pp. 1-17 (2015) (18 pages).
Jensen, T.G., "Cutaneous gene therapy", Annals of Medicine., 39, pp. 108-115 (2007) (8 pages).
Jia, Z. et al., "Fatty Acid Transport Protein 4 Is the Principal Very Long Chain Fatty Acyl-CoA Synthetase in Skin Fibroblasts", Journal of Biological Chemistry, 282(28), pp. 20573-20583 (Jul. 13, 2007) (12 pages).
Jiang, Y. et al., "Alzheimer's-related endosome dysfunction in Down syndrome is Aβ-independent but requires APP and is reversed by BACE-1 inhibition", PNAS, 107(4), pp. 1630-1635 (Jan. 26, 2010) (6 pages).
Jin, J.-K. et al., "Expression of calsenilin in neurons and astrocytes in the Alzheimer's disease brain", NeuroReport, 16(5), pp. 451-455 (Apr. 4, 2005) (5 pages).
Jin, L.-W. et al., "Novel Tricyclic Pyrone Compounds Prevent Intracellular APP C99-lnduced Cell Death", Journal of Molecular Neuroscience, 19, pp. 57-61 (2002) (5 pages).
Jin, J.-K. et al., "Phospholipase D1 is up-regulated in the mitochondrial fraction from the brains of Alzheimer's disease patients", Neuroscience Letters, 407, pp. 263-267 (2006) (5 pages).
Jo, D.-G., et al. "Induction ofpro-apoptotic calsenilin/DREAM/KChIP3 in Alzheimer's disease and cultured neurons after amyloid-β exposure", J. Neurochem., 88, pp. 604-611 (2004) (8 pages).
Jo, D.-G., et al., "Overexpression of calsenllin enhances γ-secretase activity", Neuroscience Letters, 378, pp. 59-64 (2005) (6 pages).
Johnson, P.A. et al., "Effects of gene transfer into cultured CNS neurons with a replication-defective herpes simplex virus type 1 vector", Molecular Brain Research, 12, pp. 95-102 (1992) (8 pages).
Jones, C.T. et al., "Mutation in codon 713 of the β amyloid precursor protein gene presenting with schizophrenia", Nature Genetics, 1, pp. 306-309 (Jul. 1992) (4 pages).

(56) References Cited

OTHER PUBLICATIONS

Jorba, N. et al., "Oligomerization of the influenza virus polymerase complex in vivo", Journal of general Virology, 89, pp. 520-524 (2008) (5 pages).
Jousset, H. et al., "STIM1 Knockdown Reveals That Store-operated $Ca^{2+}$ Channels Located Close to Sarco/Endoplasmic $Ca^{2+}$ ATPases (SERCA) Pumps Silently Refill the Endoplasmic Reticulum", The Journal of Biological Chemistry, 282(15), pp. 11456-11464 (Apr. 13, 2007) (10 pages).
Jung, C.G.et al., "Auraptene Increases the Production of Amyloid-β via c-Jun N-Terminal Kinase-Dependent Activation of γ-Secretase", J. Alzheimer's Dis. 43, pp. 1215-1228 (2015) (14 pages).
Kaasik, A. et al., "Energetic Crosstalk Between Organelles: Architectural Integration of Energy Production and Utilization", Circulation Research, 89, pp. 153-159 (Jul. 20, 2001) (8 pages).
Kadonaga, J.T. et al., "Affinity purification of sequence-specific DNA binding proteins", Proc. Natl. Acad. Sci. USA, 83, pp. 5889-5893 (Aug. 1986) (5 pages).
Kaether, C. et al., "Amyloid Precursor Protein and Notch Intracellular Domains are Generated after Transport of their Precursors to the Cell Surface", Traffic, 7, pp. 408-415 (2006) (8 pages).
Kaether, C. et al., "Presenilin-1 affects trafficking and processing of βAPP and is targeted in a complex with nicastrin to the plasma membrane", The Journal of Cell Biology, 158(3), pp. 551-561 Aug. 5, 2002) (11 pages).
Kajiwara, K. et al., "Yeast ARV1 Is Required for Efficient Delivery of an Early GPI Intermediate to the First Mannosyltransferase during GPI Assembly and Controls Lipid Flow from the Endoplasmic Reticulum", Molecular Biology of the Cell, 19, pp. 2069-2082 (May 2008) (14 pages).
Kalos, M. et al., "T cells with Chimeric Antigen Receptors Have Potent Antitumor Effects and Can Establish Memory in Patients with Advanced Leukemia", Science Translation Medicine, 3(95), pp. 1-11 (Aug. 10, 2011) (11 pages).
Kalota, A. et al., "Progress in the Development of Nucleic Acid Therapeutics", HEP, 173, pp. 173-196 (2006) (24 pages).
Kamal, A. et al., "Axonal Transport of Amyloid Precursor Protein Is Mediated by Direct Binding to the Kinesin Light Chain Subunit of Kinesin-I", Neuron, 28, pp. 449-459 (Nov. 2000) (11 pages).
Bass, B.L., "RNA Interference. The short answer", Nature, 411, pp. 428-429 (May 24, 2001) (2 pages).
Chen, S. et al., "Gene therapy for brain tumors: Regression of experimental gliomas by adenovirus-mediated gene transfer in vivo", Proc. Natl. Acad. Sci. USA, 91, pp. 3054-3057 (Apr. 1994) (4 pages).
Beel, A.J. et al., "Direct Binding of Cholesterol to the Amyloid Precursor Protein: An Important Interaction in Lipid-Alzheimer's Disease Relationships?" Author manuscript published in final edited form as: Biochim Biophys Acta., 1801(8), pp. 975-982 (Aug. 2010) (18 pages).
Beel, A.J. et al., "Structural Studies of the Transmembrane C-Terminal Domain of the Amyloid Precursor Protein (APP): Does APP Function as a Cholesterol Sensor?" Author Manuscript Published in final edited form as: Biochemistry, 47(36), pp. 9428-9446 (Sep. 9, 2008) (35 pages).
Begley, J.G. et al., "Altered Calcium Homeostasis and Mitochondrial Dysfunction in Cortical Synaptic Compartments of Presenilin-1 Mutant Mice", Journal of Neurochemistry, 72(3), pp. 1030-1039 (1999) (10 pages).
Berger-Sweeney, J. et al., "Impairments in learning and memory accompanied by neurodegeneration in mice transgenic for the carboxyl-terminus of the amyloid precursor protein", Mol. Brain Res., 66, pp. 150-162 (1999) (13 pages).
Berkner, K.L., "Expression of Heterologous Sequences in Adenoviral Vectors", Curr. Top. Microbiol. Immunol., 158, pp. 39-66 (1992) (28 pages).
Bermejo-Bescós, P. et al., "Processing of the Platelet Amyloid Precursor Protein in the Mild Cognitive Impairment (MCI)", Neurochem. Res., 38, pp. 1415-1423 (2013) (9 pages).
Bernhardt, W.M. et al., "Inhibition of Prolyl Hydroxylases Increases Erythropoietin Production in ESRD", J. Am. Soc. Nephrol., 21, pp. 2151-2156 (2010) (6 pages).
Berridge, M.J., "The endoplasmic reticulum: a multifunctional signaling organelle", Cell Calcium, 32(5-6), pp. 235-249 (2002) (15 pages).
Bettens, K. et al., "*DNMBP* is genetically associated with Alzheimer dementia in the Belgian population", Neurobiology of Aging, 30, pp. 2000-2009,(2009), available online Mar. 24, 2008 (10 pages).
Beutner, G. et al., "Identification of a Ryanodine Receptor in Rat Heart Mitochondria", The Journal of Biological Chemistry, 276(24), pp. 21482-21488 (Jun. 15, 2001) (8 pages).
Bezprozvanny, I. et al., "Neuronal Calcium Mishandling and the Pathogenesis of Alzheimer's Disease", Author Manuscript Published in final edited form as: Trends Neurosci., 31(9), pp. 454-463 (Sep. 2008) (18 pages).
Bijur, G.N, et al., "Glycogen synthase kinase-3β is highly activated in nuclei and mitochondria", Neurochemistry NeuroReport, 14(18), pp. 2415-2419 (Dec. 19, 2003) (5 pages).
Bionda, C. et al., "Subcellular compartmentalization of ceramide metabolism: MAM (mitochondria-associated membrane) and/or mitochondria?", Biochem. J., 382, pp. 527-533 (May 14, 2004) (7 pages).
Blondelle, S.E. et al., "Novel antimicrobial compounds identified using synthetic combinatorial library technology", Trends in Biotechnology, 14, pp. 60-65 (Feb. 1996) (6 pages).
Boehm-Cagan, A. et al., "ABCA1 Agonist Reverses the ApoE4-Driven Cognitive and Brain Pathologies", Author Manuscript—Journal of Alzheimer's disease (Aug. 2016) (16 pages).
Bonilla, E. et al., "Chapter 12: Neurologic and Neuropathologic Features of Mitochondrial Encephalomyopathies", Mitochondria and Free Radicals in Neurodegenerative Diseases, pp. 271-279 (1997) (9 pages).
Borchelt, D.R. et al., "Familial Alzheimer's Disease-Linked Presenilin 1 Variants Elevate Aβ1-42/1-40 Ratio In Vitro and In Vivo", Neuron, 17, pp. 1005-1013 (Nov. 1996) (9 pages).
Bossy, B. et al., "S-Nitrosylation of DRP1 Does Not Affect Enzymatic Activity and is Not Specific to Alzheimer's Disease", Author manuscript published in final edited form as: J. Alzheimers Dis. 20(Suppl 2), pp. S513-S526 (2010) (22 pages).
Bozidis, P. et al., "Mitochondrial and Secretory Human Cytomegalovirus UL37 Proteins Traffic into Mitochondrion-Associated Membranes of Human Cells", Journal of Virology, 82(6), pp. 2715-2726 (Jan. 16, 2008) (12 pages).
E. Braak, et al., "Alzheimer's disease: transiently developing dendritic changes in pyramidal cells of sector CA1 of the Ammon's horn", Acta Neuropathol., 93, pp. 323-325 (1997) (3 pages).
Breakefield, X.O., et al., "Gene Transfer into the Nervous System", Mol. Neurobiol., 1(4), pp. 339-371 (1987) (33 pages).
Breckenridge, D.G. et al., "Caspase cleavage product of BAP31 induces mitochondrial fission through endoplasmic reticulum calcium signals, enhancing cytochrome c release to the cytosol", The Journal of Cell Biology, 160(7), pp. 1115-1127 (Mar. 31, 2003) (13 pages).
Brini, M. et al., "A calcium signaling defect in the pathogenesis of a mitochondrial DNA inherited oxidative phosphorylation deficiency", Nature Medicine, 5(8), pp. 951-954 (Aug. 1999) (4 pages).
Brock, R. et al., "Comparison of Fixation Protocols for Adherent Cultured Cells Applied to a GFP Fusion Protein of the Epidermal Growth Factor Receptor", Cytometry, 35, pp. 353-362 (1999) (10 pages).
Brower, V., "Naked DNA vaccines come of age", Nature Biotechnology, 16, pp. 1304-1305 (Dec. 1998) (2 pages).
Browman, D.T. et al., "Erlin-1 and erlin-2 are novel members of the prohibitin family of proteins that define lipid-raft-like domains of the ER", J. Cell Sci., 119(15), pp. 3149-3160 (2006) (12 pages).
Brown, M.S. et al., "A proteolytic pathway that controls the cholesterol content of membranes, cells, and blood", Proc. Natl. Acad. Scl. USA, 96, pp. 11041-11048 (Sep. 1999) (8 pages).
Brown, A.M. et al., "Testing for Linkage and Association Across the Dlhydrolipoyl Dehydrogenase Gene Region with Alzheimer's Disease in Three Sample Populations", Neurochem. Res., 32, pp. 857-869 (Mar. 7, 2007) (13 pages).

(56) References Cited

OTHER PUBLICATIONS

Brunkan, A.L. et al., "Presenilin function and γ-secretase activity", Journal of Neurochemistry, 93, pp. 769-792 (2005) (24 pages).
Bryleva, E.Y. et al., "ACAT1 gene ablation increases 24(S)-hydroxycholesterol content in the brain and ameliorates amyloid pathology in mice with AD", Proc. Natl. Acad. Sci. USA, 107, pp. 3081-3086 (Feb. 16, 2010) (6 pages).
Buckman, J.F. et al., "MitoTracker labeling in primary neuronal and astrocytic cultures: influence of mitochondrial membrane potential and oxidants", Journal of Neuroscience Methods, 104, pp. 165-176 (2001) (12 pages).
Bui, M. et al., "Rab32 Modulates Apoptosis Onset and Mitochondria-associated Membrane (MAM) Properties", The Journal of Biological Chemistry, 285(41), pp. 31590-31602 (Oct. 8, 2010) (14 pages).
Busciglio, J. et al., "Neuronal Localization of Presenilin-1 and Association with Amyloid Plaques and Neurofibrillary Tangles in Alzheimer's Disease", The Journal of Neuroscience, 17(13), pp. 5101-5107 (Jul. 1, 1997) (7 pages).
Bustamante, H.A et al., "Turnover of C99 is Controlled by a Crosstalk Between ERAD and Ubiquitin-Independent Lysosomal Degradation in Human Neuroglioma Cells", PLOS One, 8(12), e83096, pp. 1-14 (Dec. 20, 2013) (14 pages).
Bustos, V. et al., "Bidirectional regulation of Aβ levels by Presenilin 1", Proc. Natl. Acad. Sci. USA, 114(27), pp. 7142-7147 (Jul. 3, 2017) (6 pages).
Bustos, V. et al., "Phosphorylated Presenilin 1 decreases β-amyloid by facilitating autophagosome-lysosome fusion", Proc. Natl. Acad. Sci. USA, 114(27), pp. 7148-7153 (Jul. 3, 2017) (6 pages).
Buxbaum et al., "Calsenilin: a calcium-binding protein that interacts with the presenilins and regulates the levels of a presenilin fragment", Nat. Med., 4(10), pp. 1177-1181 (1998) (5 pages).
Cai, D. et al., "Presenilin-1 Regulates Intracellular Trafficking and Cell Surface Delivery of β-Amyloid Precursor Protein", The Journal of Biological Chemistry, 278(5), pp. 3446-3454 (Jan. 31, 2003) (10 pages).
Cai, Q. et al., "Syntabulin-mediated anterograde transport of mitochondria along neuronal processes", The Journal of Cell Biology, 170(6), pp. 959-969 (Sep. 12, 2005) (11 pages).
Cai, C. et al., "The Presenilin-2 Loop Peptide Perturbs Intracellular Ca2+ Homeostasis and Accelerates Apoptosis", The Journal of Biological Chemistry, 281(24), pp. 16649-16655 (Jun. 16, 2006) (8 pages).
Canevari, L. et al., "Alzheimer's Disease and Cholesterol: The Fat Connection", Neurochem. Res., 32(4-5), pp. 739-750 (2007) (12 pages).
Capell, A. et al., "Cellular Expression and Proteolytic Processing of Presenilin Proteins Is Developmentally Regulated During Neuronal Differentiation", Journal of Neurochemistry, 69(6), pp. 2432-2440 (1997) (9 pages).
Capell, A. et al., "Nicastrin Interacts with γ-Secretase Complex Components via the N-terminal Part of Its Transmembrane Domain", J. Biol. Chem., 278(52), pp. 52519-52523 (Dec. 26, 2003) (6 pages).
Carter, D.A. et al., "More missense in amyloid gene", Nature Genetics, 2, pp. 255-256 (Dec. 1992) (2 pages).
Casley, C.S et al., "β-Amyloid inhibits integrated mitochondrial respiration and key enzyme activities", J. Neurochem., 80, pp. 91-100 (2002) (10 pages).
Castellani, R. et al., "Role of Mitochondrial Dysfunction in Alzheimer's Disease", Journal of Neuroscience Research, 70, pp. 357-360 (2002) (4 pages).
Castello, M.A. et al., "Moving beyond anti-amyloid therapy for the prevention and treatment of Alzheimer's disease", BMC Neurol., 14:169, (2014) (5 pages).
Cataldo, A.M. et al., "Gene Expression and Cellular Content of Cathepsin D in Alzheimer's Disease Brain: Evidence for Early Up-Regulation of the Endosomal-Lysosomal System", Neuron, 14, pp. 671-680 (Mar. 1995) (10 pages).
Chada, S.R. et al., "Review: Mitochondrial movement and positioning in axons: the role of growth factor signaling", The Journal of Experimental Biology, 206, pp. 1985-1992 (2003) (8 pages).
Chai, et al., "Activation of $\beta_2$ -adrenergic receptor promotes dendrite ramification and spine generation in APP/PS1 mice", Neurosci. Lett., 636, pp. 158-164 (2017), available online Nov. 6, 2016 (7 pages).
Chan, R.B. et al. "Comparative Lipidomic Analysis of Mouse and Human Brain with Alzheimer Disease", J. Biol. Chem., 287(4), pp. 2678-2688 (Jan. 20, 2012) (11 pages).
Chan, S.L. et al., "ATP-binding cassette transporter A7 regulates processing of amyloid precursor protein in vitro", J. Neurochem., 106, pp. 793-804 (2008) (12 pages).
Chang, D. et al., "Mitochondrial trafficking and morphology in healthy and injured neurons", Progress in Neurobiology, 80, pp. 241-268 (2006) (28 pages).
Chang, D. et al., "Mutant huntingtin aggregates impair mitochondrial movement and trafficking in cortical neurons", Neurobiology of Disease, 22, pp. 388-400 (Available online Feb. 9, 2006) (13 pages).
Chartier-Harlin et al., "Early-onset Alzheimer's disease caused by mutations at codon 717 of the β-amyloid precursor protein gene", Nature, 353, pp. 844-846 (Oct. 31, 1991) (3 pages).
Dimitrov, M. et al., "Alzheimer's disease mutations in APP but not γ-secretase modulators affect epsilon-cleavage-dependent AICD production", Nature Communications, 4:2246, (Aug. 2, 2013) (10 pages).
Dinkla, S. et al., "Functional consequences of sphingomyelinase-induced changes in erythrocyte membrane structure", Cell Death and Disease, 3, e410, pp. 1-12 (Oct. 18, 2012) (12 pages).
Doan, A. et al., "Protein Topology of Presenilin 1", Neuron, 17, pp. 1023-1030 (Nov. 1996) (8 pages).
Doghman-Bouguerra, M. et al., "FATE1 antagonizes calcium- and drug-induced apoptosis by uncoupling ER and mitochondria", EMBO reports 17(9), 1264-1280 (Jul. 11, 2016) (17 pages).
Dong, H. et al., "Spatial Relationship Between Synapse Loss and β-Amyloid Deposition in Tg2576 Mice", Author Manuscript published in final edited form as: J Comp Neurol., 500(2), pp. 311-321 (Jan. 10, 2007) (20 pages).
Donohue, M.C. et al., "Longitudinal plasma amyloid beta in Alzheimer's disease clinical trials", Author manuscript published in final edited form as: Alzheimer's Dement., 11(9), pp. 1069-1079 (Sep. 2015) (22 pages).
Donoviel, D.B. et al., "Mice lacking both presenilin genes exhibit early embryonic patterning defects", Genes & Development, 13, pp. 2801-2810 (1999) (10 pages).
Du, H. et al., "Cyclophilin D deficiency attenuates mitochondrial and neuronal perturbation and ameliorates learning and memory in Alzheimer's disease", Author manuscript published in final edited form as: Nat Med., 14(10), pp. 1097-1105 (Oct. 2008) (18 pages).
Du, H. et al., "Early deficits in synaptic mitochondria in an Alzheimer's disease mouse model", PNAS, 107(43), p. 18670-18675 (Oct. 26, 2010) (6 pages).
Duff, K. et al., "Increased amyloid-β42(43) in brains of mice expressing mutant presenilin 1", Nature, 383, pp. 710-713 (Oct. 24, 1996) (4 pages).
During, M.J. et al., "Controlled Release of Dopamine from a Polymeric Brain Implant: In Vivo Characterization," Annals of Neurology, 25(4), pp. 351-356 (Apr. 1989) (6 pages).
Dzau, V.J. et al., "Chapter 8: Gene Therapy for Cardiovascular Disease", in An Introduction to Molecular Medicine and Gene Therapy, Edited by Thomas F. Kresina, PhD., Wiley-Liss, Inc. Hoboken, New Jersey, pp. 183-201,2001 (19 pages).
Ebneth, A. et al., "Overexpression of Tau Protein Inhibits Kinesin-dependent Trafficking of Vesicles, Mitochondria, and Endoplasmic Reticulum: Implications for Alzheimer's Disease", The Journal of Cell Biology, 143(3), pp. 777-794 (Nov. 2, 1998) (18 pages).
Eckman, C.B. et al., "A new pathogenic mutation in the APP gene (I716V) increases the relative proportion of Aβ42(43)", Human Molecular Genetics, 6(12), pp. 2087-2089 (1997) (3 pages).
Edgington, L.E. et al., "Functional Imaging of Legumain in Cancer Using a New Quenched Activity-Based Probe", Author Manuscript published in final edited form as: J Am Chem Soc., 135(1), pp. 174-182 (Jan. 9, 2013) (18 pages).
Eggett, C.J. et al., "Development and Characterisation of a Glutamate-Sensitive Motor Neuron Cell Line", J. Neurochem., 74, pp. 1895-1902 (2000) (8 pages).

(56) References Cited

OTHER PUBLICATIONS

Elbashir, S. et al., "Duplexes of 21-nucleotide RNAs mediate RNA interference in cultured mammalian cells", Nature, 411, pp. 494-498 (May 24, 2001) (5 pages).
Eliyahu, H. et al., "Polymers for DNA Delivery", Molecules, 10(1), pp. 34-64 (2005) (31 pages).
Elojeimy, S. et al., "New insights on the use of desipramine as an inhibitor for acid ceramidase", FEBS Letters, 580, pp. 4751-4756 (2006) (6 pages).
Emoto, K. et al., "Isolation of a Chinese hamster ovary cell mutant defective in intramitochondrial transport of phosphatidylserine", PNAS, 96(22), pp. 12400-12405 (Oct. 26, 1999) (6 pages).
Endo, S. et al., "Possible mechanism for the decrease of mitochondrial aspartate aminotransferase activity in ischemic and hypoxic rat retinas", Biochimica et Biophysica Acta, 1450, pp. 385-396 (1999) (12 pages).
Engel, T. et al., "3β,5α,6β-Cholestanetriol and 25-hydroxycholesterol accumulate in ATP-binding cassette transporter G1 (ABCG1)-deficiency," Atherosclerosis, 235, pp. 122-129 (2014) (8 pages).
Ernster, L. et al., "Mitochondria: A Historical Review", The Journal of Cell Biology, 91(3, Pt. 2), pp. 227s-255s (Dec. 1981) (29 pages).
European Extended Search Report issued in EP 16845160.7, dated May 22, 2019 (13 pages).
European Extended Search Report issued in European Patent Application No. 19217065.2, dated Sep. 7, 2020 (15 pages).
Fan, J. et al., "Small molecule inducers of ABCA1 and apoE that act through indirect activation of the LXR pathway", Journal of Lipid Research, 59, pp. 830-842 (2018) (13 pages).
Farrer, L.A. et al., "Effects of Age, Sex, and Ethnicity on the Association Between Apolipoprotein E Genotype and Alzheimer Disease: A Meta-analysis", JAMA, 278(16), pp. 1349-1356 (Oct. 22/29, 1997) (8 pages).
Fassbender, K. et al., "Simvastatin strongly reduces levels of Alzheimer's disease β-amyloid peptides Aβ42 and Aβ40 in vitro and in vivo", PNAS, 98(10), pp. 5856-5861 (May 8, 2001) (6 pages).
Feldkamp, T. et al., "Assessment of mitochondrial membrane potential in proximal tubules after hypoxia-reoxyqenation", Am J Physiol Renal Physiol, 288, pp. F1092-F1102 (Jun. 2005) (11 pages).
Felsenstein, K.M. et al., "Altered cleavage and secretion of a recombinant β-APP bearing the Swedish familial Alzheimer's disease mutation", Nature Genetics, 6, pp. 251-256 (Mar. 1994) (6 pages).
Felsenstein, K.M. et al., "Reversal of the Swedish familial Alzheimer's disease mutant phenotype in cultured cells treated with phorbol 12,13-dibutyrate", Neuroscience Letters, 174, pp. 173-176 (1994) (4 pages).
Ferreirinha, F. et al., "Axonal degeneration in paraplegin-deficient mice is associated with abnormal mitochondria and impairment of axonal transport", The Journal of Clinical Investigation, 113(2), pp. 231-242 (Jan. 2004) (12 pages).
Fiers, W. et al., "Complete nucleotide sequence of SV40 DNA", Nature, 273, pp. 113-120 (May 11, 1978) (8 pages).
Figuera-Losada, M. et al., "Cambinol, a Novel Inhibitor of Neutral Sphingomyelinase 2 Shows Neuroprotective Properties", PLOS One, 10, e0124481, (May 26, 2015) (18 pages).
Filippin, L. et al., "Improved strategies for the delivery of GFP-based $Ca^{2+}$ sensors into the mitochondrial matrix", Cell Calcium, 37, pp. 129-136 (2005) (8 pages).
Filippov, V. et al., "Increased Ceramide in Brains with Alzheimer's and Other Neurodegenerative Diseases", Author manuscript, published in final edited form as: J. Alzheimer's Dis., 29(3), pp. 537-547 (2012) (16 pages).
Fink, D.J. et al., "In Vivo Expression of β-Galactosidase in Hippocampal Neurons by HSV-Mediated Gene Transfer", Human Gene Therapy, 3, pp. 11-19 (1992) (11 pages).
Fliegner, K.H. et al., "Expression of the Gene for the Neuronal Intermediate Filament Protein α-Internexin Coincides With the Onset of Neuronal Differentiation in the Developing Rat Nervous System", The Journal of Comparative Neurology, 342, pp. 161-173 (1994) (13 pages).
Foster, L.J. et al., "Chapter 4: Lipid Raft Proteomics: More Than Just Detergent-Resistant Membranes", in Subcellular Proteomics, vol. 43, Eds. Bertrand, et al., Springer, The Netherlands, pp. 35-47 (2007) (15 pages).
Fransson, A. et al., "Atypical Rho GTPases Have Roles in Mitochondrial Homeostasis and Apoptosis", The Journal of Biological Chemistry, 278(8), pp. 6495-6502 (Feb. 21, 2003) (9 pages).
Fransson, A. et al., "The atypical Rho GTPases Miro-1 and Miro-2 have essential roles in mitochondrial trafficking", Biochemical and Biophysical Research Communications, 344, pp. 500-510 (Available online Apr. 3, 2006) (11 pages).
Frechin, M. et al., "Cell-intrinsic adaptation of lipid composition to local crowding drives social behaviour", Nature, 2 (2015) (21 pages).
Freese, A. et al., "HSV-1 Vector Mediated Neuronal Gene Delivery: Strategies for Molecular Neuroscience and Neurology", Biochemical Pharmacology, 40(10), pp. 2189-2199(1990) (11 pages).
Friede, R.L. et al., "The Relation of Axonal Transport of Mitochondria With Microtubulesand Other Axoplasmic Organelles", J. Physiol., 265, pp. 507-519 (1977) (18 pages).
Friedman, J.R. et al., "ER Tubules Mark Sites of Mitochondrial Division", Author Manuscript published in final edited form as: Science, 334(6054), pp. 358-362 (Oct. 21, 2011) (11 pages).
Friedman, W. J. et al., "Differential Actions of Neurotrophins in the Locus Coeruleus and Basal Forebrain", Experimental Neurology, 119, pp. 72-78 (1993) (7 pages).
Friedmann, T., "Progress toward human gene therapy.", Science, 244, pp. 1275-1281 (1989) (10 pages).
Fukumoto, H. et al., "β-Secretase Protein and Activity Are Increased in the Neocortex in Alzheimer Disease", Arch. Neurol., 59, pp. 1381-1389; Correction in Arch Neurol, 60, p. 828 (2002) (10 pages).
Funamoto, S. et al., "Substrate ectodomain is critical for substrate preference and inhibition of ɣ-secretase", Nature Communications, 4, pp. 1-12 (Oct. 9, 2013) (12 pages).
Gaigg, B. et al., "Characterization of a microsomal subtraction associated with mitochondria of the yeast, *Saccharomyces cerevisiae*. Involvement in synthesis and import of phospholipids into mitochondria", Biochimica et Biophysica Acta, 1234, pp. 214-220 (1995) (7 pages).
Games, D. et al., "Alzheimer-type neuropathology in transgenic mice overexpressing V717F β-amyloid precursor protein", Nature, 373, pp. 523-527 (Feb. 9, 1995) (5 pages).
Gandy, S., "The role of cerebral amyloid β accumulation in common forms of Alzheimer disease", The Journal of Clinical Investigation, 115(5), pp. 1121-1129 (May 2005) (9 pages).
Ganesan, S. et al., "A dark yellow fluorescent protein (YFP)-based Resonance Energy-Accepting Chromoprotein (REACh) for Förster resonance energy transfer with GFP", PNAS, 103(11), pp. 4089-4094 (Mar. 14, 2006) (6 pages).
Garcia-Calvo M. et al., "The target of ezetimibe is Niemann-Pick C1-Like 1 (NPC1L1)" PNAS, 102(23), pp. 8132-8137 (Jun. 7, 2005) (6 pages).
Georgakopoulos, A. et al., "Presenilin-1 Forms Complexes with the Cadherin/Catenin Cell-Cell Adhesion System and Is Recruited to Intercellular and Synaptic Contacts", Molecular Cell, 4, pp. 893-902 (Dec. 1999) (10 pages).
Ghanbarabadi, M. et al., "Neuroprotective and memory enhancing effects of auraptene in a rat model of vascular dementia: Experimental study and histopathological evaluation", Neuroscience Letters, 623, pp. 13-21 (2016) (9 pages).
Giannakopoulos, P. et al., "Presenilin-1 expression in Pick's disease", Acta Neuropathol., 98, pp. 488-492 (1999) (5 pages).
Giedraitis, V. et al., "New Alzheimer's disease locus on chromosome 8", J Med Genet, 43, pp. 931-935 (2006) (5 pages).
Shimada, T. et al., "Targeted and Highly Efficient Gene Transfer into $CD4^+$ Cells by a Recombinant Human Immunodeficiency Virus Retroviral Vector", The Journal of Clinical Investigation, Inc., 88, pp. 1043-1047 (Sep. 1991) (5 pages).

(56) References Cited

OTHER PUBLICATIONS

Shimizu, T. et al., "Isoaspartate Formation and Neurodegeneration in Alzheimer's Disease", Archives of Biochemistry and Biophysics, 381 (2), pp. 225-234 (Sep. 15, 2000) (10 pages).
Shivamurthy, V.K.N. et al., "Brain FDG PET and the Diagnosis of Dementia", AJR, 204, pp. W76-W85 (Jan. 2015) (10 pages).
Silva, L.C. et al., "Lipid Raft Composition Modulates Sphingomyelinase Activity and Ceramide-Induced Membrane Physical Alterations", Biophysical Journal, 96(8), pp. 3210-3222 (Apr. 2009) (13 pages).
Siman, R. and Velji, J., "Localization of presenilin-nicastrin complexes and γ-secretase activity to the *trans*-Golgl network", Journal of Neurochemistry, 84, pp. 1143-1153 (2003) (11 pages).
Siman, R. et al., "Presenilin-1 P264L Knock-In Mutation: Differential Effects on Aβ Production, Amyloid Deposition, and Neuronal Vulnerability", The Journal of Neuroscience, 20(23), pp. 8717-8726 (Dec. 1, 2000) (10 pages).
Siman, R. and Scott, R.W., "Strategies to alter the progression of Alzheimer's disease", Current Opinion in Biotechnology, 7, pp. 601-607 (1996) (7 pages).
Simmen, T. et al., "Oxidative protein folding in the endoplasmic reticulum: Tight links to the mitochondria-associated membrane (MAM)", Biochimica et Biophysica Acta, 1798, pp. 1465-1473 (2010) (9 pages).
Simmen, T. et al., "PACS-2 controls endoplasmic reticulum mitochondria communication and Bid-mediated apoptosis", The EMBO Journal, 24(4), pp. 717-729 (2005) (13 pages).
Simons, K. and Ikonen, E., "How Cells Handle Cholesterol", Science, 290, pp. 1721-1726 (Dec. 1, 2000) (7 pages).
Simons, K. and Vaz, W.L.C., "Model Systems, Lipid Rafts, and Cell Membranes", Annu. Rev. Biophys. Biomol. Struct., 33, pp. 269-295 (published online Feb. 2, 2004) (30 pages).
Sims, N.R., "Rapid Isolation of Metabolically Active Mitochondria from Rat Brain and Subregions Using Percoll Density Gradient Centrifugation", Journal of Neurochemistry, 55(2), pp. 698-707 (1990) (10 pages).
Singer, O. and Verma, I.M., "Applications of Lentiviral Vectors for shRNA Delivery and Transgenesis", Author Manuscript Published in final edited form as: Curr Gene Ther., 8(6), pp. 483-488 (Dec. 2008) (12 pages).
Singh, N. et al., "The Role of Alzheimer's Disease-Related Presenilin 1 in Intercellular Adhesion", Experimental Cell Research, 263, pp. 1-13 (Mar. 2001) (14 pages).
Siskind, L.J. et al., "Anti-apoptotic Bcl-2 Family Proteins Disassemble Ceramide Channels", Journal of Biological Chemistry, 283(11), pp. 6622-6630 (Mar. 14, 2008) (9 pages).
Slotte, J.P. and Bierman, E.L., "Depletion of plasma-membrane sphingomyelin rapidly alters the distribution of cholesterol between plasma membranes and intracellular cholesterol pools in cultured fibroblasts", Biochem. J., 250, pp. 653-658 (1988) (6 pages).
Slotte, J.P. et al., "Effects of sphingomyelin degradation on cell cholesterol oxidizability and steady-state distribution between the cell surface and the cell interior", Biochimica et Biophysica Acta, 985, pp. 90-96 (1989) (7 pages).
Slotte, J.P. et al., "Intracellular transport of cholesterol in type C Niemann-Pick fibroblasts", Biochimica et Biophysica Acta, 1005, pp. 303-309 (1989) (7 pages).
Slunt, H.H. et al., "Nucleotide sequence of the chromosome 14-encoded *S182* cDNA and revised secondary structure prediction", Amyloid: Int. J. Exp. Clin. Invest., 2, pp. 188-190 (1995) (4 pages).
Smaili, S.S. et al., "Mitochondria, calcium and pro-apoptotic proteins as mediators in cell death signaling", Brazilian Journal of Medical and Biological Research, 36, pp. 183-190 (2003) (8 pages).
Small, D.H. et al., "Alzheimer's disease and Aβ toxicity: from top to bottom", Nature Reviews Neuroscience, 2, pp. 595-598 (Aug. 2001) (4 pages).
Smith, I.F. et al., "Calcium dysregulation in Alzheimer's disease: Recent advances gained from genetically modified animals", Cell Calcium, 38, pp. 427-437 (2005) (11 pages).
Song, Y. et al., "Cholesterol as a co-solvent and a ligand for membrane proteins", Protein Science, 23, pp. 1-22 (2014) (22 pages).
Sorbi, S. et al., "ApoE allele frequencies in Italian sporadic and familial Alzheimer's disease", Neuroscience Letters, 177, pp. 100-102 (1994) (3 pages).
Sorge, J. et al., "Amphotropic Retrovirus Vector System for Human Cell Gene Transfer", Molecular and Cellular Biology, 4(9), pp. 1730-1737 (Sep. 1984) (9 pages).
Spasic, D. and Annaert, W., "Building γ-secretase—the bits and pieces", Journal of Cell Science, 121(4), pp. 413-420 (2008) (8 pages).
St George-Hyslop, P.H. et al., "Molecular biology and genetics of Alzheimer's disease", C.R. Biologies, 328, pp. 119-130 (2004) (12 pages).
Stachel, S. J. et al., "Identification and in Vivo Evaluation of Liver X Receptor β-Selective Agonists for the Potential Treatment of Alzheimer's Disease", J. Med. Chem., 59, pp. 3489-3498 (Mar. 24, 2016) (10 pages).
Starkov, A.A. et al., "Mitochondrial α-Ketoglutarate Dehydrogenase Complex Generates Reactive Oxygen Species", The Journal of Neuroscience, 24(36), pp. 7779-7788 (Sep. 8, 2004) (10 pages).
Stefani, M. and Liguri, G., "Cholesterol in Alzheimer's Disease: Unresolved Questions", Current Alzheimer Research, 6(1), pp. 15-29 (2009) (15 pages).
Steinberg, S. et al., "Loss-of-function variants in *ABCA7* confer risk of Alzheimer's disease", Nature Genetics, 47, pp. 445-447, doi:10.1038/ng.3246, pp. 1-4 (published online Mar. 25, 2015) (4 pages).
Steiner, H. et al., "A Loss of Function Mutation of Presenilin-2 Interferes with Amyloid β-Peptide Production and Notch Signaling", The Journal of Biological Chemistry, 274(40), pp. 28669-28673 (1999) (6 pages).
Stokin, G.B. et al., "Axonopathy and Transport Deficits Early in the Pathogenesis of Alzheimer's Disease", Science, 307(5713), pp. 1282-1288 (Feb. 25, 2005) (8 pages).
Stone, S.J. and Vance, J.E., "Phosphatidylserine Synthase-1 and -2 are Localized to Mitochondria-associated Membranes", The Journal of Biological Chemistry, 275(44), pp. 34534-34540 (Nov. 3, 2000) (8 pages).
Stowers, R.S. et al., "Axonal Transport of Mitochondria to Synapses Depends on Milton, a Novel *Drosophila* Protein", Neuron, 36, pp. 1063-1077 (Dec. 19, 2002) (15 pages).
Stratford-Perricaudet, L.D. et al., "Evaluation of the Transfer and Expression in Mice of an Enzyme-Encoding Gene Using a Human Adenovirus Vector," Human Gene Therapy, 1, pp. 241-256 (1990) (24 pages).
Strittmatter, W.J. et al., "Apolipoprotein E: High-avidity binding to β-amyloid and increased frequency of type 4 allele in late-onset familial Alzheimer disease", Proc. Natl. Acad. Sci. USA, 90, pp. 1977-1981 (Mar. 1993) (5 pages).
Su, B. et al., "Abnormal Mitochondrial Dynamics—A Novel Therapeutic Target for Alzheimer's Disease?", Author Manuscript Published in final edited form as: Mol Neurobiol, 41(2-3), pp. 87-96 (Jun. 2010) (17 pages).
Suhara, T. et al., "Aβ42 generation is toxic to endothelial cells and inhibits eNOS function through an Akt/GSK-3β signaling-dependent mechanism", Neurobiology of Aging, 24, pp. 437-451 (2003) (15 pages).
Sun, F-C. et al., "Localization of GRP78 to mitochondria under the unfolded protein response", Biochem. J., 396, pp. 31-39 (Jan. 24, 2006) (9 pages).
Supnet, C. and Bezprozvanny, I., "Neuronal Calcium Signaling, Mitochondrial Dysfunction, and Alzheimer's Disease", Journal of Alzheimer's Disease, 20, pp. S487-S498 (2010) (12 pages).
Sutendra, G. et al., "The role of Nogo and the Mitochondria-Endoplasmic Reticulum Unit in Pulmonary Hypertension", Science Translation Medicine, 3(88), 88ra55 (Jun. 22, 2011) (14 pages).
Suzuki, N. et al., "An Increased Percentage of Long Amyloid β Protein Secreted by Familial Amyloid β Protein Precursor ($\beta APP_{717}$) Mutants", Science, 264(5163), pp. 1336-1340 (May 27, 1994) (6 pages).
Swerdlow, R.H. et al., "The Alzheimer's Disease Mitochondrial Cascade Hypothesis: Progress and Perspectives", Author Manu-

(56) References Cited

OTHER PUBLICATIONS script Published in final edited form as: Biochim Biophys Acta., 1842(8), pp. 1219-1231 (Aug. 2014) (37 pages).
Szabadkai, G. et al., "Chaperone-mediated coupling of endoplasmic reticulum and mitochondrial $Ca^{2+}$ channels", The Journal of Cell Biology, 175(6), pp. 901-911 (Dec. 18, 2006) (11 pages).
Takashima, A. et al., "Localization of Alzheimer-Associated Presenilin 1 In Transfected COS-7 Cells", Biochemical and Biophysical Research Communications, 227(2), pp. 423-426 (1996) (4 pages).
Takashima, A. et al., "Presenilin 1 associates with glycogen synthase kinase-3β and its substrate tau", Proc. Natl. Acad. Sci. USA, 95, pp. 9637-9641 (Aug. 1998) (5 pages).
Tamayeu, R. et al., "β—but not γ-secretase proteolysis of APP causes synaptic and memory deficits in a mouse model of dementia", EMBO Mol Med, 4, pp. 171-179 (2012) (9 pages).
Tambini, M.D. et al., "ApoE4 upregulates the activity of mitochondria-associated ER membranes", EMBO reports, 17(1), pp. 27-36 (2016) (10 pages).
Tanaka, N. et al., "HMG-CoA reductase inhibitors enhance phagocytosis by upregulating ATP-binding cassette transporter A7", Atherosclerosis, 217, pp. 407-414 (2011) (8 pages).
Tanaka, N. et al., "Roles of ATP-Binding Cassette Transporter A7 in Cholesterol Homeostasis and Host Defense System", Journal of Atherosclerosis and Thrombosis, 18(4), pp. 274-281 (2011) (8 pages).
Tanaka, Y. et al., "Targeted Disruption of Mouse Conventional Kinesin Heavy Chain, *kif5B*, Results in Abnormal Perinuclear Clustering of Mitochondria", Cell, 93, pp. 1147-1158 (Jun. 26, 1998) (12 pages).
Tanji, K. and Bonilla, E., "Chapter 18: Optical Imaging Techniques (Histochemical, Immunohistochemical, and in Situ Hybridization Staining Methods) to Visualize Mitochondria", in Methods in Cell Biology, vol. 65, Academic Press, San Diego, California, pp. 311-332 (2001) (22 pages).
Tanji, K. et al., "Kearns-Sayre Syndrome: Unusual Pattern of Expression of Subunits of the Respiratory Chain in the Cerebellar System", Annals of Neurology, 45(3), pp. 377-383 (Mar. 1999) (7 pages).
Tarassishin,L. et al., "Processing of Notch and amyloid precursor protein by γ-secretase is spatially distinct", PNAS, 101(49), p. 17050-17055 (Dec. 7, 2004) (6 pages).
Tarling, E.J. and Edwards, P.A., "ATP binding cassette transporter G1 (ABCG1) is an Intracellular sterol transporter", PNAS, 108(49), pp. 19719-19724 (Dec. 6, 2011) (6 pages).
Tatebayashi, Y. et al., "Role of tau phosphorylation by glycogen synthase kinase-3β in the regulation of organelle transport", Journal of Cell Science, 117(9), pp. 1653-1663 (2004) (11 pages).
Terry, R.D. et al., "Physical Basis of Cognitive Alterations in Alzheimer's Disease: Synapse Loss Is the Major Correlate of Cognitive Impairment", Ann Neurol, 30(4), pp. 572-580 (Oct. 1991) (9 pages).
Levy, R.J. et al. "Inhibition of Calcification of Bioprosthetic Heart Valves by Local Controlled-Release Diphosphonate", Science, 228, pp. 190-192 (Apr. 12, 1985) (3 pages).
Levy, E. et al., "Mutation of the Alzheimer's Disease Amyloid Gene in Hereditary Cerebral Hemorrhage, Dutch Type", Science, 248(4959), pp. 1124-1126 (Jun. 1, 1990) (4 pages).
Levy-Lahad, E. et al., "Candidate Gene for the Chromosome 1 Familial Alzheimer's Disease Locus", Science, 269, pp. 973-977 (Aug. 18, 1995) (5 pages).
Lewin, T.M. et al., "Rat liver acyl-CoA synthetase 4 is a peripheral-membrane protein located in two distinct subcellular organelles, peroxisomes, and mitochondrial-associated membrane", Archives of Biochemistry and Biophysics, 404, pp. 263-270 (2002) (8 pages).
Li, X. and Greenwald, I., "Additional evidence for an eight-transmembrane-domain topology for Caenorhabditis elegans and human presenilins", Proc. Natl. Acad. Sci. USA, 95, pp. 7109-7114 (Jun. 1998) (6 pages).
Li, Y. et al., "Control of APP processing and Aβ generation level by BACE1 enzymatic activity and transcription", The FASEB Journal, 20, pp. 285-292 (Feb. 2006) (8 pages).
Li, R. et al., "Amyloid β peptide load is correlated with increased β-secretase activity in sporadic Alzheimer's disease patients", PNAS, 101(10), pp. 3632-3637 (Mar. 9, 2004) (6 pages).
Li, B.-L. et al., "Human Acyl-CoA: Cholesterol Acyltransferase-1 (ACAT-1) Gene Organization and Evidence That the 4.3-Kilobase ACAT-1 mRNA Is Produced from Two Different Chromosomes", The Journal of Biological Chemistry, 274(16), pp. 11060-11071 (Apr. 16, 1999) (14 pages).
Li, D. et al., "Mutations of Presenilin Genes in Dilated Cardiomyopathy and Heart Failure", The American Journal of Human Genetics, 79, pp. 1030-1039 (Dec. 2006) (10 pages).
Li, Z. et al., "The Importance of Dendritic Mitochondria in the Morphogenesis and Plasticity of Spines and Synapses", Cell, 119, pp. 873-887 (Dec. 17, 2004) (15 pages).
Liao, Y.-F., et al., "Tumor Necrosis Factor-α, Interleukin-1β, and Interferon-γ Stimulate γ-Secretase-mediated Cleavage of Amyloid Precursor Protein through a JNK-dependent MAPK Pathway", The Journal of Biological Chemistry, 279(47), pp. 49523-49532 (Nov. 19, 2004) (10 pages).
Lippincott-Schwartz, J. et al., "Development and Use of Fluorescent Protein Markers in Living Cells", Science, 300, pp. 87-91 (Apr. 4, 2003) (6 pages).
Liu, F. et al., "A Genomewide Screen for Late-Onset Alzheimer Disease in a Genetically Isolated Dutch Population", The American Journal of Human Genetics, 81, pp. 17-31 (Jul. 2007) (15 pages).
Liu, Q. et al., "Amyloid Precursor Protein Regulates Brain Apolipoprotein E and Cholesterol Metabolism through Lipoprotein Receptor LRP1 ", Neuron, 56, pp. 66-78 (Oct. 4, 2007) (13 pages).
Long. E. et al., "Stimulation of the murine Uchl1 gene promoter by the B-Myb transcription factor", Lung Cancer, 42, 9-21 (2003) (13 pages).
Lu, J. et al., "An Anti-Parkinson's Disease Drug via Targeting Adenosine $A_{2A}$ Receptor Enhances Amyloid-β Generation and γ-Secretase Activity", PLoS One, 11(11):e0166415, Nov. 11, 2016 (21 pages).
Lund-Katz, S. et al., "High Density Lipoprotein Structure-Function and Role in Reverse Cholesterol Transport", Author Manuscript Published in final edited form as: Subcell Biochem., 51, pp. 183-227 (2010) (44 pages).
Lundberg, C. et al., "Applications of Lentlviral Vectors for Biology and Gene Therapy of Neurological Disorders", Current Gene Therapy, 8(6), pp. 461-473 (2008) (14 pages).
Luo, D. et al., "Expression of a fusion protein of scFv-biotin mimetic peptide for immunoassay", Journal of Biotechnology, 65, pp. 225-228 (1998) (4 pages).
Luo, Y. et al., "Mice deficient in BACE1, the Alzheimer's β-secretase, have normal phenotype and abolished β-amyloid generation", Nature Neuroscience, 4(3), pp. 231-232 (Mar. 2001) (2 pages).
Lutzelburger, M. and Kjems, J., "Strategies to Identify Potential Therapeutic Target Sites in RNA", HEP, 173:243-259 (2006) (17 pages).
Ma, W. et al., "Methyl protodioscin increases ABCA1 expression and cholesterol efflux while inhibiting gene expressions for synthesis of cholesterol and triglycerides by suppressing SREBP transcription and microRNA 33a/b levels", Atherosclerosis, 239, pp. 566-570 (Feb. 23, 2015) (5 pages).
Macdonald, J.L. et al., "A simplified method for the preparation of detergent-free lipid rafts", Journal of Lipid Research, 46, pp. 1061-1067 (2005) (7 pages).
Machaidze, G. et al., "Specific Binding of Cinnamycin (Ro 09-0198) to Phosphatidylethanolamine. Comparison between Micellar and Membrane Environments", Biochemistry, 42(43), pp. 12570-12576 (published online Oct. 9, 2003) (7 pages).
Macé, S. et al., "ABCA2 is a strong genetic risk factor for early-onset Alzheimer's disease", Neurobiology of Disease, 18, pp. 119-125 (2005) (available online Nov. 23, 2004) (7 pages).
Madzak, C. et al., "Efficient in vivo encapsidation of a shuttle vector into pseudo-simian virus 40 virions using a shuttle virus as helper", Journal of General Virology, 73, pp. 1533-1536 (1992) (4 pages).

(56) References Cited

OTHER PUBLICATIONS

Maeda, Y. et al., "PIG-M transfers the first mannose to glycosylphosphatidylinositol on the lumenal side of the ER", The EMBO Journal, 20(1 & 2), pp. 250-261 (2001) (12 pages).
Magrane, J. et al., "Dissociation of ERK and Akt signaling in endothelial cell angiogenic responses to β-amyloid", Experimental Cell Research, 312, pp. 996-1010 (available online Jan. 20, 2006) (15 pages).
Magrane, J. et al., "Intraneuronal β-Amyloid Expression Downregulates the Akt Survival Pathway and Blunts the Stress Response", The Journal of Neuroscience, 25(47), pp. 10960-10969 (Nov. 23, 2005) (10 pages).
Makino, A. et al., "Cinnamycin (Ro 09-0198) Promotes Cell Binding and Toxicity by Inducing Transbilayer Lipid Movement", The Journal of Biological Chemistry, 278(5), pp. 3204-3209 (Jan. 31, 2003) (7 pages).
Man, W.C. et al., "Colocalization of SCD1 and DGAT2: implying preference for endogenous monounsaturated fatty acids in triglyceride synthesis", Journal of Lipid Research, 47, pp. 1928-1939 (2006) (12 pages).
Manczak, M. et al., "Mitochondria are a direct site of Aβ accumulation in Alzheimer's disease neurons: implications for free radical generation and oxidative damage in disease progression", Human Molecular Genetics, 15(9), pp. 1437-1449 (Mar. 21, 2006) (13 pages).
Manfredi, G. et al., "Rescue of a deficiency in ATP synthesis by transfer of *MTATP6*, a mitochondrial DNA-encoded gene, to the nucleus", nature genetics, 30, pp. 394-399 (published online Feb. 25, 2002) (6 pages).
Manjunath, N. et al., "Lentiviral delivery of short hairpin RNAs", Author Manuscript published in final edited form as: Adv Drug Deliv Rev., 61(9), pp. 732-745 (Jul. 25, 2009) (29 pages).
Mann, R. et al., "Varying the Position of a Retrovirus Packaging Sequence Results in the Encapsidation of Both Unspliced and Spliced RNAs", Journal of Virology, 54(2), pp. 401-407 (May 1985) (7 pages).
Mannhold, R., "Structure-Activity Relationships of $K_{ATP}$ Channel Openers", Current Topics in Medicinal Chemistry, 6(10), pp. 1031-1047 (2006) (17 pages).
Mapstone, M. et al., "Plasma phospholipids identify antecedent memory impairment in older adults", Author manuscript published in final edited form as: Nat Med., 20(4), pp. 415-418 (Apr. 2014) (16 pages).
Marambaud, P. et al., "A CBP Binding Transcriptional Repressor Produced by the PS1/ε-Cleavage of N-Cadherin Is Inhibited by PS1 FAD Mutations", Cell, 114, pp. 635-645 (Sep. 5, 2003) (11 pages).
Marambaud, P. et al., "A presenilin-1/γ-secretase cleavage releases the E-cadherin intracellular domain and regulates disassembly of adherens junctions", The EMBO Journal, 21(8), pp. 1948-1956 (2002) (9 pages).
Marchetti, P. et al., "Apoptosis-associated Derangement of Mitochondrial Function in Cells Lacking Mitochondrial DNA", Cancer Research, 56, pp. 2033-2038 (May 1, 1996) (7 pages).
Margolskee, R.F., "Epstein-Barr Virus Based Expression Vectors", Current Topics in Microbiology and Immunology, 158, pp. 67-95 (1992) (29 pages).
Marquer, C. et al., "Increasing membrane cholesterol of neurons in culture recapitulates Alzheimer's disease early phenotypes", Molecular Neurodegeneration, 9:60, http://www.molecularneurodegeneration.com/content/9/1/60 (2014) (13 pages).
McBrayer, M. et al., "Lysosome and calcium dysregulation in Alzheimer's disease: partners in crime", Biochem. Soc. Trans., 41(6), pp. 1495-1502 (2013) (8 pages).
Marquer, C. et al., "Local cholesterol increase triggers amyloid precursor protein-Bace1 clustering in lipid rafts and rapid endocytosis" The FASEB Journal, 25, pp. 1295-1305 (Apr. 2011) (11 pages).
Martínez-Abundis, E. et al., "Bax distribution into mitochondrial detergent-resistant microdomains is related to ceramide and cholesterol content in postischemic hearts", The FEBS Journal, 276, pp. 5579-5588 (2009) (10 pages).
Marwarha, G. et al., "Endoplasmic reticulum stress-induced CHOP activation mediates the down-regulation of leptin in human neuroblastoma SH-SY5Y cells treated with the oxysterol 27-hydroxycholesterol", Cellular Signalling, 24, pp. 484-492 (2012) (9 pages).
Mast, N. et al., "Cholesterol-metabolizing enzyme cytochrome P450 46A1 as a pharmacologic target for Alzheimer's disease", Articles in Press, http://dx.doi.org/10.1016/j.neuropharm.2017.06.026, Neuropharmacology (2017) (12 pages).
Mather, J.P. et al., "Culture of Testicular Cells in Hormone-Supplemented Serum-Free Medium", Annals New York Academy of Sciences, 383, pp. 44-68 (1982) (25 pages).
Mather, J., "Establishment and Characterization of Two Distinct Mouse Testicular Epithelial Cell Lines", Biology of Reproduction, 23, pp. 243-252 (1980) (10 pages).
Matsuda, S. et al., "Maturation of BRI2 generates a specific inhibitor that reduces APP processing at the plasma membrane and in endocytic vesicles", Neurobiology of Aging, 32, pp. 1400-1408 (2011) (available online Sep. 12, 2009) (9 pages).
Matsumoto, K. et al., "Effects of hypoxia on cholesterol metabolism in human monocyte-derived macrophages", Life Sciences, 67, pp. 2083-2091 (2000) (9 pages).
Matsumura, N. et al., "γ-Secretase Associated with Lipid Rafts: *Multiple Interactive Pathways in the Stepwise Processing of* β-*Carboxyl-Terminal Fragment*", The Journal of Biological Chemistry, 289(8), pp. 5109-5121 (Feb. 21, 2014) (14 pages).
Mattson, M.P. et al., "Calcium signaling in the ER: its role in neuronal plasticity and neurodegenerative disorders", Trends Neurosci., 23(5), pp. 222-229 (2000) (8 pages).
Mattson, M.P., "Pathways towards and away from Alzheimer's disease", Nature, 430, pp. 631-639 (Aug. 5, 2004) (9 pages).
Mattsson, N et al., "Independent information from cerebrospinal fluid amyloid-β and florbetapir imaging in Alzheimer's disease", Brain, 138, pp. 772-783 (2015) (12 pages).
Maulik, M. et al., "Role of Cholesterol in APP Metabolism and Its Significance in Alzheimer's Disease Pathogenesis", Mol Neurobiol, 47, pp. 37-63 (2013) (27 pages).
Maxwell, P.H. and Eckardt, K.-U., "HIF prolyl hydroxylase inhibitors for the treatment of renal anaemia and beyond", Nature Reviews, 12, pp. 157-168 (Mar. 2016) (12 pages).
Maynard, J. and Georgiou, G., "Antibody Engineering", Annu. Rev. Biomed. Eng., 02, pp. 339-376 (2000) (40 pages).
McCormack, J.G. et al., "Studies on mitochondrial $Ca^{2+}$-transport and matrix $Ca^{2+}$ using fura-2-loaded rat heart mitochondria", Biochimica et Biophysica Acta, 973, pp. 420-427 (1989) (8 pages).
McPhie, D.L. et al., "Neuronal Expression of β-Amyloid Precursor Protein Alzheimer Mutations Causes Intracellular Accumulation of a C-terminal Fragment Containing Both the Amyloid β and Cytoplasmic Domains", J. Biol. Chem., 272(40), pp. 24743-24746 (Oct. 3, 1997) (5 pages).
Medema, R.H., "Review Article: Optimizing RNA interference for application in mammalian cells", Biochem. J., 380, pp. 593-603 (2004) (11 pages).
Mehmedbasic, A. et al., "SorLA Complement-type Repeat Domains Protect the Amyloid Precursor Protein against Processing", Journal of Biological Chemistry, 290(6), pp. 3359-3376 (Feb. 6, 2015) (19 pages).
Melan, M.A. and Sluder, G., "Redistribution and differential extraction of soluble proteins in permeabilized cultured cells: Implications for immunofluorescence microscopy", Journal of Cell Science, 101, pp. 731-743 (1992) (14 pages).
Mellgren, R.L., "Detergent-resistant membrane subtractions containing proteins of plasma membrane, mitochondrial, and internal membrane origins", J. Biochem. Biophys. Methods, 70, pp. 1029-1036 (2008) (8 pages).
Mendes, C.C.P. et al., "The Type III Inositol 1,4,5-Trisphosphate Receptor Preferentially Transmits Apoptotic $Ca^{2+}$ Signals into Mitochondria", The Journal of Biological Chemistry, 280(49), pp. 40892-40900 (Dec. 9, 2005) (10 pages).

(56) References Cited

OTHER PUBLICATIONS

Meunier, J. et al., “Sigma-1 Receptors Regulate Bcl-2 Expression by Reactive Oxygen Species-Dependent Transcriptional Regulation of Nuclear Factor kB”, The Journal of Pharmacology and Experimental Therapeutics, 332(2), pp. 388-397 (2010) (11 pages).
Migliaccio, G. et al. “The Signal Sequence Receptor, Unlike the Signal Recognition Particle Receptor, Is Not Essential for Protein Translocation”, The Journal of Cell Biology, 117(1), pp. 15-25 (Apr. 1992) (11 pages).
Miller, K.E. and Sheetz, M.P., “Axonal mitochondrial transport and potential are correlated”, Journal of Cell Science, 117(13), pp. 2791-2804 (2004) (14 pages).
Miller, C.L. et al. “An Activation-Dependent, T-Lymphocyte-Specific Transcriptional Activator in the Mouse Mammary Tumor Virus env Gene”, Molecular and Cellular Biology, 12(7), pp. 3262-3272 (Jul. 1992) (11 pages).
Miller, A.D. et al., “Deletion of the gag Region from FBR Murine Osteosarcoma Virus Does Not Affect Its Enhanced Transforming Activity”, J. Virol. 55(3), pp. 521-526 (Sep. 1985) (6 pages).
Miller, A.D. et al. “Design of Retrovirus Vectors for Transfer and Expression of the Human β-Globin Gene”, Journal of Virology, 62(11), pp. 4337-4345 (Nov. 1988) (9 pages).
Miller, A.D., “Human gene therapy comes of age”, Nature, 357, pp. 455-460 (Jun. 11, 1992) (6 pages).
Miyake, Y. et al. “Serine Palmitoyltransferase is the Primary Target of a Sphingosine-Like Immunosuppressant, ISP-1/Myriocin”, Biochemical and Biophysical Research Communications, 211(2), pp. 396-403 (Jun. 15, 1995) (8 pages).
Mokhber, N. et al. “Comparison of Sertraline, Venlafaxine and Desipramine Effects on Depression, Cognition and the Daily Living Activities in Alzheimer Patients”, Pharmacopsychiatry, (2014) (11 pages).
Monaghan, P. et al. “Ultrastructural Localization of BCL-2 Protein”, The Journal of Histochemistry and Cytochemistry, 40(12), pp. 1819-1825 (1992) (7 pages).
Moore, S. et al. “APP Metabolism Regulates Tau Proteostasis in Human Cerebral Cortex Neurons”, Cell Reports, 11, pp. 689-696 (May 5, 2015) (9 pages).
Morfini, G. et al., “Fast Axonal Transport Misregulation and Alzheimer's Disease”, NeuroMolecular Medicine, 2, pp. 89-99 (2002) (11 pages).
Morfini, G. et al., “Glycogen synthase kinase 3 phosphorylates kinesin light chains and negatively regulates kinesin-based motility”, The EMBO Journal, 21(3), pp. 281-293 (2002) (13 pages).
Morrow, I.C. and Parton, R.G., “Flotillins and the PHB Domain Protein Family: Rafts, Worms and Anaesthetics”, Traffic, 6, pp. 725-740 (Oct. 2005) (17 pages).
Mosbach, K., “Molecular imprinting”, TIBS, 19, pp. 9-14 (Jan. 1994) (6 pages).
Moss, B., “Vaccinia and other poxvirus expression vectors”, Current Opinion in Biotechnology, 3, pp. 518-522 (1992) (5 pages).
Mosser, S. et al., “The adipocyte differentiation protein APMAP is an endogenous suppressor of Aβ production in the brain”, Human Molecular Genetics, 24(2), pp. 371-382 (2015) (12 pages).
Nik, S.H.M., et al., “Alzheimer's disease-related peptide PS2V plays ancient, conserved roles in suppression of the unfolded protein response under hypoxia and stimulation of γ-secretase activity”, Human Molecular Genetics, 24(13), pp. 3662-3678 (2015) (17 pages).
Mukodani, J. et al., “Effects of Hypoxia on Sterol Synthesis, Acyl-CoA:Cholesterol Acyltransferase Activity, and Efflux of Cholesterol in Cultured Rabbit Skin Fibroblasts”, Arteriosclerosis, 10(1), pp. 106-110 (Jan./Feb. 1990) (5 pages).
Mullan, M. et al., “A pathogenic mutation for probable Alzheimer's disease in the APP gene at the N-terminus of β-amyloid”. Nature Genetics, 1, pp. 345-347 (Aug. 1992) (3 pages).
Murayama, O. et al., “Enhancement of amyloid β 42 secretion by 28 different presenilin 1 mutations of familial Alzheimer's disease”, Neuroscience Letters, 265, pp. 61-63 (1999) (3 pages).
Murayama, O. et al., “Twenty-Nine Missense Mutations Linked With Familial Alzheimer's Disease Alter the Processing of Presenilin 1”, Prog. Neuro-Psychopharmacol. & Biol. Psychiat., 23, pp. 905-913 (1999) (9 pages).
Murphy, A.N. and Bredesen, D.E., “Chapters: Mitochondria, Reactive Oxygen Species, and Apoptosis”, Mitochondria and Free Radicals in Neurodegenerative Diseases, Beal, et al., Eds., Wiley-Liss, Inc., Wilmington, Delaware, pp. 159-186 (1997) (28 pages).
Murphy, E.J. et al., “Phospholipid mass is increased in fibroblasts bearing the Swedish amyloid precursor mutation”, Brain Research Bulletin, 69, pp. 79-85 (2006) (7 pages).
Murrell, J. et al., “A Mutation in the Amyloid Precursor Protein Associated with Hereditary Alzheimer's Disease”, Science, 254, pp. 97-99 (Oct. 4, 1991) (4 pages).
Muzyczka, N., “Use of Adeno-Associated Virus as a General Transduction Vector for Mammalian Cells”, Current Topics in Microbiology and Immunology, 158, pp. 97-129 (1992) (33 pages).
Myhill, N. et al., “The Subcellular Distribution of Calnexin Is Mediated by PACS-2”, Molecular Biology of the Cell, 19, pp. 2777-2788 (Jul. 2008) (12 pages).
Nagai, T. et al., “Circularly permuted green fluorescent proteins engineered to sense $Ca^{2+}$”, PNAS, 98(6), pp. 3197-3202 (Mar. 13, 2001) (6 pages).
Nakai, T. et al., “Membrane Topology of Alzheimer's Disease-related Presenilin 1: Evidence for the Existence of a Molecular Species With a Seven Membrane-Spanning and One Membrane-Embedded Structure”, The Journal of Biological Chemistry, 274(33), p. 23647-23658 (Aug. 13, 1999) (12 pages).
Nakano, Y. et al., “Short Communication: Accumulation of murine amyloidβ42 in a gene-dosage-dependent manner in PS1 ‘knock-in’ mice”, European Journal of Neuroscience, 11, pp. 2577-2581 (1999) (5 pages).
Nakaya, Y. et al., “Random Mutagenesis of Presenilin-1 Identifies Novel Mutants Exclusively Generating Long Amyloid β-Peptides” The Journal of Biological Chemistry, 280(19), pp. 19070-19077 (published online Mar. 10, 2005) (9 pages).
Nakayama, S. and Kretsinger, R.H., “Evolution of the EF-Hand Family of Proteins”, Annu. Rev. Biophys. Biomol. Struct., 23, pp. 473-507 (1994) (38 pages).
Nangaku, M. et al., “KIF1B, a Novel Microtubule Plus End-Directed Monomeric Motor Protein for Transport of Mitochondria”, Cell, 79, pp. 1209-1220 (Dec. 30, 1994) (12 pages).
Naruse, S. et al., “Effects of PS1 Deficiency on Membrane Protein Trafficking in Neurons”, Neuron, 21, pp. 1213-1221 (Nov. 1998) (9 pages).
Nelson, O. et al., “Familial Alzheimer disease-linked mutations specifically disrupt $Ca^{2+}$ leak function of presenilin 1”, The Journal of Clinical Investigation, 117(5), pp. 1230-1239 (May 2007) (10 pages).
Netzer, W.J. et al., “Gleevec shifts APP processing from a β-cleavage to a nonamyloidogenic cleavage”, PNAS, 114(6), pp. 1389-1394 (Feb. 7, 2017) (6 pages).
Neve, R.L. et al., “Transgenic Mice Expressing APP-C100 in the Brain”, Neurobiology of Aging, 17(2), pp. 191-203 (1996) (13 pages).
Newman, M. et al., “Differential, dominant activation and inhibition of Notch signalling and APP cleavage by truncations of PSEN1 in human disease”, Human Molecular Genetics, 23(3), pp. 602-617 (2014) (16 pages).
Nguyen, M. et al., “Role of Membrane Anchor Domain of Bcl-2 in Suppression of Apoptosis Caused by E1B-defective Adenovirus”, The Journal of Biological Chemistry, 269(24), pp. 16521-16524 (Jul. 1994) (5 pages).
Ni, Y. et al., “Activation of $\beta_2$-adrenergic receptor stimulates γ-secretase activity and accelerates amyloid plaque formation”, Nature Medicine, 12(12), pp. 1390-1396 (Dec. 2006) (7 pages).
Niemann, A. et al., “Ganglioside-induced differentiation associated protein 1 is a regulator of the mitochondrial network: new implications for Charcot-Marie-Tooth disease”, The Journal of Cell Biology, 170(7), pp. 1067-1078 (Sep. 26, 2005) (12 pages).
Nikolic, M. et al., “The cdk5/p35 kinase is essential for neurite outgrowth during neuronal differentiation”, Genes & Development, 10, pp. 816-825 (1996) (11 pages).

(56) References Cited

OTHER PUBLICATIONS

North, R.A., "Molecular Physiology of P2X Receptors", Physiol Rev, 82, pp. 1013-1067 (Oct. 2002) (55 pages).
Novgorodov, S.A. et al., "Developmentally Regulated Ceramide Synthase 6 Increases Mitochondrial $Ca2^+$ Loading Capacity and Promotes Apoptosis", Journal of Biological Chemistry, 286(6), pp. 4644-4658 (Feb. 11, 2011) (15 pages).
Nunomura, A. et al., "Oxidative Damage Is the Earliest Event in Alzheimer Disease", Journal of Neuropathology and Experimental Neurology, 60(8), pp. 759-767 (Aug. 2001) (9 pages).
Ohi, S. et al., "Construction and replication of an adeno-associated virus expression vector that contains human β-globin cDNA", Gene, 89, pp. 279-282 (1990) (4 pages).
Ojaimi, J. et al., "An Algal Nucleus-encoded Subunit of Mitochondrial ATP Synthase Rescues a Defect in the Analogous Human Mitochondrial-encoded Subunit", Molecular Biology of the Cell, 13, pp. 3836-3844 (Nov. 2002) (10 pages).
Okwu, A.K. et al., "Regulation of the threshold for lipoprotein-induced acyl-CoA:cholesterol O-acyltransferase stimulation in macrophages by cellular sphingomyelin content", Journal of Lipid Research, 35, pp. 644-655 (1994) (12 pages).
Olazán, J. et al., "A Blood-Based, 7-Metabolite Signature forthe Early Diagnosis of Alzheimer's Disease", Journal of Alzheimer's Disease, 45, pp. 1157-1173 (2015) (17 pages).
Oliveira, T.G. et al., "The impact of chronic stress on the rat brain lipidome", Author manuscript published in final edited form as: Mol Psychiatry, 21(1), pp. 80-88 (Jan. 2016) (19 pages).
Orme, M.H. et al., "Glycogen synthase kinase-3 and Axin function in a β-catenin-independent pathway that regulates neurite outgrowth in neuroblastoma cells", Molecular and Cellular Neuroscience, 24, pp. 673-686 (2003) (14 pages).
Wieckowskl, M.R. et al., "Isolation of mltochondrla-associated membranes and mitochondria from animal tissues and cells", Nature Protocols, 4(11), pp. 1582-1590 (2009) (9 pages).
Wiley, J.C., et al., "Phenylbutyric acid reduces amyloid plaques and rescues cognitive behavior in AD transgenic mice", Aging Cell, 10, pp. 418-428 (2011) (11 pages).
Wiley, J.C. et al., "Phenylbutyric Acid Rescues Endoplasmic Reticulum Stress-Induced Suppression of APP Proteolysis and Prevents Apoptosis in Neuronal Cells", PLoS ONE, 5(2), e9135, (Feb. 8, 2010) (17 pages).
Wley, J.C. et al., "Familial Alzheimer's disease mutations inhibit γ-secretase-mediated liberation of β-amyloid precursor protein carboxy-terminal fragment", J. Neurochem., 94, pp. 1189-1201 (2005) (13 pages).
Wilhelm, L.P. et al., "STARD3 mediates endoplasmic reticulum-to-endosome cholesterol transport at membrane contact sites" The EMBO Journal, 36(10), pp. 1412-1433 (2017) (22 pages).
Wilkinson, G.W.G. and Akrigg, A., "Constitutive and enhanced expression from the CMV major IE promoter in a defective adenovirus vector", Nucleic Acids Research., 20(9), pp. 2233-2239 (1992) (7 pages).
Williamson, C.D. and Colberg-Poley, A.M., "Access of Viral Proteins to Mitochondria Via Mitochondria-Associated Membranes", Author manuscript Published in final edited form as: Rev Med Virol, 19(3), pp. 147-164 (May 2009) (29 pages).
Wilson, C.M. et al., "DC2 and Keratinocyte-associated Protein 2 (KCP2), Subunits of the Oligosaccharyltransferase Complex, Are Regulators of the γ-Secretase-directed Processing of Amyloid Precursor Protein (APP)", The Journal of Biological Chemistry, 286(36), pp. 31080-31091 (Sep. 9, 2011) (12 pages).
Wolfe, M.S. and Kopan, R., "Intramembrane Proteolysis: Theme and Variations", Science, 305, pp. 1119-1123 (Aug. 20, 2004) (5 pages).
Wollmer, M.A. et al., "*ABCA1* modulates CSF cholesterol levels and Influences the age at onset of Alzheimer's disease", Neurobiology of Aging, 24, pp. 421-426 (2003) (6 pages).
Wong, P.C. et al., "Presenilin 1 is required for *Notch1* and *DII1* expression in the paraxial mesoderm", Nature, 387, pp. 288-292 (May 15, 1997) (5 pages).
Wood, W.G. et al., "Cholesterol as a causative factor in Alzheimer's disease: a debatable hypothesis", Journal of Neurochemistry, 129, pp. 559-572 (2014) (14 pages).
Worgall, T.S., "Chapter 9: Sphingolipid Synthetic Pathways Are Major Regulators of Lipid Homeostasis", in Sphingolipids and Metabolic Disease, Cowart, L.A., Editor, Landes Bioscience and Springer Science+Business Media, LLC, New York, New York, pp. 139-148 (2011) (10 pages).
Wu, W.-I. and Voelker, D.R., "Characterization of Phosphatidylserine Transport to the Locus of Phosphatidylserine Decarboxylase 2 in Permeabilized Yeast", The Journal of Biological Chemistry, 276(10), pp. 7114-7121 (Mar. 9, 2001) (9 pages).
Wu, W.-I. and Voelker, D.R., "Reconstitution of Phosphatidylserine Transport from Chemically Defined Donor Membranes to Phosphatidylserine Decarboxylase 2 Implicates Specific Lipid Domains in the Process", The Journal of Biological Chemistry, 279(8), pp. 6635-6642 (Feb. 20, 2004) (9 pages).
Wu, B.X. et al., "Identification of Novel Anionic Phospholipid Binding Domains in Neutral Sphingomyelinase 2 with Selective Binding Preference", The Journal of Biological Chemistry, 286(25), pp. 22362-22371 (Jun. 24, 2011) (11 pages).
Wulff, G., "Chapter 9: Molecular Recognition in Polymers Prepared by Imprinting with Templates", in Polymeric Reagents and Catalysts, Ford, Editor, ACS Symposium, Washington, DC, pp. 186-230 (May 5, 1986) (45 pages).
Xian, X. et al., "Reversal of ApoE4-induced recycling block as a novel prevention approach for Alzheimer's disease", eLIFE, 7, e40048, DOI: https://doi.org/10.7554/eLife.40048, (Oct. 30, 2018) (32 pages).
Xie, J. and Guo, Q., "PAR-4 Is Involved in Regulation of β-Secretase Cleavage of the Alzheimer Amyloid Precursor Protein", The Journal of Biological Chemistry, 280(14), p. 13824-13832 (Apr. 8, 2005) (9 pages).
Xie, H. et al., "Mitochondrial Alterations near Amyloid Plaques in an Alzheimer's Disease Mouse Model", The Journal of Neuroscience, 33(43), p. 17042-17051 (Oct. 23, 2013) (10 pages).
Xu, X. et al., "Identification of a Novel PSD-95/Dlg/ZO-1 (PDZ)-like Protein Interacting with the C Terminus of Presenilin-1", The Journal of Biological Chemistry, 274(46), pp. 32543-32546 (1999) (4 pages).
Xu, X. et al., "The Novel Presenilin-1-associated Protein Is a Proapoptotic Mitochondrial Protein", The Journal of Biological Chemistry, 277(50), pp. 48913-48922 (2002) (11 pages).
Yan, R., "Stepping closer to treating Alzheimer's disease patients with BACE1 inhibitor drugs", Translational Neurodegeneration, 5(13), (2016) (11 pages).
Yang, L.B. et al., "Elevated β-secretase expression and enzymatic activity detected in sporadic Alzheimer disease", Nature Medicine, 9(1), pp. 3-4 (Jan. 2003) (2 pages).
Yao, J. et al., "Mitochondrial bioenergetic deficit precedes Alzheimer's pathology in female mouse model of Alzheimer's disease", PNAS, 106(34), pp. 14670-14675 (Aug. 25, 2009) (6 pages).
Yao, J.K. et al., "Reduced Membrane Lipids in the Cortex of Alzheimer's Disease Transgenic Mice", Neurochem Res, 34, pp. 102-108 (2009) (7 pages).
Yi, M. et al., "Control of mitochondrial motility and distribution by the calcium signal: a homeostatic circuit", The Journal of Cell Biology, 167(4), pp. 661-672 (Nov. 22, 2004) (12 pages).
Dalia, Y. et al., "Potential of ezetimibe in memory deficits associated with dementia of Alzheimer's type in mice", Indian Journal of Pharmacology, 41(6), pp. 262-267 (Dec. 2009) (16 pages).
Yoo, A.S. et al., "Presenilin-Mediated Modulation of Capacitative Calcium Entry", Neuron, 27, pp. 561-572 (Sep. 2000) (12 pages).
Young-Pearse, T.I et al., "A Critical Function for β-Amyloid Precursor Protein in Neuronal Migration Revealed by In Utero RNA Interference", The Journal of Neuroscience, 27(52), pp. 14459-14469 (Dec. 26, 2007) (11 pages).
Yu, J.-T. et al., "Polymorphisms at the β2-adrenergic receptor gene influence Alzheimer's disease susceptibility", Brain Research, 1210, pp. 216-222 (available online Mar. 20, 2008) (7 pages).
Yu, H. et al., "APP Processing and Synaptic Plasticity in *Presenilin-1* Conditional Knockout Mice", Neuron, 31, pp. 713-726 (Sep. 13, 2001) (14 pages).

(56) References Cited

OTHER PUBLICATIONS

Yu, C. et al., "Ceramide displaces cholesterol from lipid rafts and decreases the association of the cholesterol binding protein caveolin-1", Journal of Lipid Research, 46, pp. 1678-1691 (2005) (14 pages).
Zamzami, N. et al., "Reduction in Mitochondrial Potential Constitutes an Early Irreversible Step of Programmed Lymphocyte Death In Vivo", J. Exp. Med., 181, pp. 1661-1672 (May 1, 1995) (12 pages).
Zenisek, D. and Matthews, G., "The Role of Mitochondria in Presynaptic Calcium Handling at a Ribbon Synapse", Neuron, 25, pp. 229-237 (Jan. 2000) (9 pages).
Zhang, X. and Song, W., "The role of APP and BACE1 trafficking in APP processing and amyloid-β generation", Alzheimer's Research & Therapy, 5(46), (2013) (8 pages).
Zhang, M. et al., "Control of BACE1 degradation and APP processing by ubiquitin carboxyl-terminal hydrolase L1", Journal of Neurochemistry, 120, pp. 1129-1138 (2012) (10 pages).
Zhang, J. et al., "Creating New Fluorescent Probes for Cell Biology", Nature, 3, pp. 906-918 (Dec. 2002) (13 pages).
Zhang, Z. et al., "Delta-secretase cleaves amyloid precursor protein and regulates the pathogenesis in Alzheimer's disease", Nature Communications, 6:8762 (Nov. 9, 2015) (16 pages).
Zhang, H. et al., "Elucidating a normal function of huntingtin by functional and microarray analysis of huntingtin-null mouse embryonic fibroblasts", BMC Neuroscience, 9:38, (Apr. 15, 2008) (15 pages).
Zhang, X. et al., "Hippocampal Network Oscillations in APP/APLP2-Deficient Mice", PLOS ONE, 8(4), e61198 (Apr. 2013) (7 pages).
Zhang, H. et al., "PPAR-α agonist regulates amyloid-β generation via inhibiting BACE-1 activity in human neuroblastoma SH-SY5Y cells transfected with APPswe gene", Mol Cell Biochem, 408, pp. 37-46 (2015) (10 pages).
Zhang, Y. et al., "Rat Kinesin light chain 3 associates with spermatid mitochondria", Author manuscript Published in final edited form as: Dev Biol. 275(1): 23-33 (Nov. 1, 2004) (20 pages).
Zhao, C. et al., "Charcot-Marie-Tooth Disease Type 2A Caused by Mutation in a Microtubule Motor KIF1Bβ", Cell, 105, pp. 587-597 (Jun. 1, 2001) (11 pages).
Zheng, Y.Z. et al., "Mitochondria do not contain lipid rafts, and lipid rafts do not contain mitochondrial proteins", Journal of Lipid Research, 50, pp. 988-998 (2009) (11 pages).
Zhou, S. et al., "CD147 is a regulatory subunit of the γ-secretase complex in Alzheimer's disease amyloid β-peptide production", PNAS, 102(21), pp. 7499-7504 (May 24, 2005) (6 pages).
Zhou, Y. et al., "Prediction of EF-Hand Calcium-Binding Proteins and Analysis of Bacterial EF-Hand Proteins", Proteins: Structure, Function, and Bioinformatics, 65(3), pp. 643-655 (2006) (13 pages).
Zhou, S. et al., "Regulation of γ-Secretase Activity in Alzheimer's Disease", Biochemistry, 46(10), pp. 2553-2563 (Mar. 13, 2007) (11 pages).
Zigdon, H. et al., "Ablation of Ceramide Synthase 2 Causes Chronic Oxidative Stress Due to Disruption of the Mitochondrial Respiratory Chain", The Journal of Biological Chemistry, 288(7), pp. 4947-4956 (Feb. 15, 2013) (10 pages).
International Search Report and Written Opinion issued by the U.S. Patent and Trademark Office as International Searching Authority, in International Application No. PCT/US16/51046, dated Mar. 31, 2017 (17 pages) .
Extended European Search Report issued in European Patent Application No. EP19217065, dated Sep. 7, 2020 (15 pages).

* cited by examiner

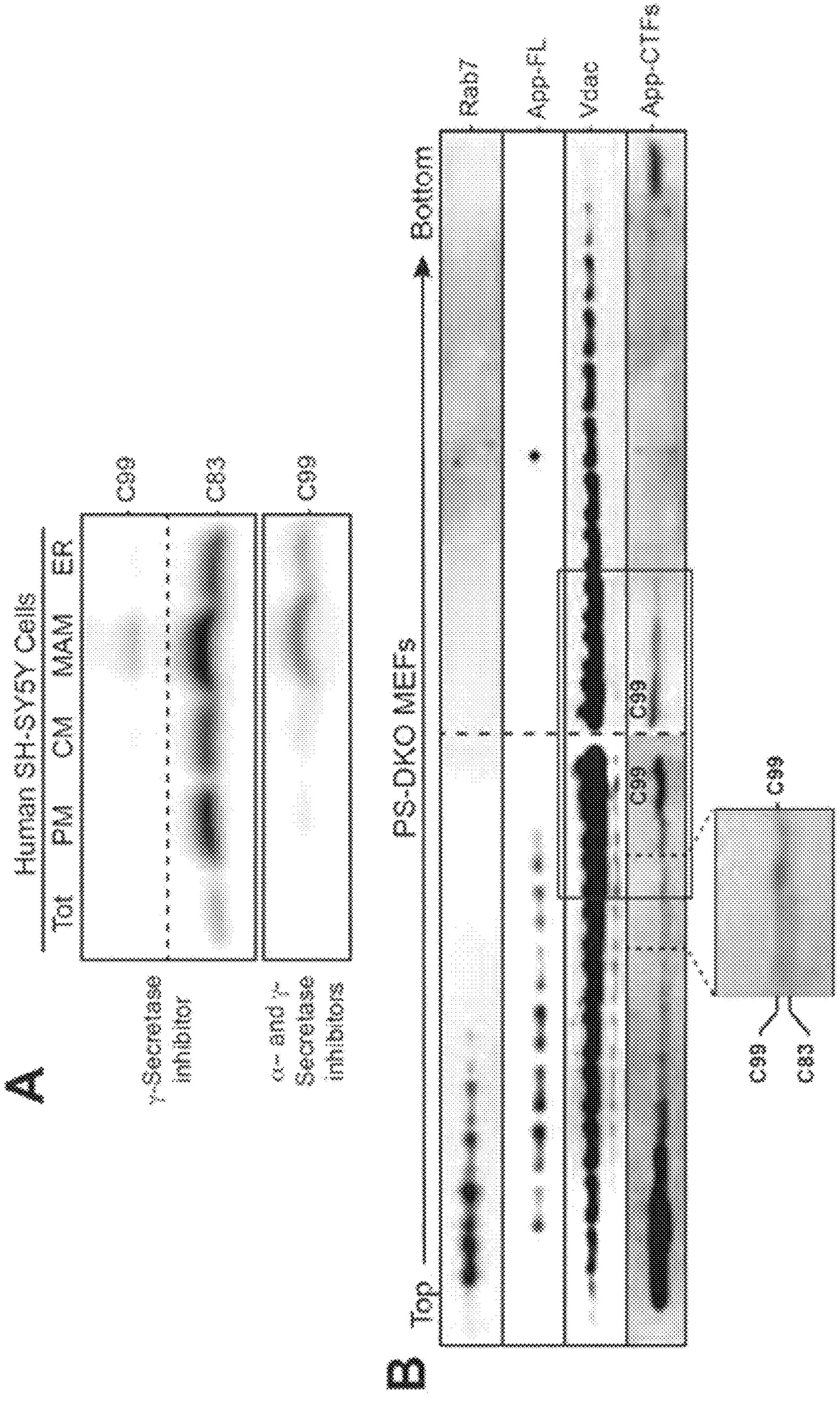
FIGS. 1A-B

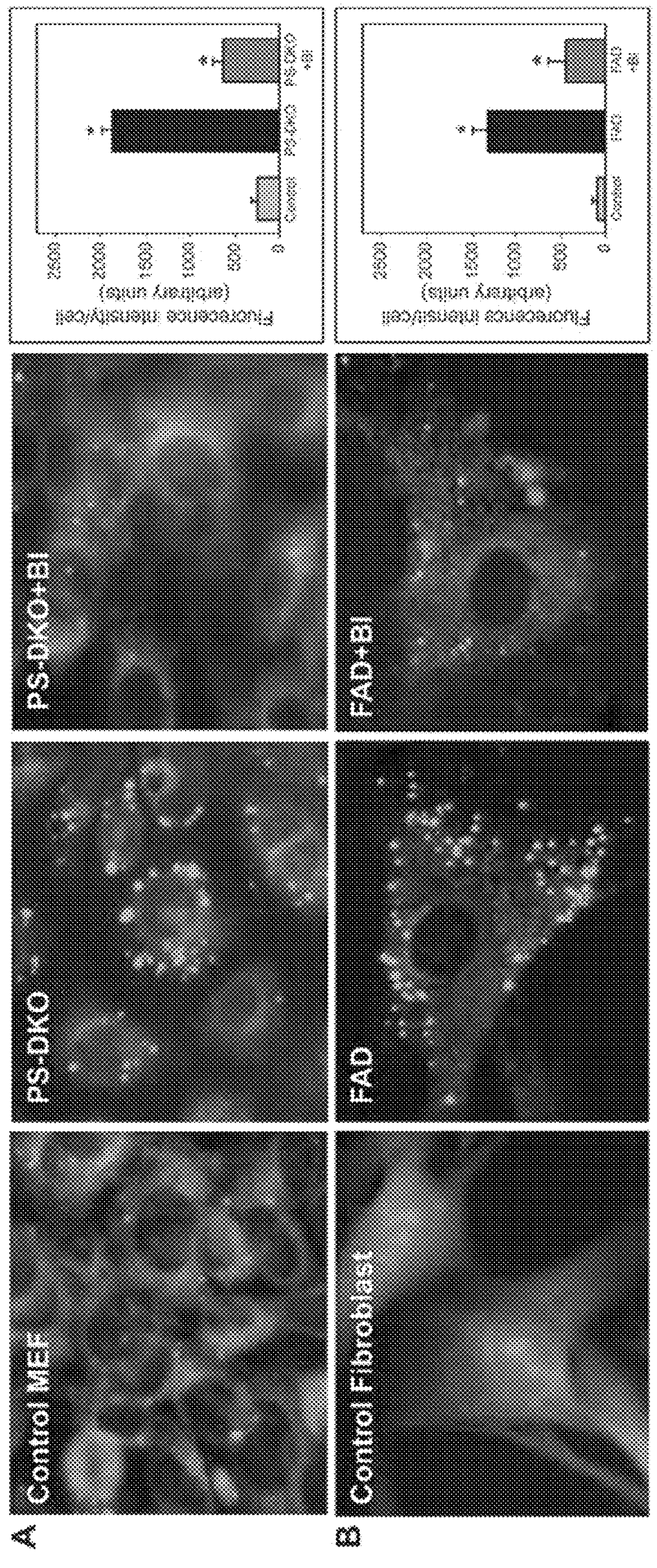
FIGS. 2A-B

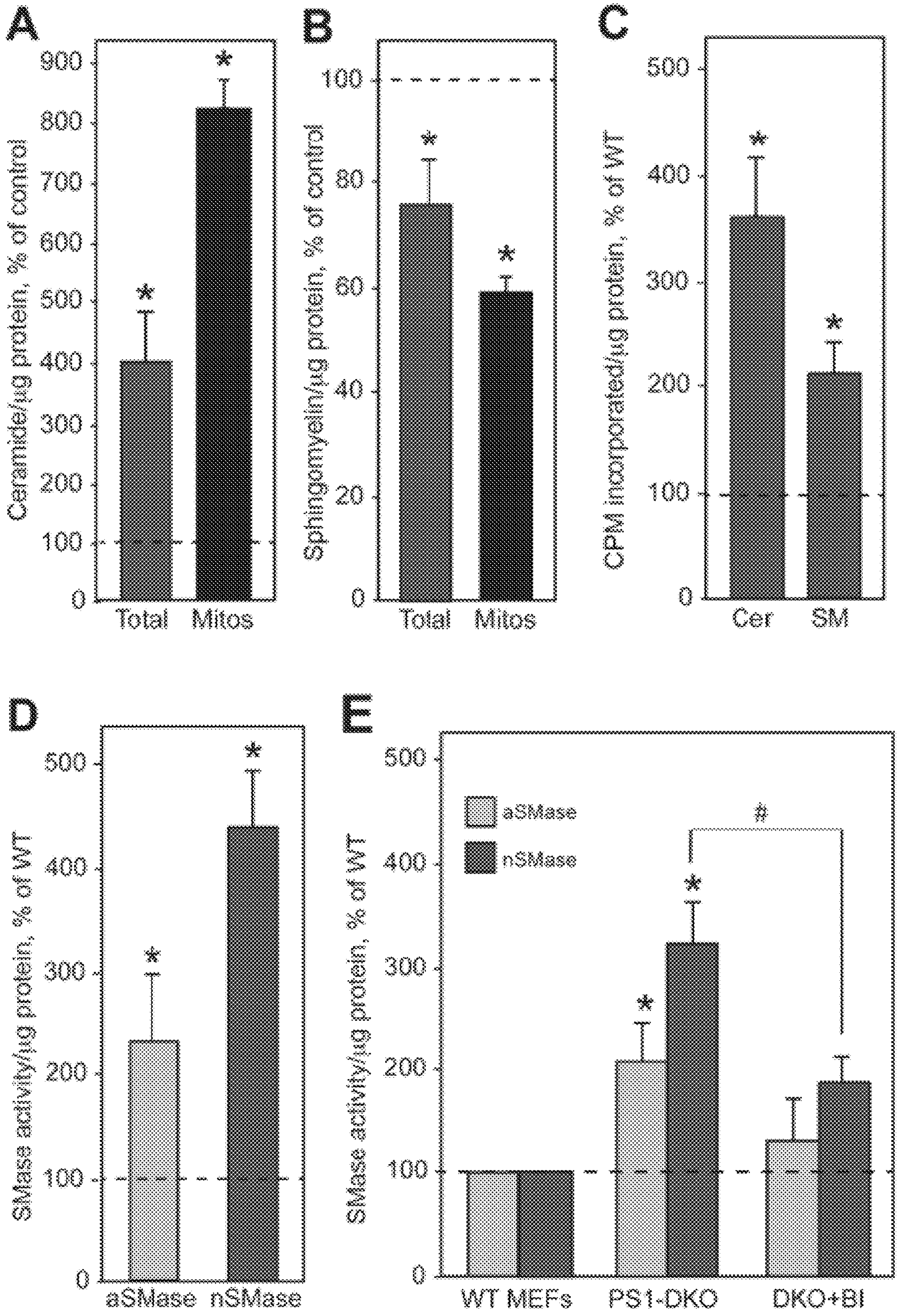
FIGS. 3A-E

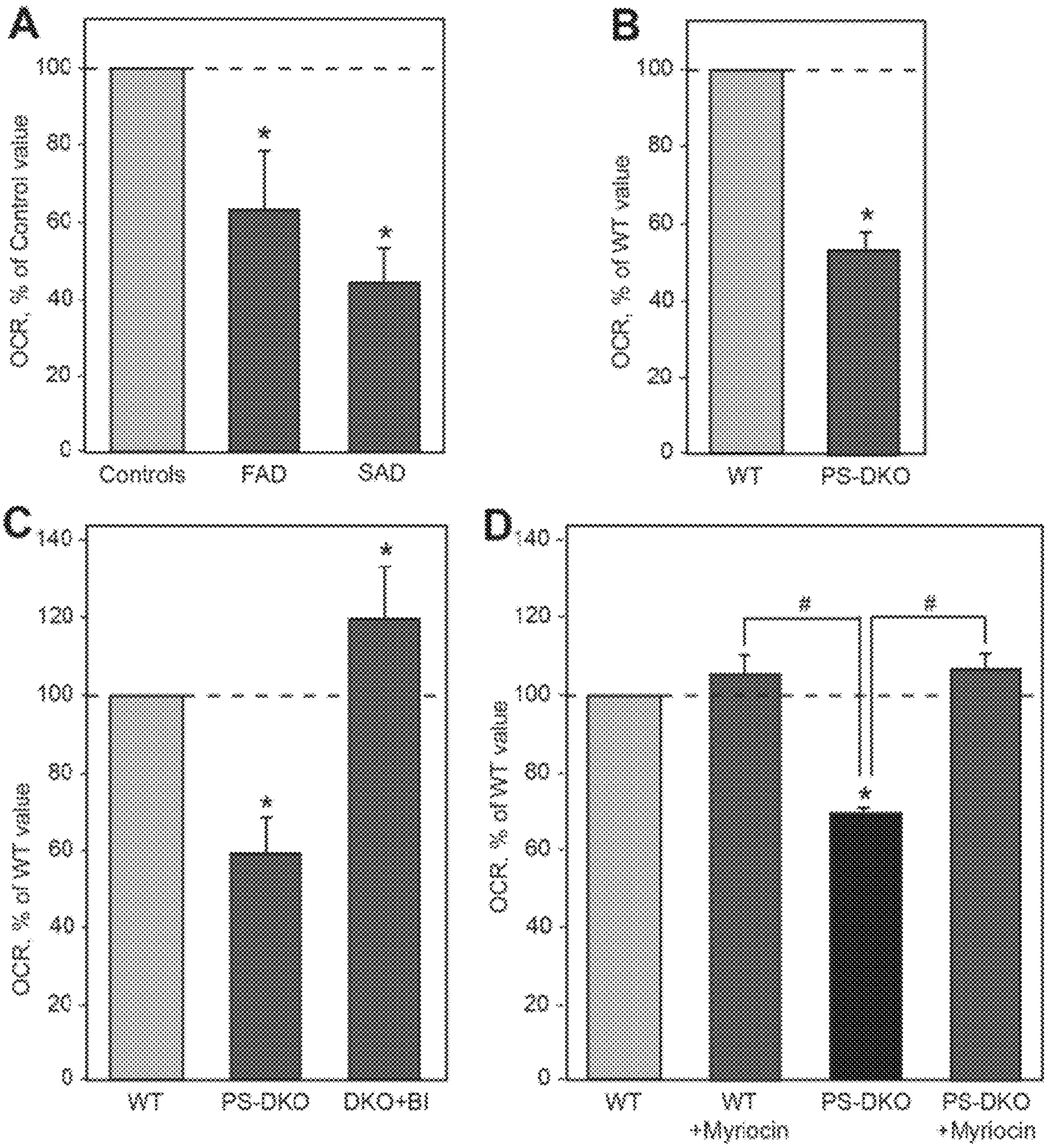
FIGS. 4A-D

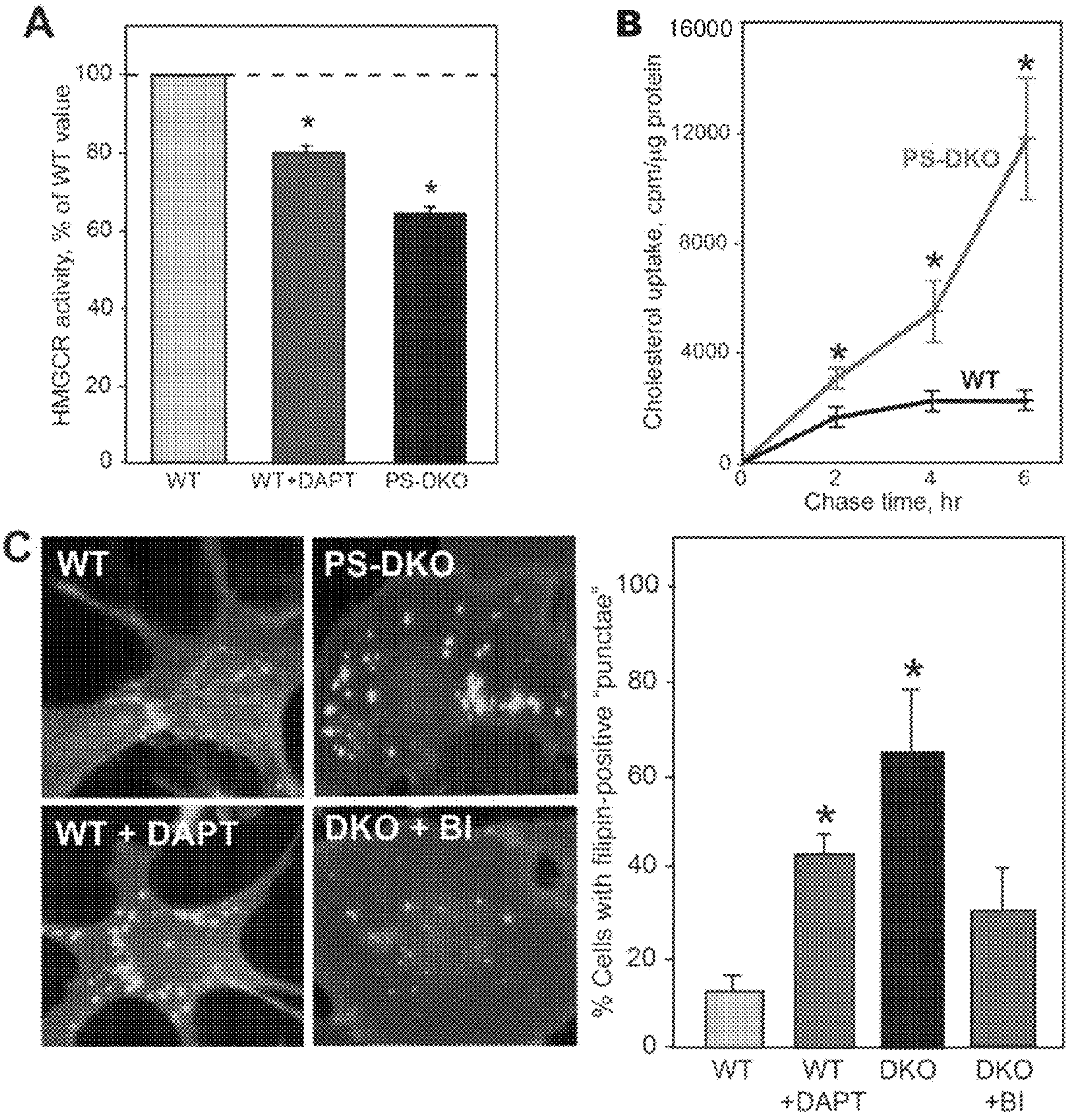
FIGS. 5A-C

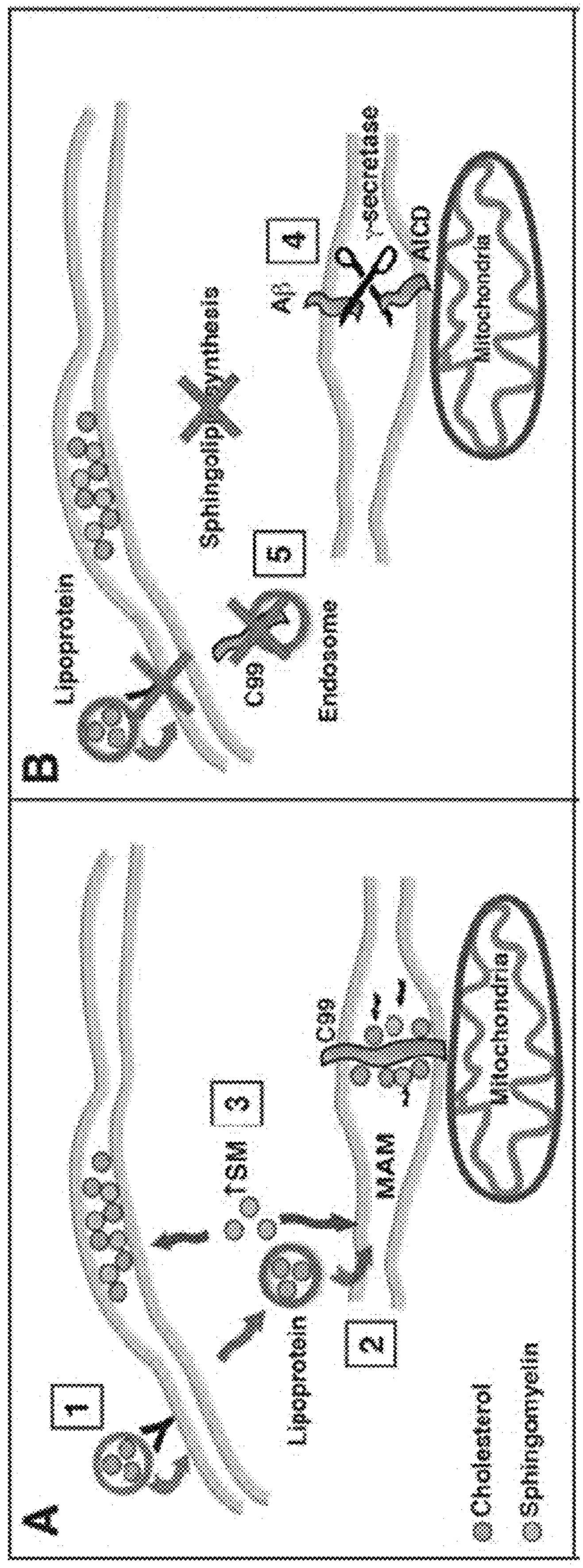
FIGS. 6A-B

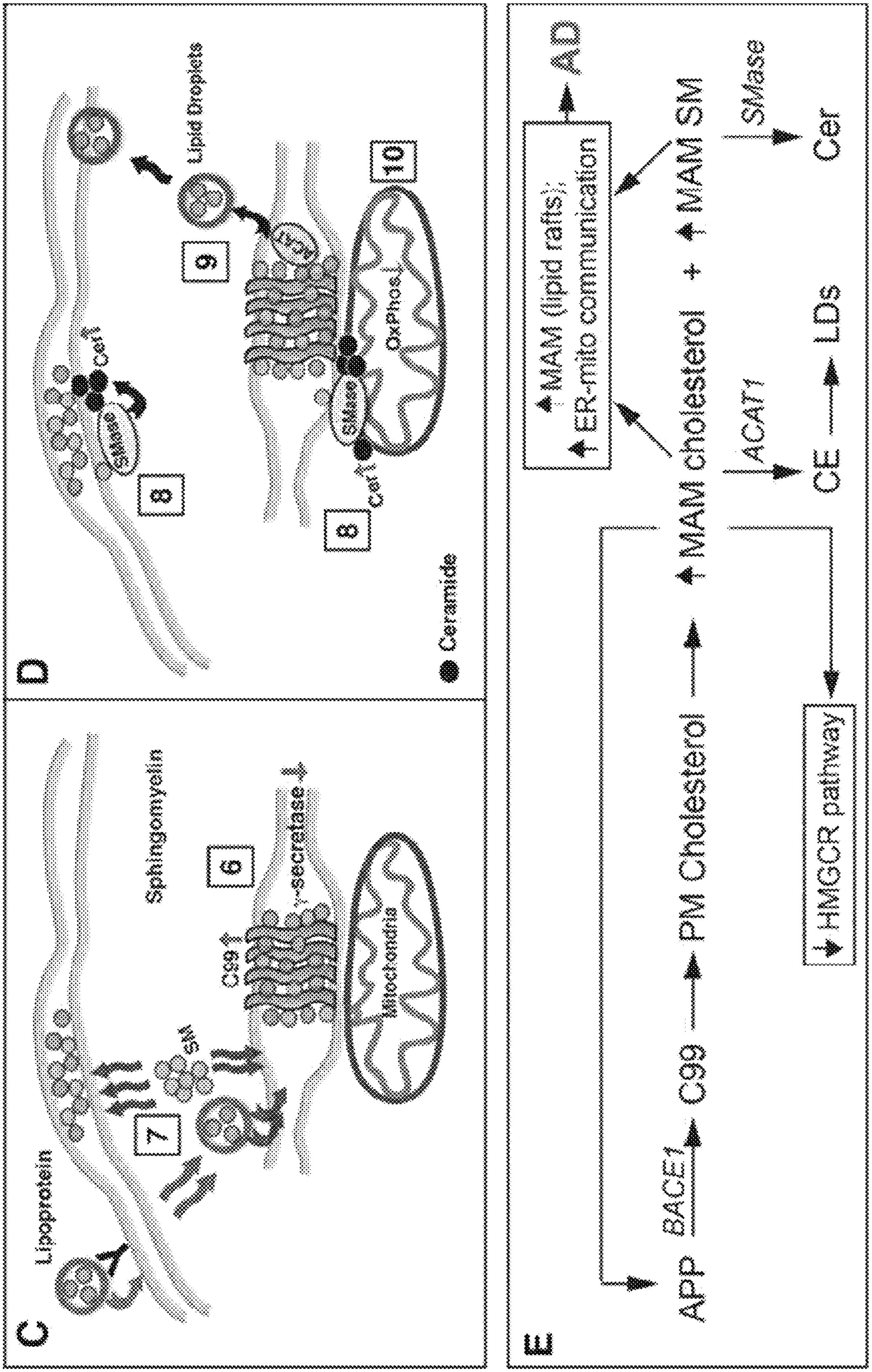
FIGS. 6C-E

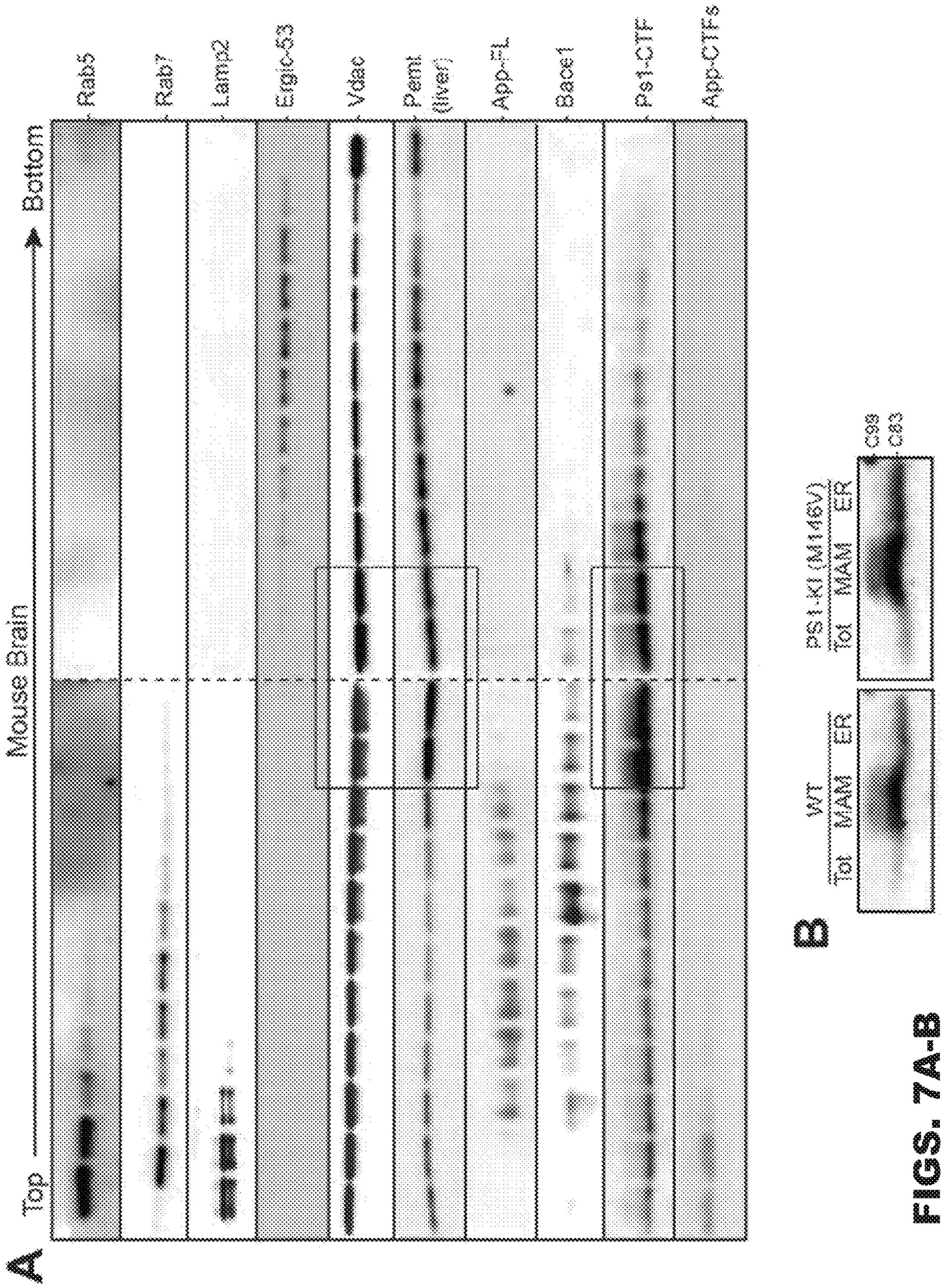
FIGS. 7A-B

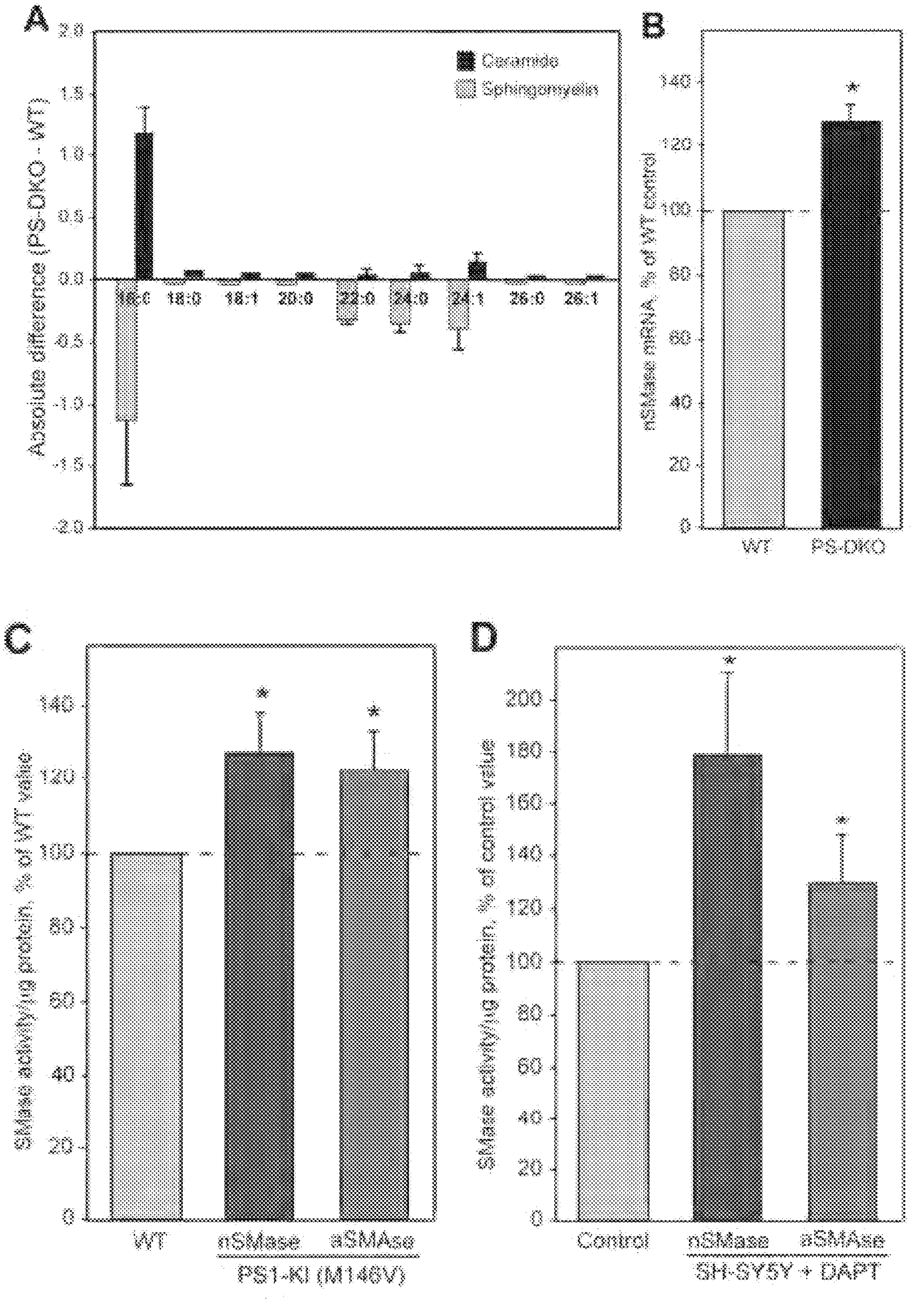
FIGS. 9A-D

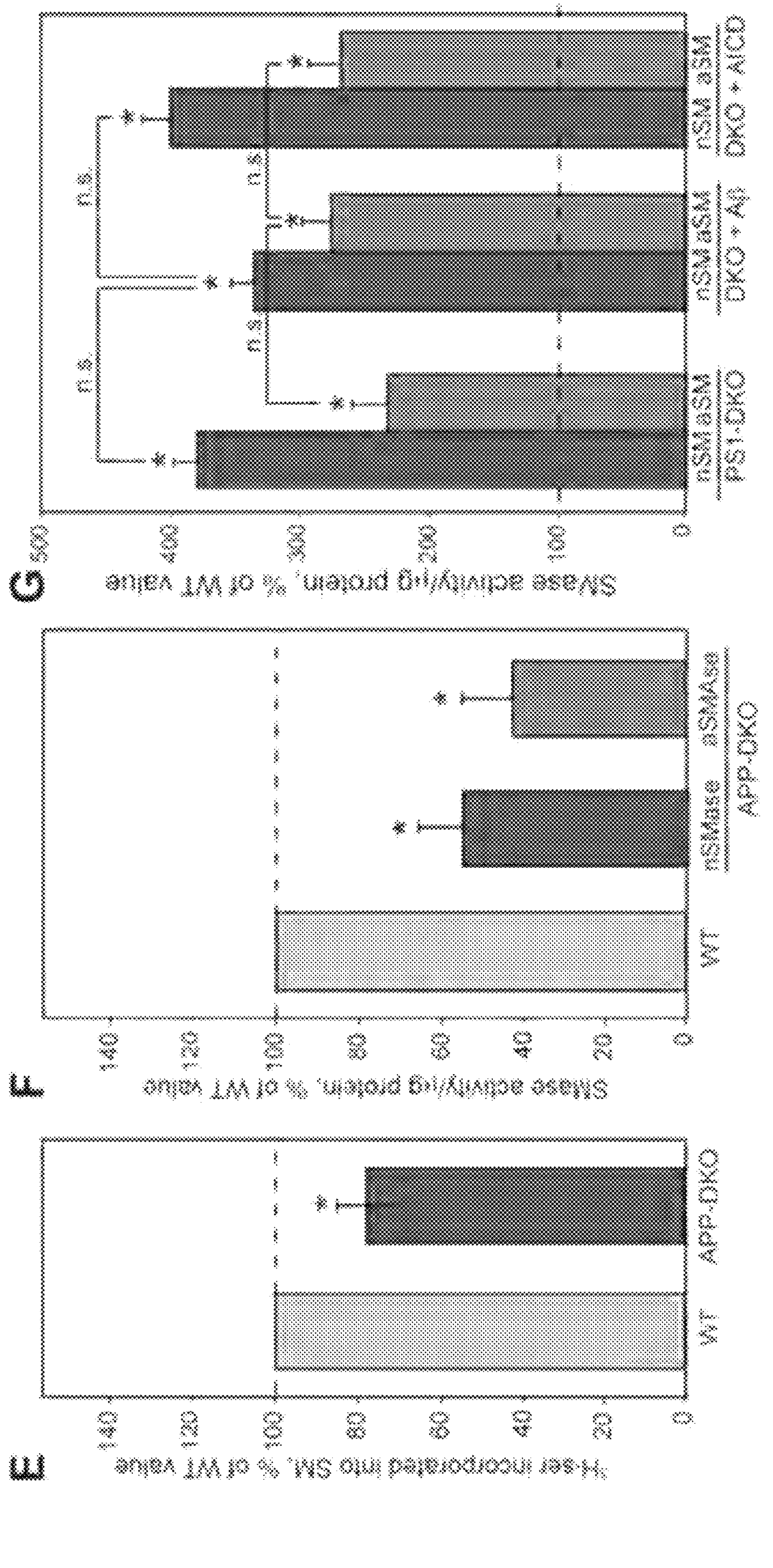
FIGS. 9E-G

H

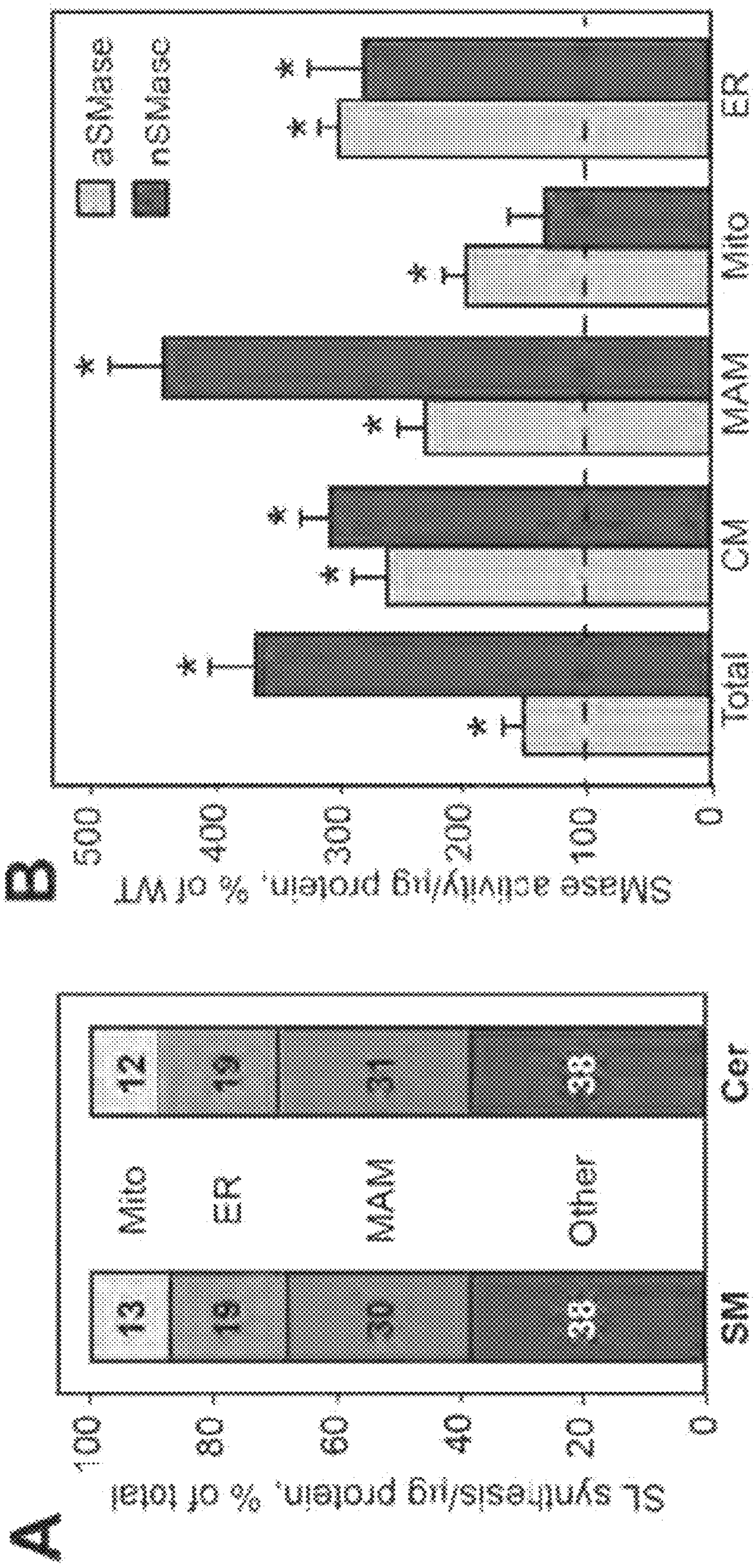
FIGS. 10A-B

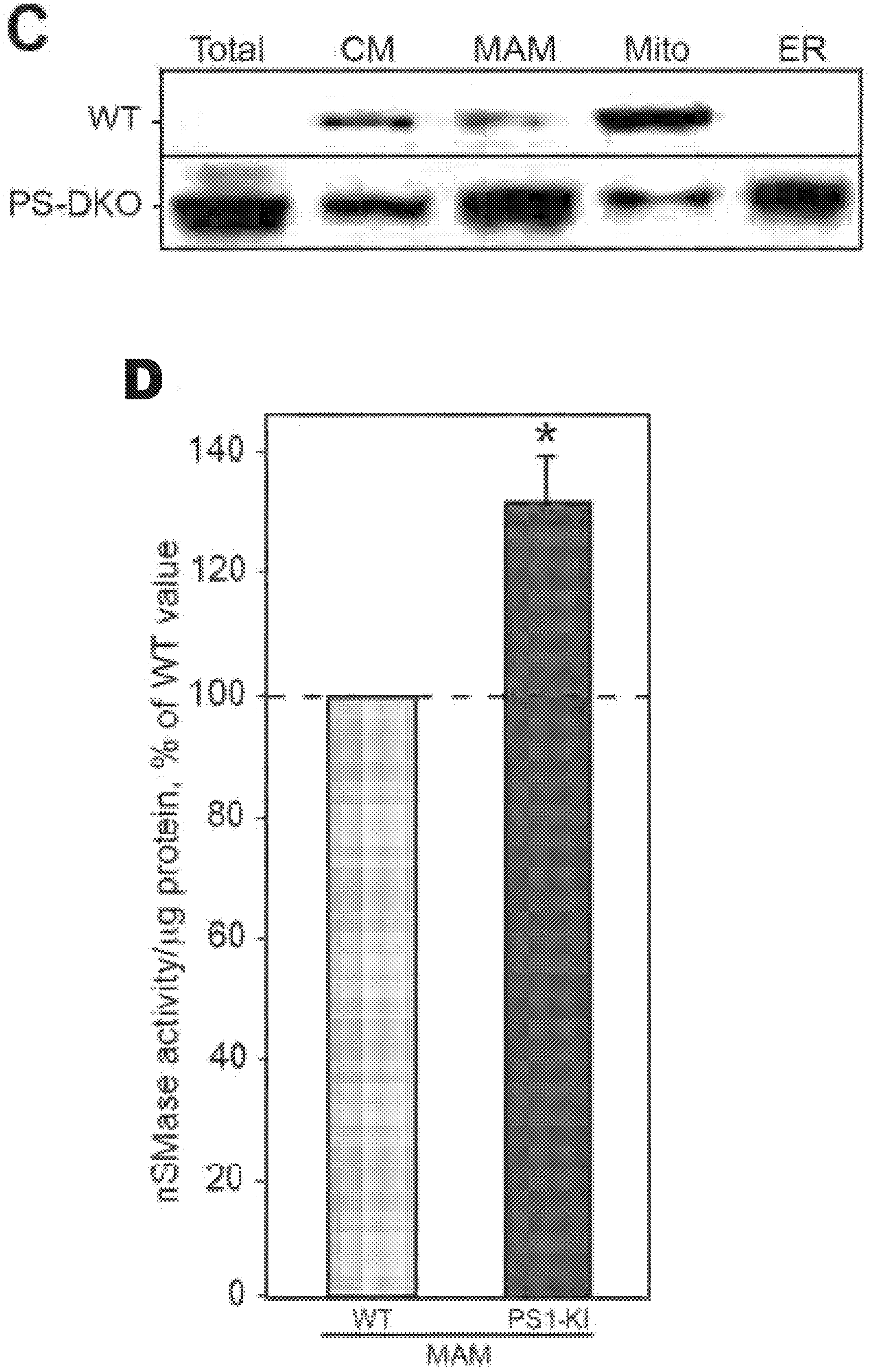
FIGS. 10C-D

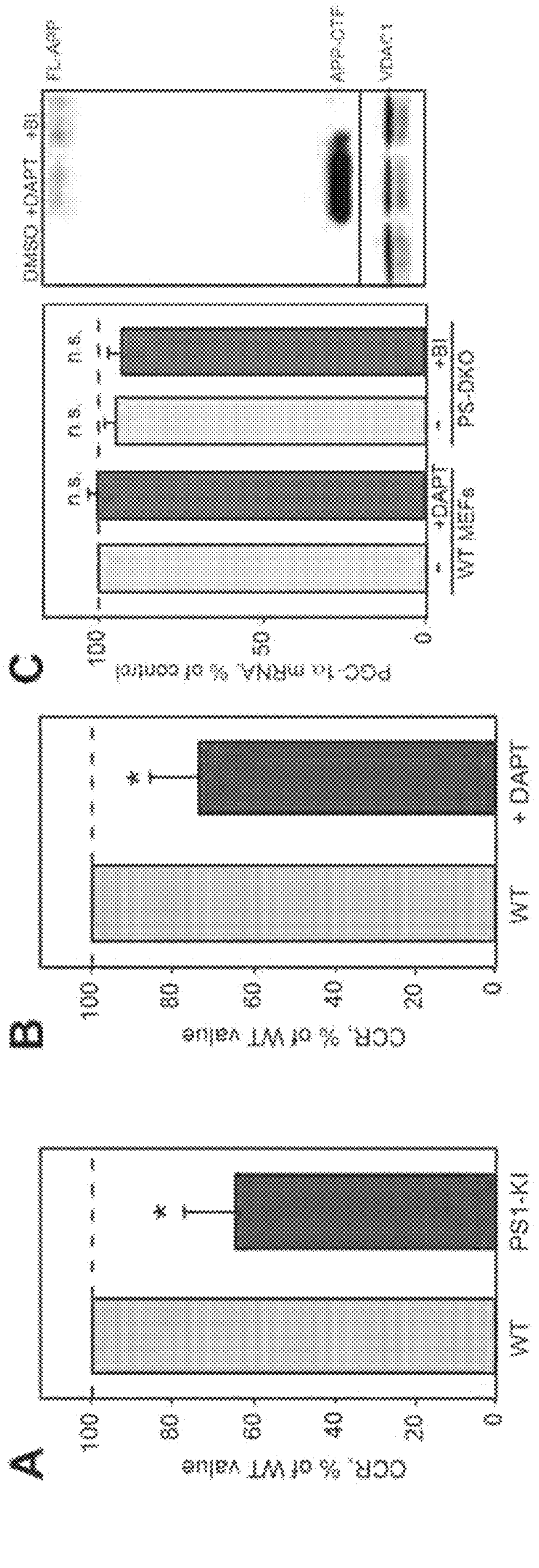
FIGS. 11A-C

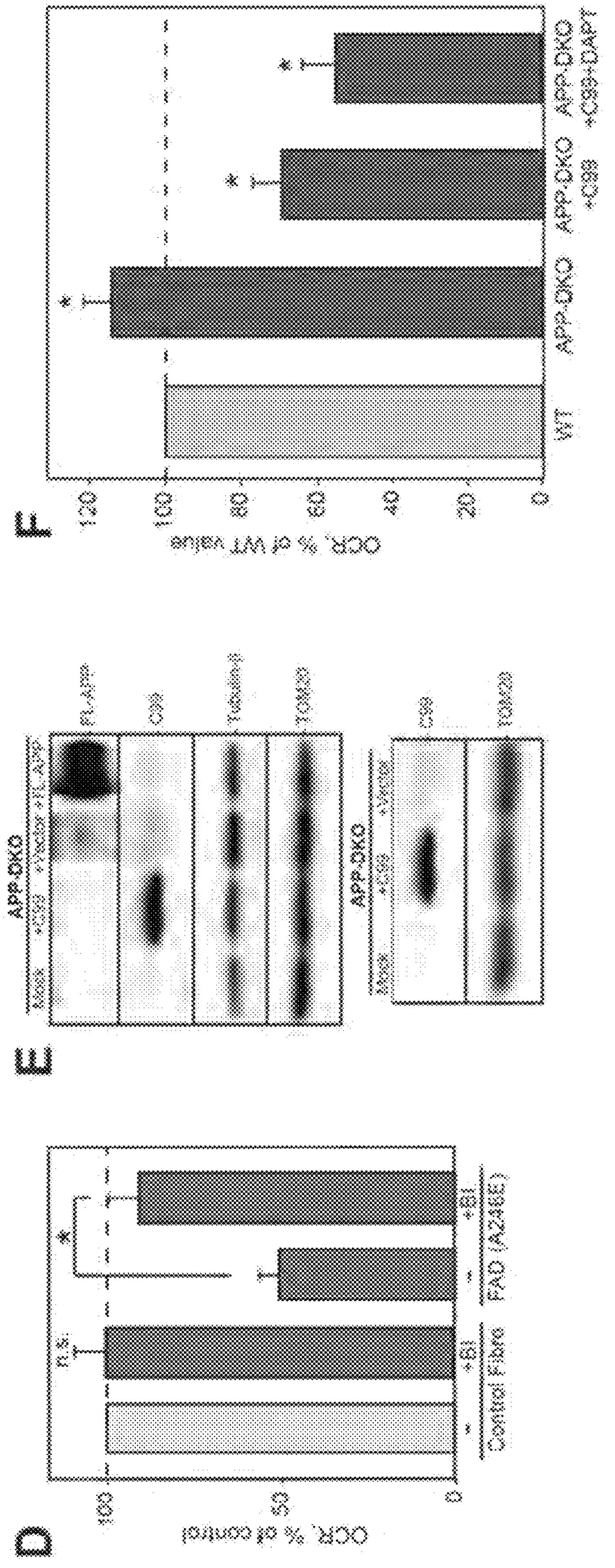
FIGS. 11D-F

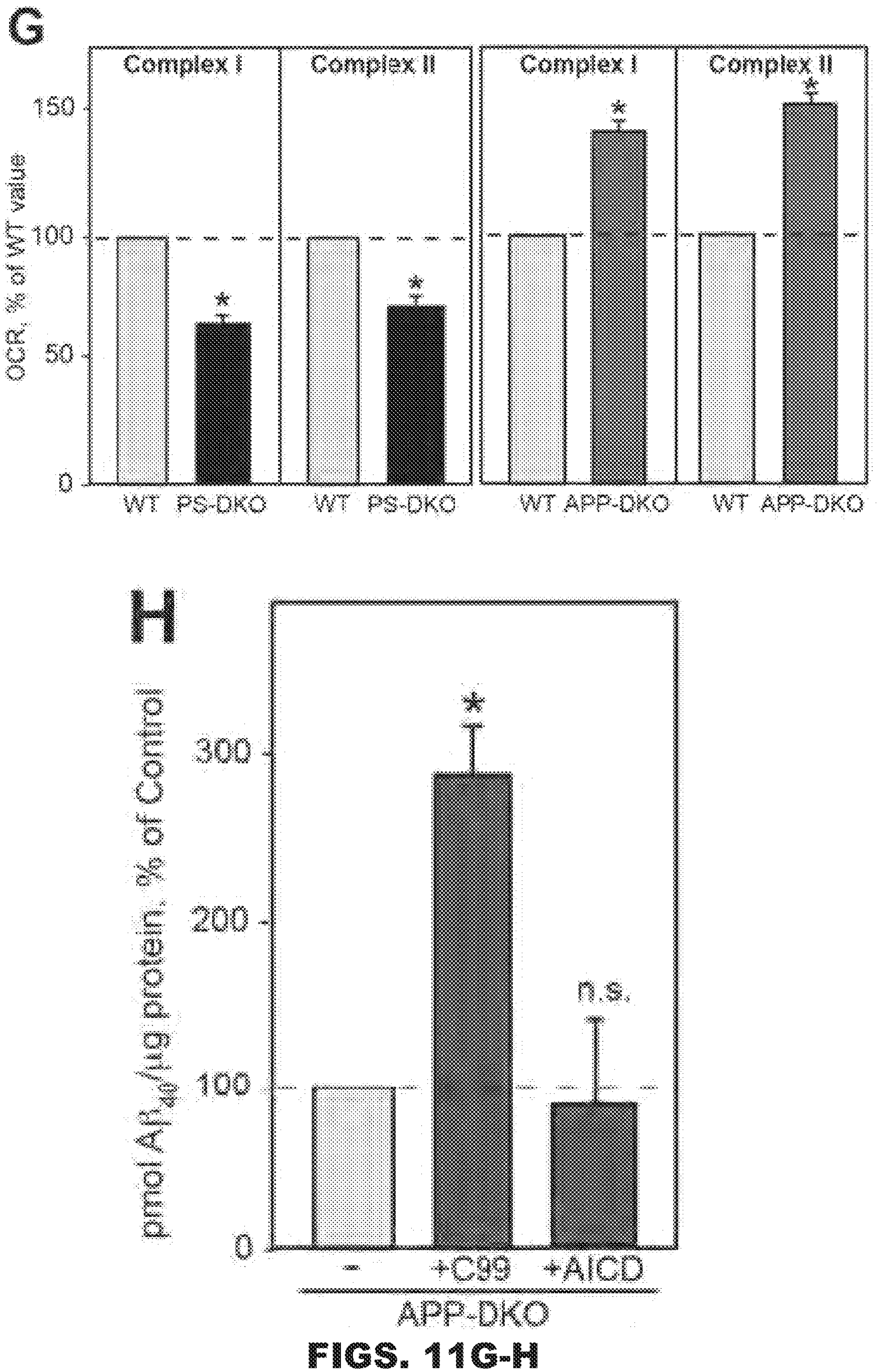
FIGS. 11G-H

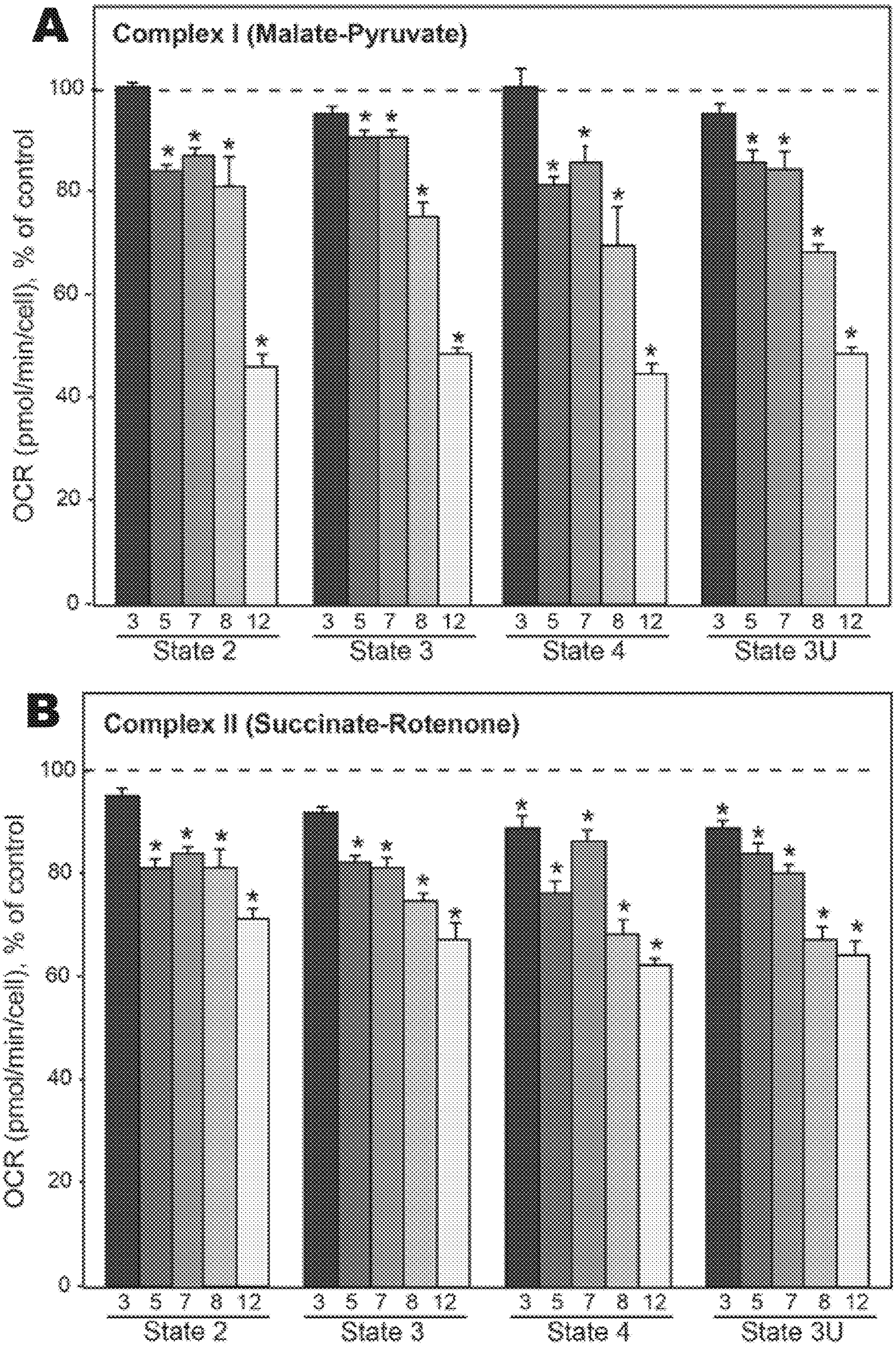
FIGS. 12A-B

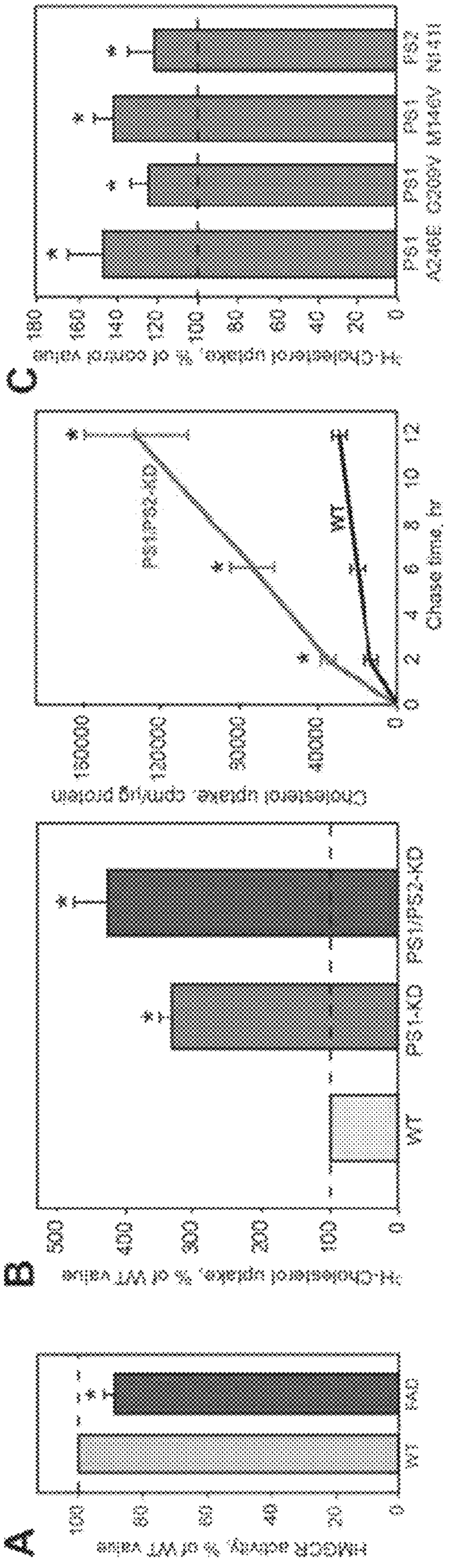
FIGS. 13A-C

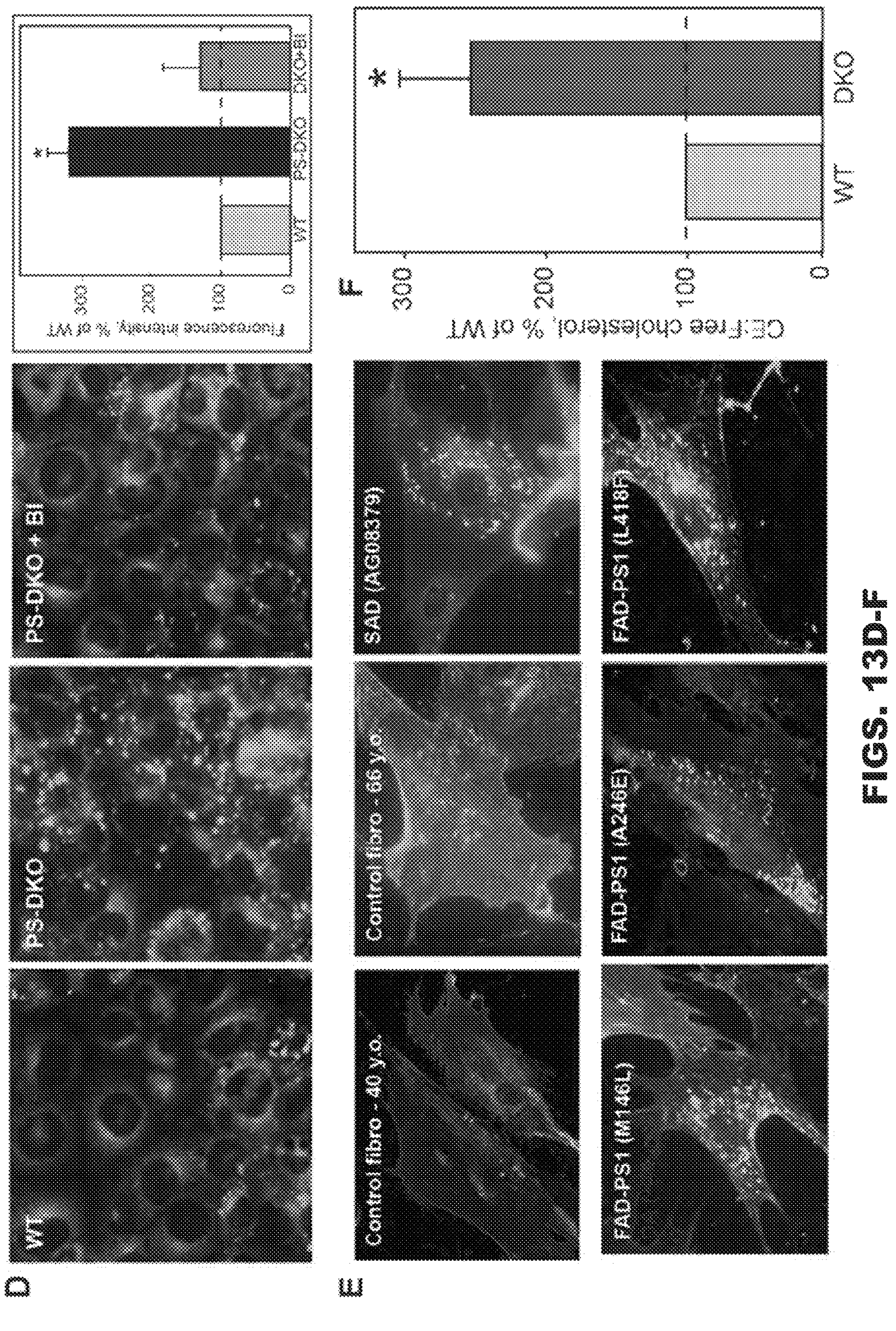
FIGS. 13D-F

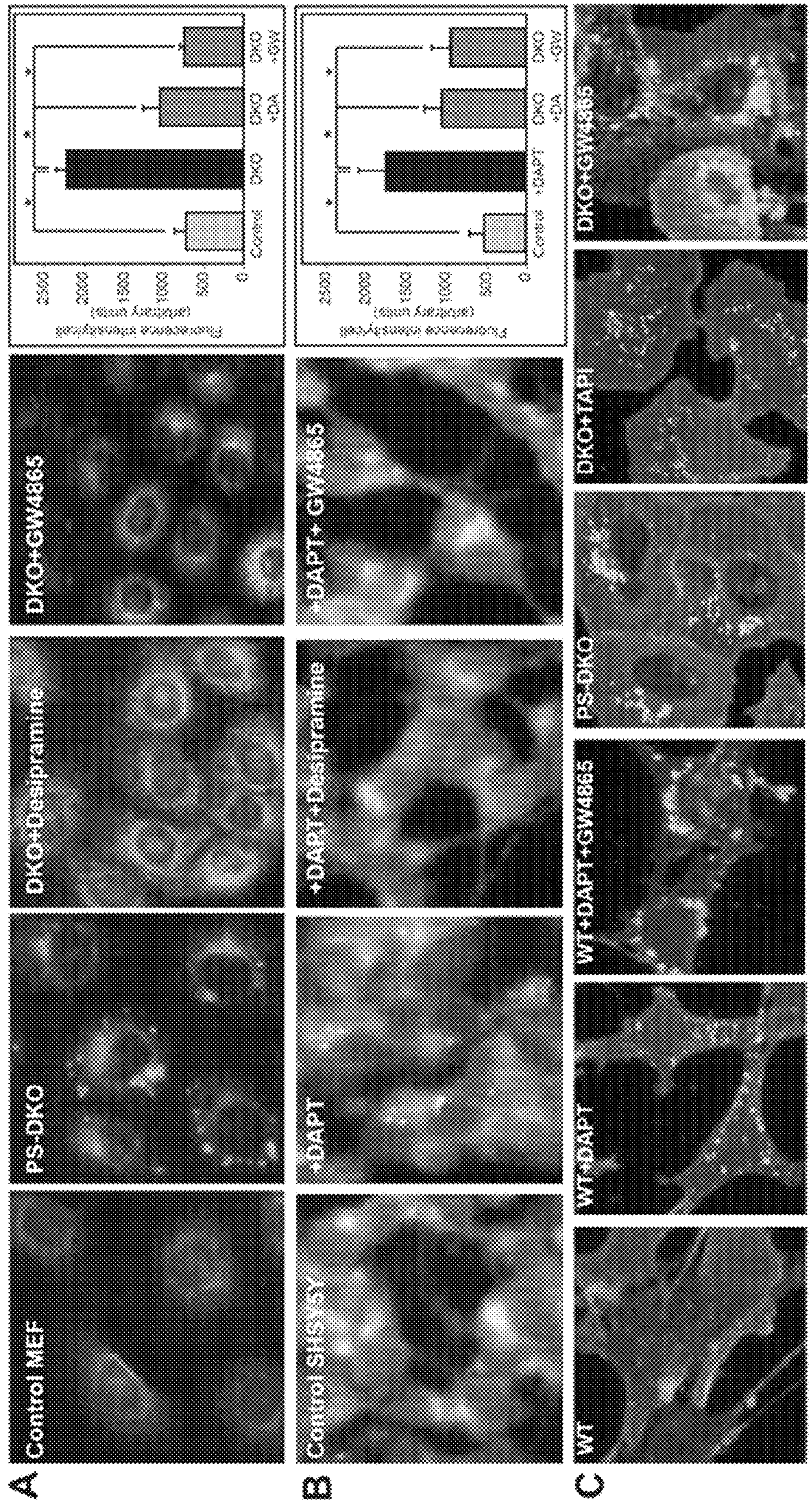
FIGS. 14A-C

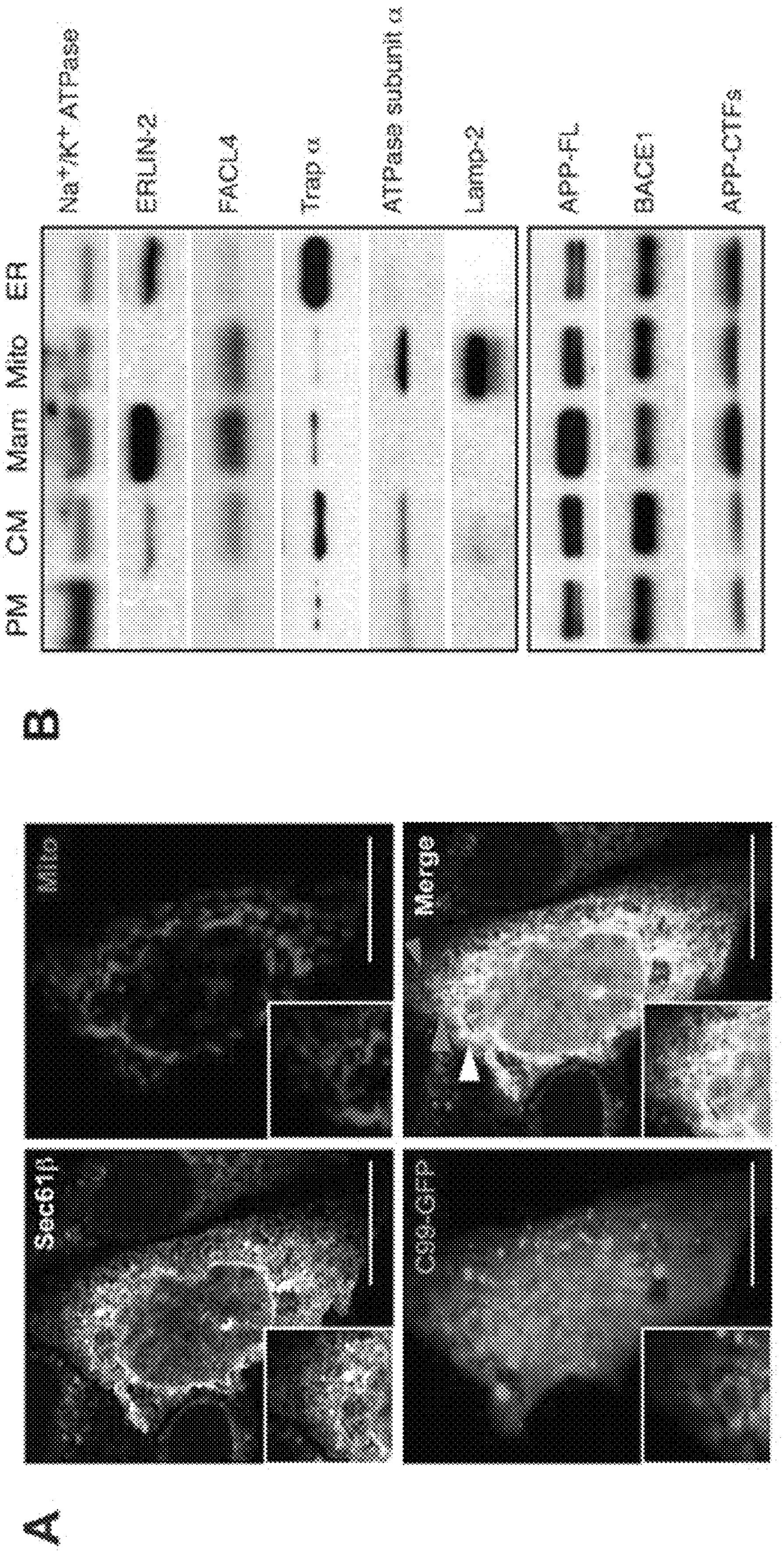
FIGS. 15A-B

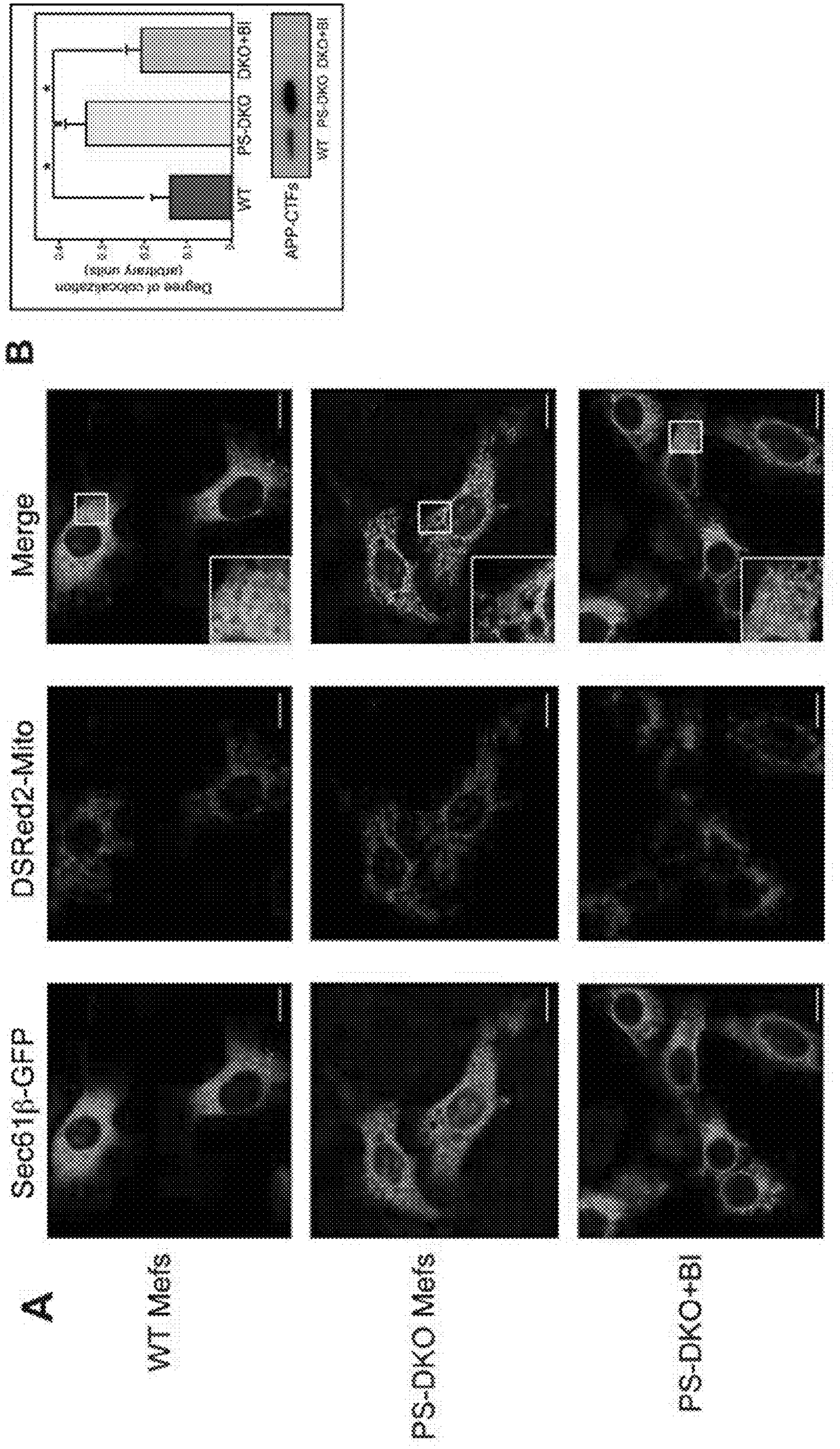
FIGS. 16A-B

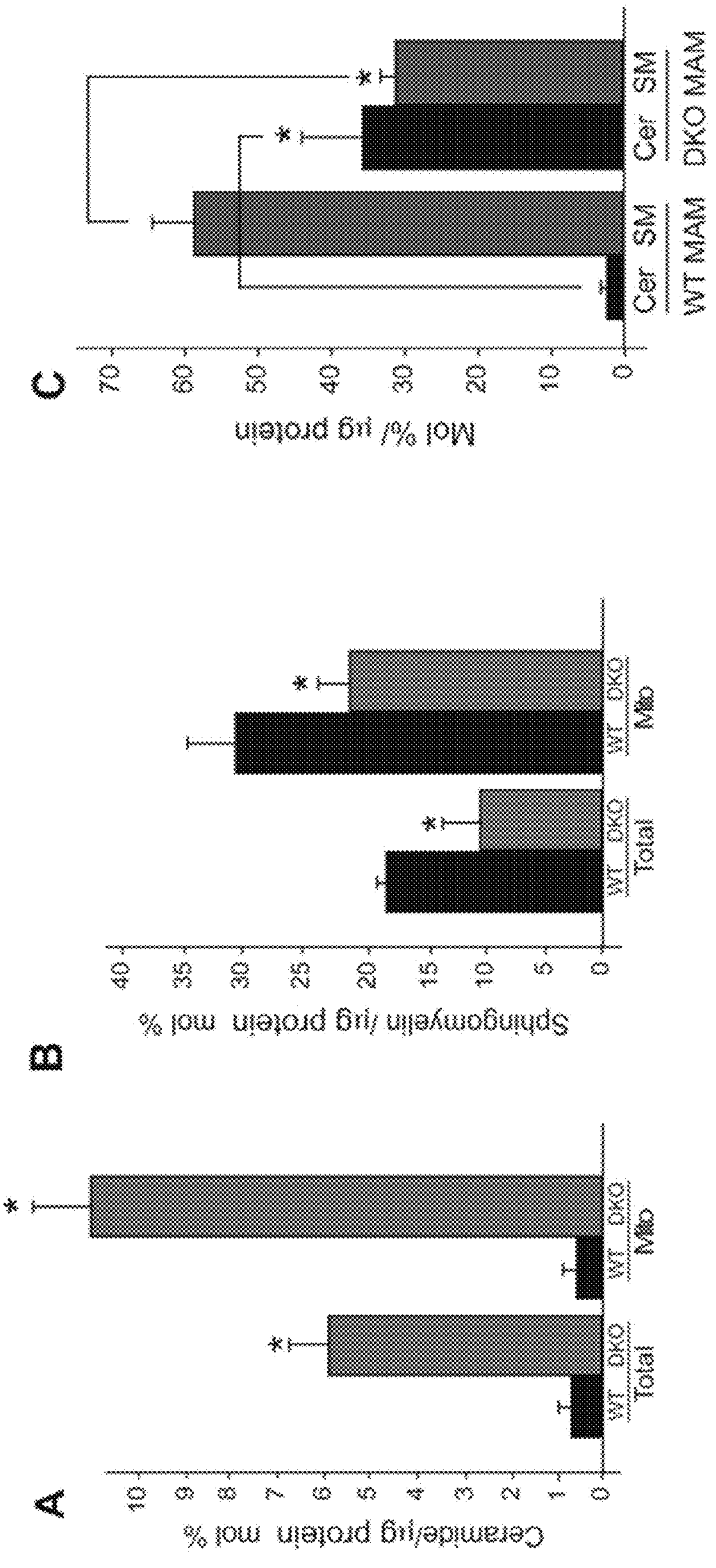
FIGS. 17A-C

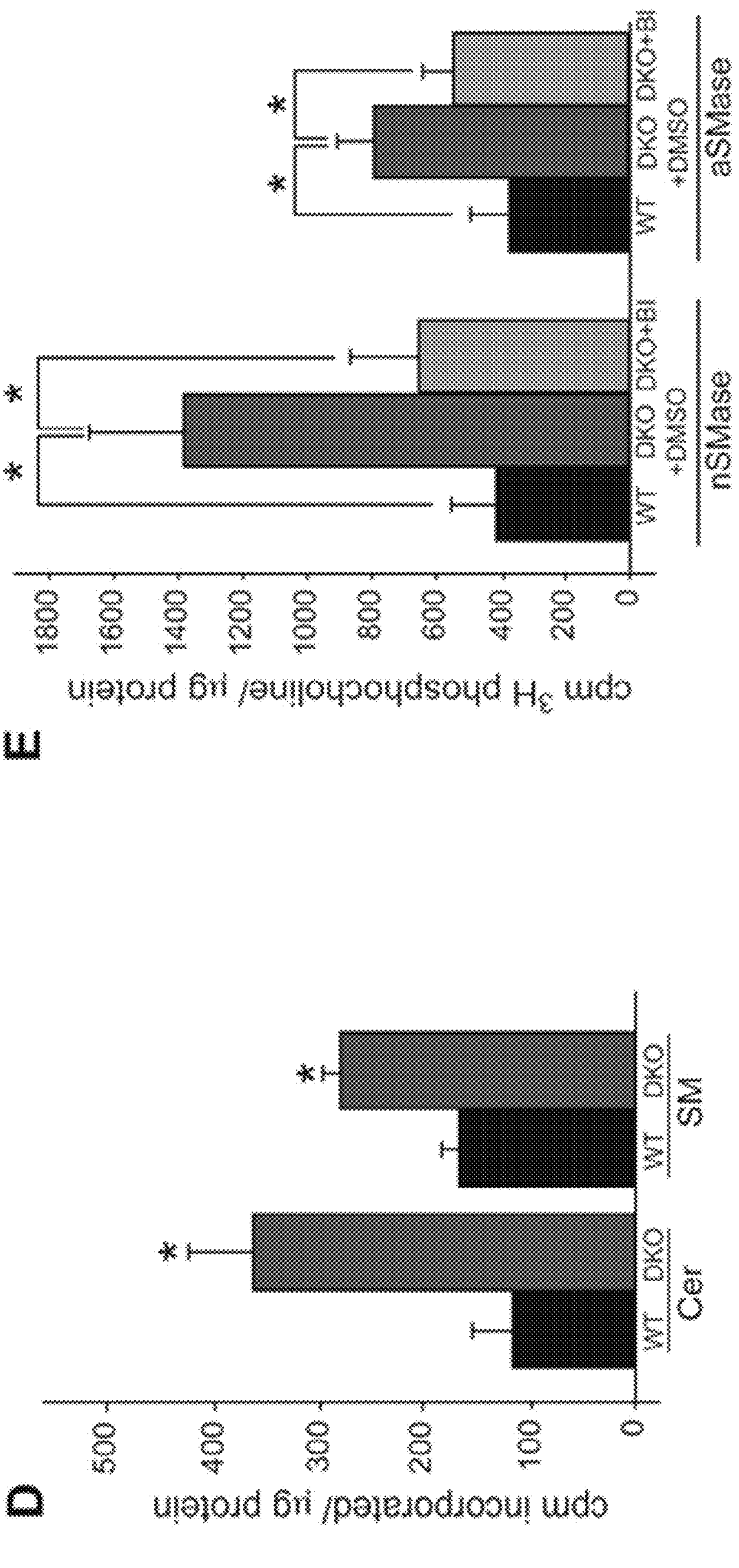
FIGS. 17D-E

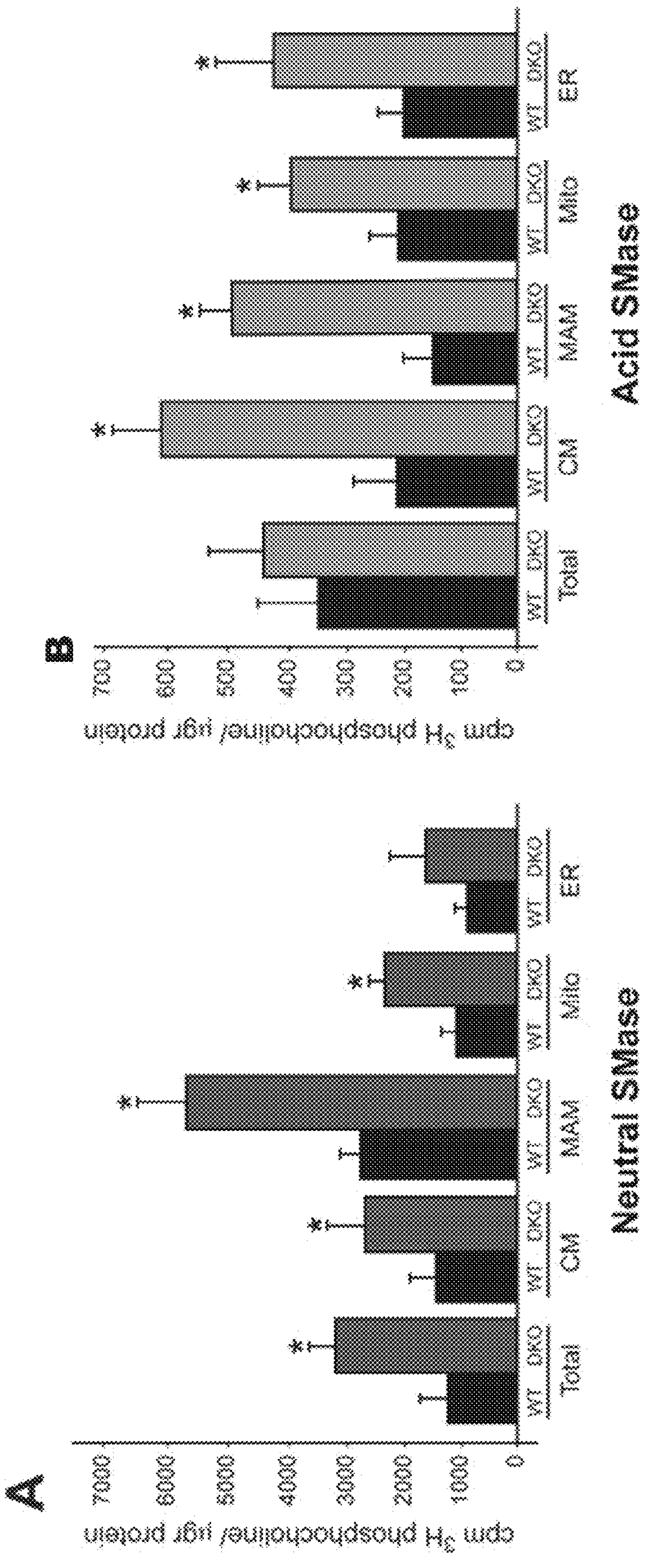
FIGS. 18A-B

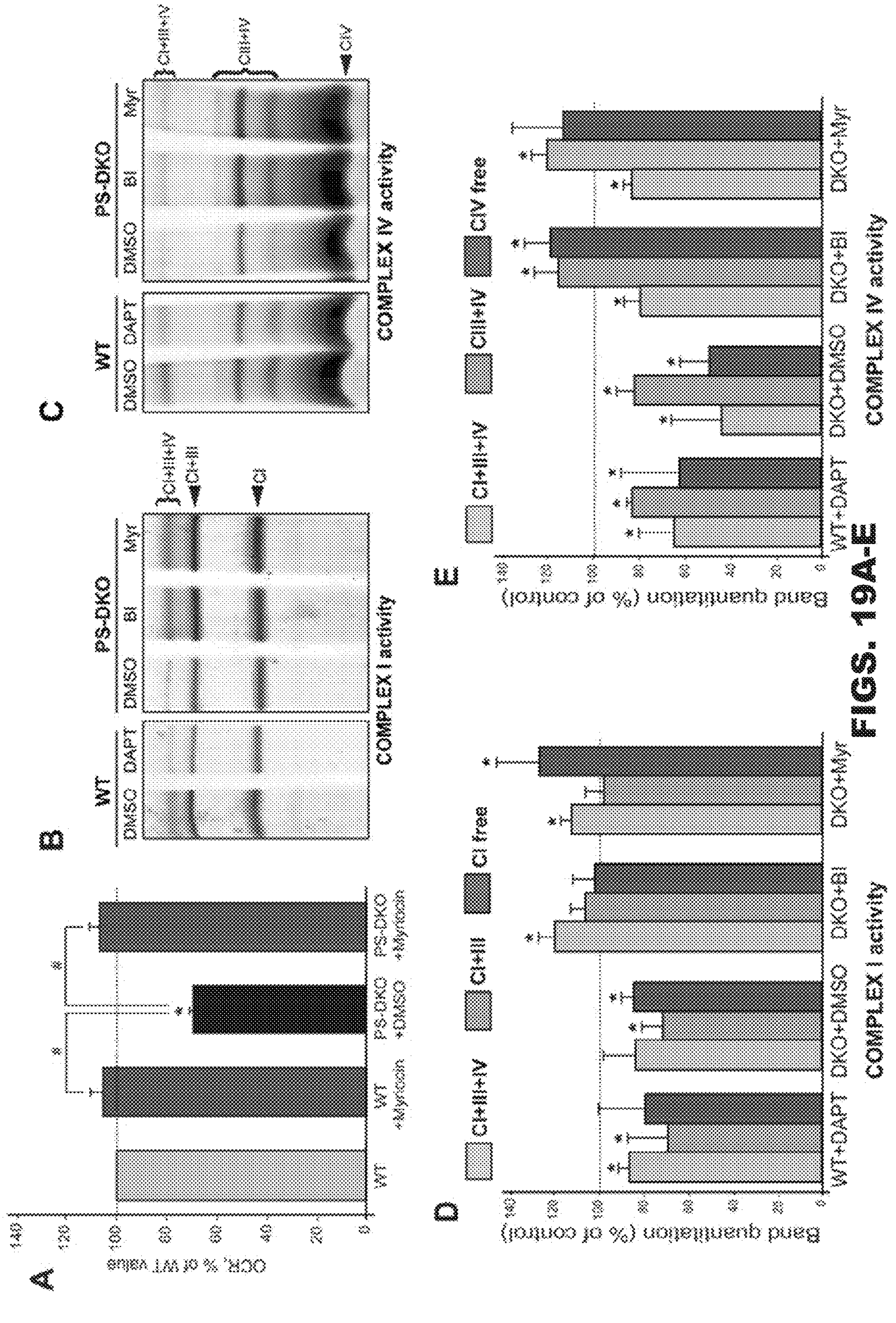
FIGS. 19A-E

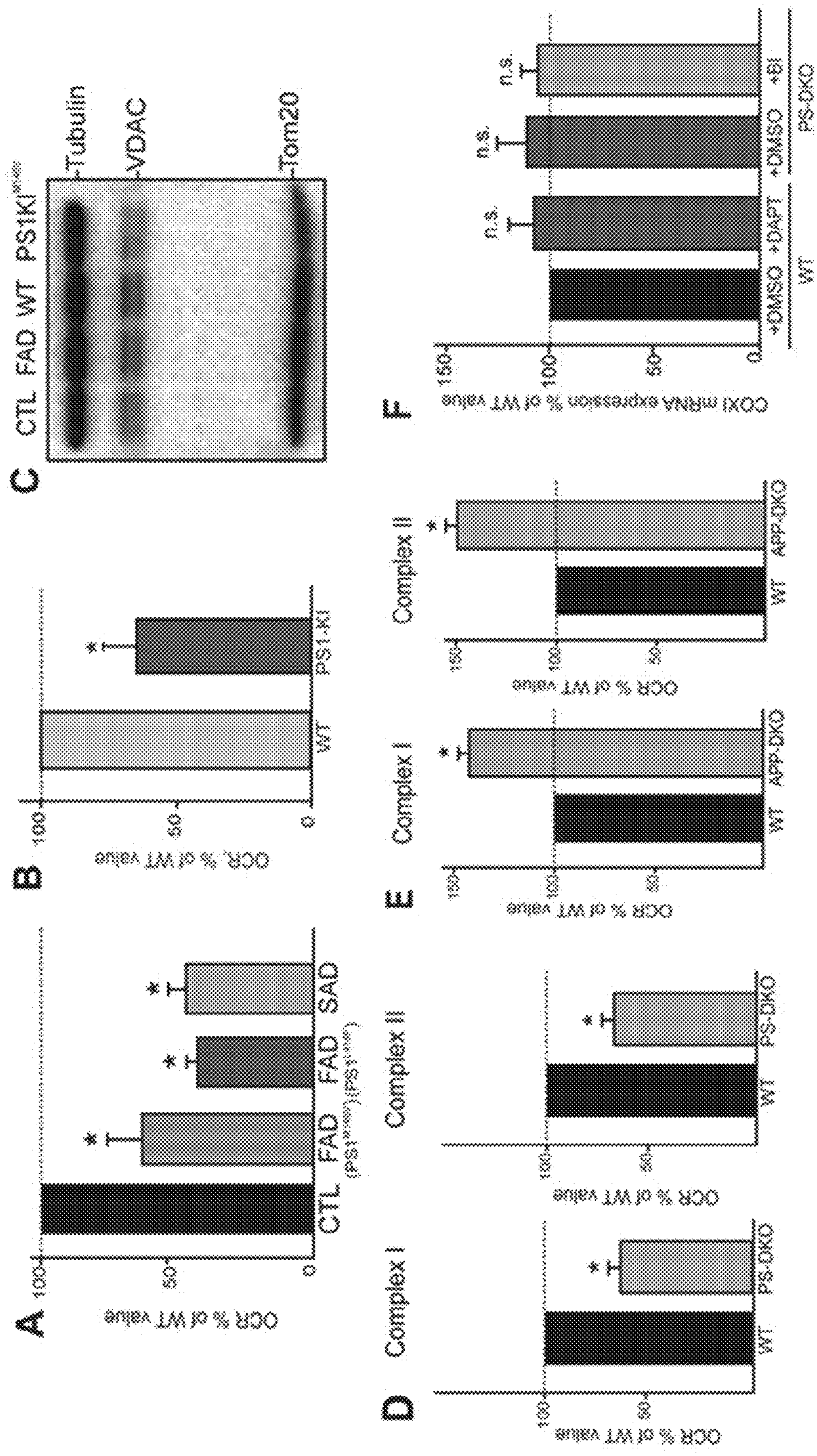
FIGS. 20A-F

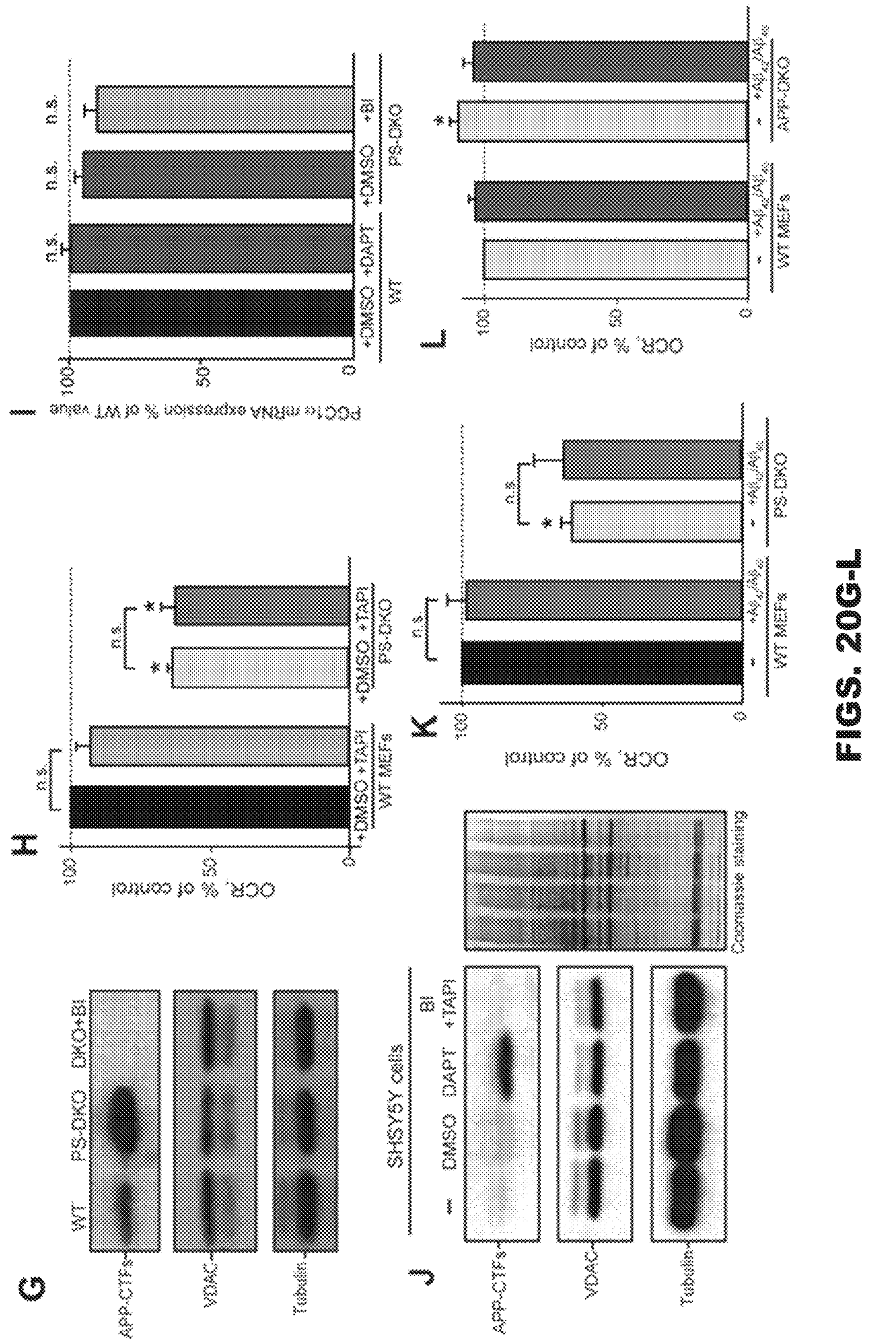
FIGS. 20G-L

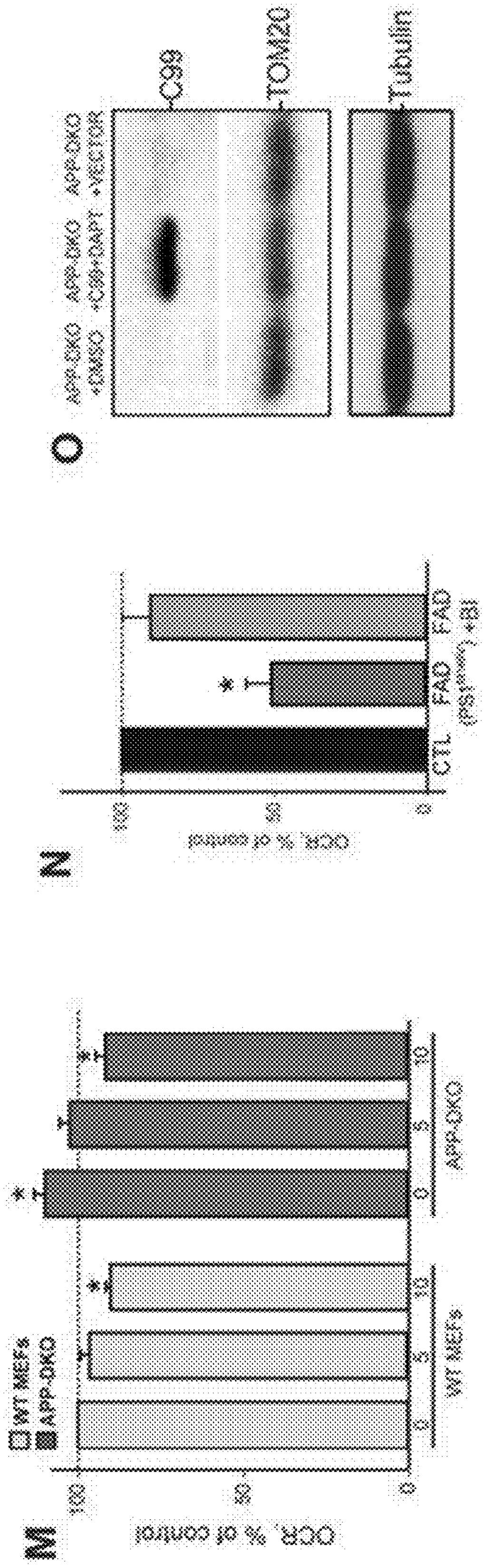
FIGS. 20M-O

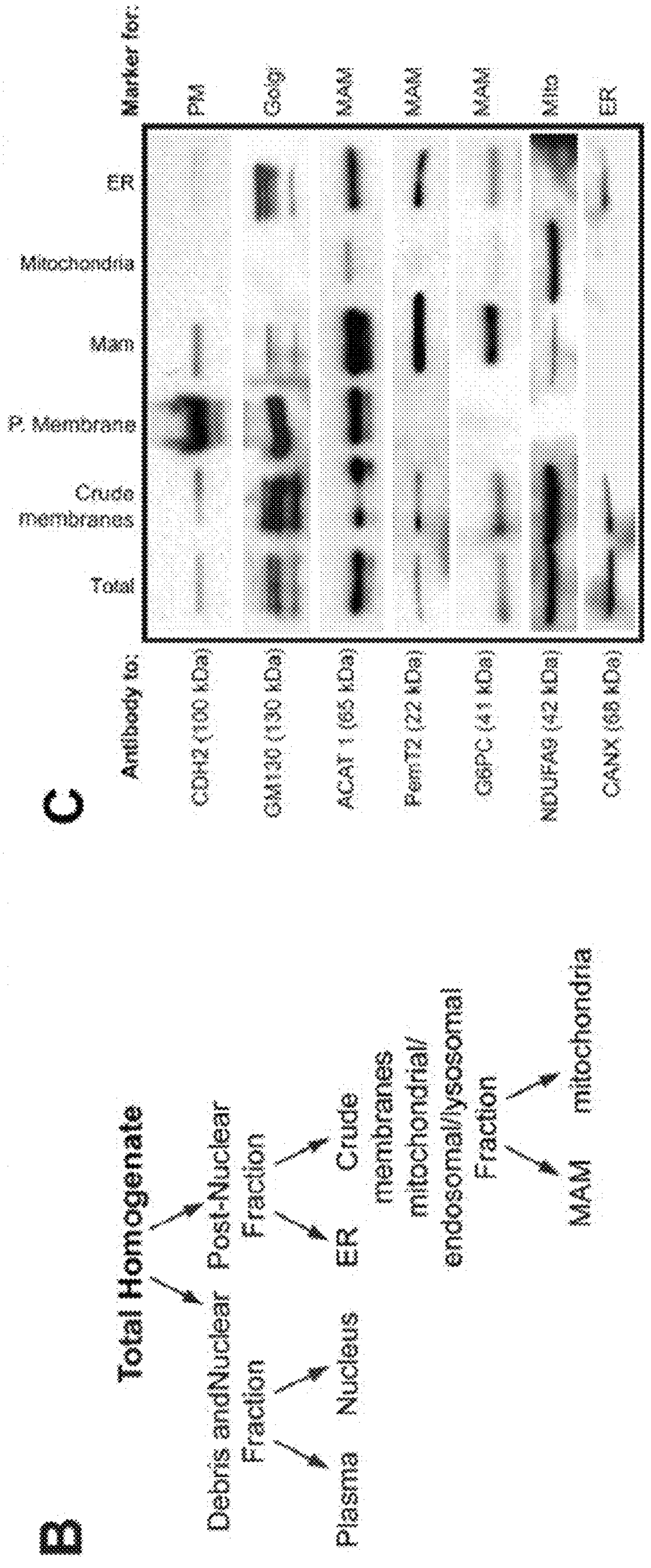
FIGS. 21B-C

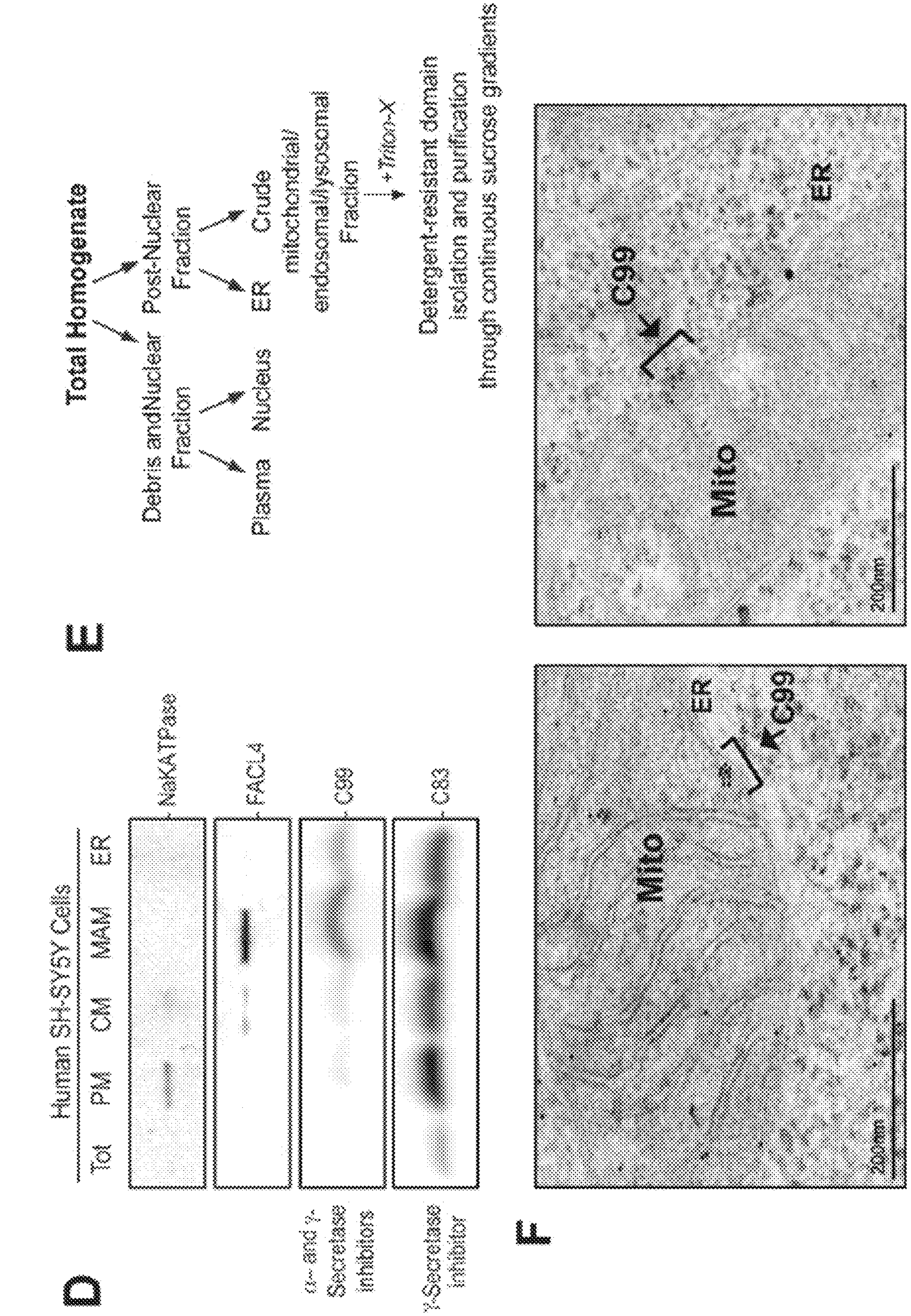
FIGS. 21D-F

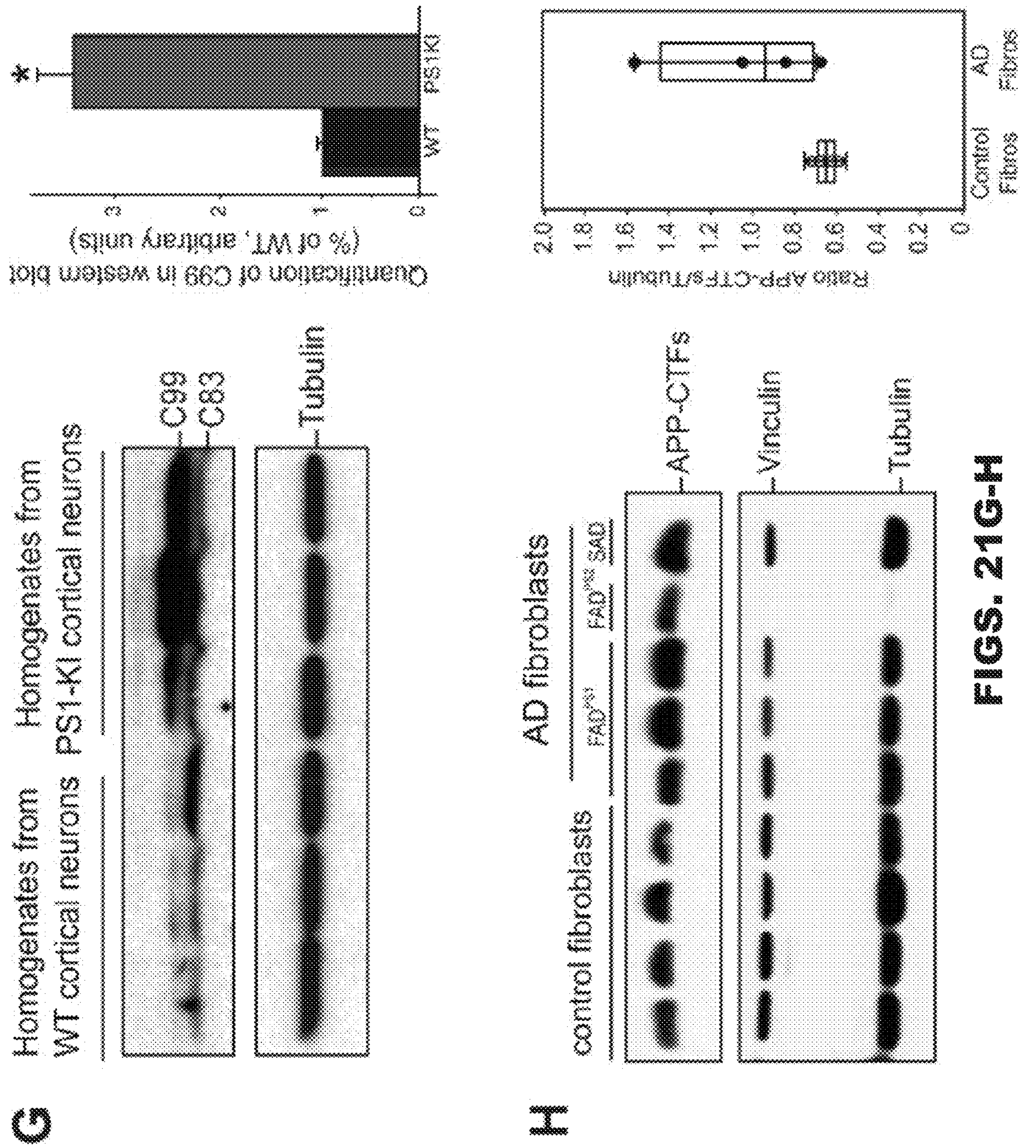
FIGS. 21G-H

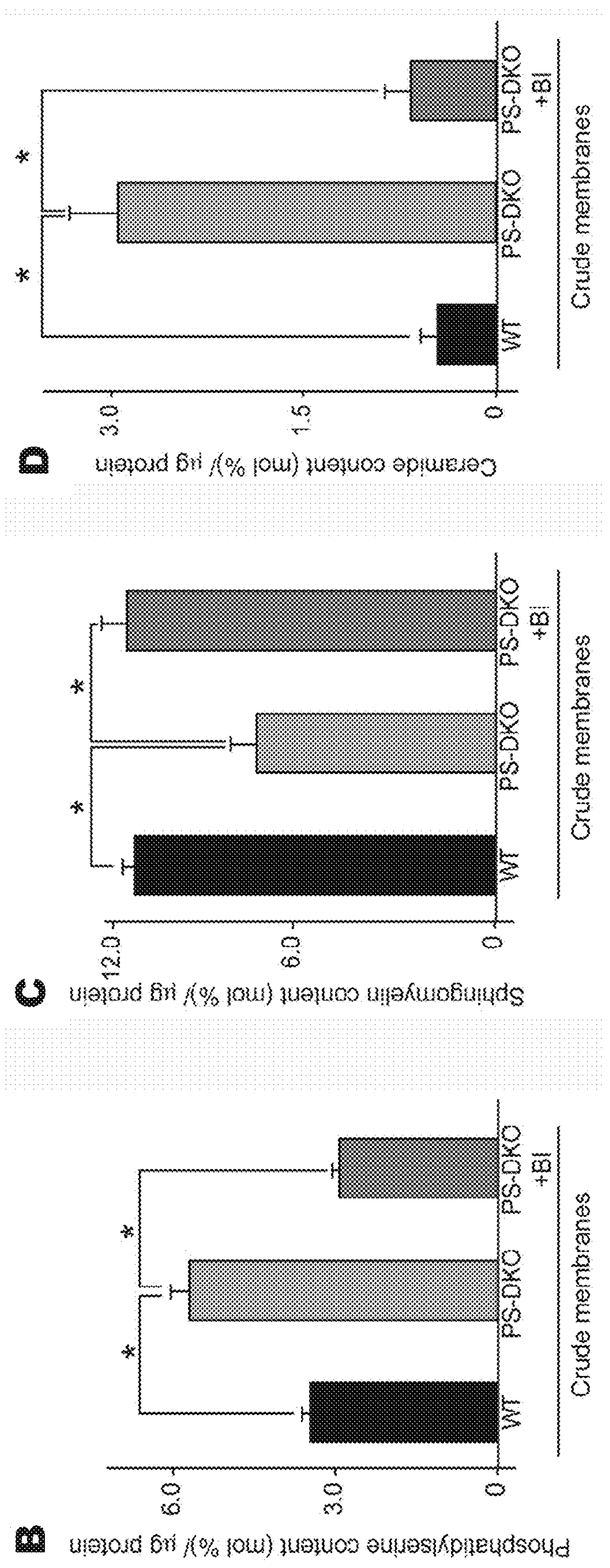
FIGS. 23B-D

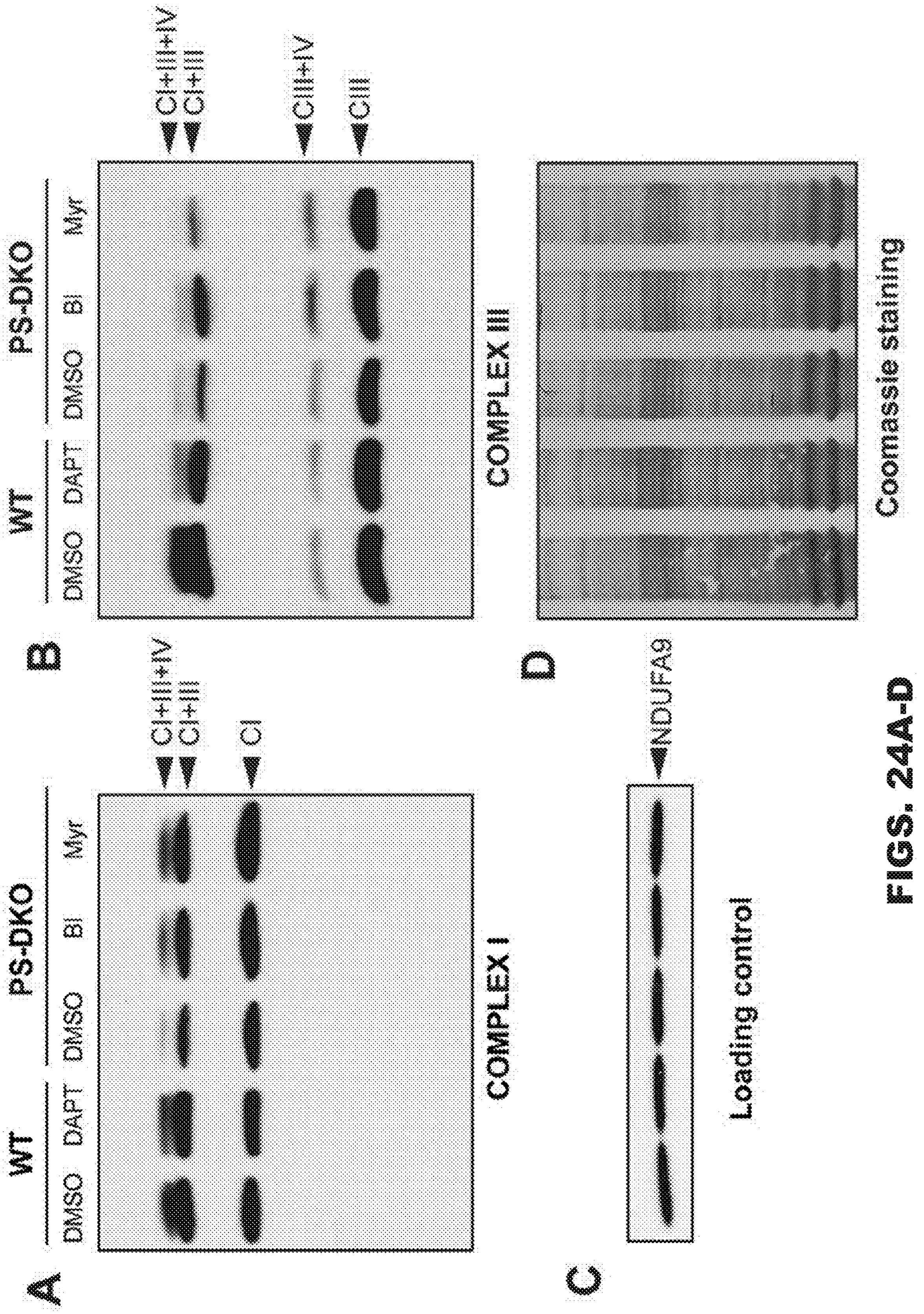
FIGS. 24A-D

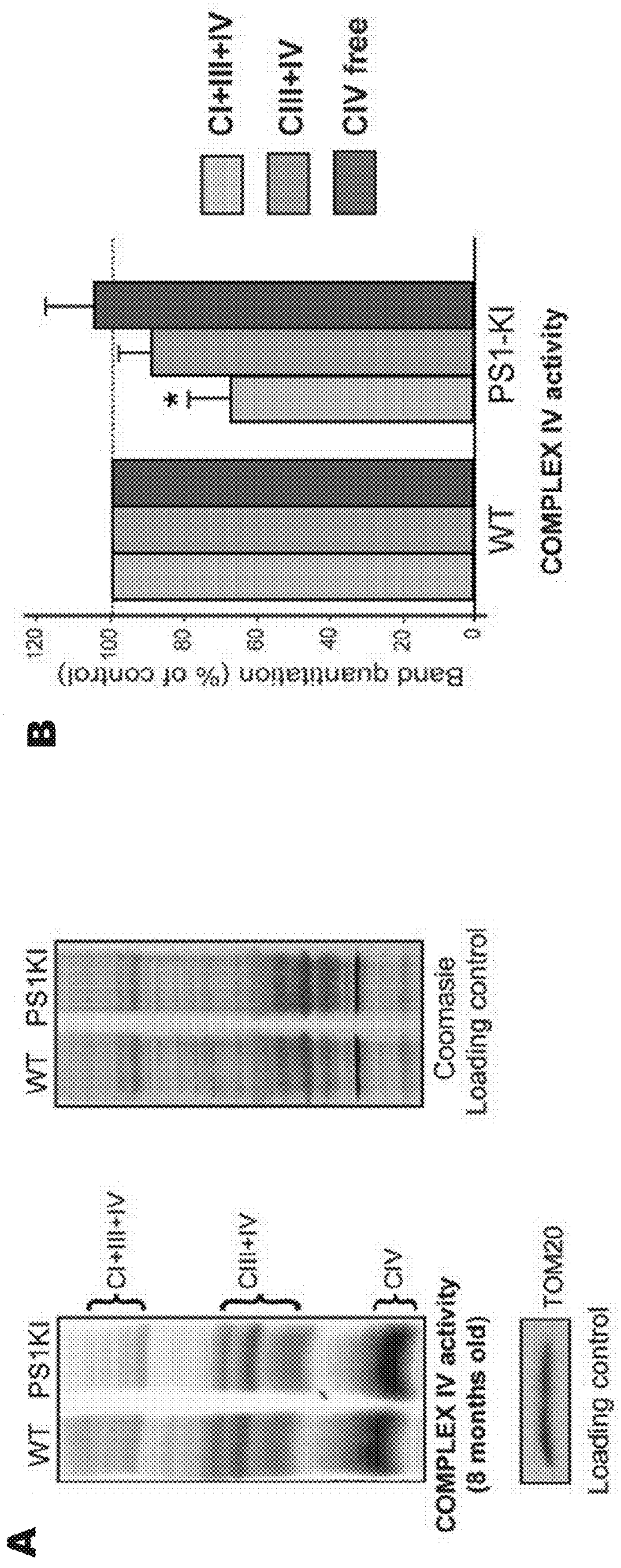
FIGS. 25A-B

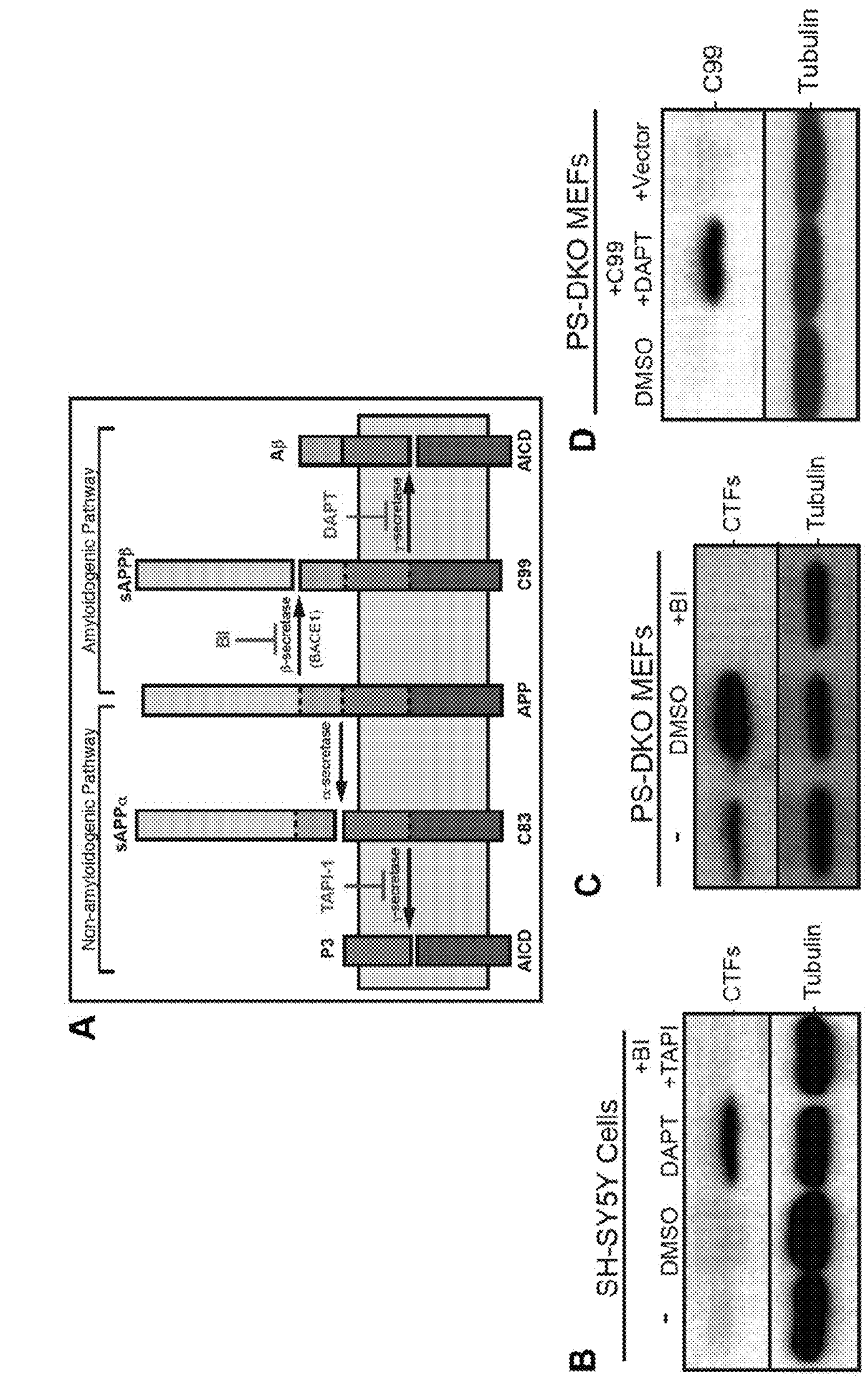
FIGS. 26A-D

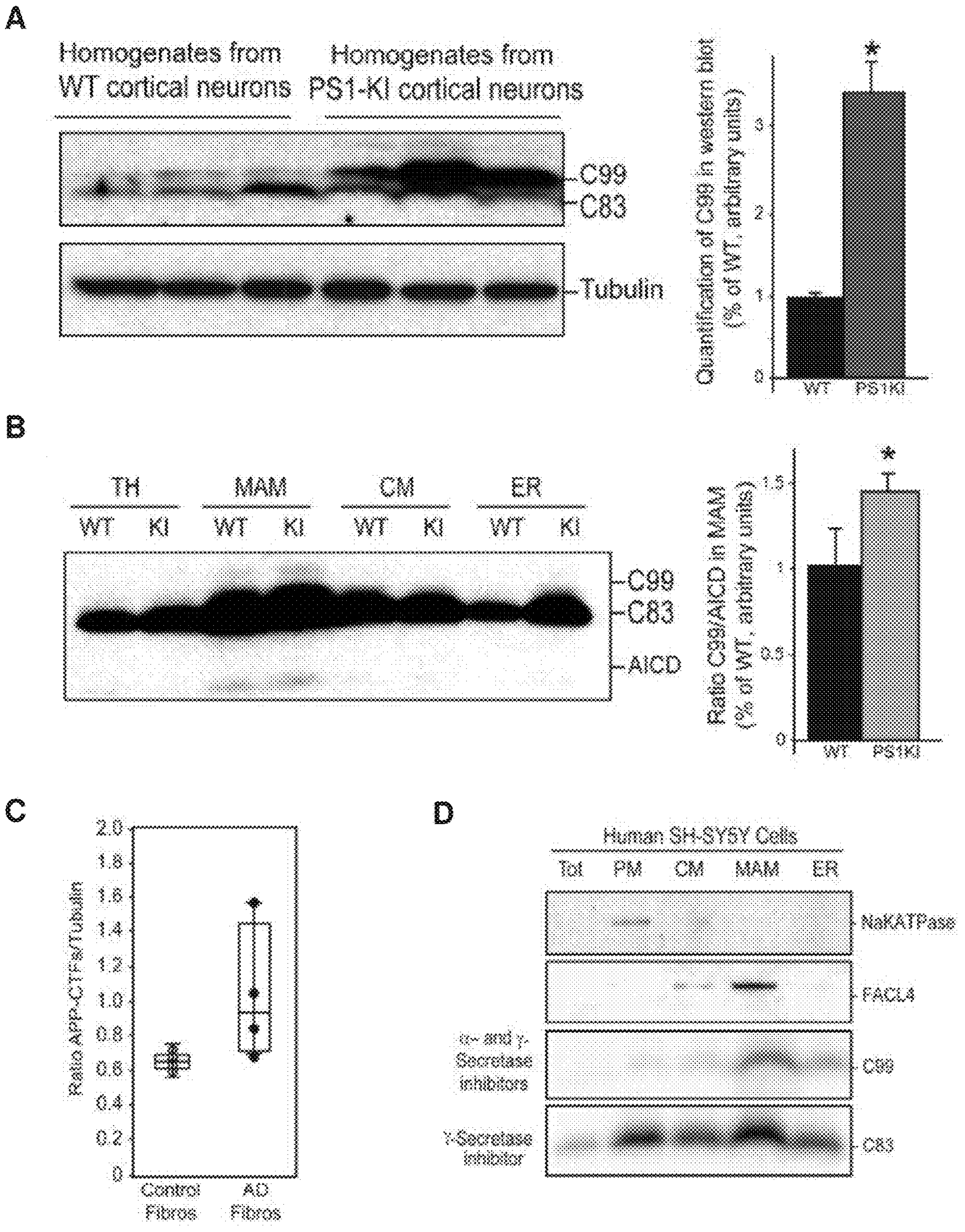
FIGS. 27A-D

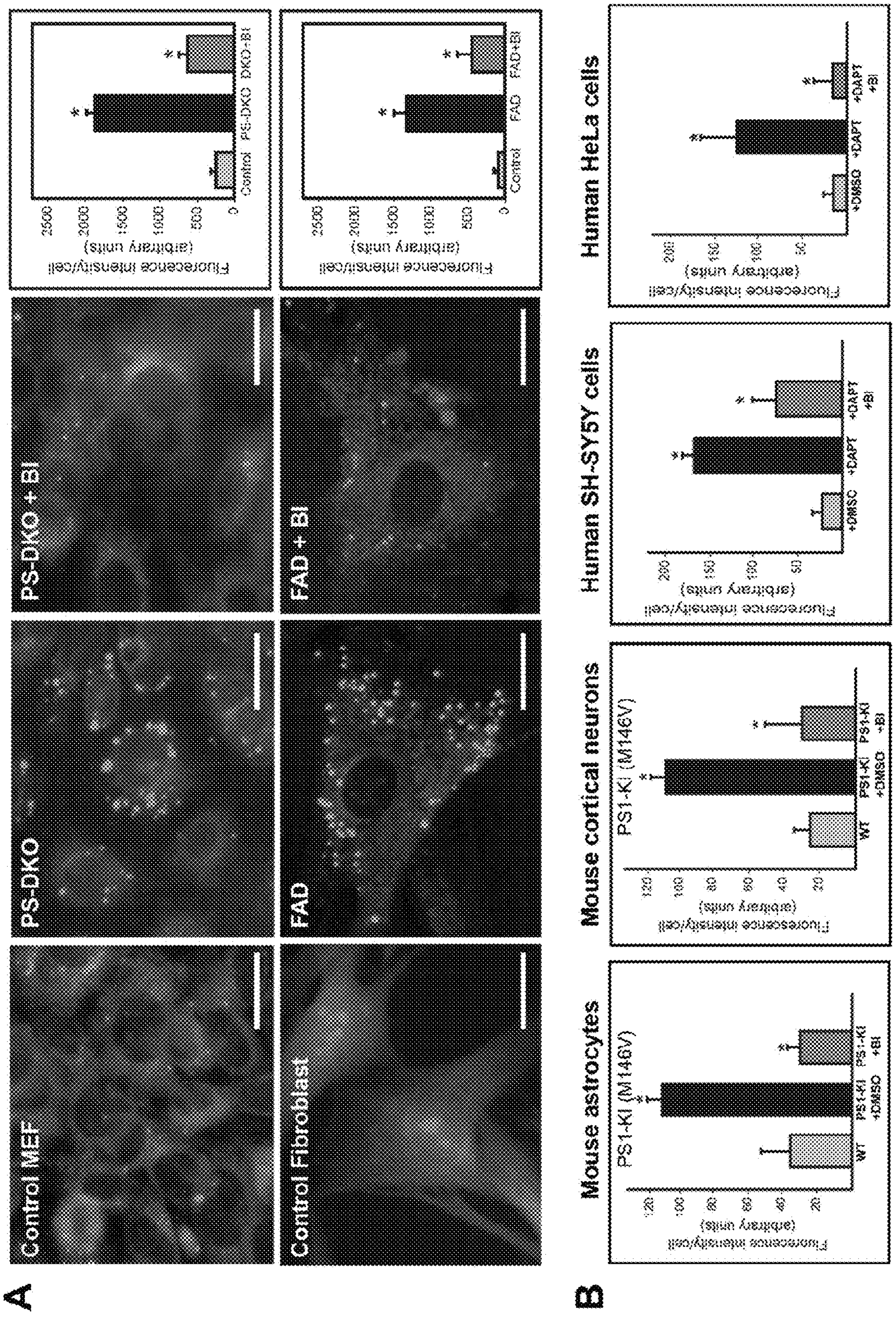
FIGS. 28A-B

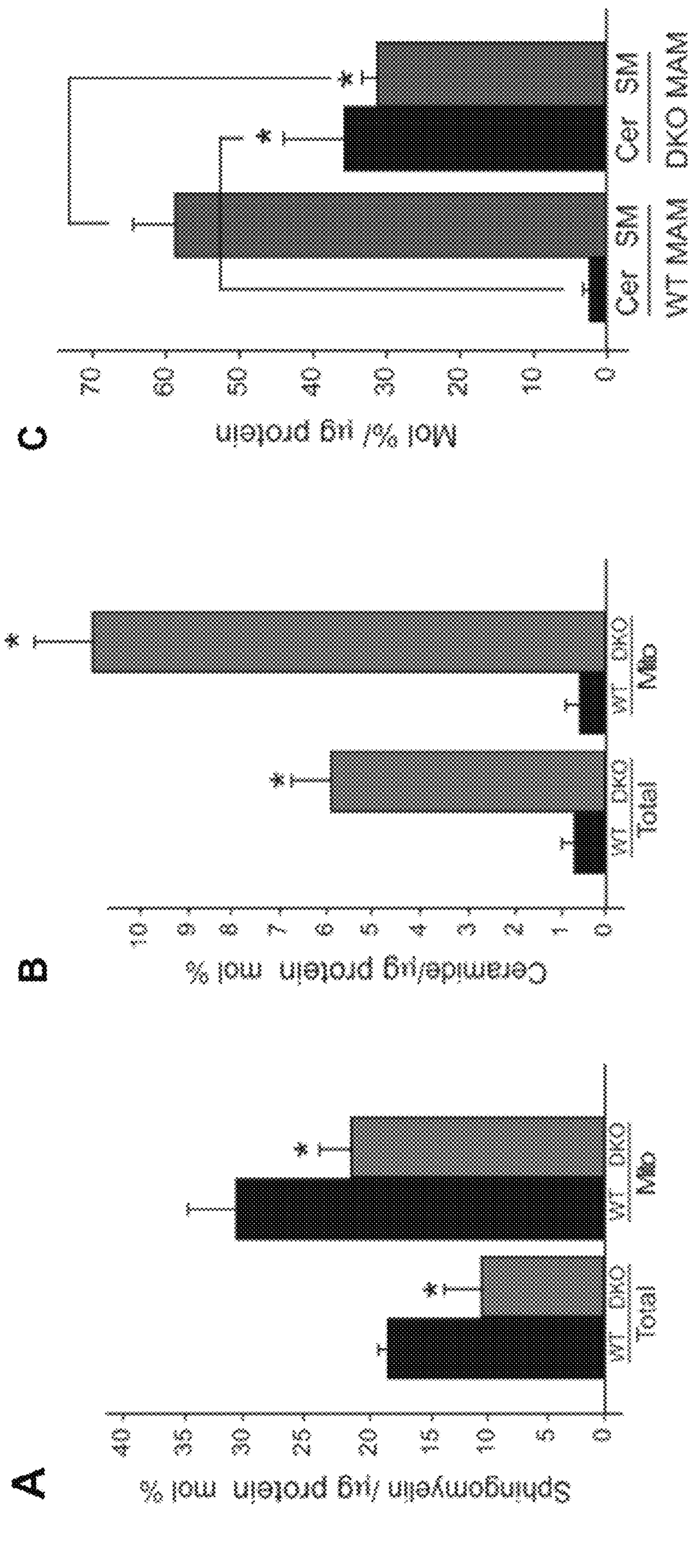
FIGS. 29A-C

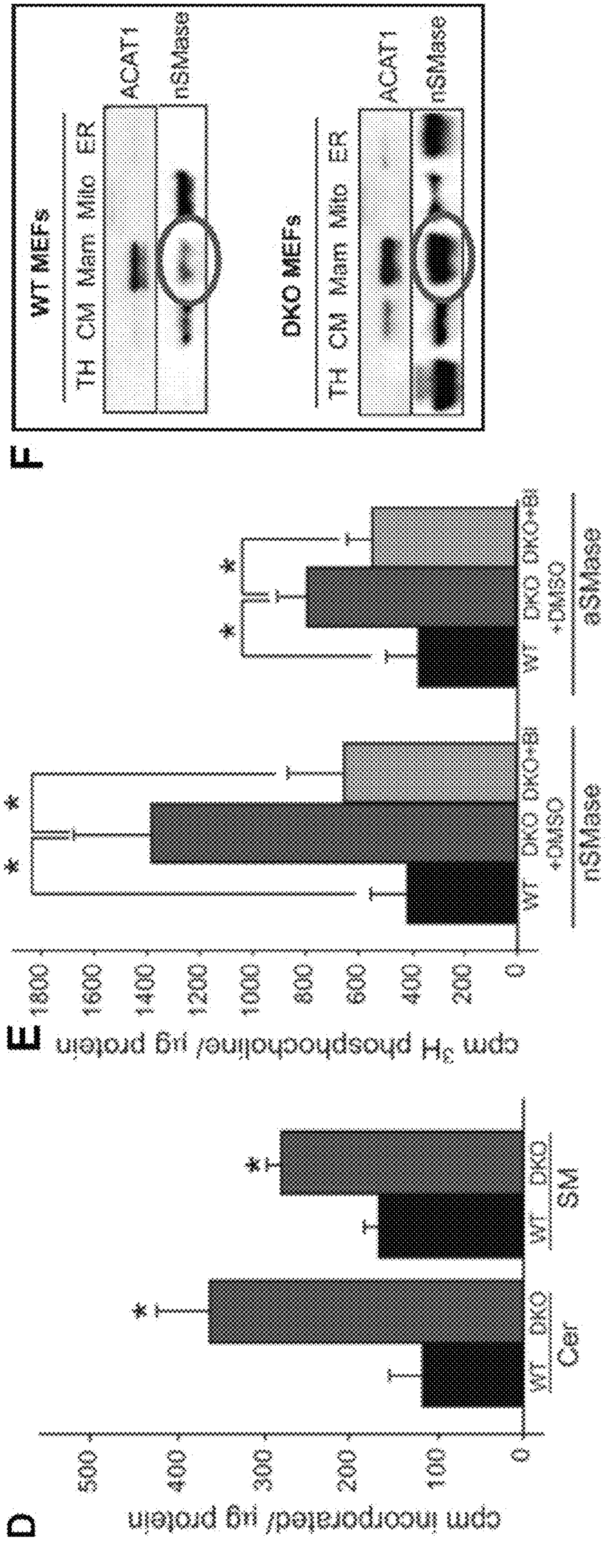
FIGS. 29D-F

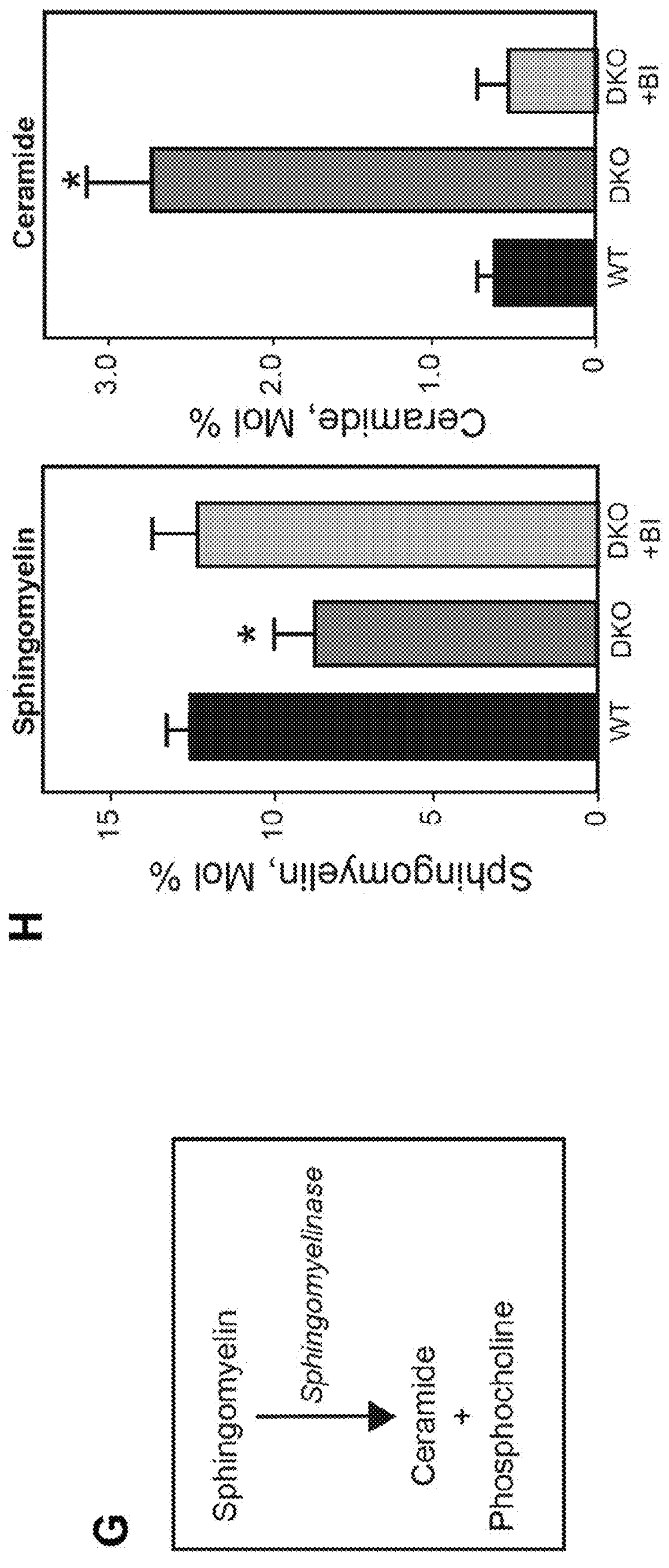
FIGS. 29G-H

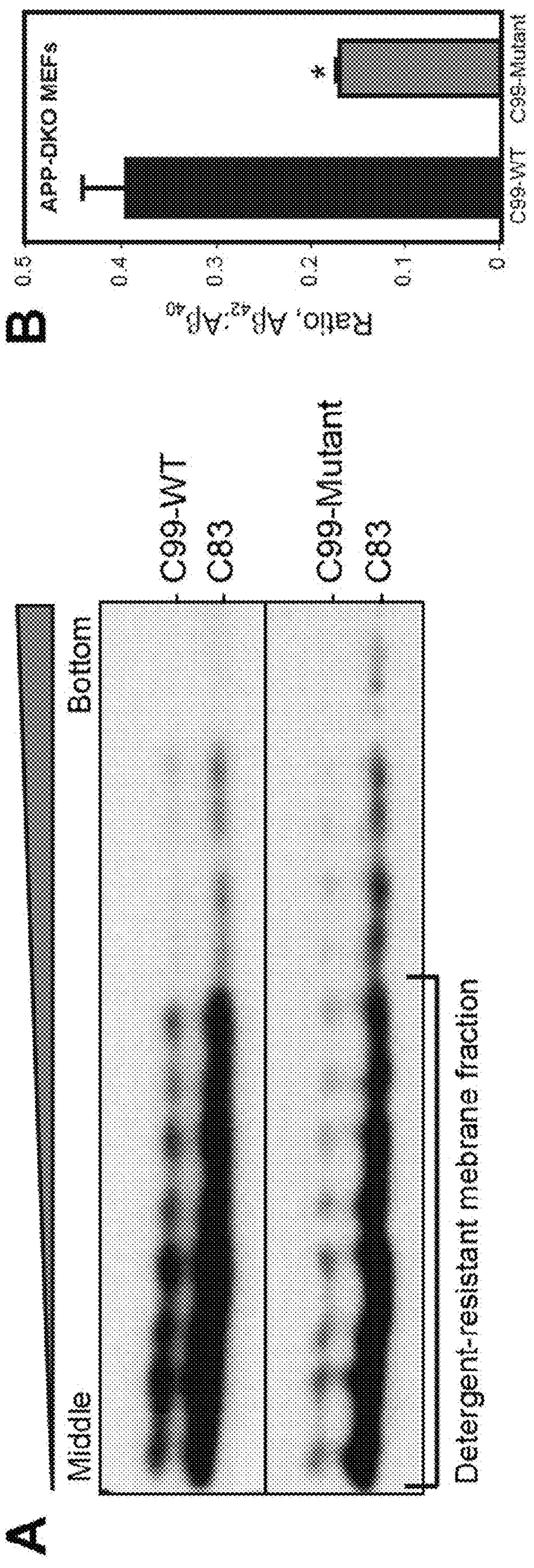
FIGS. 30A-B

A

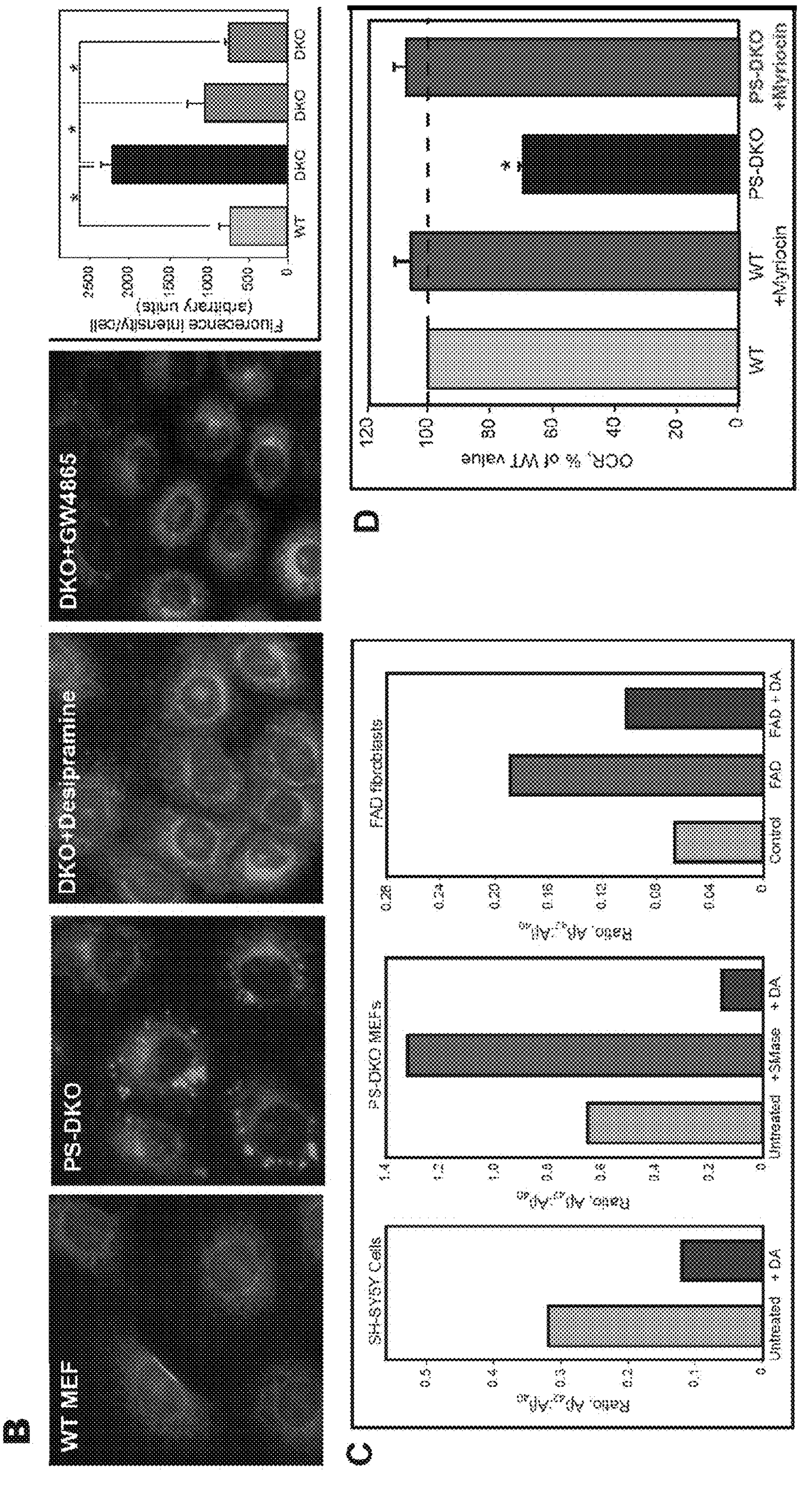
FIGS. 32B-D

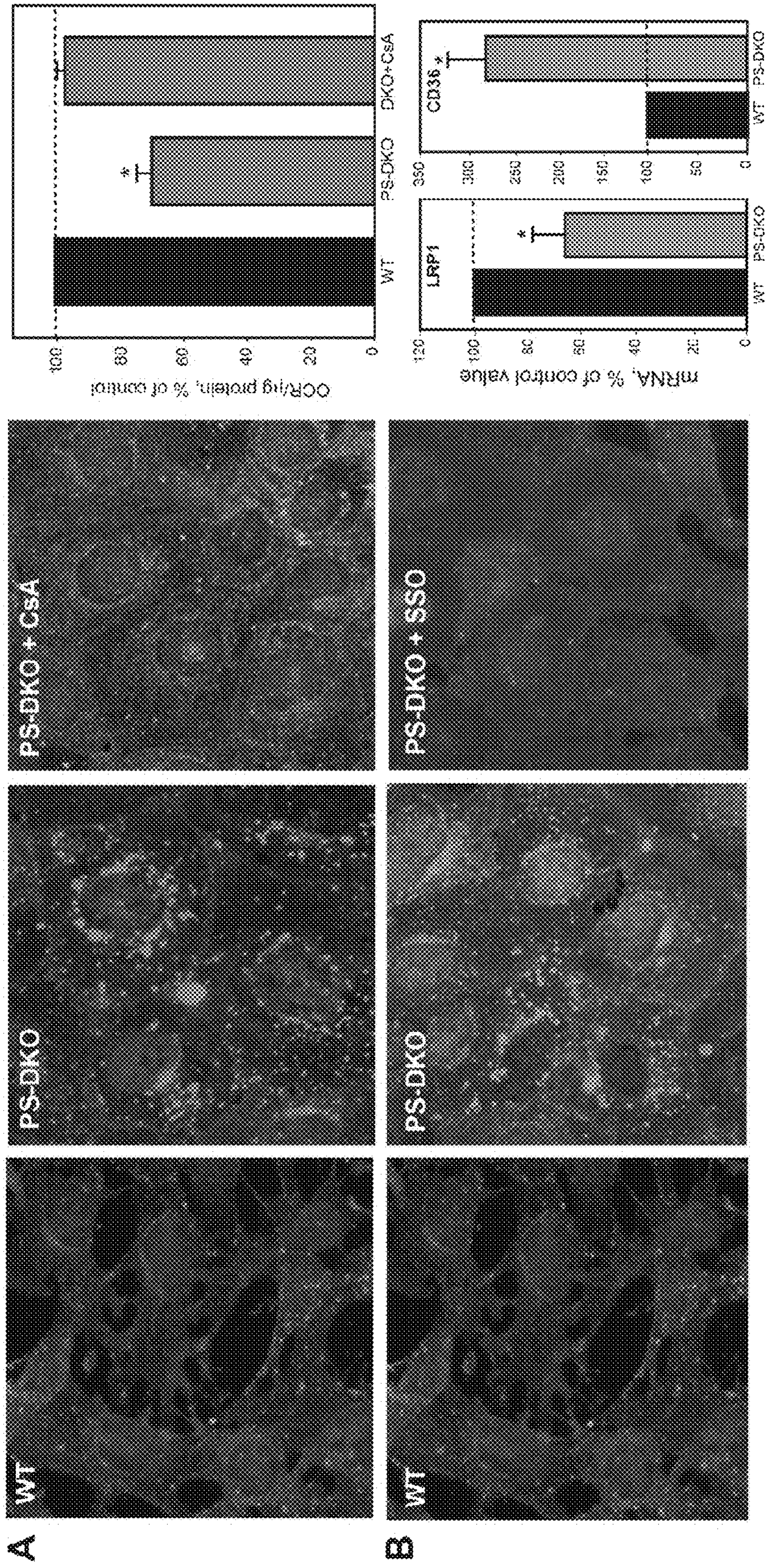
FIGS. 33A-B

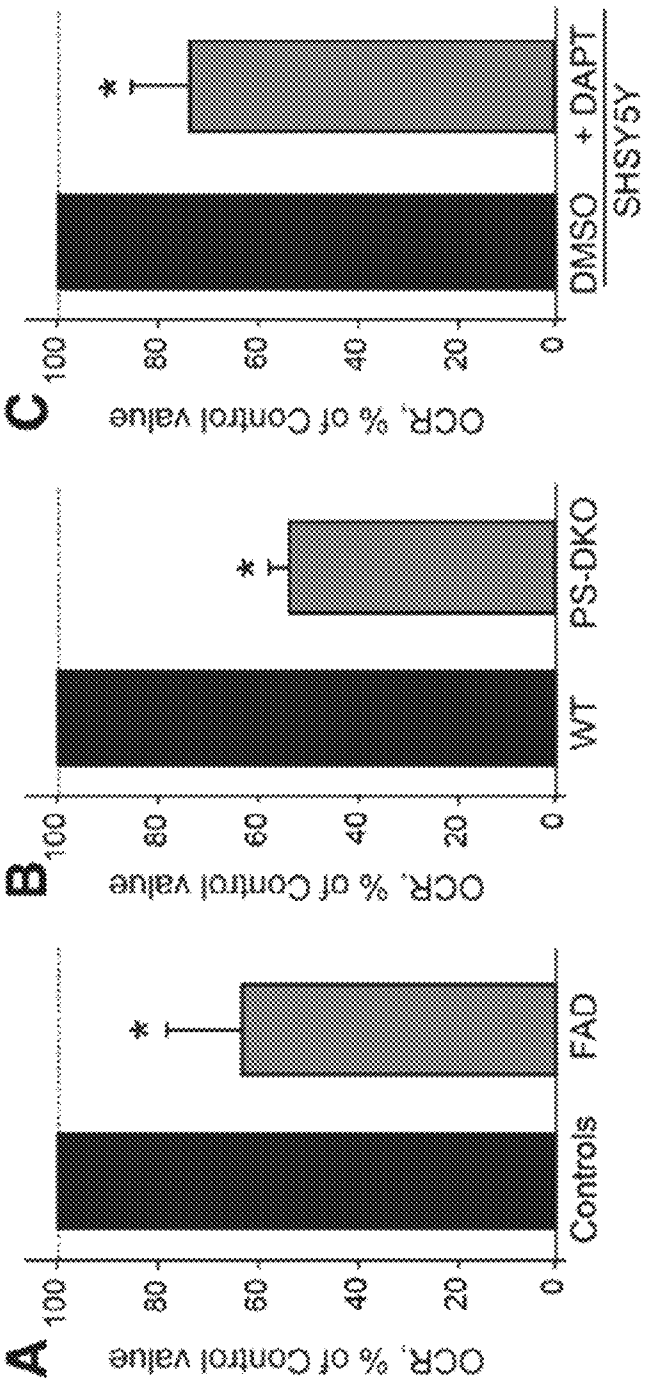
FIGS. 36A-C

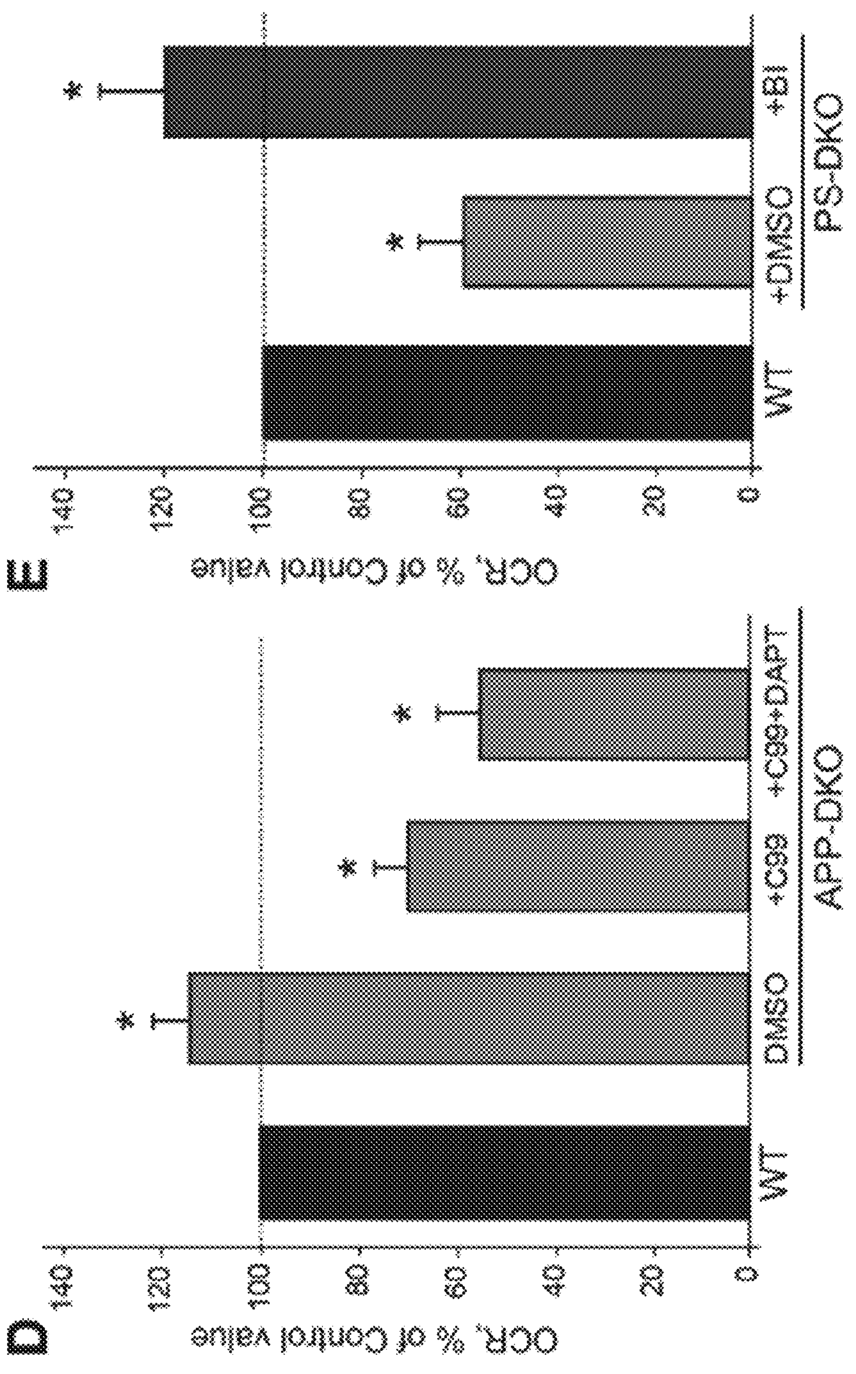
FIGS. 36D-E

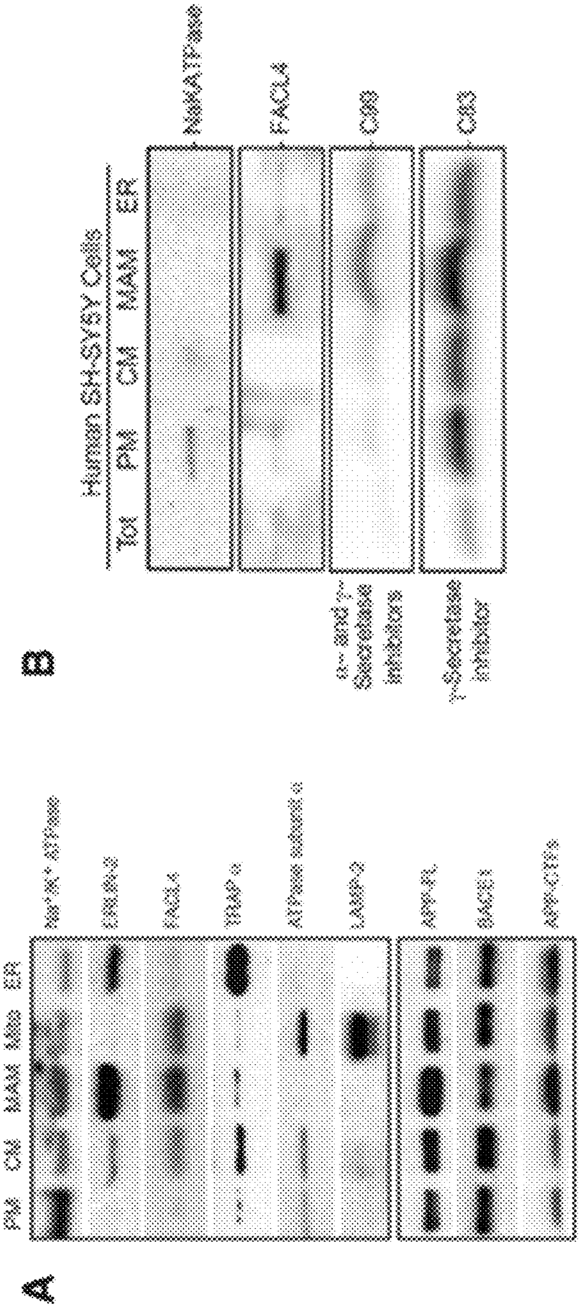
FIGS. 37A-B

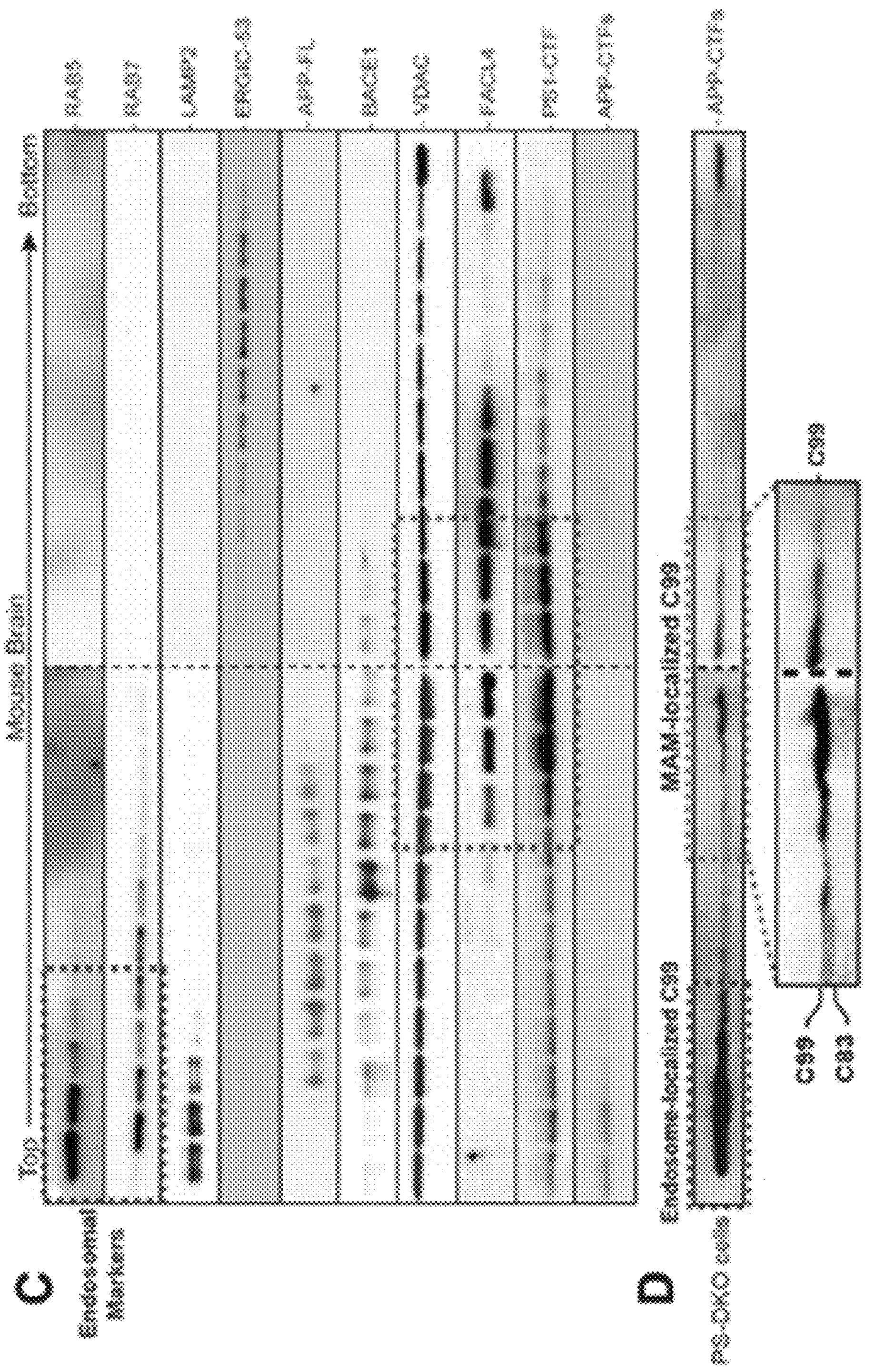
FIGS. 37C-D

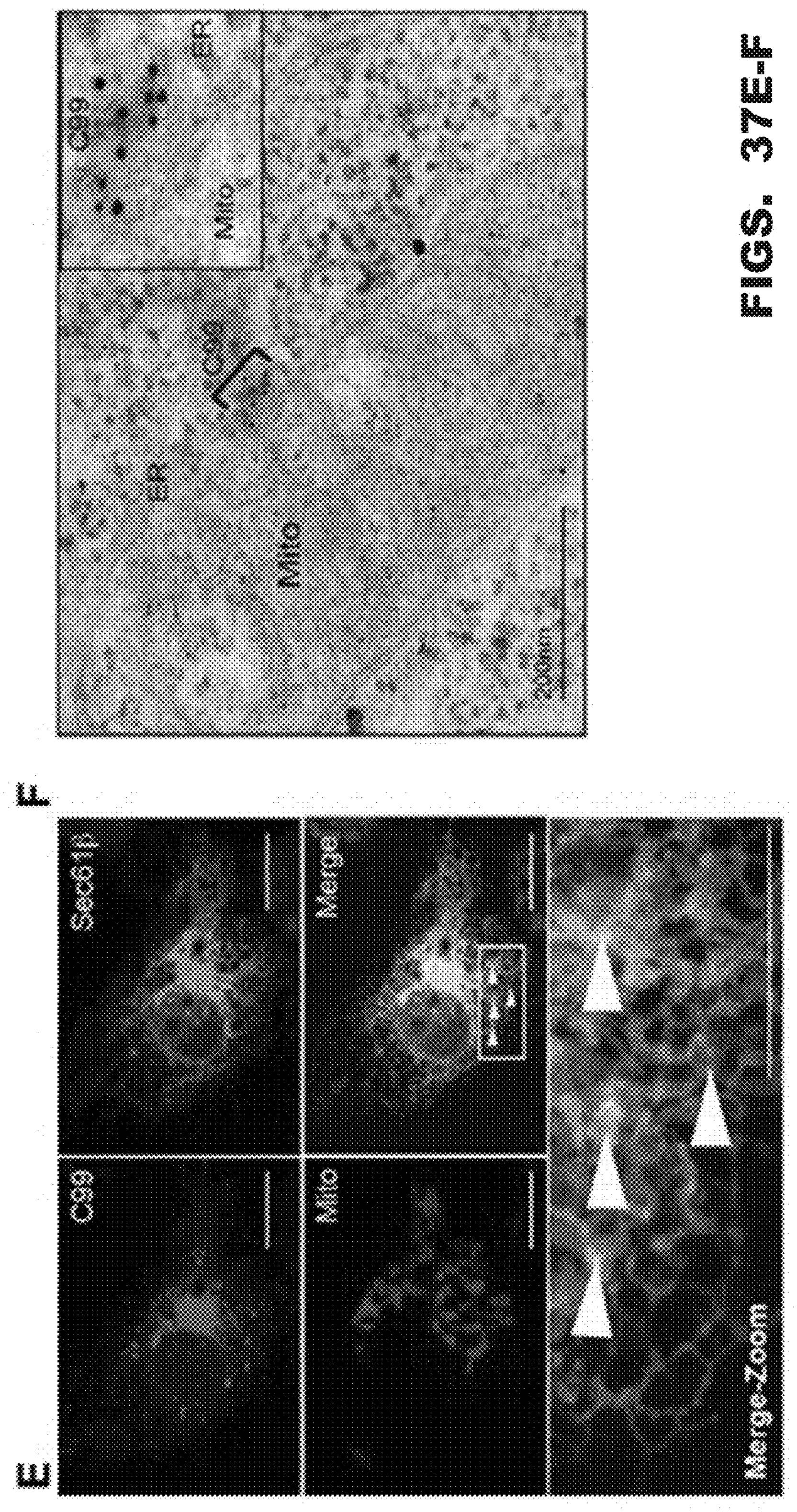
FIGS. 37E-F

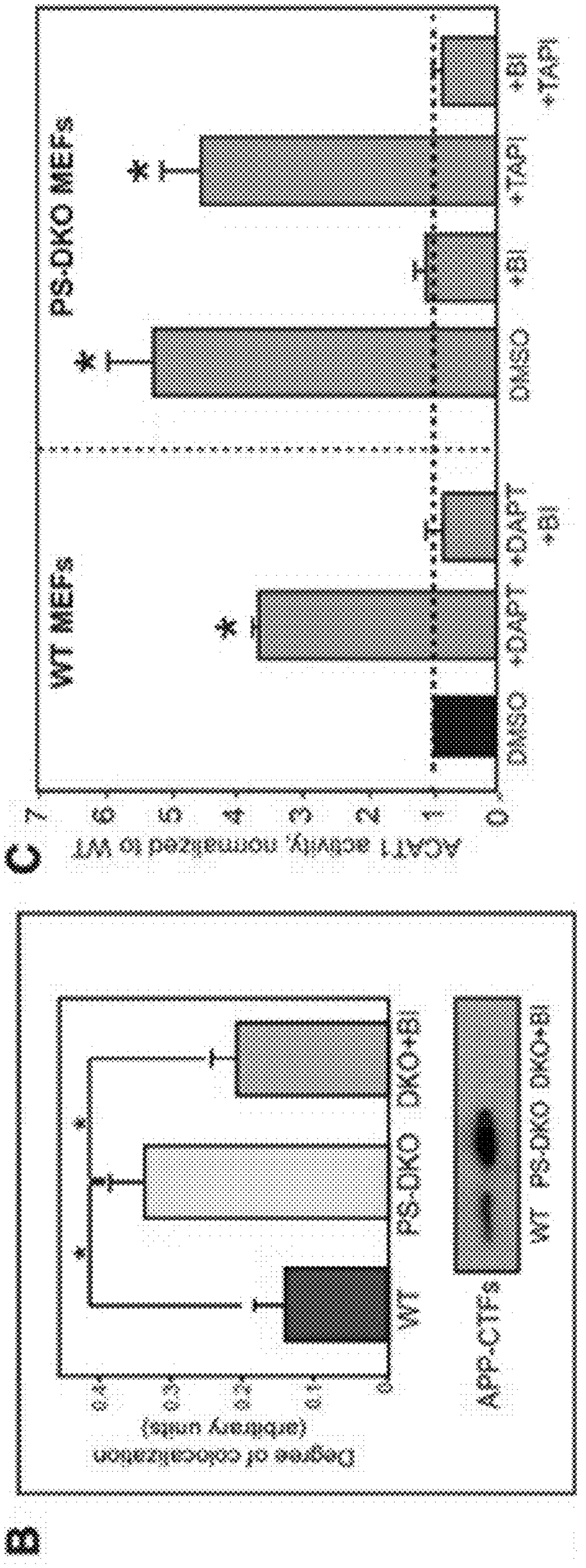
FIGS. 38B-C

D

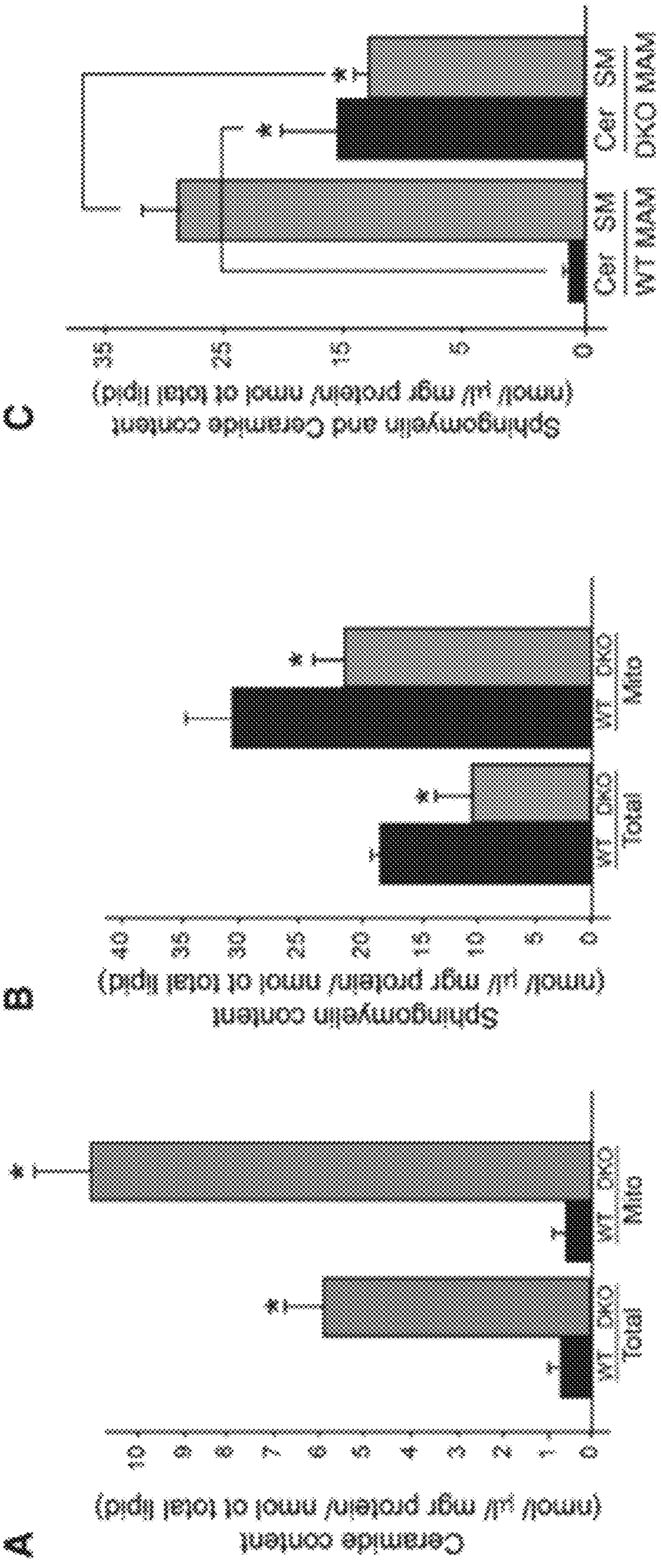
FIGS. 39A-C

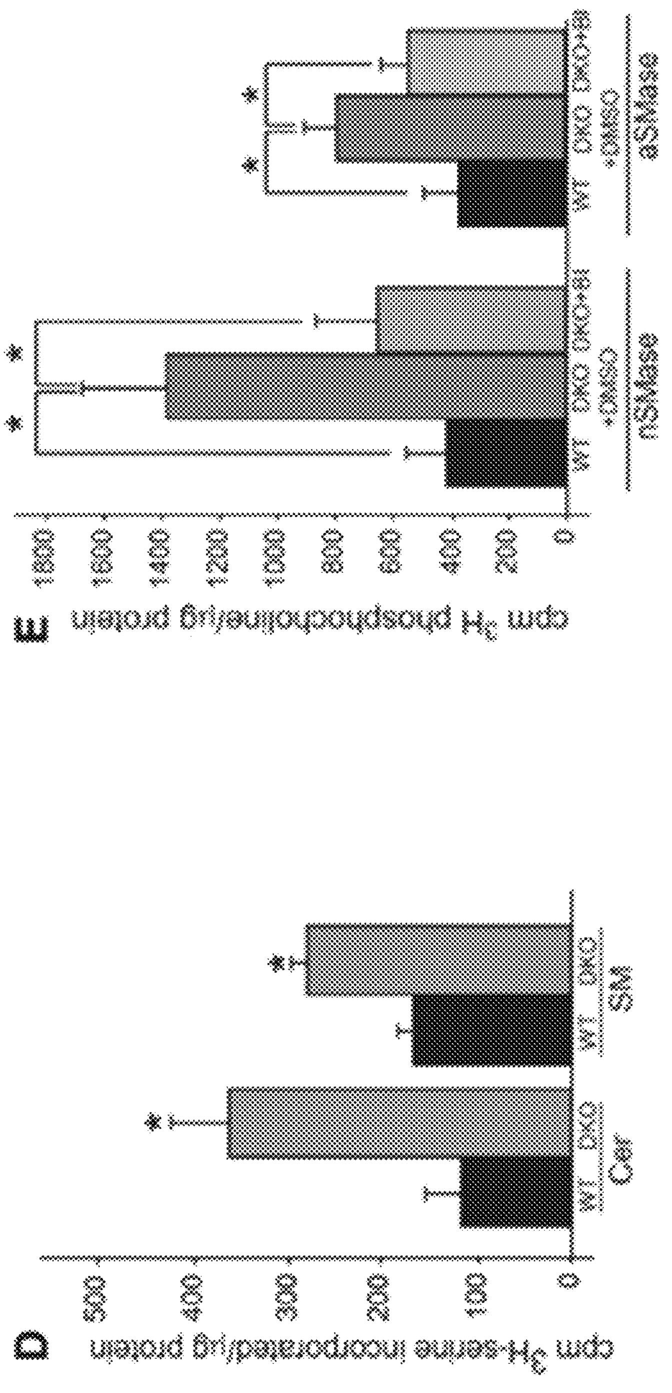
FIGS. 39D-E

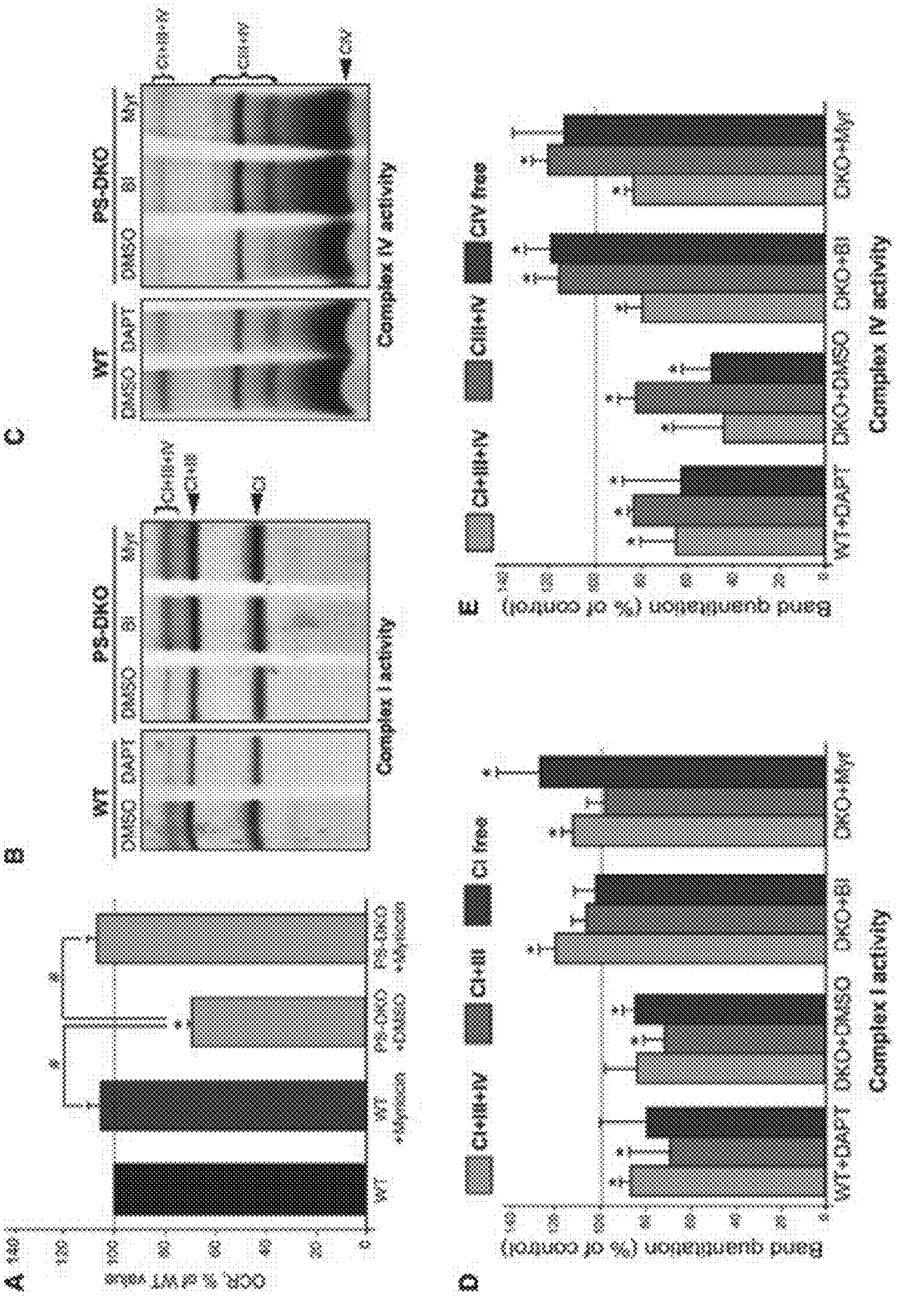
FIGS. 41A-E

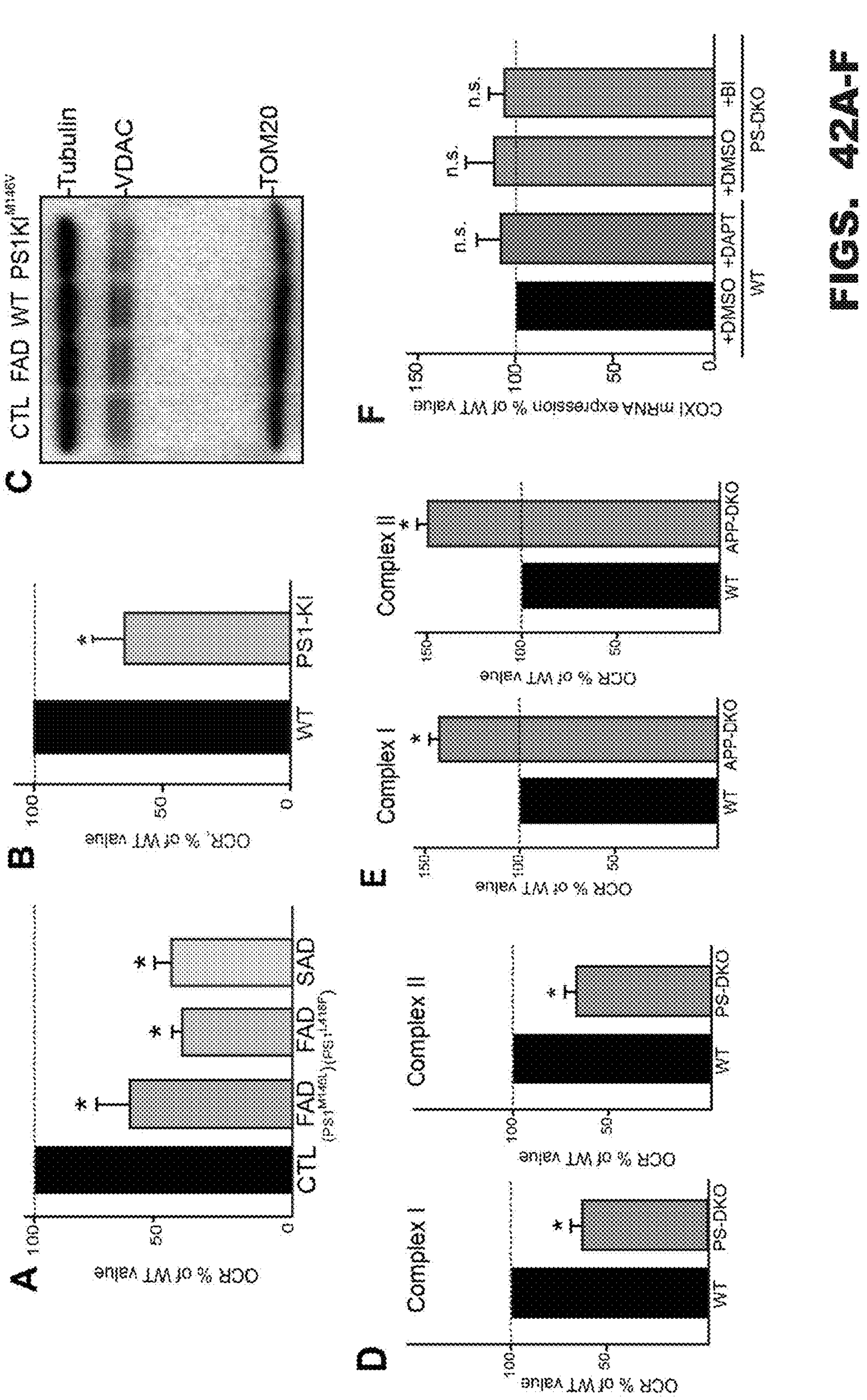
FIGS. 42A-F

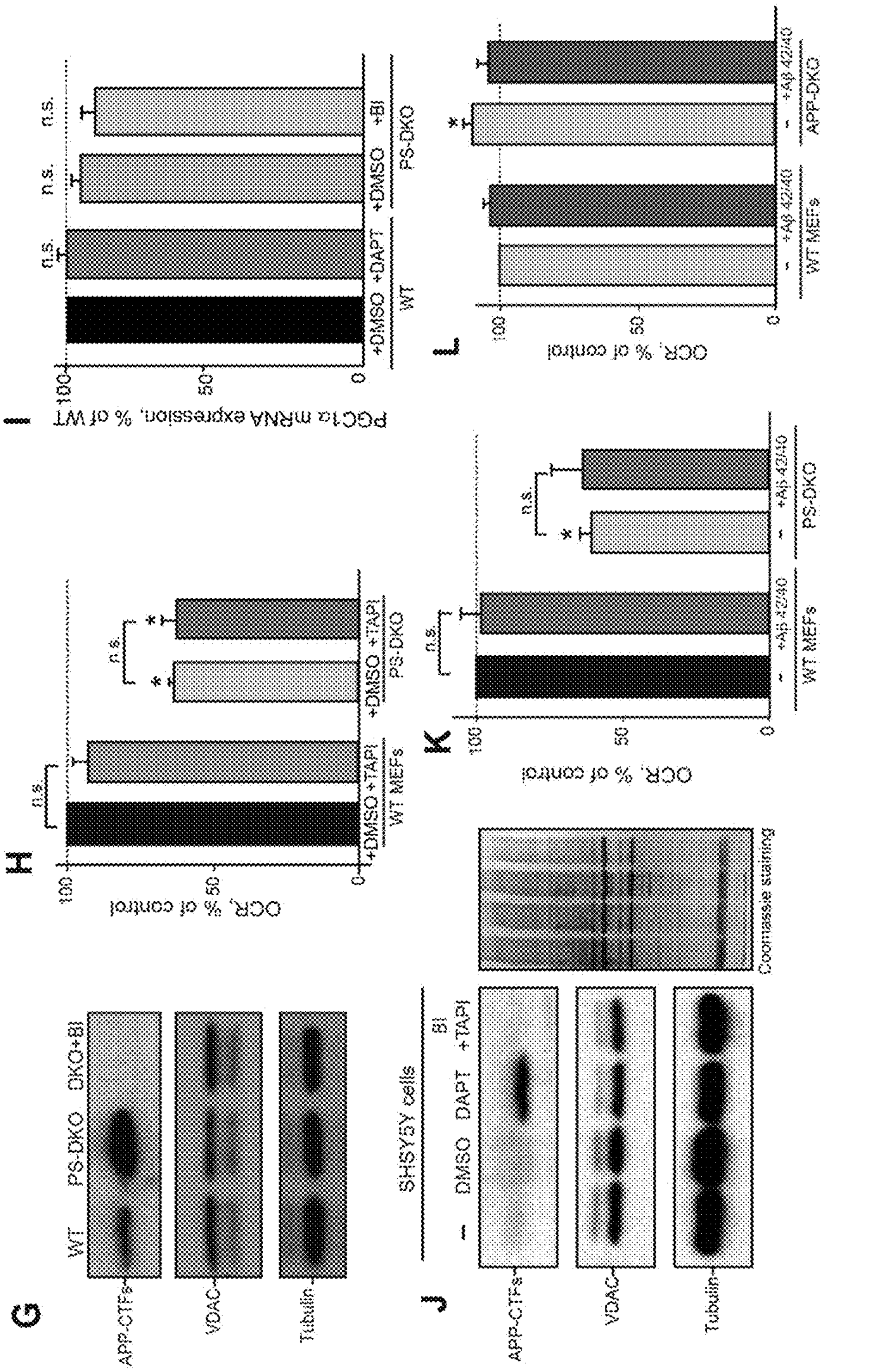
FIGS. 42G-L

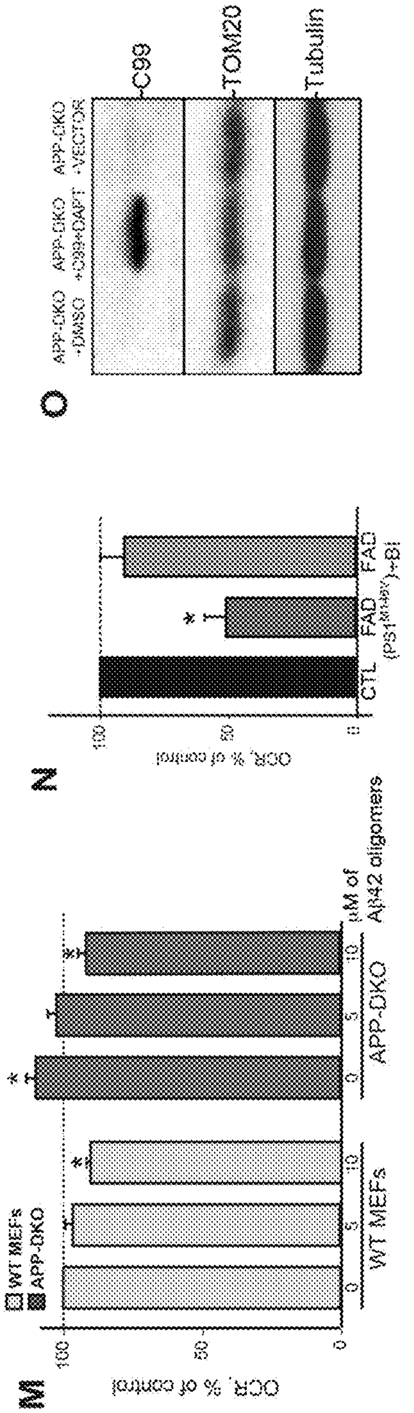
FIGS. 42M-O

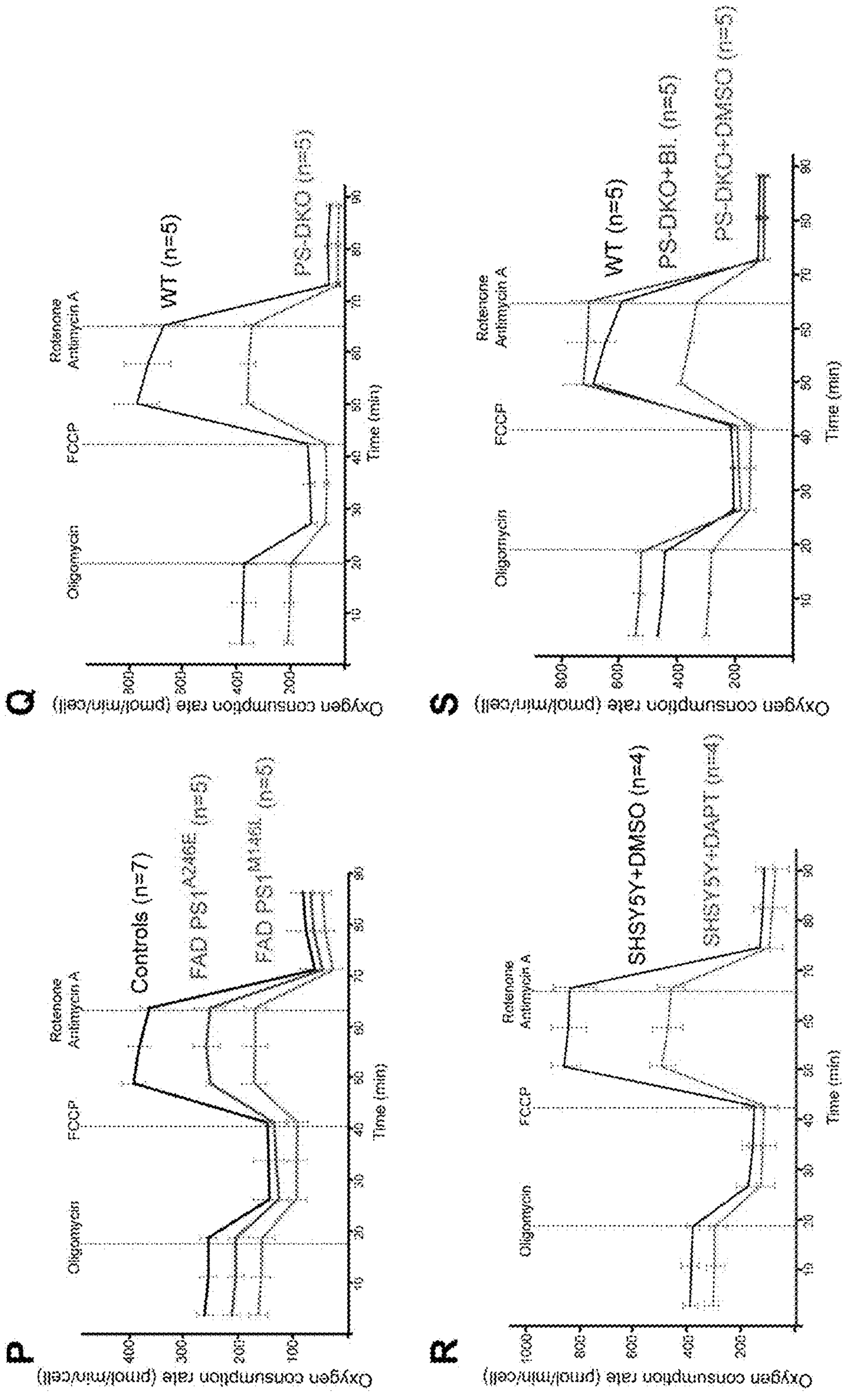
FIGS. 42P-S

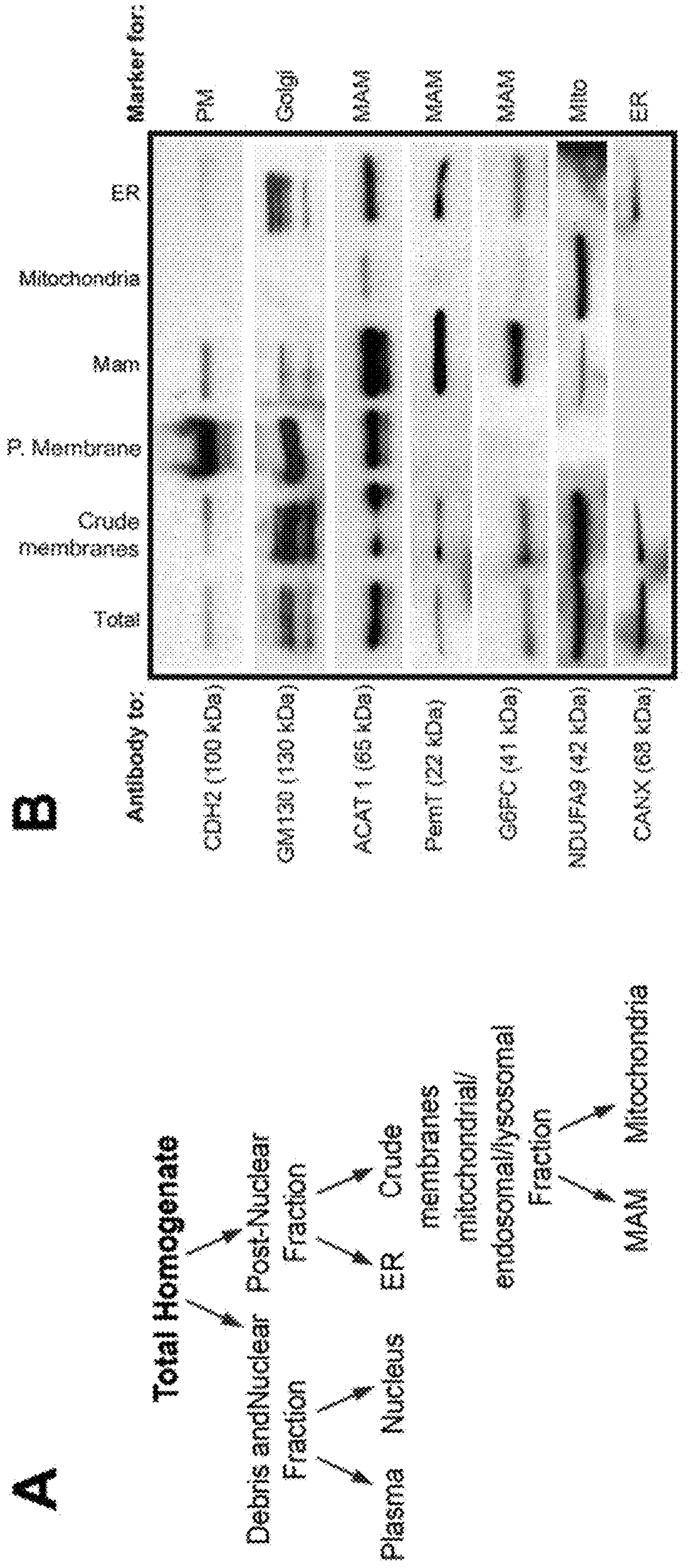
FIGS. 43A-B

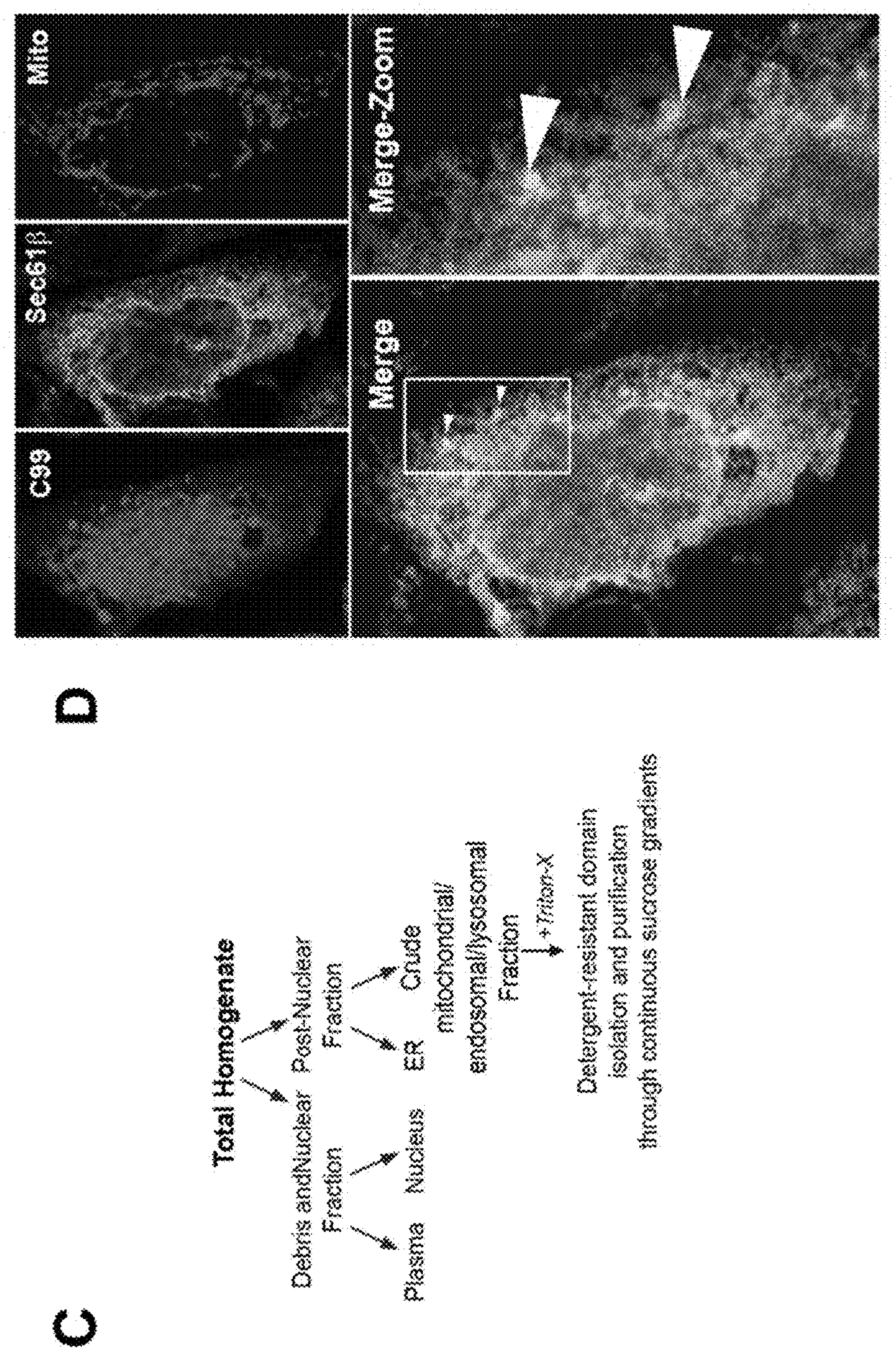
FIGS. 43C-D

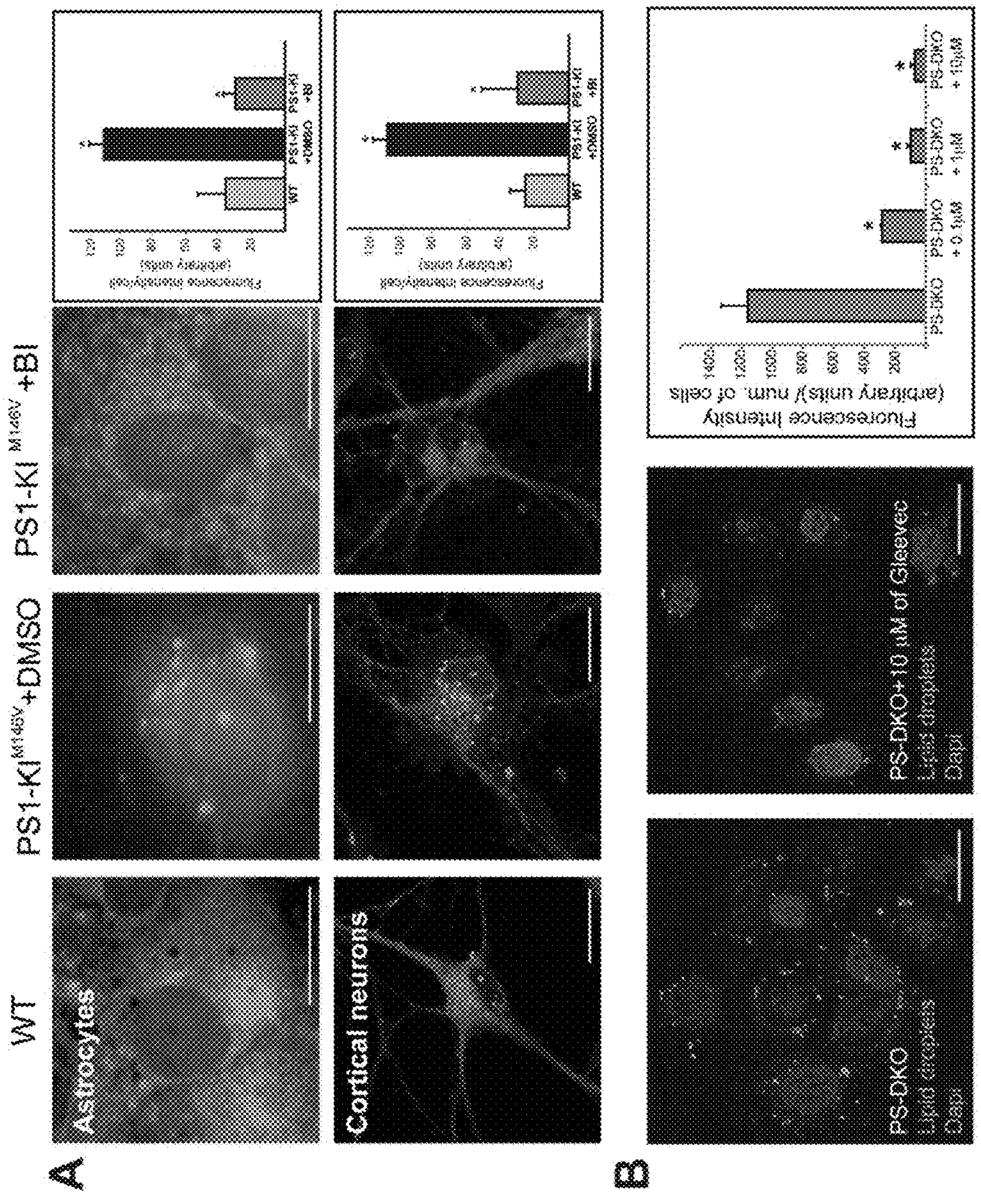
FIGS. 44A-B

FIG. 44D
CONTROL
Lipid droplets
Dapi
BACE1 KO
Lipid droplets
Dapi
Fluorescence intensity
(arbitrary units)/ num. of cells
60
40
20
n.s.
Control
BACE1-KO

D

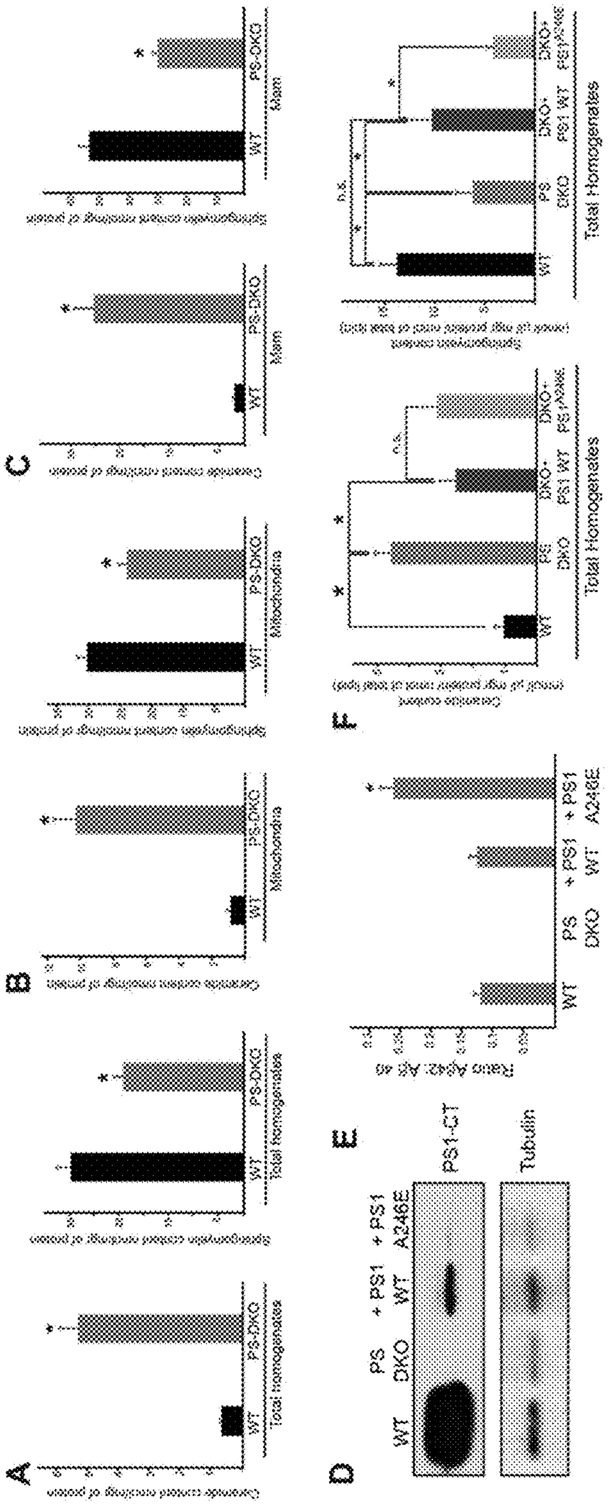
FIGS. 45A-F

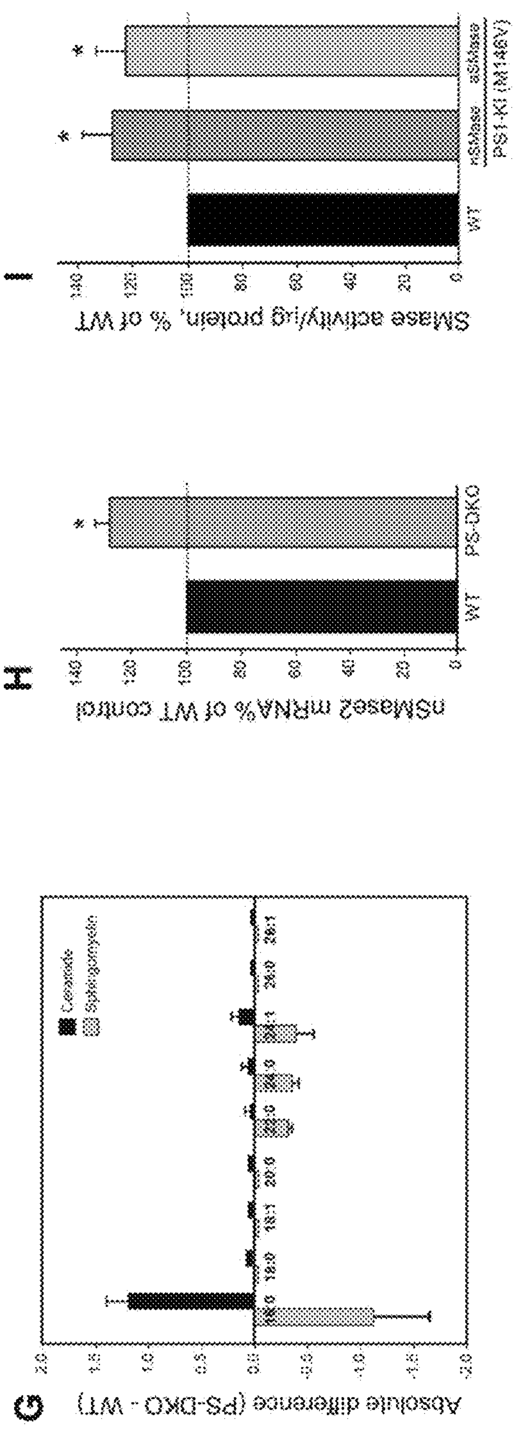
FIGS. 45G-I

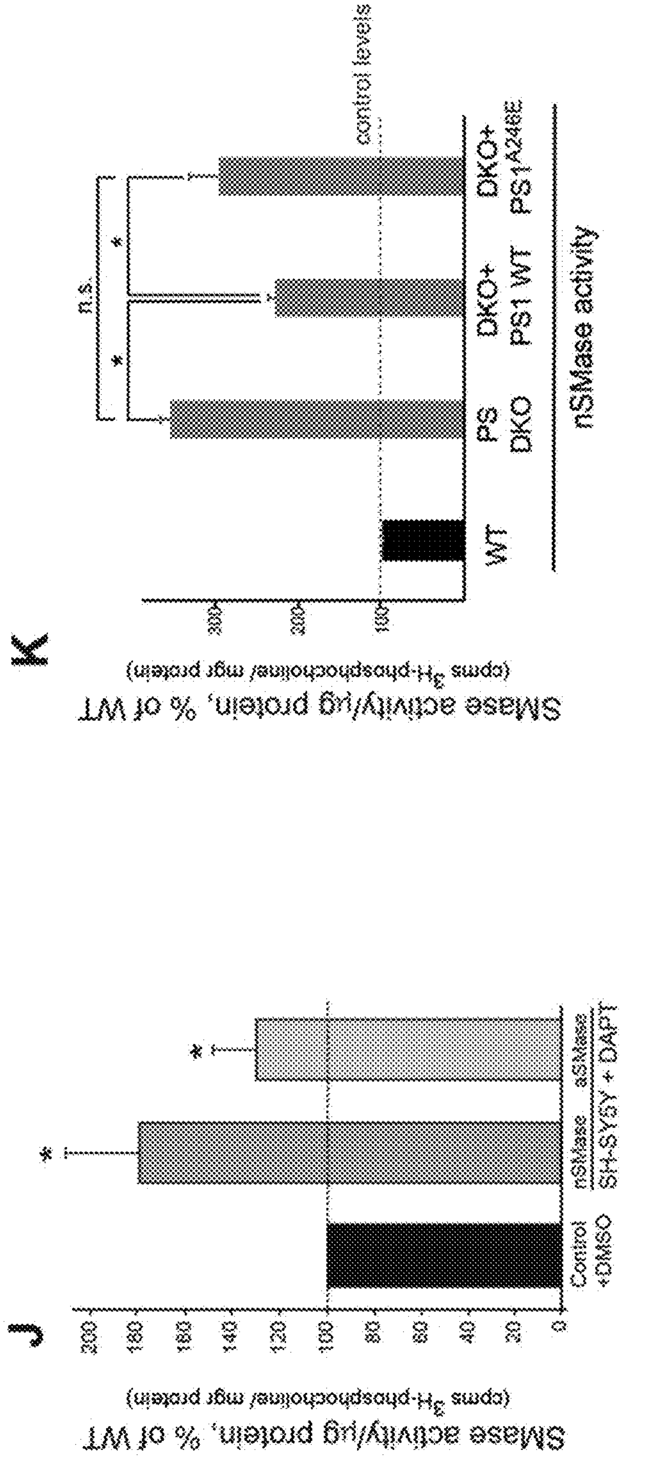
FIGS. 45J-K

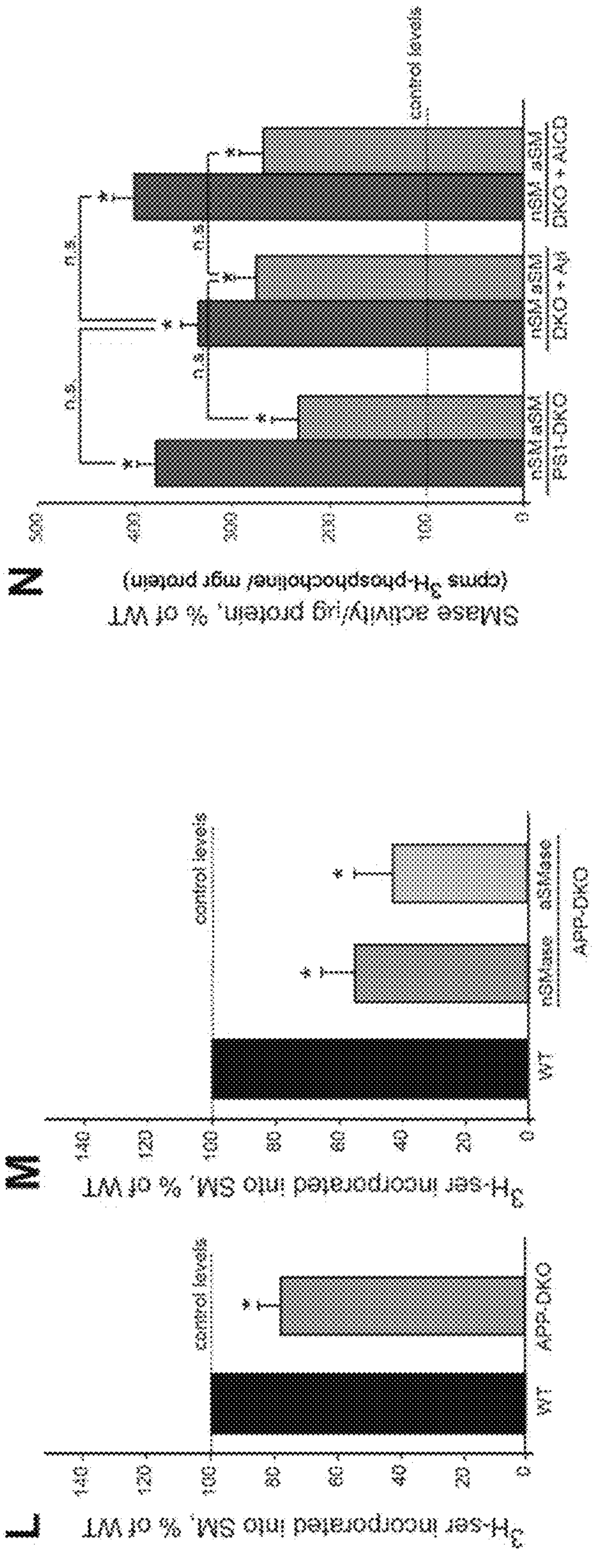
FIGS. 45L-N

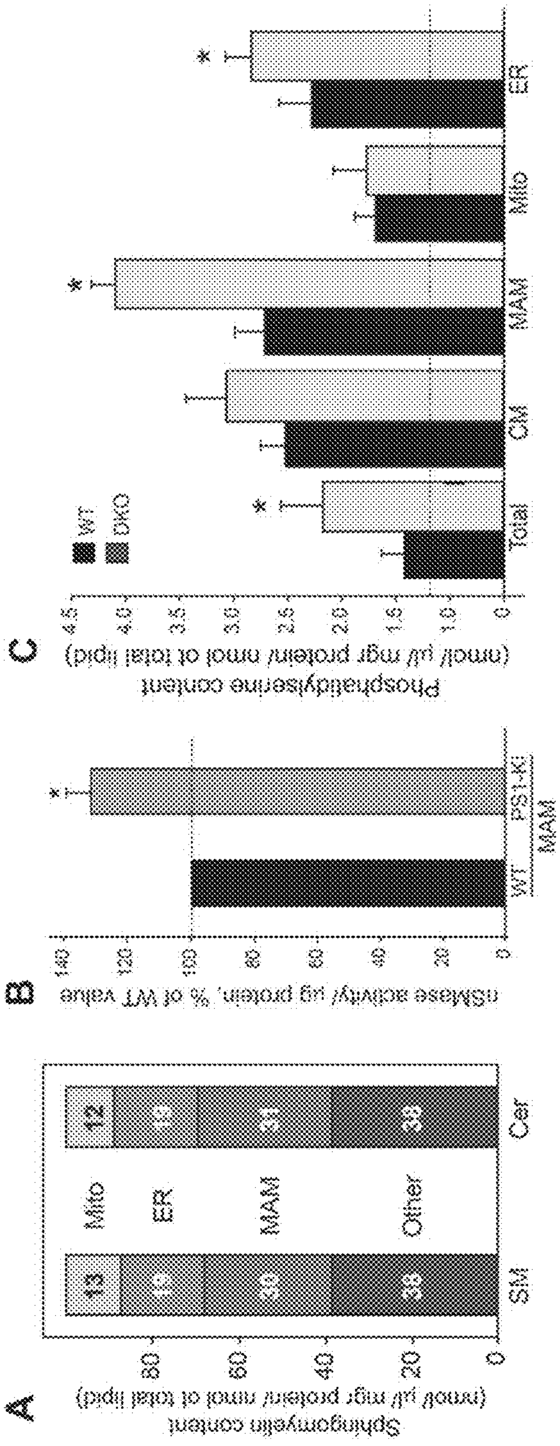
FIGS. 46A-C

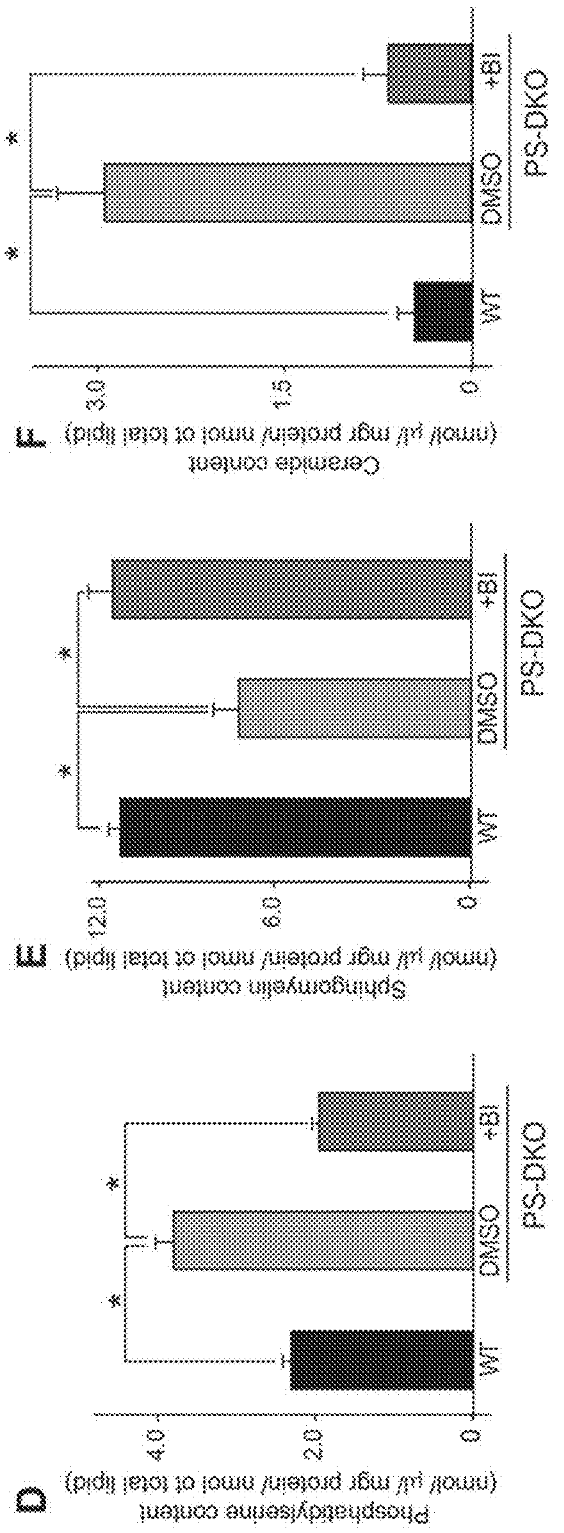
FIGS. 46D-F

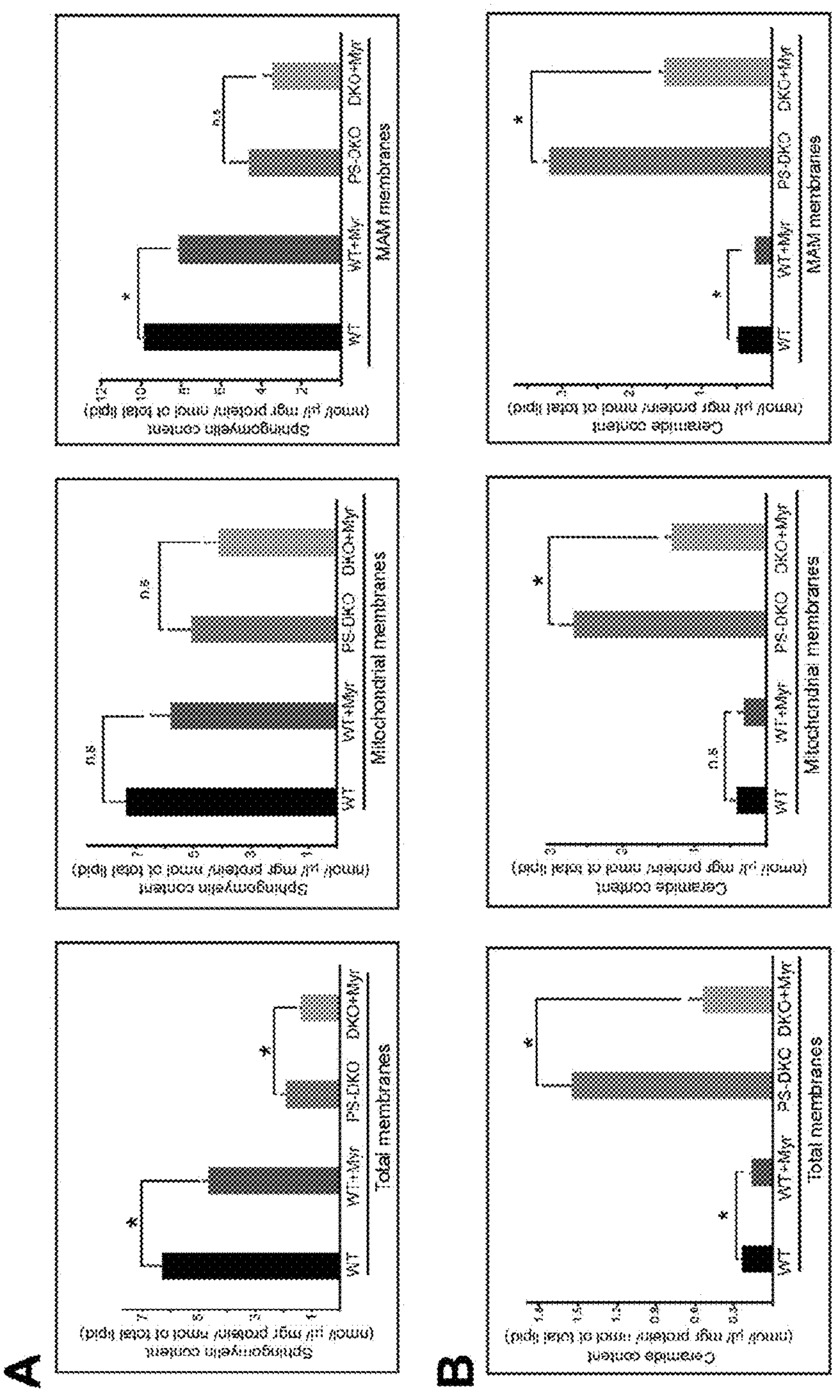
FIGS. 47A-B

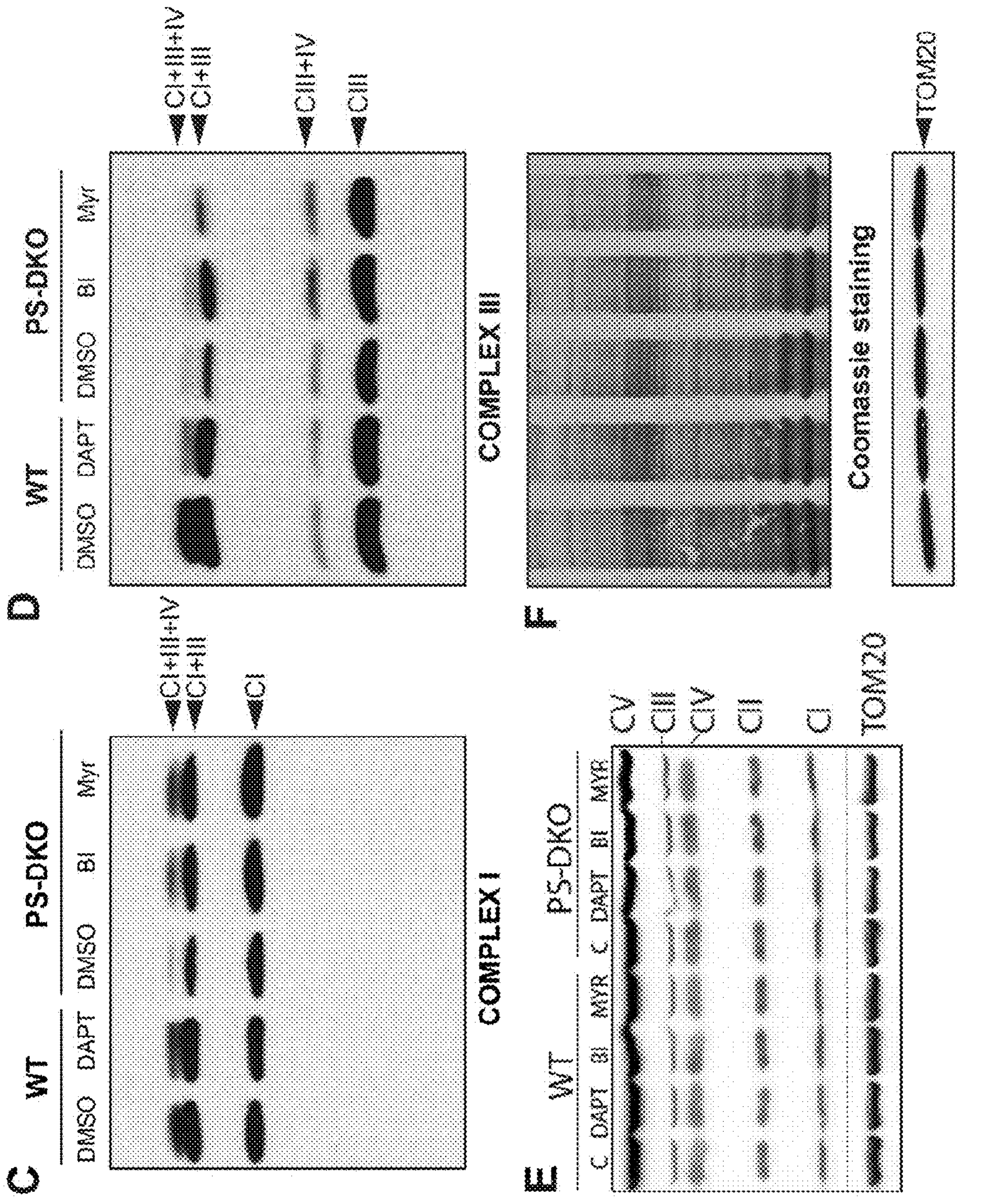
FIGS. 47C-F

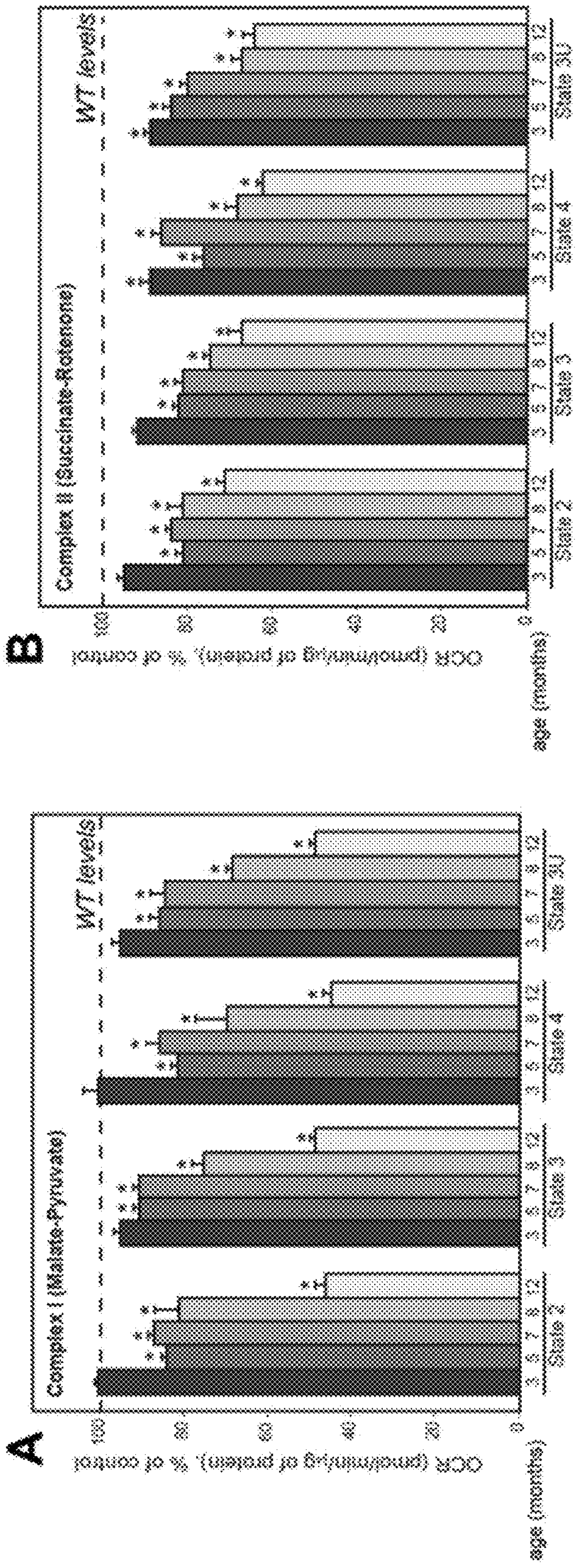
FIGS. 48A-B

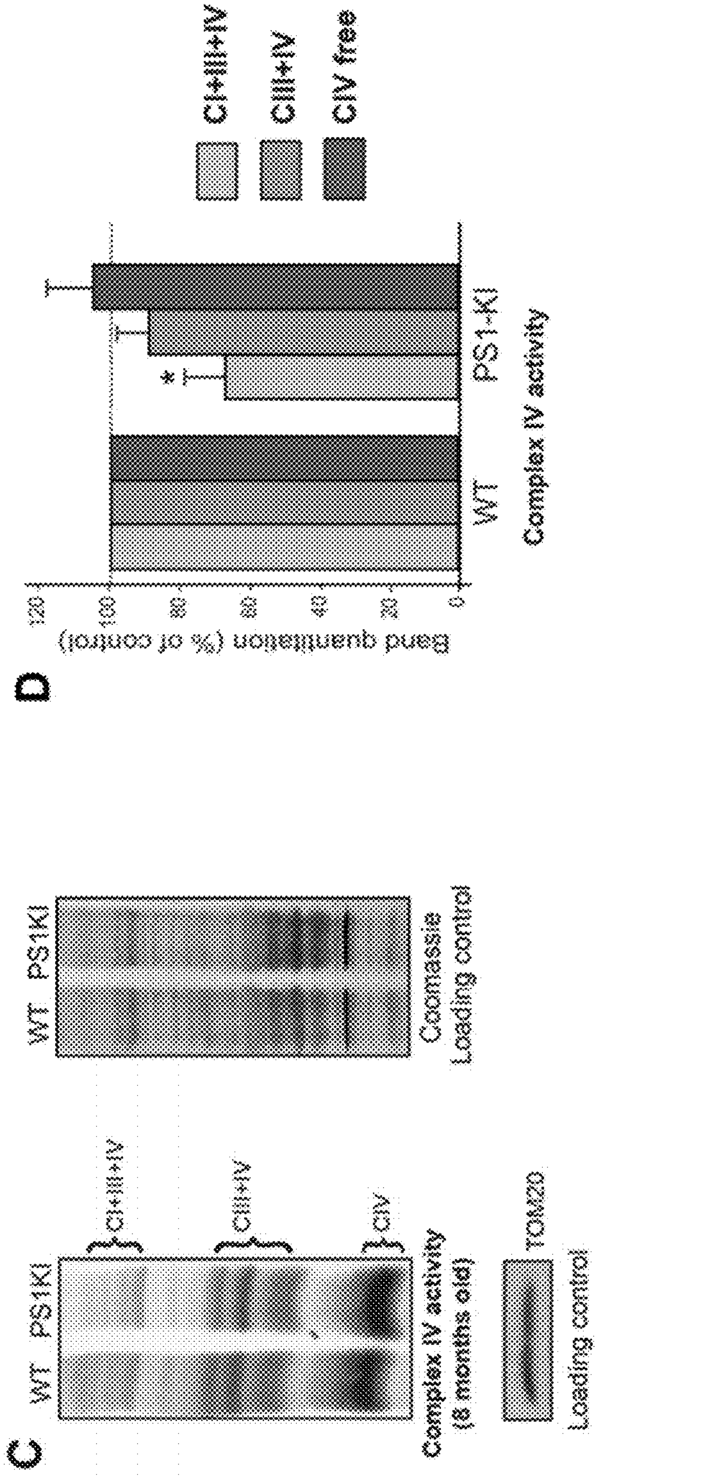
FIGS. 48C-D

SEQUENCE LISTING

<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 1

His His His His His His
1 5

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
cccgctagcc tcgagatgct gaagaagaaa cagtacacat ccattc 46

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
cccggatcca tggatgcaga attccgacat gactc 35

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
cccggatcca agcttctagt tctgcatctg ctcaaagaac ttg 43

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tgctagccgc aggcattact 20

<210> SEQ ID NO 6
<211> LENGTH: 23
<212> TYPE: DNA
<213> ORGANISM: Artificial Sequence
<220> FEATURE:

-continued

```
<223> OTHER INFORMATION: Description of Artificial Sequence: Synthetic
      primer

<400> SEQUENCE: 6

cgggatcaaa gaaagttgtg ttt                                          23
```

REDUCTION OF ER-MAM-LOCALIZED APP-C99 AND METHODS OF TREATING ALZHEIMER'S DISEASE

This application is a continuation-in-part of International Application No. PCT/US2016/051046 filed Sep. 9, 2016, which claims the benefit of and priority to U.S. Application Ser. No. 62/216,198 filed Sep. 9, 2015, the entire contents of each of which are hereby incorporated by reference in their entireties.

GOVERNMENT SUPPORT

This invention was made with government support under Grant Nos. P01-HD080642, P01-HD032062, NS071571, HD071593, R01-NS056049, P50-AG008702, and K01-AG045335 awarded by the National Institute of Health. This invention was also made with government support under Grant Nos. W911NF-12-1-9159 and W911F-15-1-0169 awarded by the U.S. Department of Defense. The Government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosure of these publications in their entireties are hereby incorporated by reference into this application in order to more fully describe the state of the art as known to those skilled therein as of the date of the invention described herein.

SEQUENCE LISTING

The instant application contains a Sequence Listing which has been submitted electronically in ASCII format and is hereby incorporated by reference in its entirety. Said ASCII copy, created on May 14, 2018, is named 19240_1104_US2_SL.txt and is 1,733 bytes in size.

BACKGROUND OF THE INVENTION

Neurodegenerative diseases are a major public health concern. The increasing number of patients with neurodegenerative diseases imposes a major financial burden on health systems around the world.

Alzheimer disease (AD) is the most common neurodegenerative disorder, whose exact pathogenetic causes are still not well defined. The vast majority of AD is sporadic (SAD), but the ε4 allele of apolipoprotein E (ApoE4) is a major risk factor for developing the disease. The familial, autosomal dominant, form of AD (FAD) is characterized by the inheritance of mutations in genes encoding presenilin-1 (PS1), presenilin-2 (PS2), and the amyloid precursor protein (APP). Aberrant processing of APP plays a central, but still unclear, role in AD pathogenesis.

More than half of the patients with dementia have Alzheimer's disease (AD). The prevalence of AD between the age 60-69 years is 0.3%, 3.2% between that age 70-79 years, and 10.8% between 80-89 years of age. Survival time after the onset of AD is in the range of 5 to 12 years.

Thus there remains a need for methods of treating, preventing, diagnosing, or inhibiting AD and for methods to identify compounds suitable for the treatment, prevention, or inhibition of AD.

SUMMARY OF THE INVENTION

The present invention provides methods that are useful for the treatment of Alzheimer's disease (AD) and for the screening of compounds or therapeutic agents for treating AD. The methods pertain in part to reducing endoplasmic reticulum-mitochondrial-associated membrane (ER-MAM) localized APP-C99 (i.e. the ~99-amino acid C-terminal fragment of APP). The methods also pertain in part to reducing the function of ER-MAM localized APP-C99.

As would be apparent to one of ordinary skill in the art, any method or composition described herein can be implemented with respect to any other method or composition described herein.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

In certain aspects, the invention provides a method of treating Alzheimer's Disease in a subject in need thereof, comprising reducing the level of endoplasmic reticulum-mitochondrial-associated membrane (ER-MAM) localized APP-C99 in cells of the subject.

In certain aspects, the invention provides a method of treating Alzheimer's Disease in a subject in need thereof, comprising reducing the function of endoplasmic reticulum-mitochondrial-associated membrane (ER-MAM) localized APP-C99 in cells of the subject.

In some embodiments, the level of ER-MAM localized APP-C99 is reduced in cells of the subject by increasing ER-MAM localized γ-secretase activity. In some embodiments, ER-MAM localized γ-secretase activity is increased by administering to the subject an effective amount of phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), or auraptene (7-geranyloxycoumarin). In some embodiments, ER-MAM localized γ-secretase activity is increased by administering to the subject an effective amount of a composition that increases the level of, activates, or agonises OCIAD2, TNF-α, interleukin-1β, interferon-γ, MEKK1, OSTC, KRTCAP2, KCNIP3, ADRB2, CREB, APMAP, CRF, PS1, PS2, or EGR1. In some embodiments, the composition that increases the level of OCIAD2, TNF-α, interleukin-1β, interferon-γ, MEKK1, OSTC, KRTCAP2, KCNIP3, ADRB2, CREB, APMAP, CRF, PS1, PS2, or EGR1 comprises a polypeptide or nucleic acid encoding OCIAD2, TNF-α, interleukin-1β, interferon-γ, MEKK1, OSTC, KRTCAP2, KCNIP3, ADRB2, CREB, APMAP, CRF, PS1, PS2, or EGR1. In some embodiments, the ADRB2 agonist is isoproterenol or clenbuterol. In some embodiments, the CREB activator is PBA. In some embodiments, the CRF activity is increased by administering a composition comprising GSK561679 or Corticorelin/Xerecept. In some embodiments, the PS2 level is increased by administering a composition comprising TPA. In some embodiments, the MEK1/2 inhibitor is PD98059, PD0325901, U0126, or Trametinib. In some embodiments, ER-MAM localized γ-secretase activity is increased by administering to the subject an effective amount of a composition that inactivates, antagonizes, or decreases the level of ADORA2A. In some embodiments, the ADORA2A antagonist is istradefylline, preladenant, or tozadenant.

In some embodiments, the level of ER-MAM localized APP-C99 is reduced in cells of the subject by administering to the subject an ER-MAM localized γ-secretase activator or agonist.

In some embodiments, the level of ER-MAM localized APP-C99 is reduced in cells of the subject by administering to the subject an effective amount of a composition comprising mifepristone, miR-106b or a nucleic acid encoding miR-106b, an ITM2B inhibitor, or a TRPC6 inhibitor. In some embodiments, the TRPC6 inhibitor is larixyl acetate.

In some embodiments, the level of ER-MAM localized APP-C99 is reduced in cells of the subject by administering to the subject an effective amount of a composition that increases phosphorylation of APP at Thr668.

In some embodiments, the level of ER-MAM localized APP-C99 is reduced in cells of the subject by administering to the subject an effective amount of an antibody or a peptide that binds to C99.

In some embodiments, the level of ER-MAM localized APP-C99 is reduced in cells of the subject by administering to the subject an effective amount of a composition that increases the level of, activates, or agonises PICALM, PIMT, ADAM10, or ADAM17. In some embodiments, the composition that increases the level of PICALM, PIMT, ADAM10, or ADAM17 comprises a polypeptide or nucleic acid encoding PICALM, PIMT, ADAM10, or ADAM17.

In some embodiments, the level of ER-MAM localized APP-C99 is reduced in cells of the subject by administering to the subject an effective amount of a composition that inhibits endosome-to-MAM movement. In some embodiments, inhibiting endosome-to-MAM movement comprises reducing the level of FAM21, or a component of the WASH complex. In some embodiments, the level of FAM21 activity is reduced by administering an effective amount of a FAM21 RNAi.

In some embodiments, the level of ER-MAM localized APP-C99 is reduced in cells of the subject by administering to the subject an effective amount of a composition that inhibits, antagonizes, or decreases the levels of ErbB2. In some embodiments, the ErbB2 inhibitor is CL-387,785. In some embodiments, the level of ER-MAM localized APP-C99 is reduced in cells of the subject by administering to the subject an effective amount of a composition that promotes or increases the levels of phosphorylated PS1 on Ser367. In some embodiments, phosphorylation of PS1 on Ser367 is promoted or increased by casein kinase 1γ2. In some embodiments, the level of ER-MAM localized APP-C99 is reduced in cells of the subject by administering to the subject an effective amount of a composition that inhibits, antagonizes, or decreases the levels of Aβ/C99-mediated cell death. In some embodiments, the Aβ/C99-mediated cell death inhibitor is CP2, a tricyclic pyrone molecule.

In some embodiments, the level of ER-MAM localized APP-C99 is reduced in cells of the subject by reducing BACE1 activity. In some embodiments, the BACE1 is localized to endosomes.

In some embodiments, the level of ER-MAM localized APP-C99 is reduced in cells of the subject by administering to the subject a BACE1 inhibitor or antagonist. In some embodiments, the BACE1 activity is reduced by administering an effective amount of a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, all-trans retinoic acid (atRA), or a legumain inhibitor. In some embodiments, the PPAR-α inhibitor is GW7647. In some embodiments, the legumain inhibitor is NN1, NN4, or LE28. In some embodiments, the BACE1 activity is reduced by administering an effective amount of a composition that increases the level of, activates, or agonises ABCA1, UCHL1, LXR, or p38α-MAPK. In some embodiments, the composition that increases the level of ABCA1, UCHL1, LXR, MAPK11, MAPK12, MAPK13, or MAPK14 comprises a polypeptide or nucleic acid encoding ABCA1, UCHL1, LXR, MAPK11, MAPK12, MAPK13, or MAPK14. In some embodiments the endosome-localized BACE1 activity is reduced by administering an effective amount of a sterol-modified BACE1 inhibitor. In some embodiments, the LXR agonist is T090317, or Compound 9.

In some embodiments, the BACE1 activity is reduced by administering an effective amount of a composition that reduces, inhibits, antagonizes, or decreases the levels of BACE1 cleavage. In some embodiment, the composition that reduces BACE1 cleavage is an antibody to the BACE1 cleavage site. In some embodiments, the composition that inhibits BACE1 cleavage is verubacest (MK-8931) or JNJ-54861911 or AZD3293/LY3314814 or E2609 or CNP520. In some embodiments, the composition that inhibits BACE1 cleavage is Gleevec or DV2-103.

In some embodiments, the level or function of ER-MAM localized APP-C99 is reduced in cells of the subject by administering to the subject Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a CypD inhibitor, or U18666a. In some embodiments, the level or function of ER-MAM localized APP-C99 is reduced in cells of the subject by administering to the subject an effective amount of a composition that increases the level of, activates, or agonises ABCA1, SOAT1, cholesterol 25-hydroxylases (e.g. CH25H, CYP46A1), PICALM, ABCA7, ABCG1, SORL1 or TRPML1-3. In some embodiments, the composition that increases the level of ABCA1, SOAT1, CH25H, CYP46A1, PICALM, ABCA7, ABCG1, SORL1, or TRPML1-3 comprises a polypeptide or nucleic acid encoding ABCA1, SOAT1, CH25H, CYP46A1, PICALM, ABCA7, ABCG1, SORL1, or TRPML1-3. In some embodiments, the PTK2 inhibitor is PF-562271. In some embodiments, the TRPML1-3 agonist is ML-SA1. In some embodiments, the ABCA1 agonist is peptide CS-6253. In some embodiments, the SREBP inhibitor or miR33a/b inhibitor is methyl protodioscin. In some embodiments, the CypD inhibitor is cyclosporin A.

In some embodiments, the level or function of ER-MAM localized APP-C99 is reduced in cells of the subject by administering to the subject an effective amount of a LDL receptor inhibitor. In some embodiments, the LDL receptor is LRP1, LRP2, LRP5, LRP6, LRP8, LRP1B, LDLR, VLDLR, LRAD3, or CD36. In some embodiments, the CD36 LDL receptor inhibitor is sulfo-N-succinimidyl oleate (SSO).

In some embodiments, the level or function of ER-MAM localized APP-C99 is reduced in cells of the subject by administering to the subject an effective amount of a composition that reduces, downregulates, inhibits, antagonizes, or decreases the levels of SREBP2. In some embodiments, the composition that reduces SREBP2 is osmotin.

In some embodiments, the level or function of ER-MAM localized APP-C99 is reduced in cells of the subject by administering to the subject an effective amount of a composition that reduces, or decreases the levels of cholesterol. In some embodiments, the composition that reduces cholesterol is cyclodextrin.

In some embodiments, the level or function of ER-MAM localized APP-C99 is reduced in cells of the subject by administering to the subject an effective amount of a composition that inhibits, antagonizes, or decreases the levels of Cyclophilin D (CypD). In some embodiments, the composition that inhibits, antagonizes, or decreases the levels of Cyclophilin D (CypD) is Cyclosporin A (CsA).

In some embodiments, the level or function of ER-MAM localized APP-C99 is reduced in cells of the subject by administering to the subject an effective amount of a composition that inhibits, antagonizes, or decreases the levels of the scavenger receptor CD36. In some embodiments, the composition that inhibits, antagonizes, or decreases the levels of the scavenger receptor CD36 is sulfo-N-succinimidyl oleate (SSO).

In some embodiments, the level or function of ER-MAM localized APP-C99 is reduced in cells of the subject by administering to the subject an effective amount of a composition that activates, agonizes, or increases the levels of CYP11A1. In some embodiments, the composition that activates, agonizes or increases the levels of CYP11A1 is efavirenz.

In some embodiments, the level or function of ER-MAM localized APP-C99 is reduced in cells of the subject by reducing ER-mitochondrial connectivity. In some embodiments, ER-mitochondrial connectivity is reduced in cells of the subject by administering to the subject an effective amount of acetylcholine, a MFN2 inhibitor, a PACS2 inhibitor, a Reticulon-1 inhibitor, a MARCH5 inhibitor, a VAPB inhibitor. In some embodiments, ER-mitochondrial connectivity is reduced in cells of the subject by administering to the subject an effective amount of a composition that increases the level of, activates, or agonises, TCHP, Reticulon-4, Nogo-B, or FATE1. In some embodiments, the composition that increases the level of TCHP, Reticulon 4, NogoB, or FATE1 comprises a polypeptide or nucleic acid encoding TCHP, Reticulon 4, NogoB, or FATE1. In some embodiments, ER-mitochondrial connectivity is reduced in cells of the subject by administering to the subject an effective amount of a composition that inhibits, inactivates, antagonizes, or decreases the levels of GRP75. In some embodiments, the GRP inhibitor is MKT-077.

In some embodiments, the level or function of ER-MAM localized APP-C99 is reduced in cells of the subject by increasing hypoxia. In some embodiments, hypoxia is increased in cells of the subject by administering to the subject an effective amount of a composition that activates, agonises, or increases the level of HIF-α. In some embodiments, hypoxia is increased in cells of the subject by administering to the subject an effective amount of a composition that inactivates, antagonizes, or decreases the level of cholesterol synthesis. In some embodiments, hypoxia is increased in cells of the subject by administering to the subject an effective amount of a composition that activates, agonizes, or increases the levels of PS2V. In some embodiments, hypoxia is increased in cells of the subject by administering to the subject an effective amount of a composition that activates, agonizes, or increases the levels of ACAT1. In some embodiments, hypoxia is increased in cells of the subject by administering to the subject an effective amount of a composition that activates, agonizes, or increases the levels of cholesterol esterification. In some embodiments, hypoxia is increased in cells of the subject by administering to the subject an effective amount of a composition that activates, agonizes, or increases the levels of Recticulon4/Nogo-B. In some embodiments, the composition that activates, agonizes, or increases the levels of hypoxia in the cells of the subject is hypoxic conditions, such as exposing a subject to high altitude environment. In some embodiments, hypoxia is increased in cells of the subject by administering to the subject an effective amount of a composition that inactivates, antagonizes, inhibits, or decreases the levels of prolyl hydroxylase (PHD1/EGLN1, PHD2/EGLN2, or PHD3/EGLN3). In some embodiments, the composition that inactivates, antagonizes, inhibits, or decreases the levels of prolyl hydroxylase (PHD1/EGLN1, PHD2/EGLN2, or PHD3/EGLN3) is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

In certain aspects, the invention provides a method of treating Alzheimer's Disease in a subject in need thereof, comprising administering an effective amount of a composition comprising an ER-MAM localized γ-secretase activator or agonist, phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), auraptene (7-geranyloxycoumarin), mifepristone, miR-106b or a nucleic acid encoding miR-106b, an ITM2B inhibitor, a TRPC6 inhibitor, a composition that increases phosphorylation of APP at Thr668, an antibody or a peptide that binds to C99, an endosome-to-MAM movement inhibitor, a BACE1 inhibitor or antagonist, a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, or all-trans retinoic acid (atRA), a legumain inhibitor, Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a LDL receptor inhibitor, acetylcholine, a CypD inhibitor, U18666a, a MFN2 inhibitor, a PACS2 inhibitor, a Reticulon-1 inhibitor, a MARCH5 inhibitor, a VAPB inhibitor, a ADORA2A inhibitor or antagonist, an ErbB2 inhibitor or antagonist, a casein kinase 1γ2 agonist, a tricyclic pyrone molecule such as CP2, verubacest (MK-8931), JNJ-54861911, AZD3293/LY3314814, E2609, CNP520, Gleevec, DV2-103, a SREBP2 inhibitor or antagonist, cyclodextrin, a CypD inhibitor or antagonist, a CD36 inhibitor or antagonist, a CYP11A1 agonist, a GRP75 inhibitor or antagonist, a HIFα agonist, a PS2V agonist, a Reticulon4/Nogo-B agonist, a prolyl hydroxylase (PHD1/EGLN1, PHD2/EGLN2, or PHD3/EGLN3) inhibitor or antagonist. In some embodiments, the ADORA2A inhibitor or antagonist is istradefylline, preladenant, or tozadenant. In some embodiments, the ErbB2 inhibitor or antagonist is CL-387,785. In some embodiments, the composition that reduces SREBP2 is osmotin. In some embodiments, the CypD inhibitor or antagonist is Cyclosporin A (CsA). In some embodiments, the CD36 inhibitor or antagonist is sulfo-N-succinimidyl oleate (SSO). In some embodiments, the CYP11A1 agonist is efavirenz. In some embodiments, the GRP inhibitor or antagonist is MKT-077. In some embodiments, the prolyl hydroxylase (PHD1/EGLN1, PHD2/EGLN2, or PHD3/EGLN3) inhibitor or antagonist is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

In certain aspects, the invention provides a method of treating Alzheimer's Disease in a subject in need thereof, comprising administering an effective amount of a composition that increases the level of, activates, or agonises OCIAD2, TNF-α, interleukin-1β, interferon-γ, MEKK1, OSTC, KRTCAP2, KCNIP3, CREB, ADRB2, APMAP, CRF, PS1, PS2, EGR1, PICALM, PIMT, ADAM10, ADAM17, ABCA1, UCHL1, LXR, p38α-MAPK, SOAT1, cholesterol 25-hydroxylases (e.g. CH25H, CYP46A1), ABCA7, ABCG1, SORL1 or TRPML1-3, miR-106b, TCHP, Reticulon-4, NogoB, FATE1, CYP11A1, HIFα, PS2V, or ACAT1. In some embodiments, the composition that increases the level of OCIAD2, TNF-α, interleukin-1β, interferon-γ, MEKK1, OSTC, KRTCAP2, KCNIP3, CREB, ADRB2, APMAP, CRF, PS1, PS2, EGR1, PICALM, PIMT, ADAM10, ADAM17, ABCA1, UCHL1, LXR, MAPK11, MAPK12, MAPK13, MAPK14, SOAT1, CH25H, CYP46A1, ABCA7, ABCG1, SORL1, TRPML1-3, miR-106b, TCHP, Reticulon-4, NogoB, FATE1, CYP11A1, HIFα, PS2V, or ACAT1 comprises a polypeptide or nucleic acid encoding OCIAD2, TNF-α, interleukin-1β, interferon-γ, MEKK1, OSTC, KRTCAP2, KCNIP3, CREB, ADRB2, APMAP, CRF, PS1, PS2, EGR1, PICALM, PIMT, ADAM10, ADAM17, ABCA1, UCHL1, LXR, MAPK11, MAPK12, MAPK13, MAPK14, SOAT1, CH25H, CYP46A1, ABCA7, ABCG1, SORL1, TRPML1-3, miR-106b, TCHP, Reticulon-4, NogoB, FATE1, CYP11A1, HIFα, PS2V, or ACAT1. In some embodiments, the ADRB2 agonist is isoproterenol or clenbuterol. In some embodiments, the MEK1/2 inhibitor is PD98059, PD0325901, U0126, or Trametinib. In some embodiments, the TRPC6 inhibitor is larixyl acetate. In some embodiments, the endosome-to-MAM movement inhibitor is a FAM21 RNAi. In some embodiments, the LXR agonist is T090317, or Compound 9. In some embodiments, the legumain inhibitor is NN1, NN4, or LE28. In some embodiments, the BACE1 inhibitor is sterol-modified. In some embodiments, the TRPML1-3 agonist is ML-SA1. In some embodiments, the ABCA1 agonist is peptide CS-6253. In some embodiments, the PPAR-α inhibitor is GW7647. In some embodiments, the PTK2 inhibitor is PF-562271. In some embodiments, the SREBP inhibitor or miR33a/b inhibitor is methyl protodioscin. In some embodiments, the CypD inhibitor is cyclosporin A. In some embodiments, the LDL receptor is LRP1, LRP2, LRP5, LRP6, LRP8, LRP1B, LDLR, VLDLR, LRAD3, or CD36. In some embodiments, the CD36 LDL receptor inhibitor is sulfo-N-succinimidyl oleate (SSO).

In certain aspects, the invention provides a method of treating Alzheimer's Disease in a subject in need thereof, comprising exposing the subject to a high altitude environment. In some embodiments, the high altitude environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the high altitude environment is a treatment room with an artificial environment that simulates high altitudes.

In certain aspects, the invention provides a method of treating Alzheimer's Disease in a subject in need thereof, comprising exposing the subject to a low oxygen (hypoxic) environment. In some embodiments, the low oxygen (hypoxic) environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the low oxygen (hypoxic) environment is a treatment room with an artificial environment that simulates hypoxic conditions.

In some embodiments, the composition reduces the level of ER-MAM localized APP-C99 in cells of the subject.

In some embodiments, the level of APP-C99 is measured by measuring the number of lipid-droplets, the cholesterol content, the level of cholesterol esters, the level of oxidized cholesterol, the level of neutral sMase (nSMase) activity, or a combination thereof, in cells of the subject. In some embodiments the level of nSMase activity is measured by measuring the conversion of sphingomyelin to ceramide and phosphocholine.

In some embodiments, the composition reduces the ratio of cholesterol esters to free cholesterol in a sample from the subject compared to the ratio of cholesterol esters to free cholesterol in a sample from the subject prior to administration of the composition.

In some embodiments, the composition reduces the ratio of ceramide to sphingomyelin in a sample from the subject compared to the ratio of ceramide to sphingomyelin in a sample from the subject prior to administration of the composition.

In some embodiments, the composition reduces the ratio of C99 to total Aβ in a sample from the subject compared to the ratio of C99 to total Aβ in a sample from the subject prior to administration of the composition.

In some embodiments, the composition decreases the level of MAM-mediated phospholipid transport and/or synthesis in a sample from the subject compared to the level of MAM-mediated phospholipid transport and/or synthesis in a sample from the subject prior to administration of the composition.

In certain aspects, the invention provides a method of treating Alzheimer's Disease (AD) in a subject in need thereof, comprising: (a) determining the ratio of cholesterol esters to free cholesterol in a sample from the subject; and (b) administering a treatment for AD to the subject if the ratio of cholesterol esters to free cholesterol in a sample from the subject is higher than the ratio of cholesterol esters to free cholesterol in a sample from a subject that does not have AD.

In certain aspects, the invention provides a method of treating AD in a subject in need thereof, comprising: (a) determining the ratio of ceramide to sphingomyelin in a sample from the subject; and (b) administering a treatment for AD to the subject if the ratio of ceramide to sphingomyelin in a sample from the subject is higher than the ratio of ceramide to sphingomyelin in a sample from a subject that does not have AD.

In certain aspects, the invention provides a method of treating AD in a subject in need thereof, comprising: (a) determining the ratio of C99 to total Aβ in a sample from the subject; and (b) administering a treatment for AD to the subject if the ratio of C99 to total Aβ in a sample from the subject is higher than the ratio of C99 to total Aβ in a sample from a subject that does not have AD.

In certain aspects, the invention provides a method of treating AD in a subject in need thereof, comprising: (a) determining the level of MAM-mediated phospholipid transport and/or synthesis in a sample from the subject; and (b) administering a treatment for AD to the subject if the level of MAM-mediated phospholipid transport and/or synthesis in a sample from the subject is higher than the level of MAM-mediated phospholipid transport and/or synthesis in a sample from a subject that does not have AD.

In some embodiments, the treatment for AD comprises an ER-MAM localized γ-secretase activator or agonist, phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), auraptene (7-geranyloxycoumarin), mifepristone, miR-106b or a nucleic acid encoding miR-106b, an ITM2B inhibitor, a TRPC6 inhibitor, a composition that increases phosphorylation of APP at Thr668, an antibody or a peptide that binds to C99, an endosome-to-MAM movement inhibitor, a BACE1 inhibitor or antagonist, a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, or all-trans retinoic acid (atRA), a legumain inhibitor, Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a LDL receptor inhibitor, acetylcholine, a CypD inhibitor, U18666a, a MFN2 inhibitor, a PACS2 inhibitor, a Reticulon-1 inhibitor, a MARCH5 inhibitor, a VAPB inhibitor, a ADORA2A inhibitor or antagonist, an ErbB2 inhibitor or antagonist, a casein kinase 1γ2 agonist, a tricyclic pyrone molecule such as CP2, verubacest (MK-8931), JNJ-54861911, AZD3293/LY3314814, E2609, CNP520, Gleevec, DV2-103, a SREBP2 inhibitor or antagonist, cyclodextrin, a CypD inhibitor or antagonist, a CD36 inhibitor or antagonist, a CYP11A1 agonist, a GRP75 inhibitor or antagonist, a HIFα agonist, a PS2V agonist, a Reticulon4/Nogo-B agonist, a prolyl hydroxylase (PHD1/EGLN1, PHD2/EGLN2, or PHD3/EGLN3) inhibitor or antagonist, or a composition that increases the level of, activates, or agonises OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, p38α-MAPK, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1.

In some embodiments, the ADORA2A inhibitor or antagonist is istradefylline, preladenant, or tozadenant. In some embodiments, the ErbB2 inhibitor or antagonist is CL-387,785. In some embodiments, the composition that reduces SREBP2 is osmotin. In some embodiments, the CypD inhibitor or antagonist is Cyclosporin A (CsA). In some embodiments, the CD36 inhibitor or antagonist is sulfo-N-succinimidyl oleate (SSO). In some embodiments, the CYP11A1 agonist is efavirenz. In some embodiments, the GRP inhibitor or antagonist is MKT-077. In some embodiments, the prolyl hydroxylase (PHD1/EGLN1, PHD2/EGLN2, or PHD3/EGLN3) inhibitor or antagonist is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

In some embodiments, the treatment for AD comprises exposing the subject to a high altitude environment. In some embodiments, the high altitude environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the high altitude environment is a treatment room with an artificial environment that simulates high altitudes.

In some embodiments, the treatment for AD comprises exposing the subject to a low oxygen (hypoxic) environment. In some embodiments, the low oxygen (hypoxic) environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the low oxygen (hypoxic) environment is a treatment room with an artificial environment that simulates hypoxic conditions.

In certain aspects the invention provides, a method of reducing the level of endoplasmic reticulum-mitochondrial-associated membrane (ER-MAM) localized APP-C99 in cells of the subject, comprising: (a) determining the ratio of cholesterol esters to free cholesterol in a sample from the subject; and (b) administering a composition that reduces the level of ER-MAM localized APP-C99 in cells of the subject if the ratio of cholesterol esters to free cholesterol in a sample from the subject is higher than the ratio of cholesterol esters to free cholesterol in a sample from a subject that does not have Alzheimer's Disease.

In certain aspects the invention provides a method of reducing the level of endoplasmic reticulum-mitochondrial-associated membrane (ER-MAM) localized APP-C99 in cells of the subject, comprising: (a) determining the ratio of ceramide to sphingomyelin in a sample from the subject; and (b) administering a composition that reduces the level of ER-MAM localized APP-C99 in cells of the subject if the ratio of ceramide to sphingomyelin in a sample from the subject is higher than the ratio of ceramide to sphingomyelin in a sample from a subject that does not have Alzheimer's Disease.

In certain aspects the invention provides a method of reducing the level of endoplasmic reticulum-mitochondrial-associated membrane (ER-MAM) localized APP-C99 in cells of the subject, comprising: (a) determining the ratio of C99 to total Aβ in a sample from the subject; and (b) administering a composition that reduces the level of ER-MAM localized APP-C99 in cells of the subject if the ratio of C99 to total Aβ in a sample from the subject is higher than the ratio of C99 to total Aβ in a sample from a subject that does not have Alzheimer's Disease.

In certain aspects the invention provides a method of reducing the level of endoplasmic reticulum-mitochondrial-associated membrane (ER-MAM) localized APP-C99 in cells of the subject, comprising: (a) determining the level of MAM-mediated phospholipid transport and/or synthesis in a sample from the subject; and (b) administering a composition that reduces the level of ER-MAM localized APP-C99 in cells of the subject if the level of MAM-mediated phospholipid transport and/or synthesis in a sample from the subject is higher than the level of MAM-mediated phospholipid transport and/or synthesis in a sample from a subject that does not have Alzheimer's Disease.

In some embodiments, the composition that reduces the level of ER-MAM localized APP-C99 comprises an ER-MAM localized γ-secretase activator or agonist, phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), auraptene (7-geranyloxycoumarin), mifepristone, miR-106b or a nucleic acid encoding miR-106b, an ITM2B inhibitor, a TRPC6 inhibitor, a composition that increases phosphorylation of APP at Thr668, an antibody or a peptide that binds to C99, an endosome-to-MAM movement inhibitor, a BACE1 inhibitor or antagonist, a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, or all-trans retinoic acid (atRA), a legumain inhibitor, Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a LDL receptor inhibitor, acetylcholine, a CypD inhibitor, U18666a, a MFN2 inhibitor, a PACS2 inhibitor, a Reticulon-1 inhibitor, a MARCH5 inhibitor, a VAPB inhibitor, a ADORA2A inhibitor or antagonist, an ErbB2 inhibitor or antagonist, a casein kinase 1γ2 agonist, a tricyclic pyrone molecule such as CP2, verubacest (MK-8931), JNJ-54861911, AZD3293/LY3314814, E2609, CNP520, Gleevec, DV2-103, a SREBP2 inhibitor or antagonist, cyclodextrin, a CypD inhibitor or antagonist, a CD36 inhibitor or antagonist, a CYP11A1 agonist, a GRP75 inhibitor or antagonist, a HIFα agonist, a PS2V agonist, a Reticulon4/Nogo-B agonist, a prolyl hydroxylase (PHD1/EGLN1, PHD2/EGLN2, or PHD3/EGLN3) inhibitor or antagonist, or a composition that increases the level of, activates, or agonises OCIAD2, TNF-α, interleukin-13, interferon-γ, MEKK1, OSTC, KRTCAP2, KCNIP3, CREB, ADRB2, APMAP, CRF, PS1, PS2, EGR1, PIMT, ADAM10, ADAM17, LXR, p38α-MAPK, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, osmotin, PS2V, or ACAT1.

In some embodiments, the ADORA2A inhibitor or antagonist is istradefylline, preladenant, or tozadenant. In some embodiments, the ErbB2 inhibitor or antagonist is CL-387,785. In some embodiments, the composition that reduces SREBP2 is osmotin. In some embodiments, the CypD inhibitor or antagonist is Cyclosporin A (CsA). In some embodiments, the CD36 inhibitor or antagonist is sulfo-N-succinimidyl oleate (SSO). In some embodiments, the CYP11A1 agonist is efavirenz. In some embodiments, the GRP inhibitor or antagonist is MKT-077. In some embodiments, the prolyl hydroxylase (PHD1/EGLN1, PHD2/EGLN2, or PHD3/EGLN3) inhibitor or antagonist is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

In some embodiments, instead of administering a composition that reduces the level of ER-MAM localized APP-C99, the subject or cells are exposed to a high altitude environment. In some embodiments, the high altitude environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the high altitude environment is a treatment room with an artificial environment that simulates high altitudes.

I In some embodiments, instead of administering a composition that reduces the level of ER-MAM localized APP-C99, the subject or cells are exposed to a low oxygen (hypoxic) environment. In some embodiments, the low oxygen (hypoxic) environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the low oxygen (hypoxic) environment is a treatment room with an artificial environment that simulates hypoxic conditions.

In certain aspects the invention provides a method of determining if a subject has or is at risk of developing AD, comprising: (a) determining the ratio of cholesterol esters to free cholesterol in a sample from the subject; and (b) determining that the subject has or is at risk of developing AD if the ratio of cholesterol esters to free cholesterol in a sample from the subject is higher than the ratio of cholesterol esters to free cholesterol in a sample from a subject that does not have AD.

In certain aspects the invention provides a method of determining if a subject has or is at risk of developing AD, comprising: (a) determining the ratio of ceramide to sphingomyelin in a sample from the subject; and (b) determining that the subject has or is at risk of developing AD if the ratio of ceramide to sphingomyelin in a sample from the subject is higher than the ratio of ceramide to sphingomyelin in a sample from a subject that does not have AD.

In certain aspects the invention provides a method of determining if a subject has or is at risk of developing AD, comprising: (a) determining the ratio of C99 to total Aβ in a sample from the subject; and (b) determining that the subject has or is at risk of developing AD if the ratio of C99 to total Aβ in a sample from the subject is higher than the ratio of C99 to total Aβ in a sample from a subject that does not have Alzheimer's Disease.

In certain aspects the invention provides a method of determining if a subject has or is at risk of developing AD, comprising: (a) determining the level of MAM-mediated phospholipid transport and/or synthesis in a sample from the subject; and (b) determining that the subject has or is at risk of developing AD if the level of MAM-mediated phospholipid transport and/or synthesis in a sample from the subject is higher than the level of MAM-mediated phospholipid transport and/or synthesis in a sample from a subject that does not have Alzheimer's Disease.

In some embodiments, the sample is a blood sample. In some embodiments, the sample comprises cells of the subject.

BRIEF DESCRIPTION OF THE FIGURES

The patent or application file contains at least one drawing executed in clor. Copies of this patent or patent application publication with color drawing(s) will be provided by the United States Patent and Trademark Office upon request and payment of the necessary fee.

FIGS. 1A-C show the localization of C99 to MAM. (A) Western blots of fractions from SH-SY5Y cells (Tot, total homogenate; PM, plasma membrane; CM, crude mitochondria-endosomal fraction) treated with α- and/or γ-secretase inhibitors. The upper blot was exposed for different times to reveal C83 vs C99 (dotted line). (B) Western blots of a gradient (two parallel gels [separated by the vertical vertical dotted line]) from PS-DKO MEF CM fractions to reveal the differential distribution of C83 vs C99. Box denotes MAM-rich region. (C) ER-mitochondrial apposition: ER (light gray) and mitochondria (dark gray) in the indicated MEFs without and with BI (inhibiting C99 formation; see Western). *, Significant difference vs control; #, significant difference before and after BI addition.

FIGS. 2A-B show lipid droplet formation in γ-secretase-deficient cells. (A, B) Staining of the indicated cells with LipidTox Green to detect lipid droplets; quantitation at right.

FIGS. 3A-E show sphingolipid metabolism in PS-DKO MEFs. (A, B) Ceramide and sphingomyelin levels in total homogenate and in crude mitochondrial fractions. (C) De novo synthesis of ceramide (Cer) and sphingomyelin (SM). (D) Activities of acid (aSMase) and neutral (nSMase) sphingomyelinases. (E) SMase activity before and after BI. Dotted lines denote baseline levels.

FIGS. 4A-D show mitochondrial respiration (resting oxygen consumption rate [OCR]) in γ-secretase-deficient cells. (A) AD fibroblasts. (B) PS-DKO MEFs. (C) PS-DKO MEFs treated with BI. (D) PS-DKO MEFs treated with myriocin.

FIGS. 5A-C show cholesterol homeostasis in PS-DKO MEFs. (A) HMGCR activity. (B) Pulse-chase analysis of 3H-cholesterol uptake. (C) Cholesterol content visualized by filipin staining. Note increased "punctae" after treatment with DAPT (left panels) and its abrogation after treatment with BI (right panels). Quantitation at right.

FIGS. 6A-E show a model of AD pathogenesis. (A) In the normal situation (A, B), the relatively small amount of unprocessed C99 stimulates cholesterol uptake [1]. After filling the PM pools, cholesterol traffics to MAM to maintain lipid homeostasis [2]. As cholesterol gets incorporated into membranes, sphingomyelin (SM) synthesis is concomitantly stimulated [3], forming lipid raft domains. (B) The increase in cholesterol content in MAM activates γ-secretase cleavage of C99 [4]. Subsequently, C99 cleavage stops cholesterol uptake and sphingolipid synthesis [5]. (C) In AD (C-E), defective γ-secretase cleavage causes C99 to accumulate in the MAM [6], triggering the uptake of extracellular cholesterol from lipoproteins, and the synthesis of sphingomyelin [7], thereby expanding the pool of cholesterol at the PM and the MAM. (D) As cholesterol levels exceed a threshold, SMases are also activated, hydrolyzing SM to Cer [8] and mobilizing more cholesterol to the MAM. In a futile effort to re-establish homeostasis, the HMGCR pathway is shut off, excess cholesterol at the MAM is converted into cholesteryl esters (CE) by ACAT1 and stored in lipid droplets [9]. The excess cholesterol and the concomitant increase in MAM-localized SM increase the physical area of ER-mitochondrial apposition, inducing many of the MAM-mediated features of AD, including mitochondrial deficits [10]. (E) This cycle, coupled with the deleterious effects of increased ER-mitochondrial apposition, ultimately converge to produce AD. Citations refer to references listed in Example 1.

FIGS. 7A-B show localization of C99 to MAM in mice. (A) Western blots of normal mouse brain CM fractions from a gradient (two parallel gels [dotted line]), probed as in FIG. 1B. Boxes denote MAM-rich regions. (B) Western blots of brain fractions from PS1-KI$^{M146V}$ mice (Tot, total brain homogenate). Note that as compared to C83, C99 is located predominantly in the MAM fraction in both WT and KI mice. Moreover, in the KI mice (in which γ-secretase activity is reduced), both species are increased compared to the levels in the WT mice (30 μg total protein loaded in each lane).

FIGS. 9A-H show acid (aSMase) and neutral (nSMase) sphingomyelinase activities in various cell types. (A) Species of ceramide and sphingomyelin in crude mitochondrial fractions from WT and PS-DKO MEFs. (B) Transcription of a gene encoding the neutral sphingomyelinase 2 (nSMase2; gene SMPD3), in WT and PS-DKO MEFs, by quantitative reverse transcriptase-polymerase chain reaction (qRT-PCR). (C) SMase activities in brain from PS1-KI$^{M146V}$ mice. Note increased SMase in the mutant cells, which have reduced γ-secretase activity (and increased C99) compared to WT. (D) SMase activities in SH-SY5Y cells. Note significantly increased SMase activities following inhibition of γ-secretase activity (and increased C99). (E) SM synthesis in APP-DKO MEFs. (F) SMase activities in APP-DKO MEFs (lacking C99). (G) Both aSMase (aSM) and nSMase (nSM), but particularly nSMase, are increased significantly in PS-DKO MEFs (containing C99 but lacking both Aβ and AICD) vs WT cells. These activities are essentially unchanged in the presence of either Aβ (monomers of Aβ40 and Aβ42 added to the medium at a ratio of Aβ40:Aβ42 of 10:1; 6 ng/ml total concentration of Aβ) or AICD (expressed transiently from a plasmid). n.s., not significant. (H) Sphingolipid levels after addition of fluorescent sphingomyelin (left, detection; right, quantitation).

FIGS. 10A-D show analysis of sphingolipid metabolism in WT and PS1-DKO MEFs. (A) Approximate distribution of steady-state levels of SM and Cer in various cell compartments in WT MEFs (numbers in boxes denote % of the total in the indicated compartment). The "Other" value was derived from subtracting the MAM+ER+Mito values from those in the total homogenate; we consider this compartment to be mainly Golgi and plasma membrane. (B) Distribution of SMase activity in the indicated subcellular compartments in PS-DKO MEFs normalized to the corresponding values in the WT MEFs (dotted lines). Note the overall increase in nSMAse levels in the DKO cells. (C) Western blot to detect nSMase protein in the indicated compartments (analyzed in panel b). (D) Increased nSMAse activity in MAM isolated from PS1-KI$^{M146V}$ brain compared to WT brain. *, significant difference vs control value (dotted lines), $p<0.01$.

FIGS. 11A-I show mitochondrial bioenergetics in γ-secretase-deficient cells. All respiratory chain (R.C.) assays, measured as initial oxygen consumption rate (OCR), were performed using the Seahorse XF24 Flux Analyzer. (A) Mitochondria from PS1-KI$^{M146V}$ brain. (B) SH-SY5Y cells treated with DAPT. (C) qRT-PCR to measure mRNA levels of PGC-1α (left panel), a master regulator of mitochondrial biogenesis, in SH-SY5Y cells before and after addition of DAPT and BI (which do not affect mitochondrial biogenesis, as assayed by a western to VDAC1 [right panel]). Note lack of an effect on PGC-1α levels in γ-secretase-deficient cells. n.s., not significant. (D) R.C. deficiency in fibroblasts from an FAD patient (AG06840) was rescued following treatment with a BACE1 inhibitor (in which C99 production is abrogated). (E) Western blot to confirm plasmid-based expression of FL-APP (upper panel) or C99 (lower panel) in APP-DKO MEFs. (F) APP-DKO MEFs. (G) Complex I and II activities in which malate-pyruvate or succinate-rotenone, respectively, were added to permeabilized PS-DKO MEFs (left) and APP-DKO MEFs (right). Note significant decrease in OCR in PS-DKO MEFs but an increase in APP-DKO MEFs. (H) ELISA demonstrating that plasmid-expressed C99 is processed correctly by endogenous γ-secretase to generate Aβ40. AICD, a negative control, had no effect. (I) Left: OCR in WT or PS-DKO cells is unaffected by treatment with the α-secretase inhibitor TAPI-1. Center: Addition of Aβ42 oligomers to APP-DKO cells. Right: Addition of monomers of Aβ40 and Aβ42 to APPDKO cells (added at a ratio of 10:1 Aβ40:Aβ42, total concentration of Aβ was 6 ng/ml).

FIGS. 12A-B shows OCR in crude mitochondrial extracts isolated from brain homogenates from PS1-KI$^{M146V}$ mice analyzed at various ages (indicated in months) compared to that in the corresponding WT mice (dotted lines). In each assay, OCR is first measured at baseline; this is State 2 (i.e. initial respiration in the presence of added substrates [e.g. malate+pyruvate to measure complex I (A); succinate+rotenone to measure complex II](B)). ADP is then added; this is State 3 (i.e. maximum respiration in the presence of the added substrates). Oligomycin is then added to inhibit ATP synthase; this mimics State 4 (i.e. respiration after added ADP has been consumed and ATP can no longer be produced). Finally the uncoupler FCCP is added; this is State 3U (i.e. state 3 "uncoupled," the maximum uncoupler-activated respiration that does not inhibit respiration [also called "noncoupled" respiration]. Note the steady decline in OCR that appears to accelerate at 8 months of age. n=3.

FIGS. 13A-F show cholesterol metabolism in γ-secretase-deficient cells. (A) HMGCR activity in FAD fibroblasts (patient GG3). *, $p<0.01$. (B) 3H-cholesterol uptake at steady-state (left) and by pulse-chase analysis (right) in PS-knockdown mouse CCL131 cells. (C) 3H-cholesterol uptake in FAD fibroblasts compared to that in age-matched controls (dotted lines). (D) Uptake of Bodipy-labeled fluorescent cholesterol in PS-DKO MEFs; quantitation at right. Note reduced uptake following treatment with a BACE1 inhibitor. (E) Filipin staining of fibroblasts from two controls (OA [40 years old] and AG08517 [66 y.o.]), one SAD patient (AG08379; 60 y.o.), and 3 FAD patients (GG3 [M146L mutation; ~40 y.o.]; AG06840 [A246E; 18 y.o.]; and WA [L418F mutation; 33 y.o.]). Other analyses on these cells have been reported elsewhere (5). (F) Ratio of CE:free cholesterol in WT vs PS-DKO MEFs.

FIGS. 14A-C show inhibition of SMases affects lipid droplet formation. (A) Example of the treatment of PS1-DKO MEFs with desipramine (DA) and GW4869 (GW) to inhibit aSMAses and nSMases, respectively, followed by visualization of lipid droplets with LipidTox Green. Quantitation of lipid droplets is at right. (B) Treatment of SH-SY5Y cells, as in (A). (C) Visualization of cellular cholesterol by staining with filipin in WT MEFs treated with DAPI or with the nSMAse inhibitor GW4869 (first 3 panels) and in PS-DKO MEFs treated with the α-secretase inhibitor TAPI-1 or with GW4869 (last 3 panels).

FIGS. 15A-C show localization of C99 to MAM. (A) Representative confocal image of a WT MEF show that C99 and mitochondria partially colocalize in those areas where ER (white) is also present (i.e. MAM). Note how C99 colocalizes with areas where mitochondria and ER are apposed (left-most arrow), compared to those of "free" mitochondria (right-most arrow) that do not contain C99 (middle arrow). Size bars=20 μm (B) Western blot of fractions from mouse brain (Tot, total homogenate; PM, Plasma membrane; CM, crude membrane fractions) probed with the indicated antibodies. (C) Representative immunoelectron microscopy image of PS-KO cells incubated with antibodies against APP-CTF conjugated with immunogold particles show significant labeling in MAM regions.

FIGS. 16A-B show ER-mitochondrial apposition is regulated by C99. (A) ER (Sec61β-GFP) and mitochondria (DSRed2-Mito) in the indicated MEFs without and with BI (inhibiting C99 formation; see Western). Large boxes are enlargements of the small boxes. Size bars=20 μm (Average of n=4 independent experiments±SD. * $p<0.05$). (B) Quantitation by ImageJ analysis of the colocalization of ER and mitochondrial signals from experiments like the one shown in (A). The Western blot indicates the APP-CTF levels in the indicated cells. Average of n=4 independent experiments±SD; * $p<0.05$).

FIGS. 17A-E show sphingolipid metabolism in PS-DKO MEFs. (A, B) Ceramide (A) and sphingomyelin (B) levels in total homogenate and in crude mitochondrial fractions in WT and PS-DKO MEFs. Lipid units are represented as molar mass over total moles of lipids analyzed (mol %) (average of n=5 independent experiments±S.D. * $p<0.05$). (C) Ceramide and sphingomyelin levels in MAM isolated from WT and PS-DKO MEFs. Lipid units are represented as molar mass over total moles of lipids analyzed (mol %) (average of n=3 independent experiments±S.D. * $p<0.05$). (D) De novo synthesis of ceramide (Cer) and sphingomyelin (SM) in WT and PS-DKO MEFs (average of n>5 independent experiments±S.D. * $p<0.05$). (E) Activities of acid (aSMase) and neutral (nSMase) sphingomyelinases before and after BI (average of n=5 independent experiments±S.D. * $p<0.05$).

FIGS. 18A-C show MAM participates in the regulation of sphingolipid metabolism. (A-B) Distribution of SMase activity in the indicated subcellular compartments in WT and PS-DKO MEFs. Note the overall increase in nSMAse (A) levels in the PS-DKO cells (average of n=5 independent experiments±SD * $p<0.05$). (C) Western blot of the indicated fractions from WT and PS-KO MEFs (probed with antibodies against the indicated markers) to detect the levels of nSMase protein in the indicated compartments. (TH, total homogenate; CM, crude membrane fraction; C.I., complex I (NDUFA9)).

FIGS. 19A-E show mitochondrial dysfunction is the consequence of increased sphingolipid turnover. (A) Respiratory chain deficiency (as measured by initial oxygen consumption rate [OCR]) in PS-DKO cells was rescued after treatment with myriocin (inhibitor of the de novo sphingolipid synthesis pathway) (average of n=3 independent experiments±S.D. * $p<0.05$). (B, C) In-gel complex I (B) and complex IV (C) activity staining in mitochondria from WT and PS-DKO cells after the indicated treatments. (D, E) Quantification of specific bands shown in (B) and (C). Note that chemical or genetic inhibition of γ-secretase results in decreased supercomplex I+III+IV activity. This effect can be rescued by inhibition of C99 production (with a BACE1 inhibitor [BI]) or by inhibition of ceramide production with myriocin (Myr). Dotted lines denote baseline levels (average of n=3 independent experiments±S.D. * $p<0.05$ vs baseline levels).

FIGS. 20A-O show mitochondrial bioenergetics in γ-secretase-deficient cells. All respiratory chain assays (initial oxygen consumption rate [OCR]) were performed using the Seahorse XF24 Flux Analyzer. (A) Fibroblasts from FAD and SAD patients. (B) Mitochondria from PS1-$KI^{M146V}$ brain. (C) Western blot from homogenates from the indicated cells probed against mitochondrial markers (VDAC and TOM20) and loading controls (D, E) Complex I and II activities in which malate-pyruvate or succinate-rotenone, respectively, were added to permeabilized PS-DKO MEFs (D) and APP-DKO MEFs (E). Note significant decrease in OCR in PS-DKO MEFs but an increase in APP-DKO MEFs. (F) qRT-PCR to measure mRNA levels of mtDNA-encoded COX1 as a as measure of mtDNA in WT and PS-DKO cells before and after addition of DAPT and BI. (n.s.=not significant). (G) Western blot of total homogenates of WT, PS-DKO, and PS-DKO cells treated with BACE1 inhibitor (BI). Note that BI treatment eliminates the accumulation of APP C-terminal fragments in PS-DKO MEFs, without changes in the levels of mitochondria (VDAC). (H) OCR in WT or PS-DKO cells is unaffected by treatment with the γ-secretase inhibitor TAPI-1. (I) qRT-PCR to measure mRNA levels of PGC-1α, a master regulator of mitochondrial biogenesis, in WT and PS-DKO cells before and after addition of DAPT and BI (which do not affect mitochondrial biogenesis). Note lack of an effect on PGC-1α levels in γ-secretase-deficient cells. n.s., not significant. (J) Western blot from total homogenates of SHSY5Y cells treated with DMSO and α-, β-, and γ-secretase inhibitors probed with the indicated antibodies. Note that none of the treatments change the levels of mitochondria (VDAC). Loading control in the right panel. (K, L) Addition of monomers of Aβ40 and Aβ42 (added at a ratio of 10:1 Aβ40:Aβ42, total concentration of Aβ was 6 ng/ml) to PS-DKO cells (K), or to APP-DKO cells (L) did not affect mitochondrial respiration. (M) Addition of Aβ42 oligomers to WT and APP-DKO cells at a 10 μM concentration decreased respiration. (N) Respiratory chain deficiency in fibroblasts from an FAD patient (AG06840) was rescued following treatment with a BACE1 inhibitor (in which C99 production was abrogated) (M) Western blot showing how transient transfection of C99 in APP-DKO cells did not affect mitochondrial levels (TOM20) (all experiments represent the average of n>5 independent experiments; n.s., non significant).

FIGS. 21A-I show localization of C99 to MAM in PS1-KI$^{M146V}$ mice. (A) Representatice confocal images from COS-7 cells transfected with C99, mitochondria, and Sec6β to label ER. Arrows indicate areas of colocalization between ER and C99 and contact areas between ER and mitochondria where C99 is present. (B) Scheme showing the protocol followed to isolate the subcellular fractions analyzed by Western blot. (C) Example of western blot analysis of subcellular fractions from mouse liver obtained using the protocol shown in S2B, probed against specific markers for each indicated compartment. (D) Western blot of subcellular fractions from SHSY5Y cells treated with α and γ-secretase inhibitors to reveal the differential localization of APP CTF fragments. Note that as compared to C83, C99 is located predominantly in the MAM fraction. (E) Scheme showing the protocol followed to purify subcellular fractions by continuous sucrose gradients analyzed by Western blot in FIG. 7A. (F) Representative electron microscopy images of PS-DKO cells incubated with antibodies against APP-CTF conjugated with immunogold particles show significant labeling in MAM regions (brackets; ER regions are shaded to facilitate its visualization). (G, H) Western blot of total homogenates of embryonic cortical neurons explanted from WT and PS1KI$^{M146V}$ mice (G), and fibroblasts from AD patients (H) show higher levels of C99 in mutant samples vs. controls. Tubulin and vinculin are loading controls. Quantifications of western blot bands normalized by loading controls are shown in the right panels. (I) Western blot of subcellular fractions isolated from WT and PS1-KI$^{M46V}$ show increased levels of C99 in total homogenates (TH), ER and MAM fractions. Note that AICD levels are not significantly changed compared to C99 (quantification on the right panel).

FIGS. 23A-D shows analysis of sphingolipid metabolism in WT and PS1-DKO MEFs. (A) Phosphatidylserine (PtdSer) content in subcellular fractions isolated from WT and PS-DKO cells. Lipid values are represented as molar mass over total lipids isolated (mol %) per unit of protein. Note the substantial increase in PtdSer in MAM fractions (values represent the average of n=3 independent experiments±S.D. * p<0.05 vs corresponding WT value; n.s., not significant). (B) PtdSer content in crude membranes isolated from WT, PS-DKO, and PS-DKO cells treated with BACE1 inhibitor. Lipid values ae represented as molar mass over total lipids isolated (mol %) per unit of protein. Note the substantial decrease in PtdSer content in mutant cells after inhibiting the production of C99 (values represent the average of n=3 independent experiments±S.D. * p<0.05; n.s., not significant). (C, D) Sphingomyelin (C) and ceramide (D) levels in crude membranes isolated from WT, PS-DKO, and PS-DKO cells treated with BACE inhibitors. Lipid values are represented as molar mass over total lipids isolated (mol %) per unit of protein. Note that BI treatment rescues sphingolipid homestasis in mutant cells (values represent the average of n=3 independent experiments±S.D. * p<0.05; n.s., not significant).

FIGS. 24A-D show supercomplex assembly is altered in γ-secretase deficient cells. (A) Western blot of blue-native PAGE gels to detect complex I (A), and complex III (B) to reveal respiratory supercomplexes in mitochondria from WT and PS-DKO cells after the indicated treatments. Note that chemical or genetic inhibition of γ-secretase results in decreased supercomplex I+III+IV assembly. Inhibition of C99 production by BACE inhibitor (BI) or inhibition of ceramide production by myriocin (Myr) increase the assembly of supercomplexes I+III and I+III+IV as measured by anti-complex I antibodies, and of supercomplex III+IV as measured by anti-complex III antibodies. (C) As loading control, the same samples from (A) and (B) were analyzed by western blot to reveal Tom20 (a protein localized in the mitochondrial outer membrane. (D) Coomasie staining of membranes analyzed in (A) and (B) show no differences in sample loading.

FIGS. 25A-B show mitochondrial dysfunction in PS1-KI$^{M146V}$ mice. The steady decline in OCR that appears to accelerate at 8 months of age, correlating with (A) a significant decrease in supercomplex activity, as measured by in-gel staining complex IV activity in mitochondria isolated from brain samples from 8 months old mice (left panel). As loading control, same membranes were analyzed by Coomasie staining, and the same samples were examined by western blot to detect Tom20 (right panel). (B) Quantification of bands from (A) by densitometry (all experiments represent the average of n=3 independent experiments±S.D. * p<0.05; n.s., not significant).

FIGS. 26A-D show the effects of secretase inhibitors on APP processing. (A) APP processing pathways and APP processing inhibitors (TAPI-1; BI; DAPT). TAPI-1 inhibits α-secretase (thereby abrogating C83 production), BACE1 inhibitor IV inhibits β-secretase (thereby abrogating C99 production), and DAPT inhibits γ-secretase (thereby increasing C99 production by abrogating Aβ/AICD production). Note that once produced, Aβ is exported from the cell whereas AICD travels to the nucleus. (B-D) Western blots using antibodies to detect APP C-terminal fragments (CTFs). Note in (D) that C99 was transfected into APP-DKO cells.

FIGS. 27A-D show the localization of C99 to MAM in mice and humans. (A) Western blots of total homogenates of embryonic cortical neurons explanted from WT and PS1-KI$^{M146V}$ mice, showing higher levels of C99 in mutant mice vs controls. Tubulin is a loading control. Quantifications of the western blot bands normalized to tubulin are shown in the right panel. (B) Western blot of subcellular fractions isolated from WT and PS1-KI$^{146V}$ mice show increased levels of C99, especially in the MAM fractions (quantitation at right panel). TH, total homogenate. (C) Quantitation of western blot signals of CTFs in fibroblasts from control and AD patients, showing their accumulation in patient cells. (D) Western blots of subcellular fractions from human SH-SY5Y cells treated with α- and γ-secretase inhibitors to reveal the differential localization of APP-CTF fragments (i.e. C83 and C99). Note that as compared to C83, C99 is located predominantly in the MAM fraction. *, $p<0.05$.

FIGS. 28A-B show accumulation of lipid droplets (containing cholesteryl esters) is regulated by C99. (A) Example of staining of the indicated cells with LipidTox Green to detect lipid droplets (LDs), before and after addition of BACE1 inhibitor (BI) to decrease C99. Quantitation of lipid droplets at right. Size bars=20 μm. (B) Quantitation of LDs in the indicated cells, treated as in (A). Note the rescue of LD formation upon treatment with BI to reduce C99, in all cell types examined.

FIGS. 29A-H show accumulation of C99 in PS-DKO MEFs alters sphingolipid metabolism. (A, B) Sphingolipid levels are decreased (A) and ceramide levels are correspondingly increased (B) in total homogenates and in crude mitochondrial fractions (containing MAM) in PS-DKO MEFs compared to WT cells. (C) These changes are even more pronounced in MAM isolated from WT and PS-DKO MEFs. (D) De novo synthesis of ceramide (Cer) and sphingomyelin (SM) is upregulated in PS-DKO MEFs vs WT. (E) The activities of acid (aSMase) and neutral (nSMase) sphingomyelinases are reduced significantly upon inhibition of BACE1 (BI), implying that increased C99 is responsible for these effects. (F) In agreement with (E), there is a dramatic upregulation of SMase activity, and a striking relocalization of SMase protein to the MAM compartment (circles) in PS-DKO MEFs. (G) These data are consistent with the biochemistry, in which sphingomyelin is converted into ceramide by sphingomyelinases. (H) Treatment of PS-DKO cells with a BACE1 inhibitor reverses the changes in sphingomyelin and ceramide, demonstrating that C99, and not Aβ, is the cause of the sphingolipid alterations. *, $p<0.05$.

FIGS. 30A-C show consequences of mutating C99. Point mutations were introduced into the cholesterol-binding domain of C99, and the WT and mutant C99 constructs were transfected (with and without GFP-appended to their C-termini) into MEFs. (A) Western blots of the detergent-resistant membrane fraction from crude mitochondria isolated from C99-WT and C99-Mutant constructs transfected into APP-DKO MEFs, treated with Triton X-100, and loaded onto a sucrose gradient. Equal amounts of material were loaded in each gradient. Note the ~50% decrease in the amount of C99-Mutant localized to the detergent-resistant membrane fraction (i.e. MAM) compared to WT. (B) The decrease of C99-Mutant in the MAM resulted in a significant reduction (i.e. improvement) in the $A\beta_{42}$:$A\beta_{40}$ ratio, a well-recognized marker of AD pathology. *, $p<0.05$. (C) Immunolocalization of the WT and C99-Mutant constructs tagged with GFP at their C-termini (left) and of mitochondria (DsRed2-Mito; middle) transfected into WT-MEFs. Note the distribution of MAM-localized C99-WT-GFP near mitochondria (white) compared to that of C99-Mutant-GFP, which is much less colocalized with both ER and mitochondria than is C99-WT-GFP. Note also that a portion of the GFP signal from C99-WT-GFP is present in the nucleus: this is the AICD fragment derived from cleavage of C99 by MAM-localized γ-secretase activity. Importantly, there is essentially no nuclear GFP signal in the cells transfected with C99-Mutant-GFP, consistent with the idea that C99-mutant is not cleaved into AICD because it is essentially absent from the MAM compartment. Thus, mutating C99 reduces its localization to MAM.

FIGS. 32A-D shows two related AD treatment strategies designed to reduce C99-mediated increases in ceramide levels. (A) Ceramide synthesis pathways and inhibitors. (B) Lipid droplet formation (i.e. cholesterol ester synthesis) was rescued after treatment of PS-DKO cells (with increased C99) with desipramine and GW4869, inhibitors of aSMases and nSMases, respectively. Quantitation at right. (C) Desipramine treatment in the indicated cells significantly reduced the $A\beta_{42}$:$A\beta_{40}$ ratio. (D) Mitochondrial dysfunction (as measured by reduced initial oxygen consumption rate [OCR]) in PS-DKO cells, due to elevated ceramide, was rescued by treatment with myriocin, an inhibitor of de novo ceramide synthesis. These experiments indicate that interdicting the sphingolipid pathway is a strategy to treat AD driven by accumulations of C99. *, $p<0.05$ vs baseline WT levels.

FIGS. 33A-B show two related AD treatment strategies designed to reduce C99-mediated increases in cholesterol levels in presenilin-mutant cells. Staining of cells with filipin to visualize free cholesterol. (A) Inhibition of Cyclophilin D with 100 nM cyclosporin A (CsA) reduces cholesterol levels in presenilin-mutant cells. Quantitation at right. (B) Inhibition of CD36, a multifunctional receptor that imports cholesterol into cells, with 250 nM sulfo-N-succinimidyl oleate (SSO), reduces cholesterol levels in presenilin-mutant cells. Note that in response to the C99-mediated perturbation of cholesterol homeostasis, the expression of the low-density lipoprotein receptor LRP1, which is normally a preferred cholesterol receptor, is significantly downregulated, whereas that of the CD36 (also called fatty acid translocase, or FAT) is massively upregulated. This likely explains why SSO was so effective in reducing cholesterol levels in the DKO cells. *, $p<0.05$.

FIGS. 36A-E show mitochondrial respiration [oxygen consumption rate (OCR)] in γ-secretase-deficient cells. A.

Figure 1C:
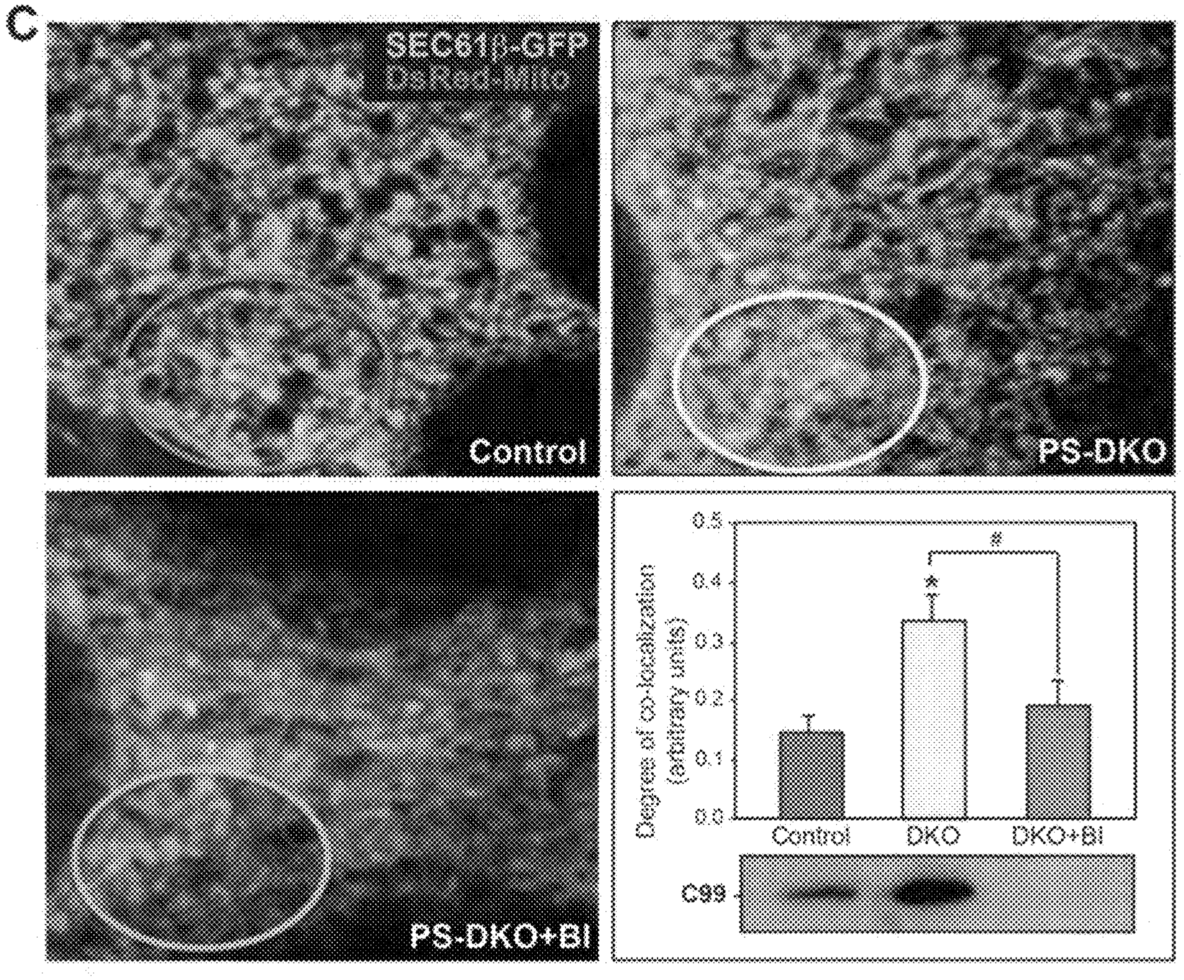

Oxygen consumption rate in AD fibroblasts (FAD). B. Oxygen consumption rate in PS—DKO MEFs. C. Oxygen consumption rate in SH-SY5Y cells treated with DAPT, an inhibitor of γ-secretase activity. C. Oxygen consumption rate in APP-DKO MEFs before and after overexpression of C99. PS-DKO MEFs treated with BACE inhibitor (BI). Data information: Data represent averages of n>5 independent experiments±SD. *P<0.05. Analysis by unpaired t-test.

FIGS. 37A-F show localization of C99 to MAM. A Western blot of fractions from mouse brain probed with the indicated antibodies (30 lg of protein per lane). PM, plasma membrane; CM, crude membrane fractions. B Western blot of subcellular fractions from SH-SY5Y cells treated with α- and γ-secretase inhibitors to reveal the differential localization of APP-CTF fragments. Note that C99 is located predominantly in the MAM fraction (30 μg of protein per lane). Tot, Total homogenate. C The crude membrane fraction (CM) from mouse brain was treated with detergent, purified on a continuous sucrose gradient, and gradient fractions were analyzed by Western blot [two parallel gels (dotted line)], probing with antibodies to detect the indicated marker proteins. Blue dotted boxes indicate areas of the gradient enriched in endosomal and lysosomal markers. Pink dotted boxes indicate areas of the gradient enriched in MAM markers. D The same analysis using crude membrane fractions from PS-DKO MEFs to reveal the differential distribution of C83 vs. C99. E Representative confocal image of a DAPT-treated COS-7 cell shows that uncleaved C99 (red) and mitochondria (blue) can colocalize only in those areas where ER (green) is also present (i.e., MAM). Note how C99 colocalizes with areas where mitochondria and ER are apposed [white arrows in Merge (boxed), also shown in the expanded view (Merge-Zoom)]. Scale bars=20 μm in top panels, 10 μm in bottom (Merge-Zoom) panel. F Representative immunoelectron microscopy image of PS-DKO cells incubated with antibodies against APP-CTF conjugated with immunogold particles, showing retention of C99 in MAM areas of the ER. The ER is colored in green, and the mitochondrial outer membrane in red. Note significant labeling in MAM regions (bracketed area, highlighted in inset).

FIGS. 38A-D show ER-mitochondrial apposition is regulated by C99. A Localization of ER (green) and mitochondria (red) in the indicated MEFs without and with BACE1 inhibitor (inhibiting C99 formation; see Western in panel B). Large boxes in the Merge are enlargements of the small boxes. Scale bars=20 μm. B Quantitation by ImageJ analysis of the colocalization of ER and mitochondrial signals from experiments like the one shown in (A) (average of n=4 independent experiments±SD). *P<0.05. Analysis by unpaired t-test. The Western blot indicates the APP-CTF levels in the indicated cells (30 μg of protein per lane). C ACAT1 activity in WT and PS-DKO MEFs in the presence and absence of α-, β-, and/or γ-secretase inhibitors (average of n=4 independent experiments±SD). *P<0.05. Analysis by unpaired t-test. ACAT activity was normalized by controls (WT incubated with vehicle [DMSO]). D Staining of the indicated cells with LipidTox Green to detect lipid droplets. Scale bars=20 μm.

FIGS. 39A-E show sphingolipid metabolism in PS-DKO MEFs. A, B Ceramide (A) and sphingomyelin (B) levels in total homogenate and in crude mitochondrial fractions in WT and PS-DKO MEFs. Lipid units are represented as molar mass over total moles of lipids analyzed (mol %) (average of n=5 independent experiments±SD). C Ceramide and sphingomyelin levels in MAM isolated from WT and PS-DKO MEFs. Lipid units are represented as nmol/μg of protein over total nmoles of lipids analyzed (average of n=3 independent experiments±SD). D De novo synthesis of ceramide (Cer) and sphingomyelin (SM) in WT and PS-DKO MEFs (average of n>5 independent experiments±SD). E Activities of acid (aSMase) and neutral (nSMase) sphingomyelinases before and after BI (average of n=5 independent experiments±SD). Data information: *P<0.05. Analysis by unpaired t-test.

Figure 40A:
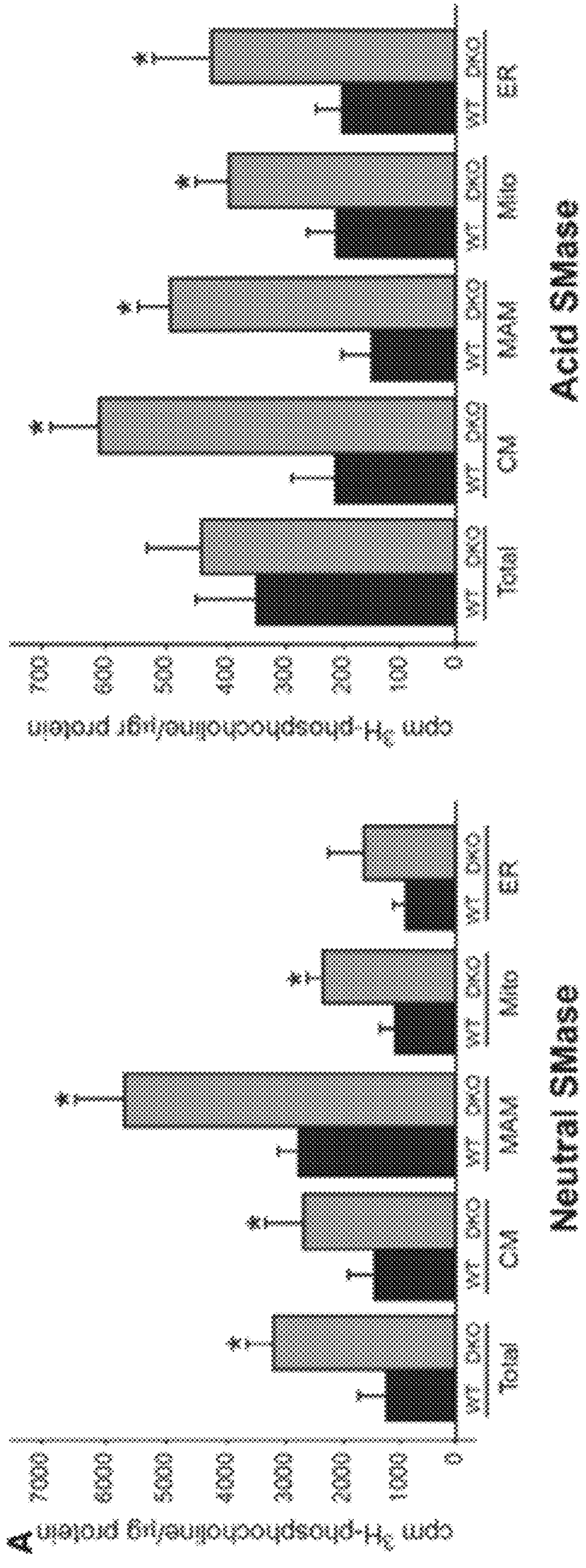
Figure 40B:
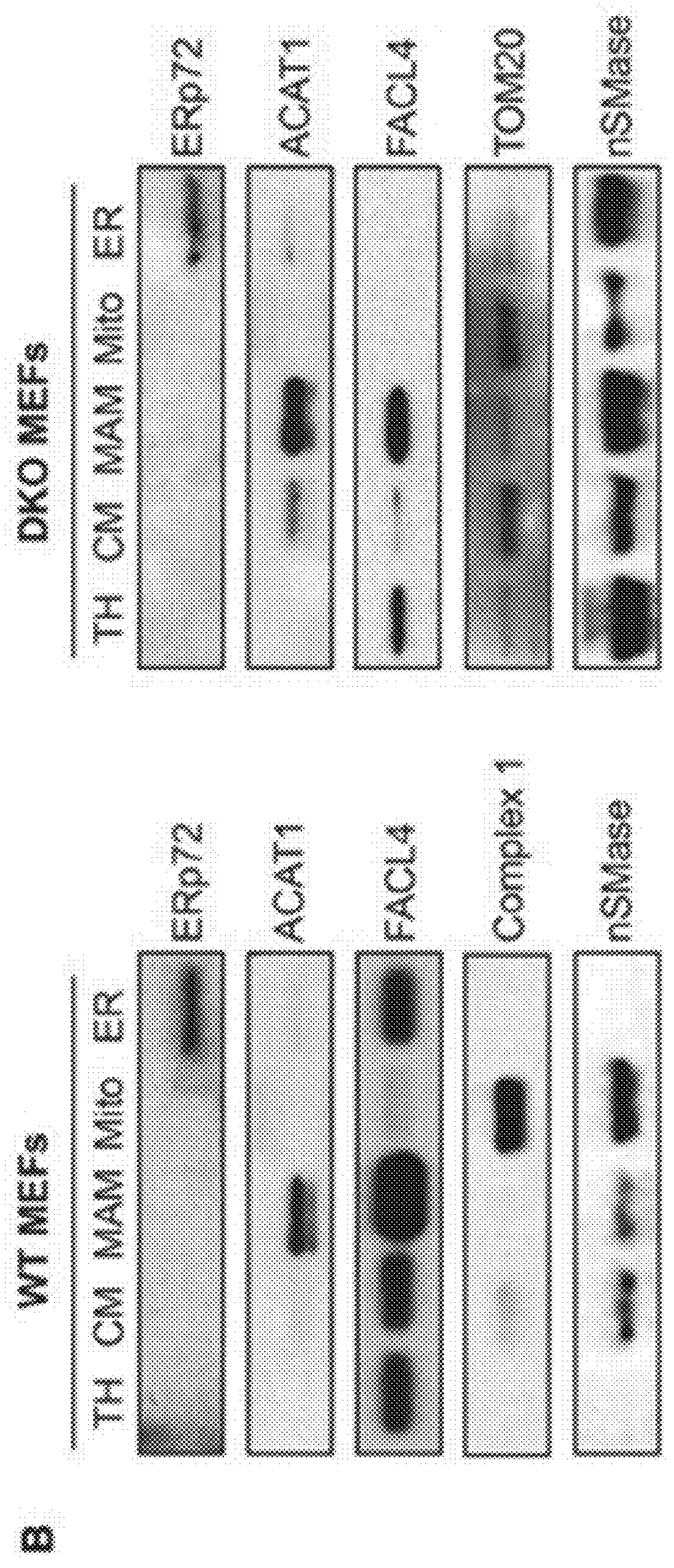
Figure 40C:
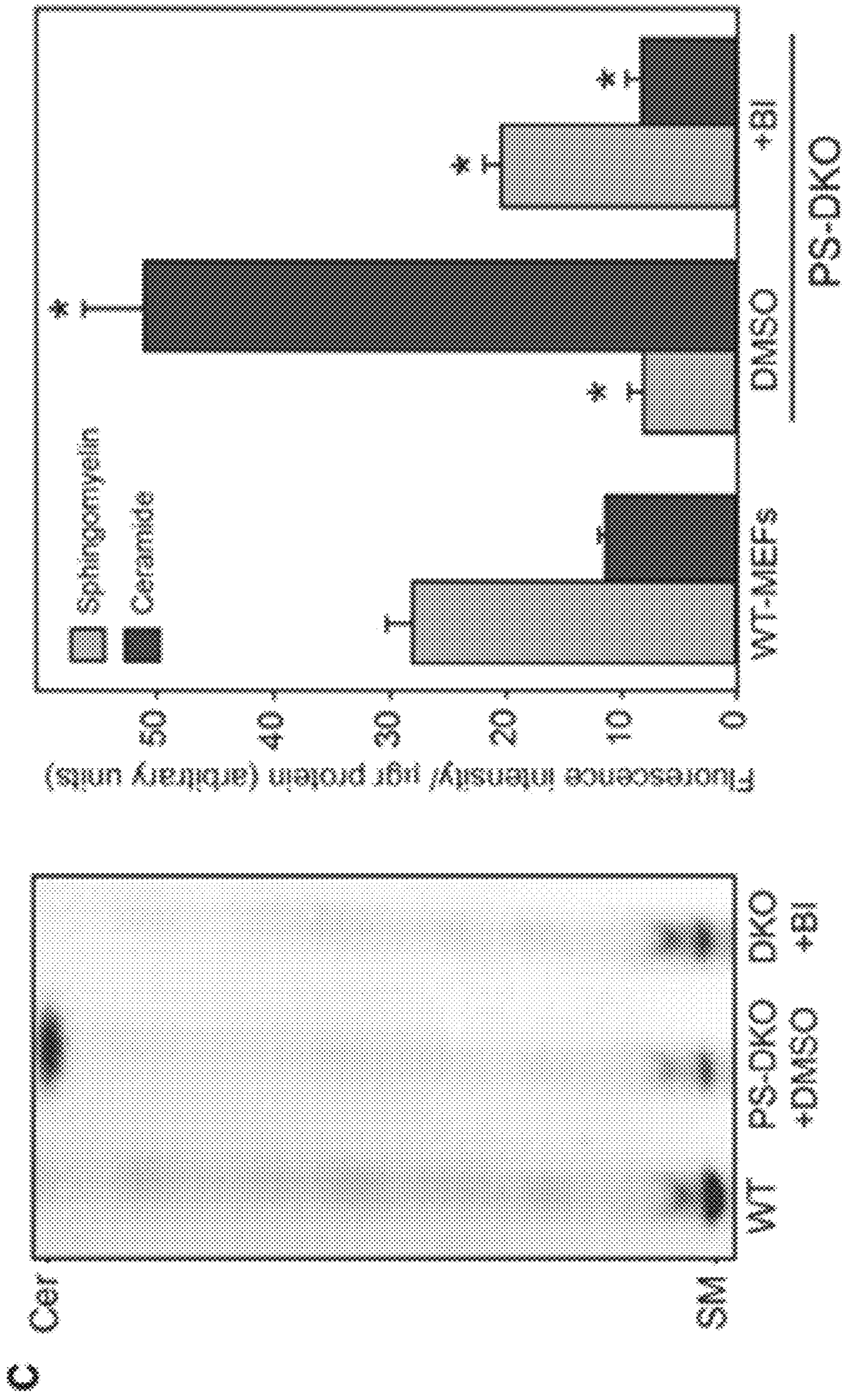

FIGS. 40A-C show MAM participates in the regulation of sphingolipid metabolism. Distribution of SMase activity in the indicated subcellular compartments in WT and PS-DKO MEFs. Note the overall increase in nSMase levels in the PS-DKO cells (average of n=5 independent experiments±SD). *P<0.05. Analysis by unpaired t-test. Western blot of the indicated fractions from WT and PS-DKO MEFs (probed with antibodies against the indicated markers) to detect the levels of nSMase protein in the indicated compartments (30 μg of protein per lane). TH, total homogenate; CM, crude membrane fraction. Sphingolipid levels in mitochondrial membranes extracted from the indicated cells after addition of fluorescent sphingomyelin (left, detection in TLC plates; right, quantitation) (average of n=5 independent experiments±SD). *P<0.05 vs. WT levels. Analysis by unpaired t-test.

FIGS. 41A-E show mitochondrial dysfunction is the consequence of increased sphingolipid turnover. A Respiratory chain deficiency [as measured by initial oxygen consumption rate (OCR)] in PS-DKO cells was rescued after treatment with myriocin (inhibitor of the de novo sphingolipid synthesis pathway) (average of n=3 independent experiments±SD). *P<0.05, compared to WT; # P<0.05, comparisons indicated on graph. Analysis by unpaired t-test. B, C In-gel complex I (B) and complex IV (C) activity staining in mitochondria from WT and PS-DKO cells after the indicated treatments. D, E Quantification of specific bands shown in (B) and (C). Note that chemical or genetic inhibition of γ-secretase results in decreased supercomplex I+III+IV activity. This effect can be rescued by inhibition of C99 production [with a BACE1 inhibitor (BI)] or by inhibition of ceramide production with myriocin (Myr). Dotted lines denote baseline levels (average of n=3 independent experiments±SD). *P<0.05 vs. baseline levels. Analysis by unpaired t-test.

Figure 42T:
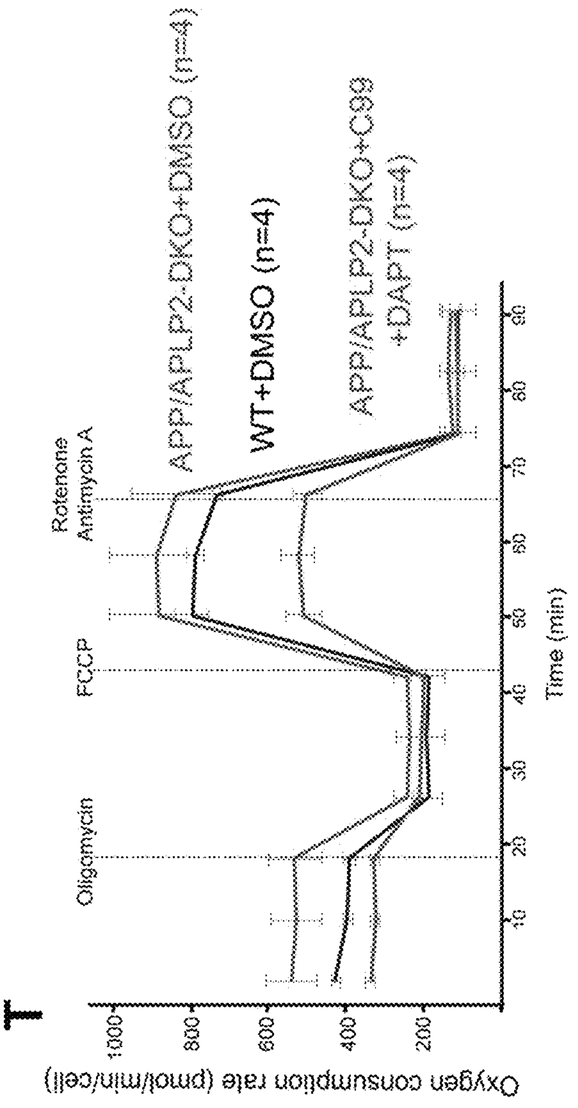

FIGS. 42A-T show mitochondrial bioenergetics in γ-secretase-deficient cells. All respiratory chain assays (OCR) were performed using the Seahorse XF24 Flux Analyzer. (A) Fibroblasts from FAD and SAD patients, (B) Mitochondria from PS1-KI$^{M146V}$ brain. (C) Western blot from homogenates from the indicated cells probed against mitochondrial markers (VDAC and TOM20) and the tubulin loading controls (30 μg of protein per lane). (D, E) Complex I and II activities in which malate-pyruvate or succinate-rotenone, respectively, were added to permeabilized PS-DKO MEFs (D) and to APP-DKO MEFs (E). Note significant decrease in OCR in PS-DKO MEFs but an increase in APP-DKO MEFs. (F) qRT-PCR to measure mRNA levels of mitochondrial encoded Cox1 as a measure of mitochondrial DNA in WT and PS-DKO cells before and after addition of DAPT and BI. n.s.=not significant. (G) Western blot from total homogenates of WT, PS-DKO, and PS-DKO cells treated with BACE1 inhibitor (BI); 30 μg of protein per lane). Note that BI treatment eliminates the accumulation of APP C-terminal fragments in PS-DKO MEFs, without changes in mitochondria (VDAC, TOM20). (H) OCR in WT or PS-DKO cells is unaffected by treatment with the α-secretase inhibitor TAPI-1. (I) qRTPCR to measure mRNA levels of PGC-1α, a master regulator of mitochondrial biogenesis, in WT and PS-DKO cells before and after addition of DAPT and BI (which do not affect mitochondrial biogenesis). Note lack of an effect on PGC-1α levels in γ-secretase-deficient cells. n.s., not significant. (J) Western blot from total homogenates of SHSY5Y cells treated with DMSO and α-, β-, and γ-secretase inhibitors probed with the indicated antibodies. Note that none of the treatments change the levels of mitochondria (VDAC). Loading control in the right panel 30 μg of protein per lane). (K, L) Addition of monomers of Aβ40 and Aβ42 (added at a ratio of 10:1 Aβ40:Aβ42, total concentration of Aβ was 6 ng/ml) to PS-KO cells (K), or to APP-DKO cells (L) did not affect mitochondria respiration. (M) Addition of 0, 5, and 10 μM of Aβ42 oligomers to WT and APP-DKO cells shows that only at a high-non-physiological concentration (10 μM) of Aβ42 oligomers, mitochondrial respiration is slightly decreased. (N) Respiratory chain deficiency in fibroblasts from an FAD patient (AG06840. PS1A246E) was rescued following treatment with a BACE1 inhibitor. (0) Western blot showing how transient transfection of C99 in APP-DKO cells did not affect mitochondrial levels (TOM20). Tubulin is revealed as loading controls. All western blots were performed on the same membranes consecutively. (P-T) Seahorse graphs of representative experiments shown in FIG. 1. All experiments represent the average of n>4 independent experiments; n.s., non significant; 30 μg of protein per lane.

FIGS. 43A-H show localization of C99 to MAM in PS1-KI$^{M146V}$ mice. (A) Scheme showing the protocol followed to isolate the subcellular fractions analyzed by Western blot. (B) Example of western blot analysis of subcellular fractions from mouse liver obtained using the protocol shown in panel S2A, probed against specific markers for each indicated compartment (30 μg of protein per lane). (C) Scheme showing the protocol followed to purify subcellular fractions by continuous sucrose gradients analyzed by Western blot as shown in FIG. 2C. (D) Representative confocal images from WT MEFs non-treated with DAPT and transfected with C99 (red), Sec6β to label ER (green), and mitochondria (blue). White arrowheads indicate areas of contact between ER and mitochondria where C99 is present. Red signal in the nucleus corresponds to the APP intracellular domain (AICD) produced after the γ-secretase cleavage of the transfected C99-red construct (compare to DAPT-treated COS-7 cells in FIG. 2E, where no AICD is produced after γ-secretase inhibition). (E) Representative electron microscopy images of PS-DKO cells incubated with antibodies against APP-CTF conjugated with immunogold particles show significant labeling in MAM regions (brackets). (F) Western blots of total homogenates of embryonic cortical neurons explanted from WT and PS1-KI$^{M146V}$ mice, and of fibroblasts from AD patients (G) show higher levels of C99 in mutant samples vs. controls (30 μg of protein per lane). All samples were run on the sample gel. Dotted line indicates an empty lane cut out. Quantifications of western blot bands normalized to the loading controls (tubulin and vinculin) are shown in the panels at right. (H) Western blot of subcellular fractions isolated from WT and PS1-KI$^{M146V}$ shows increased levels of C99 in total homogenates (TH), crude membranes (CM), ER, and MAM fractions. Note that AICD levels are not significantly changed compared to C99 (quantification in the panel at right) (Western blots of total homogenates of embryonic cortical neurons explanted from WT and PS1-KI$^{M146V}$ mice, and of fibroblasts from AD patients (G) show higher levels of C99 in mutant samples vs. controls (30 μg of protein per lane). Quantifications of western blot bands normalized to the loading controls (tubulin and vinculin) are shown in the panels at right.

FIGS. 44A-D show cholesteryl ester and lipid droplet formation in γ-secretase-deficient cells. (A) Staining with LipidTox Green to detect lipid droplets in the indicated explanted astrocytes (size bar=20 μm) and cortical neurons (size bar=25 μm) from WT and PS1-KI$^{M146V}$ mice. (B) Staining of LDs as in (A) of PS-DKO cells untreated and treated with 10 μM of Gleevec. Quantitation of lipid droplets after incubation of PS-DKO cells with increasing concentrations of Gleevec is shown at right. All values represent the average of n=3 independent experiments±SD; * p<0.01. (C) Staining of SH-SY5Y cells (upper panels) or HeLa cells (lower panels) treated with DAPT (to increase C99 accumulation) or with DAPT+BI (to inhibit C99 production) (size bar=20 μm). Quantitation of lipid droplets is shown at right. All values represent the average of n=3 independent experiments±SD; * p<0.01. (D) Staining of BACE1-KO cells. Quantitation of lipid droplets is shown at right. All values represent the average of n=3 independent experiments±SD; * p<0.01. (n.s.=non significant).

FIGS. 45A-N show acid (aSMase) and neutral (nSMase) sphingomyelinase activities in various cell types. (A-C) Ceramide and sphingomyelin levels in total homogenates (A), mitochondria (B), and MAM (C) from WT and PS-DKO cells, represented as nmol per μg of protein. (D) Western blot of WT and PS-DKO cell homogenates to reveal PS1 levels after transfection with the indicated plasmids. (E) Ratio of Aβ42:Aβ40 produced by cells shown in (D). Note the increase in the ratio of Aβ42:Aβ40 in cells transfected with mutant PS1A246E. (F) Ceramide and sphingomyelin levels in PS-DKO cells transfected with the indicated plasmids. Note partial “rescue” of ceramide levels after transfection with WT-PS1, but not with PS1A246E, plasmids. (G) Molecular species of ceramide and sphingomyelin in mitochondrial fractions from WT and PS-DKO MEFs. (H) Transcription of a gene encoding neutral sphingomyelinase 2 (nSMAse2; [SMPD3]), in WT and PS-DKO MEFs, by qRT-PCR. (I) Acid (aSMase) and neutral SMase (nSMAse) activities in brain from PS1-KI$^{M146V}$ mice. Note increased SMase in the mutant cells compared to WT. (J) SMase activities in SH-SY5Y cells. Note significantly increased SMase activities following inhibition of γ-secretase activity (and increased C99) with DAPT. (K) Neutral SMase (nSMAse) activities in PS-DKO cells transfected with the indicated plasmids. Note decreased SMase in the mutant cells transfected with WT-PS1, but not with PS1A246E, plasmids. (L) Sphingomyelin (SM) synthesis in APP-DKO MEFs. (M) Sphingomyelin hydrolysis or sphingomyelinase activities in APP-DKO MEFs (lacking C99). (N) Both aSMase (aSM) and nSMase (nSM), but particularly nSMase activity, are increased significantly in PSDKO MEFs (containing C99 but lacking both Aβ and AICD) vs WT cells. These activities are essentially unchanged in the presence of either Aβ (monomers of Aβ40 and Aβ42 added to the medium at a ratio of Aβ40:Aβ42 of 10:1; 6 ng/ml total Aβ concentration) or AICD (expressed transiently from a plasmid). All experiments represent the average of n=5 independent experiments±S.D. * p<0.05; n.s., not significant.

FIGS. 46A-F show analysis of sphingolipid metabolism in WT and PS-DKO MEFs. (A) Approximate distribution of steady-state levels of sphingomyelin (SM) and ceramide (Cer) in cell compartments in WT MEFs (numbers in boxes denote % of the total present in the indicated compartment). The “Other” value was derived from subtracting the MAM+ER+Mito values from those in the total homogenate. (B) Increased nSMase activity in MAM isolated from PS1-

$KI^{M146V}$ brain compared to WT brain (data represent the average of 4 independent experiments±S.D. * p<0.05; n.s., not significant). (C) Phosphatidylserine (PtdSer) content in fractions isolated from WT and PS-DKO cells. Lipid values are represented as nmol normalized per unit of protein and total lipid extracted. Note the increase in PtdSer in MAM fractions (values represent the average of n=3 independent experiments±S.D. * p<0.05; n.s., not significant). (D) PtdSer content in membranes isolated from WT, PS-DKO, and PS-DKO cells treated with BACE inhibitor. Note the decrease in PtdSer content in mutant cells after inhibiting the production of C99 with BI. Values represent the average of 3 independent experiments±S.D. * p<0.05; n.s., not significant. (E, F) Sphingomyelin (E) and ceramide (F) levels in membranes isolated from WT, PS-DKO, and PS-DKO cells treated with a BACE1 inhibitor. Note that BI treatment rescues sphingolipid homeostasis in mutant cells. Values represent the average of n=3 independent experiments±S.D. * p<0.05; n.s., not significant.

FIGS. 47A-F show supercomplex assembly is altered in γ-secretase deficient cells. (A, B) Sphingomyelin (A) and ceramide (B) levels in total homogenates, mitochondria, and MAM membranes from WT and PS-DKO cells untreated and treated with myriocin. Note significant reductions in sphingolipid levels after de novo synthesis of sphingolipids by myriocin. (C, D) Western blot of blue-native PAGE gels to detect complex I (C), and complex III (D) to reveal respiratory supercomplexes in mitochondria from WT and PS-DKO cells after the indicated treatments. Note that chemical or genetic inhibition of γ-secretase results in decreased supercomplex I+III+IV assembly. Inhibition of C99 production by BACE inhibitor (BI) or inhibition of ceramide production by myriocin (Myr) increases the assembly of supercomplexes I+III and I+III+IV as measured by anti-complex I antibodies, and of supercomplex III+IV as measured by anti-complex III antibodies. All values represent the average of n=3 independent experiments±SD; * p<0.05; n.s., not significant. (E) Western blot of mitochondria isolated from WT and PS-DKO cells after the indicated treatments to reveal individual subunit complexes and TOM20. (F) As a loading control, the samples from (A) and (B) were analyzed by Coomasie staining or western blot to reveal TOM20 (a protein localized in the mitochondrial outer membrane). Dotted lines indicate a second western blot performed on the same membrane. Note that chemical or genetic inhibition of γ-secretase results in decreased supercomplex I+III+IV assembly. Inhibition of C99 production by BACE1 inhibitor (BI) or inhibition of ceramide production by myriocin (Myr) increases the assembly of supercomplexes I+III and I+III+IV as measured by anti-complex I antibody, and of supercomplex III+IV as measured by anti-complex III antibodies. All experiments represent the average of n=3 independent experiments±S.D. * p<0.05; n.s., not significant.

FIGS. 48A-D shows mitochondrial dysfunction in PS1-$KI^{M146V}$ mice. (A, B) Oxygen consumption in mitochondria isolated from brain homogenates from PS1-$KI^{M146V}$ mice analyzed at various ages (indicated in months) compared to that in the corresponding WT mice (set as 100%; dotted lines). In each assay, respiration is first measured at baseline; this is State 2 (i.e. initial respiration in the presence of added substrates [e.g. malate+pyruvate to measure complex I; succinate+rotenone to measure complex II]). ADP is then added; this is State 3 (i.e. maximum respiration in the presence of substrates). Oligomycin is then added to inhibit ATP synthase; this mimics State 4 (i.e. respiration after added ADP has been consumed). Finally, the uncoupler FCCP is added; this is State 3U (i.e. state 3 "uncoupled," [also called "noncoupled" respiration]. Note the steady decline in OCR that appears to accelerate at 8 months of age, correlating with (C) a decrease in supercomplexes activity, as measured by in-gel staining complex IV activity in mitochondria isolated from brain samples from 8 months old mice (upper left panel). As loading control, same membranes were analyzed by Coomassie staining (right panel), and the same samples were examined by western blot to detect Tom20 (bottom left panel). (D) Quantification 18 of bands from (C) by densitometry. All experiments represent the average of n=3 independent experiments±S.D. * p<0.05; n.s., not significant.

DETAILED DESCRIPTION OF THE INVENTION

The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, $21^{st}$ Edition (University of the Sciences in Philadelphia, ed., Lippincott Williams & Wilkins 2005); and Handbook of Pharmaceutical Excipients, $7^{th}$ Edition (Raymond Rowe et al., ed., Pharmaceutical Press 2012); each hereby incorporated by reference in its entirety.

The terms “animal,” “subject” and “patient” as used herein includes all members of the animal kingdom including, but not limited to, mammals, animals (e.g., cats, dogs, horses, swine, etc.) and humans.

As used herein, the term “presenilin” refers to the family of related multipass transmembrane proteins that can function as a part of the γ-secretase protease complex. The term “presenilin” includes presenilin-1 (PS1) and presenilin-2 (PS2). There are at least 7 members of the presenilin family in humans including; PS1 (gene PSEN1; Chr 14q24.2), PS2 (gene PSEN2; Chr 1q42.13), PSL1 (gene SPPL2B; Chr 19p13.3), PSL2 (gene SPPL2A Chr 15q21.2; thought to be in endosomes), PSL3 (gene HM13; Chr 20q11.21), PSL4 (gene SPPL3, Chr 12q24.31), PSL5 (gene IMPS; Chr 17q21.31; no introns)

In certain aspects, the invention provides a method of treating Alzheimer’s Disease in a subject in need thereof, comprising reducing the level of endoplasmic reticulum-mitochondrial-associated membrane (ER-MAM) localized APP-C99 in cells of the subject.

In certain aspects, the invention provides a method of treating Alzheimer’s Disease in a subject in need thereof, comprising reducing the function of endoplasmic reticulum-mitochondrial-associated membrane (ER-MAM) localized APP-C99 in cells of the subject.

Alzheimer’s Disease

The present invention provides compositions and methods that are useful the treatment of Alzheimer’s disease in a subject and in the identification of compounds or therapeutic agents for treating Alzheimer’s disease.

Alzheimer disease (AD) is the most common neurodegenerative disorder, whose exact pathogenetic causes are still not well defined. The vast majority of AD is sporadic (SAD), but the ε4 allele of apolipoprotein E (ApoE4) is a major risk factor for developing the disease. The familial, autosomal dominant, form of AD (FAD) is characterized by the inheritance of mutations in genes encoding presenilin-1 (PS1), presenilin-2 (PS2), and the amyloid precursor protein (APP). Aberrant processing of APP plays a central, but still unclear, role in AD pathogenesis. APP is first cleaved by either α-secretase or β-secretase (BACE1) to produce C-terminal fragments (CTFs) 83 aa (C83) or 99 aa (C99) in length, respectively. PS1 and PS2 are the catalytic subunits of the γ-secretase complex that then cleaves C83 and C99 to produce either p3 (~25 aa) or β-amyloid (Aβ; ~40 aa), respectively, along with the APP intracellular domain (AICD; ~50 aa). The pathological accumulation of longer toxic forms of Aβ (e.g. ~42 aa) results in the formation of neuritic plaques that, along with the accumulation of neurofibrillary tangles, are key histopathological hallmarks of AD. In addition to the deleterious effects of the Aβ peptide, its precursor, C99, has also been shown to contribute to AD pathogenesis. At the molecular level, AD cells suffer significant alterations in numerous processes, such as autophagy, inflammation, calcium homeostasis, and mitochondrial function, often occurring early in the course of the disease (i.e. prior to the appearance of plaques and tangles).

In some embodiments, AD cells can comprise, but are not limited to, cells with a PS1 mutation, cells with a PS2 mutation, cells with an APP mutation, human skin fibroblasts derived from patients carrying FAD-causing presenilin mutations, mouse skin fibroblasts, cultured embryonic primary neurons, and any other cells derived from PS1-knock out transgenic mice (containing null mutation in the PS1 gene), cells having AD-linked familial mutations, cells having genetically associated AD allelic variants, cells having sporadic AD, cells having ApoE mutations or cells having mutations associated with sporadic AD.

Exemplary AD mutations include, but are not limited to APP V717 I APP V717F, APP V717G, APP A682G, APP K/M670/671N/L, APP A713V, APP A713T, APP E693G, APP T673A, APP N665D, APP I 716V, APP V715M, PS 1 113Δ4, PS 1 A79V, PS 1 V82L, PS 1 V96F, PS1 113Δ 4, PS1 Y115C, PS1 Y115H, PS1 T116N, PS1 P117L, PS1 E120D, PS1 E120K, PS1 E123K, PS1 N135D, PS1 M139, PS1 I M139T, PS1 M139VJ 143F, PS1 1143T, PS1 M461, PS1 I M146L, PS1 M146V, PS1 H163R, PS1 H163Y, PS1 S169P, PS1 S169L, PS1 L171P, PS1 E184D, PS1 G209V, PS1 I213T, PS1 L219P, PS1 A231T, PS1 A231V, PS1 M233T, PS1 L235P, PS1 A246E, PS1 L250S, PS1 A260V, PS1 L262F, PS1 C263R, PS1 P264L, PS1 P267S, PS1 R269G, PS1 R269H, PS1 E273A, PS1 R278T, PS1 E280A, PS1 E280G, PS11 L282R, PS1 A285V, PS1 L286V, PS1 S290C (A9), PS1 E318G, PS1 G378E, PS1 G384A, PS1 L392V, PS1 C410Y, PS1 L424R, PS1 A426P, PS1 P436S, PS1 P436Q, PS2 R62H, PS2 N141I, PS2 VI 481, or PS2 M293V. For example, the cells obtained can be, but are not limited to, an AD model cell, a neuron, a fibroblast, a skin biopsy, a blood cell (e.g. a lymphocyte), an epithelial cell and cells found in urine sediment.

Presenilins

PS1 and PS2 share an overall 67% amino acid sequence homology. Primary structure analysis indicates they are integral membrane proteins with 6 to 8 transmembrane domains (Slunt et al, Amyloid-Int. J Exp. Clin. Invest., 1995, 2, 188-190; Doan et al, Neuron, 1996, 17, 1023-1030). The presenilin proteins are processed proteolytically through two intracellular pathways. Under normal conditions, accumulation of 30 kDa N-terminal and 20 kDa C-terminal proteolytic fragments occurs in the absence of the full-length protein. This processing pathway is regulated and appears to be relatively slow, accounting for turnover of only a minor fraction of the full-length protein. The remaining fraction is degraded in a second pathway by the proteasome (Thinakaran et al, Neuron, 1996, 17, 181-190; Kim et al, J. Biol. Chem., 1997, 272, 11006-11010).

FAD linked to the presenilin mutations is highly penetrant. The aggressive nature of the disease indicates that the mutant protein participates in a seminal pathway of AD pathology. To date, over seventy FAD mutations have been identified in PS1, and three FAD mutations have been found in PS2. Most of the FAD mutations occur in conserved positions between the two presenilin proteins, indicating that they affect functionally or structurally important amino acid residues. All but two of the presenilin mutations are missense mutations. One exception results in an aberrant RNA splicing event that eliminates exon 9, creating an internally-deleted mutant protein (Perez-Tur et al., NeuroReport, 1995, 7, 297-301; Sato et al, Hum. Mutat. Suppl, 1998, 1, S91-94; and Prihar et al, Nature Med., 1999, 5, 1090). The other results in two deletion transcripts (Δ4 and A4cryptic) and one full-length transcript with the amino acid Thr inserted between codons 1-13 and 1-14 (DeJonghe et al., Hum. Molec. Genet., 1999, 8, 1529-1540). The latter transcript leads to the AD pathophysiology.

Presenilins form the catalytic subunit of the γ-secretase complex that produces the Aβ peptide. Most mutations in APP, PS1, and PS2 result in an increase in the ratio of a 42-residue form of Aβ (Aβ42) versus 40-residue Aβ (Aβ40). Aβ peptides ending at residue 42 or 43 (long tailed Aβ) are more fibrillogenic and more neurotoxic than Aβ ending at residue 40, which is the predominant isoform produced during normal metabolism of βAPP (St. George-Hyslop, P. H., & Petit, A., C. R. Biologies (2004) 328: 1 19-130; Selkoe, D. J., J Clin Invest (2002) 1 10: 1375-1381).

Elevated levels of Aβ1-42 are also found in cells transfected with mutant PS1 or PS2 and in mice expressing mutant PS1 (Borchelt et al, Neuron, 1996, 17, 1005-1013; Duff et al, Nature, 1996, 383, 710-713; Citron et al, Nature Med., 1997, 3, 67-72; Murayama et al, Prog. Neuro-Psychopharmacol. Biol. Psychiatr., 1999, 23, 905-913; Murayama et al, Neurosci. Lett., 1999, 265, 61-63; Nakano et al, Eur. J. Neurosci., 1999, 11, 2577-2581). The mechanism by which the mutant presenilins affect APP processing is not known. PS1-comprised γ-secretase and PS2-comprised γ-secretase, can also be involved in Notch signaling (Shen et al (1997)).

PS1 has been localized to numerous regions of the cell, including the plasma membrane (Georgakopoulos et al, 1999; Baki et al, 2001; Marambaud et al, 2002; Marambaud et al, 2003; Tarassishin, 2004), the Golgi (Siman et al, 2003; Kimura et al, 2001), and the endoplasmic reticulum (De Strooper et al, 1997; Wolfe et al, 2004), endosomes/lysosomes, the nuclear envelope (Wolfe et al, 2004), and adherens junctions (Marambaud et al, 2002). PS1 has not been found in mitochondria, except for reports from one group that used Western blotting and immunoelectron microscopy, not immunohistochemistry, to localize PS1 to the rat mitochondrial inner membrane (Ankarcrona et al, 2002; Hansson et al, 2005). Another group used immunoelectron microscopy and found PS1 in the ER, in the perinuclear region, and at the plasma membrane (at areas of cell-to-cell contact), but not in mitochondria (Takashima et al, 1996). Using immunoelectron microscopy and Western blotting, APH1, NCT, and PEN2 were found to reside in rat mitochondria (Ankarcrona et al, 2002, Hansson et al, 2004).

Lipid Metabolism in AD

Lipid metabolism is also perturbed in AD, especially altered cholesterol and sphingolipid homeostasis, and the altered lipid content of blood has been proposed as a biomarker for the early diagnosis of the disease. Moreover, cholesterol esterification by acyl-CoA:cholesterol acyltransferase 1 (ACAT1 [gene SOAT1])—the source of the cholesteryl esters that are deposited in lipid droplets that accumulate in AD—enhances Aβ production. Regarding sphingolipids, the ceramide content in brains and cells from AD patients and in cell models is increased, likely as a result of the upregulation of de novo ceramide synthesis and of the activity of sphingomyelinase (SMase), which converts sphingomyelin to ceramide.

The parallel alteration in the metabolism of these two classes of lipids is not coincidental, as sterol and sphingolipid levels are co-regulated in the cell. While the mechanism is unknown, there is an affinity and interaction between the two lipid types that keeps them in equilibrium. The interaction between sterols and sphingolipids helps to establish liquid-ordered membrane domains ("lipid rafts") that form highly-regulated signaling platforms. This relationship between cholesterol and sphingolipids is relevant to AD, as APP processing has been shown to occur preferentially in lipid rafts that also contain APP-CTFs.

Mitochondria-Associated ER Membranes ("ER-MAM" or "MAM")

As used herein, the terms "ER-MAM" or "MAM" refer to Mitochondria-associated ER membranes that constitute a subdomain of the ER that links it, both physically and biochemically, to mitochondria. Notably, MAM is rich in cholesterol and sphingolipids, giving it the properties of a lipid raft that distinguishes it from "free" ER. More than 100 proteins have been reported to be concentrated in MAM, including those involved in calcium homeostasis, lipid metabolism, cholesterol metabolism, and the transfer of lipids between the ER and mitochondria. Contacts between the two organelles are maintained by proteins such as phosphofurin acidic cluster sorting protein 2 (PACS2), which stabilizes and regulates the interaction of ER and mitochondria, and mitofusin-2 (MFN2), which is also involved in mitochondrial fusion.

ER-Mitochondrial Communication and MAM Function are Upregulated in AD

It was recently shown that PS1 and PS2 are present mainly in the ER, but not homogeneously; rather, they are highly enriched in the MAM. Equally remarkably, it was also found that γ-secretase activity itself was significantly higher in the MAM than in free ER. The fact that MAM is an intracellular lipid raft implies that the lipid rafts in which PS1 and γ-secretase activity are known to reside may be located not at the plasma membrane (PM), as previously thought, but intracellularly, in the MAM. More recently, it was shown that: (1) not only altered Aβ levels, but also many of the other phenotypes in AD (e.g. perturbed phospholipid and cholesterol metabolism; deposition of lipid droplets; aberrant calcium homeostasis; perinuclear mitochondria) result from significantly upregulated MAM function, and (2) this upregulation is detectable not only in cells from patients with FAD, but, remarkably, also in those from patients with SAD in which the presenilin and APP genes are normal. It was also found that a massive increase in the area of contact between ER and mitochondria, implying that the increased biochemical activity of MAM in PS-mutant and AD patient cells is due, at least in part, to an increased physical association between the two organelles. These results imply that altered ER-mitochondrial communication is an early, and critical, event in the pathogenesis of AD.

ApoE4 Affects MAM Function

APOE encodes apolipoprotein E (ApoE), a component of the lipoproteins that transport cholesterol and lipids throughout the body. In the brain, cholesterol is synthesized mainly by astrocytes, but not by neurons, with astrocyte-derived cholesterol delivered to neurons via high-density lipoproteins (HDL). Different isoforms of APOE are the most common and validated risk factors in sporadic AD. Individuals carrying one copy of the 84 variant (ApoE4) have ~4-fold increased risk for developing AD compared to individuals carrying ApoE3, the most common isotype, while those carrying 2 copies are at ~12-fold greater risk. The rarest variant, ApoE2, is protective against AD. It is unclear how the amino acid differences that determine the APOE genotype modulate AD risk, or whether they are related to the normal physiological function of ApoE in cholesterol and lipid homeostasis.

Methods of Treatment

The present disclosure provides methods for the treatment and/or prevention of Alzheimer's Disease. In one aspect, the disclosure provides a method of treating, preventing or delaying the onset of sporadic or familial Alzheimer's Disease in a subject.

In certain aspects, the invention provides a method of treating Alzheimer's Disease in a subject in need thereof, comprising reducing the level of endoplasmic reticulum-mitochondrial-associated membrane (ER-MAM) localized APP-C99 in cells of the subject.

In certain aspects, the invention provides a method of treating Alzheimer's Disease in a subject in need thereof, comprising reducing the function of endoplasmic reticulummitochondrial-associated membrane (ER-MAM) localized APP-C99 in cells of the subject.

In some embodiments, the level of ER-MAM localized APP-C99 is reduced in cells of the subject by increasing ER-MAM localized γ-secretase activity. In some embodiments, ER-MAM localized γ-secretase activity is increased by administering to the subject an effective amount of phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), or auraptene (7-geranyloxycoumarin). In some embodiments, ER-MAM localized γ-secretase activity is increased by administering to the subject an effective amount of a composition that increases the level of, activates, or agonises OCIAD2, TNF-α, interleukin-1β, interferon-γ, MEKK1, OSTC, KRTCAP2, KCNIP3, CREB, ADRB2, APMAP, CRF, PS1, PS2, or EGR1. In some embodiments, the composition that increases the level of OCIAD2, TNF-α, interleukin-1β, interferon-γ, MEKK1, OSTC, KRTCAP2, KCNIP3, CREB, ADRB2, APMAP, CRF, PS1, PS2, or EGR1 comprises a polypeptide or nucleic acid encoding OCIAD2, TNF-α, interleukin-1β, interferon-γ, MEKK1, OSTC, KRTCAP2, KCNIP3, CREB, ADRB2, APMAP, CRF, PS1, PS2, or EGR1. In some embodiments, the ADRB2 agonist is isoproterenol or clenbuterol. In some embodiments, the CREB activator is PBA. In some embodiments, the CRF activity is increased by administering a composition comprising GSK561679 or Corticorelin/Xerecept. In some embodiments, the PS2 level is increased by administering a composition comprising TPA. In some embodiments, the MEK1/2 inhibitor is PD98059, PD0325901, U0126, or Trametinib. In some embodiments, ER-MAM localized γ-secretase activity is increased by administering to the subject an effective amount of a composition that inactivates, antagonizes, or decreases the level of ADORA2A. In some embodiments, the ADORA2A antagonist is istradefylline, preladenant, or tozadenant.

In some embodiments, the level of ER-MAM localized APP-C99 is reduced in cells of the subject by administering to the subject an ER-MAM localized γ-secretase activator or agonist.

In some embodiments, the level of ER-MAM localized APP-C99 is reduced in cells of the subject by administering to the subject an effective amount of a composition comprising mifepristone, miR-106b or a nucleic acid encoding miR-106b, an ITM2B inhibitor, or a TRPC6 inhibitor. In some embodiments, the TRPC6 inhibitor is larixyl acetate.

In some embodiments, the level of ER-MAM localized APP-C99 is reduced in cells of the subject by administering to the subject an effective amount of a composition that increases phosphorylation of APP at Thr668. As used herein, Thr668 refers to numbering based on APP-695. In some embodiments, the phosphorylation of APP at Thr668 is mediated by a kinase including, but not limited to, JNK, CDK5, CDC2, GSK3B, c-Jun.

In some embodiments, the level of ER-MAM localized APP-C99 is reduced in cells of the subject by administering to the subject an effective amount of a composition that increases the level of, activates, or agonises PICALM, PIMT, ADAM10, or ADAM17. In some embodiments, the composition that increases the level of PICALM, PIMT, ADAM10, or ADAM17 comprises a polypeptide or nucleic acid encoding PICALM, PIMT, ADAM10, or ADAM17.

In some embodiments, the level of ER-MAM localized APP-C99 is reduced in cells of the subject by administering to the subject an effective amount of a composition that inhibits endosome-to-MAM movement. In some embodiments, inhibiting endosome-to-MAM movement comprises reducing the level of FAM21, or a component of the WASH complex. In some embodiments, the level of FAM21 activity is reduced by administering an effective amount of a FAM21 RNAi.

In some embodiments, the level of ER-MAM localized APP-C99 is reduced in cells of the subject by administering to the subject an effective amount of a composition that inhibits, antagonizes or decreases the levels of ErbB2. In some embodiments, the ErbB2 inhibitor is CL-387,785. In some embodiments, the level of ER-MAM localized APP-C99 is reduced in cells of the subject by administering to the subject an effective amount of a composition that promotes or increases the levels of phosphorylated PS1 on Ser367. In some embodiments, phosphorylation of PS1 on Ser367 is promoted or increased by casein kinase 1γ2. In some embodiments, the level of ER-MAM localized APP-C99 is reduced in cells of the subject by administering to the subject an effective amount of a composition that inhibits, antagonizes, or decreases the levels of Aβ/C99-mediated cell death. In some embodiments, the Aβ/C99-mediated cell death inhibitor is CP2, a tricyclic pyrone molecule.

In some embodiments, the level of ER-MAM localized APP-C99 is reduced in cells of the subject by administering to the subject an effective amount of a composition that increases cholesterol efflux or increases cholesterol oxidation and/or esterification. In some embodiments the treatment comprises increasing the level of PICALM, ABCA1, SOAT1, CH25H, CYP46A1, ABCA7, ABCG1, SORL1, or TRPML1-3. In some embodiments, the composition comprises a polypeptide or nucleic acid encoding PICALM, ABCA1, SOAT1, CH25H, CYP46A1, ABCA7, ABCG1, SORL1, or TRPML1-3.

In some embodiments, the level of ER-MAM localized APP-C99 is reduced in cells of the subject by administering to the subject an effective amount of an antibody or a peptide that binds to C99.

In some embodiments, the level of ER-MAM localized APP-C99 is reduced in cells of the subject by reducing BACE1 activity. In some embodiments, the BACE1 is localized to endosomes.

In some embodiments, the level of ER-MAM localized APP-C99 is reduced in cells of the subject by administering to the subject a BACE1 inhibitor or antagonist. In some embodiments, the BACE1 activity is reduced by administering an effective amount of a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, all-trans retinoic acid (atRA), or a legumain inhibitor. In some embodiments, the PPAR-α inhibitor is GW7647. In some embodiments, the legumain inhibitor is NN1, NN4, or LE28. In some embodiments, the BACE1 activity is reduced by administering an effective amount of a composition that increases the level of, activates, or agonises ABCA1, UCHL1, or LXR, p38α-MAPK. In some embodiments, the composition that increases the level of ABCA1, UCHL1, LXR, MAPK11, MAPK12, MAPK13, or MAPK14 comprises a polypeptide or nucleic acid encoding ABCA1, UCHL1, LXR, MAPK11, MAPK12, MAPK13, or MAPK14. In some embodiments the endosome-localized BACE1 activity is reduced by administering an effective amount of a sterol-modified BACE1 inhibitor. In some embodiments, the LXR agonist is T090317, or Compound 9.

In some embodiments, the BACE1 activity is reduced by administering an effective amount of a composition that reduces, inhibits, antagonizes, or decreases the levels of BACE1 cleavage. In some embodiment, the composition that reduces BACE1 cleavage is an antibody to the BACE1 cleavage site. In some embodiments, the composition that inhibits BACE1 cleavage is verubacest (MK-8931) or JNJ-54861911 or AZD3293/LY3314814 or E2609 or CNP520. In some embodiments, the composition that inhibits BACE1 cleavage is Gleevec or DV2-103.

In some embodiments, the level or function of ER-MAM localized APP-C99 is reduced in cells of the subject by administering to the subject Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a CypD inhibitor, or U18666a. In some embodiments, the level or function of ER-MAM localized APP-C99 is reduced in cells of the subject by administering to the subject an effective amount of a composition that increases the level, activates, or agonises ABCA1, SOAT1, cholesterol 25-hydroxylases (e.g. CH25H, CYP46A1), PICALM, ABCA7, ABCG1, SORL1 or TRPML1-3. In some embodiments, the composition that increases the level of ABCA1, SOAT1, CH25H, CYP46A1, PICALM, ABCA7, ABCG1, SORL1, TRPML1-3 comprises a polypeptide or nucleic acid encoding ABCA1, SOAT1, CH25H, CYP46A1, PICALM, ABCA7, ABCG1, SORL1, or TRPML1-3. In some embodiments, the PTK2 inhibitor is PF-562271. In some embodiments, the TRPML1-3 agonist is ML-SA1. In some embodiments, the ABCA1 agonist is peptide CS-6253. In some embodiments, the SREBP inhibitor or miR33a/b inhibitor is methyl protodioscin. In some embodiments, the CypD inhibitor is cyclosporin A.

In some embodiments, the level or function of ER-MAM localized APP-C99 is reduced in cells of the subject by administering to the subject an effective amount of a composition that reduces, downregulates, inhibits, antagonizes, or decreases the levels of SREBP2. In some embodiments, the composition that reduces SREBP2 is osmotin.

In some embodiments, the level or function of ER-MAM localized APP-C99 is reduced in cells of the subject by administering to the subject an effective amount of a composition that reduces, or decreases the levels of cholesterol. In some embodiments, the composition that reduces cholesterol is cyclodextrin.

In some embodiments, the level or function of ER-MAM localized APP-C99 is reduced in cells of the subject by administering to the subject an effective amount of a composition that inhibits, antagonizes, or decreases the levels of Cyclophilin D (CypD). In some embodiments, the composition that inhibits, antagonizes, or decreases the levels of Cyclophilin D (CypD) is Cyclosporin A (CsA).

In some embodiments, the level or function of ER-MAM localized APP-C99 is reduced in cells of the subject by administering to the subject an effective amount of a composition that inhibits, antagonizes, or decreases the levels of the scavenger receptor CD36. In some embodiments, the composition that inhibits, antagonizes, or decreases the levels of the scavenger receptor CD36 is sulfo-N-succinimidyl oleate (SSO).

In some embodiments, the level or function of ER-MAM localized APP-C99 is reduced in cells of the subject by administering to the subject an effective amount of a composition that activates, agonizes, or increases the levels of CYP11A1. In some embodiments, the composition that activates, agonizes or increases the levels of CYP11A1 is efavirenz.

In some embodiments, the level or function of ER-MAM localized APP-C99 is reduced in cells of the subject by administering to the subject an effective amount of a LDL receptor inhibitor. In some embodiments, the LDL receptor is LRP1, LRP2, LRP5, LRP6, LRP8, LRP1B, LDLR, VLDLR, LRAD3, or CD36. In some embodiments, the CD36 LDL receptor inhibitor is sulfo-N-succinimidyl oleate (SSO).

In some embodiments, the level or function of ER-MAM localized APP-C99 is reduced in cells of the subject by reducing ER-mitochondrial connectivity. In some embodiments, ER-mitochondrial connectivity is reduced in cells of the subject by administering to the subject an effective amount of acetylcholine, a MFN2 inhibitor, a PACS2 inhibitor, a Reticulon-1 inhibitor, a MARCH5 inhibitor, a VAPB inhibitor. In some embodiments, ER-mitochondrial connectivity is reduced in cells of the subject by administering to the subject an effective amount of a composition that increases the level of, activates, or agonises, TCHP, Reticulon-4, Nogo-B, or FATE1. In some embodiments, the composition that increases the level of TCHP, Reticulon 4, NogoB, or FATE1 comprises a polypeptide or nucleic acid encoding TCHP, Reticulon 4, NogoB, or FATE1.

In some embodiments, ER-mitochondrial connectivity is reduced in cells of the subject by administering to the subject an effective amount of a composition that inhibits, inactivates, antagonizes, or decreases the levels of GRP75. In some embodiments, the GRP inhibitor is MKT-077.

In some embodiments, the level or function of ER-MAM localized APP-C99 is reduced in cells of the subject by increasing hypoxia. In some embodiments, hypoxia is increased in cells of the subject by administering to the subject an effective amount of a composition that activates, agonises, or increases the level of HIF-α. In some embodiments, hypoxia is increased in cells of the subject by administering to the subject an effective amount of a composition that inactivates, antagonizes, or decreases the level of cholesterol synthesis. In some embodiments, hypoxia is increased in cells of the subject by administering to the subject an effective amount of a composition that activates, agonizes, or increases the levels of PS2V. In some embodiments, hypoxia is increased in cells of the subject by administering to the subject an effective amount of a composition that activates, agonizes, or increases the levels of ACAT1. In some embodiments, hypoxia is increased in cells of the subject by administering to the subject an effective amount of a composition that activates, agonizes, or increases the levels of cholesterol esterification. In some embodiments, hypoxia is increased in cells of the subject by administering to the subject an effective amount of a composition that activates, agonizes, or increases the levels of Recticulon4/Nogo-B. In some embodiments, the composition that activates, agonizes, or increases the levels of hypoxia in the cells of the subject is hypoxic conditions, exposing a subject to high altitude environment. In some embodiments, hypoxia is increased in cells of the subject by administering to the subject an effective amount of a composition that inactivates, antagonizes, inhibits or decreases the levels of prolyl hydroxylase (PHD1/EGLN1, PHD2/EGLN2, or PHD3/EGLN3). In some embodiments, the composition that inactivates, antagonizes, inhibits or decreases the levels of prolyl hydroxylase (PHD1/EGLN1, PHD2/EGLN2, or PHD3/EGLN3) is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

In certain aspects, the invention provides a method of treating Alzheimer's Disease in a subject in need thereof, comprising administering an effective amount of a composition comprising an ER-MAM localized γ-secretase activator or agonist, phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), auraptene (7-geranyloxycoumarin), mifepristone, miR-106b or a nucleic acid encoding miR-106b, an ITM2B inhibitor, a TRPC6 inhibitor, a composition that increases phosphorylation of APP at Thr668, an antibody or a peptide that binds to C99, an endosome-to-MAM movement inhibitor, a BACE1 inhibitor or antagonist, a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, or all-trans retinoic acid (atRA), a legumain inhibitor, Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a LDL receptor inhibitor, acetylcholine, a CypD inhibitor, U18666a, a MFN2 inhibitor, a PACS2 inhibitor, a Reticulon-1 inhibitor, a MARCH5 inhibitor, a VAPB inhibitor, a ADORA2A inhibitor or antagonist, an ErbB2 inhibitor or antagonist, a casein kinase 1γ2 agonist, a tricyclic pyrone molecule such as CP2, verubacest (MK-8931), JNJ-54861911, AZD3293/LY3314814, E2609, CNP520, Gleevec, DV2-103, a SREBP2 inhibitor or antagonist, cyclodextrin, a CypD inhibitor or antagonist, a CD36 inhibitor or antagonist, a CYP11A1 agonist, a GRP75 inhibitor or antagonist, a HIFα agonist, a PS2V agonist, a Reticulon4/Nogo-B agonist, a prolyl hydroxylase (PHD1/EGLN1, PHD2/EGLN2, or PHD3/EGLN3) inhibitor or antagonist. In some embodiments, the ADORA2A inhibitor or antagonist is istradefylline, preladenant, or tozadenant. In some embodiments, the ErbB2 inhibitor or antagonist is CL-387,785. In some embodiments, the composition that reduces SREBP2 is osmotin. In some embodiments, the CypD inhibitor or antagonist is Cyclosporin A (CsA). In some embodiments, the CD36 inhibitor or antagonist is sulfo-N-succinimidyl oleate (SSO). In some embodiments, the CYP11A1 agonist is efavirenz. In some embodiments, the GRP inhibitor or antagonist is MKT-077. In some embodiments, the prolyl hydroxylase (PHD1/EGLN1, PHD2/EGLN2, or PHD3/EGLN3) inhibitor or antagonist is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

In certain aspects, the invention provides a method of treating Alzheimer's Disease in a subject in need thereof, comprising administering an effective amount of a composition that increases the level of, activates, or agonises OCIAD2, TNF-α, interleukin-1β, interferon-γ, MEKK1, OSTC, KRTCAP2, KCNIP3, CREB, ADRB2, APMAP, CRF, PS1, PS2, EGR1, PICALM, PIMT, ADAM10, ADAM17, ABCA1, UCHL1, LXR, p38α-MAPK, SOAT1, cholesterol 25-hydroxylases (e.g. CH25H, CYP46A1), ABCA7, ABCG1, SORL1 or TRPML1-3, miR-106b, TCHP, Reticulon-4, NogoB, FATE1, CYP11A1, HIFα, PS2V, or ACAT1. In some embodiments, the composition that increases the level of OCIAD2, TNF-α, interleukin-1β, interferon-γ, MEKK1, OSTC, KRTCAP2, KCNIP3, CREB, ADRB2, APMAP, CRF, PS1, PS2, EGR1, PICALM, PIMT, ADAM10, ADAM17, ABCA1, UCHL1, LXR, MAPK11, MAPK12, MAPK13, MAPK14, SOAT1, CH25H, CYP46A1, ABCA7, ABCG1, SORL1, TRPML1-3, miR-106b, TCHP, Reticulon-4, NogoB, FATE1, CYP11A1, HIFα, PS2V, or ACAT1 comprises a polypeptide or nucleic acid encoding OCIAD2, TNF-α, interleukin-1β, interferon-γ, MEKK1, OSTC, KRTCAP2, KCNIP3, CREB, ADRB2, APMAP, CRF, PS1, PS2, EGR1, PICALM, PIMT, ADAM10, ADAM17, ABCA1, UCHL1, LXR, MAPK11, MAPK12, MAPK13, MAPK14, SOAT1, CH25H, CYP46A1, ABCA7, ABCG1, SORL1, TRPML1-3, miR-106b, TCHP, Reticulon-4, NogoB, FATE1, CYP11A1, HIFα, PS2V, or ACAT1. In some embodiments, the ADRB2 agonist is isoproterenol or clenbuterol. In some embodiments, the MEK1/2 inhibitor is PD98059, PD0325901, U0126, or Trametinib. In some embodiments, the TRPC6 inhibitor is larixyl acetate. In some embodiments, the endosome-to-MAM movement inhibitor is a FAM21 RNAi. In some embodiments, the LXR agonist is T090317, or Compound 9. In some embodiments, the legumain inhibitor is NN1, NN4, or LE28. In some embodiments, the BACE1 inhibitor is sterol-modified. In some embodiments, the TRPML1-3 agonist is ML-SA1. In some embodiments, the ABCA1 agonist is peptide CS-6253. In some embodiments, the PPAR-α inhibitor is GW7647. In some embodiments, the PTK2 inhibitor is PF-562271. In some embodiments, the SREBP inhibitor or miR33a/b inhibitor is methyl protodioscin. In some embodiments, the CypD inhibitor is cyclosporin A. In some embodiments, the LDL receptor is LRP1, LRP2, LRP5, LRP6, LRP8, LRP1B, LDLR, VLDLR, LRAD3, or CD36. In some embodiments, the CD36 LDL receptor inhibitor is sulfo-N-succinimidyl oleate (SSO).

In certain aspects, the invention provides a method of treating Alzheimer's Disease in a subject in need thereof, comprising exposing the subject to a high altitude environment. In some embodiments, the high altitude environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the high altitude environment is a treatment room with an artificial environment that simulates high altitudes.

In certain aspects, the invention provides a method of treating Alzheimer's Disease in a subject in need thereof, comprising exposing the subject to a low oxygen (hypoxic) environment. In some embodiments, the low oxygen (hypoxic) environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the low oxygen (hypoxic) environment is a treatment room with an artificial environment that simulates hypoxic conditions.

In certain aspects, the invention provides a method of treating Alzheimer's Disease in a subject in need thereof, comprising reducing the level of endoplasmic reticulum-mitochondrial-associated membrane (ER-MAM) localized APP-C99 in cells of the subject, comprising administering an effective amount of an acid sphingomyelinase inhibitor, a neutral sphinomyelinase inhibitor, a ceramide salvage pathway inhibitor, a ceramide synthesis pathway inhibitor, a CypD inhibitor, or a CD36 inhibitor.

In some embodiments, the acid sphingomyelinase inhibitor is desipramine. In some embodiments, the neutral sphingomyelinase inhibitor is GW4869. In some embodiments, the ceramide synthesis pathway inhibitor is myriocin. In some embodiments, the CypD inhibitor is cyclosporin A. In some embodiments, the CD36 inhibitor is sulfo-N-succinimidyl oleate (SSO).

In certain aspects, the invention provides a method of treating Alzheimer's Disease in a subject in need thereof, comprising administering an effective amount of an acid sphingomyelinase inhibitor, a neutral sphinomyelinase inhibitor, a ceramide salvage pathway inhibitor, a ceramide synthesis pathway inhibitor, a CypD inhibitor, or a CD36 inhibitor.

In some embodiments, the acid sphingomyelinase inhibitor is desipramine. In some embodiments, the neutral sphingomyelinase inhibitor is GW4869. In some embodiments, the ceramide synthesis pathway inhibitor is myriocin. In some embodiments, the CypD inhibitor is cyclosporin A. In some embodiments, the CD36 inhibitor is sulfo-N-succinimidyl oleate (SSO).

In some embodiments, the composition reduces the level of ER-MAM localized APP-C99 in cells of the subject.

In some embodiments, the level of APP-C99 is measured by measuring the number of lipid-droplets, the cholesterol content, the level of cholesterol esters, the level of oxidized cholesterol, the level of neutral sMase (nSMase) activity, or a combination thereof, in cells of the subject. In some embodiments the level of nSMase activity is measured by measuring the conversion of sphingomyelin to ceramide and phosphocholine.

In one embodiment, the treating or preventing comprises reducing the level of ER-MAM localized APP-C99 in cells of the subject as compared to the level of ER-MAM localized APP-C99 in cells of the subject prior to administration of the compositions of the invention.

In some embodiments, the composition reduces the ratio of cholesterol esters to free cholesterol in a sample from the subject compared to the ratio of cholesterol esters to free cholesterol in a sample from the subject prior to administration of the compositions of the invention.

In some embodiments, the composition reduces the ratio of ceramide to sphingomyelin in a sample from the subject compared to the ratio of ceramide to sphingomyelin in a sample from the subject prior to administration of the compositions of the invention.

In some embodiments, the composition reduces the ratio of C99 to total Aβ in a sample from the subject compared to the ratio of C99 to total Aβ in a sample from the subject prior to administration of the compositions of the invention.

In some embodiments, the composition reduces the level of MAM-mediated phospholipid transport and/or synthesis in a sample from the subject compared to the level of MAM-mediated phospholipid transport and/or synthesis in a sample from the subject prior to administration of the compositions of the invention.

In certain aspects the invention provides a method of treating Alzheimer's Disease (AD) in a subject in need thereof, comprising: (a) determining the ratio of cholesterol esters to free cholesterol in a sample from the subject; and (b) administering a treatment for AD to the subject if the ratio of cholesterol esters to free cholesterol in a sample from the subject is higher than the ratio of cholesterol esters to free cholesterol in a sample from a subject that does not have AD.

In certain aspects the invention provides a method of treating AD in a subject in need thereof, comprising: (a) determining the ratio of ceramide to sphingomyelin in a sample from the subject; and (b) administering a treatment for AD to the subject if the ratio of ceramide to sphingomyelin in a sample from the subject is higher than the ratio of ceramide to sphingomyelin in a sample from a subject that does not have AD.

In certain aspects the invention provides a method of treating AD in a subject in need thereof, comprising: (a) determining the ratio of C99 to total Aβ in a sample from the subject; and (b) administering a treatment for AD to the subject if the ratio of C99 to total Aβ in a sample from the subject is higher than the ratio of C99 to total Aβ in a sample from a subject that does not have AD.

In certain aspects the invention provides a method of treating AD in a subject in need thereof, comprising: (a) determining the level of MAM-mediated phospholipid transport and/or synthesis in a sample from the subject; and (b) administering a treatment for AD to the subject if the level of MAM-mediated phospholipid transport and/or synthesis in a sample from the subject is higher than the level of MAM-mediated phospholipid transport and/or synthesis in a sample from a subject that does not have AD.

In some embodiments, the treatment for AD comprises an ER-MAM localized γ-secretase activator or agonist, phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), auraptene (7-geranyloxycoumarin), mifepristone, miR-106b or a nucleic acid encoding miR-106b, an ITM2B inhibitor, a TRPC6 inhibitor, a composition that increases phosphorylation of APP at Thr668, an antibody or a peptide that binds to C99, an endosome-to-MAM movement inhibitor, a BACE1 inhibitor or antagonist, a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, or all-trans retinoic acid (atRA), a legumain inhibitor, Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a LDL receptor inhibitor, acetylcholine, a CypD inhibitor, U18666a, a MFN2 inhibitor, a PACS2 inhibitor, a Reticulon-1 inhibitor, a MARCH5 inhibitor, a VAPB inhibitor, a ADORA2A inhibitor or antagonist, an ErbB2 inhibitor or antagonist, a casein kinase 1γ2 agonist, a tricyclic pyrone molecule such as CP2, verubacest (MK-8931), JNJ-54861911, AZD3293/LY3314814, E2609, CNP520, Gleevec, DV2-103, a SREBP2 inhibitor or antagonist, cyclodextrin, a CypD inhibitor or antagonist, a CD36 inhibitor or antagonist, a CYP11A1 agonist, a GRP75 inhibitor or antagonist, a HIFα agonist, a PS2V agonist, a Reticulon4/Nogo-B agonist, a prolyl hydroxylase (PHD1/EGLN1, PHD2/EGLN2, or PHD3/EGLN3) inhibitor or antagonist, or a composition that increases the level of, activates, or agonises OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, p38α-MAPK, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1.

In some embodiments, the ADORA2A inhibitor or antagonist is istradefylline, preladenant, or tozadenant. In some embodiments, the ErbB2 inhibitor or antagonist is CL-387,785. In some embodiments, the composition that reduces SREBP2 is osmotin. In some embodiments, the CypD inhibitor or antagonist is Cyclosporin A (CsA). In some embodiments, the CD36 inhibitor or antagonist is sulfo-N-succinimidyl oleate (SSO). In some embodiments, the CYP11A1 agonist is efavirenz. In some embodiments, the GRP inhibitor or antagonist is MKT-077. In some embodiments, the prolyl hydroxylase (PHD1/EGLN1, PHD2/EGLN2, or PHD3/EGLN3) inhibitor or antagonist is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

In some embodiments, the treatment for AD comprises exposing the subject to a high altitude environment. In some embodiments, the high altitude environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the high altitude environment is a treatment room with an artificial environment that simulates high altitudes.

In some embodiments, the treatment for AD comprises exposing the subject to a low oxygen (hypoxic) environment. In some embodiments, the low oxygen (hypoxic) environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the low oxygen (hypoxic) environment is a treatment room with an artificial environment that simulates hypoxic conditions.

In certain aspects the invention provides, a method of reducing the level of endoplasmic reticulum-mitochondrial-associated membrane (ER-MAM) localized APP-C99 in cells of the subject, comprising: (a) determining the ratio of cholesterol esters to free cholesterol in a sample from the subject; and (b) administering a composition that reduces the level of ER-MAM localized APP-C99 in cells of the subject if the ratio of cholesterol esters to free cholesterol in a sample from the subject is higher than the ratio of cholesterol esters to free cholesterol in a sample from a subject that does not have Alzheimer's Disease.

In certain aspects the invention provides a method of reducing the level of endoplasmic reticulum-mitochondrial-associated membrane (ER-MAM) localized APP-C99 in cells of the subject, comprising: (a) determining the ratio of ceramide to sphingomyelin in a sample from the subject; and (b) administering a composition that reduces the level of ER-MAM localized APP-C99 in cells of the subject if the ratio of ceramide to sphingomyelin in a sample from the subject is higher than the ratio of ceramide to sphingomyelin in a sample from a subject that does not have Alzheimer's Disease.

In certain aspects the invention provides a method of reducing the level of endoplasmic reticulum-mitochondrial-associated membrane (ER-MAM) localized APP-C99 in cells of the subject, comprising: (a) determining the ratio of C99 to total Aβ in a sample from the subject; and (b) administering a composition that reduces the level of ER-MAM localized APP-C99 in cells of the subject if the ratio of C99 to total Aβ in a sample from the subject is higher than the ratio of C99 to total Aβ in a sample from a subject that does not have Alzheimer's Disease.

In certain aspects the invention provides a method of reducing the level of endoplasmic reticulum-mitochondrial-associated membrane (ER-MAM) localized APP-C99 in cells of the subject, comprising: (a) determining the level of MAM-mediated phospholipid transport and/or synthesis in a sample from the subject; and (b) administering a composition that reduces the level of ER-MAM localized APP-C99 in cells of the subject if the level of MAM-mediated phospholipid transport and/or synthesis in a sample from the subject is higher than the level of MAM-mediated phospholipid transport and/or synthesis in a sample from a subject that does not have Alzheimer's Disease.

In some embodiments, the composition that reduces the level of ER-MAM localized APP-C99 comprises an ER-MAM localized γ-secretase activator or agonist, phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), auraptene (7-geranyloxycoumarin), mifepristone, miR-106b or a nucleic acid encoding miR-106b, an ITM2B inhibitor, a TRPC6 inhibitor, a composition that increases phosphorylation of APP at Thr668, an antibody or a peptide that binds to C99, an endosome-to-MAM movement inhibitor, a BACE1 inhibitor or antagonist, a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, or all-trans retinoic acid (atRA), a legumain inhibitor, Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a LDL receptor inhibitor, acetylcholine, a CypD inhibitor, U18666a, a MFN2 inhibitor, a PACS2 inhibitor, a Reticulon-1 inhibitor, a MARCH5 inhibitor, a VAPB inhibitor, a ADORA2A inhibitor or antagonist, an ErbB2 inhibitor or antagonist, a casein kinase 1γ2 agonist, a tricyclic pyrone molecule such as CP2, verubacest (MK-8931), JNJ-54861911, AZD3293/LY3314814, E2609, CNP520, Gleevec, DV2-103, a SREBP2 inhibitor or antagonist, cyclodextrin, a CypD inhibitor or antagonist, a CD36 inhibitor or antagonist, a CYP11A1 agonist, a GRP75 inhibitor or antagonist, a HIFα agonist, a PS2V agonist, a Reticulon4/Nogo-B agonist, a prolyl hydroxylase (PHD1/EGLN1, PHD2/EGLN2, or PHD3/EGLN3) inhibitor or antagonist, or a composition that increases the level of, activates, or agonises OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, p38α-MAPK, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1.

In some embodiments, the ADORA2A inhibitor or antagonist is istradefylline, preladenant, or tozadenant. In some embodiments, the ErbB2 inhibitor or antagonist is CL-387,785. In some embodiments, the composition that reduces SREBP2 is osmotin. In some embodiments, the CypD inhibitor or antagonist is Cyclosporin A (CsA). In some embodiments, the CD36 inhibitor or antagonist is sulfo-N-succinimidyl oleate (SSO). In some embodiments, the CYP11A1 agonist is efavirenz. In some embodiments, the GRP inhibitor or antagonist is MKT-077. In some embodiments, the prolyl hydroxylase (PHD1/EGLN1, PHD2/EGLN2, or PHD3/EGLN3) inhibitor or antagonist is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

In some embodiments, instead of administering a composition that reduces the level of ER-MAM localized APP-C99, the subject or cells are exposed to a high altitude environment. In some embodiments, the high altitude environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the high altitude environment is a treatment room with an artificial environment that simulates high altitudes.

In some embodiments, instead of administering a composition that reduces the level of ER-MAM localized APP-C99, the subject or cells are exposed to a low oxygen (hypoxic) environment. In some embodiments, the low oxygen (hypoxic) environment includes, but is not limited to, altitudes of over 1500 meters, 1600 meters, 1700 meters, 1800 meters, 1900 meters, 2000 meters, 2100 meters, 2200 meters, 2300 meters, 2,400 meters, or 2500 meters and above. In some embodiments the low oxygen (hypoxic) environment is a treatment room with an artificial environment that simulates hypoxic conditions.

Methods of Diagnosis

In certain aspects the invention provides a method of determining if a subject has or is at risk of developing AD, comprising: (a) determining the ratio of cholesterol esters to free cholesterol in a sample from the subject; and (b) determining that the subject has or is at risk of developing AD if the ratio of cholesterol esters to free cholesterol in a sample from the subject is higher than the ratio of cholesterol esters to free cholesterol in a sample from a subject that does not have AD.

In certain aspects the invention provides a method of determining if a subject has or is at risk of developing AD, comprising: (a) determining the ratio of ceramide to sphingomyelin in a sample from the subject; and (b) determining that the subject has or is at risk of developing AD if the ratio of ceramide to sphingomyelin in a sample from the subject is higher than the ratio of ceramide to sphingomyelin in a sample from a subject that does not have AD.

In certain aspects the invention provides a method of determining if a subject has or is at risk of developing AD, comprising: (a) determining the ratio of C99 to total Aβ in a sample from the subject; and (b) determining that the subject has or is at risk of developing AD if the ratio of C99 to total Aβ in a sample from the subject is higher than the ratio of C99 to total Aβ in a sample from a subject that does not have Alzheimer's Disease.

In certain aspects the invention provides a method of determining if a subject has or is at risk of developing AD, comprising: (a) determining the level of MAM-mediated phospholipid transport and/or synthesis in a sample from the subject; and (b) determining that the subject has or is at risk of developing AD if the level of MAM-mediated phospholipid transport and/or synthesis in a sample from the subject is higher than the level of MAM-mediated phospholipid transport and/or synthesis in a sample from a subject that does not have Alzheimer's Disease.

In some embodiments, the sample is a blood sample. In some embodiments, the sample comprises cells of the subject, for example, but not limited to skin fibroblasts, or cells of the subject present in a blood sample. For example, the cells obtained can be, but are not limited to, a neuron, a fibroblast, a skin biopsy, a blood cell (e.g. a lymphocyte), an epithelial cell and cells found in urine sediment.

Methods of detecting C99, Aβ, and other polypeptides of the invention are known in the art and are described herein. For example, C99, Aβ, and other polypeptides of the invention can be detected by Western blot, or ELISA. In some embodiments, C99 is detected by Western blot. In some embodiments Aβ is measured by ELISA. Methods for determining the level of cholesterol esters, free cholesterol, ceramide, sphingomyelin are known in the art and are described herein. For example, the level of cholesterol esters, free cholesterol, ceramide, or sphingomyelin can be measured using thin-layer chromatography. In some embodiments, the level of cholesterol esters can be determined by measuring the level of total cholesterol and the level of free cholesterol, and subtracting the level of free cholesterol from the level of total cholesterol. In some embodiments the level of free and total cholesterol can be measured using a colorimetric assay.

For example, cells which contain a nucleic acid encoding a particular protein or polypeptide, and which subsequently express a protein encoded by the gene, can be identified by various procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a nucleic acid encoding a particular protein or polypeptide can be detected by DNA-DNA or DNA-RNA hybridization or amplification using probes or fragments of nucleic acids encoding the protein or polypeptide. Nucleic acid amplification-based assays involve the use of oligonucleotides selected from sequences encoding a polypeptide encoded by a gene to detect transformants which contain a nucleic acid encoding said protein or polypeptide.

Protocols for detecting and measuring the expression of a polypeptide encoded by a gene, using either polyclonal or monoclonal antibodies specific for the polypeptide are well established. Non-limiting examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a polypeptide encoded by a gene, can be used, or a competitive binding assay can be employed.

Labeling and conjugation techniques are known by those skilled in the art and can be used in various nucleic acid and amino acid assays. Methods for producing labeled hybridization or PCR probes for detecting sequences related to nucleic acid sequences encoding a protein, include, but are not limited to, oligolabeling, nick translation, end-labeling, or PCR amplification using a labeled nucleotide.

Alternatively, nucleic acid sequences encoding a polypeptide encoded by a gene, can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, and/or magnetic particles.

Compositions of the Invention

In certain aspects, the invention provides a method of treating Alzheimer's Disease in a subject in need thereof, comprising administering an effective amount of a composition that increases the level of, activates, or agonises OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, p38α-MAPK, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1. In some embodiments, the composition that increases the level of OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1 comprises a polypeptide or nucleic acid encoding OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1. In some embodiments, the level of ER-MAM localized APP-C99 is reduced in cells of the subject by administering the composition that increases the level of OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, p38α-MAPK, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1.

As used herein, the compositions for increasing the level of a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIF-α, PS2V or ACAT1) can refer to proteins or polypeptides (or a fragment thereof) encoded by the gene, or to a nucleic acid (including, for example, genomic DNA, complementary DNA (cDNA), synthetic DNA, as well as any form of corresponding RNA) which encodes a polypeptide corresponding to the gene, or fragment thereof. For example, Nogo-B is a spliced isoform of Reticulon-4. Table 1 shows the genes and gene products of the invention. The genes and gene products described herein may be referred to either by their gene name or protein name. For example, a gene or gene product of the invention can be encoded by a recombinant nucleic acid encoding a protein, or fragment thereof. The molecules of the invention can be obtained from various sources and can be produced according to various techniques known in the art. For example, a nucleic acid that encodes a gene or gene product of the invention can be obtained by screening DNA libraries, or by amplification from a natural source. Molecules of the invention can include a fragment or portion of a protein, and/or a variant of the above described examples, such as a fragment thereof. Such a variant can comprise a naturally-occurring variant due to allelic variations between individuals (e.g., polymorphisms), mutated alleles, or alternative splicing forms.

TABLE 1

Genes and gene products of the invention. The names below refer to the corresponding proteins or polypeptides encoded by the genes as shown.

| Description | Protein | Gene |
|---|---|---|
| ATP binding cassette subfamily A member 1 | ABCA1 | ABCA1 |
| ATP binding cassette subfamily A member 2 | ABCA2 | ABCA2 |
| ATP binding cassette subfamily A member 7 | ABCA7 | ABCA7 |
| ATP binding cassette subfamily G member 1 | ABCG1 | ABCG1 |
| sterol O-acyltransferase 1 | ACAT1 | SOAT1 |
| ADAM metallopeptidase domain 10 | ADAM10 | ADAM 10 |
| ADAM metallopeptidase domain 17 | ADAM17 | ADAM17 |
| adipocyte plasma membrane associated protein | APMAP | APMAP |
| β-Secretase | BACE1 | BACE1 |
| β-2 Adrenergic receptor | ADRB2 | ADRB2 |
| cAMP responsive element binding protein 1 | CREB | CREB1 |
| corticotropin releasing factor/hormone | CRF (also known as CRH) | CRF |
| Cholesterol 25-hydroxylase | CH25H | CH25H |
| Cholesterol 24-hydroxylase/cytochrome P450 family 46 subfamily A member 1 | CYP46A1 | CYP46A1 |
| cyclophilinD/peptidylprolyl isomerase F | CYPD | PPIF |
| early growth response 1 | EGR1 | EGR1 |
| mitogen-activated protein kinase 3 | ERK1 | MAPK3 |
| mitogen-activated protein kinase 1 | ERK2 | MAPK1 |
| protein tyrosine kinase 2 | Focal adhesion kinase-1 (FAK1) | PTK2 |
| fetal and adult testis expressed 1 | FATE | FATE1 |
| family with sequence similarity 21 | FAM21 | FAM21 |
| golgi associated, gamma adaptin ear containing, ARF binding protein 1 | GGA1 | GGA1 |
| integral membrane protein 2B | BRI2 | ITM2B |
| Interferon-γ | IFNG | IFNG |
| Interleukin-1β | IL-1 | IL1B |
| potassium voltage-gated channel interacting protein 3 | Calsenilin | KCNIP3 |
| keratinocyte associated protein 2 | KRTCAP2 | KRTCAP2 |
| low density lipoprotein receptor | LDLR | LDLR |
| low density lipoprotein receptor class A domain containing 3 | LRAD3 | LDLRAD3 |
| legumain | LGMN | LGMN |
| LDL receptor related protein 1 | LRP1 | LRP1 |
| LDL receptor related protein 1B | LRP1B | LRP1B |
| LDL receptor related protein 2 | LRP2 | LRP2 |
| LDL receptor related protein 5 | LRP5 | LRP5 |
| LDL receptor related protein 6 | LRP6 | LRP6 |
| LDL receptor related protein 8 | LRP8 | LRP8 |
| nuclear receptor subfamily 1 group H | LXR-b | NR1H2 |

TABLE 1-continued

Genes and gene products of the invention. The names below refer to the corresponding proteins or polypeptides encoded by the genes as shown.

| Description | Protein | Gene |
|---|---|---|
| member 2 | | |
| nuclear receptor subfamily 1 group H member 3 | LXR-a | NR1H3 |
| membrane associated ring-CH-type finger 5 | MARCH5 | MARCH5 |
| mitogen-activated protein kinase kinase 1 | MEK1 | MAP2K1 |
| mitogen-activated protein kinase kinase 2 | MEK2 | MAP2K2 |
| mitogen-activated protein kinase kinase kinase 1 | MEKK1 | MAP3K1 |
| mitogen-activated protein kinase 11 | p38α-MAPK | MAPK11 |
| mitogen-activated protein kinase 12 | | MAPK12 |
| mitogen-activated protein kinase 13 | | MAPK13 |
| mitogen-activated protein kinase 14 | | MAPK14 |
| mucolipin 1 | TRPML1-3 | MCOLN1-3 |
| Mitofusin-2 | MFN2 | MFN2 |
| mannosyl (beta-1,4-)-glycoprotein beta-1,4-N-acetylglucosaminyltransferase | MGAT3 | MGAT3 |
| OCIA domain containing 2 | OCIAD2 | OCIAD2 |
| oligosaccharyltransferase complex non-catalytic subunit | OSTC | OSTC |
| presenilin-1 | PS1 | PS1 |
| presenilin-2 | PS2 | PS2 |
| phosphofurin acidic cluster sorting protein 2 | PACS2 | PACS2 |
| pro-apoptotic WT1 regulator | PAR4 | PAWR |
| phosphatidylinositol binding clathrin assembly protein | PICALM | PICALM |
| protein L-isoaspartyl O-methyltransferase | PIMT | PIMT |
| peroxisome proliferator activated receptor alpha | PPAR-α | PPARA |
| Reticulon-1 | RTN1 | RTN1 |
| Reticulon-4 (Nogo-B) | RTN4 | RTN4 |
| sortilin related receptor 1 | SORLA (LR11) | SORL1 |
| sterol regulatory element binding transcription factor 1 | SREBP1 | SREBF1 |
| sterol regulatory element binding transcription factor 2 | SREBP2 | SREBF2 |
| trichoplein keratin filament binding | TCHP (mitostatin) | TCHP |
| tumor necrosis factor | TNF-α | TNF |
| transient receptor potential cation channel subfamily C member 6 | TRPC6 | TRPC6 |
| ubiquitin C-terminal hydrolase L1 | UCHL1 | UCHL1 |
| VAMP associated protein B and C | VAPB | VAPB |
| very low density lipoprotein receptor | VLDLR | VLDLR |
| adenosine receptor A2A | Adenosine receptor A2A | ADORA2A |
| erb-b2 receptor tyrosine kinase 2 | ErbB2 | ErbB2 |
| cyclophilin D | CypD | Cyclophilin D |
| cluster of differentiation 36/scavenger receptor | CD36 | CD36 |
| glucose-regulated protein 75 | GRP75 | GRP75 |
| prolyl hydroxylase | PHD | PHD |
| cytochrome P450 family 11 subfamily A member 1 | CYP11A1 | CYP11A1 |
| hypoxia inducible factor-alpha | HIF-α | HIF-α |
| presenilin 2 peptide | PS2V | PS2 |
| acetyl-Co enzyme A acetyltransferase 1 | ACAT1 | ACAT1 |
| osmotin | osmotin | osmotin |

The nucleic acid can be any type of nucleic acid, including genomic DNA, complementary DNA (cDNA), synthetic or semi-synthetic DNA, as well as any form of corresponding RNA. The nucleic acid can be a non-naturally occurring nucleic acid created artificially (such as by assembling, cutting, ligating or amplifying sequences). It can be double-stranded or single-stranded.

The invention further provides for nucleic acids that are complementary to a nucleic acid of a gene or gene product of the invention. Complementary nucleic acids can hybridize to the nucleic acid sequence described above under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

According to the invention, protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture.

In one embodiment, a composition for increasing the level of a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1), according to the methods described herein can be administered to a subject as a recombinant protein. In another embodiment, a composition for increasing the level of a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1), can be administered to a subject as a modified recombinant protein. In a further embodiment, a composition for increasing the level of a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1), according to the methods described herein can be administered to a subject by delivery of a nucleic acid encoding a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1), or fragment thereof. For example, nucleic acids can be delivered to a subject using a viral vector.

The polypeptide and nucleic acids sequence of the gene or gene products of the invention (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1) are accessible in public databases such as GenBank.

A gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1) of the invention can also encompass ortholog genes, which are genes conserved among different biological species such as humans, dogs, cats, mice, and rats, that encode proteins (for example, homologs (including splice variants), mutants, and derivatives) having biologically equivalent functions as the human-derived protein. Orthologs of a protein include any mammalian ortholog inclusive of the ortholog in humans and other primates, experimental mammals (such as mice, rats, hamsters and guinea pigs), mammals of commercial significance (such as horses, cows, camels, pigs and sheep), and also companion mammals (such as domestic animals, e.g., rabbits, ferrets, dogs, and cats). A gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1) of the invention can comprise a protein encoded by a nucleic acid sequence homologous to the human nucleic acid, wherein the nucleic acid is found in a different species and wherein that homolog encodes a protein similar to a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1) of the invention.

The invention utilizes conventional molecular biology, microbiology, and recombinant DNA techniques available to one of ordinary skill in the art. Such techniques are well known to the skilled worker and are explained fully in the literature. See, e.g., Maniatis, Fritsch & Sambrook, "*DNA Cloning: A Practical Approach*," Volumes I and II (D. N. Glover, ed., 1985); "Oligonucleotide Synthesis" (M. J. Gait, ed., 1984); "*Nucleic Acid Hybridization*" (B. D. Hames & S. J. Higgins, eds., 1985); "*Transcription and Translation*" (B. D. Hames & S. J. Higgins, eds., 1984); "*Animal Cell Culture*" (R. I. Freshney, ed., 1986); "*Immobilized Cells and Enzymes*" (IRL Press, 1986): B. Perbal, "*A Practical Guide to Molecular Cloning*" (1984), and Sambrook, et al., "*Molecular Cloning: a Laboratory Manual*" (2001).

One skilled in the art can obtain a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1) of the invention in several ways, which include, but are not limited to, isolating the protein via biochemical means or expressing a nucleotide sequence encoding the protein of interest by genetic engineering methods.

In one embodiment, a fragment of a nucleic acid sequence that comprises a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1) of the invention can encompass any portion of at least about 8 consecutive nucleotides. In one embodiment, the fragment can comprise at least about 10 nucleotides, at least about 15 nucleotides, at least about 20 nucleotides, or at least about 30 nucleotides. Fragments include all possible nucleotide lengths between about 8 and about 100 nucleotides, for example, lengths between about 15 and about 100 nucleotides, or between about 20 and about 100 nucleotides.

In one embodiment, a fragment of a protein encodied by a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, or ACAT1) of the invention can encompass any portion of at least about 8 consecutive amino acids. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 80 consecutive amino acids, at least about 90 consecutive amino acids, at least about 100 consecutive amino acids, at least about 110 consecutive amino acids, or at least about 120 consecutive amino acids. Fragments include all possible amino acid lengths between about 8 and 80 about amino acids, for example, lengths between about 10 and about 80 amino acids, between about 15 and about 80 amino acids, between about 20 and about 80 amino acids, between about 35 and about 80 amino acids, between about 40 and about 80 amino acids, between about 50 and about 80 amino acids, or between about 70 and about 80 amino acids.

Recombinant Proteins

One skilled in the art understands that polypeptides can be obtained in several ways, which include but are not limited to, expressing a nucleotide sequence encoding the protein of interest, or fragment thereof, by genetic engineering methods.

In certain aspects, the invention provides a method of treating Alzheimer's Disease in a subject in need thereof, comprising administering an effective amount of a composition comprising a OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIF-α, PS2V, osmotin, or ACAT1 polypeptide.

In one embodiment, the nucleic acid is expressed in an expression cassette, for example, to achieve overexpression in a cell. The nucleic acids of the invention can be an RNA, cDNA, cDNA-like, or a DNA of interest in an expressible format, such as an expression cassette, which can be expressed from the natural promoter or an entirely heterologous promoter. The nucleic acid of interest can encode a protein, and may or may not include introns. Any recombinant expression system can be used, including, but not limited to, bacterial, mammalian, yeast, insect, or plant cell expression systems.

Host cells transformed with a nucleic acid sequence encoding a protein of interest, can be cultured under conditions suitable for the expression and recovery of the protein from cell culture. The polypeptide produced by a transformed cell can be secreted or contained intracellularly depending on the sequence and/or the vector used. Expression vectors containing a nucleic acid sequence encoding a protein of interest can be designed to contain signal sequences which direct secretion of soluble polypeptide molecules encoded by a nucleic acid, through a prokaryotic or eukaryotic cell membrane.

Nucleic acid sequences that encode a polypeptide can be synthesized, in whole or in part, using chemical methods known in the art. Alternatively, proteins can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of a protein can be separately synthesized and combined using chemical methods to produce a full-length molecule.

A synthetic peptide can be substantially purified via high performance liquid chromatography (HPLC). The composition of a synthetic protein can be confirmed by amino acid analysis or sequencing. Additionally, any portion of an amino acid sequence comprising a protein can be altered during direct synthesis and/or combined using chemical methods with sequences from other proteins to produce a variant polypeptide or a fusion protein.

In another embodiment, the polypeptide can be modified, such as by glycosylations and/or acetylations and/or chemical reaction or coupling, and can contain one or several non-natural or synthetic amino acids.

Expression Systems

Bacterial Expression Systems. One skilled in the art understands that expression of desired protein products in prokaryotes is most often carried out in *E. coli* with vectors that contain constitutive or inducible promoters. Some non-limiting examples of bacterial cells for transformation include the bacterial cell line *E. coli* strains DH5a or MC1061/p3 (Invitrogen Corp., San Diego, Calif.), which can be transformed using standard procedures practiced in the art, and colonies can then be screened for the appropriate plasmid expression. In bacterial systems, a number of expression vectors can be selected. Non-limiting examples of such vectors include multifunctional *E. coli* cloning and expression vectors such as BLUESCRIPT (Stratagene). Some *E. coli* expression vectors (also known in the art as fusion-vectors) are designed to add a number of amino acid residues, usually to the N-terminus of the expressed recombinant protein. Such fusion vectors can serve three functions: 1) to increase the solubility of the desired recombinant protein; 2) to increase expression of the recombinant protein of interest; and 3) to aid in recombinant protein purification by acting as a ligand in affinity purification. In some instances, vectors, which direct the expression of high levels of fusion protein products that are readily purified, may also be used. Some non-limiting examples of fusion expression vectors include pGEX, which fuse glutathione S-tranferase (GST) to desired protein; pcDNA 3.1/V5-His A B & C (Invitrogen Corp, Carlsbad, Calif.) which fuse 6×-His (SEQ ID NO: 1) to the recombinant proteins of interest; pMAL (New England Biolabs, MA) which fuse maltose E binding protein to the target recombinant protein; the *E. coli* expression vector pUR278 (Ruther et al., (1983) EMBO 12:1791), wherein the coding sequence may be ligated individually into the vector in frame with the lac Z coding region in order to generate a fusion protein; and pIN vectors (Inouye et al., (1985) Nucleic Acids Res. 13:3101-3109; Van Heeke et al., (1989) J. Biol. Chem. 24:5503-5509. Fusion proteins generated by the likes of the above-mentioned vectors are generally soluble and can be purified easily from lysed cells via adsorption and binding of the fusion protein to an affinity matrix. For example, fusion proteins can be purified from lysed cells via adsorption and binding to a matrix of glutathione agarose beads subsequently followed by elution in the presence of free glutathione. For example, the pGEX vectors are designed to include thrombin or factor Xa protease cleavage sites so that the cloned target can be released from the GST moiety.

Plant, Insect, and Yeast Expression Systems.

Other suitable cell lines, in addition to microorganisms such as bacteria (e.g., *E. coli* and *B. subtilis*) transformed with recombinant bacteriophage DNA, plasmid DNA or cosmid DNA expression vectors containing coding sequences for a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, osmotin, or ACAT1) of the invention may alternatively be used to produce the molecule of interest. A non-limiting example includes plant cell systems infected with recombinant virus expression vectors (for example, tobacco mosaic virus, TMV; cauliflower mosaic virus, CaMV) or transformed with recombinant plasmid expression vectors (e.g., Ti plasmid) containing coding sequences for a protein of the invention. If plant expression vectors are used, the expression of sequences encoding a protein of the invention can be driven by any of a number of promoters. For example, viral promoters such as the 35S and 19S promoters of CaMV can be used alone or in combination with the omega leader sequence from tobacco mosaic virus TMV. Alternatively, plant promoters such as the small subunit of RUBISCO or heat shock promoters, can be used. These constructs can be introduced into plant cells by direct DNA transformation or by pathogen-mediated transfection.

In another embodiment, an insect system also can be used to express a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIF-α, PS2V, osmotin, or ACAT1) of the invention. For example, in one such system *Autographa californica* nuclear polyhedrosis virus (AcNPV) is used as a vector to express foreign genes in *Spodoptera frugiperda* cells or in *Trichoplusia* larvae. Sequences encoding a nucleic acid of the invention can be cloned into a non-essential region of the virus, such as the polyhedrin gene, and placed under control of the polyhedrin promoter. Successful insertion of the nucleic acid sequences of a nucleic acid of the invention will render the polyhedrin gene inactive and produce recombinant virus lacking coat protein. The recombinant viruses can then be used to infect *S. frugiperda* cells or *Trichoplusia* larvae in which a protein of the invention can be expressed.

In another embodiment, a yeast (for example, *Saccharomyces* sp., *Pichia* sp.) system also can be used to express a protein of the invention. Yeast can be transformed with recombinant yeast expression vectors containing coding sequences for a protein of the invention.

Mammalian Expression Systems.

Mammalian cells (such as BHK cells, VERO cells, CHO cells and the like) can also contain an expression vector (for example, one that harbors a nucleotide sequence encoding a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, osmotin, or ACAT1) for expression of a desired product. Expression vectors containing such a nucleic acid sequence linked to at least one regulatory sequence in a manner that allows expression of the nucleotide sequence in a host cell can be introduced via methods known in the art. A number of viral-based expression systems can be used to express a protein of the invention in mammalian host cells. The vector can be a recombinant DNA or RNA vector, and includes DNA plasmids or viral vectors. For example, if an adenovirus is used as an expression vector, sequences encoding a nucleic acid of the invention can be ligated into an adenovirus transcription/translation complex comprising the late promoter and tripartite leader sequence. Insertion into a non-essential E1 or E3 region of the viral genome can be used to obtain a viable virus which is capable of expressing a protein of the invention in infected host cells. Transcription enhancers, such as the Rous sarcoma virus (RSV) enhancer, can also be used to increase expression in mammalian host cells. In addition, viral vectors can be constructed based on, but not limited to, adeno-associated virus, retrovirus, adenovirus, lentivirus or alphavirus.

Regulatory sequences are well known in the art, and can be selected to direct the expression of a protein of the invention in an appropriate host cell as described in Goeddel, *Gene Expression Technology: Methods in Enzymology* 185, Academic Press, San Diego, Calif. (1990). Non-limiting examples of regulatory sequences include: polyadenylation signals, promoters (such as CMV, ASV, SV40, or other viral promoters such as those derived from bovine papilloma, polyoma, and Adenovirus 2 viruses (Fiers, et al., 1973, *Nature* 273:113; Hager G L, et al., *Curr Opin Genet-Dev,* 2002, 12(2):137-41) enhancers, and other expression control elements. Practitioners in the art understand that designing an expression vector can depend on factors, such as the choice of host cell to be transfected and/or the type and/or amount of desired protein to be expressed.

Enhancer regions, which are those sequences found upstream or downstream of the promoter region in non-coding DNA regions, are also known in the art to be important in optimizing expression. If needed, origins of replication from viral sources can be employed, such as if a prokaryotic host is utilized for introduction of plasmid DNA. However, in eukaryotic organisms, chromosome integration is a common mechanism for DNA replication.

For stable transfection of mammalian cells, a small fraction of cells can integrate introduced DNA into their genomes. The expression vector and transfection method utilized can be factors that contribute to a successful integration event. For stable amplification and expression of a desired protein, a vector containing DNA encoding a protein of interest is stably integrated into the genome of eukaryotic cells (for example mammalian cells, such as HEK293 cells), resulting in the stable expression of transfected genes. An exogenous nucleic acid sequence can be introduced into a cell (such as a mammalian cell, either a primary or secondary cell) by homologous recombination as disclosed in U.S. Pat. No. 5,641,670, the contents of which are herein incorporated by reference.

A gene that encodes a selectable marker (for example, resistance to antibiotics or drugs, such as ampicillin, neomycin, G418, and hygromycin) can be introduced into host cells along with the gene of interest in order to identify and select clones that stably express a gene encoding a protein of interest. The gene encoding a selectable marker can be introduced into a host cell on the same plasmid as the gene of interest or can be introduced on a separate plasmid. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein molecule.

A host cell strain can be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

An exogenous nucleic acid can be introduced into a cell via a variety of techniques known in the art, such as lipofection, microinjection, calcium phosphate or calcium chloride precipitation, DEAE-dextrin-mediated transfection, or electroporation. Electroporation is carried out at approximate voltage and capacitance to result in entry of the DNA construct(s) into cells of interest. Other methods used to transfect cells can also include modified calcium phosphate precipitation, polybrene precipitation, liposome fusion, and receptor-mediated gene delivery.

Animal or mammalian host cells capable of harboring, expressing, and secreting large quantities of a protein of the invention into the culture medium for subsequent isolation and/or purification include, but are not limited to, Human Embryonic Kidney 293 cells (HEK-293) (ATCC CRL-1573); Chinese hamster ovary cells (CHO), such as CHO-K1 (ATCC CCL-61), DG44 (Chasin et al., (1986) *Som. Cell Molec. Genet,* 12:555-556; Kolkekar et al., (1997) *Biochemistry,* 36:10901-10909; and WO 01/92337 A2), dihydrofolate reductase negative CHO cells (CHO/dhfr-, Urlaub et al., (1980) *Proc. Natl. Acad. Sci. U.S.A.,* 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293 cells subcloned for growth in suspension culture, Graham et al., (1977) *J Gen. Virol.,* 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4; Mather (1980) *Biol. Reprod.,* 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather (1982) *Annals NY Acad. Sci.,* 383:44-68); MCR 5 cells; FS4 cells. A cell line transformed to produce a protein of the invention can also be an immortalized mammalian cell line of lymphoid origin, which include but are not limited to, a myeloma, hybridoma, trioma or quadroma cell line. The cell line can also comprise a normal lymphoid cell, such as a B cell, which has been immortalized by transformation with a virus, such as the Epstein Barr virus (such as a myeloma cell line or a derivative thereof).

A host cell strain, which modulates the expression of the inserted sequences, or modifies and processes the nucleic acid in a specific fashion desired also may be chosen. Such modifications (for example, glycosylation and other post-translational modifications) and processing (for example, cleavage) of protein products may be important for the function of the protein. Different host cell strains have characteristic and specific mechanisms for the post-translational processing and modification of proteins and gene products. As such, appropriate host systems or cell lines can be chosen to ensure the correct modification and processing of the foreign protein expressed. Thus, eukaryotic host cells possessing the cellular machinery for proper processing of the primary transcript, glycosylation, and phosphorylation of the gene product may be used. Non-limiting examples of mammalian host cells include HEK-293, 3T3, W138, BT483, Hs578T, CHO, VERY, BHK, Hela, COS, BT2O, T47D, NSO (a murine myeloma cell line that does not endogenously produce any immunoglobulin chains), CRL7030, MDCK, 293, HTB2, and HsS78Bst cells.

Various culturing parameters can be used with respect to the host cell being cultured. Appropriate culture conditions for mammalian cells are well known in the art (Cleveland W L, et al., *J Immunol Methods,* 1983, 56(2): 221-234) or can be determined by the skilled artisan (see, for example, *Animal Cell Culture: A Practical Approach* 2*nd Ed*., Rickwood, D. and Hames, B. D., eds. (Oxford University Press: New York, 1992)). Cell culturing conditions can vary according to the type of host cell selected. Commercially available medium can be utilized.

Cells suitable for culturing can contain introduced expression vectors, such as plasmids or viruses. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 201, *Molecular Cloning, A Laboratory Manual*, Cold Spring Harbor Press, Cold Spring Harbor, N.Y. and in F. M. Ausubel et al., 1989, *Current Protocols in Molecular Biology*, John Wiley & Sons, New York, N.Y.

Purification of Recombinant Proteins

A polypeptide can be purified from any human or non-human cell which expresses the polypeptide, including those which have been transfected with expression constructs that express a protein of the invention. A purified protein can be separated from other compounds which normally associate with the protein, in the cell, such as certain other proteins, carbohydrates, or lipids, using methods practiced in the art. For protein recovery, isolation and/or purification, the cell culture medium or cell lysate is centrifuged to remove particulate cells and cell debris. The desired polypeptide molecule is isolated or purified away from contaminating soluble proteins and polypeptides by suitable purification techniques. Non-limiting purification methods for proteins include: size exclusion chromatography; affinity chromatography; ion exchange chromatography; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anion-exchange resins, in which the more acidic fraction(s) is/are collected.

Compounds of the Invention

In certain aspects, the invention provides a method of treating Alzheimer's Disease in a subject in need thereof, comprising administering an effective amount of a composition comprising an ER-MAM localized γ-secretase activator or agonist, phenylbutyric acid (PBA), an ADRB2 agonist, 4-hydroxynonenal, an ERK1/2 inhibitor, a MEK1/2 inhibitor, GSK561679, Corticorelin/Xerecept, 12-O tetradecanoylphorbol-13-acetate (TPA), auraptene (7-geranyloxycoumarin), mifepristone, miR-106b or a nucleic acid encoding miR-106b, an ITM2B inhibitor, a TRPC6 inhibitor, a composition that increases phosphorylation of APP at Thr668, an antibody or a peptide that binds to C99, an endosome-to-MAM movement inhibitor, a BACE1 inhibitor or antagonist, a MGAT3 inhibitor, a LXR agonist, a phorbol ester, zaragozic acid, C99 blocking peptides, BACE1 RNAi, a PAWR inhibitor, a GGA1 inhibitor, a PPAR-α inhibitor, or all-trans retinoic acid (atRA), a legumain inhibitor, Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a LDL receptor inhibitor, acetylcholine, a CypD inhibitor, U18666a, a MFN2 inhibitor, a PACS2 inhibitor, a Reticulon-1 inhibitor, a MARCH5 inhibitor, or a VAPB inhibitor, a ADORA2A inhibitor or antagonist, an ErbB2 inhibitor or antagonist, a casein kinase 1γ2 agonist, a tricyclic pyrone molecule such as CP2, verubacest (MK-8931), JNJ-54861911, AZD3293/LY3314814, E2609, CNP520, Gleevec, DV2-103, a SREBP2 inhibitor or antagonist, cyclodextrin, a CypD inhibitor or antagonist, a CD36 inhibitor or antagonist, a CYP11A1 agonist, a GRP75 inhibitor or antagonist, a HIFα agonist, a PS2V agonist, a Reticulon4/Nogo-B agonist, a prolyl hydroxylase (PHD1/EGLN1, PHD2/EGLN2, or PHD3/EGLN3) inhibitor or antagonist. In some embodiments, the ADORA2A inhibitor or antagonist is istradefylline, preladenant, or tozadenant. In some embodiments, the ErbB2 inhibitor or antagonist is CL-387,785. In some embodiments, the composition that reduces SREBP2 is osmotin. In some embodiments, the CypD inhibitor or antagonist is Cyclosporin A (CsA). In some embodiments, the CD36 inhibitor or antagonist is sulfo-N-succinimidyl oleate (SSO). In some embodiments, the CYP11A1 agonist is efavirenz. In some embodiments, the GRP inhibitor or antagonist is MKT-077. In some embodiments, the prolyl hydroxylase (PHD1/EGLN1, PHD2/EGLN2, or PHD3/EGLN3) inhibitor or antagonist is succinate, L-mimosime, 3,4-dihydroxybenzoate (3,4-DHB), S956711, FG-2216, FG-4592 (ASP1517, roxadustat), BAY85-3934 (molidustat), GSK1278863 (daprodustat), AKB-6548, or JTZ-951.

An aspect of the invention also provides a method for inhibiting the protein product of certain genes in a subject having AD, wherein the method comprises administering to the subject an effective amount of a composition comprising an inhibitor compound. In some embodiments, the inhibitor decreases expression of a gene or protein of interest (e.g. ER-MAM localized γ-secretase, ERK1/2, MEK1/2, ITM2B, ER-MAM localized APP-C99, BACE1, MGAT3, PAWR, GGA1, PPAR-α, PTK2, ABCA2, SREBP, miR33a/b, LDL receptor, MFN2, PACS2, Reticulon-1, MARCH5, TRPC6, FAM21, legumain, VAPB, ADORA2A, ErbB2, SREBP2, Cyclophilin D, CD36, GRP75, or prolyl hydroxylase [PHD1/EGLN1, PHD2/EGLN2, or PHD3/EGLN3]), thereby decreasing its expression in the subject. In some embodiments, the composition comprises modulator compounds of a gene or protein of interest (e.g. ER-MAM localized γ-secretase, ADRB2, ERK1/2, MEK1/2, ITM2B, ER-MAM localized APP-C99, BACE1, MGAT3, PAWR, GGA1, PPAR-α, PTK2, ABCA2, SREBP, miR33a/b, SORL1, LDL receptor, MFN2, PACS2, Reticulon-1, MARCH5, VAPB, TRPC6, FAM21, LXR, legumain, OCIAD2, TNF-α, interleukin-1β, interferon-γ, MEKK1, OSTC, KRTCAP2, KCNIP3, CREB, APMAP, CRF, PS1, PS2, EGR1, PIMT, ADAM10, ADAM17, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, ACAT1, VAPB, ADORA2A, ErbB2, SREBP2, Cyclophilin D, CD36, GRP75, or prolyl hydroxylase [PHD1/EGLN1, PHD2/EGLN2, or PHD3/EGLN3]). In some embodiments, the compound comprises an antibody or a peptide that specifically binds to a gene or protein of interest (e.g. ER-MAM localized γ-secretase, ERK1/2, MEK1/2, ITM2B, ER-MAM localized APP-C99, BACE1, MGAT3, PAWR, GGA1, PPAR-α, PTK2, ABCA2, SREBP, miR33a/b, LDL receptor, MFN2, PACS2, Reticulon-1, MARCH5, TRPC6, FAM21, legumain, VAPB, ADORA2A, ErbB2, SREBP2, Cyclophilin D, CD36, GRP75, or prolyl hydroxylase [PHD1/EGLN1, PHD2/EGLN2, or PHD3/EGLN3]) or a fragment thereof, an antisense RNA or antisense DNA that inhibits expression of a gene or protein of interest (e.g. ER-MAM localized γ-secretase, ERK1/2, MEK1/2, ITM2B, ER-MAM localized APP-C99, BACE1, MGAT3, PAWR, GGA1, PPAR-α, PTK2, ABCA2, SREBP, miR33a/b, LDL receptor, MFN2, PACS2, Reticulon-1, MARCH5, TRPC6, FAM21, legumain, VAPB, ADORA2A, ErbB2, SREBP2, Cyclophilin D, CD36, GRP75, or prolyl hydroxylase [PHD1/EGLN1, PHD2/EGLN2, or PHD3/EGLN3]); a siRNA that specifically targets a gene or protein of interest (e.g. ER-MAM localized γ-secretase, ERK1/2, MEK1/2, ITM2B, ER-MAM localized APP-C99, BACE1, MGAT3, PAWR, GGA1, PPAR-α, PTK2, ABCA2, SREBP, miR33a/b, LDL receptor, MFN2, PACS2, Reticulon-1, MARCH5, TRPC6, FAM21, legumain, VAPB, ADORA2A, ErbB2, SREBP2, Cyclophilin D, CD36, GRP75, or prolyl hydroxylase [PHD1/EGLN1, PHD2/EGLN2, or PHD3/EGLN3]); a shRNA that specifically targets a gene or protein of interest (e.g. ER-MAM localized γ-secretase, ERK1/2, MEK1/2, ITM2B, ER-MAM localized APP-C99, MGAT3, PAWR, GGA1, PPAR-α, PTK2, ABCA2, SREBP, miR33a/b, LDL receptor, MFN2, PACS2, Reticulon-1, MARCH5, TRPC6, FAM21, legumain, VAPB, ADORA2A, ErbB2, SREBP2, Cyclophilin D, CD36, GRP75, or prolyl hydroxylase [PHD1/EGLN1, PHD2/EGLN2, or PHD3/EGLN3]); or a combination thereof. In some embodiments, the compound comprises an antibody or a peptide that specifically binds to the BACE1 cleavage site.

The present invention also relates to screening and identification of compounds or therapeutic agents for treating AD which can reduce endoplasmic reticulum-mitochondrial-associated membrane (ER-MAM) localized APP-C99. The present invention also realtes to screening and identification of compounds or therapeutic agents for treating AD which can reduce the function of endoplasmic reticulum-mitochondrial-associated membrane (ER-MAM) localized APP-C99. The methods can comprise the identification of test compounds or agents (e.g., peptides (such as antibodies or fragments thereof), small molecules, nucleic acids (such as siRNA or antisense RNA), or other agents) that can reduce endoplasmic reticulum-mitochondrial-associated membrane (ER-MAM) localized APP-C99, and subsequently determining whether these compounds can have an effect on AD in an in vitro or an in vivo assay.

As used herein, a "modulating compound" refers to a compound that interacts with a gene or protein of interest and modulates its activity and/or its expression. The compound can either increase or decrease an activity or expression. The compound can be a inhibitor, agonist, or antagonist. Some non-limiting examples of modulating compounds include peptides (such as peptide fragments, or antibodies or fragments thereof), small molecules, and nucleic acids (such as siRNA or antisense RNA specific for a gene of interest). Agonists of a molecule can be molecules which, when bound to a protein increase the expression, or increase or prolong the activity of said protein. Antagonists can be molecules which, when bound to a protein of interest, decrease the amount or the duration of the activity of said protein.

The term "modulate", as it appears herein, refers to a change in the activity or expression of a nucleic acid or protein of the invention. For example, modulation can cause an increase or a decrease in protein activity, binding characteristics, or any other biological, functional, or immunological properties of a nucleic acid or protein of the invention.

A compound, for example, an agonist or antagonist, can be a protein, such as an antibody (monoclonal, polyclonal, humanized, chimeric, or fully human), or a binding fragment thereof. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and $(Fab')_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) *Ann. Rev. Biomed. Eng.* 2:339-76; Hudson (1998) *Curr. Opin. Biotechnol.* 9:395-402). Antibodies can be obtained commercially, custom generated, or synthesized against an antigen of interest according to methods established in the art (Janeway et al., (2001) *Immunobiology,* 5th ed., Garland Publishing).

Inhibition of RNA encoding a protein of the invention can effectively modulate the expression of the gene from which the RNA is transcribed. Inhibitors are selected from the group comprising: siRNA, interfering RNA or RNAi; dsRNA; RNA Polymerase III transcribed DNAs; shRNAs; ribozymes; and antisense nucleic acid, which can be RNA, DNA, or artificial nucleic acid.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the DNA sequence encoding a polypeptide can be synthesized, e.g., by conventional phosphodiester techniques (Dallas et al., (2006) *Med. Sci. Monit.* 12(4):RA67-74; Kalota et al., (2006) *Handb. Exp. Pharmacol.* 173:173-96; Lutzelburger et al., (2006) *Handb. Exp. Pharmacol.* 173:243-59; each herein incorporated by reference in its entirety).

siRNA comprises a double stranded structure containing from about 15 to about 50 base pairs, for example from about 21 to about 25 base pairs, and having a nucleotide sequence identical or nearly identical to an expressed target gene or RNA within the cell. Antisense nucleotide sequences include, but are not limited to: morpholinos, 2'-O-methyl polynucleotides, DNA, RNA and the like. RNA polymerase III transcribed DNAs contain promoters, such as the U6 promoter. These DNAs can be transcribed to produce small hairpin RNAs in the cell that can function as siRNA or linear RNAs that can function as antisense RNA. The modulating compound can contain ribonucleotides, deoxyribonucleotides, synthetic nucleotides, or any suitable combination such that the target RNA and/or gene is inhibited. In addition, these forms of nucleic acid can be single, double, triple, or quadruple stranded. See for example Bass (2001) *Nature,* 411, 428 429; Elbashir et al., (2001) *Nature,* 411, 494 498; and PCT Publication Nos. WO 00/44895, WO 01/36646, WO 99/32619, WO 00/01846, WO 01/29058, WO 99/07409, WO 00/44914; each of which are herein incorporated by reference in its entirety.

siRNA can be produced chemically or biologically, or can be expressed from a recombinant plasmid or viral vector (for example, see U.S. Pat. Nos. 7,294,504; 7,148,342; and 7,422,896; the entire disclosures of which are herein incorporated by reference). Exemplary methods for producing and testing dsRNA or siRNA molecules are described in U.S. Publication No. 2002/0173478 to Gewirtz, and in U.S. Publication No. 2007/0072204 to Hannon et al., the entire disclosures of which are herein incorporated by reference.

A modulating compound can additionally be a short hairpin RNA (shRNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., 2002, *Genes Dev,* 16:948-58; McCaffrey et al., 2002, *Nature,* 418:38-9; McManus et al., 2002, *RNA,* 8:842-50; Yu et al., 2002, *Proc Natl Acad Sci USA,* 99:6047-52; each herein incorporated by reference in its entirety. Such hairpin RNAs are engineered in cells or in an animal to ensure continuous and stable suppression of a desired gene. It is known in the art that siRNAs can be produced by processing a hairpin RNA in the cell.

When a nucleic acid such as RNA or DNA is used that encodes a protein or peptide of the invention, it can be delivered into a cell in any of a variety of forms, including as naked plasmid or other DNA, formulated in liposomes, in an expression vector, which includes a viral vector (including RNA viruses and DNA viruses, including adenovirus, lentivirus, alphavirus, and adeno-associated virus), by biocompatible gels, via a pressure injection apparatus such as the Powderject™ system using RNA or DNA, or by any other convenient means. Again, the amount of nucleic acid needed to sequester an Id protein in the cytoplasm can be readily determined by those of skill in the art, which also can vary with the delivery formulation and mode and whether the nucleic acid is DNA or RNA. For example, see Manjunath et al., (2009) *Adv Drug Deliv Rev.* 61(9):732-45; Singer and Verma, (2008) *Curr Gene Ther.* 8(6):483-8; and Lundberg et al., (2008) *Curr Gene Ther.* 8(6):461-73; each herein incorporated by reference in its entirety.

A modulating compound can also be a small molecule that binds to a nucleic acid or protein of the invention and disrupts its function, or conversely, enhances its function. Small molecules are a diverse group of synthetic and natural substances having low molecular weights. They can be isolated from natural sources (for example, plants, fungi, microbes and the like), are obtained commercially and/or available as libraries or collections, or synthesized. Candidate small molecules that modulate a nucleic acid or protein of the invention can be identified via in silico screening or high-throughput (HTP) screening of combinatorial libraries. Most conventional pharmaceuticals, such as aspirin, penicillin, and many chemotherapeutics, are small molecules, can be obtained commercially, can be chemically synthesized, or can be obtained from random or combinatorial libraries as described herein (Werner et al., (2006) *Brief Funct. Genomic Proteomic* 5(1):32-6; herein incorporated by reference in its entirety).

Knowledge of the primary sequence of a molecule of interest, and the similarity of that sequence with proteins of known function, can provide information as to the inhibitors or antagonists of the protein of interest in addition to agonists. Identification and screening of agonists and antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Test compounds, for example, an agonist or antagonist, can be screened from large libraries of synthetic or natural compounds (see Wang et al., (2007) *Curr Med Chem,* 14(2):133-55; Mannhold (2006) *Curr TopMed Chem,* 6 (10):1031-47; and Hensen (2006) *Curr Med Chem* 13(4): 361-76). Numerous means are currently used for random and directed synthesis of saccharide, peptide, and nucleic acid based compounds. Synthetic compound libraries are commercially available from Maybridge Chemical Co. (Trevillet, Cornwall, UK), AMRI (Albany, N.Y.), ChemBridge (San Diego, Calif.), and MicroSource (Gaylordsville, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) *Tib Tech* 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. For example, libraries can also include, but are not limited to, peptide-on-plasmid libraries, synthetic small molecule libraries, aptamer libraries, in vitro translation-based libraries, polysome libraries, synthetic peptide libraries, neurotransmitter libraries, and chemical libraries.

Screening the libraries can be accomplished by any variety of commonly known methods.

Small molecule combinatorial libraries can also be generated and screened. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address.

Computer modeling and searching technologies permit the identification of compounds, or the improvement of already identified compounds, that can treat or prevent AD. Other methods for preparing or identifying peptides that bind to a target are known in the art. Molecular imprinting, for instance, can be used for the de novo construction of macromolecular structures such as peptides that bind to a molecule. See, for example, Kenneth J. Shea, Molecular Imprinting of Synthetic Network Polymers: The De Novo synthesis of Macromolecular Binding and Catalytic Sites, TRIP Vol. 2, No. 5, May 1994; Mosbach, (1994) *Trends in Biochem. Sci.,* 19(9); and Wulff, G., in *Polymeric Reagents and Catalysts* (Ford, W. T., Ed.) *ACS Symposium Series* No. 308, pp 186-230, American Chemical Society (1986). One method for preparing such structures involves the steps of: (i) polymerization of functional monomers around a known substrate (the template) that exhibits a desired activity; (ii) removal of the template molecule; and then (iii) polymerization of a second class of monomers in, the void left by the template, to provide a new molecule which exhibits one or more desired properties which are similar to that of the template. In addition to preparing peptides in this manner other binding molecules such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are prepared by the free radical polymerization of functional monomers, resulting in a compound with a nonbiodegradable backbone. Other methods for designing such molecules include for example drug design based on structure activity relationships, which require the synthesis and evaluation of a number of compounds and molecular modeling.

Screening Assays.

Test compounds or agents can be identified by two types of assays: (a) cell-based assays; or (b) cell-free assays. The assay can be a binding assay comprising direct or indirect measurement of the binding of a test compound. The assay can also be an activity assay comprising direct or indirect measurement of the activity of a compound. The assay can also be an expression assay comprising direct or indirect measurement of the expression of mRNA nucleic acid sequences or a protein encoded by a gene of interest. The various screening assays can be combined with an in vivo assay comprising measuring the effect of the test compound on the symptoms of AD, on the defects observed in cells with an increases level of ER-MAM localized APP-C99, or on the ratio of cholesterol esters to free cholesterol, the ratio of ceramide to sphingomyelin, the ratio of C99 to total Aβ, and the level of MAM-mediated phospholipid transport and synthesis. An in vivo assay can also comprise assessing the effect of a test compound on an AD model in known mammalian models.

Functional Assays.

Compounds can be tested for the ability to decrease the level of ER-MAM localized APP-C99. Activity can be measured after contacting, a cell membrane preparation, or an intact cell with a test compound. A test compound that decreases the level of ER-MAM localized APP-C99, the ratio of cholesterol esters to free cholesterol, the ratio of ceramide to sphingomyelin, the ratio of C99 to total Aβ, or MAM-mediated phospholipid transport and synthesis by at least about 10%, at least about 20%, at least about 30%, at least about 40%, at least about 50%, at least about 60%, at least about 70%, at least about 75%, at least about 80%, at least about 90%, at least about 95% or 100% is identified as a potential agent for decreasing the level of ER-MAM localized APP-C99 or for treating AD.

As used herein, an "inhibitor" refers to a compound that interacts with a gene or a protein or polypeptide, and inhibits its activity and/or its expression. The compound can decrease the activity or expression of a protein encoded by the gene.

As used herein, an "activator" or "agonist" refers to a compound that interacts with a gene or a protein or polypeptide, and enhances its activity and/or its expression. The compound can increase the activity or expression of a protein encoded by a gene.

Any suitable agonist or antagonist, inhibitor or activator, of a gene or protein, can be used. Such compounds may be, for example, small molecule drugs, peptide agents, peptidomimetic agents, antibodies (including, but not limited to monoclonal, poycloncal, humanized, and fully human antibodies, as well as antibody fragments), inhibitory RNA molecules (such as siRNA) and the like. One of skill in the art will understand that these and other types of agents may be used to inhibit or activate the targets disclosed herein.

Nucleotide-Based Compounds

In one aspect, a compound of the invention is a nucleotide-based agonist or antagonist, inhibitor or activator. Such inhibitors or antagonists include, but are not limited to siRNAs, shRNAs, dsRNAs, microRNAs, antisense RNA molecules, and ribozymes, that inhibit the expression or activity of a target. Such nucleotide-based inhibitors may comprise ribonucleotides, deoxyribonucleotides, or various artificial nucleotide derivatives.

Peptides and Peptidomimetics

In another aspect, a compound of the invention is a peptide or peptidomimetic agonist or antagonist, inhibitor or activator. Peptides may be synthesized by methods well known in the art, including chemical synthesis and recombinant DNA methods. A peptidomimetic is a compound that is structurally similar to a peptide, such that the peptidomimetic retains the functional characteristics of the peptide. Peptidomimetics include organic compounds and modified peptides that mimic the three-dimensional shape of a peptide.

The invention encompasses a composition comprising one or more peptides provided for by the invention and a pharmaceutically acceptable carrier. The invention also encompasses a composition comprising one or more peptidomimetics provided for by the invention and a pharmaceutically acceptable carrier.

Antibodies

In one aspect, a compound of the invention is an antibody agonist or antagonist, inhibitor or activator, or a fragment thereof. The invention encompasses a composition comprising one or more antibodies provided for by the invention and a pharmaceutically acceptable carrier. The invention also encompasses a composition comprising one or more hybridoma cells provided for by the invention and a pharmaceutically acceptable carrier.

Small Molecules

In another aspect of the invention, a compound of the invention is a small molecule inhibitor, antagonist, activator, or agonist. Within the scope of the invention, the small molecule comprises an organic molecule. Also within the scope of the invention, the small molecule comprises an inorganic molecule. Protein-protein interaction inhibitors may act directly via inhibition at the protein-protein interface, or indirectly via binding to a site not at the interface and inducing a conformational change in the protein such that the protein is prohibited from engaging in the protein-protein interaction (Pagliaro et al., Curr Opin Chem Biol 8:442-449 (2004)).

A compound of the invention can also be a small molecule that binds to a protein and disrupts its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules that modulate a protein can be identified via in silico screening or high-through-put (HTP) screening of combinatorial libraries. Most conventional pharmaceuticals, such as aspirin, penicillin, and many chemotherapeutics, are small molecules, can be obtained commercially, can be chemically synthesized, or can be obtained from random or combinatorial libraries (Werner et al., (2006) *Brief Funct. Genomic Proteomic* 5(1):32-6). In some embodiments, the agent is a small molecule that binds, interacts, or associates with a target protein or RNA. Such a small molecule can be an organic molecule that, when the target is an intracellular target, is capable of penetrating the lipid bilayer of a cell to interact with the target. Small molecules include, but are not limited to, toxins, chelating agents, metals, and metalloid compounds. Small molecules can be attached or conjugated to a targeting agent so as to specifically guide the small molecule to a particular cell.

One of skill in the art will understand that other agents may be useful as agonist or antagonist, inhibitor or activator, and may be used in conjunction with the methods of the invention.

Methods of Administration

Nucleic Acid Delivery Methods.

In certain aspects, the invention provides a method of treating Alzheimer's Disease in a subject in need thereof. In some embodiments, the method can comprise administering to the subject a polypeptide or nucleic acid encoding OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, osmotin, or ACAT1.

Various approaches can be carried out to restore the activity or function of a gene or gene product (e.g. OCIAD2, TNF-α, interleukin-1β, interferon-γ, MEKK1, OSTC, KRT- CAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, osmotin, or ACAT1) of the invention in a subject. Increasing a gene expression level or activity can be accomplished through gene or protein therapy.

A nucleic acid encoding a gene or gene product (e.g. OCIAD2, TNF-α, interleukin-1β, interferon-γ, MEKK1, OSTC, KRTCAP2, KCNIP3, CREB, ADRB2, APMAP, CRF, PS1, PS2, EGR1, PIMT, ADAM10, ADAM17, LXR, MAPK11, MAPK12, MAPK13, MAPK14, PICALM, ABCA1, SOAT1, CH25H, CYP46A1, ABCA7, ABCG1, SORL1, UCHL1, miR-106b, TCHP, Reticulon-4, NogoB, TRPML1-3, FATE1, CYP11A1, HIFα, PS2V, osmotin, or ACAT1) of the invention can be introduced into the cells of a subject. For example, the wild-type gene (or fragment thereof) can also be introduced into the cells of the subject in need thereof using a vector as described herein. The vector can be a viral vector or a plasmid. The gene can also be introduced as naked DNA. The gene can be provided so as to integrate into the genome of the recipient host cells, or to remain extra-chromosomal. Integration can occur randomly or at precisely defined sites, such as through homologous recombination. Further techniques include gene gun, liposome-mediated transfection, or cationic lipid-mediated transfection. Gene therapy can be accomplished by direct gene injection, or by administering ex vivo prepared genetically modified cells expressing a functional polypeptide.

Delivery of nucleic acids into viable cells can be effected ex vivo, in situ, or in vivo by use of vectors, and more particularly viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (see, for example, Anderson, Nature, supplement to vol. 392, no. 6679, pp. 25-20 (1998)). Introduction of a nucleic acid or a gene encoding a polypeptide of the invention can also be accomplished with extrachromosomal substrates (transient expression) or artificial chromosomes (stable expression). Cells may also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., (1992) *J Gen Virol.* 73(Pt 6):1533-6), adenovirus (Berkner (1992) *Curr Top Microbiol Immunol.* 158: 39-66; Berkner (1988) *Biotechniques,* 6(7):616-29; Gorziglia and Kapikian (1992) *J Virol.* 66(7):4407-12; Quantin et al., (1992) *Proc Natl Acad Sci USA.* 89(7):2581-4; Rosenfeld et al., (1992) *Cell.* 68(1):143-55; Wilkinson et al., (1992) *Nucleic Acids Res.* 20(9):2233-9; Stratford-Perricaudet et al., (1990) *Hum Gene Ther.* 1(3):241-56), vaccinia virus (Moss (1992) *Curr Opin Biotechnol.* 3(5):518-22), adeno-associated virus (Muzyczka, (1992) *Curr Top Microbiol Immunol.* 158:97-129; Ohi et al., (1990) *Gene.* 89(2): 279-82), herpesviruses including HSV and EBV (Margolskee (1992) *Curr Top Microbiol Immunol.* 158:67-95; Johnson et al., (1992) *Brain Res Mol Brain Res.* 12(1-3): 95-102; Fink et al., (1992) *Hum Gene Ther.* 3(1): 11-9; Breakefield and Geller (1987) *Mol Neurobiol.* 1(4):339-71; Freese et al., (1990) *Biochem Pharmacol.* 40(10):2189-99), and retroviruses of avian (Bandyopadhyay and Temin (1984) *Mol Cell Biol.* 4(4):749-54; Petropoulos et al., (1992)*J Virol.* 66(6):3391-7), murine (Miller et al. (1992) *Mol Cell Biol.* 12(7):3262-72; Miller et al., (1985) *J Virol.* 55(3):521-6; Sorge et al., (1984) *Mol Cell Biol.* 4(9):1730-7; Mann and Baltimore (1985)*J Virol.* 54(2):401-7; Miller et al., (1988)*J Virol.* 62(11):4337-45), and human origin (Shimada et al., (1991) *J Clin Invest.* 88(3): 1043-7; Helseth et al., (1990) *J Virol.* 64(12):6314-8; Page et al., (1990) *J Virol.* 64(11):5270-6; Buchschacher and Panganiban (1992) *J Virol.* 66(5):2731-9).

Non-limiting examples of in vivo gene transfer techniques include transfection with viral (typically retroviral) vectors (see U.S. Pat. No. 5,252,479, which is incorporated by reference in its entirety) and viral coat protein-liposome mediated transfection (Dzau et al., Trends in Biotechnology 11:205-210 (1993), incorporated entirely by reference). For example, naked DNA vaccines are generally known in the art; see Brower, Nature Biotechnology, 16:1304-1305 (1998), which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of gene therapy protocols and methods see Anderson et al., Science 256:808-813 (1992); U.S. Pat. Nos. 5,252,479, 5,747,469, 6,017,524, 6,143,290, 6,410,010 6,511,847; 8,398,968; and 8,404,653 which are all hereby incorporated by reference in their entireties. For an example of gene therapy treatment in humans see Porter et al., NEJM 2011 365:725-733 and Kalos et al. Sci. Transl. Med. 2011. 201 3(95):95. For additional reviews of gene therapy technology, see Friedmann, Science, 244:1275-1281 (1989); Verma, Scientific American: 68-84 (1990); Miller, Nature, 357: 455-460 (1992); Kikuchi et al., J Dermatol Sci. 2008 May; 50(2):87-98; Isaka et al., Expert Opin Drug Deliv. 2007 September; 4(5):561-71; Jager et al., Curr Gene Ther. 2007 August; 7(4):272-83; Waehler et al., Nat Rev Genet. 2007 August; 8(8):573-87; Jensen et al., Ann Med. 2007; 39(2):108-15; Herweijer et al., Gene Ther. 2007 January; 14(2):99-107; Eliyahu et al., Molecules, 2005 Jan. 31; 10(1):34-64; and Altaras et al., Adv Biochem Eng Biotechnol. 2005; 99:193-260, all of which are hereby incorporated by reference in their entireties.

These methods described herein are by no means all-inclusive, and further methods to suit the specific application is understood by the ordinary skilled artisan. Moreover, the effective amount of the compositions can be further approximated through analogy to compounds known to exert the desired effect.

Protein Delivery Methods.

Protein replacement therapy can increase the amount of protein by exogenously introducing wild-type or biologically functional protein by way of infusion. A replacement polypeptide can be synthesized according to known chemical techniques or may be produced and purified via known molecular biological techniques. Protein replacement therapy has been developed for various disorders. For example, a wild-type protein can be purified from a recombinant cellular expression system (e.g., mammalian cells or insect cells-see U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al. and U.S. Pat. No. 5,879,680 to Ginns et al.), human placenta, or animal milk (see U.S. Pat. No. 6,188,045 to Reuser et al.), or other sources known in the art. After the infusion, the exogenous protein can be taken up by tissues through non-specific or receptor-mediated mechanism.

A protein of the invention can also be delivered in a controlled release system. For example, the protein can be administered using intravenous infusion, an implantable osmotic pump, a transdermal patch, liposomes, or other modes of administration. In one embodiment, a pump can be used (see Sefton (1987) *Biomed. Eng.* 14:201; Buchwald et al. (1980) *Surgery* 88:507; Saudek et al. (1989) *N. Engl. J. Med.* 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); *Ranger and Peppas*, (1983) *J. Macromol. Sci. Rev. Macromol. Chem.* 23:61; see also Levy et al. (1985) *Science* 228:190; During et al. (1989) *Ann. Neurol.* 25:351; Howard et al. (1989) *J. Neurosurg.* 71:105). In yet another embodiment, a controlled release system can be placed in proximity of the therapeutic target thus requiring only a fraction of the systemic dose (see, e.g., Goodson, in *Medical Applications of Controlled Release*, supra, vol. 2, pp. 115-138 (1984)). Other controlled release systems are discussed in the review by Langer (Science (1990) 249:1527-1533).

Pharmaceutical Compositions, Methods of Administration and Combination Treatments In some embodiments, a composition of the invention can be supplied in the form of a pharmaceutical composition, comprising an isotonic excipient prepared under sufficiently sterile conditions for human administration. Choice of the excipient and any accompanying elements of a composition of the invention will be adapted in accordance with the route and device used for administration. In some embodiments, a composition of the invention can also comprise, or be accompanied with, one or more other ingredients that facilitate the delivery or functional mobilization of the composition.

These methods described herein are by no means all-inclusive, and further methods to suit the specific application is understood by the ordinary skilled artisan. Moreover, the effective amount of the compositions can be further approximated through analogy to compounds known to exert the desired effect.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

A composition of the invention can be administered to the subject one time (e.g., as a single dose). Alternatively, a composition of the invention can be administered once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof. Furthermore, a composition of the invention can be co-administrated with another therapeutic.

The compositions of this invention can be formulated and administered to reduce the symptoms associated with AD by any means that produce contact of the active ingredient with the agent's site of action in the body of a human or non-human subject. For example, the compositions of this invention can be formulated and administered to reduce the symptoms associated with AD. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa. ($20^{th}$ ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers, such as PBS, Hank's solution, or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

Any of the therapeutic applications described herein can be applied to any subject in need of such therapy, including, for example, a mammal such as a dog, a cat, a cow, a horse, a rabbit, a monkey, a pig, a sheep, a goat, or a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). The composition must be sterile and fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition of the invention in the required amount in an appropriate solvent with one or a combination of ingredients enumerated herein, as required, followed by filtered sterilization. Dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art A composition of the invention can be administered to a subject in need thereof. Subjects in need thereof can include but are not limited to, for example, a mammal such as a dog, a cat, a cow, a horse, a rabbit, a monkey, a pig, a sheep, a goat, or a human.

A composition of the invention can also be formulated as a sustained and/or timed release formulation. Such sustained and/or timed release formulations can be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the invention (e.g., that have a therapeutic effect) can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, can be readily selected for use with the pharmaceutical compositions of the invention. Single unit dosage forms suitable for oral administration, such as, but not limited to, tablets, capsules, gel-caps, caplets, or powders, that are adapted for sustained release are encompassed by the invention.

The dosage administered can be a therapeutically effective amount of the composition sufficient to result in treatment of AD, and can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

In one embodiment, a composition of the invention is administered at least once daily. In another embodiment, a composition of the invention is administered at least twice daily. In some embodiments, a composition of the invention is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 18 weeks, for at least 24 weeks, for at least 36 weeks, for at least 48 weeks, or for at least 60 weeks. In further embodiments, a composition of the invention is administered in combination with a second therapeutic agent or with a surgical procedure.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

Experimental animals can be used as models for human disease. For example, mice can be used as a mammalian model system. The physiological systems that mammals possess can be found in mice, and in humans, for example. Certain diseases can be induced in mice by manipulating their environment, genome, or a combination of both. For example, a knock-in mouse expressing human PS1 containing a pathogenic AD-causing mutation, M146V, at the mouse PS1 locus (Q. Guo et al. Nat. Med. 5, 101-106 (1999)).

Administration of a composition of the invention is not restricted to a single route, but may encompass administration by multiple routes. Multiple administrations may be sequential or concurrent. Other modes of application by multiple routes will be apparent to one of skill in the art.

EXAMPLES

The following examples illustrate the present invention, and are set forth to aid in the understanding of the invention, and should not be construed to limit in any way the scope of the invention as defined in the statements of the invention which follow thereafter.

The Examples described below are provided to illustrate aspects of the present invention and are not included for the purpose of limiting the invention.

Example 1—Accumulation of MAM-Localized APP-C99 Triggers the Pathogenesis of Alzheimer Disease In the amyloidogenic pathway associated with Alzheimer disease (AD), the amyloid precursor protein (APP) is cleaved by β-secretase to generate a 99-aa C-terminal fragment (C99) that is then cleaved by γ-secretase to generate the β-amyloid (Aβ) found in senile plaques. It was recently showed that γ-secretase activity is enriched in mitochondria-associated endoplasmic reticulum (ER) membranes (MAM), and that ER-mitochondrial connectivity and MAM function are upregulated in AD. We now show that C99 is localized to MAM, where it mediates cellular cholesterol and sphingolipid homeostasis. Whereas C99 is normally processed rapidly, it accumulates in cells from AD patients and animal models, resulting in disrupted lipid homeostasis and increased MAM functionality. The data described herein indicate that the biochemical cause of AD is C99-mediated perturbation of cholesterol and sphingolipid metabolism, which in turn triggers the functional cause of AD, namely increased ER-mitochondrial connectivity and upregulated MAM function. Without being bound by theory, aberrant APP processing in AD results in the accumulation of MAM-localized C99, which is the fundamental effector of the pathogenesis of AD.

Familial AD (FAD) is characterized by mutations in presenilin-1 (PS1), presenilin-2 (PS2), and APP. APP is first cleaved by either α-secretase or β-secretase (BACE1) to produce C-terminal fragments (CTFs) 83 aa (C83) or 99 aa (C99) in length, respectively. PS1 and PS2 are the catalytic subunits of the γ-secretase complex that cleaves C83 and C99 to produce either p3 or β-amyloid (Aβ), respectively, along with the APP intracellular domain (AICD). The accumulation of longer forms of Aβ (e.g. ~42 aa) results in plaques that are hallmarks of AD. In addition, its precursor, C99, has also been shown to contribute to pathogenesis (1).

Altered cholesterol and sphingolipid homeostasis are early and important events in the pathogenesis of AD (2), but its cause, and its relationship to APP processing, are unclear (3). Cholesterol stimulates APP internalization and processing (4), whereas cholesterol-lowering drugs decrease Aβ (5). Moreover, cholesterol esterification by acyl-CoA:cholesterol acyltransferase 1 (ACAT1) is required for Aβ production (6). Regarding sphingolipids, ceramide is increased in AD (7), due to upregulated de novo ceramide synthesis (8) and increased sphingomyelinase (SMase) activity (7), which converts sphingomyelin to ceramide. Sterol and sphingolipid levels are co-regulated (9) so as to maintain them in equilibrium (10) to establish liquid-ordered membrane domains ("lipid rafts") (11). This equilibrium is relevant to AD, as APP processing occurs in lipid rafts (12) that also contain APP-CTFs (13).

Presenilins and γ-secretase activity localize to MAM (14-16), a lipid raft subdomain of the ER (17). Moreover, MAM functionality (17) and ER-mitochondrial apposition are increased in AD (17, 18). Described herein is demonstration that C99 is localized to MAM, and that its accumulation triggers the features of AD, via altered cholesterol and sphingolipid homeostasis.

C99 Localizes to MAM

To determine the distribution of C83 and C99, subcellular fractions from SH-SH5Y cells treated with DAPT, a γ-secretase inhibitor, and with DAPT and G1254023X, an α-secretase inhibitor were analyzed. C83 was enriched in the plasma membrane (PM) and MAM, but C99 was located preferentially in the MAM (FIG. 1A). The distribution of C83 and C99 from mouse brain in density gradients, compared to markers for other compartments, was then examined. Full-length APP (App-FL) and BACE1 partially co-migrated with mature endosomes (Rab7), but not with lysosomal, ER-intermediate, or MAM markers (FIG. 7A). In agreement with the "spatial paradox" (19), APP-CTFs co-migrated with early endosomal and lysosomal markers, whereas PS1 behaved as a MAM protein (14-16). The difficulty in seeing APP-CTFs and PS1 together was probably due to the rapid cleavage of CTFs by γ-secretase once both are in the same compartment. To reduce this rapid cleavage, the same experiment was repeated using PS1+PS2 double-knockout (PS-DKO) mouse embryonic fibroblasts (MEFs) (20); a significant fraction of C99, but not C83, now co-migrated with MAM markers (FIG. 1B). C99 in brain from knock-in (KI) mice expressing the M146V mutation in PS1 (PS-KI$^{M146V}$) (21) was also analyzed. Similar to other FAD mice (22), PS-KI$^{M146V}$ mice showed significantly more CTFs, and especially more C99, than did controls (FIG. 7B). These results suggest that C99 is targeted to MAM, and that both pathogenic mutations in PS1 and reductions in γ-secretase activity cause an accumulation of C99 in MAM. The mechanism by which C99 translocates from endosomes to the MAM is currently unknown, but may be via ER-endosome contacts (23).

An accumulation of C99 is consistent with a reduction in γ-secretase activity, supporting the view that presenilin mutations can cause a loss of function (24). Importantly, AD tissues always show increased C99 compared to the total amount of amyloid produced (25). Therefore, AD, which is typically defined by an elevated Aβ42:Aβ40 ratio (26), could also be defined by a reduced ratio of total Aβ:C99. Thus it is believed that γ-secretase defects in AD result in a loss of function in both the "quality" of the cleavage (i.e. position of the cut) and in the "quantity" of the cleaved product relative to the amount of available C99, and both should be taken into account when considering the effects of altered γ-secretase.

Accumulated C99 Causes Increased ER-Mitochondrial Apposition and MAM Dysfunction Given that reduced γ-secretase activity causes an accumulation of C99 at the MAM, it was asked if elevated C99 could be the cause of this, and other, AD-related MAM phenotypes (17). To determine if C99 plays a role in the increased apposition of ER to mitochondria (17), control and PSDKO cells were transfected with plasmids expressing markers of ER and mitochondria, and measured their colocalization (17, 27) in the absence or presence of a BACE1 inhibitor (BI) that prevents the generation of C99. Remarkably, incubation of the PS-DKO cells with BI reduced the degree of ER-mitochondrial co-localization significantly (FIG. 1C).

Figure 8A:
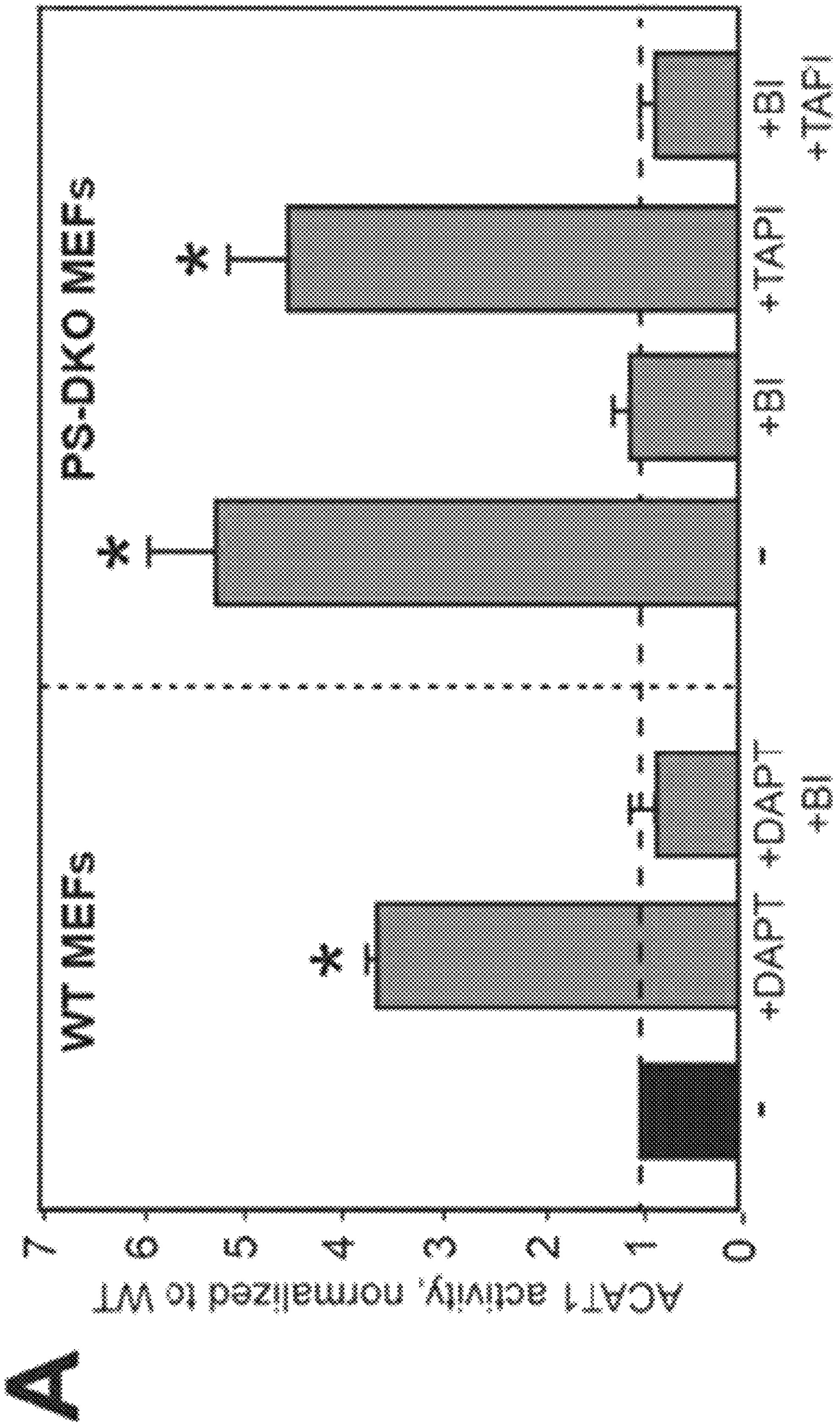
FIGS. 8A-C show cholesteryl ester and lipid droplet formation in γ-secretase-deficient cells. (A) ACAT1 activity in WT and PS-DKO MEFs in the presence and absence of α-, β-, and/or γ-secretase inhibitors. (B) Staining with LipidTox Green to detect lipid droplets in explanted brain cells from WT and PS1-KI$^{M146V}$ mice. (C) Staining of SH-SY5Y cells treated with DAPT (to increase C99 accumulation) or with DAPT+BI (to inhibit C99 production). Quantitations of lipid droplets at right.
Figure 8B:
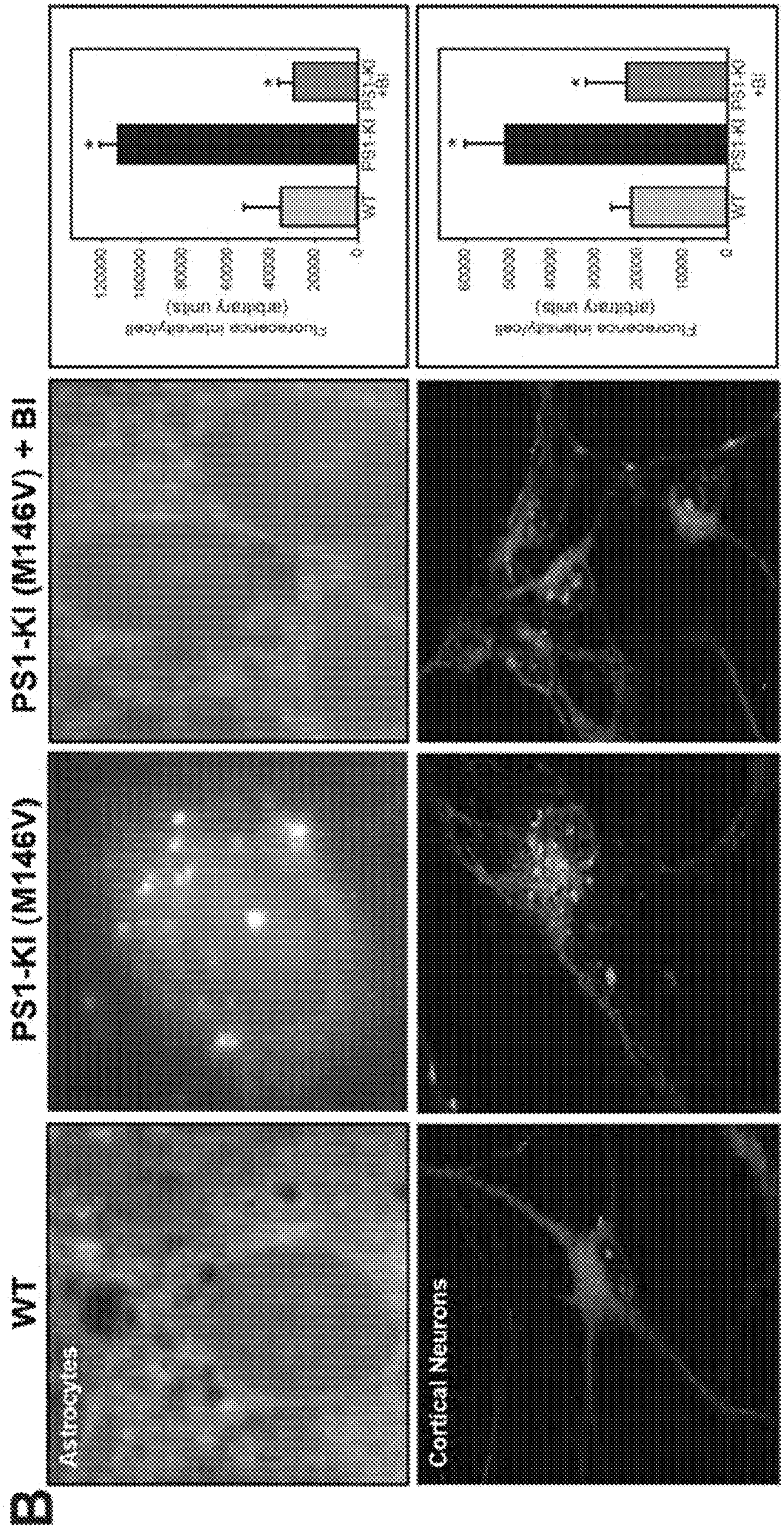
Figure 8C:
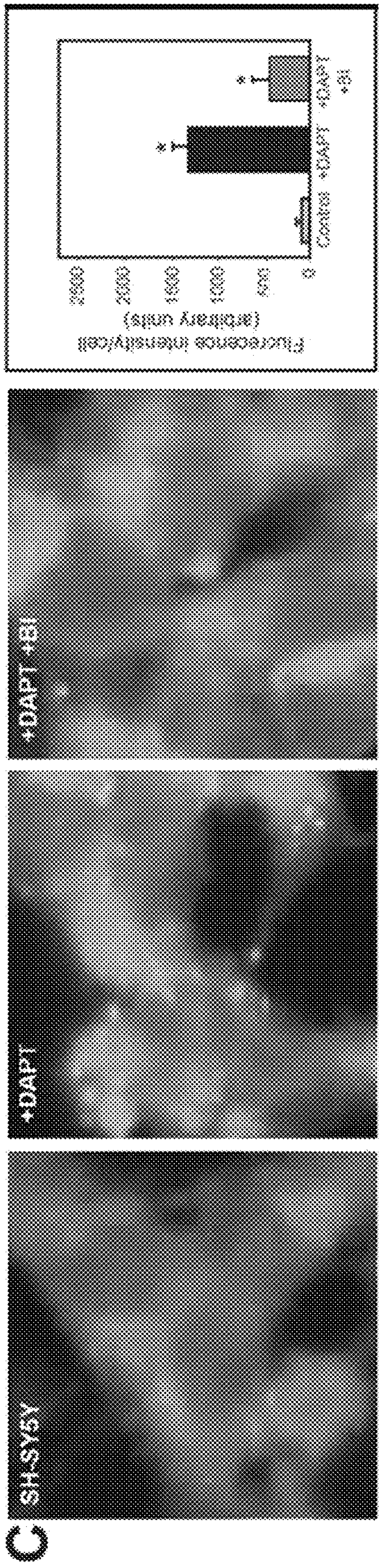

To assess the affect of C99 on MAM functionality, the conversion of cholesterol to cholesteryl esters by ACAT1, a MAM-resident enzyme (17), were measured by measuring ACAT1 activity and by monitoring the accumulation of newly-synthesized cholesteryl esters into lipid droplets (LDs) (17). Treatment with BI reduced significantly the incorporation of radiolabeled cholesterol into cholesterol esters in PS-DKO cells (FIG. 8A), and reduced the number of LDs in PS-DKO cells (FIG. 2A), in fibroblasts from AD patients (FIG. 2B), and in cortical neurons and astrocytes from PS1-KI$^{M146V}$ mice (FIG. 8B). LDs also accumulated in SH-SY5Y cells treated with DAPT alone (to inhibit C99 cleavage), and this was reversed in cells treated with DAPT+BI (to inhibit C99 production) (FIG. 8C).

Taken together, these results show that the accumulation of C99 induces both the physical and functional enhancement of the connections between ER and mitochondria.

Sphingolipid Metabolism is Perturbed in AD-Mutant Cells

Given that MAM is a lipid raft (17), it was speculated that C99 regulates MAM and ER-mitochondrial connectivity through changes in MAM lipid composition (11). Lipidomic analysis of total homogenates was therefore performed and fractions containing MAM and mitochondria from PS-DKO MEFs and controls. It was found that a significant increase in ceramide (FIG. 3A) and a parallel decrease in sphingomyelin in mutant cells (FIG. 3B), which was more pronounced in the mitochondrial fraction. There was an inverse relationship between the amounts of individual species of ceramide and those of the corresponding species of sphingomyelin (FIG. 9A), suggesting an increase in the hydrolysis of sphingomyelin and subsequent de novo synthesis to replace its loss. In agreement with this, PS-DKO cells showed a significantly higher synthesis of both ceramide and sphingomyelin (FIG. 4C). In addition, acidic (aSMAse) and neutral (nSMase) SMase activities were increased significantly in PS-DKO MEFs (FIG. 4D), with a more dramatic upregulation of nSMase activity that correlated with an increase in the expression of neutral sphingomyelinase 2 (gene SMPD3) (FIG. 9B). Increases in both SMase activities in PS1-KI$^{M146V}$ mouse brain (FIG. 9C) were also observed.

Figure 9H:
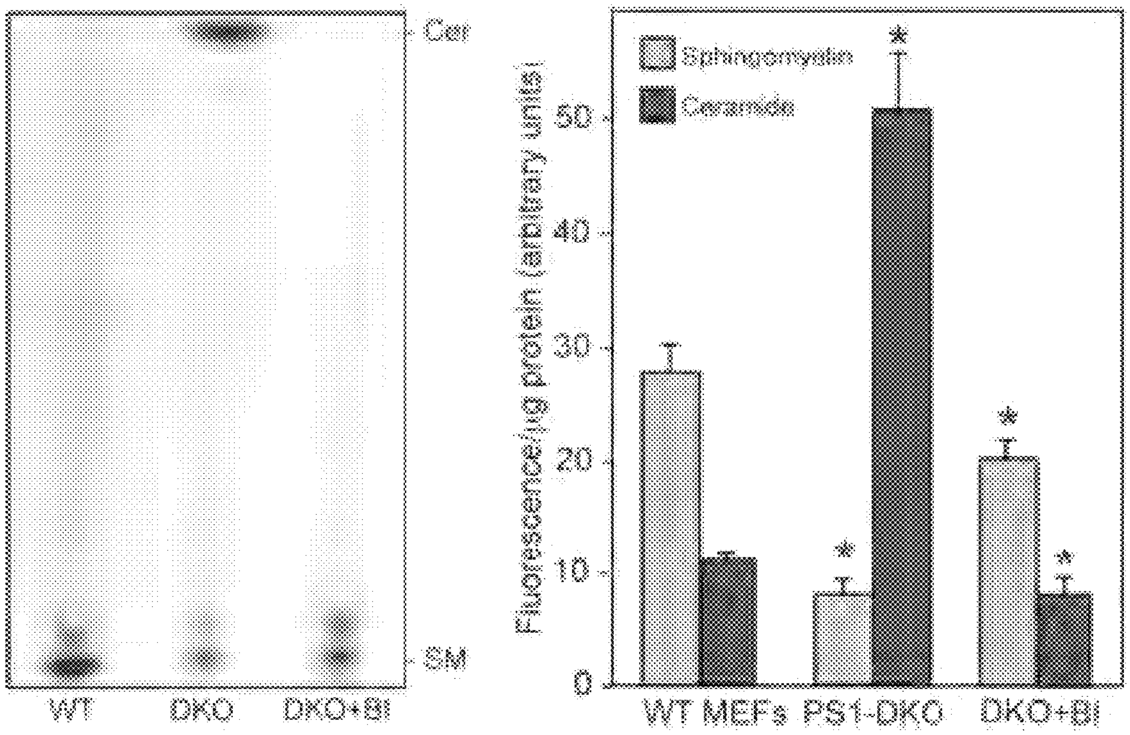

The increase in SMase activity in SH-SY5Y cells was replicated by inhibiting γ-secretase activity with DAPT (FIG. 9D), suggesting that the effects of mutated presenilins on sphingolipid metabolism were via their roles as proteases in γ-secretase, but it was unclear whether this effect was direct or was mediated by APP and/or its cleavage products. SMase activity was therefore measured in MEFs lacking APP and APLP2 (APP-DKO) (28). Contrary to what was found in PS-DKO and DAPT-treated cells, APP-DKO cells showed significant decreases in both sphingolipid synthesis (FIG. 9E) and SMase activities (FIG. 9F). Given that both PS-DKO and APP-DKO cells lack Aβ and AICD, these results suggest that the difference in sphingolipid regulation between the two cell types was due to the presence or absence of FL-APP and/or its cleavage products C88/C99. To test this, SMases was measured in PSDKO cells treated with α- and β-secretase inhibitors, to abrogate the production of C83 and C99, respectively. As controls, the γ-secretase products Aβ and AICD were also added back (FIG. 9G). Remarkably, only the inhibition of BACE1 activity (FIG. 3E) resulted in an attenuation of SMase activity, suggesting that among the APP processing products, it is the accumulation of C99 that plays a role in the regulation of SMase. For corroboration in vivo, PS-DKO and control cells were incubated with a fluorescent analog of sphingomyelin and analyzed its conversion to ceramide. PS-mutant cells showed a decrease in sphingomyelin and a concomitant increase in ceramide; as before, this increase disappeared when mutant cells were treated with BI (FIG. 9H). These data indicate that increased levels of C99 perturb sphingolipid metabolism.

MAM Contains SMase Protein and Activity

Given these results, it was asked whether MAM plays a role in sphingolipid metabolism. Sphingolipid activities are located mainly in ER and Golgi (29), although MAM may also play a role, affecting mitochondrial function (30). In fact, mitochondria have been reported to contain ceramide, probably generated at the MAM (31). It was hypothesized that the increased ceramide in the mitochondrial fraction of the mutant cells (FIG. 3A) was a consequence of deranged sphingolipid metabolism at ER-mitochondrial connections. Indeed, measurement of de novo sphingolipid synthesis and SMase activities in subcellular fractions from WT and PS-DKO MEFs showed that MAM participates in these functions (FIGS. 10A, B). Interestingly, the nSMase activity was significantly higher than the aSMAse activity (FIG. 10B), and Western blot analysis revealed a remarkable increase in the expression of nSMase at ER-mitochondrial contacts in γ-secretase-deficient cells (FIG. 10C). A significantly increased nSMase activity in MAM from PS1-KI$^{M146V}$ mouse brain (FIG. 10D) was also observed.

It is concluded that the accumulation of C99 in the MAM causes an upregulation of both the synthesis and catabolism of sphingomyelin, either directly or as a consequence of an upstream event. In addition, SMase activity is also upregulated at the ER-mitochondrial interface in PS-deficient cells (FIG. 10B, D), likely accounting for the observed increase in ceramide on mitochondrial membranes (FIG. 3A). This increase in ceramide promotes the amplification of lipid rafts, such as MAM (32). Notably, in addition to upregulated MAM function, AD cells show a physical elongation of MAM, resulting in a higher degree of apposition between ER and mitochondria (17, 18). Likewise, MAM is dependent on a cholesterol and sphingolipid core for its integrity; thus, changes in MAM's lipid composition caused by the accumulation of C99 may also alter the regulation of the proteins localized in this functional ER domain.

C99 Inhibits Mitochondrial Respiration in PS-Mutant Cells

Mitochondrial bioenergetics is reduced in AD (33), for unclear reasons. In view of the inverse relationship between mitochondrial ceramide content and bioenergetics (31), it was asked whether the upregulated SMase activity and sphingolipid synthesis in the MAM (FIGS. 3 and 10) could result in increased ceramide in apposed mitochondrial membranes, thereby affecting oxidative phosphorylation (OxPhos).

Figure 11I:
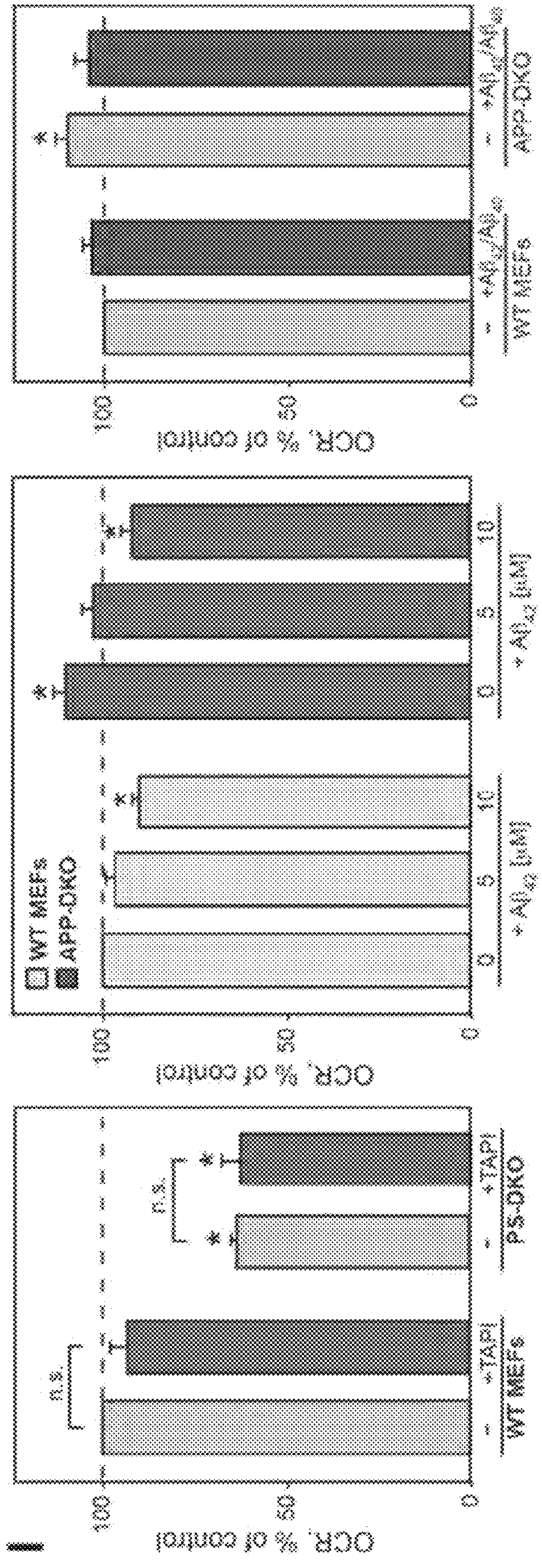

In agreement with previous findings, a marked reduction in mitochondrial respiration in AD fibroblasts (FIG. 4A) and in mitochondria from PS1-KI$^{M146V}$ mice (FIG. 11A) was observed. Similarly, a significant decrease in respiration in PS-DKO cells (FIG. 4B) and in SH-SY5Y cells treated with DAPT (FIG. 11B) was found. Importantly, this decrease in respiration was not due to a decrease in mitochondrial mass as measured by protein and PGC-1α levels (FIG. 11C). These results indicate that from the mitochondrial perspective, mutations in presenilins behave as loss-of-function alleles.

Remarkably, treatment with BI reversed the defect in mitochondrial respiration seen in PS-DKO cells (FIG. 4C) and in FAD fibroblasts (FIG. 11D), implying that accumulated C99 plays a role in the mitochondrial dysfunction seen in AD.

Similarly, APP-DKO cells expressing C99 (FIG. 11E) showed a significant reduction in OxPhos, whereas in untransfected APP-DKO cells respiration was increased over that in WT cells (FIGS. 11F,G). In distinction to the effect of C99, addition of Aβ and AICD did not rescue the mitochondrial respiration defect in these cells (FIGS. 11H, I).

Next it was asked whether the effect of C99 on OxPhos occurred via increased deposition of ceramide at mitochondrial membranes (31) (FIGS. 3A-E). Respiration in PS-DKO cells treated with myriocin, a specific inhibitor of serine palmitotyltransferase, which catalyzes the first step in the de novo ceramide synthesis pathway, was measured. As expected, inhibition of ceramide synthesis reversed the respiratory defect in these cells (FIG. 4D).

The data described herein imply that the accumulation of C99 triggers bioenergetic dysfunction in AD via increased ceramide at the mitochondria (31). First, ceramide interacts with respiratory complexes, disrupting their activity and increasing reactive oxidative species (34). Second, accumulation of ceramide on mitochondria provokes mitochondrial outer membrane permeabilization and apoptosis (35). Third, increased ceramide correlates with increased calcium uptake by mitochondria (36), consistent with the known deregulation of mitochondrial calcium in AD (37). Finally, the data described herein are consistent with previous data ascribing the localization of C99 to mitochondria from AD model mice that had a respiratory chain deficiency that could be rescued by deletion of BACE1 (38). These results show that mitochondrial dysfunction, while occurring early in AD, is nevertheless downstream of deranged lipid homeostasis and MAM dysregulation. Supporting this view, defects in respiration in PS1-KI$^{M146V}$ mice became significant only after MAM alterations and lipid deregulation became evident (FIGS. 12A-B).

What Upregulates Sphingolipid Metabolism in AD?

Cholesterol, which can either be synthesized de novo or taken up from circulating lipoproteins (39), is transferred mainly to the plasma membrane to expand the different pools of cholesterol (40), with concomitant increases in sphingomyelin to "accommodate" the new load of free cholesterol. In order to maintain homeostasis, beyond a certain threshold sphingomyelin is hydrolyzed by SMases, thereby increasing ceramide, which creates an unfavorable environment for cholesterol (41). This cholesterol, in turn, will be mobilized from the membrane towards those regions of the ER where ACAT activity is localized (i.e. MAM) to be esterified and stored in lipid droplets that will eventually be effluxed. Thus, co-activation of SMases (42, 43) and ACAT1 (44) is a regulatory mechanism by which cells "detoxify" membranes from an excess of free cholesterol. This pathway is controlled by an as-yet unknown sensor in the ER that regulates the transport of cholesterol from the plasma membrane to the ER and that operates in a feedback loop to maintain appropriate levels of cholesterol in both compartments (44).

Knowing this, it was hypothesized that the increased sphingolipid metabolism, cholesterol esterification, and lipid doplet formation observed in AD cells is triggered by increased free cholesterol. However, de novo cholesterol synthesis—as measured by quantification of 3-hydroxy-3-methylglutaryl-CoA reductase (HMGCR) activity—was reduced in γ-secretase-deficient cells (FIG. 5A) and in FAD fibroblasts (FIG. 13A), in agreement with others (45). On the other hand, the rate of uptake of extracellular cholesterol-measured by pulse-chase analysis—was enhanced significantly in PS-DKO cells (FIG. 5B), in neuronal cell lines silenced for PS1 and/or PS2 (FIG. 13B), and in FAD fibroblasts (FIG. 13C). Supporting this result, the uptake of extracellular fluorescently-labeled cholesterol was also increased significantly in PS-DKO cells (FIG. 13D). Surprisingly, this latter increase in cholesterol uptake was abrogated upon inhibition of BACE1 (FIG. 13D), indicating that C99 might play a role in cholesterol homeostasis.

The distribution of free cholesterol, as visualized by filipin staining, was markedly changed in PSDKO cells (FIG. 5C) and AD fibroblasts (FIG. 13E) vs controls, indicating a higher degree of internalization of cholesterol from the plasma membrane. This enhanced trafficking of cholesterol in AD cells was also reflected in the increased ratio of cholesteryl esters:free cholesterol in PS-DKO cells (FIG. 13F) (42). Importantly, this phenotype was recapitulated by treating WT MEFs with DAPT, and to reverse it after incubation with the BACE1 inhibitor (FIG. 5C), strongly suggesting that increased C99 was behind this phenomenon.

Finally, given that the mobilization of cholesterol is triggered by activation of SMases, inhibition of SMases should inhibit this process and reduce lipid droplet formation in γ-secretase-deficient cells. PS-DKO cells and controls were treated with desipramine and GW4869, inhibitors of aSMases and nSMases, respectively (46), and then stained them with LipidTox Green, a dye that visualizes lipid droplets. Incubation with both compounds reduced the accumulation of lipid droplets in PS-DKO cells to near-control levels (FIG. 14A).

Similar results were obtained with DAPT-treated SH-SY5Y cells (FIG. 14B). Thus, the increase in ACAT1 activity and in lipid droplet production that was seen in AD cells was likely due to upregulated SMase activity. However, the augmented cholesterol uptake and altered pattern of filipin staining was not reversed by incubation of mutant cells with SMase inhibitors (FIG. 14C), indicating that SMase upregulation is likely not a cause, but rather a consequence, of a prior enrichment in free cholesterol in cellular membranes.

In conclusion, the data described herein show that the loss of sphingolipid homeostasis is a consequence of the continuous uptake of extracellular cholesterol and its mobilization from the PM to the MAM, triggered by the accumulation of C99.

Discussion

Described herein is an intersection between the APP processing intermediate C99 and lipid homeostasis (specifically, that of cholesterol and sphingolipids) in the pathogenesis of AD. Normally, C99 is rapidly cleaved by γ-secretase to produce Aβ and AICD. We (14) and others (16) have found that this cleavage occurs primarily in the MAM. In AD, however, C99 accumulates above normal levels, triggering a cascade of events that result in perturbed cholesterol and sphingolipid metabolism, and in bioenergetics dysfunction. These changes cause a massive increase in the connectivity between ER and mitochondria at the MAM, a cholesterol- and sphingolipid-rich lipid raft subdomain of the ER, which, in turn, gives rise to the features of AD (17).

Cholesterol metabolism has always been known to play a central role in AD pathogenesis, but the mechanism has been unclear (3). It is nored that once free cholesterol in the PM reaches a threshold, the excess is transported to the ER pool, where it inhibits its own de novo synthesis and activates ACAT in order to maintain lipid homeostasis (47). Thus, cholesterol production (e.g. via the HMGCR pathway), uptake (e.g. via lipoproteins), and elimination (e.g. via esterification) is mediated by the communication between the PM and ER pools. It has been suggested that this response is regulated by a cholesterol-sensing protein and/or a specific cholesterol-sensing membrane phase or domain (44). Based on previous studies (48) and the results presented here, we propose that C99 is in fact this sensor, and that MAM is the specific ER "regulatory-pool" (42) that acts as the ER signaling platform to maintain cholesterol homeostasis. Notably, the transmembrane segment of C99 contains a cholesterol-binding domain (49). Thus, it is possible that C99 stimulates the formation of cholesterol-rich regions (50) needed for its cleavage by γ-secretase (12). In the context of deficient γ-secretase activity (as in AD), unprocessed C99 accumulates, increasing the recruitment of cholesterol to MAM, reorganizing the membrane composition at this site. Moreover, cholesterol associates with itself and sphingolipids, enhancing the formation of these rafts.

A model is proposed in which increased levels of C99 in the MAM result in a vicious cycle, divided into two phases (FIGS. 6A-E). In the first phase, the accumulation of C99 in the MAM triggers the uptake of lipoproteins, via an unknown mechanism. The lipoprotein-derived free cholesterol is incorporated into the plasma membrane, stimulating sphingomyelin production (consistent with upregulated sphingolipid synthesis in AD (2)). Once the cholesterol reaches a threshold level in the plasma membrane (40) it will be mobilized to the ER, where it induces feedback responses to maintain cholesterol homeostasis (51). In the second phase, cholesterol mobilization is triggered by sphingomyelin hydrolysis (41, 52) for esterification by ACAT1 in the MAM and storage in lipid droplets (39) (consistent with increased SMase activity (7), ACAT1 activity (17), and LDs (17) in AD). Closing the cycle, the continuous uptake of cholesterol induces APP internalization and its interaction with, and cleavage by, BACE1 (53) (generating more C99) and downregulates α-secretase (54), and likely explains the increased Aβ42:Aβ40 ratio in AD (55).

This two-phase model is supported by the fact that SMase inhibition, while capable of blocking cholesterol esterification, cannot prevent the uptake of cholesterol induced by the accumulation of C99. The uncoupling of cholesterol uptake from its esterification also occurs in Niemann-Pick disease, where SMase deficiency results in a higher uptake of cholesterol (56), induced APP endocytosis (53), and increased BACE1 cleavage (56). This increased rate of cholesterol influx is counterbalanced by a compensatory degree of efflux and downregulation of de novo cholesterol synthesis (45); thus, the trafficking dynamics, but not the steady-state level, of cellular cholesterol is affected, which may underlie the controversy surrounding cholesterol levels in AD (3). Taken together, this "MAM hypothesis" (57, 58) provides a new framework to help understand the role of both APP processing and cholesterol as seminal effectors in the pathogenesis of AD.

REFERENCES FOR EXAMPLE 1

1. Y. Jiang et al., *Proc. Natl. Acad. Sci. USA* 107, 1630-1635 (2010).
2. T. Hartmann, J. Kuchenbecker, M. O. Grimm, *J. Neurochem.* 103 Suppl 1, 159-170 (2007).
3. W. G. Wood, L. Li, W. E. Muller, G. P. Eckert, *J. Neurochem.* 129, 559-572 (2014).
4. C. Marquer et al., *FASEB J.* 25, 1295-1305 (2011).
5. K. Fassbender et al., *Proc. Natl. Acad. Sci. USA* 98, 5856-5861 (2001).
6. L. Puglielli, B. C. Ellis, L. A. Ingano, D. M. Kovacs, *J. Mol. Neurosci.* 24, 93-96 (2004).
7. V. Filippov et al., *J. Alzheimers Dis.* 29, 537-547 (2012).
8. M. O. Grimm et al., *Int. J. Alzheimers Dis.* 2011, 695413 (2011).
9. S. Gulati, Y. Liu, A. B. Munkacsi, L. Wilcox, S. L. Sturley, *Prog. Lipid Res.* 49, 353-365 (2010).
10. X. L. Guan et al., *Mol. Biol. Cell* 20, 2083-2095 (2009).
11. K. Simons, W. L. Vaz, *Annu. Rev. Biophys. Biomol. Struct.* 33, 269-295 (2004).
12. J. M. Cordy, N. M. Hooper, A. J. Turner, *Mol. Membr. Biol.* 23, 111-122 (2006).
13. J. Hare, *Biochem. Biophys. Res. Commun.* 401, 219-224 (2010).
14. E. Area-Gomez et al., *Am. J. Pathol.* 175, 1810-1816 (2009).
15. M. Newman et al., *Hum. Mol. Genet.* 23, 602-617 (2014).
16. B. Schreiner, L. Hedskog, B. Wiehager, M. Ankarcrona, *J. Alzheimers Dis.* 43, 369-374 (2015).
17. E. Area-Gomez et al., *EMBO J.* 31, 4106-4123 (2012).
18. L. Hedskog et al., *Proc. Natl. Acad. Sci. USA* 110, 7916-7921 (2013).
19. P. Cupers et al., *J. Cell Biol.* 154, 731-740 (2001).
20. A. Herreman et al., *Nat. Cell Biol.* 2, 461-462 (2000).
21. Q. Guo et al., *Nat. Med.* 5, 101-106 (1999).
22. D. L. McPhie et al., *J. Biol. Chem.* 272, 24743-24746 (1997).
23. A. A. Rowland, P. J. Chitwood, M. J. Phillips, G. K. Voeltz, *Cell* 159, 1027-1041 (2014).
24. E. A. Heilig, U. Gutti, T. Tai, J. Shen, R. J. Kelleher, 3rd, *J. Neurosci.* 33, 11606-11617 (2013).
25. I. Lauritzen et al., *J. Neurosci.* 32, 16243-16255a (2012).
26. L. Chavez-Gutierrez et al., *EMBO J* 31, 2261-2274 (2012).
27. O. M. de Brito, L. Scorrano, *Nature* 456, 605-610 (2008).
28. X. Zhang et al., *PLoS One* 8, e61198 (2013).
29. T. S. Worgall, *Adv. Exp. Med. Biol.* 721, 139-148 (2011).
30. D. Ardail et al., *Biochem. J.* 371, 1013-1019 (2003).
31. A. Kogot-Levin, A. Saada, *Biochimie* 100, 88-94 (2014).
32. J. M. Holopainen, M. Subramanian, P. K. Kinnunen, *Biochemistry* 37, 17562-17570 (1998).
33. R. H. Swerdlow, J. M. Burns, S. M. Khan, *Biochim. Biophys. Acta* 1842, 1219-1231 (2014).
34. M. Di Paola, T. Cocco, M. Lorusso, *Biochemistry* 39, 6660-6668 (2000).
35. L. J. Siskind, R. N. Kolesnick, M. Colombini, *Mitochondrion* 6, 118-125 (2006).
36. S. A. Novgorodov et al., *J Biol. Chem.* 286, 4644-4658 (2011).

37. C. Supnet, I. Bezprozvanny, *J. Alzheimers Dis.* 20 Suppl 2, S487-498 (2010).
38. L. Devi, M. Ohno, *Neurobiol. Dis.* 45, 417-424 (2012).
39. K. Simons, E. Ikonen, *Science* 290, 1721-1726 (2000).
40. A. Das, M. S. Brown, D. D. Anderson, J. L. Goldstein, A. Radhakrishnan, *eLife* 3, e02882 (2014).
41. C. Yu, M. Alterman, R. T. Dobrowsky, *J. Lipid Res.* 46, 1678-1691 (2005).
42. J. P. Slotte, E. L. Bierman, *Biochem. J.* 250, 653-658 (1988).
43. J. P. Slotte, G. Hedstrom, S. Rannstrom, S. Ekman, *Biochim. Biophys. Acta* 985, 90-96 (1989).
44. Y. Lange, J. Ye, M. Rigney, T. L. Steck, *J. Lipid Res.* 40, 2264-2270 (1999).
45. N. Pierrot et al., *EMBO Mol. Med.* 5, 608-625 (2013).
46. A. Delgado, J. Casas, A. Llebaria, J. L. Abad, G. Fabrias, *Biochim. Biophys. Acta* 1758, 1957-1977(2006).
47. J. P. Slotte, G. Hedstrom, E. L. Bierman, *Biochim. Biophys. Acta* 1005, 303-309 (1989).
48. A. J. Beel et al., *Biochemistry* 47, 9428-9446 (2008).
49. P. J. Barrett et al., *Science* 336, 1168-1171 (2012).
50. Y. Song, A. K. Kenworthy, C. R. Sanders, *Protein Sci.* 23, 1-22 (2014).
51. M. S. Brown, J. L. Goldstein, *Proc. Natl. Acad. Sci. USA* 96, 11041-11048 (1999).
52. S. Scheek, M. S. Brown, J. L. Goldstein, *Proc. Natl. Acad. Sci. USA* 94, 11179-11183 (1997).
53. J. C. Cossec et al., *Biochim. Biophys. Acta* 1801, 846-852 (2010).
54. W. Wang et al., *FASEB J.* 28, 849-860 (2014).
55. C. Marquer et al., *Mol. Neurodegener.* 9, 60 (2014).
56. M. Kosicek, M. Malnar, A. Goate, S. Hecimovic, *Biochem. Biophys. Res. Commun.* 393, 404-409 (2010).
57. E. A. Schon, E. Area-Gomez, *J. Alzheimers Dis.* 20, S281-S292 (2010).
58. E. A. Schon, E. Area-Gomez, *Mol. Cell. Neurosci.* 55, 26-36 (2013).

Materials And Methods

Animals $PS1^{M146V}$ knock-in mice ($PS1\text{-}KI^{M146V}$) were generated as described (1, 2). All experiments were performed according to a protocol approved by the Institutional Animal Care and Use Committee of the Columbia University Medical Center and were consistent with the National Institutes of Health Guide for the Care and Use of Laboratory Animals. Mice were housed and bred according to international standard conditions, with a 12-h light, 12-h dark cycle, and sacrificed at 3, 5, 7, 8, and 12 months of age. Brain was removed and homogenized, either for Western blot and Seahorse analysis. All the experiments were performed in at least three mice per group.

Cells and Reagents

WT, PS1-KO, PS2-KO, and PS1/2-DKO (called PS-DKO) mouse MEFs were gifts of Dr. Bart De Strooper (University of Leuven). APP/APLP2-KO (called APP-DKO) and WT mice were the kind gift of Dr. Huaxi Xu (Sanford Burnham Institute). PS1-mutant FAD cells were the kind gift of Dr. Gary E. Gibson (Cornell University). Other AD and control cell lines were obtained from the Coriell Institute for Medical Research (Camden, N.J.). SH-SY5Y and CCL13 cells were obtained from the American Type Culture Collection. Antibodies to APP C-terminal (Sigma; A8717, polyclonal), APP C99 (Covance; SIG-39320-200 [6E10], monoclonal), the α-subunit of mitochondrial ATP synthase (complex V) (Invitrogen; 459240), BACE1 (Cell Signaling; D10E5) Erlin-2 (Cell Signaling; #2959), SMPD2/nSMAseI (Thermo Scientific; PA5-24614), TOM20 (Santa Cruz; sc-11415), β-tubulin (Sigma; T4026), and VDAC1 (Abcam; 34726) were used. Thin layer chromatography (TLC) silica plates were from EMD Biosciences (5748-7). Ceramide (22244), sphingomyelin (S0756), cholesteryl palmitate (C6072), cholesteryl oleate (C9253), lipid markers for TLC (P3817), α-secretase inhibitor TAPI-1 (SML0739), GI254023X (SML0789), β-secretase inhibitor IV (Calbiochem; 565788), γ-secretase inhibitor DAPT (D5942), serine palmitoyltransferase inhibitor myriocin (M1177), and sphingomyelinase inhibitor desipramine (D3900) were from Sigma. Sphingomyelinase inhibitor GW4869 (13127) was from Cayman. Fluorescent lipids BODIPY-FL C6 ceramide complexed to BSA (N22651) and BODIPY-FL C12-sphingomyelin (D7711) were from Invitrogen.

Radiolabelled 3H-serine and 3H-cholesterol were from Perkin Elmer; fatty acid-free bovine serum albumin (FAF-BSA) was from MP Biomedical (820472). Amyloid β peptides 40-aa and 42-aa were obtained from Biopolymer Laboratory (UCLA) and APP intracellular domain (AICD) peptide was from Genescript Corporation (Piscataway, N.J.).

Culture of Primary Mouse Cortical Neurons

Cortex from four 14-day-old embryos were cut in pieces and washed in 45% glucose in PBS. After that, brain tissues were resuspended in 1 ml trypsin diluted in 45% glucose in PBS (1:1 v/v) and incubated at 37° C. for 20 min. Samples were added to 500 μl horse serum and 10 units of DNase and incubated for 10 min at room temperature until debris sank to the bottom of the tubes. The non-debris fraction was pelleted at 800×g for 10 min and resuspended in Neurobasal Medium (Life Technologies; 21103-049) supplemented with 200 mM glutamine. Cells were counted and seeded on coverslips coated with polyomithine and laminin.

Plasmid Constructs and Transfections

Plasmids were constructed using standard methodological techniques. In brief, APP fragments AICD, and C99 were amplified from pCAX APP-695 (3), using forward primer 5'-cccgctagcctcgagATGCTGAAGAAGAAACAGTACAC ATCCATTC-3' (SEQ ID NO: 2) for AICD and 5'-ccc ggatccATGGATGCAGAATTCCGACATGACTC-3' (SEQ ID NO: 3) for C99, with a single reverse primer 5'-ccc ggatccaagcttCTAGTTCTGCATCTGCTCAAAGAACTTG-3' (SEQ ID NO: 4) for both; restriction sites for subcloning are underlined and the start/stop codons are in bold. The PCR products were cut with XhoI+BamHI (for AICD) or with BamHI (for C99) and subcloned into the corresponding sites in pGFPN3 (Clontech). All plasmids were verified by restriction analysis and sequencing. Cells were transfected using Lipofectamine® Transfection Reagent (Thermo Fisher Scientific, Life Technologies) according to the manufacturer's instructions.

Subcellular Fractionation and Western Blotting

Purification of ER, MAM, and mitochondria was performed and analyzed as described (4).

Analysis of ER-Mitochondrial Apposition

Interactions between mitochondria and ER were performed as described (5).

Inhibition of α-, β- and γ-Secretase Activity

To inhibit γ-secretase activity, cells were treated with 10 μM DAPT, a highly specific inhibitor of this enzyme complex. For β-secretase inhibition, cells were treated with 100 nM β-secretase inhibitor IV (BI). Inhibition of aSMase and the nSMase activities was performed using 10 μM desipramine or 5 μM GW4869, respectively. Finally, to inhibit serine-palmitoyl transferase activity the cells were treated with 5 μM myriocin. Incubations with all drugs were for 12-16 h.

Quantification of Cholesterol Species

Quantification of total cholesterol and cholesteryl esters was performed using the Cholesterol/Cholesteryl Ester Quantitation kit from Calbiochem (428901). Staining of lipid droplets Staining of lipid droplets was performed using HCS LipidTox™ Deep Green neutral lipid stain (Invitrogen H34475) according to the manufacturer's instructions. Lipid droplet staining was quantified using ImageJ. The different values represent the product of the intensity and the area covered by the fluorescent signal above background in every cell examined.

Sphingolipid Synthesis in Cultured Cells

Cells were incubated for 2 h with serum-free medium to ensure removal of exogenous lipids. The medium was then replaced with MEM containing 2.5 μCi/ml of 3H-serine for the indicated periods of time. The cells were washed and collected in PBS, pelleted at 2500×g for 5 min at 4° C., and resuspended in 0.5 ml water, removing a small aliquot for protein quantification. Lipid extraction was done in 3 volumes of chloroform:methanol:HCl (2:1:0.5 v/v/v) added to the samples. Samples were vortexed and centrifuged at 8000×g for 5 min, organic phase was blown and dried under nitrogen. Dried lipids were resuspended in 30 μl of chloroform:methanol (2:1 v/v) and applied to a TLC plate. Sphingolipids were separated using a solvent composed of chloroform/methanol/0.22% CaCl2 (60:35:8 v/v/v). Development was performed by exposure of the plate to iodine vapor. The spots corresponding to the relevant sphingolipids (identified using co-migrating standards) were scraped and counted in a scintillation counter (Packard Tri-Carb 2900TR).

Lipidomic Analyses

Lipid extracts were prepared via chloroform-methanol extraction, spiked with appropriate internal standards, and analyzed using a 6490 Triple Quadrupole LC/MS system (Agilent Technologies, Santa Clara, Calif.) as described previously (6, 7). Glycerophospholipids and sphingolipids were separated with normal-phase HPLC using an Agilent Zorbax Rx-Sil column (inner diameter 2.1×100 mm) under the following conditions: mobile phase A (chloroform:methanol:1 M ammonium hydroxide, 89.9:10:0.1, v/v) and mobile phase B (chloroform:methanol:water:ammonium hydroxide, 55:39.9:5:0.1, v/v); 95% A for 2 min, linear gradient to 30% A over 18 min and held for 3 min, and linear gradient to 95% A over 2 min and held for 6 min. Quantification of lipid species was accomplished using multiple reaction monitoring (MRM) transitions that were developed in earlier studies (6) in conjunction with referencing of appropriate internal standards: ceramide d18:1/17:0 and sphingomyelin d18:1/12:0 (Avanti Polar Lipids, Alabaster, Ala.).

Analysis of Sphingolipid Synthesis in Subcellular Fractions

Cellular fractions were isolated from MEFs as described (4). Two hundred μg were incubated in a final volume of 200 μl of 100 mM HEPES pH 7.4, 5 mM DTT, 10 mM EDTA, 50 μM piridoxal phosphate, 0.15 mM palmitoyl-CoA and 3 μCi/ml 3H-Ser for 20 min at 37° C. The reaction was stopped by addition of 3 volumes of chloroform/methanol (2:1 v/v). Lipid extraction and TLC analysis was performed as described above.

Analysis of Sphingomyelinase Activity

One hundred μg of protein were assayed in 100 mM of the appropriate buffer (Tris/glycine for pH 7.0-9.0 and sodium acetate for pH 4.0-5.0), 1.55 mM Triton X-100, 0.025% BSA, 1 mM MgCl2, and 400 μM bovine brain sphingomyelin spiked with 22000 dpm of [3H]-bovine sphingomyelin (1 ncurie/sample). Reactions were carried out in borosilicate glass culture tubes at 37° C., overnight, followed by quenching with 1.2 ml of ice-cold 10% trichloroacetic acid, incubation at 4° C. for 30 min, and centrifugation at 2000 rpm at 4° C. for 20 min. One ml of supernatant was transferred to clean tubes, 1 ml of ether was added, the mixture vortexed, and centrifuged at 2000 rpm for 5 min. Eight hundred μl of the bottom phase was transferred to scintillation vials, 5 ml of Scintiverse BD (Fisher Scientific, Fair Lawn, N.J.) was added, and samples were counted.

Assay of Cholesterol Uptake and ACAT Activity

To measure cholesterol uptake in vivo, cultured cells were incubated in serum-free medium for 2 h to remove all exogenous lipids. After that, 2.5 μCi/ml of 3H-cholesterol was added to FBS-free DMEM containing 2% FAF-BSA, allowed to equilibrate for at least 30 min at 37° C., and the radiolabeled medium was added to the cells for the indicated periods of time. Cells were then washed and collected in DPBS, removing a small aliquot for protein quantification. Lipids were extracted in 3 volumes of chloroform:methanol (2:1 v/v). After vortexing and centrifugation at 8000×g for 5 min, the organic phase was blown to dryness under nitrogen. Dried lipids were resuspended in 30 μl of chloroform:methanol (2:1 v/v) and applied to a TLC plate along with unlabeled standards. A mixture of hexanes/diethyl ether/acetic acid (80:20:1 v/v/v) was used as solvent. Iodine-stained bands corresponding to cholesterol and cholesteryl esters were scraped and counted.

To measure uptake of fluorescent cholesterol, cultured cells were incubated with 1 μM Bodipylabeled cholesterol (Avanti Lipids; 810255P) for 12 h. Alternatively, Bodipy-cholesterol was complexed with methyl-β-cyclodextrin at a 1:10 molar ratio of sterol:cyclodextrin and added to cultured cells to a final concentration of 25 μg/ml for 6-8 h. Cholesterol droplets were visualized by microscopy and fluorescence was quantified by ImageJ.

Filipin Staining

Cells were washed in PBS and fixed in 3% paraformaldehyde at room temperature for 1 h. After washing in PBS three times, samples were incubated in 1.5 mg/ml glycine in 1×PBS to quench the paraformaldehyde and then incubated in 0.05 mg/ml of filipin in PBS/10% FBS for 2 h at room temperature. Free cholesterol signal was visualized in by microscopy and quantified by ImageJ.

Quantification of De Novo Cholesterol Biosynthesis

HMG-CoA reductase activity was determined using the HMGCR assay kit from Sigma (CS 1090) following the manufacturer's instructions.

Analysis of ER-Mitochondrial Apposition

Cells under were co-transfected with GFP-Sec61-β (Addgene plasmid #15108) and DsRed-Mito (Clontech, #632421) at a 1:1 ratio, using Lipofectamine 2000 (Invitrogen, #11668-027) in serum-free DMEM. Twelve hours post-transfection, cells were analyzed as described (8).

Transcriptional Silencing

To knock down mouse Ps1 and Ps2 in cells, shRNAs against Psen1 and Psen2 (Sigma SASI_Mm01_00048853 and SASI_Mm02_00310708) were transfected transiently together, according to the manufacture's instructions. Briefly, cells plated at low confluence were transfected with each shRNA to a final concentration of 30 nM, using Lipofectamine 2000 (Invitrogen, 11668-027) to a 1:1 ratio in serum-free DMEM. After 5 h, medium was changed to 2%

FBS DMEM and cells were incubated for 12 more hours. Successful silencing of the targeted proteins was checked by Western blot.

ELISA to Detect Aβ

Aβ40 was measured using the Human/Rat β-amyloid ELISA Kit Wako II (Wako 294-64701) according to the manufacturer's instructions.

Preparation of Synthetic A/f in Different States of Aggregation

Lyophilized Aβ40 and Aβ42 peptides (American Peptide; 62-0-80; UCLA) were equilibrated at room temperature for 30 min and then resuspended in hexafluro-2-propanol (HIFP) (Sigma; H8508) to 1 mM using a glass-tight Hamilton syringe with Teflon plunger. HIFP was allowed to evaporate in a fume hood and dried under vacuum in a SpeedVac (Savant Instruments) and kept at −20° C. Immediately prior to use, an aliquot was resuspended to 5 mM in DMSO followed by bath sonication for 10 min.

To analyze the effect of Aβ addition, a mix of Aβ40/Aβ42 at a ratio 10:1 was added to the cultured cells to a final concentration of 6000 pg/ml for 24 h. For Aβ42 oligomer formation, 5 mM of Aβ42 in DMSO was diluted to 100 μM in ice-cold media, vortexed for 30 seconds, and incubated at 4° C. for 24 h. Aβ42 Oligomers were added to the cultured cells to a final concentration of 5 or 10 μM for 24 h.

Quantitative Reverse Transcription-Polymerase Chain Reaction (qRT-PCR)

Total RNA was extracted from MEFs using TRIzol® Reagent (Invitrogen 15596-018) according to the manufacture's instructions, and was quantified by NanoDrop2000 (Thermo Scientific). One mg of total RNA was used to obtain cDNA by RT-PCR using a High Capacity cDNA Reverse Transcription Kit (Applied Biosystems; PN 4368813, 4374966). Real-Time PCR was performed in triplicate in a StepOnePlus™ Real-Time PCR System (Applied Biosystems; 4376600). The expression of each gene under study was analyzed using specific predesigned TaqMan Probes (PGC-1α, ppargc1 Mm01208835_m1; aSMase, smpd1 Mm00488319_g1; nSMase, smpd3 Mm00491359_m1). The expression of each gene under study was analyzed using specific predesigned TaqMan Probes and normalizing against Gapdh expression (Applied Biosystems, 4352339E) as an internal standard.

Statistical Analyses

Tests of significance employed student's t-test at $p<0.05$, unless indicated otherwise; all error bars in the figures are SD. For the determination of ER-mitochondrial apposition, the "colocalization" data sets were compared using Mander's coefficient.

REFERENCES FOR MATERIALS AND METHODS

1. Q. Guo et al., *Nat. Med.* 5, 101-106 (1999).
2. P. C. Wong et al., *Nature* 387, 288-292 (1997).
3. T. L. Young-Pearse et al., *J. Neurosci.* 27, 14459-14469 (2007).
4. E. Area-Gomez et al., *Am. J. Pathol.* 175, 1810-1816 (2009).
5. E. Area-Gomez et al., *EMBO J.* 31, 4106-4123 (2012).
6. R. B. Chan et al., *J. Biol. Chem.* 287, 2678-2688 (2012).
7. T. G. Oliveira et al., *Mol. Psychiatry* in press, (2015).
8. C. Guardia-Laguarta et al., *J. Neurosci.* 34, 249-259 (2014).

Example 2—Strategies to Treat Alzheimer Disease

As described herein, the "MAM hypothesis" proposes that increased ER-mitochondrial connectivity is the cause of the phenotypes seen in AD, and that this connectivity is the result of two interrelated processes, namely, elevated C99 in the MAM and cholesterol dyshomeostasis. Therefore, targeted strategies to reduce C99 accumulation in MAM can be used to treat AD. Identified below are methods, and specific compounds, to accomplish that goal.

Strategies to Reduce C99 Accumulation in MAM

Increase γ-Secretase Activity

Increase γ-secretase cleavage of APP with phenylbutyric acid (PBA) [1], a phenyl derivative of GABA that activates CREB [2] and is a CNS depressant/tranquilizer. PBA decreases UPR signalling and blocks ER stress [1, 3]. It also reverses the UPR-induced decrease in γ-secretase cleavage of APP (and increases AICD) [1]. PBA stimulates both α- and γ-cleavage of APP [1], rescues cholesterol defects [4-6] and cognition [7] in AD mice, and rescues ER-stress toxicity induced by the oxysterol 27-OH cholesterol [8]. Finally, C99 is regulated by ER-associated degradation (ERAD) [9].

Increase γ-secretase activity by activating he β2-adrenergic receptor (gene ADRB2) with β2-AR agonists Isoproterenol or Clenbuterol [10] (ADRB2 mutations G16R, Q27E increase AD risk [11]). Note, however, that β2-AR antagonists (ICI-118551) have been reported to decrease AD incidence [12] and decrease plaques [10]). P2-AR interacts with β-arrestin 2 (gene ARRB2), which associates with APH1 and sends γ-secretase to detergent-resistant membranes (DRMs; lipid rafts) [13]; isoproterenol reduces this interaction [13]. Also, it was reported that activating β2-AR with Clenbuterol increased α-secretase, decreased Aβ, and reduced Thr668p [Chai, G-s. et al.].

Increase γ-secretase activity by inactivating the adenosine receptor A2A (A2A-AR; gene ADORA2A) with the related but non-identical A2A-AR antagonists Istradefylline (Kyowa (Sigma SML0422)), Preladenant (Merck) and Tozadenant (Biotie) [Lu, J. et al.]. $\alpha_{2A}$-AR colocalizes with γ-secretase in endosomes and physically interacts with PS1 [Lu, J. et al.]. All 3 drugs increased γ-secretase activity and increased Aβ42 [Lu, J. et al.].

Increase γ-secretase activity by modifying nicastrin with 4-hydroxynonenal (HNE) [14], thereby stabilizing γ-secretase [15].

Increase γ-secretase activity by inhibiting ERK1/2, which is a negative regulator of γ-secretase [16], probably via phosphoryation of nicastrin that reduces γ-secretase activity [16].

Increase γ-secretase activity by inhibiting MEK1/2 (which stimulates ERK1/2) with, e.g., PD98059, PD0325901, or U0126 [16]. The MEK inhibitor Trametinib is FDA approved for use in melanoma.

Increase γ-secretase activity by upregulating adipocyte-associated plasma membrane protein (APMAP) [17].

Increase γ-secretase activity by increasing corticotropin releasing factor (CRF) [18], e.g. with GSK561679 or with the synthetic hormone peptide Corticorelin/Xerecept.

Increase γ-secretase activity by increasing OCIAD2, a MAM-localized protein [19, 20] that binds nicastrin [19] and cholesterol [21].

Increase γ-secretase activity by upregulating PS2 with 12-O tetradecanoylphorbol-β-acetate (TPA), which induces transcription factor EGR1, which binds to the neuronal-specific promoter element P2 upstream of PS2 [22].

Increase γ-secretase activity by upregulating TNF-α, interleukin-1β, interferon-γ, or MEKK1 [23]. TNF-α stimulates γ-secretase via JNK-mediated phosphorylation/stabilization of presenilin and nicastrin [23, 24].

Increase γ-secretase activity by increasing oligosaccharyltransferase subunits DC2 (gene OSTC) and KCP2 (gene KRTCAP2), which are required for APP maturation [25].

Increase γ-secretase activity by increasing calsenilin (gene KCNIP3) [26], a brain-specific protein that binds to PS1 and PS2 [27-29]; we note, however, that calsenilin is already up in AD brain [30, 31].

Increase γ-secretase activity with auraptene (7-geranyloxycoumarin) via activation of JNK [Jung C-G et al.]; enhances memory [Ghanbarabadi et al.].

Reduce C99 Levels in the MAM

Reduce C99 (and C83) with mifepristone (Mifeprex) [32].

Reduce C99 by increasing expression of miR-106b, which normally decreases ABCA1 expression, impairs cholesterol efflux, increases Aβ, and decreases C99 [33].

Reduce C99 by increasing its processing, by enhancing JNK-mediated phosphorylation of APP at Thr668 [34].

Reduce C99 by upregulating PICALM (a known SAD risk gene) to degrade C99 via autophagy [35].

Reduce C99 by reducing or inhibiting BRI2 (gene ITM2B), which blocks C99 processing [36].

Reduce C99 by blocking its function with a monoclonal antibody [37].

Reduce C99 by inhibiting TRPC6, which binds to C99 and inhibits its cleavage by γ-secretase [Wang, J et al.], using larixyl acetate (Sigma, Santa Cruz), a specific inhibitor of TRPC6 [Urban, N et al.]. Notably, PS2 regulates TRPC6 activity by inhibiting TRPC6 activation [Lessard, C. B. et al.].

Reduce C99 by overexpressing PIMT (protein 1-isoaspartyl o-methyltransferase), which is up in AD [Shimizu, T. et al], via upregulation of ADAM10/ADAM17 (i.e. α-secretases) [Bae, N. et al].

Reduce trafficking of C99 from endosomes to ER/MAM by inhibiting endosome-to-MAM movement genetically (e.g. knock-down of FAM21, a relevant component of the "WASH" complex [Rowland, A. A. et al]).

Reduce C99 by inhibiting ErbB2, which is a negative regulator of C99 autophagy (e.g. with CL-387,785) [Wang, B J. et al].

Degrade C99 via autophagy by promoting phosphorylation of PS1 on Ser367 (e.g. casein kinase 1γ2) [Bustos, V. et al. (a); Bustos, V. at al. (b)].

Prevent Aβ/C99-mediated cell death with the tricyclic pyrone molecule CP2 [Jin, L-W. et al].

Reduce BACE1 Activity/Cleavage

Reduce BACE1 activity by inhibiting its "bisecting" N-acetylglucosamination (GlcNac) by MGAT3 [38, 39].

Reduce BACE1 by activating the liver X receptor (LXR) with T0901317, a synthetic oxysterol ligand (perhaps via upregulated ABCA1) [40], or Compound 9, an LXR agonist [Stachel et al.].

Reduce BACE1 activity with phorbol esters [41].

Reduce BACE1 with zaragozic acid, which inhibits squalene synthase and increases α-secretase [42].

Reduce BACE1 cleavage with blocking peptides that bind to C99 [43].

Reduce BACE1 transcription [44].

Reduce BACE1 expression and C99 production by overexpressing UCHL1 [45] via, e.g., B-Myb [46].

Reduce BACE1 activity by inhibiting its binding partner PAR4 (gene PAWR) [47].

Reduce BACE1 trafficking/sorting by inhibiting its partner GGA1 [48].

Reduce BACE1 activity by inhibiting PPAR-α, for example, with GW7647 [49].

Reduce BACE1 transcription with all-trans retinoic acid (atRA), which binds the BACE1 promoter [50].

Reduce BACE1 specifically in endosomes (where only APP is cleaved by BACE1 [Ben Halima, S. et al.]) with a sterol-modified BACE1 inhibitor [Ben Halima, S. et al.; Rajendran, L. et al.].

Reduce BACE1 activity by inhibiting legumain (AEP; LGMN), which is a 6-secretase that cleaves APP at N-585 and stimulates BACE1 cleavage of the resulting C-terminal fragment [Zhang, Z. et al.] (e.g. with NN1 or NN4, [Lee, J. et al.] or LE28 [Edgington, L. E. et al.]; see also US 20120251459 A1.

Degrade BACE1 with p38α-MAPK [Schnoder, L. et al.].

Reduce BACE1 cleavage with an antibody to the BACE1 cleavage site [Arbel, M. et al.].

Inhibit BACE1 cleavage with Merck's verubacest (MK-8931), which is in clinical trials [Kennedy, M E. et al.]. Also in clinical trials are JNJ-54861911 (Janssen/Shionogi), AZD3293/LY3314814 (Astra-Zeneca/Lilly), E2609 (Eisei/Biogen), and CNP520 (Novartis/Amgen), all in clinical trials [Yan, R. 2016].

Reduce BACE1 cleavage specifically in endolysosomes with Gleevec (Novartis; now generic [Sun Pharmaceuticals]) and DV2-103 (Sloan-Kettering Institute) [Netzer, W J.].

Strategies to Re-Normalize Cholesterol Homeostasis

Block extracellular cholesterol absorption with Ezetimibe, which blocks cholesterol absorption by binding to NPC1L1, which contains a SCAP-like sterol sensing domain [51] and improves memory in AD mice [52].

Reduce ceramide production with myriocin [53], which inhibits serine palmitoyltransferase (SPT) [54], the first step of de novo ceramide synthesis [55, 56].

Reduce ceramide production by inhibiting sphingomyelinase (SMase) with desipramine [57] or zoledronic acid [58] (for acidic SMase) [59], and with GW4869 [59], altenusin [60], or cambinol [61] (for neutral SMase) [62, 63]. Note: Desipramine also inhibits acid ceramidase [64] and neutral SMase.

Reduce cholesterol and sphingolipid levels by overexpressing ABCA1 [65, 66].

Upregulate ACAT1 (gene SOAT1) to esterify cholesterol [67, 68] (ACAT1 inhibition with CP-113,818 reduces Aβ [69]).

Upregulate cholesterol 25-hydroxylases (e.g. CH25H and CYP46A1) to oxidize cholesterol [70, 71]. Both are risk factors in AD [72].

Cholesterol-related proteins (genes APOA4, APOE, CYP46A1, LPL, LIPA, OLR1, SOAT1) as risk factors in AD [73].

Increase PICALM to normalize cholesterol homeostasis and decrease LDLR [74].

Treat with osmotin, a plant homolog of adiponectin, which downregulates SREBP2 [Shah, S A. et al.].

Block LDL receptors (LRP1/ApoER; LRP2; LRP5; LRP6; LRP8/ApoER2; LRP1B; LDLR; VLDLR), focusing on LRP1, LDLR [75, 76], and LRAD3 (which binds C99 [77]).

Block LRP1, APOE receptor in brain [78].

Increase activity of ABCA1, which effluxes cholesterol [79]. ABCA1 mutation R219K reduces CSF cholesterol and AD risk [79, 80]). ABCA1 is positively regulated by SREBP2 (i.e. under high cholesterol, ABCA1 mRNA and protein are increased) [81, 82]. ABCA1 and ABCG1 transport cholesterol to ApoE [83]. ABCA1 regulates PtdSer flipping in membranes [84, 85].

Increase expression of ABCA1 by reducing FAK (gene PTK2) [86] with, e.g. PF-562,271.

Inhibit ABCA2 (which is a genetic risk factor for AD [87]; expressed mainly in brain [88]), which inhibits the conversion of plasma membrane-derived cholesterol to cholesteryl esters (CE) by ACAT1, by modulating sphingolipid metabolism [89].

Increase activity of ABCA7, perhaps with atorvastatin [90]. ABCA7 loss-of-function mutations increase AD risk [91]. ABCA7 regulates cholesterol efflux (to ApoE [92]) and HDL formation [82, 93], and also regulates APP processing [92]. ABCA7 traffics to the plasma membrane (PM) with LRP1 [94]. ABCA7 may also regulate cellular ceramide homeostasis [95]. ABCA7 binds APOA1 and may function in apolipoprotein-mediated phospholipid efflux from cells [96, 97], but perhaps not cholesterol efflux [97]. ABCA7 is negatively regulated by SREBP2 (i.e. under high cholesterol, ABCA7 mRNA and protein are reduced) [81, 82].

Increase activity of ABCA1 with methyl protodioscin, which inhibits SREBP and miR33a/b transcription [98].

Increase activity of ABCG1, which effluxes cholesterol [99] and 25-OH cholesterol [100].

Inhibit cholesterol trafficking with U18666a to reduce C99 [David W, Jr. et al.].

Reduce cholesterol by activating TRPML1-3 (MCOLN1-3) with the TRPML agonist ML-SA1 (Sigma SML0267), which enhances TRPML1-mediated lysosomal $Ca^{2+}$ release [Shen, D. et al.] and reduces cholesterol [Shen, D. et al.] (and perhaps sphingomyelin as well).

Enhance cholesterol efflux with ABCA1 agonist peptide CS-6253 [Hafiane, A. et al.].

Reduce cholesterol levels with cyclodextrins [Coisne, C. et al.].

Inhibit Cyclophilin D (CypD), an ostensibly mitochondrial protein associated with ER-mitochondrial calcium trafficking (and not associated with cholesterol trafficking), and which has recently shown to be in the MAM [Paillard, M. et al.; Tubbs, E. et al.], with Cyclosporin A (CsA).

Inhibit the scavenger receptor CD36, which is a fatty acid transporter that binds and imports cholesterol [Nassir, F. et al.; Rodrigue-Way, A. et al.], and which appears to be a major receptor for cholesterol, with sulfo-N-succinimidyl oleate (SSO) [Harmon, C M. et al.].

Increase cholesterol efflux by activating CYP11A1 with the anti-HIV drug efavirenz [Mast, N. et al.].

Strategies to Reduce ER-Mitochondrial Connectivity

Inhibit function of mitofusin-2 (MFN2) [101].

Inhibit function of PACS2 [102].

Stimulate function of Reticulon4/Nogo-B [103].

Inhibit ER-mitochondrial connectivity with acetylcholine [104].

Inhibit function of any factor known to increase ER-mitochondrial apposition.

Stimulate function of any factor known to decrease ER-mitochondrial apposition.

Inhibit GRP75 (on MAM), which couples to VDAC (on MOM) [Schwarzer, C. et al.], with MKT-077 [Honrath, B. et al.].

Increase the level of fetal and adult testis activator (FATE1) [Doughman-Bouguerra et al.]. FATE1, a cancer-testis antigen, has a role in the regulation of ER-mitochondria distance and Ca2+ uptake by mitochondria.

Strategies to Promote Hypoxia

The promotion of hypoxia to treat Alzheimer's disease is counterintuitive as hypoxia is normally associated with promoting Alzheimer's disease.

Promote hypoxia to increase γ-secretase activity by upregulating HIF-α, which binds to, and activates γ-secretase [Villa, J C. et al.; De Gasperi, R. et al.; Kaufmann, M R, et al.].

Promote hypoxia to block cholesterol synthesis [DeBose-Boyd, R A. et al.], upregulate PS2V [Sharman, M J. et al.; Moussavi Nik, S H. et al.]; and upregulate ACAT1 and cholesterol esterification [Matsumoto, K. et al.; Mukodani, J. et al].

Promote hypoxia to activate Reticulon4/Nogo-B and thereby decrease ER-mitochondrial tethering [Sutendra, G. et al.].

Hypoxia can be induced by (1) placing patients in hypoxic conditions (e.g. at high altitude [Thielke, S. et al.]), or (2) inhibiting prolyl hydroxylase (PHD1/EGLN1, PHD2/EGLN2, and PHD3/EGLN3) (which degrades HIF-α) with succinate [Selak, M A. et al], or with L-mimosime, 3,4-dihydroxybenzoate (3,4-DHB), and S956711 [Warnecke, C. et al.] or with FG-2216, an oxoglutarate analog [Bernhardt, W M. et al], or with ~6 other similar compounds in trials [Maxwell, P H. et al.].

REFERENCES FOR EXAMPLE 2

1. Wiley J C, Meabon J S, Frankowski H, Smith E A, Schecterson L C, et al (2010). Phenylbutyric acid rescues endoplasmic reticulum stress-induced suppression of APP proteolysis and prevents apoptosis in neuronal cells. PloS One 5, e9135.
2. Corbett G T, Roy A, Pahan K (2013). Sodium phenylbutyrate enhances astrocytic neurotrophin synthesis via protein kinase C (PKC)-mediated activation of cAMP-response element-binding protein (CREB): implications for Alzheimer disease therapy. J. Biol. Chem. 288, 8299-8312.
3. Basseri S, Lhotak S, Sharma A M, Austin R C (2009). The chemical chaperone 4-phenylbutyrate inhibits adipogenesis by modulating the unfolded protein response. J. Lipid Res. 50, 2486-2501.
4. Barbero-Camps E, Fernandez A, Baulies A, Martinez L, Fernandez-Checa J C, et al (2014). Endoplasmic reticulum stress mediates amyloid β neurotoxicity via mitochondrial cholesterol trafficking. Am. J. Pathol. 184, 2066-2081.
5. Cuadrado-Tejedor M, Ricobaraza A L, Torrijo R, Franco R, Garcia-Osta A (2013). Phenylbutyrate is a multifaceted drug that exerts neuroprotective effects and reverses the Alzheimers disease-like phenotype of a commonly used mouse model. Curr. Pharm. Des. 19, 5076-5084.
6. Wiley J C, Pettan-Brewer C, Ladiges W C (2011). Phenylbutyric acid reduces amyloid plaques and rescues cognitive behavior in A D transgenic mice. Aging Cell 10, 418-428.
7. Ricobaraza A, Cuadrado-Tejedor M, Perez-Mediavilla A, Frechilla D, Del Rio J, et al (2009). Phenylbutyrate ameliorates cognitive deficit and reduces tau pathology in an Alzheimer's disease mouse model. Neuropsychopharmacology 34, 1721-1732.
8. Marwarha G, Dasari B, Ghribi O (2012). Endoplasmic reticulum stress-induced CHOP activation mediates the down-regulation of leptin in human neuroblastoma SH-SY5Y cells treated with the oxysterol 27-hydroxycholesterol. Cell. Signal. 24, 484-492.
9. Bustamante H A, Rivera-Dictter A, Cavieres V A, Munoz V C, Gonzalez A, et al (2013). Turnover of C99 is controlled by a crosstalk between ERAD and ubiquitin-independent lysosomal degradation in human neuroglioma cells. PloS One 8, e83096.
10. Ni Y, Zhao X, Bao G, Zou L, Teng L, et al (2006). Activation of β2-adrenergic receptor stimulates γ-secretase activity and accelerates amyloid plaque formation. Nat. Med. 12, 1390-1396.
11. Yu J-T, Tan L, Ou J-R, Zhu J-X, Liu K, et al (2008). Polymorphisms at the β2-adrenergic receptor gene influence Alzheimer's disease susceptibility. Brain Res. 1210, 216-222.
12. Khachaturian A S, Zandi P P, Lyketsos C G, Hayden K M, Skoog I, et al (2006). Antihypertensive medication use and incident Alzheimer disease: the Cache County Study. Arch. Neurol. 63, 686-692.
13. Thathiah A, Horre K, Snellinx A, Vandewyer E, Huang Y, et al (2013). β-arrestin 2 regulates Aβ generation and γ-secretase activity in Alzheimer's disease. Nat. Med. 19, 43-49.
14. Gwon A R, Park J-S, Arumugam T V, Kwon Y-K, Chan S L, et al (2012). Oxidative lipid modification of nicastrin enhances amyloidogenic γ-secretase activity in Alzheimer's disease. Aging Cell 11, 559-568.
15. Capell A, Kaether C, Edbauer D, Shirotani K, Merkl S, et al (2003). Nicastrin interacts with γ-secretase complex components via the N-terminal part of its transmembrane domain. J. Biol. Chem. 278, 52519-52523.
16. Kim S-K, Park H-J, Hong H S, Baik E J, Jung M W, et al (2006). ERK1/2 is an endogenous negative regulator of the γ-secretase activity. FASEB J. 20, 157-159.
17. Mosser S, Alattia J-R, Dimitrov M, Matz A, Pascual J, et al (2015). The adipocyte differentiation protein APMAP is an endogenous suppressor of Aβ production in the brain. Hum. Mol. Genet. 24, 371-382.
18. Park H-J, Ran Y, Jung J I, Holmes O, Price A R, et al (2015). The stress response neuropeptide CRF increases amyloid-beta production by regulating gamma-secretase activity. EMBO J. 34, 1674-1686.
19. Han J, Jung S, Jang J, Kam T-I, Choi H, et al (2014). OCIAD2 activates γ-secretase to enhance amyloid beta production by interacting with nicastrin. Cell. Mol. Life Sci. 71, 2561-2576.
20. Poston C N, Krishnan S C, Bazemore-Walker C R (2013). In-depth proteomic analysis of mammalian mitochondria-associated membranes (MAM). J. Proteomics 79, 219-230.
21. Hulce J J, Cognetta A B, Niphakis M J, Tully S E, Cravatt B F (2013). Proteome-wide mapping of cholesterol-interacting proteins in mammalian cells. Nat. Methods 10, 259-264.
22. Renbaum P, Beeri R, Gabai E, Amiel M, Gal M, et al (2003). Egr-1 upregulates the Alzheimer's disease presenilin-2 gene in neuronal cells. Gene 318, 113-124.
23. Liao Y-F, Wang B-J, Cheng H-T, Kuo L-H, Wolfe M S (2004). Tumor necrosis factor-α, interleukin-1β, and interferon-γ stimulate γ-secretase-mediated cleavage of amyloid precursor protein through a JNK-dependent MAPK pathway. J. Biol. Chem. 279 , 49523-49532.
24. Kuo L-H, Hu M-K, Hsu W-M, Tung Y-T, Wang B-J, et al (2008). Tumor necrosis factor-α-elicited stimulation of γ-secretase is mediated by c-Jun N-terminal kinase-dependent phosphorylation of presenilin and nicastrin. Mol. Biol. Cell 19, 4201-4212.
25. Wilson C M, Magnaudeix A, Yardin C, Terro F (2011). DC2 and keratinocyte-associated protein 2 (KCP2), subunits of the oligosaccharyltransferase complex, are regulators of the γ-secretase-directed processing of amyloid precursor protein (APP). J. Biol. Chem. 286, 31080-31091.
26. Jo D-G, Jang J, Kim B-J, Lundkvist J, Jung Y-K (2005). Overexpression of calsenilin enhances γ-secretase activity. Neurosci. Lett. 378, 59-64.
27. Buxbaum J D, Choi E K, Luo Y, Lilliehook C, Crowley A C, et al (1998). Calsenilin: a calcium-binding protein that interacts with the presenilins and regulates the levels of a presenilin fragment. Nat. Med. 4, 1177-1181.
28. Choi E K, Zaidi N F, Miller J S, Crowley A C, Merriam D E, et al (2001). Calsenilin is a substrate for caspase-3 that preferentially interacts with the familial Alzheimer's disease-associated C-terminal fragment of presenilin 2. J. Biol. Chem. 276, 19197-19204.
29. Jang C, Choi J-K, Na Y-J, Jang B, Wasco W, et al (2011). Calsenilin regulates presenilin 1/γ-secretase-mediated N-cadherin ε-cleavage and β-catenin signaling. FASEB journal: official publication of the Federation of American Societies for Experimental Biology 25, 4174-4183.
30. Jin J-K, Choi J-K, Wasco W, Buxbaum J D, Kozlowski P B, et al (2005). Expression of calsenilin in neurons and astrocytes in the Alzheimer's disease brain. Neuroreport 16, 451-455.
31. Jo D-G, Lee J-Y, Hong Y-M, Song S, Mook-Jung I, et al (2004). Induction of pro-apoptotic calsenilin/DREAM/KChIP3 in Alzheimer's disease and cultured neurons after amyloid-β exposure. J. Neurochem. 88, 604-611.
32. Baglietto-Vargas D, Medeiros R, Martinez-Coria H, LaFerla F M, Green K N (2013). Mifepristone alters amyloid precursor protein processing to preclude amyloid beta and also reduces tau pathology. Biol. Psychiatry 74, 357-366.
33. Kim J, Yoon H, Ramirez C M, Lee S-M, Hoe H-S, et al (2012). MiR-106b impairs cholesterol efflux and increases Abeta levels by repressing ABCA1 expression. Exp. Neurol. 235, 476-483.
34. Vingtdeux V, Hamdane M, Gompel M, Begard S, Drobecq H, et al (2005). Phosphorylation of amyloid precursor carboxy-terminal fragments enhances their processing by a γ-secretase-dependent mechanism. Neurobiol. Dis. 20, 625-637.
35. Tian Y, Chang J C, Fan E Y, Flajolet M, Greengard P (2013). Adaptor complex AP2/PICALM, through interaction with LC3, targets Alzheimer's APP-CTF for terminal degradation via autophagy. Proc. Natl. Acad. Sci. USA 110, 17071-17076.
36. Matsuda S, Matsuda Y, Snapp E L, D'Adamio L (2011). Maturation of BRI2 generates a specific inhibitor that reduces APP processing at the plasma membrane and in endocytic vesicles. Neurobiol. Aging 32, 1400-1408.
37. Houacine J, Bolmont T, Aeschbach L, Oulad-Abdelghani M, Fraering P C (2012). Selective neutralization of APP-C99 with monoclonal antibodies reduces the production of Alzheimer's Abeta peptides. Neurobiol. Aging 33, 2704-2714.
38. Hanashima S, Korekane H, Taniguchi N, Yamaguchi Y (2014). Synthesis of N-glycan units for assessment of substrate structural requirements of N-acetylglucosaminyltransferase III. Bioorganic Med. Chem. Lett. 24, 4533-4537.
39. Kizuka Y, Kitazume S, Fujinawa R, Saito T, Iwata N, et al (2015). An aberrant sugar modification of BACE1 blocks its lysosomal targeting in Alzheimer's disease. EMBO Mol. Med. 7, 175-189.
40. Cui W, Sun Y, Wang Z, Xu C, Xu L, et al (2011). Activation of liver X receptor decreases BACE1 expression and activity by reducing membrane cholesterol levels. Neurochem. Res. 36, 1910-1921.

41. Felsenstein K M, Ingalls K M, Hunihan L W, Roberts S B (1994). Reversal of the Swedish familial Alzheimer's disease mutant phenotype in cultured cells treated with phorbol 12,13-dibutyrate. Neurosci. Lett. 174, 173-176.
42. Kojro E, Fuger P, Prinzen C, Kanarek A M, Rat D, et al (2010). Statins and the squalene synthase inhibitor zaragozic acid stimulate the non-amyloidogenic pathway of amyloid-β protein precursor processing by suppression of cholesterol synthesis. J. Alzheimers Dis. 20, 1215-1231.
43. Funamoto S, Sasaki T, Ishihara S, Nobuhara M, Nakano M, et al (2013). Substrate ectodomain is critical for substrate preference and inhibition of γ-secretase. Nat. Commun. 4, 2529.
44. Li Y, Zhou W, Tong Y, He G, Song W (2006). Control of APP processing and Aβ generation level by BACE1 enzymatic activity and transcription. FASEB J. 20, 285-292.
45. Zhang M, Deng Y, Luo Y, Zhang S, Zou H, et al (2012). Control of BACE1 degradation and APP processing by ubiquitin carboxyl-terminal hydrolase L1. J. Neurochem. 120, 1129-1138.
46. Long E M, Long M A, Tsirigotis M, Gray D A (2003). Stimulation of the murine Uchl1 gene promoter by the B-Myb transcription factor. Lung Cancer 42, 9-21.
47. Xie J, Guo Q (2005). PAR-4 is involved in regulation of β-secretase cleavage of the Alzheimer amyloid precursor protein. J. Biol. Chem. 280, 13824-13832.
48. von Amim CAF, Spoelgen R, Peltan I D, Deng M, Courchesne S, et al (2006). GGA1 acts as a spatial switch altering amyloid precursor protein trafficking and processing. J. Neurosci. 26, 9913-9922.
49. Zhang H, Gao Y, Qiao P F, Zhao F L, Yan Y (2015). PPAR-α agonist regulates amyloid-β generation via inhibiting BACE-1 activity in human neuroblastoma SH-SY5Y cells transfected with APPswe gene. Mol Cell Biochem. in press.
50. Wang R, Chen S, Liu Y, Diao S, Xue Y, et al (2015). All-trans retinoic acid reduces BACE1 expression under inflammatory conditions via modulation of NFκB signaling. J. Biol. Chem. in press.
51. Garcia-Calvo M, Lisnock J, Bull H G, Hawes B E, Burnett D A, et al (2005). The target of ezetimibe is Niemann-Pick C1-Like 1 (NPC1L1). Proc. Natl. Acxad. Sci. USA 102, 8132-8137.
52. Dalla Y, Singh N, Jaggi A S, Singh D, Ghulati P (2009). Potential of ezetimibe in memory deficits associated with dementia of Alzheimer's type in mice. Indian J. Pharmacol. 41, 262-267.
53. Sawamura N, Ko M, Yu W, Zou K, Hanada K, et al (2004). Modulation of amyloid precursor protein cleavage by cellular sphingolipids. J. Biol. Chem. 279, 11984-11991.
54. Miyake Y, Kozutsumi Y, Nakamura S, Fujita T, Kawasaki T (1995). Serine palmitoyltransferase is the primary target of a sphingosine-like immunosuppressant, ISP-1/myriocin. Biochem. Biophys. Res. Commun. 211, 396-403.
55. Cutler R G, Kelly J, Storie K, Pedersen W A, Tammara A, et al (2004). Involvement of oxidative stress-induced abnormalities in ceramide and cholesterol metabolism in brain aging and Alzheimer's disease. Proc. Natl. Acad. Sci. USA 101, 2070-2075.
56. Colon-Saez J O, Yakel J L (2011). The α7 nicotinic acetylcholine receptor function in hippocampal neurons is regulated by the lipid composition of the plasma membrane. J. Physiol. 589, 3163-3174.
57. Hurwitz R, Ferlinz K, Sandhoff K (1994). The tricyclic antidepressant desipramine causes proteolytic degradation of lysosomal sphingomyelinase in human fibroblasts. Biol. Chem. Hoppe-Seyler 375, 447-450.
58. Roth A G, Drescher D, Yang Y, Redmer S, Uhlig S, et al (2009). Potent and selective inhibition of acid sphingomyelinase by bisphosphonates. Angew. Chem. Int. Ed. Engl. 48, 7560-7563.
59. Pera M, Larrea D, Guardia-Laguarta C, Chan R B, Mehler F, et al (2015). Accumulation of APP-C99 in mitochondria-associated ER membranes disrupts lipid homeostasis and triggers early events in the pathogenesis of Alzheimer disease. Manuscript in preparation.
60. Uchida R, Tomoda H, Dong Y, Omura S (1999). Alutenusin, a specific neutral sphingomyelinase inhibitor, produced by Penicillium sp. FO-7436. J. Antibiot. 52, 572-574.
61. Figuera-Losada M, Stathis M, Dorskind J M, Thomas A G, Bandaru VVR, et al (2015). Cambinol, a novel inhibitor of neutral sphingomyelinase 2 shows neuroprotective properties. PLoS One 10, e0124481.
62. Delgado A, Casas J, Llebaria A, Abad J L, Fabrias G (2006). Inhibitors of sphingolipid metabolism enzymes. Biochim. Biophys. Acta 1758, 1957-1977.
63. Mokhber N, Abdollahian E, Soltanifar A, Samadi R, Saghebi A, et al (2014). Comparison of sertraline, venlafaxine and desipramine effects on depression, cognition and the daily living activities in Alzheimer patients. Pharmacopsychiatry 47, 131-140.
64. Elojeimy S, Holman D H, Liu X, El-Zawahry A, Villani M, et al (2006). New insights on the use of desipramine as an inhibitor for acid ceramidase. FEBS Lett. 580, 4751-4756.
65. Polzhofer H (2010). Linking cholesterol sensing at the plasma membrane to its production at the endoplasmic reticulum. Thesis ETH Zurich, 144.
66. Damm E-M, Snijder B, Stergiou L, Guan X L, Polzhofer H, et al (2010). Focal adhesion kinase establishes lipid rafts on the cell surface by controlling transcription of the cholesterol transporter ABCA1. Unpublished.
67. Area-Gomez E, Del Carmen Lara Castillo M, Tambini M D, Guardia-Laguarta C, de Groof A J C, et al (2012). Upregulated function of mitochondria-associated ER membranes in Alzheimer disease. EMBO J 31, 4106-4123.
68. Puglielli L, Ellis B C, Ingano L A, Kovacs D M (2004). Role of acyl-coenzyme A: cholesterol acyltransferase activity in the processing of the amyloid precursor protein. J. Mol. Neurosci. 24, 93-96.
69. Hutter-Paier B, Huttunen H J, Puglielli L, Eckman C B, Kim D Y, et al (2004). The ACAT inhibitor CP-113, 818 markedly reduces amyloid pathology in a mouse model of Alzheimer's disease. Neuron 44, 227-238.
70. Bryleva E Y, Rogers M A, Chang CCY, Buen F, Harris B T, et al (2010). ACAT1 gene ablation increases 24(S)-hydroxycholesterol content in the brain and ameliorates amyloid pathology in mice with A D. Proc. Natl. Acad. Sci. USA 107, 3081-3086.
71. Papassotiropoulos A, Lambert J-C, Wavrant-De Vrieze F, Wollmer M A, von der Kammer H, et al (2005). Cholesterol 25-hydroxylase on chromosome 10q is a susceptibility gene for sporadic Alzheimer's disease. Neurodegener. Dis. 2, 233-241.
72. Papassotiropoulos A, Streffer J R, Tsolaki M, Schmid S, Thal D, et al (2003). Increased brain β-amyloid load, phosphorylated tau, and risk of Alzheimer disease associated with an intronic CYP46 polymorphism. Arch. Neurol. 60, 29-35.
73. Papassotiropoulos A, Wollmer M A, Tsolaki M, Brunner F, Molyva D, et al (2005). A cluster of cholesterol-related genes confers susceptibility for Alzheimer's disease. J. Clin. Psychiatry 66, 940-947.
74. Mercer J L, Argus J P, Crabtree D M, Keenan M M, Wilks M, et al (2015). Modulation of PICALM levels perturbs cellular cholesterol homeostasis. PLoS One 10, e0129776.
75. Holtzman D M, Herz J, Bu G (2012). Apolipoprotein E and apolipoprotein E receptors: normal biology and roles in Alzheimer disease. Cold Spr. Harb. Perspect. Med. 2, a006312.
76. Tambini M D, Pera M, Kanter E, Yang H, Holtzman D M, et al (2015). ApoE4 upregulates the activity of mitochondria-associated ER membranes. EMBO Rep. Submitted.
77. Ranganathan S, Noyes N C, Migliorini M, Winkles J A, Battey F D, et al (2011). LRAD3, a novel low-density lipoprotein receptor family member that modulates amyloid precursor protein trafficking. J. Neurosci. 31, 10836-10846.
78. Liu Q, Zerbinatti C V, Zhang J, Hoe H-S, Wang B, et al (2007). Amyloid precursor protein regulates brain apolipoprotein E and cholesterol metabolism through lipoprotein receptor LRP 1. Neuron 56, 66-78.
79. Wollmer M A, Streffer J R, Lutjohann D, Tsolaki M, Iakovidou V, et al (2003). ABCA1 modulates CSF cholesterol levels and influences the age at onset of Alzheimer's disease. Neurobiol. Aging 24, 421-426.
80. Katzov H, Chalmers K, Palmgren J, Andreasen N, Johansson B, et al (2004). Genetic variants of ABCA1 modify Alzheimer disease risk and quantitative traits related to β-amyloid metabolism. Hum. Mutat. 23, 358-367.
81. Iwamoto N, Abe-Dohmae S, Sato R, Yokoyama S (2006). ABCA7 expression is regulated by cellular cholesterol through the SREBP2 pathway and associated with phagocytosis. J. Lipid Res. 47, 1915-1927.
82. Tanaka N, Abe-Dohmae S, Iwamoto N, Yokoyama S (2011). Roles of ATP-binding cassette transporter A7 in cholesterol homeostasis and host defense system. J. Atheroscler. Thromb. 18, 274-281.
83. Kim W S, Rahmanto A S, Kamili A, Rye K-A, Guillemin G J, et al (2007). Role of ABCG1 and ABCA1 in regulation of neuronal cholesterol efflux to apolipoprotein E discs and suppression of amyloid-beta peptide generation. J. Biol. Chem. 282, 2851-2861.
84. Albrecht C, McVey J H, Elliott J I, Sardini A, Kasza I, et al (2005). A novel missense mutation in ABCA1 results in altered protein trafficking and reduced phosphatidylserine translocation in a patient with Scott syndrome. Blood 106, 542-549.
85. Alder-Baerens N, Muller P, Pohl A, Korte T, Hamon Y, et al (2005). Headgroup-specific exposure of phospholipids in ABCA1-expressing cells. J. Biol. Chem. 280, 26321-26329.
86. Frechin M, Stoeger T, Daetwyler S, Gehin C, Battich N, et al (2015). Cell-intrinsic adaptation of lipid composition to local crowding drives social behaviour. Nature 523, 88-91.
87. Mace S, Cousin E, Ricard S, Genin E, Spanakis E, et al (2005). ABCA2 is a strong genetic risk factor for early-onset Alzheimer's disease. Neurobiol. Dis. 18, 119-125.
88. Schmitz G, Kaminski W E (2002). ABCA2: a candidate regulator of neural transmembrane lipid transport. Cell. Mol. Life Sci. 59, 1285-1295.
89. Davis W, Jr. (2014). The ATP-binding cassette transporter-2 (ABCA2) regulates esterification of plasma membrane cholesterol by modulation of sphingolipid metabolism. Biochim. Biophys. Acta 1841, 168-179.
90. Tanaka N, Abe-Dohmae S, Iwamoto N, Fitzgerald M L, Yokoyama S (2011). HMG-CoA reductase inhibitors enhance phagocytosis by upregulating ATP-binding cassette transporter A7. Atherosclerosis 217, 407-414.
91. Steinberg S, Stefansson H, Jonsson T, Johannsdottir H, Ingason A, et al (2015). Loss-of-function variants in ABCA7 confer risk of Alzheimer's disease. Nat. Genet. 47, 445-447.
92. Chan S L, Kim W S, Kwok J B, Hill A F, Cappai R, et al (2008). ATP-binding cassette transporter A7 regulates processing of amyloid precursor protein in vitro. J. Neurochem. 106, 793-804.
93. Abe-Dohmae S, Ikeda Y, Matsuo M, Hayashi M, Okuhira K-i, et al (2004). Human ABCA7 supports apolipoprotein-mediated release of cellular cholesterol and phospholipid to generate high density lipoprotein. J. Biol. Chem. 279, 604-611.
94. Jehle A W, Gardai S J, Li S, Linsel-Nitschke P, Morimoto K, et al (2006). ATP-binding cassette transporter A7 enhances phagocytosis of apoptotic cells and associated ERK signaling in macrophages. J. Cell Biol. 174, 547-556.
95. Kielar D, Kaminski W E, Liebisch G, Piehler A, Wenzel J J, et al (2003). Adenosine triphosphate binding cassette (ABC) transporters are expressed and regulated during terminal keratinocyte differentiation: a potential role for ABCA7 in epidermal lipid reorganization. J. Invest. Dermatol. 121, 465-474.
96. Ikeda Y, Abe-Dohmae S, Munehira Y, Aoki R, Kawamoto S, et al (2003). Posttranscriptional regulation of human ABCA7 and its function for the apoA-I-dependent lipid release. Biochem. Biophys. Res. Commun. 311, 313-318.
97. Wang N, Lan D, Gerbod-Giannone M, Linsel-Nitschke P, Jehle A W, et al
(2003). ATP-binding cassette transporter A7 (ABCA7) binds apolipoprotein A-I and mediates cellular phospholipid but not cholesterol efflux. J. Biol. Chem. 278, 42906-42912.
98. Ma W, Ding H, Gong X, Liu Z, Lin Y, et al (2015). Methyl protodioscin increases ABCA1 expression and cholesterol efflux while inhibiting gene expressions for synthesis of cholesterol and triglycerides by suppressing SREBP transcription and microRNA 33a/b levels. Atherosclerosis 239, 566-570.
99. Tarling E J, Edwards P A (2011). ATP binding cassette transporter G1 (ABCG1) is an intracellular sterol transporter. Proc. Natl. Acad. Sci. USA 108, 19719-19724.
100. Engel T, Fobker M, Buchmann J, Kannenberg F, Rust S, et al (2014). 3β,5α,6β-Cholestanetriol and 25-hydroxycholesterol accumulate in ATP-binding cassette transporter G1 (ABCG1)-deficiency. Atherosclerosis 235, 122-129.
101. de Brito O M, Scorrano L (2008). Mitofusin 2 tethers endoplasmic reticulum to mitochondria. Nature 456, 605-610.
102. Simmen T, Aslan J E, Blagoveshchenskaya A D, Thomas L, Wan L, et al (2005). PACS-2 controls endoplasmic reticulum-mitochondria communication and Bid-mediated apoptosis. EMBO J. 24, 717-729.

103. Sutendra G, Dromparis P, Wright P, Bonnet S, Haromy A, et al (2011). The role of Nogo and the mitochondria-endoplasmic reticulum unit in pulmonary hypertension. Science Transl. Med. 3, 88ra55.

104. He X, Bi X-y, X.-z. L, Zhao M, Yu X-j, et al (2015). Reduction of mitochondria-endoplasmic reticulum interactions by acetylcholine protects human umbilical vein endothelial cells from hypoxia/reoxygenation injury. Arterioscler. Thromb. Vasc. Biol. 35, 1623-1634.

Jung C-G, Uhm K-O, Horike H, Kim M-J, Misumi S, et al (2015). Auraptene increases the production of amyloid-β via c-Jun N-terminal kinase-dependent activation of γ-secretase. J. Alzheimer's Dis. 43, 1215-12128.

Ghanbarabadi M, Iranshahi M, Amoueian S, Mehri S, Motamedshariaty V S, Mohajeri S A (2016). Neuroprotective and memory enhancing effects of auraptene in a rat model of vascular dementia: Experimental study and histopathological evaluation. Neurosci. Lett. 623, 13-21.

Wang J, Lu R, Yang J, Li H, He Z, Jing N, Wang X, Wang Y (2015). TRPC6 specifically interacts with APP to inhibit its cleavage by gamma-secretase and reduce Abeta production. Nat. Commun. 6, 8876.

Urban N, Wang L, Kwiek S, Rademann J, Kuebler W M, Schaefer M (2016). Identification and validation of larixyl acetate as a potent TRPC6 inhibitor. Mol. Pharmacol. 89, 197-213.

Lessard C B, Lussier M P, Cayouette S, Bourque G, Boulay G (2005). The overexpression of presenilin2 and Alzheimer's-disease-linked presenilin2 variants influences TRPC6-enhanced Ca2+ entry into HEK293 cells. Cell. Signal. 17, 437-445.

Shimizu T, Watanabe A, Ogawara M, Mori H, Shirasawa T (2000). Isoaspartate formation and neurodegeneration in Alzheimer's disease. Arch, Biochem. Biophys. 381, 225-234.

Bae N, Byeon S E, Song J, Lee S-J, Kwon M, Mook-Jung I, Cho J Y, Hong S (2011). Knock-down of protein L-isoaspartyl O-methyltransferase increases beta-amyloid production by decreasing ADAM10 and ADAM17 levels. Acta pharmacol. Sin. 32, 288-294.

Rowland A A, Chitwood P J, Phillips M J, Voeltz G K (2014). E R contact sites define the position and timing of endosome fission. Cell 159, 1027-1041.

Stachel S J, Zerbinatti C, Rudd M T, Cosden M, Suon S, et al (2016). Identification and in vivo evaluation of liver X receptor β-selective agonists for the potential treatment of Alzheimer's disease. J. Med. Chem. 59, 3489-3498.

Ben Halima S, Mishra S, Raja KMP, Willem M, Baici A, et al (2016). Specific inhibition of β-secretase processing of the Alzheimer disease amyloid precursor protein. Cell Rep. 14, 2127-2141.

Rajendran L, Schneider A, Schlechtingen G, Weidlich S, Ries J, et al (2008). Efficient inhibition of the Alzheimer's disease β-secretase by membrane targeting. Science 320, 520-523.

Zhang Z, Song M, Liu X, Su Kang S, Duong D M, et al (2015). Delta-secretase cleaves amyloid precursor protein and regulates the pathogenesis in Alzheimer's disease. Nat. Commun. 6, 8762.

Lee J, Bogyo M (2012). Synthesis and evaluation of aza-peptidyl inhibitors of the lysosomal asparaginyl endopeptidase, legumain. Bioorg. Med. Chem. lett. 22, 1340-1343.

Edgington L E, Verdoes M, Ortega A, Withana N P, Lee J, Syed S, Bachmann M H, Blum G, Bogyo M (2013). Functional imaging of legumain in cancer using a new quenched activity-based probe. J. Am. Chem. Soc. 135, 174-182.

Schnoder L, Hao W, Qin Y, Liu S, Tomic I, Liu X, Fassbender K, Liu Y (2016). Deficiency of neuronal p38α-MAPK attenuates amyloid pathology in Alzheimer's mouse and cell models through facilitating lysosomal degradation of BACE1. J. Biol. Chem. 291, 2067-2079.

Davis W, Jr. (2008). The cholesterol transport inhibitor U18666a regulates amyloid precursor protein metabolism and trafficking in N2aAPP "Swedish" cells. Curr. Alz. Res. 5 , 448-456.

Shen D, Wang X, Li X, Zhang X, Yao Z, et al (2012). Lipid storage disorders block lysosomal trafficking by inhibiting a TRP channel and lysosomal calcium release. Nat. Commun. 3, 731.

Hafiane A, Bielicki J K, Johansson J O, Genest J (2015). Novel Apo E-derived ABCA1 agonist peptide (CS-6253) promotes reverse cholesterol transport and induces formation of preβ-1 HDL in vitro. PloS One 10, e0131997.

Doghman-Bouguerra M, Granatiero V, Sbiera S, Sbiera I, Lacas-Gervais S, Brau F, Fassnacht M, Rizzuto R, Lalli E (2016) FATE1 antagonizes calcium- and drug-induced apoptosis by uncoupling E R and mitochondria. EMBO Rep. 17, 1264-1280.

Chai G-s, Wang Y-y, Zhu D, Yasheng A, Zhao P (2016). Activation of $\beta_2$-adrenergic receptor promotes dendrite ramification and spine generation in APP/PS1 mice. Neurosci. Lett. in press.

Wang B J, Her G M, Hu M K, Chen Y W, Tung Y T, et al (2017). ErbB2 regulates autophagic flux to modulate the proteostasis of APP-CTFs in Alzheimer's disease. Proc. Natl. Acad. Sci. USA 114, E3129-E3138.

Bustos V, Pulina M V, Bispo A, Lam A, Flajolet M, Gorelick F S, Greengard P (a) (2017). Phosphorylated Presenilin 1 decreases beta-amyloid by facilitating autophagosome-lysosome fusion. Proc. Natl. Acad. Sci. USA 114, 7148-7153.

Bustos V, Pulina M V, Kelahmetoglu Y, Sinha S C, Gorelick F S, Flajolet M, Greengard P (b) (2017). Bidirectional regulation of Abeta levels by Presenilin 1. Proc. Natl. Acad. Sci. USA 114, 7142-7147.

Jin L-W, Hua D H, Shie F-S, Maezawa I, Sopher B, Martin G M (2002). Novel tricyclic pyrone compounds prevent intracellular APP C99-induced cell death. J. Mol. Neurosci. 19, 57-61.

Arbel M, Solomon B (2007). A novel immunotherapy for Alzheimer's disease: antibodies against the beta-secretase cleavage site of APP. Curr. Alzheimer Res. 4, 437-445.

Kennedy M E, Stamford A W, Chen X, Cox K, Cumming J N, et al (2016). The BACE1 inhibitor verubecestat (MK-8931) reduces CNS β-amyloid in animal models and in Alzheimer's disease patients. Sci. Transl. Med. 8, 363ra150.

Yan R (2016). Stepping closer to treating Alzheimer's disease patients with BACE1 inhibitor drugs. Transl. Neuridegen. 5, 13.

Netzer W J, Bettayeb K, Sinha S C, Flajolet M, Greengard P, Bustos V (2017). Gleevec shifts APP processing from a beta-cleavage to a nonamyloidogenic cleavage. Proc. Natl. Acad. Sci. USA 114, 1389-1394.

Shah S A, Yoon G H, Chung S S, Abid M N, Kim T H, Lee H Y, Kim M O (2017). Novel osmotin inhibits SREBP2 via the AdipoR1/AMPK/SIRT1 pathway to improve Alzheimer's disease neuropathological deficits. Mol. Psychiatry 22, 407-416.

Coisne C, Tilloy S, Monflier E, Wils D, Fenart L, Gosselet F (2016). Cyclodextrins as emerging therapeutic tools in the treatment of cholesterol-associated vascular and neurodegenerative diseases. Molecules in press.

Paillard M, Tubbs E, Thiebaut P-A, Gomez L, Fauconnier J, et al (2013). Depressing mitochondria-reticulum interactions protects cardiomyocytes from lethal hypoxia-reoxygenation injury. Circulation 128, 1555-1565.

Tubbs E, Theurey P, Vial G, Bendridi N, Bravard A, et al (2014). Mitochondria-associated endoplasmic reticulum membrane (MAM) integrity is required for insulin signaling and is implicated in hepatic insulin resistance. Diabetes 63, 3279-3294.

Nassir F, Wilson B, Han X, Gross R W, Abumrad N A (2007). CD36 is important for fatty acid and cholesterol uptake by the proximal but not distal intestine. J. Biol. Chem. 282 , 19493-19501.

Rodrigue-Way A, Caron V, Bilodeau S, Keil S, Hassan M, Levy E, Mitchell G A, Tremblay A (2014). Scavenger receptor CD36 mediates inhibition of cholesterol synthesis via activation of the PPARγ/PGC-1α pathway and Insig1/2 expression in hepatocytes. FASEB J. 28, 1910-1923.

Harmon C M, Luce P, Beth A H, Abumrad N A (1991). Labeling of adipocyte membranes by sulfo-N-succinimidyl derivatives of long-chain fatty acids: inhibition of fatty acid transport. J. Membr. Biol. 121, 261-268.

Mast N, Saadane A, Valencia-Olvera A, Constans J, Maxfield E, Arakawa H, Li Y, Landreth G, Pikuleva I A (2017). Cholesterol-metabolizing enzyme cytochrome P450 46A1 as a pharmacologic target for Alzheimer's disease. Neuropharmacology 123, 465-476.

Schwarzer C, Bamikol-Watanabe S, Thinnes F P, Hilschmann N (2002). Voltage-dependent anion-selective channel (VDAC) interacts with the dynein light chain Tctex1 and the heat-shock protein PBP74. Int. J. Biochem. Cell Biol. 34, 1059-1070.

Honrath B, Metz I, Bendridi N, Rieusset J, Culmsee C, Dolga A M (2017). Glucose-regulated protein 75 determines E R-mitochondrial coupling and sensitivity to oxidative stress in neuronal cells. Cell Death Discov. 3, 17076.

Villa J C, Chiu D, Brandes A H, Escorcia F E, Villa C H, et al (2014). Nontranscriptional role of Hif-1 α in activation of γ-secretase and notch signaling in breast cancer. Cell Rep. 8, 1077-1092.

De Gasperi R, Sosa MAG, Dracheva S, Elder G A (2010). Presenilin-1 regulates induction of hypoxia inducible factor-1α: altered activation by a mutation associated with familial Alzheimer's disease. Mol. Neurodegen. 5, 38.

Kaufmann M R, Barth S, Konietzko U, Wu B, Egger S, et al (2013). Dysregulation of hypoxia-inducible factor by presenilin/γ-secretase loss-of-function mutations. J. Neurosci. 33, 1915-1926.

DeBose-Boyd R A (2008). Feedback regulation of cholesterol synthesis: sterol-accelerated ubiquitination and degradation of HMG CoA reductase. Cell research 18, 609-621.

Sharman M J, Moussavi Nik S H, Chen M M, Ong D, Wijaya L, et al (2013). The guinea pig as a model for sporadic Alzheimer's fisease (A D): The impact of cholesterol intake on expression of A D-related genes. PloS One 8, e66235.

Moussavi Nik S H, Newman M, Wilson L, Ebrahimie E, Wells S, Musgrave I, Verdile G, Martins R N, Lardelli M (2015). Alzheimer's disease-related peptide PS2V plays ancient, conserved roles in suppression of the unfolded protein response under hypoxia and stimulation of γ-secretase activity. Hum. Mol. Genet. 24, 3662-3678.

Matsumoto K, Taniguchi T, Fujioka Y, Shimizu H, Ishikawa Y, Yokoyama M (2000). Effects of hypoxia on cholesterol metabolism in human monocyte-derived macrophages. Life Sciences 67, 2083-2091.

Mukodani J, Ishikawa Y, Fukuzaki H (1990). Effects of hypoxia on sterol synthesis, acyl-CoA: cholesterol acyltransferase activity, and efflux of cholesterol in cultured rabbit skin fibroblasts. Arteriosclerosis 10, 106-110.

Sutendra G, Dromparis P, Wright P, Bonnet S, Haromy A, et al (2011). The role of Nogo and the mitochondria-endoplasmic reticulum unit in pulmonary hypertension. Science Transl. Med. 3, 88ra55.

Thielke S, Slatore C G, Banks W A (2015). Association Between Alzheimer Dementia Mortality Rate and Altitude in California Counties. JAMA Psychiatry 72, 1253-1254.

Selak M A, Armour S M, MacKenzie E D, Boulahbel H, Watson D G, et al (2005). Succinate links TCA cycle dysfunction to oncogenesis by inhibiting HIF-α prolyl hydroxylase. Cancer Cell 7, 77-85.

Warnecke C, Griethe W, Weidemann A, Jurgensen J S, Willam C, et al (2003). Activation of the hypoxia-inducible factor-pathway and stimulation of angiogenesis by application of prolyl hydroxylase inhibitors. FASEB J. 17, 1186-1188.

Bernhardt W M, Wiesener M S, Scigalla P, Chou J, Schmieder R E, Gunzler V, Eckardt K-U (2010). Inhibition of prolyl hydroxylases increases erythropoietin production in ESRD. J. Am. Soc. Nephrol. 21, 2151-2156.

Maxwell P H, Eckardt K-U (2016). HIF prolyl hydroxylase inhibitors for the treatment of renal anaemia and beyond. Nat. Rev. Nephrol. 12, 157-168.

Example 3—Accumulation of APP-C99 in Mitochondria-Associated ER Membranes Causes Mitochondrial Dysfunction in Alzheimer Disease In the amyloidogenic pathway associated with Alzheimer disease (AD), the amyloid precursor protein (APP) is cleaved by 3-secretase to generate a 99-aa C-terminal fragment (C99) that is then cleaved by γ-secretase to generate the β-amyloid (Aβ) found in senile plaques. In previous reports, γ-secretase activity has been shown to be enriched in mitochondria-associated endoplasmic reticulum (ER) membranes (MAM), and that ER-mitochondrial connectivity and MAM function are upregulated in AD. Described herein are results that show C99 is localized to MAM, where it is normally processed rapidly. In AD, however C99 accumulates above normal levels in MAM regions, resulting in increased sphingolipid turnover and an altered lipid composition of both MAM and mitochondrial membranes. In turn, this change in mitochondrial membrane composition interferes with the proper assembly and activity of mitochondrial respiratory supercomplexes, thereby likely contributing to the bioenergetic defects characteristic of AD.

Familial AD (FAD) is characterized by mutations in presenilin-1 (PS1), presenilin-2 (PS2), and APP. APP is first cleaved by either α-secretase or β-secretase (BACE1) to produce C-terminal fragments (CTFs) 83 aa (C83) or 99 aa (C99) long, respectively. PS1 and PS2 are the catalytic subunits of the γ-secretase complex that cleaves C83 and C99 to produce either p3 or β-amyloid (Aβ), respectively, along with the APP intracellular domain (AICD). The accumulation of longer forms of Aβ (e.g. ~42 aa) results in plaques that, together with Tau tangles, are hallmarks of AD.

The deleterious effects of Aβ deposition during symptomatic stages of AD are undeniable (Hardy and Higgins, 1992), but the role of Aβ in earlier phases of the disease is still debated.

During these early stages, AD cells exhibit alterations in numerous metabolic processes (McBrayer and Nixon, 2013; Wang et al., 2014). Among these, perturbed mitochondrial function, including reduced respiratory chain activity and ATP production, and increased oxidative stress (Du et al., 2010), have been described extensively (Swerdlow et al., 2014), occurring before the appearance of plaques (Wang et al., 2014; Yao et al., 2009). Nevertheless, the cause of these mitochondrial deficits in AD it is still unknown.

In addition to mitochondrial dysfunction, alterations in lipid metabolism are another feature of AD (Mapstone et al., 2014), but their origin and relationship to APP metabolism are unclear. Among these alterations, abnormal sphingolipid metabolism has been reported in AD tissues (van Echten-Deckert and Walter, 2012). Specifically, there is an upregulation of de novo ceramide synthesis (Grimm et al., 2011), and an increase in sphingomyelinase activity (SMase), which catabolyzes sphingomyelin (SM) into ceramide (Filippov et al., 2012). These alterations act synergistically to increase ceramide content in AD brains (Filippov et al., 2012).

As these metabolic alterations occur early in AD, they cannot be explained by the accumulation of plaques or tangles. Moreover, unsuccessful efforts directed towards modifying Aβ production as a treatment for AD (Castello et al., 2014) have raised the possibility that other aspects of APP cleavage may be contributing to these metabolic changes. In this regard, increased levels of the C99 fragment have also been shown to contribute to AD pathogenesis (Lauritzen et al., 2012; Lee et al., 2006), suggesting a role for C99 in the early stages of pathogenesis. This processing of APP occurs in lipid raft domains (LRs) (Cordy et al., 2006), which are membrane regions enriched in cholesterol and sphingolipids (Pike, 2009). While most of these domains are found in the plasma membrane, intracellular LRs have also been described (Browman et al., 2006). One of these intracellular lipid raft-like domains is called mitochondria-associated ER membranes (MAM), a functional subdomain of the ER located in close apposition to mitochondria that regulates key cellular metabolic functions (Vance, 2014). It has been shown previously that presenilins and γ-secretase activity localize to MAM (Area-Gomez et al., 2009; Newman et al., 2014; Schreiner et al., 2015). Moreover, MAM functionality (Area-Gomez et al., 2012) and ER-mitochondrial apposition are increased in AD (Area-Gomez et al., 2012; Hedskog et al., 2013).

Described herein are results that show that unprocessed C99 accumulates at the MAM in AD. This MAM-localized C99 is associated with the activation of sphingolipid synthesis and hydrolysis, and with the subsequent increase in ceramide levels observed in AD, particularly in mitochondrial membranes. Finally, it is shown that these higher levels of ceramide on mitochondria cause reduced respiratory chain activity. Given these results, without being bound by theory, a critical component of AD pathogenesis appears to be mediated by C99 toxicity through its effects on MAM and mitochondria.

Results

C99 Inhibits Mitochondrial Respiration in Presenilin-Mutant Cells

Current hypotheses regarding mitochondrial dysfunction in AD propose that it is the consequence of the accumulation of Aβ in mitochondria (Manczak et al., 2006), but the mechanism is unclear. To address the reasons for mitochondrial dysfunction in AD, mitochondrial respiration was measured in fibroblasts from FAD patients with pathogenic mutations in PS1 (M146L and A246E) and in age-matched controls, as well as in mitochondria from the brain of a knock-in (KI) mouse model expressing the M146V mutation in PS1 (PS-KI$^{M146V}$) (Guo et al., 1999). A reduced respiration in FAD patient cells was observed (FIGS. 4A and 20A), and in mitochondria isolated from PS-KI$^{M146V}$ mouse brain (FIG. 20B). To understand the consequences of presenilin mutations and the effect of amyloid on mitochondrial function in AD, respiration in mouse embryonic fibroblasts (MEFs) ablated for both Psen1 and Psen2 (PS-DKO)(Herreman et al., 2000) were measured. As above, decreased respiration in the PS-DKO cells was found compared to controls (FIG. 4B). Additionally, measurements of oxygen consumption rate, both in isolated mitochondria and in permeabilized cultures of PS-DKO cells, showed clear defects in respiration (FIG. 20D). Importantly, the decrease in respiration was not due to reductions in mitochondrial content or biogenesis (FIGS. 20C, 20F, 20G, and 20I). Together, these results suggest that, from the mitochondrial perspective, mutations in and ablation of presenilins behave similarly, causing decreases in mitochondrial function that do not depend on Aβ production.

To determine whether mutations in presenilins affect mitochondria via its role as the catalytic core of γ-secretase, mitochondrial respiration in human neuroblastoma SH-SY5Y cells treated with 10 μM of the γ-secretase inhibitor DAPT was measured. This inhibition caused a significant reduction in respiration compared to that in untreated cells (FIG. 11B), without altering mitochondrial content or biogenesis (FIGS. 20F, 20I, and 20J). This result implies that the catalytic activity of presenilins is necessary to maintain respiratory function. In addition, given that neither PS-DKO nor DAPT-treated cells produce Aβ, the results described herein raise the possibility that the mitochondrial deficits in AD are independent of Aβ production. Equally possible, alterations in full-length APP (FL-APP) or in any of its cleavage products may play a role in regulating mitochondrial respiration. To test this, oxygen consumption was measured in cells in which APP and its paralog APLP2 were knocked out (APP-DKO) (Zhang et al., 2013). Contrary to what was found in presenilin-mutant cells, elimination of APP and APLP2 had no detrimental effects on respiration (FIG. 11F). Surprisingly, the oxygen consumption rate in permeabilized APP-DKO cells was slightly increased compared to that in controls (FIGS. 11D and 20E).

Considering that PS-DKO cells and APP-DKO cells both lack Aβ and AICD, our results suggest that the difference in mitochondrial function between these two cell models was due to the presence or absence of FL-APP or its cleavage products, C99 and C83. Therefore, respiration was measured in PS-DKO cells treated with BACE1 inhibitor IV (BI) (FIG. 4C) and with an α-secretase inhibitor (TAPI-1) (FIG. 20H) to abrogate the production of C99 and/or C83, respectively. As controls, physiological concentrations of Aβ and oligomers of Aβ42 were added back (FIGS. 20K, 20L and 20M). Remarkably, only BI treatment rescued the respiration defects, both in PS-DKO cells (FIG. 4C) and in FAD fibroblasts (FIG. 20N), suggesting that the accumulation of C99, rather than the levels of Aβ, plays a role in the mitochondrial dysfunction seen in AD. Supporting this, addition of Aβ to APP-DKO cells had little effect on respiration (FIG. 20M), whereas APP-DKO cells expressing C99 suffered a significant decrease in respiration, which was accentuated by adding DAPT (FIG. 11F), without changes in the content of mitochondria (FIG. 20O).

C99 Localizes to MAM

APP and its cleavage products have been shown to colocalize with almost every membranous compartment in the cell, including mitochondria. Thus, it is possible that C99, as previously suggested for Aβ (Casley et al., 2002), accumulates on mitochondrial membranes, disrupting its regulation.

Figure 21A:
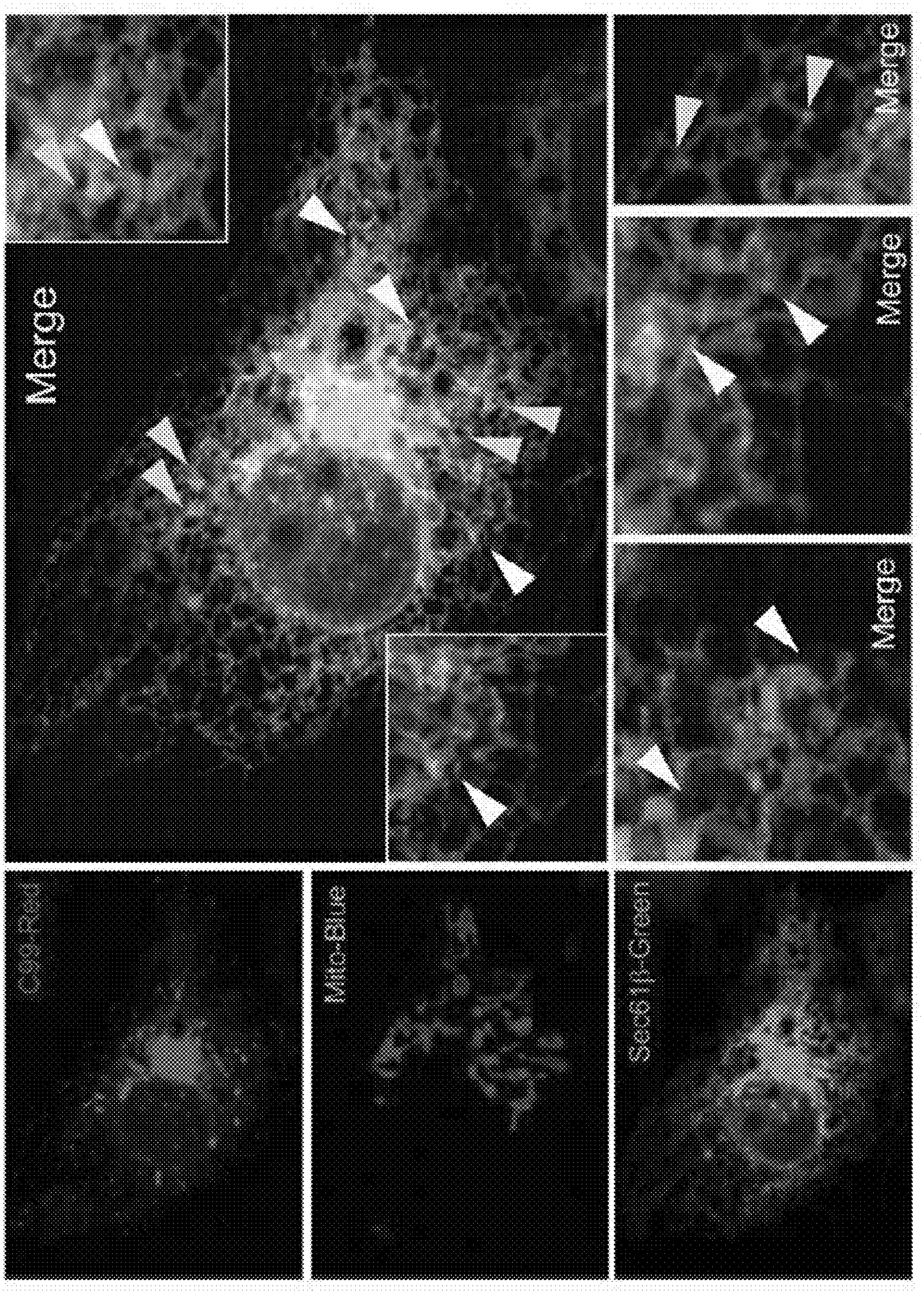

To test this, the spatial relationship between mitochondria and C99 was analyzed, by transfecting wild-type (WT) MEFs and COS-7 cells with fluorescently-tagged C99, and with plasmids expressing mitochondrial and ER markers. Confocal microscopy analysis revealed that C99 colocalized with mitochondria, but only in the perinuclear area. In fact, co-localization of C99 and mitochondria occurred only in regions where both ER and mitochondria were present (FIGS. 15A and 21A), suggesting that, like presenilins (Area-Gomez et al., 2009), C99 localizes to areas of the ER apposed to mitochondria, i.e. MAM (Area-Gomez et al., 2009) and is consistent with the fact that γ-secretase activity is enriched in MAM (Area-Gomez et al., 2009; Schreiner et al., 2015).

To explore further the localization of C99 and C83, subcellular fractions were isolated from brain samples (FIG. 21B) (Area-Gomez, 2014) and analyzed by western blot (which was also validated in an identical fractionation of mouse liver [FIG. 21C]), using specific markers for each compartment (FIG. 15B). It was found that APP CTF fragments were indeed enriched significantly in MAM regions of the ER. In addition, subcellular fractions from SH-SH5Y cells treated with DAPT (to prevent cleavage of C99 and C83), and with DAPT and TAPI-1 (to analyze C99 localization in the absence of C83) showed that while C83 was present in all fractions, C99 was located preferentially in MAM (FIG. 21D).

To eliminate the possibility of cross-contamination with other compartments crude membranes were further purified from mouse brain through continuous sucrose gradients (FIG. 21E) and examined the distribution of C83 and C99 compared to markers for other compartments (FIG. 7A). FL-APP and BACE1 co-migrated partially with a marker for endosomes (Rab7), but not with lysosomal, ER-intermediate, or MAM markers (FIG. 7A). In agreement with other reports (Das et al., 2016; Haass et al., 2012), the majority of APP-CTFs co-migrated with endosomal and lysosomal markers, whereas PS1 co-migrated with MAM markers such as FACL4 (Area-Gomez et al., 2009; Newman et al., 2014; Schreiner et al., 2015). The difficulty in seeing APP-CTFs and PS1 together was probably due to the rapid cleavage of CTFs by γ-secretase once both are in the same compartment. Thus, to circumvent this rapid cleavage, the same analysis was repeated using PS-DKO cells (Herreman et al., 2000), in which APP-CTFs are not cleaved, and accumulate (FIG. 20G). Interestingly, western blot analysis showed that, when unprocessed, a significant fraction of C99 co-migrated with MAM markers (FIG. 1B).

Figure 15C:
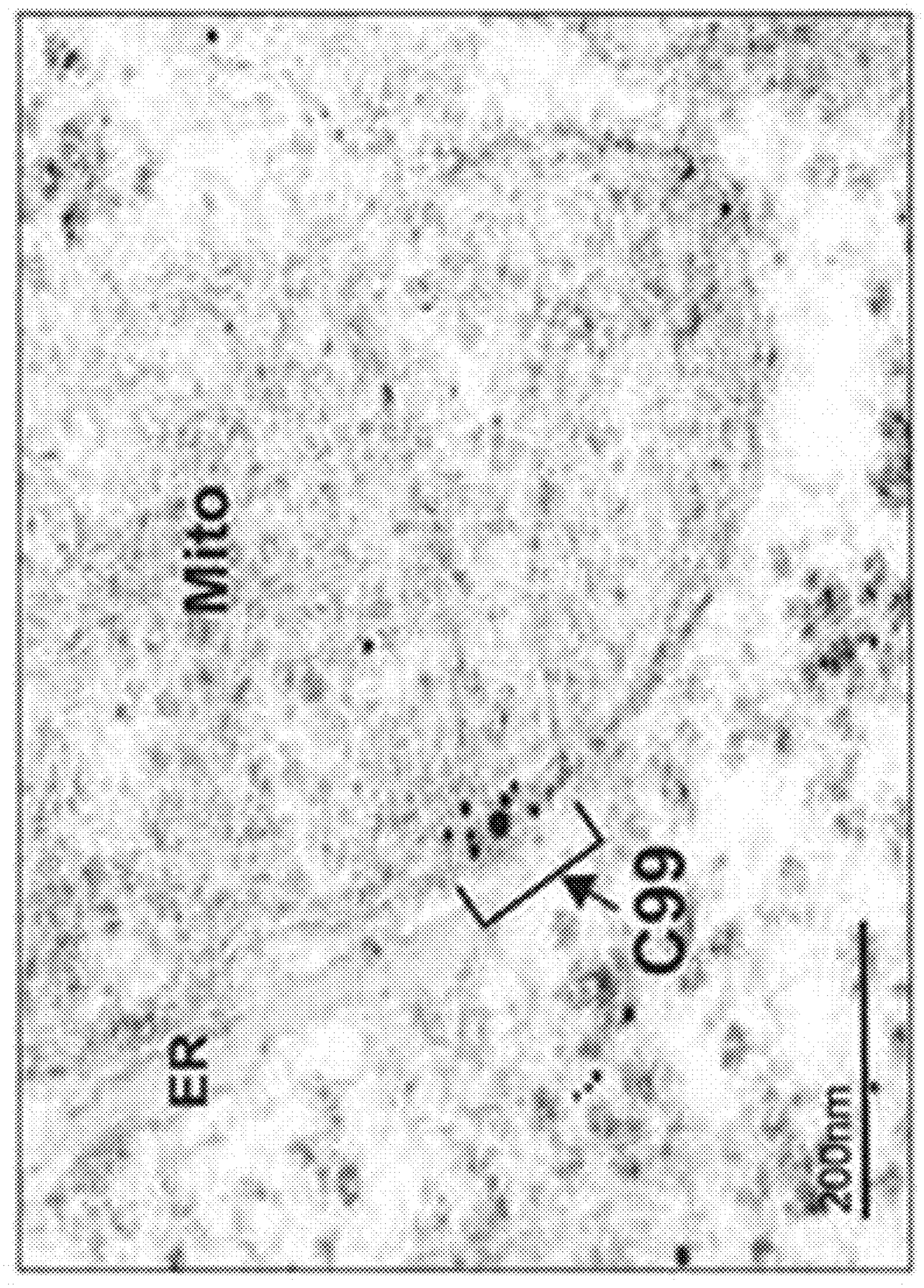

To corroborate this result the localization of unprocessed C99 in PS-DKO cells it was analyzed by immunogold electron microscopy (iEM), using antibodies against C-terminal regions of APP. In agreement with the confocal and western blot analysis, iEM images indicated that, when uncleaved, C99 accumulates in MAM regions of the ER (FIGS. 15C and 21F).

Figure 21I:
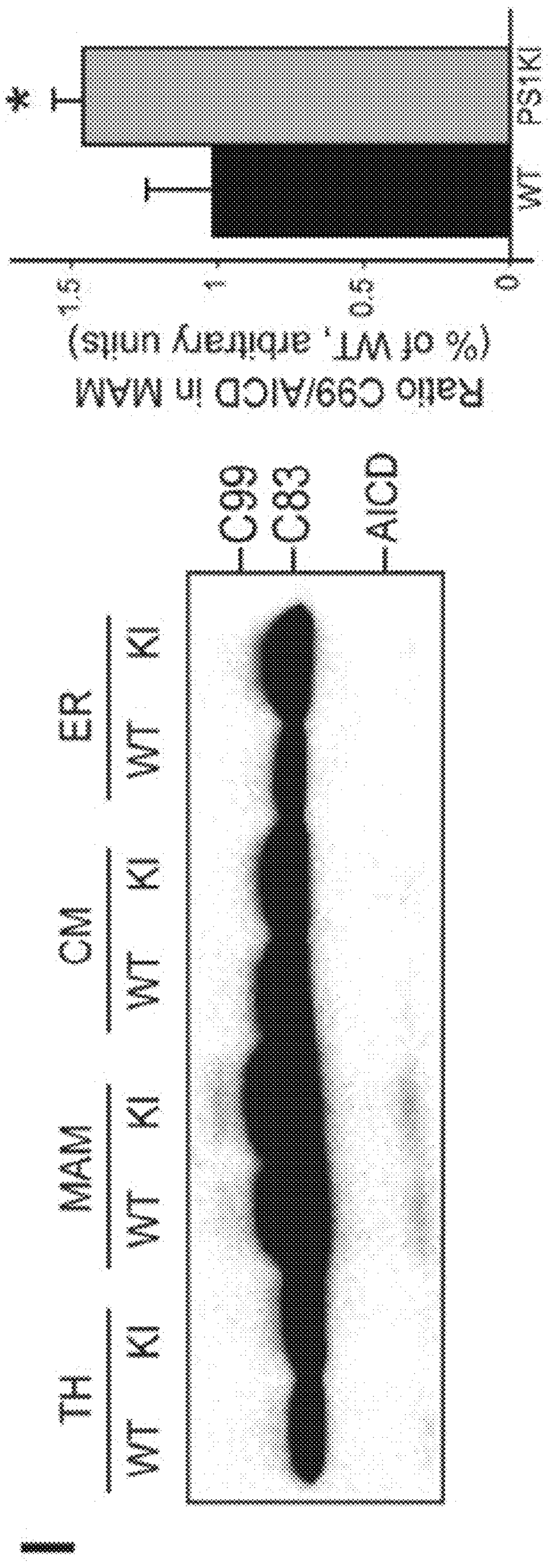

Next, it was asked if the accumulation of C99 in the MAM also occurred in the context of AD, as tissues from AD patients and animal models show increases in this fragment (Holsinger et al., 2002). To test this, C99 levels were measured by western blot in homogenates from embryonic cortical neurons from WT and PS-KI$^{M146V}$ mouse brain (Guo et al., 1999) (FIG. 21G), as well as in cells from AD patients and controls (FIG. 21H). Notably, there was more C99 in the homogenates of mutant neurons and cells from AD patients and than in WT (FIGS. 21G and 21H), similar to previous findings in other AD pateints and in FAD mice (McPhie et al., 1997; Rockenstein et al., 2005; Yang et al., 2003). In addition, western blot analysis of subcellular fractions isolated from WT and PS-KI$^{M146V}$ mouse brain also showed an increase in the levels of C99, in the mutant samples, and especially in the MAM fractions, than in that of controls (FIG. 21I), while the relative concentration of AICD was not significantly changed (FIG. 21I).

Taken together, our results suggest that C99, after being produced in endocytic compartments (Das et al., 2016) is targeted to MAM, via an as-yet unknown mechanism, to be rapidly cleaved by γ-secretase. Moreover, both pathogenic mutations in PS1 and reductions in γ-secretase activity cause an accumulation of this fragment in this region of the ER that is in close apposition to mitochondria.

Accumulated C99 Increases MAM Function and ER-Mitochondrial Apposition

Given that reduced γ-secretase activity causes an accumulation of C99 at the MAM, it was asked if elevated C99 could be the cause of the increased ER-mitochondria apposition and MAM upregulation seen in AD (Area-Gomez et al., 2012). To assess apposition, control and PS-DKO cells were transfected with markers of ER and mitochondria, and their co-localization measured (Area-Gomez et al., 2012; de Brito and Scorrano, 2008) in the absence or presence of BI to prevent the generation of C99. Remarkably, incubation with BI rescued the upregulation of ER-mitochondria apposition in mutant cells (FIGS. 16A and 16B).

Figure 22:
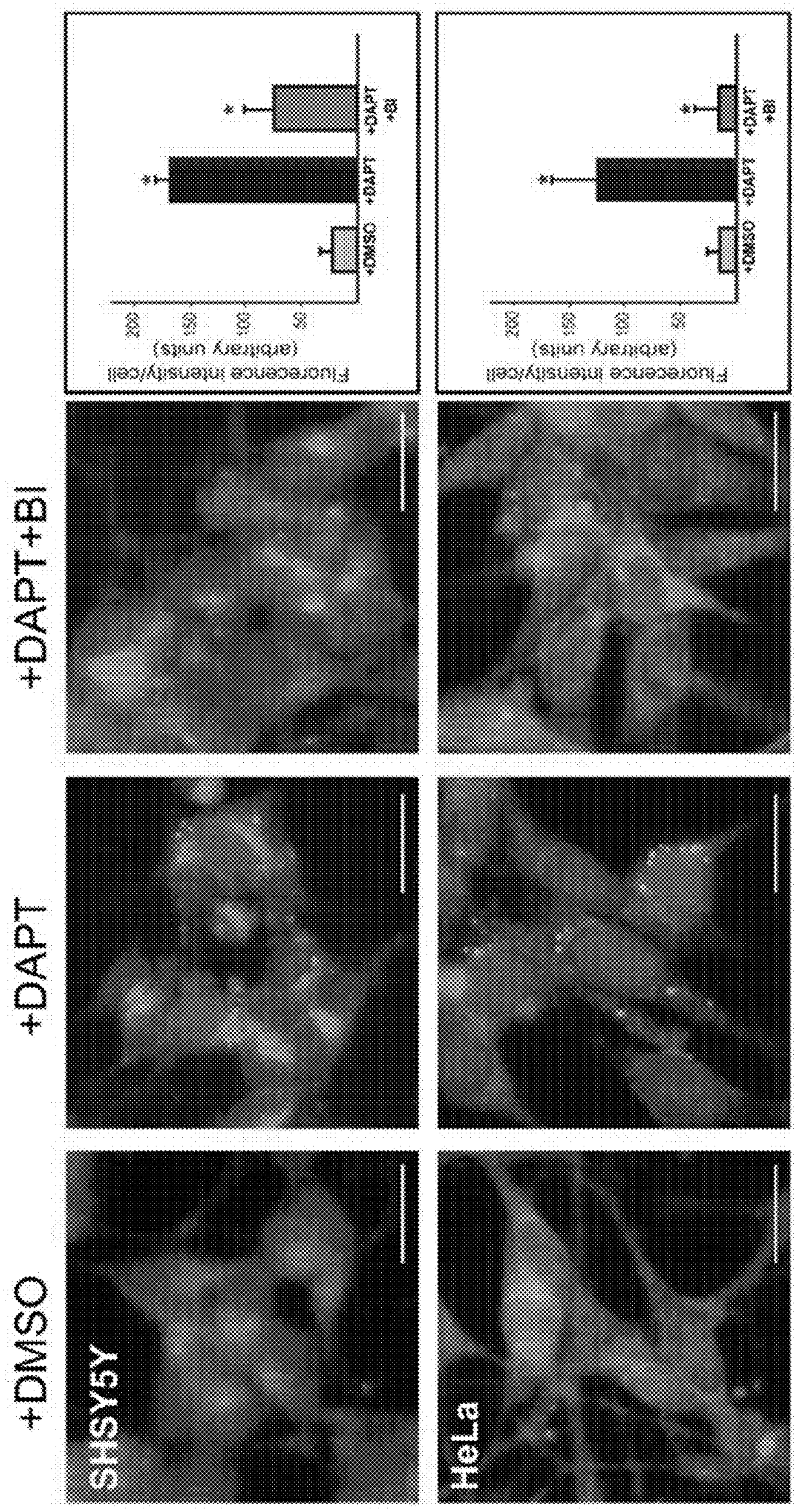
FIG. 22 shows cholesteryl ester and lipid droplet formation in γ-secretase-deficient cells. Staining of SH-SY5Y cells (upper panels) or HeLa cells (lower panels) treated with DAPT (to increase C99 accumulation) or with DAPT+BI (to inhibit C99 production) (size bar=20 μM). Quantitation of lipid droplets is shown at right (all values represent the average of n=3 independent experiments±SD; * p<0.01).

To assess the effect of C99 on MAM functionality, the conversion of cholesterol to cholesteryl esters by ACAT1, a MAM-resident enzyme (Area-Gomez et al., 2012) was measured, and the accumulation of newly-synthesized cholesteryl esters into lipid droplets (LDs)(Area-Gomez et al., 2012) was monitored. Treatment with BI reduced the incorporation of cholesterol into cholesteryl esters (FIG. 8A) and reduced the number of LDs in PS-DKO cells, in AD patient fibroblasts (FIGS. 2A-B), and in PS1-KI$^{M146V}$ mouse astrocytes and cortical neurons (FIG. 8B). LDs also accumulated in SH-SY5Y and HeLa cells treated with DAPT alone, which was reversed in cells treated with DAPT+BI (FIG. 22). Taken together, these results show that the accumulation of C99 in the MAM induces both the physical and functional enhancement of ER-mitochondria connections.

Sphingolipid Metabolism is Perturbed in AD-Mutant Cells

Given that MAM is a lipid raft (Area-Gomez et al., 2012), it was speculated that C99 regulates MAM and ER-mitochondrial connectivity through changes in MAM lipid composition (Simons and Vaz, 2004). Lipidomic analyses of total homogenates, mitochondrial fractions and isolated MAM from PS-DKO MEFs and controls was therefore performed. A significant increase in ceramide was found (FIG. 17A) and a parallel decrease in sphingomyelin in mutant cells (FIG. 17B), which was more pronounced in mitochondrial (FIGS. 17A and 17B) and MAM (FIG. 17C) fractions than in total homogenates. Moreover, there was an inverse relationship between the amounts of individual sphingomyelin species and those of the corresponding ceramide species (FIG. 9A). This latter result suggested an increase in the hydrolysis of sphingomyelin by sphingomyelinases (SMases), and subsequent de novo synthesis of SM to replace its loss. In agreement with this idea, PS-DKO cells showed a significantly higher synthesis of both ceramide and sphingomyelin (FIG. 17D). In addition, acidic (aSMase) and neutral (nSMase) SMase activities were increased in PS-DKO cells (FIG. 17E), with a more dramatic upregulation of nSMase activity correlating with increased expression of neutral sphingomyelinase 2 (nSMase2; gene SMPD3) (FIG. 9B). Increases in both acid and neutral SMase activities were also observed in PS1-KI$^{M146V}$ mouse brain (FIG. 9C). Likewise, the increase in SMase activity was replicated in SH-SY5Y cells by inhibiting γ-secretase activity (FIG. 9D), suggesting that the effects of mutated presenilins on sphingolipid metabolism occur via their roles as proteases in γ-secretase.

Because it was unclear whether these effects were direct or were mediated by APP and/or its cleavage products, SMase activity in APP-DKO cells was measured. Contrary to what was found in PS-DKO and DAPT-treated cells, APP-DKO cells showed significant decreases in both sphingolipid synthesis (FIG. 9E) and SMase activities (FIG. 9F).

As mentioned previously, both PS-DKO and APP-DKO cells lack Aβ and AICD. Therefore, any difference in sphingolipid regulation between the two cell types must be due to the presence or absence of FL-APP and/or C88 and C99. Therefore, SMases were measured in PS-DKO cells treated with α- and γ-secretase inhibitors to test the effect of C83 and C99, respectively, as well as in PS-DKO cells in which Aβ and AICD were added back (FIG. 9G). Interestingly, only the inhibition of C99 production (by BI) resulted in an attenuation of sphingolipid turnover (FIG. 17E). These results indicate that it is unprocessed C99 that causes the upregulation of sphingolipid metabolism, resulting in the previously described increases in ceramide in AD (Filippov et al., 2012). However, they did not clarify why ceramide is elevated specifically in MAM and mitochondrial membranes.

MAM Participates in the Regulation of Sphingolipid Metabolism

Previous reports have suggested that MAM is involved in regulating sphingolipid metabolism, affecting mitochondrial activity (Ardail et al., 2003). In fact, mitochondria are reported to contain ceramide, probably generated at MAM (Kogot-Levin and Saada, 2014). Taking this and our data into account, it was hypothesized that an increase in ceramide synthesis and in SMase activity at ER-mitochondria connections could explain the increased ceramide in mitochondrial membranes in AD.

Figure 18C:
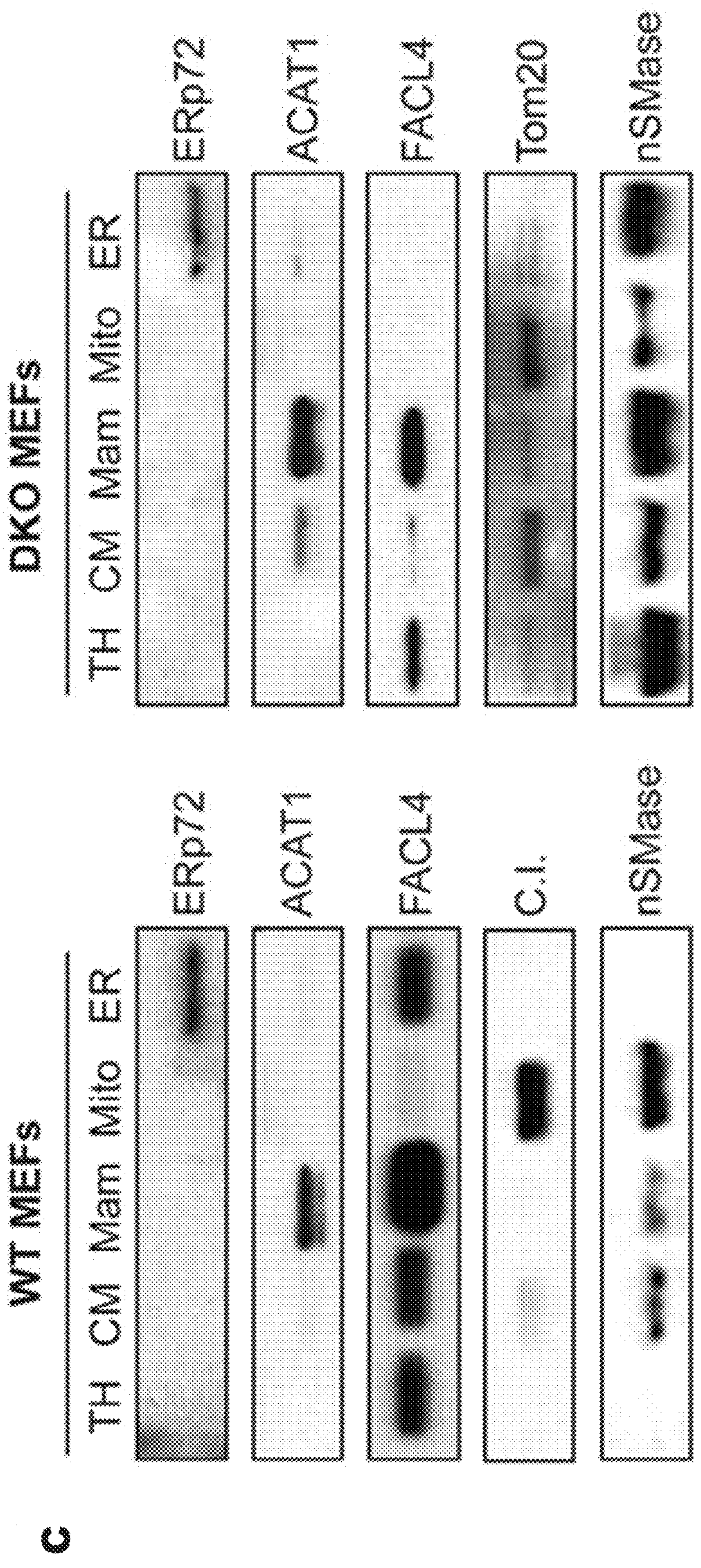

To address this, ceramide synthesis and SMase activity was analyzed in vitro, using subcellular fractions from WT and PS-DKO cells. The results indicate that MAM indeed participates in regulating sphingolipid metabolism (FIGS. 18A-B and 10A). Moreover, SMase activities were significantly upregulated in subcellular fractions from PS-DKO cells compared to controls (FIGS. 18A-B), as well as in MAM from PS1-KI$^{M146V}$ mouse brain (FIG. 10E). In agreement with these results, western blot analysis revealed a remarkable increase in the localization of nSMase to MAM in mutant cells compared to WT (FIG. 18B), suggesting higher recruitment of SMase to these ER-mitochondria contacts.

To explore this further, PS-DKO and control cells were incubated with a fluorescent sphingomyelin (FL-SM) and its localization and conversion to ceramide in mitochondrial membranes was analyzed by thin-layer chromatography (TLC). Presenilin-mutant cells showed a substantial decrease in FL-SM intensity (FIG. 9H), which was paralleled by an increase in ceramide (FIG. 9H), implying that upregulated SMase activity may be responsible for this inverse behavior. Remarkably, the elevated deposition of ceramide at mitochondria disappeared when mutant cells were treated with BI (FIG. 9H). These data suggest that the effect of BACE1 inhibition in enhancing mitochondrial respiration (FIGS. 4C and 20N) may occur via the attenuation of sphingolipid metabolism in mutant cells.

Figure 23A:
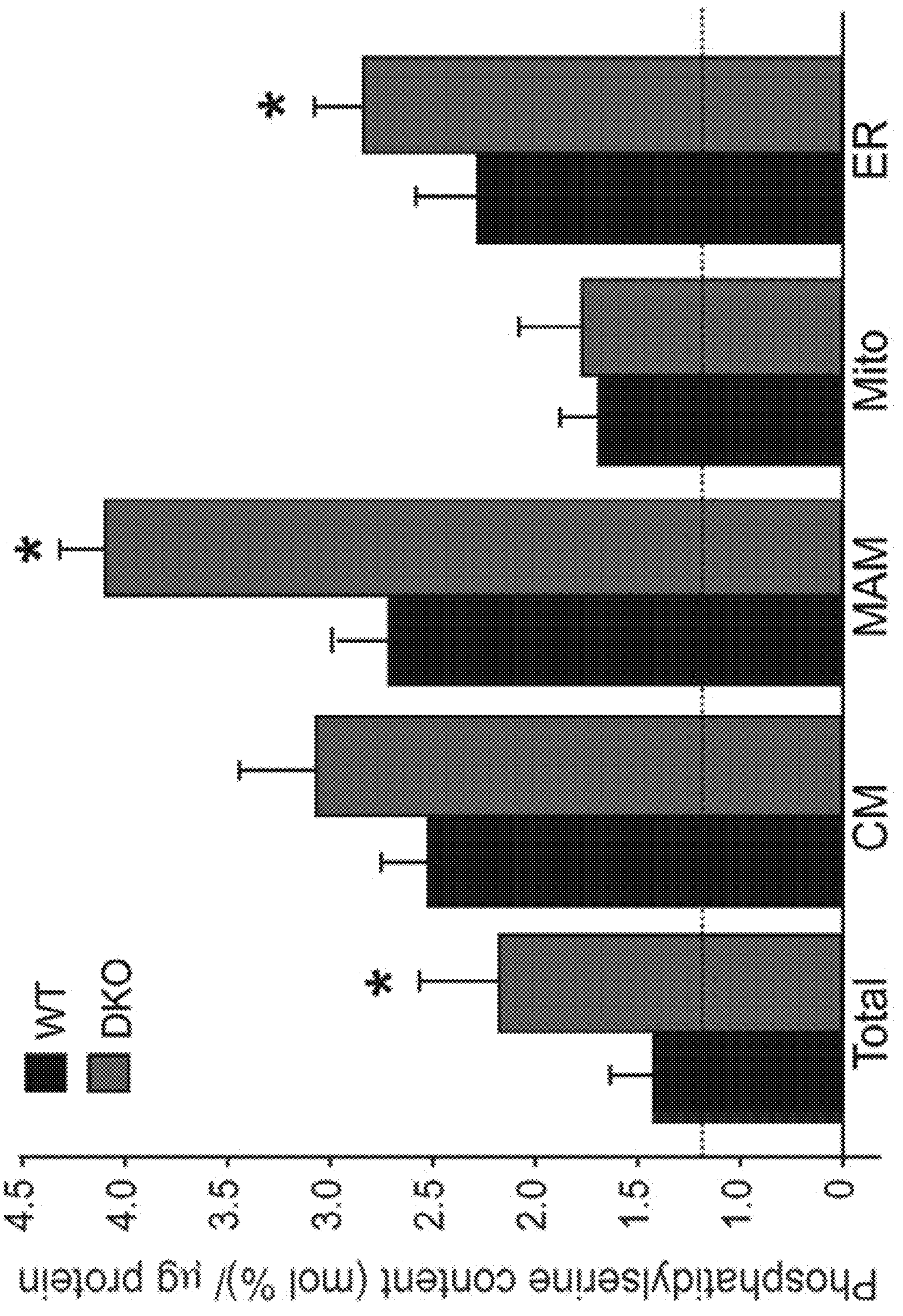

Why is there an increased recruitment of nSMase to these ER regions in PS-mutant cells? It is well known that SMase activity is modulated by membrane characteristics and lipid composition (De Tullio et al., 2007). Notably, SMase activity is higher in lipid raft-like domains, such as MAM, where liquid ordered and disordered phases coexist (Silva et al., 2009). In addition, nSMase shows increased affinity for membranes enriched in anionic phopholipids (Wu et al., 2011). In particular, the activity of nSMase2 (gene SPMD3) is stimulated upon its binding to phosphatidylserine (PtdSer) (Wu et al., 2011). To see whether elevated PtdSer might be behind the increased recruitment of nSMase activity to MAM in mutant cells, the content of PtdSer in WT and PS-DKO homogenates and in subcellular fractions was analyzed. In agreement with this idea, a significant increase in the amount of PtdSer in PS-DKO membranes was found, which was most pronounced in the MAM domains of the ER (FIGS. 23A-D). This result also supports the idea that increases in PtdSer due to C99-mediated upregulation of MAM is driving the increased SMase activity. Consistent with this proposed mechanism, inhibition of C99 production reduced the PtdSer content of PS-DKO membranes to control levels (FIG. 23B), while at the same time reversing the alterations in both sphingomyelin (FIG. 23C) and ceramide (FIG. 23D).

Taken together, it is concluded that the accumulation of C99 in MAM upregulates both the synthesis and catabolism of sphingomyelin in presenilin-deficient cells, likely accounting for the increased ceramide in mitochondrial membranes (FIG. 17A) via ER-mito connections.

Mitochondrial Dysfunction in AD is Caused by Upregulated Sphingolipid Turnover

The detrimental effects of ceramide on mitochondrial functionality have been shown extensively (Kogot-Levin and Saada, 2014). Thus, it was speculated that the upregulation of SM turnover at MAM and the subsequent increase in ceramide could be the underlying cause of the respiratory deficits seen in AD (Du et al., 2010; Swerdlow et al., 2014). To test this idea, respiration was measured in PS-DKO mutant cells treated with 5 μM myriocin, a specific inhibitor of serine-palmitoyltransferase, the first step in the de novo pathway to synthesize sphingolipids, including ceramide. In agreement with the hypothesis, inhibition of sphingolipid synthesis rescued the bioenergetic defect in these cells (FIG. 19A).

Ceramide has been shown to provoke changes in mitochondrial lipid composition, altering its membrane potential and permeability (Kogot-Levin and Saada, 2014). Notably, the lipid composition of mitochondrial membranes is crucial for the stabilization and assembly of mitochondrial respiratory complexes into supercomplexes (also called respirasomes) necessary for optimal respiratory chain function (Acin-Perez and Enriquez, 2014). Therefore, it is possible that ceramide interferes with bioenergetics by destabilizing or preventing supercomplex assembly. To assess this, blue-native gel electrophoresis (Acin-Perez et al., 2008) was used to examine the activity (FIGS. 19B and 19C) and assembly status (FIGS. 24A-D) of supercomplexes in mitochondria from WT and PS-DKO cells, from DAPT-treated WT cells, and from PS-DKO cells incubated with BI and myriocin (FIG. 19B). Measurements by in-gel staining of the activities of respiratory chain complexes I and IV (FIGS. 19B and 19C) and western blotting to detect subunits of complexes I and III from PS-DKO and DAPT-treated WT cells (FIGS. 24A-D) showed a decrease in the activity of supercomplexes I+III+IV, I+III and III+IV, which could be rescued after treatment with BI and myriocin (FIGS. 19D and 19E).

To corroborate these results in vivo, mitochondrial respiration and supercomplex activity was analyzed in mitochondria isolated from brain tissue from PS1-KI$^{M146V}$ mice at various ages (FIG. 12). Interestingly, while MAM defects were already present in fetal cortical neurons (FIG. 8B), decreases in mitochondrial respiration became significant only after 3 months of age (FIG. 12). In agreement with previous results, this bioenergetic defect correlated with a significant decrease in supercomplex activity in mutant samples compared to controls (FIGS. 25A and 25B).

Taken together, these results indicate that the bioenergetic defects in AD are likely to be the consequence of upregulated sphingolipid turnover and increased ceramide content triggered by the accumulation of C99 at the MAM. This elevation in ceramide levels alters mitochondrial membrane properties, hindering the assembly and activity of respiratory supercomplexes. Moreover, these data suggest that while mitochondrial dysfunction is an early and significant defect in AD, it is not a primary insult in the pathogenesis of the disease, but rather is a consequence of MAM dysfunction.

Discussion

In previous reports it has been shown that γ-secretase activity is enriched in MAM (Area-Gomez et al., 2009) and that alterations in its activity result in the upregulation of MAM function and in increased ER-mitochondria apposition (Area-Gomez et al., 2012). Described herein are results that show that the γ-secretase substrate C99 is also enriched in MAM. Thus, both the γ-secretase enzyme activity and its direct substrate are located in the same compartment, where the former can cleave the latter. Moreover, chemical and genetic alterations of γ-secretase activity provoke an accumulation of this APP processing fragment in ER-MAM regions that, in turn, causes deregulation of sphingolipid homeostasis, MAM deficits, and downstream mitochondrial dysfunction.

These results support a model in which, in addition to Aβ, C99 accumulation in AD plays an early role in AD pathogenesis. In fact, increases in C99 were already shown to contribute to the pathogenesis of the disease (Lauritzen et al., 2012; Saito et al., 2011), including endosomal dysfunction (Jiang et al., 2010), hippocampal degeneration (Lauritzen et al., 2012), and altered Tau proteostasis (Moore et al., 2015). In addition, elevations in C99 are toxic to neurons (Neve et al., 1996), correlating with symptoms of the disease (Rockenstein et al., 2005; Tamayev et al., 2012). Importantly, it is noted that although much of the data described herein were obtained using FAD models and cells from FAD patients containing mutations in presenilins, alterations in γ-secretase activity and increased levels of C99 have also been detected in sporadic AD patients as well (Fukumoto et al., 2002; Li et al., 2004; Pera et al., 2013; Yang et al., 2003).

It is proposed that, while the majority of C99 resides in endosomes, C99 can traffic to MAM regions in the ER, where it is rapidly cleaved by γ-secretase to produce Aβ and AICD (Area-Gomez et al., 2009; Schreiner et al., 2015). It is noted that although the mechanism of C99 translocation to ER-MAM is unknown, recent work has elegantly demonstrated the existence of ER-endosome contacts (Rowland et al., 2014) (FIG. 22A) where lipid and protein exchange may occur. Thus, it is possible that C99 is delivered through a similar mechanism to ER where it regulates the interaction with mitochondria. Furthermore, the localization of C99 at MAM clarifies why C99, an ER-localized protein concentrated in lipid rafts (Matsumura et al., 2014), is also detected in mitochondria (Devi and Ohno, 2012). Similarly, since C99 processing occurs at MAM, this could explain why Aβ has been found to colocalize with mitochondria (Hansson Petersen et al., 2008; Xie et al., 2013).

Described herein are results that show that chemical or genetic alteration of γ-secretase results in the accumulation of unprocessed C99 in MAM. This, in turn, provokes the upregulation of sphingolipid turnover via increased expression and recruitment of SMase activity in MAM. These results help clarify a number of previous observations. First, as MAM contains γ-secretase and SMase activities, the data described herein help explain why changes in APP processing can induce alterations in sphingolipid regulation (Filippov et al., 2012; Lee et al., 2014). Second, upregulation of SMase and the resulting increase in ceramide are known to alter the size and composition of lipid raft domains (Dinkla et al., 2012), such as MAM. Therefore, the accumulation of C99 in MAM may explain the upregulation of ER-mitochondria connections and MAM functionality seen in AD (Area-Gomez et al., 2012; Hedskog et al., 2013). These findings have mechanistic implications. Specifically, one of the MAM functions that is increased in AD is the synthesis of PtdSer by phosphatidylserine synthases 1 and 2 (PtdSS1/2) (Area-Gomez et al., 2012; Vance, 2014), resulting in higher levels of this phospholipid in MAM and other membranes in AD cells and tissues. Considering the affinity of nSMase for PtdSer (Wu et al., 2011), it is believed that nSMase activation is due, at least in part, to the upregulation of PTDSS1/2 in MAM, triggered by the accumulation of C99. The details of this mechanism will require further investigation. Finally, given the detrimental effect of ceramide on mitochondrial supercomplex assembly and respiratory chain activity (Zigdon et al., 2013), it is concluded that its accumulation is likely to be a primary cause of mitochondrial dysfunction in AD.

This last conclusion disagrees with proposals that the accumulation of Aβ42 oligomers in mitochondria triggers the mitochondrial defects seen in AD (Manczak et al., 2006). Rather, the results described herein show that PS-DKO and DAPT-treated cells, in which Aβ production is inhibited, can nevertheless recapitulate the mitochondrial deficits seen in AD. This finding suggests that mitochondrial deficiencies are due to increased levels of C99 rather than to elevated production of longer Aβ species, since bioenergetic deficiency can occur in the absence of Aβ. It is believed that the discrepancy between the results described herein and those of others showing reductions in mitochondrial respiration after incubation with Aβ (Casley et al., 2002) is due mainly to the use of unphysiologically high concentrations of this peptide (Casley et al., 2002). Thus, it is proposed that MAM and mitochondrial alterations are caused by an increased ratio of C99:Aβ, rather than by an increased ratio of Aβ42:Aβ40. In agreement with this, the accumulation in AD of C99 in mitochondria has been described before, correlating with mitochondrial respiratory defects that could be rescued by partial deletion of BACE1 (Devi and Ohno, 2012). Finally, the results described herein linking C99, rather than higher levels of Aβ42, to mitochondrial dysfunction help explain how mitochondrial alterations can occur early in AD pathogenesis (Balietti et al., 2013), preceding the appearance of Aβ-containing plaques (Yao et al., 2009).

In summary, the data described herein demonstrate that unprocessed MAM-localized C99 is a fundamental cause of mitochondrial dysfunction in AD, mediated by the loss of sphingolipid homeostasis at ER-mitochondria connections. Equally important, while the toxicity of Aβ is undeniable, our work supports a role for C99 accumulation (Rockenstein et al., 2005) and MAM deregulation in the pathogenesis of the disease (Schon and Area-Gomez, 2010, 2013), thus providing a new framework for understanding the link between alterations in APP processing and lipid homeostasis as seminal effectors in AD pathogenesis.

Materials and Methods

Cells, Animals, and Reagents

AD and control cell lines were obtained from the Coriell Institute for Medical Research (Camden, N.J.). SH-SY5Y, COS-7, and CCL131 cells were obtained from the American Type Culture Collection. Other PS1-mutant FAD cells were the kind gift of Dr. Gary E. Gibson (Comell University). WT, PS1-KO, PS2-KO, and PS1/2-DKO (called PS-DKO) mouse MEFs were provided by Dr. Bart De Strooper (University of Leuven). APP/APLP2-KO (called APP-DKO) and WT mice were the kind gift of Dr. Huaxi Xu (Sanford Burnham Institute). PS1-KI$^{M146V}$ knock-in mice were generated as described (Guo et al., 1999). All experiments were performed according to a protocol approved by the Institutional Animal Care and Use Committee of the Columbia University Medical Center and were consistent with the National Institutes of Health Guide for the Care and Use of Laboratory Animals. Mice were housed and bred according to international standard conditions, with a 12-h light, 12-h dark cycle, and sacrificed at 3, 5, 7, 8, and 12 months of age. Brain was removed and homogenized, for Western blot and Seahorse analysis. All the experiments were performed on at least three mice per group.

We used antibodies to APP C-terminal (Sigma; A8717, polyclonal), APP-C99 (Covance; SIG-39320-200 [6E10], monoclonal), the α-subunit of mitochondrial ATP synthase (complex V) (Invitrogen; 459240), BACE1 (Cell Signaling; D10E5), complex I subunit NDUFA9 (Abcam; ab14713), complex III subunit core-1-ubiquinol-cytochrome c reductase (Abcam; ab110252), OxPhos complex IV subunit IV (COX IV) (Abcam; ab14744), Ergic53/p58 (Sigma; E1031), Erlin-2 (Cell Signaling; #2959), Lamp2 (NOVUS biologicals; NBP1-71692), Presenilin 1 (Calbiochem; PC267; NOVUS biologicals; EP1998Y), Rab5a (NOVUS Biologicals; NBP1-58880), Rab7a (NOVUS Biologicals; NBP1-87174), SMPD2/nSMAseI (Thermo Scientific; PA5-24614), TOM20 (Santa Cruz; sc-11415), β-tubulin (Sigma; T4026), and VDAC1 (Abcam; 34726). Thin layer chromatography (TLC) silica plates were from EMD Biosciences (5748-7). Ceramide (22244), sphingomyelin (S0756), cholesteryl palmitate (C6072), cholesteryl oleate (C9253), lipid markers for TLC (P3817), α-secretase inhibitor TAPI-1 (SML0739), cytochrome C from horse heart (C2506), 3,3'-diaminobenzidine tetrahydrochloride hydrate (D5637), GI254023X (SML0789), β-secretase inhibitor IV (Calbiochem; 565788), γ-secretase inhibitor DAPT (D5942), antimycin A (A8674), FCCP (carbonyl-cyanide p-(trifluoromethoxy)phenylhydrazone) (C2920), NADH Grade II, disodium salt (Roche; 10128023001), nitro blue tetrazolium (N5514-25TA1), oligomycin (04876), rotenone (R8875), serine palmitoyltransferase inhibitor myriocin (M1177) were from Sigma. Fluorescent lipids BODIPY-FL C6 ceramide complexed to BSA (N22651) and BODIPY-FL C12-sphingomyelin (D7711) were from Invitrogen. Radiolabelled $^3$H-serine and $^3$H-cholesterol were from Perkin Elmer; fatty acid-free bovine serum albumin (FAF-BSA) was from MP Biomedical (820472). Amyloid 3 peptides 40-aa and 42-aa were obtained from Biopolymer Laboratory (UCLA) and APP intracellular domain (AICD) peptide was from Genescript Corporation (Piscataway, N.J.).

Seahorse Analysis

Respirometry of cultured cells was performed using the XF24e Extracellular Flux Analyzer (Seahorse Bioscience). Oxygen consumption was measured in basal conditions (Seahorse media with 25 mM glucose and 2 mM pyruvate) and after the sequential addition of 1 μM oligomycin (Complex V inhibitor), 0.75 μM FCCP (uncoupler) and 1 μM rotenone/1 μM antimycin A (Complex I and Complex III inhibitors respectively).

For permeabilization assays, the cell culture medium was replaced by the mitochondrial assay solution (70 mM sucrose, 220 mM mannitol, 5 mM KH2PO4, 5 mM MgCl2, 2 mM HEPES, 1 mM EGTA and 0.2% fatty acid-free BSA, pH 7.4) containing 10 nM of the XF Plasma membrane permeabilizer reagent XF PMP (Seahorse Bioscience #102504-100) and pyruvate/malate (for complex I assays) or succinate/rotenone (for complex II assays). Oxygen consumption was measured at State 2, 3, 4 and uncoupling after sequential addition of 3 mM ADP, 4 μM oligomycin, 6 μM FCCP and 4.5 μM Antimycin A.

To analyze mitochondrial respiration in mouse tissues, mitochondria were isolated from WT and PS1$^{M146V}$ KI mouse brain. Mouse brains were homogenized in ~10 volumes of homogenization buffer (210 mM mannitol, 70 mM sucrose, 5 mM HEPES and 1 mM EGTA) and then centrifuged at 900×g for 10 minutes at 4° C. The remaining supernatant was centrifuged at 9000×g for 10 min at 4° C. and the resulting pellets resuspended in washing buffer (210 mM mannitol, 70 mM sucrose, 5 mM HEPES, 1 mM EGTA, and 0.5% BSA pH 7.2) and centrifuged again at 8000×g for 10 min at 4° C. The pellets, containing mitochondria, were resuspended in mitochondrial assay solution and protein was quantitated using the BCA Protein Assay kit (Thermo Scientific #23227). For complex I experiments, 8 μg of protein were added to each well and for complex II analysis 6 μg per well. Analyses in the Seahorse analyzer were performed as described in the permeabilization assays.

Culture of Primary Mouse Cortical Neurons

Cortex from four 14-day-old embryos were cut in pieces and washed in 45% glucose in PBS. After that, brain tissues were resuspended in 1 ml trypsin diluted in 45% glucose in PBS (1:1 v/v) and incubated at 37° C. for 20 min. Samples were added to 500 μl horse serum and 10 units of DNase and incubated for 10 min at room temperature until debris sank to the bottom of the tubes. The non-debris fraction was pelleted at 800×g for 10 min and resuspended in Neurobasal Medium (Life Technologies; 21103-049) supplemented with 200 mM glutamine. Cells were counted and seeded on coverslips coated with poly-omithine and laminin.

Plasmid Constructs and Transfections

Plasmids were constructed using standard methodological techniques. In brief, APP fragments AICD, and C99 were amplified from pCAX APP-695 (Young-Pearse et al., 2007), using forward primer 5'-cccgctagcctcgagATGCTGAAGAAGAAACAGTACACATCCATTC-3' (SEQ ID NO: 2 for AICD, and 5'-cccggatccATGGATGCAGAATTCCGACATGACTC-3' (SEQ ID NO: 3) for C99, with a single reverse primer 5'-cccggatccaagcttCTAGTTCTGCATCTGCTCAAAGAACTTG-3' (SEQ ID NO: 4) for both; restriction sites for subcloning are underlined and the start/stop codons are in bold. The PCR products were cut with XhoI+BamHI (for AICD) or with BamHI (for C99) and subcloned into the corresponding sites in pGFP-N3 (Clontech). All plasmids were verified by restriction analysis and sequencing. Cells were transfected using LIPO- FECTAMINE Transfection Reagent (Thermo Fisher Scientific, Life Technologies) according to the manufacturer's instructions.

Subcellular Fractionation and Western Blotting

Purification of ER, MAM, and mitochondria was performed and analyzed as described Area-Gomez et al., 2009, the contents of which is hereby incorporated by reference in its entirety.

Analysis of ER-Mitochondrial Apposition

Confocal analysis and interactions between mitochondria and ER were performed as described Area-Gomez et al., 2012 the contents of which is hereby incorporated by reference in its entirety.

Electron Microscopy Analysis

Samples were fixed in 2.5% glutaraldehyde in 0.1 M sodium cacodylate buffer, enrobed in 4% gelatin, postfixed with 1% osmium tetroxide (aq) followed by 2% uranyl acetate, dehydrated through a graded series of ethanol and embedded in LX112 resin (LADD Research Industries, Burlington Vt.). Ultrathin sections were cut onto niceel grids with a Leica Ultracut UCT (Leica Microsystems, Wetzlar, Germany).

Antigen Retrieval Immunolabeling

Sections were etched with saturated sodium metaperiodate for 1 hour, washed with PBS, blocked with 1% BSA and incubated with primary antibody overnight at 4°. The next day, they were washed and then incubated in 6 nm goat anti-rabbit gold (Aurion, NL), for two hours at RT. Sections were counter-stained with uranyl acetate and viewed on a JEOL JEM-1400Plus transmission electron microscope at 120 kv.

Inhibition of $\alpha$-, $\beta$- and $\gamma$-Secretase Activity

To inhibit $\gamma$-secretase activity, cells were treated with 10 $\mu$M DAPT, a highly specific inhibitor of this enzyme complex. For $\beta$-secretase inhibition, cells were treated with 100 nM $\beta$-secretase inhibitor IV (BI). Inhibition of aSMase and the nSMase activities was performed using 10 $\mu$M desipramine or 5 $\mu$M GW4869, respectively. Finally, to inhibit serine-palmitoyl transferase activity the cells were treated with 5 $\mu$M myriocin. Incubations with all drugs were for 12-16 h.

Staining of Lipid Droplets

Staining of lipid droplets was performed using HCS LipidTox™ Deep Green neutral lipid stain (Invitrogen H34475) according to the manufacturer's instructions. Lipid droplet staining was quantified using ImageJ. The different values represent the product of the intensity and the area covered by the fluorescent signal above background in every cell examined.

Sphingolipid Synthesis in Cultured Cells

Cells were incubated for 2 h with serum-free medium to ensure removal of exogenous lipids. The medium was then replaced with MEM containing 2.5 $\mu$Ci/ml of 3H-serine for the indicated periods of time. The cells were washed and collected in PBS, pelleted at 2500×g for 5 min at 4° C., and resuspended in 0.5 ml water, removing a small aliquot for protein quantification. Lipid extraction was done in 3 volumes of chloroform:methanol:HCl (2:1:0.5 v/v/v) added to the samples. Samples were vortexed and centrifuged at 8000×g for 5 min; the organic phase was blown and dried under nitrogen. Dried lipids were resuspended in 30 $\mu$l of chloroform:methanol (2:1 v/v) and applied to a TLC plate. Sphingolipids were separated using a solvent composed of chloroform/methanol/0.22% CaCl2 (60:35:8 v/v/v). Development was performed by exposure of the plate to iodine vapor. The spots corresponding to the relevant sphingolipids (identified using co-migrating standards) were scraped and counted in a scintillation counter (Packard Tri-Carb 2900TR).

Lipidomic Analyses

Lipids were extracted from equal amounts of material (30 $\mu$g protein/sample). Lipid extracts were prepared via chloroform-methanol extraction, spiked with appropriate internal standards, and analyzed using a 6490 Triple Quadrupole LC/MS system (Agilent Technologies, Santa Clara, Calif.) as described previously (Chan et al., 2012). Glycerophospholipids and sphingolipids were separated with normal-phase HPLC using an Agilent Zorbax Rx-Sil column (inner diameter 2.1×100 mm) under the following conditions: mobile phase A (chloroform:methanol:1 M ammonium hydroxide, 89.9:10:0.1, v/v/v) and mobile phase B (chloroform:methanol:water:ammonium hydroxide, 55:39.9:5:0.1, v/v/v); 95% A for 2 min, linear gradient to 30% A over 18 min and held for 3 min, and linear gradient to 95% A over 2 min and held for 6 min. Quantification of lipid species was accomplished using multiple reaction monitoring (MRM) transitions that were developed in earlier studies (Chan et al., 2012) in conjunction with referencing of appropriate internal standards: ceramide d18:1/17:0 and sphingomyelin d18:1/12:0 (Avanti Polar Lipids, Alabaster, Ala.). Values are represented as mole fraction with respect to total lipid (% molarity)

Analysis of Sphingolipid Synthesis in Subcellular Fractions

Cellular fractions were isolated from MEFs as described (Area-Gomez et al., 2009). Two hundred $\mu$g were incubated in a final volume of 200 $\mu$l of 100 mM HEPES pH 7.4, 5 mM DTT, 10 mM EDTA, 50 mM piridoxal phosphate, 0.15 mM palmitoyl-CoA and 3 mCi/ml 3H-Ser for 20 min at 37° C. The reaction was stopped by addition of 3 volumes of chloroform/methanol (2:1 v/v). Lipid extraction and TLC analysis was performed as described above.

Analysis of Sphingomyelinase Activity

One hundred $\mu$g of protein were assayed in 100 mM of the appropriate buffer (Tris/glycine for pH 7.0-9.0 and sodium acetate for pH 4.0-5.0), 1.55 mM Triton X-100, 0.025% BSA, 1 mM MgCl2, and 400 $\mu$M bovine brain sphingomyelin spiked with 22000 dpm of [3H]-bovine sphingomyelin (1 nCi/sample).

Reactions were carried out in borosilicate glass culture tubes at 37° C., overnight, followed by quenching with 1.2 ml of ice-cold 10% trichloroacetic acid, incubation at 4° C. for 30 min, and centrifugation at 2000 rpm at 4° C. for 20 min. One ml of supernatant was transferred to clean tubes, 1 ml of ether was added, the mixture vortexed, and centrifuged at 2000 rpm for 5 min. Eight hundred $\mu$l of the bottom phase was transferred to scintillation vials, 5 ml of Scintiverse BD (Fisher Scientific, Fair Lawn, N.J.) was added, and samples were counted.

ACAT Activity Assay

To measure cholesterol esterification in vivo, cultured cells were incubated in serum-free medium for 2 h to remove all exogenous lipids. After that, 2.5 $\mu$Ci/ml of 3H-cholesterol was added to FBS-free DMEM containing 2% FAF-BSA, allowed to equilibrate for at least 30 min at 37° C., and the radiolabeled medium was added to the cells for the indicated periods of time. Cells were then washed and collected in DPBS, removing a small aliquot for protein quantification. Lipids were extracted in 3 volumes of chloroform:methanol (2:1 v/v). After vortexing and centrifugation at 8000×g for 5 min, the organic phase was blown to dryness under nitrogen. Dried lipids were resuspended in 30 $\mu$l of chloroform:methanol (2:1 v/v) and applied to a TLC plate along with unlabeled standards. A mixture of hexanes/diethyl ether/acetic acid (80:20:1 v/v/v) was used as solvent. Iodine-stained bands corresponding to cholesterol and cholesteryl esters were scraped and counted.

Analysis of ER-Mitochondrial Apposition

Cells under were co-transfected with GFP-Sec61-β (Addgene plasmid #15108) and DsRed2-Mito (Clontech, #632421) at a 1:1 ratio, using Lipofectamine 2000 (Invitrogen, #11668-027) in serum-free DMEM. Twelve hours post-transfection, cells were analyzed as described (Guardia-Laguarta et al., 2014).

Preparation of Synthetic Aβ in Different States of Aggregation

Lyophilized Aβ40 and Aβ42 peptides (American Peptide; 62-0-80; UCLA) were equilibrated at room temperature for 30 min and then resuspended in hexafluro-2-propanol (HIFP) (Sigma; H8508) to 1 mM using a glass-tight Hamilton syringe with Teflon plunger. HIFP was allowed to evaporate in a fume hood and dried under vacuum in a SpeedVac (Savant Instruments) and kept at −20° C. Immediately prior to use, an aliquot was resuspended to 5 mM in DMSO followed by bath sonication for 10 min.

To analyze the effect of Aβ addition, a mix of Aβ40/Aβ42 at a ratio 10:1 was added to the cultured cells to a final concentration of 6000 pg/ml for 24 h. For Aβ42 oligomer formation, 5 mM of Aβ42 in DMSO was diluted to 100 μM in ice-cold media, vortexed for 30 seconds, and incubated at 4° C. for 24 h. Aβ42 Oligomers were added to the cultured cells to a final concentration of 5 or 10 μM for 24 h.

Quantitative Reverse Transcription-Polymerase Chain Reaction (qRT-PCR)

Total RNA was extracted from MEFs using TRIzol® Reagent (Invitrogen 15596-018) according to the manufacture's instructions, and was quantified by NanoDrop2000 (Thermo Scientific). One mg of total RNA was used to obtain cDNA by RT-PCR using a High Capacity cDNA Reverse Transcription Kit (Applied Biosystems; PN 4368813, 4374966). Real-Time PCR was performed in triplicate in a StepOnePlus™ Real-Time PCR System (Applied Biosystems; 4376600). The expression of each gene under study was analyzed using specific predesigned TaqMan Probes (PGC-1α, ppargcl Mm01208835_ml; aSMase, smpd1 Mm00488319_g1; nSMase, smpd3 Mm00491359_ml). The forward and reverse primers for COXI quantification were, respectively, (TGCTAGCCGCAGGCATTACT (SEQ ID NO: 5); CGGGATCAAAGAAAGTTGTGTTT (SEQ ID NO: 6)). The expression of each gene under study was analyzed using specific predesigned TaqMan Probes and normalized against Gapdh expression (Applied Biosystems, 4352339E) as an internal standard.

Supercomplex Analysis

Analysis and quantification of mitochondrial respiratory complexes by western blot and enzymatic in-gel activity were carried out as previously reported (Acin-Perez et al., 2008)

Statistical Analyses

All averages are the result of 3 or more independent experiments carried out at different times with different sets of samples. Tests of significance employed student's t-test at $p<0.05$, unless indicated otherwise; all error bars in the figures are SD. For the determination of ER-mitochondrial apposition, all images were randomly taken from a set of multiple fields. The degree of colocalization was analyzed by ImageJ and data were compared using Mander's coefficient.

REFERENCES FOR EXAMPLE 3

Acin-Perez, R., and Enriquez, J. A. (2014). The function of the respiratory supercomplexes: the plasticity model. Biochim Biophys Acta 1837, 444-450.

Acin-Perez, R., Fernandez-Silva, P., Peleato, M. L., Perez-Martos, A., and Enriquez, J. A. (2008). Respiratory active mitochondrial supercomplexes. Mol Cell 32, 529-539.

Ardail, D., Popa, I., Bodennec, J., Louisot, P., Schmitt, D., and Portoukalian, J. (2003). The mitochondria-associated endoplasmic-reticulum subcompartment (MAM fraction) of rat liver contains highly active sphingolipid-specific glycosyltransferases. Biochem J 371, 1013-1019.

Area-Gomez, E. (2014). Assessing the function of mitochondria-associated ER membranes. Methods Enzymol 547, 181-197.

Area-Gomez, E., de Groof, A. J., Boldogh, I., Bird, T. D., Gibson, G. E., Koehler, C. M., Yu, W. H., Duff, K. E., Yaffe, M. P., Pon, L. A., et al. (2009). Presenilins are enriched in endoplasmic reticulum membranes associated with mitochondria. Am. J. Pathol. 175, 1810-1816.

Area-Gomez, E., Del Carmen Lara Castillo, M., Tambini, M. D., Guardia-Laguarta, C., de Groof, A. J., Madra, M., Ikenouchi, J., Umeda, M., Bird, T. D., Sturley, S. L., et al. (2012). Upregulated function of mitochondria-associated ER membranes in Alzheimer disease. EMBO J.

Balietti, M., Giorgetti, B., Casoli, T., Solazzi, M., Tamagnini, F., Burattini, C., Aicardi, G., and Fattoretti, P. (2013). Early selective vulnerability of synapses and synaptic mitochondria in the hippocampal CA1 region of the Tg2576 mouse model of Alzheimer's disease. J Alzheimers Dis 34, 887-896.

Browman, D. T., Resek, M. E., Zajchowski, L. D., and Robbins, S. M. (2006). Erlin-1 and erlin-2 are novel members of the prohibitin family of proteins that define lipid-raft-like domains of the ER. J. Cell Sci. 119, 3149-3160.

Casley, C. S., Canevari, L., Land, J. M., Clark, J. B., and Sharpe, M. A. (2002). Beta-amyloid inhibits integrated mitochondrial respiration and key enzyme activities. J Neurochem 80, 91-100.

Castello, M. A., Jeppson, J. D., and Soriano, S. (2014). Moving beyond anti-amyloid therapy for the prevention and treatment of Alzheimer's disease. BMC Neurol 14, 169.

Chan, R. B., Oliveira, T. G., Cortes, E. P., Honig, L. S., Duff, K. E., Small, S. A., Wenk, M. R., Shui, G., and Di Paolo, G. (2012). Comparative lipidomic analysis of mouse and human brain with Alzheimer disease. J Biol Chem 287, 2678-2688.

Cordy, J. M., Hooper, N. M., and Turner, A. J. (2006). The involvement of lipid rafts in Alzheimer's disease. Mol. Membr. Biol. 23, 111-122.

Das, U., Wang, L., Ganguly, A., Saikia, J. M., Wagner, S. L., Koo, E. H., and Roy, S. (2016). Visualizing APP and BACE-1 approximation in neurons yields insight into the amyloidogenic pathway. Nat Neurosci 19, 55-64.

de Brito, O. M., and Scorrano, L. (2008). Mitofusin 2 tethers endoplasmic reticulum to mitochondria. Nature 456, 605-610.

De Tullio, L., Maggio, B., Hartel, S., Jara, J., and Fanani, M. L. (2007). The initial surface composition and topography modulate sphingomyelinase-driven sphingomyelin to ceramide conversion in lipid monolayers. Cell Biochem Biophys 47, 169-177.

Devi, L., and Ohno, M. (2012). Mitochondrial dysfunction and accumulation of the beta-secretase-cleaved C-terminal fragment of APP in Alzheimer's disease transgenic mice. Neurobiol Dis 45, 417-424. Dinkla, S., Wessels, K., Verdurmen, W. P., Tomelleri, C., Cluitmans, J. C., Fransen, J., Fuchs, B., Schiller, J., Joosten, I., Brock, R., et al. (2012). Functional consequences of sphingomyelinase-induced changes in erythrocyte membrane structure. Cell Death Dis 3, e410.

Du, H., Guo, L., Yan, S., Sosunov, A. A., McKhann, G. M., and Yan, S. S. (2010). Early deficits in synaptic mitochondria in an Alzheimer's disease mouse model. Proc Natl Acad Sci USA 107, 18670-18675.

Filippov, V., Song, M. A., Zhang, K., Vinters, H. V., Tung, S., Kirsch, W. M., Yang, J., and Duerksen-Hughes, P. J. (2012). Increased ceramide in brains with Alzheimer's and other neurodegenerative diseases. J Alzheimers Dis 29, 537-547.

Fukumoto, H., Cheung, B. S., Hyman, B. T., and Irizarry, M. C. (2002). Beta-secretase protein and activity are increased in the neocortex in Alzheimer disease. Arch Neurol 59, 1381-1389.

Grimm, M. O., Grosgen, S., Rothhaar, T. L., Burg, V. K., Hundsdorfer, B., Haupenthal, V. J., Friess, P., Muller, U., Fassbender, K., Riemenschneider, M., et al. (2011). Intracellular APP domain regulates serine-palmitoyl-CoA transferase expression and is affected in Alzheimer's disease. Int. J. Alzheimers Dis. 2011, 695413.

Guardia-Laguarta, C., Area-Gomez, E., Rub, C., Liu, Y., Magrane, J., Becker, D., Voos, W., Schon, E. A., and Przedborski, S. (2014). alpha-Synuclein is localized to mitochondria-associated ER membranes. J Neurosci 34, 249-259.

Guo, Q., Fu, W., Sopher, B. L., Miller, M. W., Ware, C. B., Martin, G. M., and Mattson, M. P. (1999). Increased vulnerability of hippocampal neurons to excitotoxic necrosis in presenilin-1 mutant knock-in mice. Nat Med 5, 101-106.

Haass, C., Kaether, C., Thinakaran, G., and Sisodia, S. (2012). Trafficking and proteolytic processing of APP. Cold Spring Harb Perspect Med 2, a006270.

Hansson Petersen, C. A., Alikhani, N., Behbahani, H., Wiehager, B., Pavlov, P. F., Alafuzoff, I., Leinonen, V., Ito, A., Winblad, B., Glaser, E., et al. (2008). The amyloid beta-peptide is imported into mitochondria via the TOM import machinery and localized to mitochondrial cristae. Proc Natl Acad Sci USA 105, 13145-13150.

Hardy, J. A., and Higgins, G. A. (1992). Alzheimer's disease: the amyloid cascade hypothesis. Science 256, 184-185.

Hedskog, L., Pinho, C. M., Filadi, R., Ronnback, A., Hertwig, L., Wiehager, B., Larssen, P., Gellhaar, S., Sandebring, A., Westerlund, M., et al. (2013). Modulation of the endoplasmic reticulum-mitochondria interface in Alzheimer's disease and related models. Proc Natl Acad Sci USA 110, 7916-7921.

Herreman, A., Semeels, L., Annaert, W., Collen, D., Schoonjans, L., and De Strooper, B. (2000). Total inactivation ofy-secretase activity in presenilin-deficient embryonic stem cells. Nat. Cell Biol. 2, 461-462.

Holsinger, R. M., McLean, C. A., Beyreuther, K., Masters, C. L., and Evin, G. (2002). Increased expression of the amyloid precursor beta-secretase in Alzheimer's disease. Ann Neurol 51, 783-786.

Jiang, Y., Mullaney, K. A., Peterhoff, C. M., Che, S., Schmidt, S. D., Boyer-Boiteau, A., Ginsberg, S. D., Cataldo, A. M., Mathews, P. M., and Nixon, R. A. (2010). Alzheimer's-related endosome dysfunction in Down syndrome is Abeta-independent but requires APP and is reversed by BACE-1 inhibition. Proc Natl Acad Sci USA 107, 1630-1635.

Kogot-Levin, A., and Saada, A. (2014). Ceramide and the mitochondrial respiratory chain. Biochimie 100, 88-94.

Lauritzen, I., Pardossi-Piquard, R., Bauer, C., Brigham, E., Abraham, J. D., Ranaldi, S., Fraser, P., St-George-Hyslop, P., Le Thuc, O., Espin, V., et al. (2012). The beta-secretase-derived C-terminal fragment of betaAPP, C99, but not Abeta, is a key contributor to early intraneuronal lesions in triple-transgenic mouse hippocampus. J Neurosci 32, 16243-16255a.

Lee, J. K., Jin, H. K., Park, M. H., Kim, B. R., Lee, P. H., Nakauchi, H., Carter, J. E., He, X., Schuchman, E. H., and Bae, J. S. (2014). Acid sphingomyelinase modulates the autophagic process by controlling lysosomal biogenesis in Alzheimer's disease. J Exp Med 211, 1551-1570.

Lee, K. W., Im, J. Y., Song, J. S., Lee, S. H., Lee, H. J., Ha, H. Y., Koh, J. Y., Gwag, B. J., Yang, S. D., Paik, S. G., et al. (2006). Progressive neuronal loss and behavioral impairments of transgenic C57BL/6 inbred mice expressing the carboxy terminus of amyloid precursor protein. Neurobiol Dis 22, 10-24.

Li, R., Lindholm, K., Yang, L. B., Yue, X., Citron, M., Yan, R., Beach, T., Sue, L., Sabbagh, M., Cai, H., et al. (2004). Amyloid beta peptide load is correlated with increased beta-secretase activity in sporadic Alzheimer's disease patients. Proc Natl Acad Sci USA 101, 3632-3637.

Manczak, M., Anekonda, T. S., Henson, E., Park, B. S., Quinn, J., and Reddy, P. H. (2006). Mitochondria are a direct site of Aβ accumulation in Alzheimer's disease neurons: implications for free radical generation and oxidative damage in disease progression. Hum. Mol. Genet. 15, 1437-1449.

Mapstone, M., Cheema, A. K., Fiandaca, M. S., Zhong, X., Mhyre, T. R., MacArthur, L. H., Hall, W. J., Fisher, S. G., Peterson, D. R., Haley, J. M., et al. (2014). Plasma phospholipids identify antecedent memory impairment in older adults. Nat Med 20, 415-418.

Matsumura, N., Takami, M., Okochi, M., Wada-Kakuda, S., Fujiwara, H., Tagami, S., Funamoto, S., Ihara, Y., and Morishima-Kawashima, M. (2014). gamma-Secretase associated with lipid rafts: multiple interactive pathways in the stepwise processing of beta-carboxyl-terminal fragment. J Biol Chem 289, 5109-5121.

McBrayer, M., and Nixon, R. A. (2013). Lysosome and calcium dysregulation in Alzheimer's disease: partners in crime. Biochem Soc Trans 41, 1495-1502.

McPhie, D. L., Lee, R. K., Eckman, C. B., Olstein, D. H., Durham, S. P., Yager, D., Younkin, S. G., Wurtman, R. J., and Neve, R. L. (1997). Neuronal expression of β-amyloid precursor protein Alzheimer mutations causes intracellular accumulation of a C-terminal fragment containing both the amyloid 3 and cytoplasmic domains. J. Biol. Chem. 272 , 24743-24746.

Moore, S., Evans, L. D., Andersson, T., Portelius, E., Smith, J., Dias, T. B., Saurat, N., McGlade, A., Kirwan, P., Blennow, K., et al. (2015). APP metabolism regulates tau proteostasis in human cerebral cortex neurons. Cell Rep 11, 689-696.

Neve, R. L., Boyce, F. M., McPhie, D. L., Greenan, J., and Oster-Granite, M. L. (1996). Transgenic mice expressing APP-C100 in the brain. Neurobiol Aging 17, 191-203.

Newman, M., Wilson, L., Verdile, G., Lim, A., Khan, I., Moussavi Nik, S. H., Pursglove, S., Chapman, G., Martins, R. N., and Lardelli, M. (2014). Differential, dominant activation and inhibition of Notch signalling and APP cleavage by truncations of PSEN1 in human disease. Hum Mol Genet 23, 602-617. Pera, M., Alcolea, D., Sanchez-Valle, R., Guardia-Laguarta, C., Colom-Cadena, M., Badiola, N., Suarez-Calvet, M., Llado, A., Barrera-Ocampo, A. A., Sepulveda-Falla, D., et al. (2013). Distinct patterns of APP processing in the CNS in autosomal-dominant and sporadic Alzheimer disease. Acta Neuropathol 125, 201-213.

Pike, L. J. (2009). The challenge of lipid rafts. J. Lipid Res. 50, S323-S328. Rockenstein, E., Mante, M., Alford, M., Adame, A., Crews, L., Hashimoto, M., Esposito, L., Mucke, L., and Masliah, E. (2005). High beta-secretase activity elicits neurodegeneration in transgenic mice despite reductions in amyloid-beta levels: implications for the treatment of Alzheimer disease. J Biol Chem 280, 32957-32967.

Rowland, A. A., Chitwood, P. J., Phillips, M. J., and Voeltz, G. K. (2014). ER contact sites define the position and timing of endosome fission. Cell 159, 1027-1041.

Saito, T., Suemoto, T., Brouwers, N., Sleegers, K., Funamoto, S., Mihira, N., Matsuba, Y., Yamada, K., Nilsson, P., Takano, J., et al. (2011). Potent amyloidogenicity and pathogenicity of Abeta43. Nat Neurosci 14, 1023-1032.

Schon, E. A., and Area-Gomez, E. (2010). Is Alzheimer's disease a disorder of mitochondria-associated membranes? J Alzheimers Dis 20 Suppl 2, S281-292.

Schon, E. A., and Area-Gomez, E. (2013). Mitochondria-associated ER membranes in Alzheimer disease. Mol Cell Neurosci 55, 26-36.

Schreiner, B., Hedskog, L., Wiehager, B., and Ankarcrona, M. (2015). Amyloid-beta peptides are generated in mitochondria-associated endoplasmic reticulum membranes. J Alzheimers Dis 43, 369-374. Silva, L. C., Futerman, A. H., and Prieto, M. (2009). Lipid raft composition modulates sphingomyelinase activity and ceramide-induced membrane physical alterations. Biophys J 96, 3210-3222.

Simons, K., and Vaz, W. L. (2004). Model systems, lipid rafts, and cell membranes. Annu. Rev. Biophys. Biomol. Struct. 33, 269-295.

Swerdlow, R. H., Burns, J. M., and Khan, S. M. (2014). The Alzheimer's disease mitochondrial cascade hypothesis: progress and perspectives. Biochim Biophys Acta 1842 , 1219-1231.

Tamayev, R., Matsuda, S., Arancio, O., and D'Adamio, L. (2012). beta-but not gamma-secretase proteolysis of APP causes synaptic and memory deficits in a mouse model of dementia. EMBO Mol Med 4, 171-179.

van Echten-Deckert, G., and Walter, J. (2012). Sphingolipids: critical players in Alzheimer's disease. Prog Lipid Res 51, 378-393.

Vance, J. E. (2014). MAM (mitochondria-associated membranes) in mammalian cells: Lipids and beyond. Biochim Biophys Acta 1841, 595-609.

Wang, X., Wang, W., Li, L., Perry, G., Lee, H. G., and Zhu, X. (2014). Oxidative stress and mitochondrial dysfunction in Alzheimer's disease. Biochim Biophys Acta 1842 , 1240-1247.

Wu, B. X., Clarke, C. J., Matmati, N., Montefusco, D., Bartke, N., and Hannun, Y. A. (2011). Identification of novel anionic phospholipid binding domains in neutral sphingomyelinase 2 with selective binding preference. J Biol Chem 286, 22362-22371.

Xie, H., Guan, J., Borrelli, L. A., Xu, J., Serrano-Pozo, A., and Bacskai, B. J. (2013). Mitochondrial alterations near amyloid plaques in an Alzheimer's disease mouse model. J Neurosci 33, 17042-17051.

Yang, L. B., Lindholm, K., Yan, R., Citron, M., Xia, W., Yang, X. L., Beach, T., Sue, L., Wong, P., Price, D., et al. (2003). Elevated beta-secretase expression and enzymatic activity detected in sporadic Alzheimer disease. Nat Med 9, 3-4.

Yao, J., Irwin, R. W., Zhao, L., Nilsen, J., Hamilton, R. T., and Brinton, R. D. (2009). Mitochondrial bioenergetic deficit precedes Alzheimer's pathology in female mouse model of Alzheimer's disease. Proc Natl Acad Sci USA 106, 14670-14675.

Young-Pearse, T. L., Bai, J., Chang, R., Zheng, J. B., LoTurco, J. J., and Selkoe, D. J. (2007). A critical function for beta-amyloid precursor protein in neuronal migration revealed by in utero RNA interference. J Neurosci 27, 14459-14469.

Zhang, X., Herrmann, U., Weyer, S. W., Both, M., Muller, U. C., Korte, M., and Draguhn, A. (2013). Hippocampal network oscillations in APP/APLP2-deficient mice. PLoS One 8, e61198.

Zigdon, H., Kogot-Levin, A., Park, J. W., Goldschmidt, R., Kelly, S., Merrill, A. H., Jr., Scherz, A., Pewzner-Jung, Y., Saada, A., and Futerman, A. H. (2013). Ablation of ceramide synthase 2 causes chronic oxidative stress due to disruption of the mitochondrial respiratory chain. J Biol Chem 288, 4947-4956.

Example 4

Overview

APP-C99 (referred to hereinafter as "C99") accumulates in AD cells and in cell and animal models of AD. Use of specific inhibitors of APP processing in cells in which C99 production is enhanced or abrogated were used to demonstrate that C99, and not Aβ, is the cause of AD phenotypes (e.g. elevated $A\beta_{42}$:$A\beta_{40}$ ratios; increased cholesteryl ester production and lipid droplet formation; altered sphingolipid metabolism and increased ceramide levels; decreased mitochondrial respiratory chain function and bioenergetics). Thus, treatments that reverse these phenotypes will reduce the amount of C99 in the MAM and/or reduce the effects of the accumulated C99 in the MAM, thereby ameliorating the symptoms of AD.

In summary, described herein is: (1) C99 is localized to MAM; (2) C99 is present in MAM at low levels in normal individuals, but accumulates in MAM in AD patients; (3) C99, and not Aβ, is the cause of the increased ER-mitochondrial communication and the phenotypes in AD; and (4) AD can be treated by strategies aimed at reducing C99 levels and/or ER-mitochondrial communication, either directly or indirectly.

Described herein is (1) an overview of the relationship of C99 to these phenotypes, paying particular attention to cell behaviors that are amenable to treatment, and (2) examples of specific treatments that improve known phenotypes of AD and that either imply or demonstrate that the effects of C99 on AD pathology have been reduced or circumvented.

The Relationship of C99 to AD Phenotypes

In broad view, the relationship of C99 to AD phenotypes was determined by perturbing APP processing (FIG. 26A), both chemically—using inhibitors of α-secretase (e.g. TAPI-1), β-secretase (e.g. BACE1 inhibitor IV), and γ-secretase (e.g. DAPT)—and genetically—using mouse embryonic fibroblasts (MEFs) lacking PS1 and PS2 (PS-DKO, in which C99 accumulates) and in MEFs lacking APP/APLP2 (APP-DKO, in which C99 is not produced).

Using these reagents, it was first demonstrated that C99 is localized to MAM, both in mice (FIGS. 27A, 27B) and in humans (FIGS. 27C, 27D). It was then showed that lipid droplets containing cholesteryl esters accumulated in various mouse and human cells, and that this accumulation was mediated by C99 (FIGS. 28A-B).

It was also shown that the accumulation of C99 in PS-DKO MEFs alters sphingolipid metabolism, with a notable decrease in the levels of sphingomyelin (SM) and a corresponding increase in ceramide (Cer) (FIGS. 29A, 29B), especially in MAM (FIG. 29C), consistent with the fact that sphingomyelin is converted to ceramide by sphingomyelinases (SMases) (FIG. 29G). These changes were associated with upregulated synthesis of these sphingolipid species (FIG. 29D), with increased SMase activities (FIG. 29E), and with a remarkable relocalization of SMase(s) to the MAM (FIG. 29F). Importantly, these changes in sphingolipid homeostasis were almost certainly driven by the accumulation of C99 at the MAM, as treatment of PS-DKO cells (containing C99 but lacking Aβ) with a BACE1 inhibitor (now also lacking C99) completely reversed the changes in SM and Cer levels (FIG. 29H, FIGS. 9A-H).

Figure 30C:
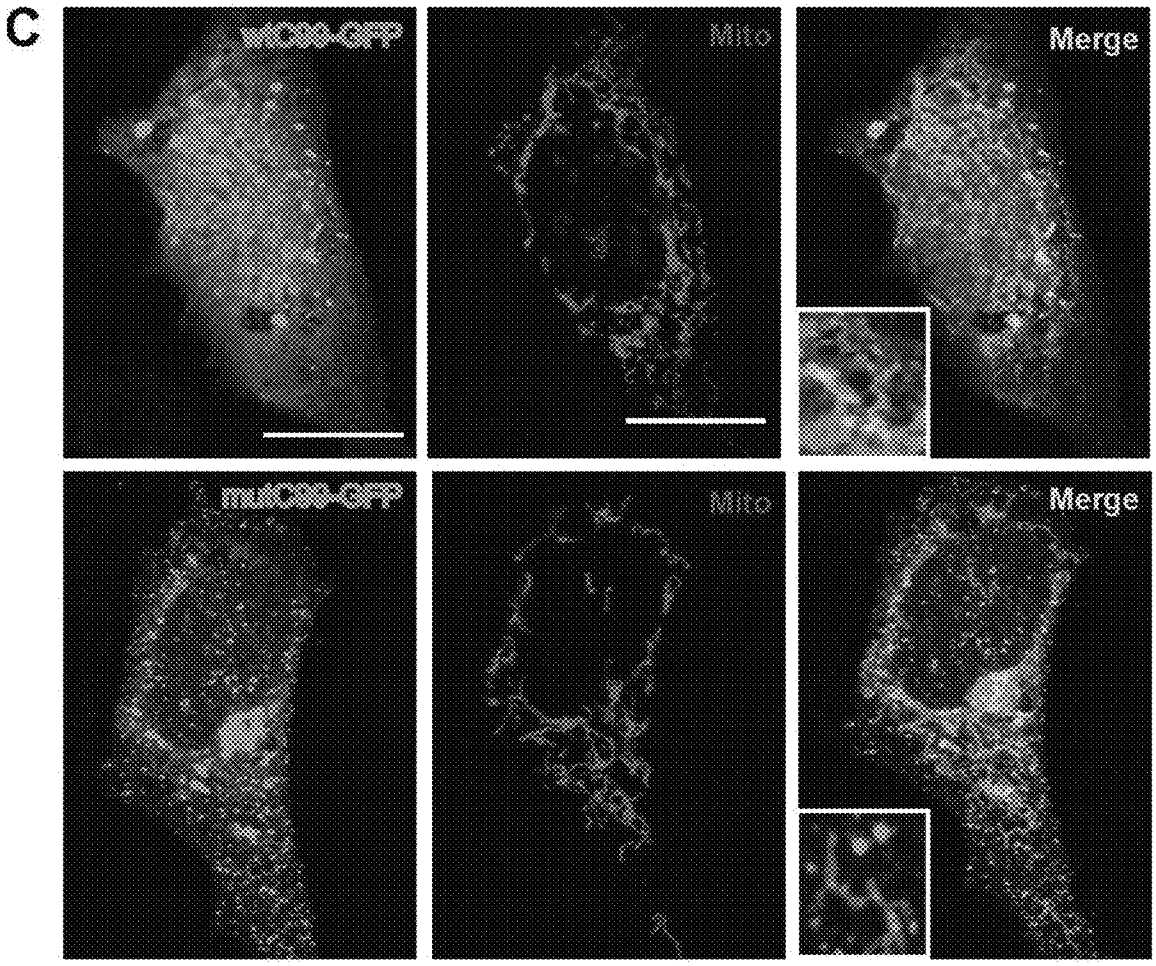
Figure 31:
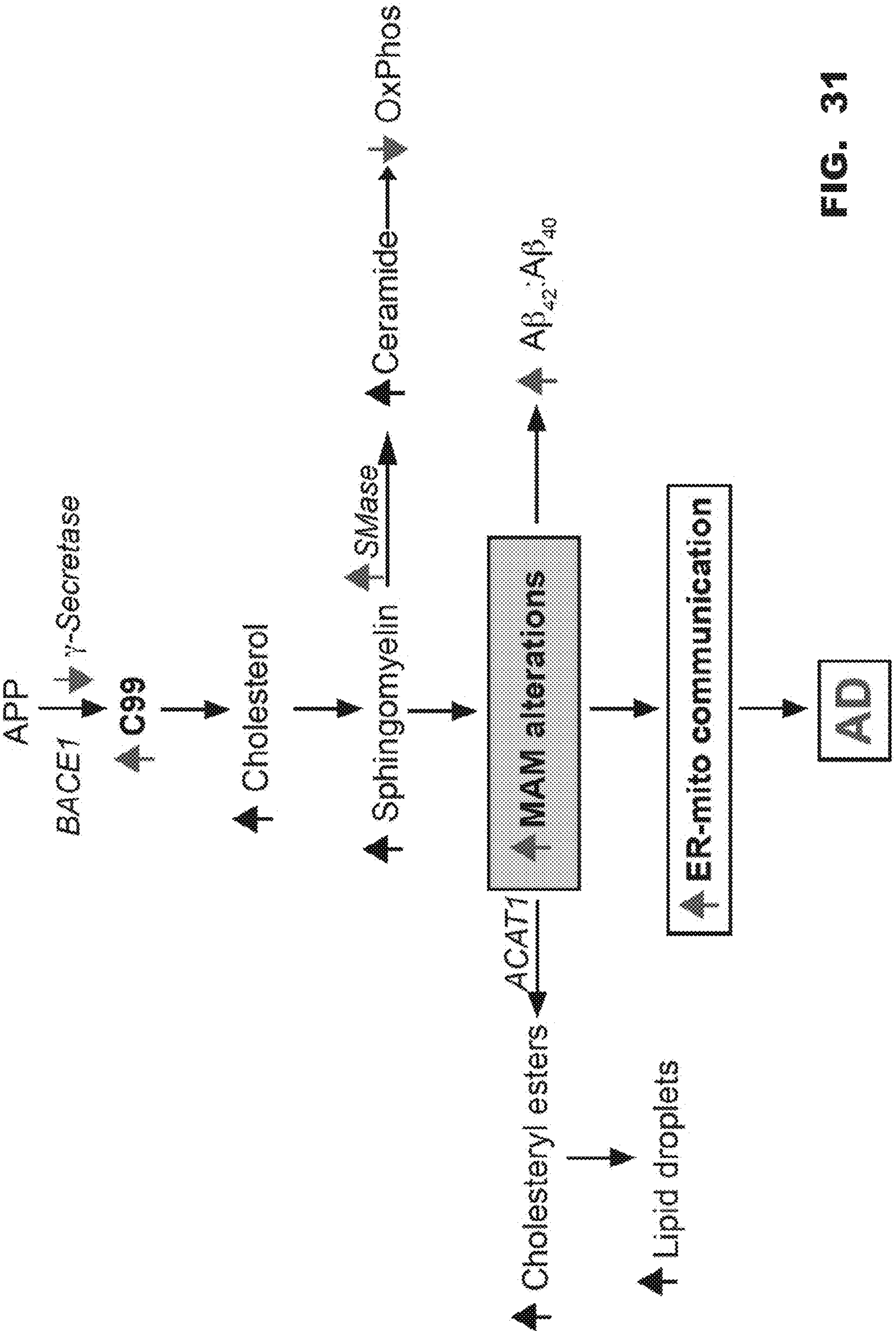
FIG. 31 shows a model of C99-mediated AD pathogenesis. Aberrant accumulation of MAM-localized C99 triggers elevated levels of intracellular cholesterol, which in turns stimulates an increase in transient levels of sphingomyelin (SM). The SM, however, is rapidly converted to ceramide (ultimately reducing steady-state SM levels). The overall derangement in lipid metabolism (most notably the inability of the cell to maintain cholesterol homeostasis) results in increased ER-mitochondrial communication, giving rise to essentially all the features of the disease.

Without being bound by theory, it is proposed that MAM-localized C99 is the driver of all the phenotypes seen in AD, including the elevated $A\beta_{42}$:$A\beta_{40}$ ratio and the reduced mitochondrial bioenergetics (see FIGS. 4A-D and 11A-I). If that is the case, reducing the amount of C99 at the MAM should reverse/rescue AD phenotypes. Since C99 contains a cholesterol binding domain [1], this domain might play a role both in the localization of C99 to MAM (which, as a lipid raft, is rich in cholesterol and sphingomyelin) and in regulating cellular lipid homeostasis. Upon mutation of this domain, it was found that, following expression of WT and C99-Mutant constructs in APP-DKO MEFs (lacking APP and C99), the amount of C99-Mutant in the MAM was severely reduced compared to that of C99-WT (FIG. 30A) and significantly, the $A\beta_{42}$:$A\beta_{40}$ ratio decreased (i.e. improved) dramatically (FIG. 30B). Moreover, upon the expression of C-terminus-tagged-GFP versions of these constructs in WT-MEFs, the C99-Mutant-GFP was re-localized away from MAM (FIG. 30C). In addition, whereas a portion of the GFP signal in the cells expressing C99-WT-GFP was present in the nucleus, as expected (due to cleavage of C99-WT-GFP into AICD-GFP [by MAM-localized γ-secretase activity (see FIGS. 26A-D)], which then is transported to the nucleus), there was essentially no nuclear GFP signal in the cells transfected with C99-Mutant-GFP, consistent with the reduction of C99-Mutant in the MAM compartment and its redistribution elsewhere in the cell. This experiment demonstrates a direct link between the amount of C99, its localization to MAM, and AD phenotypes. Notably, this latter result also supports the contention that C99 must be at the MAM, and in high amounts, in order to cause AD, and that strategies aimed at reducing MAM-localized C99, or in reducing the consequences of MAM-localized C99 (noted above), are ways to treat AD. This view is summarized in the model shown in FIG. 31 (see also FIGS. 6A-E).

Strategies to Treat AD

Described herein are two broad strategies to demonstrate proof of principle that AD can be treated by taking advantage of our discovery that MAM-localized C99 drives AD pathogenesis. The first is aimed at reversing C99-mediated sphingolipid dyshomeostasis; the second is aimed at reversing C99-mediated cholesterol dyshomeostasis.

Interdict Sphingolipid Pathways

Figure 32A:
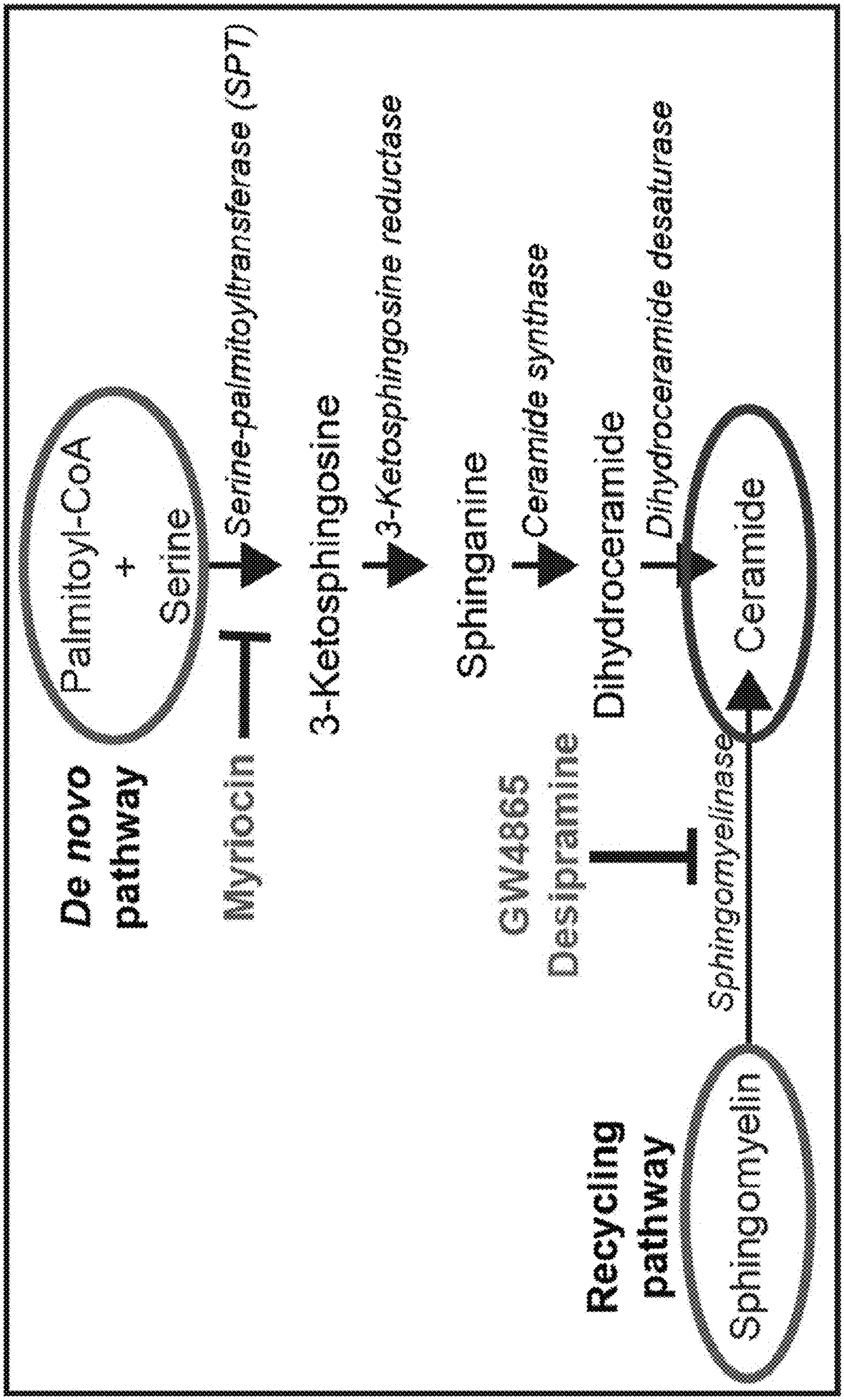

If C99 perturbs sphingolipid levels which, in turn, cause increased ER-mitochondrial apposition and the features of AD, then strategies to reduce ceramide should be salutary. PS-mutant cells were, therefore, treated with desipramine, an inhibitor of acid sphingomyelinase (aSMase), and with GW4869, an inhibitor of neutral sphingomyelinase (nSMase) (FIG. 32A). Both treatments, which were designed to inhibit the ceramide salvage pathway (see FIG. 32A), reduced lipid droplet formation (FIG. 32B). Equally strikingly, desipramine reduced the $A\beta_{42}$:$A\beta_{40}$ ratio (FIG. 32C). Treatment of these cells with myriocin, an inhibitor of the de novo pathway of ceramide synthesis (FIG. 32A), reversed the bioenergetic deficits in these cells (FIG. 32D).

Interdict Cholesterol Trafficking

If C99 causes cholesterol dyshomeostsis, interdicting the C99-mediated increase in intracellular cholesterol should be salutory. One way to reduce intracellular cholesterol is to prevent its import from the extracellular space. One way to achieve this is by blocking Cyclophilin D (CypD), which not only binds sphingomyelin [2] and regulates sterol metabolism [3], but also interacts with the MAM-localized IP3 receptor to regulate calcium trafficking [4], and which can affect MAM integrity [5]. CypD was therefore inhibited with cyclosporin A (CsA), and showed that the increased level of cholesterol seen in PS-mutant cells was reversed (FIG. 33A).

In a related approach, it was found that elevated C99 causes a downregulation of the expression of LRP1 (low density lipoprotein receptor-related protein 1), which imports cholesterol into cells, but also causes a massive upregulation of the expression of CD36/FAT, a multifunctional receptor that also imports cholesterol into cells [6] (FIG. 33B, right panel). The cells were therefore treated with sulfo-N-succinimidyl oleate (SSO), an inhibitor of CD36 [7], and found an equally marked reduction in cellular free cholesterol.

Taken together, both sets of experiments indicate that interdicting sphingolipid and cholesterol pathways is a strategy to treat AD caused by the accumulation of C99 at the MAM.

REFERENCES FOR EXAMPLE 4

1. Barrett P J, Song Y, Van Horn W D, Hustedt E J, Schafer J M, Hadziselimovic A, Beel A J, Sanders C R (2012). The amyloid precursor protein has a flexible transmembrane domain and binds cholesterol. Science 336, 1168-1171.
2. Dynarowicz-Latka P, Wnetrzak A, Makyla-Juzak K (2015). Cyclosporin A in membrane lipids environment: implications for antimalarial activity of the drug—the *Langmuir* monolayer studies. J. Membr. Biol. 248, 1021-1032.
3. Vaziri N D, Liang K, Azad H (2000). Effect of cyclosporine on HMG-CoA reductase, cholesterol 7α-hydroxylase, LDL receptor, HDL receptor, VLDL receptor, and lipoprotein lipase expressions. J Pharmacol. Exp. Therap. 294, 778-783.
4. Theurey P, Tubbs E, Vial G, Jacquemetton J, Bendridi N, et al (2016). Mitochondria-associated endoplasmic reticulum membranes allow adaptation of mitochondrial metabolism to glucose availability in the liver. J. Mol. Cell Biol. 8, 129-143.
5. Tubbs E, Theurey P, Vial G, Bendridi N, Bravard A, et al (2014). Mitochondria-associated endoplasmic reticulum membrane (MAM) integrity is required for insulin signaling and is implicated in hepatic insulin resistance. Diabetes 63, 3279-3294.

6. Nassir F, Wilson B, Han X, Gross R W, Abumrad N A (2007). CD36 is important for fatty acid and cholesterol uptake by the proximal but not distal intestine. J. Biol. Chem. 282, 19493-19501.

7. Kuda O, Pietka T A, Demianova Z, Kudova E, Cvacka J, Kopecky J, Abumrad N A (2013). Sulfo-N-succinimidyl oleate (SSO) inhibits fatty acid uptake and signaling for intracellular calcium via binding CD36 lysine 164: SSO also inhibits oxidized low density lipoprotein uptake by macrophages. J. Biol. Chem. 288, 15547-15555.

Example 5

Described herein is a major breakthrough in the understanding of the pathogenesis of Alzheimer disease, which currently is untreatable and difficult to diagnose. While the accumulation of plaques and tangles clearly plays a role in the development of the disease, these are not primary events, but rather are secondary phenomena resulting from an underlying pathogenetic process that is described herein. This process involves an unexpected relationship between APP processing and sphingolipid homeostasis that ultimately affects a subcellular compartment where these two processes intersect, namely mitochondria-associated endoplasmic reticulum (ER) membranes (MAM).

MAM is a specialized lipid raft-like subdomain of the ER (i.e. rich in cholesterol and sphingomyelin) that connects ER to mitochondria, both physically and biochemically. Presenilin-1 and -2, and γ-secretase activity itself, are located predominantly in the MAM, and that ER-mitochondrial apposition and MAM function are massively upregulated in both familial and sporadic AD. Significantly, these MAM-mediated functions—altered phospholipid and cholesterol metabolism, aberrant calcium homeostasis, abnormal mitochondrial dynamics, and altered Aβ levels—are the very features perturbed in AD, but the reason for this upregulated MAM function was unknown. However, described herein is the discovery that the aberrant processing of APP seen in AD cells perturbs intracellular sphingolipid metabolism and homeostasis, resulting in the expansion of the raft-like MAM compartment (both physically and operationally). In turn, this increase in ER-mitochondrial apposition and in MAM functionality gives rise to essentially all of the symptoms and features of AD, including the plaques.

As can be imagined, this "MAM hypothesis" of AD pathogenesis is a novel, and some might say radical, view of AD that is a major departure from the current majority view of pathogenesis (i.e. the "amyloid cascade hypothesis"). As such, it has major ramifications, not only for understanding how AD develops and progresses, but also for treating and diagnosing the disease. In this regard, it is proposed here to (1) test candidate FDA-approved compounds to treat AD and (2) develop protocols to diagnose AD rapidly, simply, and inexpensively in more easily-accessible tissues, such as skin fibroblasts and blood (6 person months), using MAM function as the readout in both cases. This work can establish a proof of principle that the MAM hypothesis is valid, that it has predictive power, and that it is translationally relevant to this relentlessly devastating neurodegenerative disorder.

Methods of Treatment

The "MAM hypothesis" proposes that increased ER-mitochondrial connectivity is the cause of the phenotypes seen in AD, and that this connectivity is the result of aberrant sphingolipid homeostasis. In addition, described herein are results that explain how and why sphingolipid metabolism is perturbed. Based on these insights, a number of strategies to reverse the lipid dyshomeostasis have been identified, in some cases using specific compounds that are FDA-approved. We were able to reverse both the sphingolipid and MAM phenotypes—including the elevated Aβ42:Aβ40 ratio—using two FDA-approved drugs. In addition, a pharmacological approach to reverse the ER-mitochondrial hyperconnectivity is being developed, based on the inhibition of mitofusin-2 (MFN2), a known positive regulator of ER-mitochondrial apposition.

There have been a number of efforts aimed at diagnosing AD in blood—including those based on measurements of APP, Aβ, PS1, BACE1, and calcium—but essentially all have poor sensitivity and/or specificity. Diagnostic tests based on elevated lipids in blood have also been proposed, but again, sensitivity and specificity were problems. Markers of AD in fibroblasts and blood components (lymphocyes, dendritic cells) can be searched for that based on the MAM hypothesis, would be altered in AD. Candidate markers would include the ratio of cholesteryl esters:free cholesterol, the ratio of ceramide:sphingomyelin, and measurement of MAM-mediated phospholipid transport and synthesis.

Fibroblasts can be obtained from patients with FAD (with mutations in PS1, PS2, and APP), patients with SAD, and controls, and attempts to "bin" them blind (i.e. without any knowledge of who is who) can be made by assaying for markers predicted by the MAM hypothesis to be altered in AD. The assays can be performed on fibroblasts from autopsy-confirmed SAD patients and on fibroblasts from FAD patients with PS1 mutations who already have AD, compared to age- and sex-matched controls (including controls matched for ApoE status). If patients can be distinguished from controls successfully, the same assays can be performed on fibroblasts from young, asymptomatic carriers from the same FAD families but who are destined to succumb to the disease, again compared to age- and sex-matched controls, blind. If these FAD samples can be "binned", it would mean that one might be able to diagnose AD even in clinically asymptomatic individuals, i.e. the diagnosis would have predictive value. Since all the data described herein imply that MAM dysfunction in SAD patients is the same as in FAD, this prognostic value would apply to all patients destined to get AD.

Example 6

Figure 34:
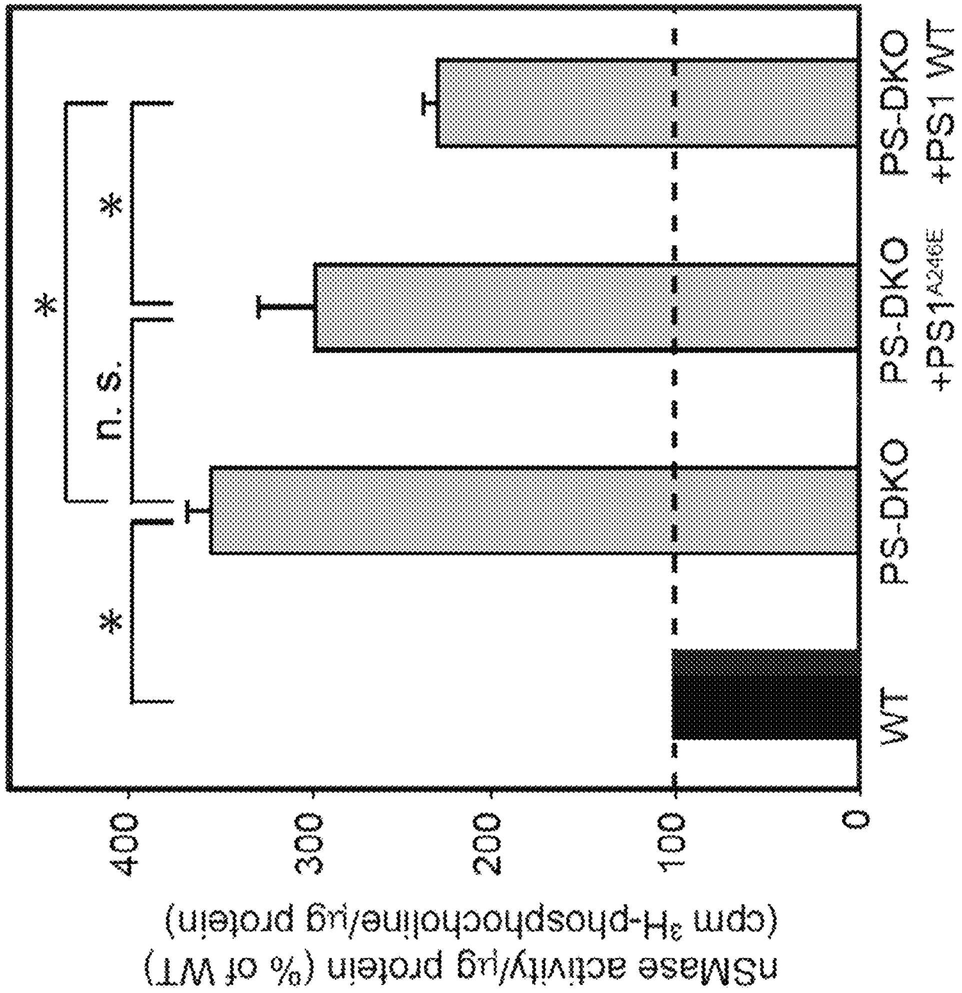
FIG. 34 shows rescue of SMase activity. Neutral SMase (nSMAse) activity is measured via conversion of 3H-sphingomyelin to ceramide+3H-phosphocholine. Mouse embryonic fibroblasts lacking PS1 and PS2 (PS-DKO) have significantly higher levels of nSMase activity compared to WT fibroblasts. Transfection of PS-DKO cells significantly reduces (i.e. improved) nSMAse activity, whereas there is no significant change in SMase activity upon transfection with PS1 harboring a known pathogenic mutation (A246E). This result demonstrates that increasing γ-secretase activity can ameliorate a MAM-related phenotype (i.e. elevated nSMase activity). *, $p<0.05$; n.s., non-significant.

Described herein is a rescue of SMase activity. Neutral SMase (nSMAse) activity can be measured via conversion of 3H-sphingomyelin to ceramide+3H-phosphocholine. Using this approach, it was discovered that mouse embryonic fibroblasts lacking PS1 and PS2 (PS-DKO) have significantly increased levels of nSMase activity (FIG. 34). Transfection of the PS-DKO cells results in a significantly reduced (i.e. improved) nSMAse activity, whereas there is no significant change in SMase activity upon transfection with PS1 harboring a known pathogenic mutation (A246E) (FIG. 34). This result demonstrates that increasing γ-secretase activity can ameliorate a MAM-related phenotype (i.e. elevated nSMase activity).

Figure 35:
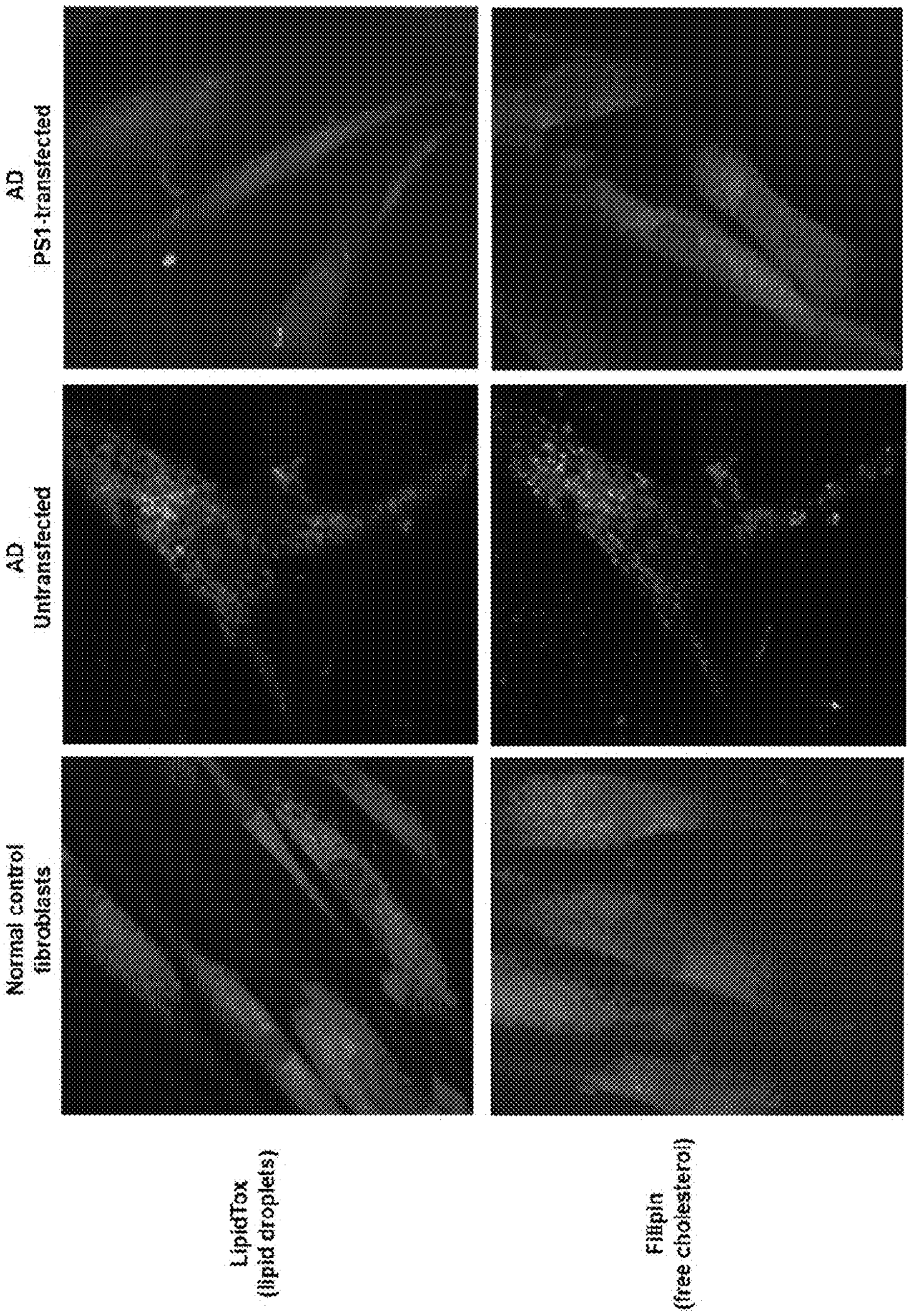
FIG. 35 shows rescue of lipid droplet deposition and free cholesterol accumulation. Staining of fibroblasts with LipidTox to visualize lipid droplets containing cholesteryl esters (LDs; in green) and with filipin to visualize free cholesterol (FC; in blue). Normal control cells have few LDs and FC whereas Alzheimer's Disease cells have numerous LDs and FC "punctae". Transient transfection of Alzheimer's Desease cells with a plasmid expressing PS1 leads to a significant decrease in the number of LDs and of FC punctae.

Described herein is a rescue of lipid droplet deposition and free cholesterol accumulation. Fibroblasts are stained with LipidTox to visualize lipid droplets containing cholesteryl esters (LDs; in green) and with filipin to visualize free cholesterol (FC; in blue) (FIG. 35). Normal control cells have few LDs and FC, whereas Alzheimer's Disease cells have numerous LDs and FC "punctae". Upon transient expression of PS1, the number of LDs and of FC punctae decreases significantly (FIG. 35). This demonstrates that increasing γ-secretase activity can ameliorate MAM-related phenotypes via a reduction in C99 as described herein.

Example 7—Increased Localization of APP-C99 in Mitochondria-Associated ER Membranes Causes Mitochondrial Dysfunction in Alzheimer Disease In the amyloidogenic pathway associated with Alzheimer disease (AD), the amyloid precursor protein (APP) is cleaved by β-secretase to generate a 99-aa C-terminal fragment (C99) that is then cleaved by γ-secretase to generate the β-amyloid (Aβ) found in senile plaques. It has been shown that γ-secretase activity is enriched in mitochondria-associated endoplasmic reticulum (ER) membranes (MAM) and that ER-mitochondrial connectivity and MAM function are upregulated in AD. Described herein is the finding that C99, in addition to its localization in endosomes, can also be found in MAM, where it is normally processed rapidly by γ-secretase. In cell models of AD, however, the concentration of unprocessed C99 increases in MAM regions, resulting in elevated sphingolipid turnover and an altered lipid composition of both MAM and mitochondrial membranes. In turn, this change in mitochondrial membrane composition interferes with the proper assembly and activity of mitochondrial respiratory supercomplexes, thereby likely contributing to the bioenergetic defects characteristic of AD.

Introduction

Familial AD (FAD) is characterized by mutations in presenilin-1 (PS1), presenilin-2 (PS2), and amyloid precursor protein (APP). APP is first cleaved by either α-secretase or 3-secretase (BACE1) to produce C-terminal fragments (CTFs) 83 aa (C83) or 99 aa (C99) long, respectively. PS1 and PS2 are the catalytic subunits of the γ-secretase complex that cleaves C83 and C99 to produce either p3 or I3-amyloid (Aβ; ~40 aa), respectively, along with the APP intracellular domain (AICD). The accumulation of Aβ, and especially its longer forms (e.g., ~42 aa), within plaques, together with Tau tangles, are the neuropathological hallmarks of AD. The deleterious effects of Aβ deposition during the symptomatic stages of AD are undeniable (Hardy & Higgins, 1992), but the role of Aβ in earlier phases of the disease is still debated.

During these early stages, AD cells exhibit alterations in numerous metabolic processes (McBrayer & Nixon, 2013; Wang et al, 2014). Among these, perturbed mitochondrial function, including reduced respiratory chain activity and ATP production, and increased oxidative stress (Du et al, 2010), have been described extensively (Swerdlow et al, 2014), occurring before the appearance of plaques (Yao et al, 2009; Wang et al, 2014). Nevertheless, the cause of the mitochondrial deficits in AD is still unknown.

In addition to mitochondrial dysfunction, alterations in lipid metabolism are another feature of AD (Mapstone et al, 2014), but their origin and relationship to APP metabolism are unclear. Among these alterations, abnormal sphingolipid metabolism has been reported in AD tissues (van Echten-Deckert & Walter, 2012). Specifically, there is an upregulation of de novo ceramide synthesis (Grimm et al, 2011) and an increase in the activity of sphingomyelinase (SMase), which catabolizes sphingomyelin (SM) into ceramide (Filippov et al, 2012). These alterations act synergistically to increase ceramide content in AD brains (Filippov et al, 2012).

As these metabolic alterations occur early in AD, they cannot be explained by the accumulation of plaques or tangles. Moreover, unsuccessful efforts directed toward modifying Aβ production as a treatment for AD (Castello et al, 2014) have raised the possibility that other aspects of APP cleavage may be contributing to these metabolic changes. In this regard, increased levels of the C99 fragment have also been shown to contribute to AD pathogenesis (Lee et al, 2006; Lauritzen et al, 2012), suggesting a role for C99 in the early stages of pathogenesis.

The processing of APP occurs in lipid raft domains (Cordy et al, 2006), which are membrane regions enriched in cholesterol and sphingolipids (Pike, 2009). While most of these domains are found in the plasma membrane, intracellular lipid rafts have also been described (Browman et al, 2006). One of these intracellular lipid rafts is called mitochondria-associated ER membranes (MAM), a functional subdomain of the ER located in close apposition to mitochondria that regulates key cellular metabolic functions (Vance, 2014).

It has been shown that presenilins and γ-secretase activity localize to MAM (Area-Gomez et al, 2009; Newman et al, 2014; Schreiner et al, 2015). Moreover, MAM functionality (Area-Gomez et al, 2012) and ER-mitochondrial apposition (Area-Gomez et al, 2012; Hedskog et al, 2013) are increased in AD.

Described herein is the finding that the concentration of unprocessed C99 at the MAM is increased in cell and animal models of AD and in cells from AD patients. This increase in MAM-localized C99 is associated with the activation of sphingolipid synthesis and hydrolysis, and with a subsequent increase in ceramide levels [notably, a feature observed in AD (Cutler et al, 2004; He et al, 2010), particularly in mitochondrial membranes (Kennedy et al, 2016)]. Finally, it is shown that these higher levels of ceramide on mitochondria cause reduced respiratory chain activity. Given these results, without being bound by theory, a critical component of AD pathogenesis is mediated by C99 toxicity through its effects on MAM and mitochondria.

Results

C99 Inhibits Mitochondrial Respiration in Presenilin-Mutant Cells

Current hypotheses regarding mitochondrial dysfunction in AD propose that this defect is the consequence of the accumulation of Aβ in mitochondria (Manczak et al, 2006), but the mechanism is unclear. To address this, mitochondrial respiration was measured in fibroblasts from FAD patients with pathogenic mutations in PS1 (M146L and A246E) and in age-matched controls, as well as in mitochondria from the brain of a knock-in (KI) mouse model expressing the M146V mutation in PS1 (PS-KIM146V) (Guo et al, 1999). We observed reduced respiration in FAD patient cells (FIG. 36A, and FIGS. 42A and P) and in mitochondria isolated from PS-KIM146V mouse brain (FIG. 42B). To understand the consequences of presenilin mutations and the effect of amyloid on mitochondrial function in AD, we measured respiration in mouse embryonic fibroblasts (MEFs) ablated for both Psen1 and Psen2 (PS-DKO) (Herreman et al, 2000). As above, we found decreased respiration in the PS-DKO cells compared to controls (FIG. 36B and FIG. 42Q). Additionally, measurements of oxygen consumption rate (OCR) in permeabilized cultures of PS-DKO cells showed clear defects in respiration (FIG. 42D). Importantly, the decrease in respiration was not due to reductions in mitochondrial content or biogenesis (FIGS. 42C, F, G, and I). Taken together, these results suggest that, from the mitochondrial perspective, cells with pathological mutations in, and ablation of, presenilins behave similarly, resulting in loss of mitochondrial respiration. Given that PS-DKO MEFs lack γ-secretase, these results suggest that mitochondrial dysfunction in these mutant cells does not depend on Aβ production.

To determine whether mutations in presenilins affect mitochondria via its role as the catalytic core of γ-secretase, we measured mitochondrial respiration in human neuroblastoma SH-SY5Y cells treated with 10 μM of the γ-secretase inhibitor DAPT. This inhibition caused a significant reduction in respiration compared to that in untreated cells (FIG. 36C and FIG. 42R) without altering mitochondrial content or biogenesis (FIGS. 42F, I, and J). This result implies that the catalytic activity of presenilins is necessary to maintain respiratory function. In addition, given that neither PS-DKO nor DAPT-treated cells produce Aβ, our results raise the possibility that the mitochondrial deficits in AD are independent of Aβ production. However, it is equally possible that alterations in full-length APP (FL-APP) or in any of its cleavage products may play a role in regulating mitochondrial respiration. To test this, we measured oxygen consumption in MEFs in which App and its paralog Aplp2 were knocked out (APP-DKO) (Zhang et al, 2013). Contrary to what we found in presenilin-mutant cells, elimination of APP and APLP2 had no detrimental effects on respiration (FIG. 36D). In fact, the OCR in permeabilized APP-DKO cells was slightly but significantly increased compared to that in controls (FIG. 36D and FIGS. 42E and T).

Considering that PS-DKO cells and APP-DKO cells both lack Aβ and AICD, our results suggest that the difference in mitochondrial function observed in these two cell models was due to the presence or absence of FL-APP or its cleavage products, C99 and C83. We therefore measured respiration in PS-DKO cells treated with BACE1 inhibitor IV (BI) (FIG. 36E and FIG. 42S) and with an α-secretase inhibitor (TAPI-1) (FIG. 42H) to abrogate the production of C99 and/or C83, respectively. As controls, we added back physiological concentrations of Aβ and oligomers of Aβ42 (FIG. 42K-M). Remarkably, only the treatment with BI rescued the respiration defects, both in PS-DKO cells (FIG. 36E and FIG. 42S) and in FAD fibroblasts (FIG. 42N), suggesting that increased levels of unprocessed C99, rather than the levels of Aβ, play a role in the mitochondrial dysfunction seen in AD. Supporting this, addition of Aβ oligomers to APP-DKO cells had little effect on respiration (FIG. 42M), whereas APP-DKO cells expressing C99 suffered a significant decrease in respiration, which was accentuated by adding DAPT (FIG. 36D and FIG. 42T), without changes in the content of mitochondria (FIG. 42O).

C99 can be Localized in MAM

APP and its cleavage products have been shown to colocalize with almost every membranous compartment in the cell, including mitochondria (Devi & Ohno, 2012). Thus, it is possible that in AD cells, C99, as previously suggested for Aβ (Casley et al, 2002), is retained on mitochondrial membranes, disrupting its regulation.

To explore the localization of C99 and C83, we isolated subcellular fractions from mouse brain (Area-Gomez, 2014) (FIG. 43A) and analyzed them by Western blot [this was also validated in an identical fractionation of mouse liver (FIG. 43B)], using specific markers for each compartment. Interestingly, we found that APP-CTF fragments, while present in all compartments, were enriched significantly in MAM regions of the ER (FIG. 37A).

To discriminate between the localization of C83 and C99, we isolated subcellular fractions from SH-SY5Y cells treated with DAPT (to prevent cleavage of C99 and C83), or treated with α- and γ-secretase inhibitors (TAPI-1 and DAPT, to prevent the generation of C83 and the cleavage of C99, respectively, thereby revealing the presence only of C99). Notably, Western blot analysis of these fractions showed that while C83 was present in all samples (i.e., cells treated only with DAPT), C99 was located preferentially in MAM (i.e., fractions from cells treated with TAPI-1 and DAPT) (FIG. 37B).

Many reports have shown that C99 is localized mainly in endosomes (Haass et al, 2012; Das et al, 2016). Therefore, it is possible that the presence of C99 in MAM regions was the result of a cross-contamination of MAM samples with endosomes during the process of subcellular fractionation. To eliminate this possibility, we isolated cellular membranes from mouse brain and separated them through continuous density sucrose gradients (FIG. 43C), to allow us to purify MAM away from endosomes and other subcellular fractions. After gradient centrifugation, we examined the distribution of C83 and C99 compared to markers for other compartments (FIG. 37C). Consistent with the data of others (Das et al, 2016), FL-APP and BACE1 co-migrated partially with a marker for endosomes (Rab7), but not with lysosomal, ER-intermediate, or MAM markers (FIG. 37C). Similarly, the APP-CTFs C83 and C99 co-migrated with endosomal and lysosomal markers (Rab5, Rab7, and LAMP-2) (Haass et al, 2012; Das et al, 2016), whereas PS1 co-migrated with MAM markers, such as FACL4 (Area-Gomez et al, 2009; Newman et al, 2014; Schreiner et al, 2015). We reasoned that the difficulty in seeing APP-CTFs and PS1 together was probably due to the rapid cleavage of the CTFs by γ-secretase once both are in the same compartment. Thus, to circumvent this rapid cleavage and determine C99 localization, we repeated the same analysis using PS-DKO cells (Herreman et al, 2000) in which APP-CTFs are not cleaved, due to the absence of presenilins (FIG. 42G). Western blot analysis in this case showed that, in addition to its localization in endosomes, a significant fraction of unprocessed C99 co-migrated with MAM markers (FIG. 37D).

To validate this result by imaging, we transfected wild-type (WT) MEFs and COS-7 cells with plasmids expressing fluorescently tagged C99 and mitochondrial and ER markers, and in the absence (FIG. 43D) or presence (FIG. 37E) of γ-secretase inhibitors. Confocal microscopy analysis revealed that C99 (in red) was present mainly in the cytosol and in ER membranes (in green), as shown previously by others (Das et al, 2016). In addition to those sites, C99 (in red) also colocalized with regions where both ER (in green) and mitochondria (in blue) were present (white arrows in FIG. 37E and FIG. 43D). This suggests that, like presenilins (Area-Gomez et al, 2009), C99 can be localized to areas of the ER apposed to mitochondria, that is, MAM, and is consistent with the fact that γ-secretase activity is present in this compartment (Area-Gomez et al, 2009; Schreiner et al, 2015).

Figure 43E:
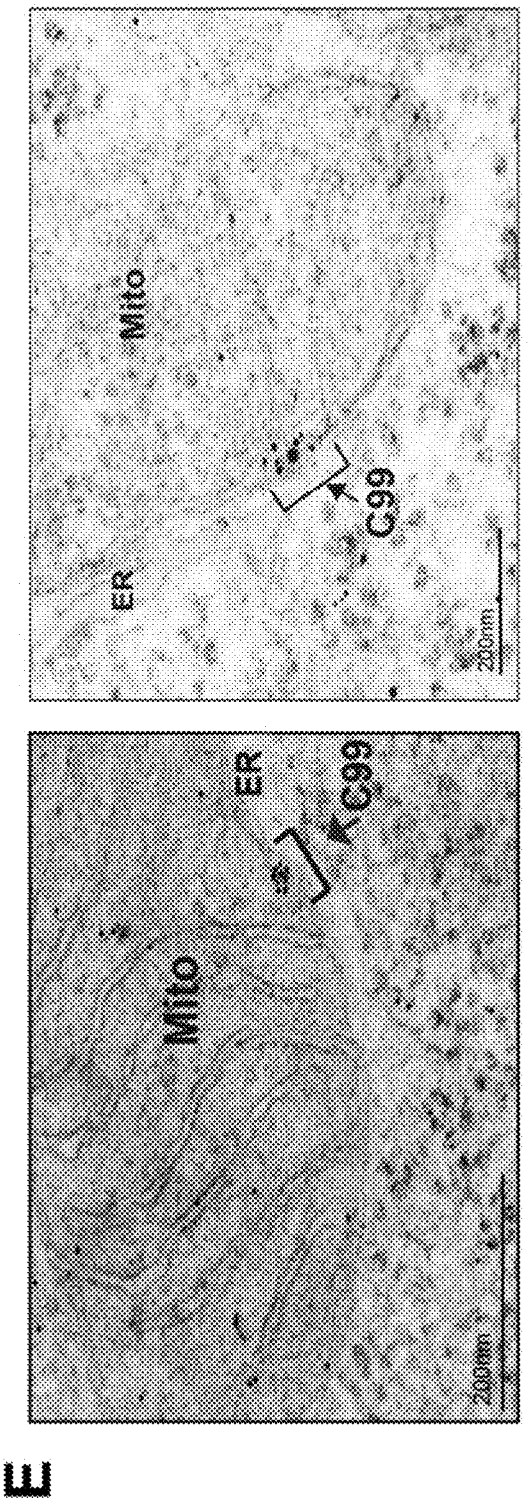
Figure 43F:
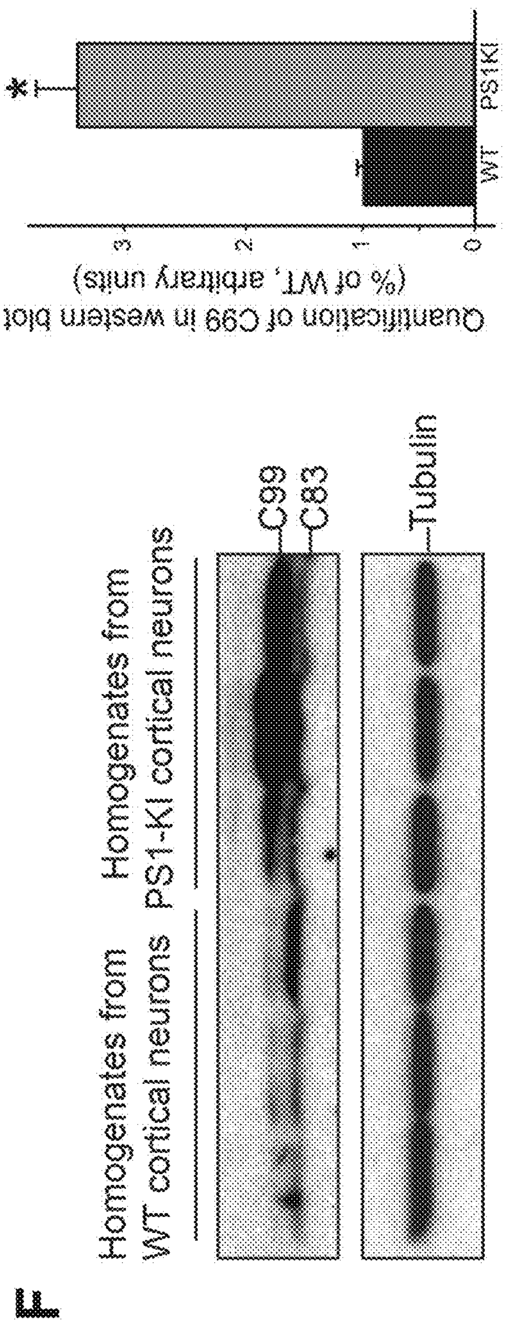

To corroborate this result, we analyzed the localization of unprocessed C99 by immunogold electron microscopy (iEM) of PS-DKO cells, using antibodies against C-terminal regions of APP. In agreement with the confocal and Western blot analyses, iEM images indicated that, when uncleaved, C99 can be localized in MAM regions of the ER (FIG. 37F and FIG. 43E).

Figure 43G:
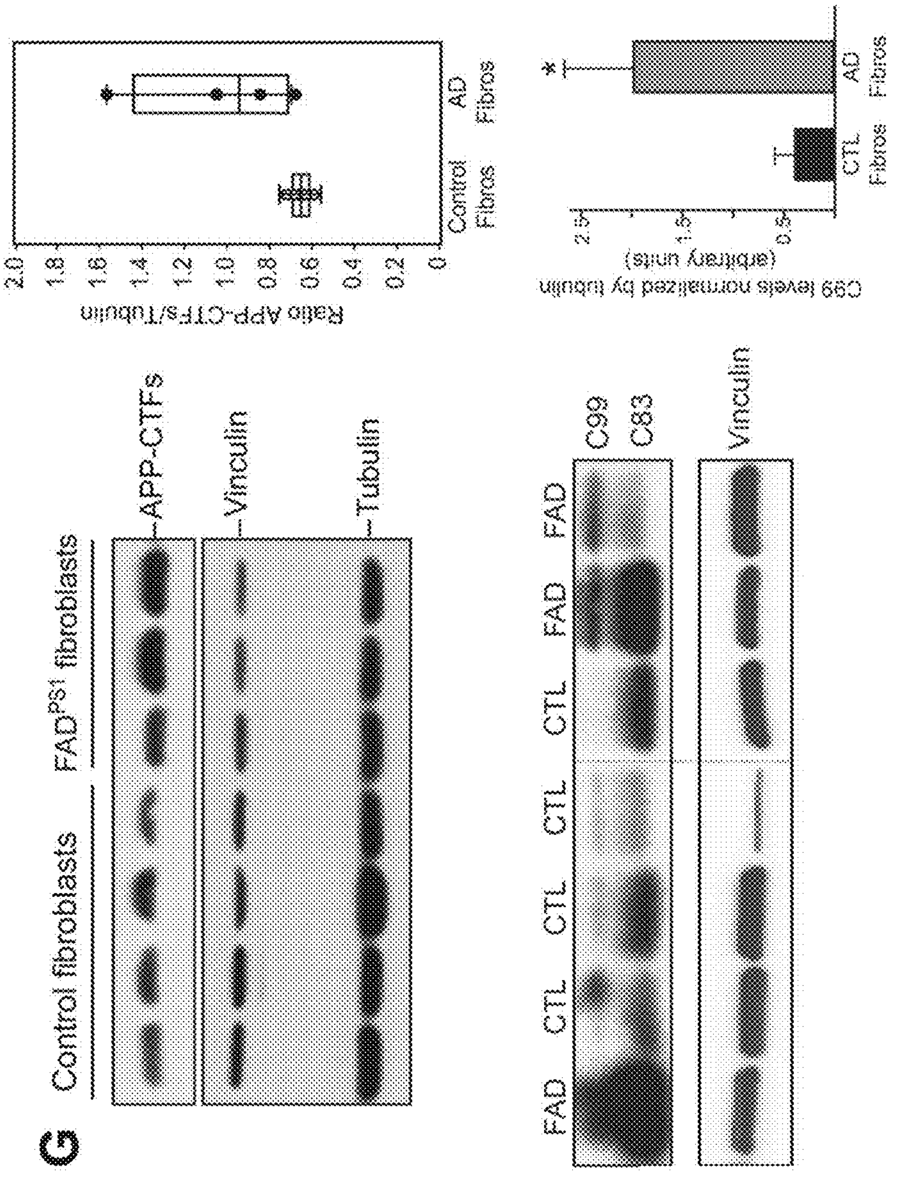
Figure 43H:
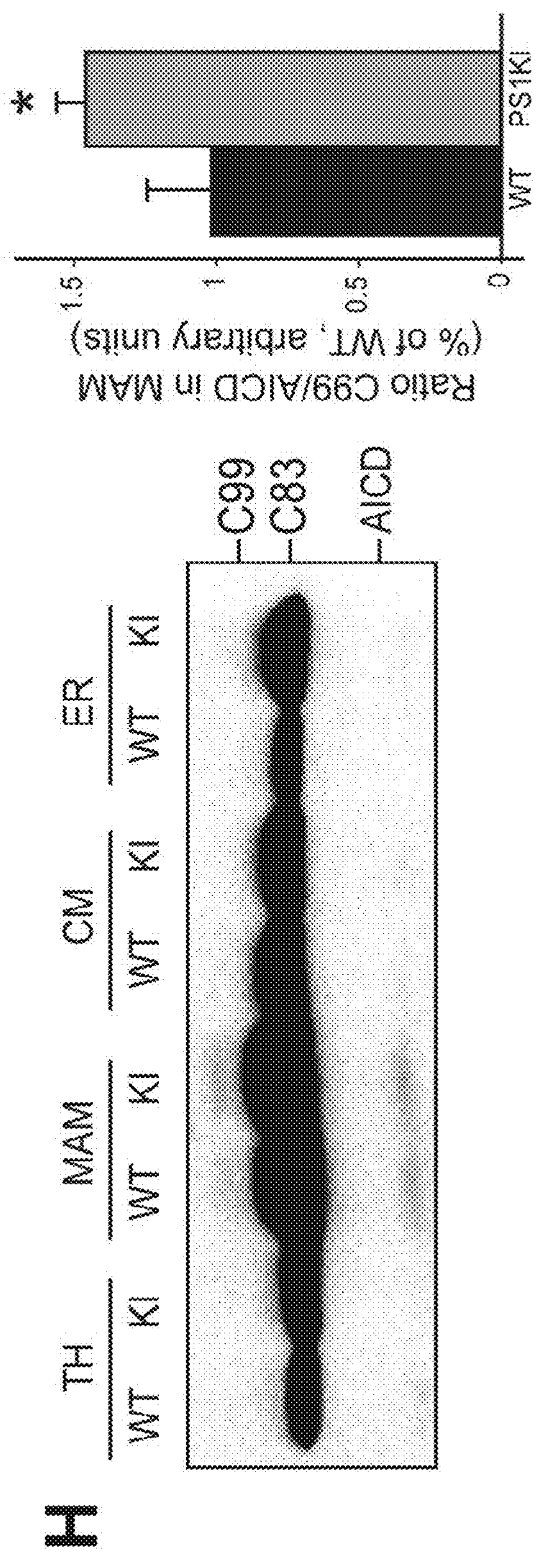

We next asked whether the increased localization of C99 in the MAM also occurred in the context of AD, as tissues from AD patients and animal models show increases in this fragment (Holsinger et al, 2002). We measured C99 levels by Western blot in homogenates from embryonic cortical neurons from WT and PS1-KIM146V mouse brain (Guo et al, 1999) (FIG. 43F), as well as from cells from AD patients and controls (FIG. 43G). Notably, there was more C99 in the homogenates of mutant neurons and of cells from AD patients, than in those from controls (FIGS. 43F and G), similar to previous findings in other AD patients and in FAD mice (McPhie et al, 1997; Yang et al, 2003; Rockenstein et al, 2005). In addition, Western blot analysis of subcellular fractions isolated from WT and PS-KIM146V mouse brain also showed an increase in the levels of C99 in the mutant samples, and especially in the MAM fractions, compared to that in controls (FIG. 43H), while the relative concentration of AICD was not changed significantly (FIG. 43H).

Taken together, the results described herein suggest that C99, after being produced in endocytic compartments (Das et al, 2016), is targeted to MAM, via an as-yet unknown mechanism, to be cleaved rapidly by γ-secretase. Moreover, both pathogenic mutations in PS1 and reductions in γ-secretase activity cause the retention of this fragment in this region of the ER that is in close apposition to mitochondria.

Figure 38A:
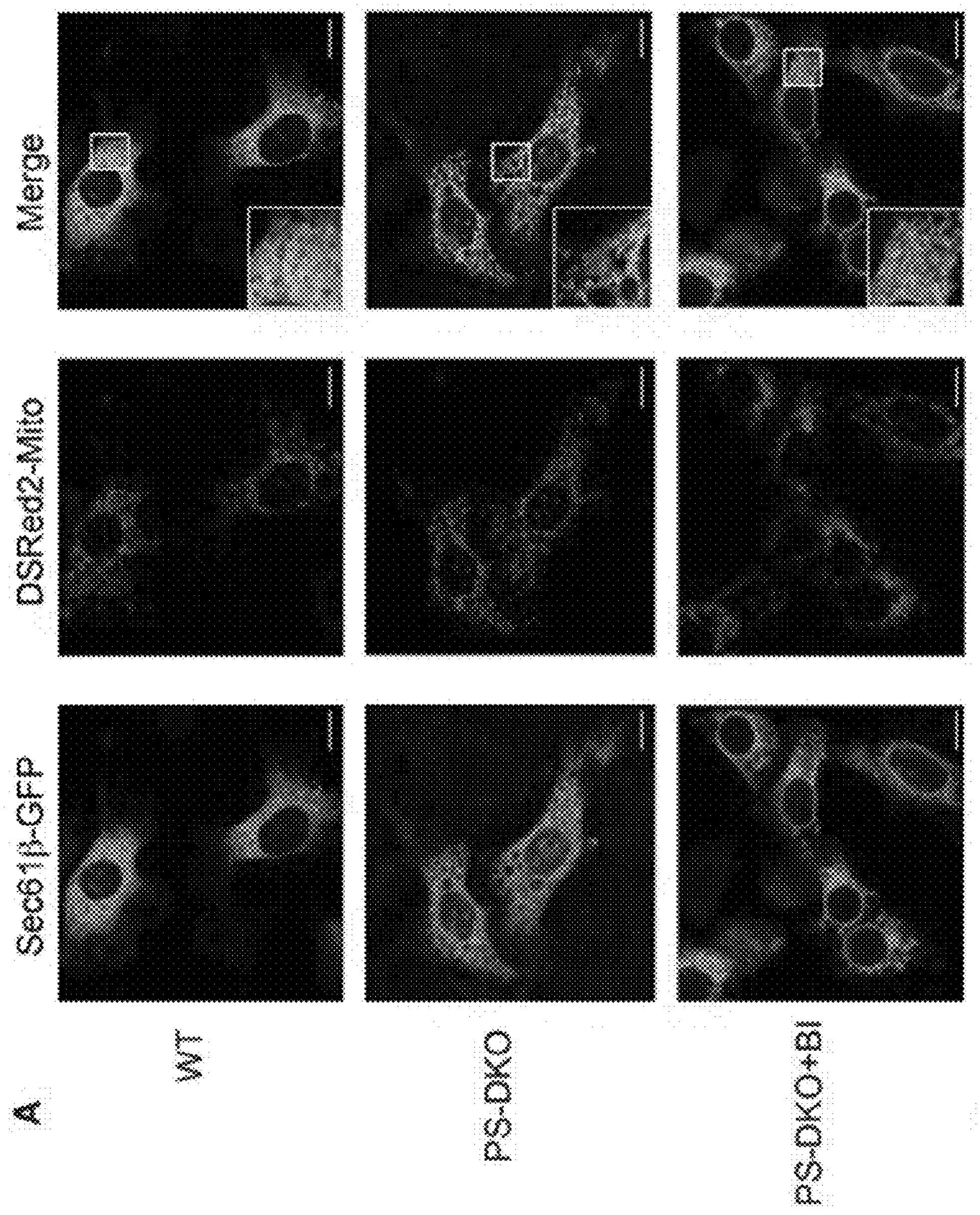
Figure 38D:
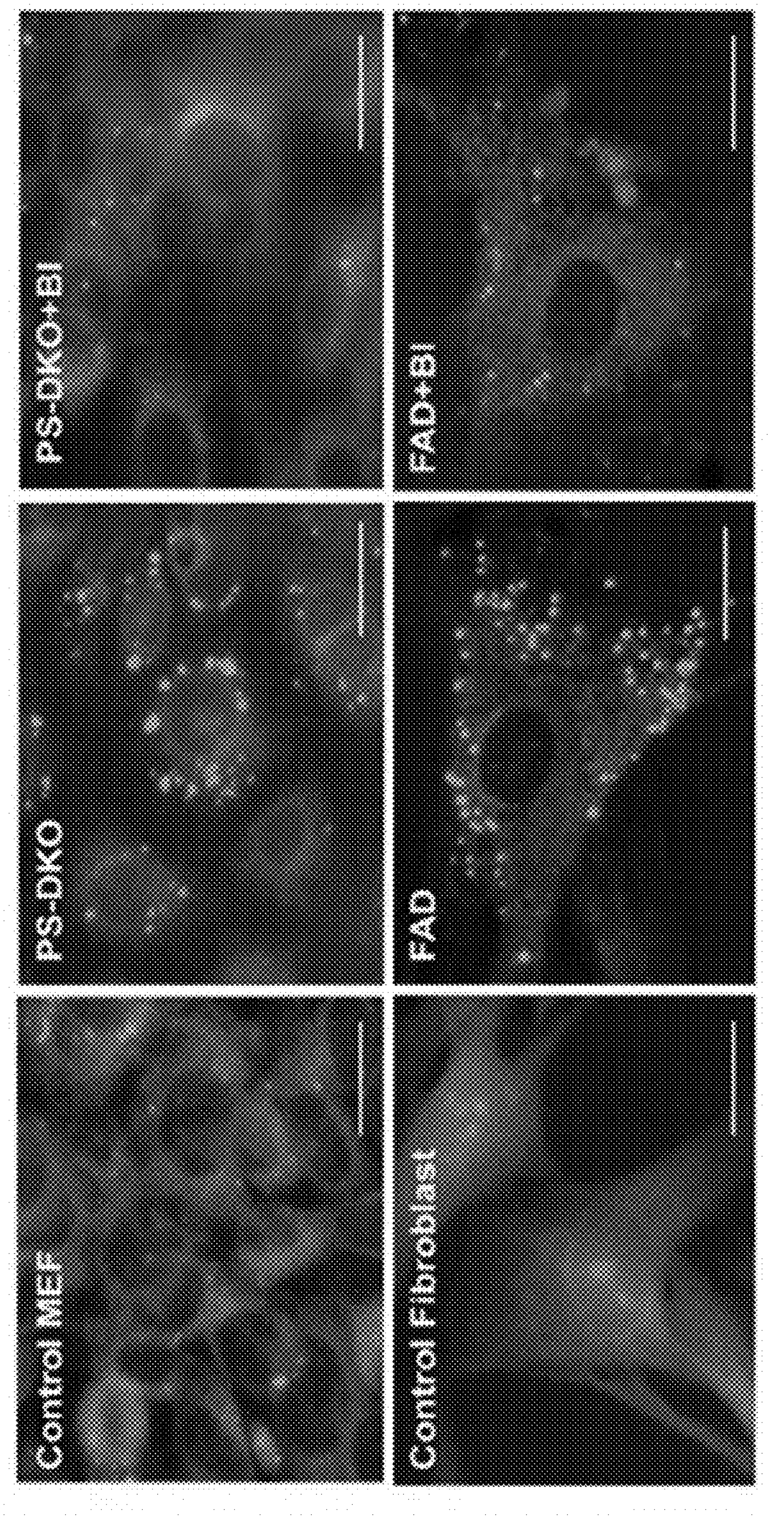

Increased Localization of C99 at MAM Upregulates MAM Functionality and ER-Mitochondrial Apposition Given that reduced γ-secretase activity causes an accumulation of C99 at the MAM, we asked whether elevated C99 could be the cause of the increased ER-mitochondria apposition and MAM upregulation seen in AD (Area-Gomez et al, 2012). To assess apposition, we transfected control and PS-DKO cells with markers of ER and mitochondria, and measured their colocalization (de Brito & Scorrano, 2008; Area-Gomez et al, 2012) in the absence or presence of BI to prevent the generation of C99; remarkably, incubation with BI rescued the upregulation of ER-mitochondria apposition seen in mutant cells (FIGS. 38A and B).

Figure 44C:
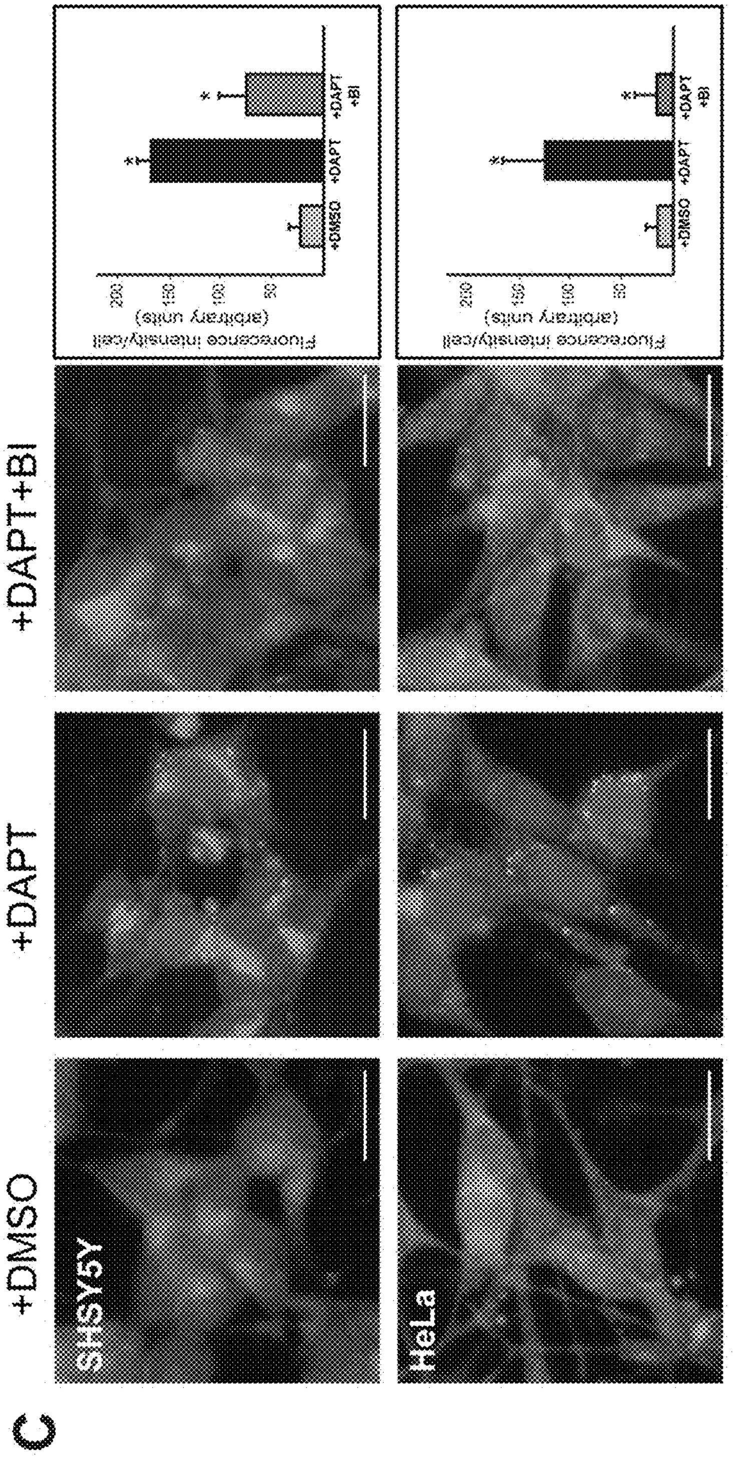
Figure 44D:

To assess the effect of C99 on MAM functionality, we measured the conversion of cholesterol to cholesteryl esters by ACAT1, a MAM-resident enzyme (Area-Gomez et al, 2012), and monitored the accumulation of newly synthesized cholesteryl esters in lipid droplets (LDs) (Area-Gomez et al, 2012). Treatment with BI reduced the incorporation of cholesterol into cholesteryl esters (FIG. 38C) and reduced the number of LDs in PS-DKO cells, in AD patient fibroblasts (FIG. 38D), and in PS1-KIM146V mouse astrocytes and cortical neurons (FIG. 44A). Similarly, treatment of PS-DKO cells with Gleevec, an anticancer drug that has been recently shown to reduce APP cleavage by BACE (Netzer et al, 2017), resulted in a significant reduction of LDs in PS-DKO cells (FIG. 44B). Lipid droplets also accumulated in SH-SY5Y and HeLa cells treated with DAPT alone (i.e., increasing C99), which was reversed in cells treated with DAPT+BI (i.e., preventing C99 formation) (FIG. 44C). Supporting these data, and contrary to what we observed in γ-secretase-deficient cells but in agreement with what we saw in the DAPT+BI treated cells, MEFs in which BACE1 had been knocked out (Luo et al, 2001) were essentially devoid of LDs in the cytosol (FIG. 44D).

Taken together, these results show that the increase in, and retention of, uncleaved C99 in the MAM induces both a physical and functional enhancement of ER-mitochondria connections.

Sphingolipid Metabolism is Perturbed in AD-Mutant Cells

Given that MAM is a lipid raft (Area-Gomez et al, 2012), C99 could have a role in MAM activity and in ER-mitochondrial connectivity through changes in MAM lipid composition (Simons & Vaz, 2004). We therefore performed lipidomic analyses of total homogenates, mitochondrial fractions, and isolated MAM from PS-DKO MEFs and controls. We found a significant increase in ceramide (FIG. 39A and FIG. 45A, left panel) and a parallel decrease in sphingomyelin in mutant cells (FIG. 39B and FIG. 45B, right panel), which was more pronounced in the mitochondrial (FIGS. 39A and B, and FIG. 45B) and MAM (FIG. 39C and FIG. 45C) fractions than in total homogenates. To confirm the presenilin-dependent nature of these lipid alterations, we transfected the PS-DKO cells with plasmids expressing either PS1WT or PS1A246E (FIGS. 45D and E). Notably, expression of PS1WT, but not PS1A246E, was capable of partially rescuing the alteration in sphingolipid content in PS-DKO cells (FIG. 45F).

Moreover, there was an inverse relationship between the amounts of individual sphingomyelin species present and those of the corresponding ceramide species (FIG. 45G). The latter result suggested that there was an increase in the hydrolysis of sphingomyelin by sphingomyelinases (SMases) and subsequent upregulation of the de novo synthesis of SM to replace its loss (FIG. 39D). In agreement with this idea, PS-DKO cells showed a significantly higher synthesis of both ceramide and sphingomyelin vs. WT (FIG. 39D). In addition, acidic (aSMase) and neutral (nSMase) SMase activities were increased in the PS-DKO cells (FIG. 39E), with a more dramatic upregulation of nSMase activity, correlating with increased expression of neutral sphingomyelinase 2 (nSMase2; gene Smpd3) (FIG. 45H). We also observed increases in both acid and neutral SMase activities in PS1-KIM146V mouse brain (FIG. 45I). Likewise, we replicated the increase in SMase activity in SH-SY5Y cells by inhibiting γ-secretase activity (FIG. 45J), suggesting that the effects of mutated presenilins on sphingolipid metabolism occur via their roles as proteases in γ-secretase. In agreement with this view and with our lipidomics results, expression of PS1WT, but not PS1A246E, significantly blunted the upregulation of nSMase activity in PS-DKO cells (FIG. 45K).

To understand whether these effects were direct or were mediated by APP and/or its cleavage products, we measured SMase activity in APP-DKO cells. Contrary to what we found in PS-DKO and DAPT-treated cells, APP-DKO cells showed significant decreases in both sphingolipid synthesis (FIG. 45L) and SMase activities (FIG. 45M). As mentioned previously, both PS-DKO and APP-DKO cells lack Aβ and AICD. Therefore, any difference in sphingolipid regulation between the two cell types must be due to the presence or absence of full-length APP and/or C83 and C99. We therefore measured SMase activities in PS-DKO cells treated with α- and β-secretase inhibitors to test the effect of C83 and C99, respectively, as well as in PS-DKO cells in which Aβ and AICD were added back (FIG. 45N). Interestingly, only the inhibition of C99 production (by BI) resulted in an attenuation of sphingolipid synthesis and hydrolysis by sphingomyelinases (FIG. 39E). These results indicate that it is the increase in C99 that causes the upregulation of sphingolipid metabolism, resulting in the previously described elevations in ceramide in AD (Filippov et al, 2012). However, they did not clarify why ceramide is particularly elevated in MAM and mitochondrial membranes.

MAM Participates in the Regulation of Sphingolipid Metabolism

Previous reports have suggested that MAM is involved in regulating sphingolipid metabolism, affecting mitochondrial activity (Ardail et al, 2003). In fact, mitochondria are reported to contain ceramide, probably generated at MAM (Kogot-Levin & Saada, 2014). Taking these and our data into account, without being bound by theory, an increase in ceramide synthesis and in SMase activity at ER-mitochondria connections could explain the increased ceramide in mitochondrial membranes in AD.

To address this, we analyzed ceramide synthesis and SMase activity in vitro, using subcellular fractions from WT and PS-DKO cells. The results indicate that MAM indeed participates in regulating sphingolipid metabolism (FIG. 40A and FIG. 46A). Moreover, SMase activities were upregulated significantly in subcellular fractions from PS-DKO cells compared to controls (FIG. 40A), as well as in MAM from PS1-KIM146V mouse brain (FIG. 46B). In agreement with these results, Western blot analysis revealed a remarkable increase in the localization of nSMase to MAM in mutant cells compared to WT (FIG. 40B), suggesting higher recruitment of SMase to these ER-mitochondria contacts.

To explore this further, we incubated PS-DKO and control cells with fluorescent sphingomyelin and analyzed its localization and conversion to ceramide in mitochondrial membranes by thin-layer chromatography (TLC). Presenilin-mutant cells showed a substantial decrease in fluorescent sphingomyelin intensity (FIG. 40C) which was paralleled by an increase in fluorescent ceramide (FIG. 40C), implying that upregulated SMase activity may be responsible for this inverse behavior. Remarkably, the elevated deposition of ceramide at mitochondria disappeared when mutant cells were treated with BI (FIG. 40C). These data suggest that the effect of BACE1 inhibition in enhancing mitochondrial respiration (FIG. 36E and FIG. 42N) may occur via the attenuation of sphingolipid metabolism in mutant cells.

We questioned why there was an increased recruitment of nSMase to these ER regions in PS-mutant cells. It is well known that SMase activity is modulated by membrane characteristics and lipid composition (De Tullio et al, 2007). Notably, SMase activity is higher in lipid raft-like domains, such as MAM, where liquid-ordered and liquid-disordered phases coexist (Silva et al, 2009). In addition, nSMase shows increased affinity for membranes enriched in anionic phospholipids (Wu et al, 2011). In particular, the activity of nSMase2 is stimulated upon its binding to phosphatidylserine (PtdSer) (Wu et al, 2011). To see whether elevated PtdSer might be behind the increased recruitment of nSMase activity to MAM in mutant cells, we analyzed the content of PtdSer in WT and PS-DKO homogenates and in subcellular fractions. We found a significant increase in the amount of PtdSer in PS-DKO membranes, which was most pronounced in the MAM domains of the ER (FIG. 46C). This result also supports the idea that increases in PtdSer due to C99-mediated upregulation of MAM are driving the increased SMase activity in these ER regions. Consistent with this proposed mechanism, inhibition of C99 production (with BI) reduced the PtdSer content of PS-DKO membranes to control levels (FIG. 46D), while at the same time reversing the alterations in both sphingomyelin (FIG. 46E) and ceramide (FIG. 46F).

Taken together, we conclude that retention of uncleaved C99 in MAM in presenilin-deficient cells upregulates both the synthesis and catabolism of sphingomyelin in these regions of the ER, likely accounting for the increased ceramide in mitochondrial membranes (FIG. 39A) via ER-mitochondrial connections.

Mitochondrial Dysfunction in AD is Caused by Upregulated Sphingolipid Turnover

The detrimental effects of ceramide on mitochondrial functionality have been shown extensively (Kogot-Levin & Saada, 2014). Thus, the upregulation of SM turnover at MAM and the subsequent local increase in ceramide could be the underlying cause of the respiratory deficits seen in AD (Du et al, 2010; Swerdlow et al, 2014). To test this idea, we measured respiration in PS-DKO mutant cells treated with 5 μM myriocin, a specific inhibitor of serine palmitoyltransferase, the first step in the de novo pathway to synthesize sphingolipids, including ceramide. Inhibition of sphingolipid synthesis by myriocin resulted in slight decreases in sphingomyelin (FIG. 47A) but in significant reductions in ceramide content (FIG. 47B) in our cell models, with changes in the latter more pronounced in PS-DKO cells (FIG. 47B). This reduction in ceramide rescued the bioenergetic defect in these mutant cells (FIG. 41A).

Ceramide has been shown to provoke changes in mitochondrial lipid composition, altering its membrane potential and permeability (Kogot-Levin & Saada, 2014). Notably, the lipid composition of mitochondrial membranes is crucial for the stabilization and assembly of mitochondrial respiratory complexes into supercomplexes (also called respirasomes) necessary for optimal respiratory chain function (Acin-Perez & Enriquez, 2014). Therefore, it is possible that ceramide interferes with bioenergetics by destabilizing or preventing supercomplex assembly. To assess this, we used blue-native gel electrophoresis (Acin-Perez et al, 2008) to examine the activity (FIGS. 41B and C) and assembly status (FIGS. 47C and D) of supercomplexes in mitochondria from WT and PS-DKO cells, from DAPT-treated WT cells, and from PS-DKO cells incubated with BI and myriocin (FIG. 41B). Measurements by in-gel staining of the activities of respiratory chain complexes I and IV (FIGS. 41B and C) and Western blotting to detect subunits of complexes I and III from PS-DKO and DAPT-treated WT cells (FIGS. 47C and D) showed a decrease in the activity of supercomplexes I+III+IV, I+III, and III+IV, which could be rescued after treatment with BI and myriocin (FIGS. 41D and E). Importantly, these changes in supercomplex activities and assembly were not due to alterations in the expression of individual complex subunits (FIG. 47E).

To corroborate these results in vivo, we analyzed mitochondrial respiration and supercomplex activity in mitochondria isolated from brain tissue from PS1-KIM146V mice at various ages (FIGS. 48A and B). Interestingly, while MAM defects were already present in fetal cortical neurons (FIG. 44A), decreases in mitochondrial respiration became significant only after 3 months of age (FIG. 48A). In agreement with our previous results, this bioenergetic defect correlated with a significant decrease in supercomplex activity in mutant samples compared to controls (FIGS. 48C and D).

Taken together, these results indicate that the bioenergetic defects in AD are likely to be the consequence of upregulated sphingolipid turnover and increased ceramide content in mitochondria, triggered by the retention of C99 at the MAM. This elevation in ceramide levels alters mitochondrial membrane properties, likely hindering the assembly and activity of respiratory supercomplexes. Moreover, these data suggest that while mitochondrial dysfunction is an early and significant defect in AD, it is not a primary insult in the pathogenesis of the disease, but rather is a consequence of MAM dysfunction.

Discussion

In previous reports, it was shown that γ-secretase activity is localized in MAM (Area-Gomez et al, 2009) and that alterations in γ-secretase activity result in the upregulation of MAM function and in increased ER-mitochondria apposition (Area-Gomez et al, 2012). Described herein is the finding that the γ-secretase substrate C99, in addition to its endosomal localization, is also present in MAM domains. Thus, both the γ-secretase enzyme activity (i.e., presenilins) and its direct substrate (i.e., C99) are located in the same compartment, where the former can cleave the latter. Moreover, chemical and genetic alterations of γ-secretase activity provoke a significant increase in the amount of this APP processing fragment in ER-MAM regions. The increased presence of C99 in MAM causes the upregulation of MAM functionality (as measured by ACAT1 activity) and greater apposition between ER and mitochondria. In addition, the higher concentration of MAM-localized C99 induces the recruitment of sphingomyelinase to this ER domain and the subsequent deregulation of sphingolipid homeostasis, followed by mitochondrial dysfunction.

These results support a model in which, in addition to Aβ, increased C99 plays an early role in AD pathogenesis, via altered MAM function. Of course, these results do not exclude the possibility that C99 has other roles in the pathogenesis of AD. In fact, increases in C99 were already shown to contribute to other aspects of the pathogenesis of the disease (Saito et al, 2011; Lauritzen et al, 2012), including endosomal dysfunction (Jiang et al, 2010), hippocampal degeneration (Lauritzen et al, 2012), and altered Tau proteostasis (Moore et al, 2015). In addition, elevations in C99 are toxic to neurons (Neve et al, 1996), correlating with symptoms of the disease (Rockenstein et al, 2005; Tamayev et al, 2012). Importantly, we note that although much of our data were obtained using FAD models and cells from FAD patients containing mutations in presenilins, alterations in γ-secretase activity and increased levels of C99 have been detected in sporadic AD patients as well (Fukumoto et al, 2002; Yang et al, 2003; Li et al, 2004; Pera et al, 2013).

Without being bound by theory, it appears that while the majority of C99 resides in endosomes, C99 can traffic to MAM regions in the ER, where it is cleaved rapidly by γ-secretase to produce Aβ and AICD (Area-Gomez et al, 2009; Schreiner et al, 2015). We note that although the mechanism by which C99 translocates to ER-MAM is unknown, recent work has demonstrated the existence of ER-endosome contacts (Rowland et al, 2014) where lipid and protein exchange may occur (Wilhelm et al, 2017). Thus, without being bound by theory, it is possible that C99 is delivered to ER via a similar mechanism, where it regulates the interaction between ER and mitochondria. Furthermore, the localization of C99 at MAM clarifies why C99, an ER-localized protein (Matsumura et al, 2014), was also detected in mitochondria (Devi & Ohno, 2012). Similarly, since C99 processing occurs at MAM, this could explain why Aβ has been found to colocalize with mitochondria (Hansson Petersen et al, 2008; Xie et al, 2013).

We show here that chemical or genetic alteration of γ-secretase activity results in an increase in unprocessed C99 in MAM. This, in turn, provokes the recruitment of SMase activity to MAM and the upregulation of sphingolipid turnover at these sites. These findings have mechanistic implications. Specifically, one of the MAM functions that is increased in AD is the synthesis of PtdSer by phosphatidylserine synthases 1 and 2 (PTDSS1/2) (Vance, 2014; Kannan et al, 2017 #2382, Wu & Voelker, 2004; Area-Gomez et al, 2012 #234), resulting in higher levels of this phospholipid in MAM and other membranes in AD cells and tissues. Considering the affinity of nSMase for PtdSer (Wu et al, 2011), the activation of nSMase by C99 is due, at least in part, to the upregulation of PTDSS1/2 in MAM, triggered by the increased concentration of this APP fragment.

These results also help clarify a number of previous observations. First, as MAM contains γ-secretase and SMase activities, the data described herein helps explain why changes in APP processing can induce alterations in sphingolipid regulation (Filippov et al, 2012; Lee et al, 2014). Second, upregulation of SMase and the resulting increase in ceramide are known to alter the size and composition of lipid raft domains (Dinkla et al, 2012), such as MAM. Therefore, an increased localization of C99 in MAM in AD may explain the upregulation of ER-mitochondria connections and MAM functionality seen in the disease (Area-Gomez et al, 2012; Hedskog et al, 2013). Finally, given the detrimental effect of ceramide on mitochondrial supercomplex assembly and respiratory chain activity (Zigdon et al, 2013), we conclude that its accumulation is likely to be a primary cause of mitochondrial dysfunction in AD.

This last conclusion disagrees with proposals that the accumulation of Aβ42 oligomers in mitochondria triggers the mitochondrial defects seen in AD (Manczak et al, 2006). Rather, our results show that PS-DKO and DAPT-treated cells, in which Aβ production is inhibited, can nevertheless recapitulate the mitochondrial deficits seen in AD. This finding suggests that mitochondrial deficiencies are due to increased levels of C99 rather than to elevated production of longer Aβ species, since bioenergetic deficiency can occur in the absence of Aβ. We believe that the discrepancy between our results and those of others showing reductions in mitochondrial respiration after incubation with Aβ (Casley et al, 2002) is due mainly to the use of unphysiologically high concentrations of this peptide (Casley et al, 2002). Thus, it is proposed that MAM and mitochondrial alterations are caused by an increased ratio of C99:Aβ, rather than by an increased ratio of Aβ42:Aβ40. In agreement with this, the increase of C99 in mitochondria in AD has been described before, correlating with mitochondrial respiratory defects that could be rescued by partial deletion of BACE1 (Devi & Ohno, 2012). Finally, our results linking C99, rather than higher levels of Aβ42, to mitochondrial dysfunction help explain how mitochondrial alterations can occur early in AD pathogenesis (Balietti et al, 2013), preceding the appearance of Aβ-containing plaques (Yao et al, 2009).

In summary, our data demonstrate that increased levels of unprocessed MAM-localized C99 are a driver of mitochondrial dysfunction in AD, mediated by the loss of sphingolipid homeostasis at ER-mitochondria connections. Equally important, while the toxicity of Aβ is undeniable, described herein is a role for elevated C99 (Rockenstein et al, 2005) and MAM deregulation (Schon & Area-Gomez, 2010, 2013) in the pathogenesis of the disease, thus providing a new framework for understanding the link between alterations in APP processing and lipid homeostasis as seminal effectors of AD pathogenesis. Further work is required to fully elucidate the mechanism by which MAM-C99 induces these alterations and validate its relevance in the pathogenesis of this devastating disease.

Materials and Methods

Cells, Animals, and Reagents

AD and control cell lines were obtained from the Coriell Institute for Medical Research (Camden, N.J., USA). SH-SY5Y and COS-7 cells were obtained from the American Type Culture Collection. Other PS1-mutant FAD cells were the kind gift of Dr. Gary E. Gibson (Cornell University). WT, PS1-KO, PS2-KO, and PS1/2-DKO (called PS-DKO) mouse MEFs were provided by Dr. Bart De Strooper (University of Leuven). APP/APLP2-KO (called APP-DKO) (Herms et al, 2004) and PS1-KIM146V knock-in mice (Guo et al, 1999). All experiments were performed according to a protocol approved by the Institutional Animal Care and Use Committee of the Columbia University Medical Center and were consistent with the National Institutes of Health Guide for the Care and Use of Laboratory Animals. Mice were housed and bred according to international standard conditions, with a 12-h light/12-h dark cycle, and sacrificed at 3, 5, 7, 8, and 12 months of age. Brains were removed and homogenized for Western blot and Seahorse analysis. All the experiments were performed on at least three mice per group.

We used antibodies to ACAT1 (Abcam, ab39327), APP C-terminal (Sigma; A8717, polyclonal), APP-C99 [Covance; SIG-39320-200 (6E10), monoclonal], the α-subunit of mitochondrial ATP synthase (complex V) (Invitrogen; 459240), the α-subunit of ATPase (Abcam, ab7671), BACE1 (Cell Signaling; D10E5), CANX (Chemicon, MAB3126), CDH2 (ref), complex I subunit NDUFA9 (Abcam; ab14713), complex III subunit core-1-ubiquinol-cytochrome c reductase (Abcam; ab110252), OxPhos complex IV subunit IV (COX IV) (Abcam; ab14744), Ergic53/p58 (Sigma; E1031), Erlin-2 (Cell Signaling; #2959), ERp72 (Cell Signaling, D70D12), FACL4 (Abgent, Aβ2536b), GM130 (BD Transduction Laboratories, 610822), G6PC (ref), Lamp2 (Novus biologicals; NBP1-71692), Na+/K+ ATPase (Abcam, ab7671), PEMT (a gift of Jean Vance, University of Alberta), Presenilin 1 (Calbiochem; PC267; NOVUS biologicals; EP1998Y), Rab5a (NOVUS Biologicals; NBP1-58880), Rab7a (Novus Biologicals; NBP1-87174), TRAP-α (ref), nSMase (Thermo Scientific; PA5-24614), total OXPHOS mouse cocktail (abcam, ab110413), TOM20 (Santa Cruz; sc-11415), β-tubulin (Sigma; T4026), vinculin (Sigma, V4505), and VDAC1 (Abcam; 34726). TLC silica plates were from EMD Biosciences (5748-7). Ceramide (22244), sphingomyelin (S0756), cholesteryl palmitate (C6072), cholesteryl oleate (C9253), lipid markers for TLC (P3817), α-secretase inhibitor TAPI-1 (SML0739), cytochrome c from horse heart (C2506), 3,3'-diaminobenzidine tetrahydrochloride hydrate (D5637), GI254023X (SML0789), β-secretase inhibitor IV (Calbiochem; 565788), γ-secretase inhibitor DAPT (D5942), antimycin A (A8674), FCCP (carbonyl-cyanide p-(trifluoromethoxy)phenylhydrazone) (C2920), NADH Grade II, disodium salt (Roche; 10128023001), nitro blue tetrazolium (N5514-25TA1), oligomycin (O4876), rotenone (R8875), imatinib mesylate (Gleevec®, SML1027), and serine palmitoyltransferase inhibitor myriocin (M1177) were from Sigma. Fluorescent lipids BODIPY-FL C6 ceramide complexed to BSA (N22651) and BODIPY-FL C12-sphingomyelin (D7711) were from Invitrogen. Radiolabelled 3H-serine and 3H-cholesterol were from Perkin Elmer; fatty acid-free bovine serum albumin (FAF-BSA) was from MP Biomedical (820472). Amyloid β peptides 40 aa and 42 aa were from Biopolymer Laboratory (UCLA), and AICD peptide was from Genescript Corporation (Piscataway, N.J., USA).

Seahorse Analysis

Respirometry of cultured cells was performed using the XF24e Extracellular Flux Analyzer (Seahorse Bioscience). Oxygen consumption was measured in basal conditions (Seahorse media with 25 mM glucose and 2 mM pyruvate) and after the sequential addition of 1 μM oligomycin (complex V inhibitor), 0.75 μM FCCP (uncoupler), and 1 μM rotenone/1 μM antimycin A (complex I and complex III inhibitors, respectively). All results were averages of five or more biological replicates. Every biological replicate consisted of three technical replicates. For every technical replicate, we plated equal number of cells (25,000 cell/well when MEFs were used, and 50,000 cells/well when human primary fibroblasts were analyzed). The number of cells was also counted after every respirometry assay to correct for cell death. All oxygen consumption (OCR) data were normalized by the number of viable cells or by protein quantity when isolated mitochondria were used.

For permeabilization assays, the cell culture medium was replaced by the mitochondrial assay solution (70 mM sucrose, 220 mM mannitol, 5 mM KH2PO4, 5 mM MgCl2, 2 mM HEPES, 1 mM EGTA and 0.2% FAF-BSA, pH 7.4) containing 10 nM of the XF Plasma membrane permeabilizer reagent XF PMP (Seahorse Bioscience #102504-100) and pyruvate/malate (for complex I assays) or succinate/rotenone (for complex II assays). Oxygen consumption was measured at States 2, 3, 4, and uncoupling after sequential addition of 3 mM ADP, 4 μM oligomycin, 6 μM FCCP, and 4.5 μM Antimycin A.

To analyze mitochondrial respiration in mouse tissues, mitochondria were isolated from WT and PS1-KIM146V mouse brain. Mouse brains were homogenized in ~10 volumes of homogenization buffer (210 mM mannitol, 70 mM sucrose, 5 mM HEPES, and 1 mM EGTA) and then centrifuged at 900×g for 10 min at 4° C. The remaining supernatant was centrifuged at 9,000×g for 10 min at 4° C., and the resulting pellets were resuspended in washing buffer (210 mM mannitol, 70 mM sucrose, 5 mM HEPES, 1 mM EGTA, and 0.5% FAF-BSA pH 7.2) and centrifuged again at 8,000×g for 10 min at 4° C. The pellets, containing mitochondria, were resuspended in mitochondrial assay solution, and protein was quantitated using the BCA Protein Assay kit (Thermo Scientific #23227). For complex I experiments, 8 μg of protein was added to each well and for complex II analysis 6 μg per well. Analyses in the Seahorse analyzer were performed as described in the permeabilization assays.

Culture of Primary Mouse Cortical Neurons

Cortexes from four 14-day-old embryos were cut in pieces and washed in 45% glucose in PBS. After that, brain tissues were resuspended in 1 ml trypsin diluted in 45% glucose in PBS (1:1 v/v) and incubated at 37° C. for 20 min. Samples were added to 500 μl horse serum and 10 units of DNase and incubated for 10 min at room temperature until debris sank to the bottom of the tubes. The non-debris fraction was pelleted at 800×g for 10 min and resuspended in Neurobasal Medium (Life Technologies; 21103-049) supplemented with 200 mM glutamine. Cells were counted and seeded on coverslips coated with poly-omithine and laminin.

Plasmid Constructs and Transfections

Plasmids were constructed using standard techniques. In brief, APP fragments AICD and C99 were amplified from pCAX APP-695 (Young-Pearse et al, 2007), using forward primer 5'-cccgctagcctcgag ATGCTGAAGAAGAAACAGTACACATCCATTC-3' (SEQ ID NO: 2) for AICD, and 5'-cccggatcc ATGGATGCAGAATTCCGACATGACTC-3' (SEQ ID NO: 3) for C99, with a single reverse primer 5'-cccggatccaagcttCTAGTTCTGCATCTGCTCAAAGAACTTG-3' (SEQ ID NO: 4) for both; restriction sites for subcloning are underlined and the start/stop codons are in bold. The PCR products were cut with XhoI+BamHI (for AICD) or with BamHI (for C99) and subcloned into the corresponding sites in pGFP-N3 (Clontech). Plasmid C99-GFP was kind gift of Dr. Albert Lleo. For the construction of this plasmid, C99 amplified from APP770 GFP using forward primer (Scott): (HindIII) 5' gcaagcttgcagaattccgacatgactcagga 3' and reverse primer cw mini LRP 3' (psectag 2B mini LRP GFP primers). The fragment was subcloned into psectag 2B with HindII/NotI. All plasmids were verified by restriction analysis and sequencing. Cells were transfected using Lipofectamine™ Transfection Reagent (Thermo Fisher Scientific, Life Technologies) according to the manufacturer's instructions.

Subcellular Fractionation and Western Blotting

Purification of ER, MAM, and mitochondria was performed and analyzed as described (Area-Gomez et al, 2009).

For C99 detection, samples were run in 4-12% Bis-Tris gels (Criterion XT Precast Midi Gels, BioRad) in XT MES buffer.

Electron Microscopy Analysis

Samples were fixed in 2.5% glutaraldehyde in 0.1 M sodium cacodylate buffer, enrobed in 4% gelatin, postfixed with 1% osmium tetroxide (aq) followed by 2% uranyl acetate, dehydrated through a graded series of ethanol, and embedded in LX112 resin (LADD Research Industries, Burlington, Vt., USA). Ultrathin sections were cut onto nickel grids with a Leica Ultracut UCT (Leica Microsystems, Wetzlar, Germany).

Antigen Retrieval Immunolabeling

Sections were etched with saturated sodium metaperiodate for 1 h, washed with PBS, blocked with 1% BSA, and incubated with primary antibody overnight at 4°. The next day, they were washed and then incubated in 6 nm goat anti-rabbit gold (Aurion, NL), for 2 h at room temperature. Sections were counterstained with uranyl acetate and viewed on a JEOL JEM-1400Plus transmission electron microscope at 120 kV.

Inhibition of α-, β-, and γ-Secretase Activity

To inhibit γ-secretase activity, cells were treated with 10 μM DAPT, a highly specific inhibitor of this enzyme complex. For β-secretase inhibition, cells were treated with 100 nM β-secretase inhibitor IV (BI) or different doses of imatinib lysate (Gleevec). To inhibit α-secretase, cells were treated with 5 μM of TAPI-1 (Enzo Life Sciences). Inhibition of aSMase and the nSMase activities was performed using 10 μM desipramine or 5 μM GW4869, respectively. To inhibit serine palmitoyltransferase activity, the cells were treated with 5 μM myriocin. Incubations with all drugs were for 12-16 h.

Staining of Lipid Droplets

Staining of lipid droplets was performed using HCS LipidTox™ Deep Green neutral lipid stain (Invitrogen H34475) according to the manufacturer's instructions. Lipid droplet staining was quantified using ImageJ. The different values represent the product of the intensity and the area covered by the fluorescent signal above background in every cell examined.

Sphingolipid Synthesis in Cultured Cells

Cells were incubated for 2 h with serum-free medium to ensure removal of exogenous lipids. The medium was then replaced with MEM containing 2.5 μCi/ml of 3H-serine for the indicated periods of time. The cells were washed and collected in PBS, pelleted at 2,500×g for 5 min at 4° C., and resuspended in 0.5 ml water, removing a small aliquot for protein quantification. Lipid extraction was done in three volumes of chloroform:methanol:HCl (2:1:0.5 v/v/v) added to the samples. Samples were vortexed and centrifuged at 8,000×g for 5 min; the organic phase was blown and dried under nitrogen. Dried lipids were resuspended in 30 μl of chloroform:methanol (2:1 v/v) and applied to a TLC plate. Sphingolipids were separated using a solvent composed of chloroform/methanol/0.22% CaCl2 (60:35:8 v/v/v). Development was performed by exposure of the plate to iodine vapor. The spots corresponding to the relevant sphingolipids (identified using co-migrating standards) were scraped and counted in a scintillation counter (Packard Tri-Carb 2900TR).

Lipidomic Analyses

Lipids were extracted from equal amounts of material (30 μg protein/sample). Lipid extracts were prepared via chloroform-methanol extraction, spiked with appropriate internal standards, and analyzed using a 6490 Triple Quadrupole LC/MS system (Agilent Technologies, Santa Clara, Calif.) as described previously (Chan et al, 2012). Glycerophospholipids and sphingolipids were separated with normal-phase HPLC using an Agilent Zorbax Rx-Sil column (inner diameter 2.1×100 mm) under the following conditions: mobile phase A (chloroform:methanol:1 M ammonium hydroxide, 89.9:10:0.1, v/v/v) and mobile phase B (chloroform:methanol:water:ammonium hydroxide, 55:39.9:5:0.1, v/v/v/v); 95% A for 2 min, linear gradient to 30% A over 18 min and held for 3 min, and linear gradient to 95% A over 2 min and held for 6 min. Quantification of lipid species was accomplished using multiple reaction monitoring (MRM) transitions that were developed in earlier studies (Chan et al, 2012) in conjunction with referencing of appropriate internal standards: ceramide d18:1/17:0 and sphingomyelin d18:1/12:0 (Avanti Polar Lipids, Alabaster, Ala., USA). Values are represented as mole fraction with respect to total lipid (% molarity). For this, lipid mass (in moles) of any specific lipid is normalized by the total mass (in moles) of all the lipids measured (Chan et al, 2012). In addition, all of our results were further normalized by protein content.

Analysis of Sphingolipid Synthesis in Subcellular Fractions

Cellular fractions were isolated from MEFs as described (Area-Gomez et al, 2009). Two hundred micrograms was incubated in a final volume of 200 μl of 100 mM HEPES pH 7.4, 5 mM DTT, 10 mM EDTA, 50 μM pyridoxal phosphate, 0.15 mM palmitoyl-CoA, and 3 μCi/ml 3H-Ser for 20 min at 37° C. The reaction was stopped by addition of three volumes of chloroform/methanol (2:1 v/v). Lipid extraction and TLC analysis were performed as described above.

Analysis of Sphingomyelinase Activity

One hundred micrograms of protein was assayed in 100 mM of the appropriate buffer (Tris/glycine for pH 7.0-9.0 and sodium acetate for pH 4.0-5.0), 1.55 mM Triton X-100, 0.025% BSA, 1 mM MgCl2, and 400 μM bovine brain sphingomyelin spiked with 22,000 dpm of [3H]-bovine sphingomyelin (1 nCi/sample). Reactions were carried out in borosilicate glass culture tubes at 37° C., overnight, followed by quenching with 1.2 ml of ice-cold 10% trichloroacetic acid, incubation at 4° C. for 30 min, and centrifugation at 2,000 rpm at 4° C. for 20 min. One milliliter of supernatant was transferred to clean tubes, 1 ml of ether was added, the mixture vortexed, and centrifuged at 2,000 rpm for 5 min. Eight hundred microliters of the bottom phase was transferred to scintillation vials, 5 ml of Scintiverse BD (Fisher Scientific, Fair Lawn, N.J., USA) was added, and samples were counted.

ACAT Activity Assay

To measure cholesterol esterification in vivo, cultured cells were incubated in serum-free medium for 2 h to remove all exogenous lipids. After that, 2.5 μCi/ml of 3H-cholesterol was added to FBS-free DMEM containing 2% FAF-BSA, allowed to equilibrate for at least 30 min at 37° C., and the radiolabeled medium was added to the cells for the indicated periods of time. Cells were then washed and collected in DPBS, removing a small aliquot for protein quantification. Lipids were extracted in three volumes of chloroform: methanol (2:1 v/v). After vortexing and centrifugation at 8,000×g for 5 min, the organic phase was blown to dryness under nitrogen. Dried lipids were resuspended in 30 μl of chloroform:methanol (2:1 v/v) and applied to a TLC plate along with unlabeled standards. A mixture of hexanes/diethyl ether/acetic acid (80:20:1 v/v/v) was used as solvent. Iodine-stained bands corresponding to cholesterol and cholesteryl esters were scraped and counted.

Analysis of ER-Mitochondrial Apposition

Cells under were co-transfected with GFP-Sec61-β (Addgene plasmid #15108) and DsRed2-Mito (Clontech, #632421) at a 1:1 ratio, using Lipofectamine 2000 (Invitrogen, #11668-027) in serum-free DMEM. Twelve hours post-transfection, cells were analyzed as described (Guardia-Laguarta et al, 2014).

Preparation of Synthetic Aβ in Different States of Aggregation and Aβ40/Aβ42 Detection Lyophilized Aβ40 and Aβ42 peptides (American Peptide; 62-0-80; UCLA) were equilibrated at room temperature for 30 min and then resuspended in hexafluoro-2-propanol (HIFP) (Sigma; H8508) to 1 mM using a glass-tight Hamilton syringe with Teflon plunger. HIFP was allowed to evaporate in a fume hood and dried under vacuum in a SpeedVac (Savant Instruments) and kept at −20° C. Immediately prior to use, an aliquot was resuspended to 5 mM in DMSO followed by bath sonication for 10 min.

To analyze the effect of Aβ addition, a mix of Aβ40/Aβ42 at a ratio 10:1 was added to the cultured cells to a final concentration of 6,000 pg/ml for 24 h. For Aβ42 oligomer formation, 5 mM of Aβ42 in DMSO was diluted to 100 μM in ice-cold media, vortexed for 30 s, and incubated at 4° C. for 24 h. Aβ42 oligomers were added to the cultured cells to a final concentration of 5 or 10 μM for 24 h.

Detection of Aβ40/Aβ42 levels in cell media was performed by ELISA following manufacturer's instructions (WAKO ELISA kit 294-64701 for Aβ40 and 292-64501 for Aβ42).

Quantitative Reverse Transcription-Polymerase Chain Reaction (qRT-PCR)

Total RNA was extracted from MEFs using TRIzol® Reagent (Invitrogen 15596-018) according to the manufacturer's instructions and was quantified by NanoDrop2000 (Thermo Scientific). One microgram of total RNA was used to obtain cDNA by RTPCR using a High Capacity cDNA Reverse Transcription Kit (Applied Biosystems; PN 4368813, 4374966). Real-Time PCR was performed in triplicate in a StepOnePlus™ Real-Time PCR System (Applied Biosystems; 4376600). The expression of each gene under study was analyzed using specific predesigned TaqMan Probes (PGC-1α, ppargcla Mm01208835_ml; aSMase, smpd1 Mm00488319_g1; nSMase, smpd3 Mm00491359_ml). The forward and reverse primers (5'→3') for Cox1 quantification were, respectively: TGCTAGCCGCAGGCATTACT (SEQ ID NO: 5) and CGGGATCAAAGAAAGTTGTGTTT (SEQ ID NO: 6). The expression of each gene under study was analyzed using specific predesigned TaqMan Probes and normalized against Gapdh expression (Applied Biosystems, 4352339E) as an internal standard.

Supercomplex Analysis

Analysis and quantification of mitochondrial respiratory complexes by Western blot and enzymatic in-gel activity were carried out as described (Acin-Perez et al, 2008).

Statistical Analyses

All averages are the result of three or more independent experiments carried out at different times with different sets of samples. Tests of significance employed Student's t-test at $P<0.05$, unless indicated otherwise; all error bars in the figures are ±SD. For the determination of ER-mitochondrial apposition, all images were taken randomly from a set of multiple fields. The degree of colocalization was analyzed by ImageJ, and data were compared using Mander's coefficient.

REFERENCES

Acin-Perez R, Fernandez-Silva P, Peleato M L, Perez-Martos A, Enriquez JA (2008) Respiratory active mitochondrial supercomplexes. Mol Cell 32: 529-539

Acin-Perez R, Enriquez J A (2014) The function of the respiratory supercomplexes: the plasticity model. Biochim Biophys Acta 1837: 444-450

Ardail D, Popa I, Bodennec J, Louisot P, Schmitt D, Portoukalian J (2003) The mitochondria-associated endoplasmic-reticulum subcompartment (MAM fraction) of rat liver contains highly active sphingolipid-specific glycosyltransferases. Biochem J 371: 1013-1019

Area-Gomez E, de Groof A J, Boldogh I, Bird T D, Gibson G E, Koehler C M, Yu W H, Duff K E, Yaffe M P, Pon L A, Schon E A (2009) Presenilins are enriched in endoplasmic reticulum membranes associated with mitochondria. Am J Pathol 175: 1810-1816

Area-Gomez E, Del Carmen Lara Castillo M, Tambini M D, Guardia-Laguarta C, de Groof A J, Madra M, Ikenouchi J, Umeda M, Bird T D, Sturley S L, Schon E A (2012) Upregulated function of mitochondria-associated ER membranes in Alzheimer disease. EMBO J 31: 4106-4123

Area-Gomez E (2014) Assessing the function of mitochondria-associated ER membranes. Methods Enzymol 547: 181-197

Balietti M, Giorgetti B, Casoli T, Solazzi M, Tamagnini F, Burattini C, Aicardi G, Fattoretti P (2013) Early selective vulnerability of synapses and synaptic mitochondria in the hippocampal CA1 region of the Tg2576 mouse model of Alzheimer's disease. J Alzheimers Dis 34: 887-896 de Brito O M, Scorrano L (2008) Mitofusin 2 tethers endoplasmic reticulum to mitochondria. Nature 456: 605-610

Browman D T, Resek M E, Zajchowski L D, Robbins S M (2006) Erlin-1 and erlin-2 are novel members of the prohibitin family of proteins that define lipid-raft-like domains of the E R. J Cell Sci 119: 3149-3160

Casley C S, Canevari L, Land J M, Clark J B, Sharpe M A (2002) Beta-amyloid inhibits integrated mitochondrial respiration and key enzyme activities. J Neurochem 80: 91-100

Castello M A, Jeppson J D, Soriano S (2014) Moving beyond anti-amyloid therapy for the prevention and treatment of Alzheimer's disease. BMC Neurol 14: 169

Chan R B, Oliveira T G, Cortes E P, Honig L S, Duff K E, Small S A, Wenk M R, Shui G, Di Paolo G (2012) Comparative lipidomic analysis of mouse and human brain with Alzheimer disease. J Biol Chem 287: 2678-2688

Cordy J M, Hooper N M, Turner A J (2006) The involvement of lipid rafts in Alzheimer's disease. Mol Membr Biol 23: 111-122

Cutler R G, Kelly J, Storie K, Pedersen W A, Tammara A, Hatanpaa K, Troncoso J C, Mattson M P (2004) Involvement of oxidative stress-induced abnormalities in ceramide and cholesterol metabolism in brain aging and Alzheimer's disease. Proc Natl Acad Sci USA 101: 2070-2075

Das U, Wang L, Ganguly A, Saikia J M, Wagner S L, Koo E H, Roy S (2016) Visualizing APP and BACE-1 approximation in neurons yields insight into the amyloidogenic pathway. Nat Neurosci 19: 55-64

De Tullio L, Maggio B, Hartel S, Jara J, Fanani M L (2007) The initial surface composition and topography modulate sphingomyelinase-driven sphingomyelin to ceramide conversion in lipid monolayers. Cell Biochem Biophys 47: 169-177
Devi L, Ohno M (2012) Mitochondrial dysfunction and accumulation of the beta-secretase-cleaved C-terminal fragment of APP in Alzheimer's disease transgenic mice. Neurobiol Dis 45: 417-424
Dinkla S, Wessels K, Verdurmen W P, Tomelleri C, Cluitmans J C, Fransen J, Fuchs B, Schiller J, Joosten I, Brock R, Bosman G J (2012) Functional consequences of sphingomyelinase-induced changes in erythrocyte membrane structure. Cell Death Dis 3: e410
Du H, Guo L, Yan S, Sosunov A A, McKhann G M, Yan S S (2010) Early deficits in synaptic mitochondria in an Alzheimer's disease mouse model. Proc Natl Acad Sci USA 107: 18670-18675
van Echten-Deckert G, Walter J (2012) Sphingolipids: critical players in Alzheimer's disease. Prog Lipid Res 51: 378-393
Filippov V, Song M A, Zhang K, Vinters H V, Tung S, Kirsch W M, Yang J, Duerksen-Hughes P J (2012) Increased ceramide in brains with Alzheimer's and other neurodegenerative diseases. J Alzheimers Dis 29: 537-547
Fukumoto H, Cheung B S, Hyman B T, Irizarry M C (2002) Beta-secretase protein and activity are increased in the neocortex in Alzheimer disease. Arch Neurol 59: 1381-1389
Grimm M O, Grosgen S, Rothhaar T L, Burg V K, Hundsdorfer B, Haupenthal V J, Friess P, Muller U, Fassbender K, Riemenschneider M, Grimm H S, Hartmann T (2011) Intracellular APP domain regulates serine-palmitoyl-CoA transferase expression and is affected in Alzheimer's disease. Int J Alzheimers Dis 2011: 695413
Guardia-Laguarta C, Area-Gomez E, Rub C, Liu Y, Magrane J, Becker D, Voos W, Schon E A, Przedborski S (2014) Alpha-Synuclein is localized to mitochondria-associated ER membranes. J Neurosci 34: 249-259
Guo Q, Fu W, Sopher B L, Miller M W, Ware C B, Martin G M, Mattson M P (1999) Increased vulnerability of hippocampal neurons to excitotoxic necrosis in presenilin-1 mutant knock-in mice. Nat Med 5: 101-106
Haass C, Kaether C, Thinakaran G, Sisodia S (2012) Trafficking and proteolytic processing of APP. Cold Spring Harb Perspect Med 2: a006270
Hansson Petersen C A, Alikhani N, Behbahani H, Wiehager B, Pavlov P F, Alafuzoff I, Leinonen V, Ito A, Winblad B, Glaser E, Ankarcrona M (2008) The amyloid beta-peptide is imported into mitochondria via the TOM import machinery and localized to mitochondrial cristae. Proc Natl Acad Sci USA 105: 13145-13150
Hardy J A, Higgins G A (1992) Alzheimer's disease: the amyloid cascade hypothesis. Science 256: 184-185
He X, Huang Y, Li B, Gong C X, Schuchman E H (2010) Deregulation of sphingolipid metabolism in Alzheimer's disease. Neurobiol Aging 31: 398-408
Hedskog L, Pinho C M, Filadi R, Ronnback A, Hertwig L, Wiehager B, Larssen P, Gellhaar S, Sandebring A, Westerlund M, Graff C, Winblad B, Galter D, Behbahani H, Pizzo P, Glaser E, Ankarcrona M (2013) Modulation of the endoplasmic reticulum-mitochondria interface in Alzheimer's disease and related models. Proc Natl Acad Sci USA 110: 7916-7921
Herms J, Anliker B, Heber S, Ring S, Fuhrmann M, Kretzschmar H, Sisodia S, Muller U (2004) Cortical dysplasia resembling human type 2 lissencephaly in mice lacking all three APP family members. EMBO J 23: 4106-4115
Herreman A, Semeels L, Annaert W, Collen D, Schoonjans L, De Strooper B (2000) Total inactivation of γ-secretase activity in presenilin-deficient embryonic stem cells. Nat Cell Biol 2: 461-462
Holsinger R M, McLean C A, Beyreuther K, Masters C L, Evin G (2002) Increased expression of the amyloid precursor beta-secretase in Alzheimer's disease. Ann Neurol 51: 783-786
Jiang Y, Mullaney K A, Peterhoff C M, Che S, Schmidt S D, Boyer-Boiteau A, Ginsberg S D, Cataldo A M, Mathews P M, Nixon R A (2010) Alzheimer's-related endosome dysfunction in Down syndrome is Abeta-independent but requires APP and is reversed by BACE-1 inhibition. Proc Natl Acad Sci USA 107: 1630-1635
Kannan M, Lahiri S, Liu L K, Choudhary V, Prinz W A (2017) Phosphatidylserine synthesis at membrane contact sites promotes its transport out of the ER. J Lipid Res 58: 1539-7262 [PMC free article]
Kennedy M A, Moffat T C, Gable K, Ganesan S, Niewola-Staszkowska K, Johnston A, Nislow C, Giaever G, Harris L J, Loewith R, Zaremberg V, Harper M E, Dunn T, Bennett S A, Baetz K (2016) A signaling lipid associated with Alzheimer's disease promotes mitochondrial dysfunction. Sci Rep 6: 19332
Kogot-Levin A, Saada A (2014) Ceramide and the mitochondrial respiratory chain. Biochimie 100: 88-94
Lauritzen I, Pardossi-Piquard R, Bauer C, Brigham E, Abraham J D, Ranaldi S, Fraser P, St-George-Hyslop P, Le Thuc O, Espin V, Chami L, Dunys J, Checler F (2012) The beta-secretase-derived C-terminal fragment of betaAPP, C99, but not Abeta, is a key contributor to early intraneuronal lesions in triple-transgenic mouse hippocampus. J Neurosci 32: 16243-16255a
Lee K W, Im J Y, Song J S, Lee S H, Lee H J, Ha H Y, Koh J Y, Gwag B J, Yang S D, Paik S G, Han P L (2006) Progressive neuronal loss and behavioral impairments of transgenic C57B L/6 inbred mice expressing the carboxy terminus of amyloid precursor protein. Neurobiol Dis 22: 10-24
Lee J K, Jin H K, Park M H, Kim B R, Lee P H, Nakauchi H, Carter J E, He X, Schuchman E H, Bae J S (2014) Acid sphingomyelinase modulates the autophagic process by controlling lysosomal biogenesis in Alzheimer's disease. J Exp Med 211: 1551-1570
Li R, Lindholm K, Yang L B, Yue X, Citron M, Yan R, Beach T, Sue L, Sabbagh M, Cai H, Wong P, Price D, Shen Y (2004) Amyloid beta peptide load is correlated with increased beta-secretase activity in sporadic Alzheimer's disease patients. Proc Natl Acad Sci USA 101: 3632-3637
Luo Y, Bolon B, Kahn S, Bennett B D, Babu-Khan S, Denis P, Fan W, Kha H, Zhang J, Gong Y, Martin L, Louis J C, Yan Q, Richards W G, Citron M, Vassar R (2001) Mice deficient in BACE1, the Alzheimer's beta-secretase, have normal phenotype and abolished beta-amyloid generation. Nat Neurosci 4: 231-232
Manczak M, Anekonda T S, Henson E, Park B S, Quinn J, Reddy P H (2006) Mitochondria are a direct site of Aβ accumulation in Alzheimer's disease neurons: implications for free radical generation and oxidative damage in disease progression. Hum Mol Genet 15: 1437-1449
Mapstone M, Cheema A K, Fiandaca M S, Zhong X, Mhyre T R, MacArthur L H, Hall W J, Fisher S G, Peterson D R, Haley J M, Nazar M D, Rich S A, Berlau D J, Peltz C B, Tan M T, Kawas C H, Federoff H J (2014) Plasma phospholipids identify antecedent memory impairment in older adults. Nat Med 20: 415-418

Matsumura N, Takami M, Okochi M, Wada-Kakuda S, Fujiwara H, Tagami S, Funamoto S, Ihara Y, Morishima-Kawashima M (2014) gamma-Secretase associated with lipid rafts: multiple interactive pathways in the stepwise processing of beta-carboxyl-terminal fragment. J Biol Chem 289: 5109-5121

McBrayer M, Nixon R A (2013) Lysosome and calcium dysregulation in Alzheimer's disease: partners in crime. Biochem Soc Trans 41: 1495-1502

McPhie D L, Lee R K, Eckman C B, Olstein D H, Durham S P, Yager D, Younkin S G, Wurtman R J, Neve R L (1997) Neuronal expression of I3-amyloid precursor protein Alzheimer mutations causes intracellular accumulation of a C-terminal fragment containing both the amyloid β and cytoplasmic domains. J Biol Chem 272: 24743-24746

Moore S, Evans L D, Andersson T, Portelius E, Smith J, Dias T B, Saurat N, McGlade A, Kirwan P, Blennow K, Hardy J, Zetterberg H, Livesey F J (2015) APP metabolism regulates tau proteostasis in human cerebral cortex neurons. Cell Rep 11: 689-696

Netzer W J, Bettayeb K, Sinha S C, Flajolet M, Greengard P, Bustos V (2017) Gleevec shifts APP processing from a beta-cleavage to a nonamyloidogenic cleavage. Proc Natl Acad Sci USA 114: 1389-1394

Neve R L, Boyce F M, McPhie D L, Greenan J, Oster-Granite M L (1996) Transgenic mice expressing APP-C100 in the brain. Neurobiol Aging 17: 191-203

Newman M, Wilson L, Verdile G, Lim A, Khan I, Moussavi Nik S H, Pursglove S, Chapman G, Martins R N, Lardelli M (2014) Differential, dominant activation and inhibition of Notch signalling and APP cleavage by truncations of PSEN1 in human disease. Hum Mol Genet 23: 602-617

Pera M, Alcolea D, Sanchez-Valle R, Guardia-Laguarta C, Colom-Cadena M, Badiola N, Suarez-Calvet M, Llado A, Barrera-Ocampo A A, Sepulveda-Falla D, Blesa R, Molinuevo J L, Clarimon J, Ferrer I, Gelpi E, Lleo A (2013) Distinct patterns of APP processing in the CNS in autosomal-dominant and sporadic Alzheimer disease. Acta Neuropathol 125: 201-213

Pike L J (2009) The challenge of lipid rafts. J Lipid Res 50: S323-S328

Rockenstein E, Mante M, Alford M, Adame A, Crews L, Hashimoto M, Esposito L, Mucke L, Masliah E (2005) High beta-secretase activity elicits neurodegeneration in transgenic mice despite reductions in amyloid-beta levels: implications for the treatment of Alzheimer disease. J Biol Chem 280: 32957-32967

Rowland A A, Chitwood P J, Phillips M J, Voeltz G K (2014) E R contact sites define the position and timing of endosome fission. Cell 159: 1027-1041

Saito T, Suemoto T, Brouwers N, Sleegers K, Funamoto S, Mihira N, Matsuba Y, Yamada K, Nilsson P, Takano J, Nishimura M, Iwata N, Van Broeckhoven C, Ihara Y, Saido T C (2011) Potent amyloidogenicity and pathogenicity of Abeta43. Nat Neurosci 14: 1023-1032

Schon E A, Area-Gomez E (2010) Is Alzheimer's disease a disorder of mitochondria-associated membranes? J Alzheimers Dis 20(Suppl 2): S281-S292

Schon E A, Area-Gomez E (2013) Mitochondria-associated ER membranes in Alzheimer disease. Mol Cell Neurosci 55: 26-36

Schreiner B, Hedskog L, Wiehager B, Ankarcrona M (2015) Amyloid-beta peptides are generated in mitochondria-associated endoplasmic reticulum membranes. J Alzheimers Dis 43: 369-374

Silva L C, Futerman A H, Prieto M (2009) Lipid raft composition modulates sphingomyelinase activity and ceramide-induced membrane physical alterations. Biophys J 96: 3210-3222

Simons K, Vaz W L (2004) Model systems, lipid rafts, and cell membranes. Annu Rev Biophys Biomol Struct 33: 269-295

Swerdlow R H, Burns J M, Khan S M (2014) The Alzheimer's disease mitochondrial cascade hypothesis: progress and perspectives. Biochim Biophys Acta 1842: 1219-1231

Tamayev R, Matsuda S, Arancio O, D'Adamio L (2012) beta-but not gamma-secretase proteolysis of APP causes synaptic and memory deficits in a mouse model of dementia. EMBO Mol Med 4: 171-179

Vance J E (2014) MAM (mitochondria-associated membranes) in mammalian cells: lipids and beyond. Biochim Biophys Acta 1841: 595-609

Wang X, Wang W, Li L, Perry G, Lee H G, Zhu X (2014) Oxidative stress and mitochondrial dysfunction in Alzheimer's disease. Biochim Biophys Acta 1842: 1240-1247

Wilhelm L P, Wendling C, Vedie B, Kobayashi T, Chenard M P, Tomasetto C, Drin G, Alpy F (2017) STARD3 mediates endoplasmic reticulum-to-endosome cholesterol transport at membrane contact sites. EMBO J 36: 1412-1433

Wu W I, Voelker D R (2004) Reconstitution of phosphatidylserine transport from chemically defined donor membranes to phosphatidylserine decarboxylase 2 implicates specific lipid domains in the process. J Biol Chem 279: 6635-6642

Wu B X, Clarke C J, Matmati N, Montefusco D, Bartke N, Hannun Y A (2011) Identification of novel anionic phospholipid binding domains in neutral sphingomyelinase 2 with selective binding preference. J Biol Chem 286: 22362-22371

Xie H, Guan J, Borrelli L A, Xu J, Serrano-Pozo A, Bacskai B J (2013) Mitochondrial alterations near amyloid plaques in an Alzheimer's disease mouse model. J Neurosci 33: 17042-17051

Yang L B, Lindholm K, Yan R, Citron M, Xia W, Yang X L, Beach T, Sue L, Wong P, Price D, Li R, Shen Y (2003) Elevated beta-secretase expression and enzymatic activity detected in sporadic Alzheimer disease. Nat Med 9: 3-4

Yao J, Irwin R W, Zhao L, Nilsen J, Hamilton R T, Brinton R D (2009) Mitochondrial bioenergetic deficit precedes Alzheimer's pathology in female mouse model of Alzheimer's disease. Proc Natl Acad Sci USA 106: 14670-14675

Young-Pearse T L, Bai J, Chang R, Zheng J B, LoTurco J J, Selkoe D J (2007) A critical function for beta-amyloid precursor protein in neuronal migration revealed by in utero RNA interference. J Neurosci 27: 14459-14469

Zhang X, Herrmann U, Weyer S W, Both M, Muller U C, Korte M, Draguhn A (2013) Hippocampal network oscillations in APP/APLP2-deficient mice. PLoS One 8: e61198

Zigdon H, Kogot-Levin A, Park J W, Goldschmidt R, Kelly S, Merrill A H Jr, Scherz A, Pewzner-Jung Y, Saada A, Futerman A H (2013) Ablation of ceramide synthase 2 causes chronic oxidative stress due to disruption of the mitochondrial respiratory chain. J Biol Chem 288: 4947-4956

What is claimed:

1. A method of reducing the level of endoplasmic reticulum-mitochondrial-associated membrane (ER-MAM) localized APP-C99 in cells of a subject, comprising:

a) determining a ratio of C99 to total Aβ in a sample from the subject;

b) determining that the ratio of C99 to total Aβ in a sample from the subject is higher than the ratio of C99 to total Aβ in a sample from a subject that does not have Alzheimer's Disease; and c) administering to the subject a composition that reduces the level of ER-MAM localized APP-C99 in cells of the subject.

2. The method of claim 1, wherein the subject has or is suspected of having Alzheimer's disease.

3. The method of claim 1, wherein the level of ER-MAM localized APP-C99 is reduced in cells of the subject by increasing ER-MAM localized γ-secretase activity.

4. The method of claim 1, wherein the composition comprises an effective amount of phenylbutyric acid (PBA), 4-hydroxynonenal, GSK561679, Corticorelin, Xerecept, 12-O tetradecanoylphorbol-13-acetate (TPA), auraptene, isoproterenol, clenbuterol, PD98059, PD0325901, U0126, or Trametinib.

5. The method of claim 1, wherein the level of ER-MAM localized APP-C99 is reduced in cells of the subject by administering to the subject a BACE1 inhibitor or antagonist.

6. The method of claim 1, wherein the level of ER-MAM localized APP-C99 is reduced in cells of the subject by administering to the subject a composition comprising Ezetimibe, myriocin, a SPT inhibitor, a SMase inhibitor, desipramine, zoledronic acid, GW4869, altenusin, cambinol, atorvastatin, a PTK2 inhibitor, an ABCA2 inhibitor, a SREBP inhibitor, a miR33a/b inhibitor, a CypD inhibitor, or U18666a.

7. The method of claim 6, wherein the SMase inhibitor is a neutral SMase inhibitor.

8. A method of treating Alzheimer's Disease in a subject in need thereof, comprising:

a) determining a ratio of C99 to total Aβ in a sample from the subject;

b) determining that the ratio of C99 to total Aβ in the sample from the subject is higher than the ratio of C99 to total Aβ in a sample from a subject that does not have Alzheimer's Disease; and c) administering to the subject a composition that reduces the level of ER-MAM localized APP-C99 in cells of the subject, wherein the composition comprises an effective amount of phenylbutyric acid (PBA), 4-hydroxynonenal, GSK561679, Corticorelin, Xerecept, 12-O tetradecanoylphorbol-13-acetate (TPA), auraptene, isoproterenol, clenbuterol, PD98059, PD0325901, U0126, or Trametinib.

* * * * *

UNITED STATES PATENT AND TRADEMARK OFFICE

CERTIFICATE OF CORRECTION

PATENT NO. : 11,266,626 B2
APPLICATION NO. : 15/917344
DATED : March 8, 2022
INVENTOR(S) : Eric A. Schon et al.

It is certified that error appears in the above-identified patent and that said Letters Patent is hereby corrected as shown below:

In the Specification

In Column 12, Lines 41-45, should read:
The patent or application file contains at least one drawing executed in color. Copies of this patent or patent application publication, with color drawing(s) will be provided by the United States Patent and Trademark Office upon request and payment of the necessary fee.

In Column 16, Lines 44 - Column 17, Lines 1-20, should read:
Figs. 20A-O show mitochondrial bioenergetics in y-secretase-deficient cells. All respiratory chain assays (initial oxygen consumption rate [OCR]) were performed using the Seahorse XF24 Flux Analyzer. (A) Fibroblasts from FAD and SAD patients. (B) Mitochondria from PS1-KIM146V brain. (C) Western blot from homogenates from the indicated cells probed against mitochondrial markers (VDAC and TOM20) and loading controls (D, E) Complex I and II activities in which malate-pyruvate or succinate-rotenone, respectively, were added to permeabilized PS-DKO MEFs (D) and APP-DKO MEFs (E). Note significant decrease in OCR in PS-DKO MEFs but an increase in APP-DKO MEFs. (F) qRT-PCR to measure mRNA levels of mtDNA-encoded COXl as a as measure ofmtDNA in WT and PS-DKO cells before and after addition ofDAPT and BI. (n.s.=not significant). (G) Western blot of total homogenates of WT, PS-DKO, and PS-DKO cells treated with BACEl inhibitor (BI). Note that BI treatment eliminates the accumulation of APP C-terminal fragments in PS-DKO MEFs, without changes in the levels of mitochondria (VDAC). (H) OCR in WT orPS-DKO cells is unaffected by treatment with the y-secretase inhibitor TAPI-1. (I) qRT-PCR to measure mRNA levels of PGC-1a, a master regulator of mitochondrial biogenesis, in WT and PS-DKO cells before and after addition ofDAPT and BI (which do not affect mitochondrial biogenesis). Note lack of an effect on PGC-1a levels in *y*-secretase-deficient cells, n.s., not significant. (J) Western blot from total homogenates of SHSY5Y cells treated with DMSO and a-, 13-, and y-secretase inhibitors probed with the indicated antibodies. Note that none of the treatments change the levels of mitochondria (VDAC). Loading control in the right panel. (K, L) Addition of monomers of Af340 and Af342 (added at a ratio of 10: 1 Af340:Af342, total concentration of Af3 was 6 ng/ml) to PS-DKO cells (K), or to APP-DKO cells (L) did not affect mitochondrial respiration. (M) Addition of Af342 oligomers to WT and APP- Signed and Sealed this
Twentieth Day of December, 2022

Katherine Kelly Vidal

Katherine Kelly Vidal
*Director of the United States Patent and Trademark Office*

DKO cells at a IOiiM concentration decreased respiration. (N) Respiratory chain deficiency in fibroblasts from an FAD patient (AG06840) was rescued following treatment with a BACEl inhibitor (in which C99 production was abrogated) .(Ql Western blot showing how transient transfection of C99 in APP-DKO cells did not affect mitochondrial levels (TOM20) (all experiments represent the average of n>5 independent experiments; n.s., non significant).

In Column 20, Lines 66 - to Column 21, Lines 1-8, should read:
Figs. 36A-E show mitochondrial respiration [o x y gen consumption rate (OCR)] in *y*-secretase-deficient cells. A Oxygen consumption rate in AD fibroblasts (FAD). B. Ox-ygen consumption rate in PS-DKO MEFs. C. Ox y gen consumption rate in SH-SY5Y cells treated with DAPT, an inhibitor of y-secretase activity. Q. Ox y gen consumption rate in APP-DKO MEFs before and after overexpression of C99. E. PS-DKO MEFs treated with BACE inhibitor (BI). Data information: Data represent averages of n > 5 independent experiments± SD. *P < 0.05. Analysis by unpaired t-test.